(12) United States Patent
Li

(10) Patent No.: US 11,034,954 B2
(45) Date of Patent: Jun. 15, 2021

(54) COMPOSITIONS AND METHODS FOR TREATING LEBER'S HEREDITARY OPTIC NEUROPATHY

(71) Applicant: WUHAN NEUROPHTH BIOLOGICAL TECHNOLOGY LIMITED COMPANY, Hubei (CN)

(72) Inventor: Bin Li, Hubei (CN)

(73) Assignee: Wuhan Neurophth Biological Technology Limited Company, Wuhan (CN)

( * ) Notice: Subject to any disclaimer, the term of this patent is extended or adjusted under 35 U.S.C. 154(b) by 0 days.

(21) Appl. No.: 16/836,644

(22) Filed: Mar. 31, 2020

(65) Prior Publication Data
US 2020/0263172 A1    Aug. 20, 2020

Related U.S. Application Data

(63) Continuation of application No. PCT/CN2019/094136, filed on Jul. 1, 2019.

(30) Foreign Application Priority Data

| Jun. 29, 2018 | (CN) | ............... | 201810702492.7 |
| Jun. 29, 2018 | (CN) | ............... | 201810703168.7 |
| Aug. 20, 2018 | (CN) | ............... | 201810948193.1 |
| Oct. 19, 2018 | (CN) | ............... | 201811221305 .X |
| Oct. 22, 2018 | (CN) | ............... | 201811230856.2 |

(51) Int. Cl.
| C12N 15/11 | (2006.01) |
| C12N 9/02 | (2006.01) |
| C12N 15/86 | (2006.01) |
| C12N 7/00 | (2006.01) |
| A61K 31/573 | (2006.01) |
| A61K 31/664 | (2006.01) |
| A61K 9/00 | (2006.01) |
| A61K 35/76 | (2015.01) |

(52) U.S. Cl.
CPC ............ *C12N 15/11* (2013.01); *A61K 9/0019* (2013.01); *A61K 9/0048* (2013.01); *A61K 31/573* (2013.01); *A61K 31/664* (2013.01); *A61K 35/76* (2013.01); *C12N 7/00* (2013.01); *C12N 9/0004* (2013.01); *C12N 15/86* (2013.01); *C12Y 106/99003* (2013.01); *C12N 2750/14143* (2013.01)

(58) Field of Classification Search
CPC ...... C12N 15/11; C12N 9/0004; C12N 15/86; C12N 7/00; C12N 2750/14143; C12N 2830/008; C12Y 106/99003; A61K 31/573; A61K 31/664; A61K 9/0019; A61K 9/0048; A61K 35/76; A61K 9/127; A61K 48/0075; A61K 48/005; A01K 2227/107

See application file for complete search history.

(56) References Cited

U.S. PATENT DOCUMENTS

| 3,625,214 | A | 12/1971 | Higuchi |
| 4,789,734 | A | 12/1988 | Pierschbacher |
| 4,897,268 | A | 1/1990 | Tice et al. |
| 4,906,474 | A | 3/1990 | Langer et al. |
| 4,925,673 | A | 5/1990 | Steiner et al. |
| 5,075,109 | A | 12/1991 | Tice et al. |
| 5,811,128 | A | 9/1998 | Tice et al. |
| 5,814,344 | A | 9/1998 | Tice et al. |
| 5,820,883 | A | 10/1998 | Tice et al. |
| 5,853,763 | A | 12/1998 | Tice et al. |
| 5,928,647 | A | 7/1999 | Rock |
| 5,942,252 | A | 8/1999 | Tice et al. |
| 6,207,392 | B1 | 3/2001 | Weiss et al. |
| 2009/0306188 | A1 | 12/2009 | Corral-Debrinski et al. |

FOREIGN PATENT DOCUMENTS

| CN | 102517304 A | 6/2012 |
| CN | 102634527 A | 8/2012 |
| CN | 104450747 A | 3/2015 |
| EP | 2913403 A1 | 9/2015 |
| WO | WO 2006/117250 A2 | 11/2006 |
| WO | WO 2008/063802 A2 | 5/2008 |
| WO | WO 2016/044023 A1 | 3/2016 |
| WO | WO 2017/011519 A1 | 1/2017 |
| WO | WO 2020/010491 A1 | 1/2020 |
| WO | WO 2020/037938 A1 | 2/2020 |
| WO | WO 2020/038352 A1 | 2/2020 |

(Continued)

OTHER PUBLICATIONS

Greenwood et al. "Current research into brain barriers and the delivery of therapeutics for neurological diseases: a report on CNS barrier congress London, UK, 2017." Fluids Barriers CNS. 2017; 14: 31. (Year: 2017).*

(Continued)

*Primary Examiner* — Titilayo Moloye
(74) *Attorney, Agent, or Firm* — Cooley LLP

(57) ABSTRACT

Disclosed herein is a recombinant nucleic acid, comprising: a mitochondrial targeting sequence; a mitochondrial protein coding sequence, wherein said mitochondrial protein coding sequence encodes a polypeptide comprising a mitochondrial protein; and a 3'UTR nucleic acid sequence. Also disclosed is a pharmaceutical composition comprising the recombinant nucleic acid and a method of treating Leber's hereditary optic neuropathy (LHON) using the pharmaceutical composition.

23 Claims, 18 Drawing Sheets
Specification includes a Sequence Listing.

(56) References Cited

FOREIGN PATENT DOCUMENTS

| WO | WO 2020/077756 A1 | 4/2020 |
|----|-------------------|--------|
| WO | WO 2020/082417 A1 | 4/2020 |

OTHER PUBLICATIONS

Hocquemiller et al. "Adeno-Associated Virus-Based Gene Therapy for CNS Diseases." Hum Gene Ther. Jul. 1, 2016; 27(7): 478-496. (Year: 2016).*
Manfredsson et al. "AAV9: a potential blood-brain barrier buster." Mol Ther. Mar. 2009; 17(3): 403-405. (Year: 2009).*
Hudry et al. "Therapeutic AAV Gene Transfer to the Nervous System: A Clinical Reality." Neuron. Mar. 6, 2019;101(5):839-862. (Year: 2019).*
Ribera et al. "Biochemical, histological and functional correction of mucopolysaccharidosis type IIIB by intra-cerebrospinal fluid gene therapy"Hum Mol Genet Apr. 1, 2015;24(7):2078-95. (Year: 2015).*
Kotterman et al. "Antibody Neutralization Poses a Barrier to Intravitreal Adeno-Associated Viral Vector Gene Delivery to Non-Human Primates." Gene Ther. Feb. 2015; 22(2): 116-126. (Year: 2015).*
Allocca et al., "Novel Adeno-Associated Virus Serotypes Efficiently Transduce Murine Photoreceptors," J Viol 81(20):11372-11380 (2007).
Bainbridge et al., "Effect of gene therapy on visual function in Leber's congenital amaurosis," N Engl J Med. 358(21):2231-2239 (2008).
Bonnet, Crystel et al The optimized allotopic expression of ND1 or ND4 genes restores respiratory chain complex I activity in fibroblasts harboring mutations in these genes Biochimica et Biophysica Acta 31 No. 10(1783):1707-1717 (2008).
Choi et al., "AAV hybrid serotypes: improved vectors for gene delivery," Curr Gene Ther. 5(3):299-310 (2005).
Cronin, et al., "Functional Genomics Study of the RdCVF-/- Mouse Model", Investigative Ophthalmology & Visual Science, vol. 49, No. 3058, 2008, D1048, 2 pages.
Cwerman-Thibault. et al. "Nuclear Expression of Mitochondrial Nd4 Leads to the Protein Assembling in Complex I and Prevents Optic Atrophy and Visual Loss," Molecular Therapy-Methods & Clinical Development. 2(15003):1-15 (2015).
Devereux et al., "A comprehensive set of sequence analysis programs for the VAX," Nucleic Acids Research 12, 387-395 (1984).
Gao et al., "Comparison of Immunosuppressive Effects and ND4 Expression among Different Immunosuppressive Strategies following AAV2-ND4 Gene Treatment for Leber Hereditary Optic Neuropathy," Acta Medicinae Universitatis Scientiae et Technologiae Huazhong 42(2):187-191 (2013).
International Search Report and Written Opinion issued by the International Searching Authority for Application No. PCT/CN2018/095023, dated Apr. 9, 2019, 14 pages including English translation of ISR.
International Search Report and Written Opinion issued by the International Searching Authority for Application No. PCT/CN2018/103937, dated Apr. 3, 2019, 19 pages including English translation of Search Report.
International Search Report and Written Opinion issued by the International Searching Authority for Application No. PCT/CN2018/118662, dated Jul. 18, 2019, 18 pages including English translation of ISR.
International Search Report and Written Opinion issued by the International Searching Authority for Application No. PCT/CN2019/070461, dated May 22, 2019, 13 pages including translation of ISR.
International Search Report and Written Opinion issued by the International Searching Authority for Application No. PCT/CN2019/094136, dated Oct. 10, 2019, 10 pages.
International Search Report and Written Opinion issued by the International Searching Authority for Application No. PCT/CN2019/101538, dated Nov. 29, 2019, 14 pages.
Karlin, S. and Altschul, S., "Applications and statistics for multiple high-scoring segments in molecular sequences," Proc. Natl. Acad. Sci. USA, 90- 5873-5877 (1993).
Koilkonda, R. D. et al. "Safety and Effects of the Vector for the Leber Hereditary Optic Neuropathy Gene Therapy Clinical Trial." JAMA Ophthalmol. 132(4):409-420 (2014).
Laughlin et al., "Spliced adenovirus-associated virus RNA.," PNAS, 76:5567-5571 (1979).
Mancuso et al., "Gene therapy for red-green colour blindness in adult primates," Nature 461:784-787 (2009).
NCBI Reference Sequence: NC_001829.1, dated Aug. 13, 2018, 3 pages.
NCBI Reference Sequence: NC_002077.1, dated Aug. 13, 2018, 3 pages.
NCBI Reference Sequence: NC_001729.1, dated Aug. 13, 2018, 3 pages.
NCBI Reference Sequence: NC_004828.1 Aug. 13, 2018, 3 pages.
NCBI Reference Sequence: NC_005889.1 Aug. 13, 2018, 3 pages.
NCBI. "Genbank Accession No. KP240659.1" GenBank, Dec. 4, 2016 (Dec. 4, 2016), 8 pages.
NCBI. "Genbank Accession No. LX309664.1" GenBank, Oct. 28, 2017 (Oct. 28, 2017).
NCBI. "Genbank Accession No. LX309670.1" GenBank, Oct. 28, 2017 (Oct. 28, 2017), 2 pages.
NCBI. "Genbank Accession No. MF522909.1" GenBank, Oct. 21, 2017 (Oct. 21, 2017), 8 pages.
NCBI. "Genbank Accession No. YP_003024026.1" GenBank, Oct. 31, 2014 (Oct. 31, 2014), 2 pages.
Sun et al., "Detection of Neutralizing Antibody to Human Adenovirus Type 5 in Marmosets," J. South Med. Univ., 36(4):582-587 (2016).
Szoka et al., "Procedure for preparation of liposomes with large internal aqueous space and high capture by reverse-phase evaporation," Proc. Natl Acad. Sci. USA 75: 4194-4198 (1978).
Wan et al., "Efficacy and Safety of rAAV2-ND4 Treatment for Leber's Hereditary Optic Neuropathy," Scientific Reports, vol. 6, Article 21587, pp. 1-10 (2016).
Wu et al., "Adeno-associated virus serotypes: vector toolkit for human gene therapy," Molecular Therapy. 14(3):316-327 (2006).
Yang et al., "Study on transfection of adeno associated virus 2-ND4 gene into mitochondria," Chinese Journal of Experimental Ophthalmology 8(32):693-695 (2014).
Yang et al., "Long-Term Outcomes of Gene Therapy for the Treatment of Leber's Hereditary Optic Neuropathy," Ebiomedicine 10:258-268 (2016).
Yang, S. et al. "Chemical and material communication between the optic nerves in rats," Clinical and Experimental Ophthalmology 43:742-748 (2015).
Yu et al. "Mutant NADH dehydrogenase subunit 4 gene delivery to mitochondria by targeting sequence-modified adeno-associated virus induces visual loss and optic atrophy in mice," Molecular Vision 18:1668-1683 (2012).
Yu et al., "Gene delivery to mitochondria by targeting modified adenoassociated virus suppresses Leber's hereditary optic neuropathy in a mouse model," PNAS, pp. EI238-EI247 (2012).
International Search Report and Written Opinion issued by the International Searching Authority for Application No. PCT/CN2018/113799, dated Aug. 5, 2019, 15 pages including English translation of Search Report.
Kushnareva et al., "Mitochondrial Dysfunction in an Op1 $Q285TOP$ Mouse Model of Dominant Optic Atrophy Results from Opa1 Haploinsufficiency," Cell Death and Disease Jul. 7, 2016(7):e-2309, 13 pages.
GenBank LX309670, dated Oct. 28, 2017, 2 pages.
GenBank LX309664, dated Oct. 28, 2017, 2 pages.
GenBank LX309667, dated Oct. 28, 2017, 2 pages.
Yang, Y, Codon and Anticodon, Foreign Medical Molecular Biology Fascicule 7(4):156-163 (1985) (English translation included).

* cited by examiner

COMPOSITIONS AND METHODS FOR TREATING LEBER'S HEREDITARY OPTIC NEUROPATHY

CROSS-REFERENCE

This application is a continuation application of PCT Application No. PCT/CN2019/094136, filed Jul. 1, 2019, which claims the benefit of PCT Application No. PCT/CN2018/095023, filed on Jul. 9, 2018; PCT Application No. PCT/CN2018/103937, filed on Sep. 4, 2018; Chinese Application Nos. CN201810703168.7 and CN201810702492.7, both filed on Jun. 29, 2018; PCT Application No. PCT/CN2018/113799, filed on Nov. 2, 2018; Chinese Application No. CN201811230856.2, filed on Oct. 22, 2018; PCT Application No. PCT/CN2018/118662, filed on Nov. 30, 2018; Chinese Application No. CN201811221305.X, filed on Oct. 19, 2018; PCT Application No. PCT/CN2019/070461, filed on Jan. 4, 2019; Chinese Application No. CN201810948193.1, filed on Aug. 20, 2018; all of which are incorporated herein by reference in their entirety.

REFERENCE TO A SEQUENCE LISTING

The instant application contains a Sequence Listing which has been submitted in ASCII format via EFS-Web and is hereby incorporated by reference in its entirety. Said ASCII copy, created on Mar. 31, 2020, is named WNBT_002_03US_ST25.txt and is 304,961 bytes in size.

BACKGROUND OF THE INVENTION

Leber's hereditary optic neuropathy (LHON) is a mitochondrially inherited (transmitted from mother to offspring) degeneration of retinal ganglion cells (RGCs) and their axons that leads to an acute or subacute loss of central vision; this affects predominantly young adult males. LHON is only transmitted through the mother, as it is primarily due to mutations in the mitochondrial (not nuclear) genome, and only the egg contributes mitochondria to the embryo. LHON is usually due to one of three pathogenic mitochondrial DNA (mtDNA) point mutations. These mutations are at nucleotide positions 11778 G to A (G11778A), 3460 G to A (G3460A) and 14484 T to C (T14484C), respectively in the NADH dehydrogenase subunit-4 protein (ND4), NADH dehydrogenase subunit-1 protein (ND1) and NADH dehydrogenase subunit-6 protein (ND6) subunit genes of complex I of the oxidative phosphorylation chain in mitochondria. Each mutation is believed to have significant risk of permanent loss of vision. It typically progresses within several weeks to several months without pain, until the binocular vision deteriorate to below 0.1, which seriously affects the quality of life of the patient. Two LHON mutants, G3460A and T14484C, results in the reduction of the patient's platelets isolated mitochondrial NADH dehydrogenase activity by 80%. Ninety percent of the Chinese LHON patients carry the G11778A mutation. The G11778A mutation changes an arginine into histidine in the ND4 protein, resulting the dysfunction and optic nerve damage in LHON patients. There is a need for developing compositions and methods for treating LHON with higher transfection efficiency and treatment efficacy.

SUMMARY OF THE INVENTION

Disclosed here recombinant nucleic acids, pharmaceutical compositions, and methods for treating LHON. In one aspect, disclosed herein is a recombinant nucleic acid, comprising: a mitochondrial targeting sequence; a mitochondrial protein coding sequence comprising a sequence that is at least 99% identical to a sequence selected from the group consisting of SEQ ID NO: 7, 8, 10, and 12; and a 3'UTR nucleic acid sequence.

In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100%0 identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising: a mitochondrial targeting sequence comprising a sequence that is at least 90% identical to a sequence selected from the group consisting of SEQ ID NO: 2, 3, 4, and 5; a mitochondrial protein coding sequence, wherein the mitochondrial protein coding sequence encodes a polypeptide comprising a mitochondrial protein; and a 3'UTR nucleic acid sequence.

In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein is selected from a group consisting of NADH dehydrogenase 4 (ND4), NADH dehydrogenase 6 (ND6), NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90% at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, mSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-84.

In another aspect, disclosed herein is a recombinant nucleic acid, comprising: a mitochondrial targeting sequence; a mitochondrial protein coding sequence comprising a sequence that is at least 90%, at least 95%, at least 97%, at least 99%, or 100% identical to a sequence selected from the group consisting of SEQ ID NO: 7, 8, 10, and 12; and a 3'UTR nucleic acid sequence.

In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATPSG3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2 or 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, mSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14.

In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a recombinant nucleic acid, comprising a mitochondrial targeting sequence that is at least 90%, at least 95%, at least 97%, at least 99%, or 100% identical to a sequence selected from the group consisting of SEQ ID NO: 2, 3, and 4. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4.

In some cases, the recombinant nucleic acid further comprises a mitochondrial protein coding sequence, wherein the mitochondrial protein coding sequence encodes a polypeptide comprising a mitochondrial protein. In some cases, the mitochondrial protein is selected from a group consisting of NADH dehydrogenase 4 (ND4), NADH dehydrogenase 6 (ND6). NADH dehydrogenase 1 (ND1), and a variant thereof. In some cases, the mitochondrial protein comprises NADH dehydrogenase 4 (ND4), or a variant thereof. In some cases, the mitochondrial protein comprises a peptide sequence that is at least 90%, at least 95%, at least 97%, at least 99%, or 100% identical to a sequence as set forth in SEQ ID NO: 160. In some cases, the mitochondrial protein coding sequence comprises a sequence that is at least 90%, at least 95%, at least 97%, at least 99%, or 100% identical to a sequence as set forth in SEQ ID NO: 6, 7, or 8. In some cases, the mitochondrial protein comprises NADH dehydrogenase 6 (ND6), or a variant thereof. In some cases, the mitochondrial protein comprises a sequence that is at least 90%, at least 95%, at least 97%, at least 99%, or 100% identical to a sequence as set forth in SEQ ID NO: 161. In some cases, the mitochondrial protein coding sequence comprises a sequence that is at least 90%, at least 95%, at least 97%, at least 99%, or 100% identical to a sequence as set forth in SEQ ID NO: 9 or 10. In some cases, the mitochondrial protein comprises NADH dehydrogenase 1 (ND1), or a variant thereof. In some cases, the mitochondrial protein comprises a sequence that is at least 90%, at least 95%, at least 97%, at least 99%, or 100% identical to a sequence as set forth in SEQ ID NO: 162. In some cases, the mitochondrial protein coding sequence comprises a sequence that is at least 90%, at least 95%, at least 97%, at least 99%, or 100% identical to a sequence as set forth in SEQ ID NO: 11 or 12.

In some cases, the recombinant nucleic acid further comprises a 3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, mSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 29-70.

In another aspect, disclosed herein is a recombinant nucleic acid, comprising a mitochondrial protein coding sequence, wherein the mitochondrial protein coding sequence encodes a polypeptide comprising a mitochondrial protein, wherein the mitochondrial protein coding sequence comprises a sequence that is at least 90%, at least 95%, at least 97%, at least 99%, or 100% identical to a sequence selected from the group consisting of SEQ ID NO: 7, 8, 10, and 12.

In some cases, the recombinant nucleic acid further comprises a mitochondrial targeting sequence. In some cases, the mitochondrial targeting sequence comprises a sequence encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATP5G3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9. In some cases, the mitochondrial targeting sequence encodes a polypeptide comprising a peptide sequence that is at least 90%, at least 95%, at least 97%, at least 99%, or 100% identical to a sequence selected from the group consisting of SEQ ID NO: 129-159. In some cases, the mitochondrial targeting sequence comprises a sequence that is at least 90%, at least 95%, at least 97%, at least 99%, or 100% identical to a sequence as set forth in SEQ ID NO: 2. In some cases, the mitochondrial targeting sequence comprises a sequence that is at least 90%, at least 95%, at least 97%, at least 99%, or 100% identical to a sequence as set forth in SEQ ID NO: 3. In some cases, the mitochondrial targeting sequence comprises a sequence that is at least 90%, at least 95%, at least 97%, at least 99%, or 100% identical to a sequence as set forth in SEQ ID NO: 4. In some cases, the mitochondrial targeting sequence comprises a sequence that is at least 90%, at least 95%, at least 97%, at least 99%, or 100% identical to a sequence as set forth in SEQ ID NO: 5.

In some cases, the mitochondrial protein coding sequence comprises a sequence that is at least 90%, at least 95%, at least 97%, at least 99%, or 100% identical to a sequence as set forth in SEQ ID NO: 7 or 8. In some cases, the mitochondrial protein coding sequence comprises a sequence that is at least 90%, at least 95%, at least 97%, at least 99%, or 100% identical to a sequence as set forth in SEQ ID NO: 10. In some cases, the mitochondrial protein coding sequence comprises a sequence that is at least 90%, at least 95%, at least 97%, at least 99%, or 100% identical to a sequence as set forth in SEQ ID NO: 12.

In some cases, the recombinant nucleic acid further comprises a 3'UTR nucleic acid sequence. In some cases, the 3'UTR nucleic acid sequence is located at 3' of the mitochondrial targeting sequence. In some cases, the 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1·hsMRPS12, hsATPSJ2, mSOD2, and hsOXA1L. In some cases, the 3'UTR nucleic acid sequence comprises a sequence that is at least 90%, at least 95%, at least 97%, at least 99%, or 100% identical to a sequence selected from the group consisting of SEQ ID NO: 111-125. In some cases, the 3'UTR nucleic acid sequence comprises a sequence that is at least 90%, at least 95%, at least 97%, at least 99%, or 100% identical to a sequence as set forth in SEQ ID NO: 13 or SEQ ID NO: 14. In some cases, the mitochondrial targeting sequence is located at 5' of the 3'UTR nucleic acid sequence. In some cases, the mitochondrial targeting sequence is located at 3' of the mitochondrial targeting sequence.

In some cases, the recombinant nucleic acid comprises a sequence that is at least 90%, at least 95%, at least 97%, at least 99%, or 100% identical to a sequence selected from the group consisting of SEQ ID NO: 17-20, 23-24, 27-28, 31-34, 37-38, 41-42, 45-48, 51-52, 55-56, 59-62, 65-66, 69-70, 73-76, 79-80, and 83-84.

In another aspect, disclosed herein is a viral vector comprising the recombinant nucleic acid disclosed herein. In some cases, the viral vector is an adeno-associated virus (AAV) vector. In some cases, the AAV vector is selected from the group consisting of AAV1, AAV2, AAV3, AAV4, AAV5, AAV6, AAV7, AAV8, AAV9, AAV10, AAV11, AAV12, AAV13, AAV14, AAV15, and AAV16 vectors. In some cases, the AAV vector is a recombinant AAV (rAAV) vector. In some cases, the rAAV vector is rAAV2 vector.

In another aspect, disclosed herein is a pharmaceutical composition, comprising an adeno-associated virus (AAV) comprising any recombinant nucleic acid disclosed herein. In some cases, the pharmaceutical composition further comprises a pharmaceutically acceptable excipient thereof. Also disclosed is a pharmaceutical composition, comprising the viral vector disclosed herein, and a pharmaceutically acceptable excipient thereof, wherein the viral vector comprises any recombinant nucleic acid disclosed herein. Also disclosed is a pharmaceutical composition, comprising: an adeno-associated virus (AAV) comprising any recombinant nucleic acid disclosed herein, wherein the recombinant nucleic acid comprises a sequence that is at least 90%, at least 95%, at least 97%, at least 99%, or 100% identical to a sequence as set forth in SEQ ID NO: 15; and a pharmaceutically acceptable excipient.

In some cases, the pharmaceutically acceptable excipient comprises phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof. In some cases, the pharmaceutically acceptable excipient is selected from phosphate-buffered saline (PBS), α,α-trehalose dehydrate, L-histidine monohydrochloride monohydrate, polysorbate 20, NaCl, $NaH_2PO_4$, $Na_2HPO_4$, $KH_2PO_4$, $K_2HPO_4$, poloxamer 188, and any combination thereof. In some cases, the pharmaceutically acceptable excipient comprises poloxamer 188. In some cases, the pharmaceutically acceptable excipient comprises 0.0001%-0.01% poloxamer 188. In some cases, the pharmaceutically acceptable excipient comprises 0.001% poloxamer 188. In some cases, the pharmaceutically acceptable excipient further comprises one or more salts. In some cases, the one or more salts comprises NaCl, $NaH_2PO_4$, $Na_2HPO_4$, and $KH_2PO_4$. In some cases, the one or more salts comprises 80 mM NaCl, 5 mM $NaH_2PO_4$, 40 mM $Na_2HPO_4$, and 5 mM $KH_2PO_4$. In some cases, the pharmaceutical composition has a pH of 6-8. In some cases, the pharmaceutical composition has a pH of 7.2-7.4. In some cases, the pharmaceutical composition has a pH of 7.3. In some cases, the pharmaceutical composition has a viral titer of at least $1.0 \times 10^{10}$ vg/mL. In some cases, the pharmaceutical composition has a viral titer of at least $5.0 \times 10^{10}$ vg/mL.

In some cases, the pharmaceutical composition is subject to five freeze/thaw cycles, the pharmaceutical composition retains at least 60%, 70%, 80%, or 90% of a viral titer as compared to the viral titer prior to the five freeze/thaw cycles. In some cases, the pharmaceutical composition, when administered to a patient with Leber's hereditary optic neuropathy, generates a higher average recovery of vision than a comparable pharmaceutical composition without the recombinant nucleic acid. In some cases, the pharmaceutical composition, when administered to a patient with Leber's hereditary optic neuropathy, generates a higher average recovery of vision than a comparable pharmaceutical composition comprising a recombinant nucleic acid as set forth in SEQ ID NO: 15.

In another aspect, disclosed herein is a method of treating an eye disorder, comprising administering any pharmaceutical composition disclosed herein to a patient in need thereof. In some cases, the eye disorder is Leber's hereditary optic neuropathy (LHON). In some cases, the method comprises administering the pharmaceutical composition to one or both eyes of the patient. In some cases, the pharmaceutical composition is administered via intraocular or intravitreal injection. In some cases, the pharmaceutical composition is administered via intravitreal injection. In some cases, about 0.01-0.1 mL of the pharmaceutical composition is administered via intravitreal injection. In some cases, about 0.05 mL of the pharmaceutical composition is administered via intravitreal injection.

In some cases, the method further comprises administering methylprednisolone to the patient. In some cases, the methylprednisolone is administered prior to the intravitreal injection of the pharmaceutical composition. In some cases, the methylprednisolone is administered orally. In some cases, the methylprednisolone is administered daily for at least 1, 2, 3, 4, 5, 6, or 7 days prior to the intravitreal injection of the pharmaceutical composition. In some cases, the methylprednisolone is administered daily. In some cases, the a daily dosage of about 32 mg/60 kg methylprednisolone is administered. In some cases, the methylprednisolone is administered after the intravitreal injection of the pharmaceutical composition. In some cases, the method further comprises administering creatine phosphate sodium to the patient. In some cases, the creatine phosphate sodium is administered intravenously. In some cases, the methylprednisolone is administered intravenously or orally. In some cases, the method comprises administering methylprednisolone intravenously for at least one day, which is followed by administering methylprednisolone orally for at least a week. In some cases, the method comprises administering methylprednisolone intravenously for about 3 days, which is followed by administering methylprednisolone orally for at least about 6 weeks. In some cases, the methylprednisolone is administered intravenously at a daily dose of about 80 mg/60 kg. In some cases, the administering the pharmaceutical composition generates a higher average recovery of vision than a comparable pharmaceutical composition without the recombinant nucleic acid. In some cases, the administering the pharmaceutical composition generates a higher average recovery of vision than a comparable pharmaceutical composition comprising a recombinant nucleic acid as set forth in SEQ ID NO: 15.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Definitions

Figure 1:
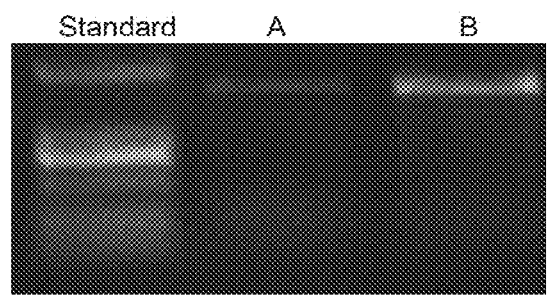
FIG. 1 shows the PCR nucleic acid electrophoresis verification of ND4 (lane A) and optimized ND4 (lane B) gene cloning results.

Unless defined otherwise, all technical and scientific terms used herein have the same meaning as commonly understood by one of the ordinary skill in the art to which this disclosure belongs. Although any methods and materials similar or equivalent to those described herein can be used in the practice or testing of the formulations or unit doses herein, some methods and materials are now described. Unless mentioned otherwise, the techniques employed or contemplated herein are standard methodologies. The materials, methods and examples are illustrative only and not limiting.

As used herein and in the appended claims, the singular forms "a," "and," and "the" include plural referents unless the context clearly dictates otherwise. Thus, for example, reference to "a compound" includes a plurality of such agents, and reference to "the salt" includes reference to one or more salts (or to a plurality of salts) and equivalents thereof known to those skilled in the art, and so forth.

As used herein, unless otherwise indicated, the term "or" can be conjunctive or disjunctive. As used herein, unless otherwise indicated, any embodiment can be combined with any other embodiment.

As used herein, unless otherwise indicated, some inventive embodiments herein contemplate numerical ranges. When ranges are present, the ranges include the range endpoints. Additionally, every subrange and value within the range is present as if explicitly written out.

The term "about" and its grammatical equivalents in relation to a reference numerical value and its grammatical equivalents as used herein can include a range of values plus or minus 10% from that value, such as a range of values plus or minus 10%, 9%, 8%, 7%, 6%, 5%, 4%, 3%, 2%, or 1% from that value. For example, the amount "about 10" includes amounts from 9 to 11.

The term "comprising" (and related terms such as "comprise" or "comprises" or "having" or "including") is not intended to exclude that in other certain embodiments, for example, an embodiment of any composition of matter, composition, method, or process, or the like, described herein, may "consist of" or "consist essentially of" the described features.

The term "subject" refers to a mammal that has been or will be the object of treatment, observation or experiment. The term "mammal" is intended to have its standard meaning, and encompasses humans, dogs, cats, sheep, and cows, for example. The methods described herein can be useful in both human therapy and veterinary applications. In some embodiments, the subject is a human.

The term "treating" or "treatment" encompasses administration of at least one compound disclosed herein, or a pharmaceutically acceptable salt thereof, to a mammalian subject, particularly a human subject, in need of such an administration and includes (i) arresting the development of clinical symptoms of the disease, such as cancer, (ii) bringing about a regression in the clinical symptoms of the disease, such as cancer, and/or (iii) prophylactic treatment for preventing the onset of the disease, such as cancer.

The term "therapeutically effective amount" of a chemical entity described herein refers to an amount effective, when administered to a human or non-human subject, to provide a therapeutic benefit such as amelioration of symptoms, slowing of disease progression, or prevention of disease.

As used herein, unless otherwise indicated, the terms "nucleic acid" and "polynucleotide" can be used interchangeably.

Nucleic Acid and Polypeptide Sequences

Table 1 discloses all the nucleic acid and polypeptide sequences disclosed herein. The first column shows the SEQ ID NO of each sequence. The second column describes the nucleic acid or polypeptide construct. For example, the construct COX10-ND6-3'UTR is a nucleic acid combining the nucleic acid sequences of COX10 (SEQ ID NO: 1), ND6 (SEQ ID NO: 9), and 3'UTR (SEQ ID NO: 13) (from 5' to 3' without linker between the nucleic acid sequences.

TABLE 1 nucleic acid and polypeptide sequences and SEQ ID NOs

| SEQ | description | sequence |
|---|---|---|
| 1 | COX10 | ATGGCCGCATCTCCGCACACTCTCTCCTCACGCCTCCTGACAGGTTGCGTAGGAGGCTCTGTCTGGT ATCTTGAAAGAAGAACT |
| 2 | opt_COX10 | ATGGCCGCCTCTCCACACACACTGAGTAGCAGACTGCTGACCGGCTGTGTTGGCGGCTCTGTGTGGT ATCTGGAACGGCGGACA |
| 3 | opt_COX10* | ATGGCCGCCAGCCCCCACACCCTGAGCAGCCGCCTGCTGACCGGCTGCGTGGGCGGCAGCGTGTG GTACCTGGAGCGCCGCACC |
| 4 | COX3 | ATGTCCGTCCTGACGCGCCTGCTGCTGCGGGGCTTGACACGGCTCGGCTCGGCGGCTCCAGTGCGG CGCGCCAGAATCCATTCGTTG |
| 5 | OPA1 | GTGCTGCCCGCCTAGAAAGGGTGAAGTGGTTGTTTCCGTGACGGACTGAGTACGGGTGCCTGTCAGG CTCTTGCGGAAGTCCATGCGCCATTGGGAGGGCCTCGGCCGCGGCTCTGTGCCCTTGCTGCTGAGG GCCACTTCCTGGGTCATTCCTGGACCGGGAGCCGGGCTGGGGCTCACACGGGGGCTCCCGCGTGG CCGTCTCGGCGCCTGCGTGACCTCCCCGCCGGCGGGATGTGGCGACTACGTCGGGCCGCTGTGGC CTG |
| 6 | ND4 | ATGCTAAAACTAATCGTCCCAACAATTATGTTACTACCACTGACATGGCTTTCCAAAAAACACATGATTT GGATCAACACAACCACCCACAGCCTAATTATTAGCATCATCCCTCTACTATTTTTTAACCAAATCAACAA CAACCTATTTAGCTGTTCCCCAACCTTTTCCTCCGACCCCCTAACAACCCCCCTCCTAATGCTAACTAC CTGGCTCCTACCCCTCACAATCATGGCAAGCCAACGCCACTTATCCAGTGAACCACTATCACGAAAAA AACTCTACCTCTCTATGCTAATCTCCCTACAAATCTCCTTAATTATGACATTCACAGCCACAGAACTAAT CATGTTTTATATCTTCTTCGAAACCACACTTATCCCCACCTTGGCTATCATCACCCGATGGGGCAACCA GCCAGAACGCCTGAACGCAGGCACATACTTCCTATTCTACACCCTAGTAGGCTCCCTTCCCCTACTCA TCGCACTAATTTACACTCACAACACCCTAGGCTCACTAAACATTCTACTACTCACTCTCACTGCCCAAG AACTATCAAACTCCTGGGCCAACAACTTAATGTGGCTAGCTTACACAATGGCTTTTATGGTAAAGATGC CTCTTTACGGACTCCACTTATGGCTCCCTAAAGCCCATGTCGAAGCCCCCATCGCTGGGTCAATGGTA CTTGCCGCAGTACTCTTAAAACTAGGCGGCTATGGTATGATGCGCCTCACACTCATTCTCAACCCCCT GACAAAACACATGGCCTACCCCTTCCTTGTACTATCCCTATGGGGCATGATTATGACAAGCTCCATCTG CCTACGACAAACAGACCTAAAATCGCTCATTGCATACTCTTCAATCAGCCACATGGCCCTCGTAGTAAC AGCCATTCTCATCCAAACCCCCTGGAGCTTCACCGGCGCAGTCATTCTCATGATCGCCCACGGGCTTA CATCCTCATTACTATTCTGCCTAGCAAACTCAAACTACGAACGCACTCACAGTCGCATCATGATCCTCT CTCAAGGACTTCAAACTCTACTCCCACTAATGGCTTTTTGGTGGCTTCTAGCAAGCCTCGCTAACCTCG CCTTACCCCCCACTATTAACCTACTGGGAGAACTCTCTGTGCTAGTAACCACGTTCTCCTGGTCAAATA TCACTCTCCTACTTACAGGACTCAACATGCTAGTCACAGCCCTATACTCCCTCTACATGTTTACCACAA CACAATGGGGCTCACTCACCCACCACATTAACAACATGAAACCCTCATTCACACGAGAAAACACCCTC ATGTTCATGCACCTATCCCCCATTCTCCTCCTATCCCTCAACCCCGACATCATTACCGGGTTTTCCTCT TAA |
| 7 | opt_ND4 | ATGCTGAAGCTGATCGTGCCCACCATCATGCTGCTGCCTCTGACCTGGCTGAGCAAGAAACACATGAT CTGGATCAACACCACCACGCACAGCCTGATCATCAGCATCATCCCTCTGCTGTTCTTCAACCAGATCA ACAACAACCTGTTCAGCTGCAGCCCCACCTTCAGCAGCGACCCTCTGACAACACCTCTGCTGATGCTG ACCACCTGGCTGCTGCCCCTCACAATCATGGCCTCTCAGAGACACCTGAGCAGCGAGCCCCTGAGCC GGAAGAAACTGTACCTGAGCATGCTGATCTCCCTGCAGATCTCTCTGATCATGACCTTCACCGCCACC GAGCTGATCATGTTCTACATCTTTTTCGAGACAACGCTGATCCCCACACTGGCCATCATCACCAGATG GGGCAACCAGCCTGAGAGACTGAACGCCGGCACCTACTTTCTGTTCTACACCCTCGTGGGCAGCCTG CCACTGCTGATTGCCCTGATCTACACCCACAACACCCTGGGCTCCCTGAACATCCTGCTGCTGACACT GACAGCCCAAGAGCTGAGCAACAGCTGGGCCAACAATCTGATGTGGCTGGCCTACACAATGGCCTTC ATGGTCAAGATGCCCCTGTACGGCCTGCACCTGTGGCTGCCTAAAGCTCATGTGGAAGCCCCTATCG CCGGCTCTATGGTGCTGGCTGCAGTGCTGCTGAAACTCGGCGGCTACGGCATGATGCGGCTGACCCT GATTCTGAATCCCCTGACCAAGCACATGGCCTATCCATTTCTGGTGCTGAGCCTGTGGGGCATGATTA TGACCAGCAGCATCTGCCTGCGGCAGACCGATCTGAAGTCCCTGATCGCCTACAGCTCCATCAGCCA CATGGCCCTGGTGGTCACCGCCATCCTGATTCAGACCCCTTGGAGCTTTACAGGCGCCGTGATCCTG ATGATTGCCCACGGCCTGACAAGCAGCCTGCTGTTTTGTCTGGCCAACAGCAACTACGAGCGGACCC ACAGCAGAATCATGATCCTGTCTCAGGGCCTGCAGACCCTCCTGCCTCTTATGGCTTTTTGGTGGCTG CTGGCCTCTCTGGCCAATCTGGCACTGCCTCCTACCATCAATCTGCTGGGCGAGCTGAGCGTGCTGG TCACCACATTCAGCTGGTCCAATATCACCCTGCTGCTCACCGGCCTGAACATGCTGGTTACAGCCCTG TACTCCCTGTACATGTTCACCACCACACAGTGGGGAAGCCTGACACACCACATCAACAATATGAAGCC CAGCTTCACCCGCGAGAACACCCTGATGTTCATGCATCTGAGCCCCATTCTGCTGCTGTCCCTGAATC CTGATATCATCACCGGCTTCTCCAGCTGA |

TABLE 1-continued nucleic acid and polypeptide sequences and SEQ ID NOs

| SEQ | description | sequence |
|---|---|---|
| 8 | opt_ND4* | ATGCTGAAGCTGATCGTGCCCACCATCATGCTGCTGCCCCTGACCTGGCTGAGCAAGAAGCACATGA<br>TCTGGATCAACACCACCACCCACAGCCTGATCATCAGCATCATCCCCCTGCTGTTCTTCAACCAGATC<br>AACAACAACCTGTTCAGCTGCAGCCCCACCTTCAGCAGCAGCCCCCTGACCACCCCCCTGCTGATGC<br>TGACCACCTGGCTGCTGCCCCTGACCATCATGGCCAGCCAGCGCCACCTGAGCAGCGAGCCCCTGA<br>GCCGCAAGAAGCTGTACCTGAGCATGCTGATCAGCCTGCAGATCAGCCTGATCATGACCTTCACCGC<br>CACCGAGCTGATCATGTTCTACATCTTCTTCGAGACCACCCTGATCCCCACCCTGGCCATCATCACCC<br>GCTGGGGCAACCAGCCCGAGCGCCTGAACGCCGGCACCTACTTCCTGTTCTACACCCTGGTGGGCA<br>GCCTGCCCCTGCTGATCGCCCTGATCTACACCCCACAACACCCCTGGGCAGCCTGAACATCCTGCTGCT<br>GACCCTGACCGCCCAGGAGCTGAGCAACAGCTGGGCAACAACCTGATGTGGCTGGCCTACACCAT<br>GGCCTTCATGGTGAAGATGCCCCTGTACGGCCTGCACCTGTGGCTGCCCAAGGCCCACGTGGAGGC<br>CCCCATCGCCGGCAGCATGGTGCTGGCCGCCGTGCTGCTGAAGCTGGGCGGCTACGGCATGATGCG<br>CCTGACCCTGATCCTGAACCCCCTGACCAAGCACATGGCCTACCCCTTCCTGGTGCTGAGCCTGTGG<br>GGCATGATCATGACCAGCAGCATCTGCCTGCGCCAGACCGACCTGAAGAGCCTGATCGCCTACAGCA<br>GCATCAGCCACATGGGCCTGGTGGTGACCGCCATCCTGATCCAGACCCCCTGGAGCTTCACCGGCG<br>CCGTGATCCTGATGATCGCCCACGGCCTGACCAGCAGCCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA<br>TCAACAACATGAAGCCCAGCTTCACCCGCGAGAACACCCTGATGTTCATGCACCTGAGCCCCATCCTG<br>CTGCTGAGCCTGAACCCCGACATCATCACCGGCTTCAGCAGCTAA |
| 9 | ND6 | ATGATGTATGCTTTGTTTCTGTTGAGTGTGGGTTTAGTAATGGGGTTTGTGGGGTTTTCTTCTAAGCCT<br>TCTCCTATTTATGGGGGTTTAGTATTGATTGTTAGCGGTGTGGTCGGGTGTGTTATTATTCTGAATTTTG<br>GGGGAGGTTATATGGGTTTAATGGTTTTTTTAATTTATTTAGGGGGAATGATGGTTGTCTTTGGATATAC<br>TACAGCGATGGCTATTGAGGAGTATCCTGAGGCATGGGGGTCAGGGGTTGAGGTCTTGGTGAGTGTT<br>TTAGTGGGGTTAGCGATGGAGGTAGGATTGGTGCTGTGGGTGAAAGAGTATGATGGGGTGGTGGTTG<br>TGGTAAACTTTAATAGTGTAGGAAGCTGGATGATTATGAAGGAGAGGGGTCAGGGTTGATTCGGGAG<br>GATCCTATTGGTGCGGGGGCTTTGTATGATTATGGGCGTTGGTTAGTAGTAGTTACTGGTTGGACATT<br>GTTTGTTGGTGTATATATTGTAATTGAGATTGCTCGGGGGAATTAG |
| 10 | opt_ND6 | ATGATGTACGCCCTGTTCCTGCTGAGCGTGGGCCTGGTGATGGGCTTCGTGGGCTTCAGCAGCAAGC<br>CCAGCCCCATCTACGGCGGCCTGGTGCTGATCGTGAGCGGCGTGGTGGGCTGCGTGATCATCCTGA<br>ACTTCGGCGGCGGCTACATGGGCCTGATGGTGTTCCTGATCTACCTGGGCGGCATGATGGTGGTGTT<br>CGGCTACACCACCGCCATGGCCATCGAGGAGTACCCCGAGGCCTGGGGCAGCGGCGTGGAGGTGC<br>TGGTGAGCGTGCTGGTGGGCCTGGCCATGGAGGTGGGCCTGGTGCTGTGGGTGAAGGAGTACGACG<br>GCGTGGTGGTGGTGGTGAACTTCAACAGCGTGGGCAGCTGGATGATCTACGAGGGCGAGGGCAGCG<br>GCCTGATCCGCGAGGACCCCATCGGCGCCGGCGCCCTGTACGACTACGGCCGCTGGCTGGTGGTG<br>GTGACCGGCTGGACCCTGTTCGTGGGCGTGTACATCGTGATCGAGATCGCCCGCGGCAACTAA |
| 11 | ND1 | ATGGCCAACCTCCTACTCCTCATTGTACCCATTCTAATCGCAATGGCATTCCTAATGCTTACCGAACGA<br>AAAATTCTAGGCTATATGCAACTACGCAAAGGCCCCAACGTTGTAGGCCCCTACGGGCTACTACAACC<br>CTTCGCTGACGCCATAAAACTCTTCACCAAAGAGCCCCTAAAACCCGCCACATCTACCATCACCCTCT<br>ACATCACCGCCCCGACCTTAGCTCTCACCATCGCTCTTCTACTATGGACCCCCCTCCCCATGCCCAAC<br>CCCCTGGTCAACCTCAACCTAGGCCTCCTATTTATTCTAGCCACCTCTAGCCTAGCCGTTTACTCAATC<br>CTCTGGTCAGGGTGGGCATCAAACTCAAACTACGCCCTGATCGGCGCACTGCGAGCAGTAGCCCAAA<br>CAATCTCATATGAAGTCACCCTAGCCATCATTCTACTATCAACATTACTAATGAGTGGCTCCTTWACCT<br>CTCCACCCTTATCACAACACAAGAACACCTCTGGTTACTCCTGCCATCATGGCCCTTGGCCATGATGT<br>GGTTTATCTCCACACTAGCAGAGACCAACCGAACCCCCTTCGACCTTGCCGAAGGGGAGTCCGAACT<br>AGTCTCAGGCTTCAACATCGAATACGCCGCAGGCCCCTTCGCCCTATTCTTCATGGCCGAATACACAA<br>ACATTATTATGATGAACACCCTCACCACTACAATCTTCCTAGGAACAACATATGACGCACTCTCCCCTG<br>AACTCTACACAACATATTTGTCACCAAGACCCTACTTCTAACCTCCCTGTTCTTATGGATTCGAACAGC<br>ATACCCCCGATTCCGCTACGACCAACTCATGCACCTCCTATGGAAAAACTTCCTACCACTCACCCTAG<br>CATTACTTATGTGGTATGTCTCCATGCCCATTACAATCTCCAGCATTCCCCTCAAACCTAA |
| 12 | opt_ND1 | ATGGCCAACCTGCTGCTGCTGATCGTGCCCATCCTGATCGCCATGGCCTTCCTGATGCTGACCGAGC<br>GCAAGATCCTGGGCTACATGCAGCTGCGCAAGGGCCCCAACGTGGTGGGCCCCTACGGCTGCTGC<br>AGCCCCTTCGCCGACGCCATCAAGCTGTTCACCAAGGAGCCCCTGAAGCCCGCCACCAGCACCATCA<br>CCTGTACATCACCGCCCCCACCCTGGCCCTGACCATCGCCCTGCTGCTGTGGACCCCCCTGCCCATG<br>CCCAACCCCCTGGTGAACCTGAACCTGGGCCTGCTGTTCATCCTGGCCACCAGCAGCCTGGCCGTGT<br>ACAGCATCCTGTGGAGCGGCTGGGCCAGCAACAGCAACTACGCCCTGATCGGCGCCCTGCGCGCCG<br>TGGCCCAGACCATCAGCTACGAGGTGACCCTGGCCATCATCCTGTCGAGCACCCTGCTGATGAGCGG<br>CAGCTTCAACCTGAGCACCCTGATCACCACCCAGGAGCACCTGTGGCTGCTGCTGCCCAGCTGGCCC<br>CTGGCCATGATGTGGTTCATCAGCACCCTGGCCGAGACCAACCGCACCCCCTTCGACCTGGCCGAGG<br>GCGAGAGCGAGCTGGTGAGCGGCTTCAACATCGAGTACGCCGCCGGCCCCTTCGCCCTGTTCTTCAT<br>GGCCGAGTACACCAACATCATCATGATGAACACCCTGACCACCACCATCTTCCTGGGCACCACCTACG<br>ACGCCCTGAGCCCCGAGCTGTACACCACCTACTTCGTGACCAAGACCCTGCTGCTGACCAGCCTGTT<br>CCTGTGGATCCGCACCGCCTACCCCGCTTCGCTACGACCAGCTGATGCACCTGCTGTGGAAGAAC<br>TTCCTGCCCCTGACCCTGGCCCTGCTGATGTGGTACGTGAGCATGCCCATCACCATCAGCAGCATCC<br>CCCCCCAGACCTAA |
| 13 | 3'UTR* | GAGCACTGGGACGCCCACCGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGGTGCTCAGTGATCACTTGAC<br>AGTTTTTTTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCTCTATTCT |

TABLE 1-continued nucleic acid and polypeptide sequences and SEQ ID NOs

| SEQ | description | sequence |
|---|---|---|
| | | GTTTCTTCCTCCTCACATGGGGGTACACATACACAGCTTCCTCTTTTGGTTCCATCCTTACCACCACAC<br>CACACGCACACTCCACATGCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACCCCCTTCCTTGTGACTGAG<br>CCAGGGCCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCAAGCT<br>GGACTGCCAGCCCCTGTCCTCCCTTCACCCCCATTGCGTATGAGCATTTCAGAACTCCAAGGAGTCAC<br>AGGCATCTTTATAGTTCACGTTAACATATAGACACTGTTGGAAGCAGTTCCTTCTAAAAGGGTAGCCCT<br>GGACTTAATACCAGCCGGATACCTCTGGCCCCCACCCCATTACTGTACCTCTGGAGTCACTACTGTGG<br>GTCGCCACTCCTCTGCTACACAGCACGGCTTTTTCAAGGCTGTATTGAGAAGGGAAGTTAGGAAGAAG<br>GGTGTGCTGGGCTAACCAGCCCACAGAGCTCACATTCCTGTCCCTTGGGTGAAAAATACATGTCCATC<br>CTGATATCTCCTGAATTCAGAAATTAGCCTCCACATGTGCAATGGCTTTAAGAGCCAGAAGCAGGGTT<br>CTGGGAATTTTGCAAGTTACCTGTGGCCAGGTGTGGTCTCGGTTACCAAATACGGTTACCTGCAGCTT<br>TTTAGTCCTTTGTGCTCCCACGGGTCTAGAGAGTCCCATCTGCCCAAAGGTCTTGAAGCTTGACAGGA<br>TGTTTTCGATTACTCAGTCTCCCAGGGCACTACTGGTCCGTAGGATTCGATTGGTCGGGGTAGGAGAG<br>TTAAACAACATTTAAACAGAGTTCTCTCAAAAATGTCTAAAGGGATTGTAGGTAGATAACATCCAATCAC<br>TGTTTGCACTTATCTGAAATCTTCCCTCTTGGCTGCCCCAGGTATTTACTGTGGAGAACATTGCATAG<br>GAATGTCTGGAAAAAGCTTCTACAACTTGTTACAGCCTTCACATTTGTAGAAGCTTT |
| 14 | 3'UTR* | GAGCACTGGGACGCCCACCGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGGTGCTCAGTGATCACTTGAC<br>AGTTTTTTTTTTTTAAATATTACCCAAAATGCTCCCAAATAAGAAATGCATCAGCTCAGTCAGTGAAT<br>ACAAAAAAGGAATTATTTTTCCCTTTGAGGGTCTTTTATACATCTCTCCTCCAACCCCACCCTCTATTCT<br>GTTTCTTCCTCCTCACATGGGGGTACACATACACAGCTTCCTCTTTTGGTTCCATCCTTACCACCACAC<br>CACACGCACACTCCACATGCCCAGCAGAGTGGCACTTGGTGGCCAGAAAGTGTGAGCCTCATGATCT<br>GCTGTCTGTAGTTCTGTGAGCTCAGGTCCCTCAAAGGCCTCGGAGCACCCCCTTCCTTGTGACTGAG<br>CCAGGGCCTGCATTTTTGGTTTTCCCCACCCCACACATTCTCAACCATAGTCCTTCTAACAATACCAAT<br>AGCTAGGACCCGGCTGCTGTGCACTGGGACTGGGGATTCCACATGTTTGCCTTGGGAGTCTCAAGCT<br>GGACTGCCA |
| 15 | COX10-ND4-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGCTAAAACTAATCGTCCCAACAATTATGTTACTACCACTGACATGGCTTTC<br>CAAAAAACACATGATTTGGATCAACACAACCACCCACAGCCTAATTATTAGCATCATCCCTCTACTATTT<br>TTTAACCAAATCAACAACAACCTATTTAGCTGTTCCCCAACCTTTTCCTCCGACCCCTAACAACCCCC<br>CTCCTAATGCTAACTACCTGGCTCCTACCCCTCACAATCATGGCAAGCCAACGCCACTTATCCAGTGA<br>ACCACTATCACGAAAAAAACTCTACCTCTCTATGCTAATCTCCCTACAAATCTCTTAATTATGACATTC<br>ACAGCCACAGAACTAATCATGTTTATATCTTCTTGAAACCACACTTATCCCCACCTTGGCTATCATCA<br>CCCGATGGGGCAACCAGCCAGAACGCCTGAACGCAGGCACATACTTCCTATTCTACACCCTAGTAGG<br>CTCCCTTCCCCTACTCATCGCACTAATTTACACTCACAACACCCTAGGCTCACTAAACATTCTACTACT<br>CACTCTCACTGCCCAAGAACTATCAAACTCCTGGGCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAATCGCTCATTGCATACTCTTCAATCAGCCAC<br>ATGGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTAAATATTACCCAAAATGCTCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCAGCCCCTGTCCTCCCTTCACCCCCATTGCGTATGAGCATT<br>TCAGAACTCCAAGGAGTCACAGGCATCTTTATAGTTCACGTTAACATATAGACACTGTTGGAAGCAGTT<br>CCTTCTAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGTATTGA<br>GAAGGGAAGTTAGGAAGAAGGGTGTGCTGGGCTAACCAGCCCACAGAGCTCACATTCCTGTCCCTTG<br>GGTGAAAAATACATGTCCATCCTGATATCTCCTGAATTCAGAAATTAGCCTCCACATGTGCAATGGCTT<br>TAAGAGCCAGAAGCAGGGTTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTAGAGAGTCCCATCTGCCCAAA<br>GGTCTTGAAGCTTGACAGGATGTTTTCGATTACTCAGTCTCCCAGGGCACTACTGGTCCGTAGGATTC<br>GATTGGTCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCAGGTATTT<br>ACTGTGGAGAACATTGCATAGGAATGTCTGGAAAAAGCTTCTACAACTTGTTACAGCCTTCACATTTGT<br>AGAAGCTTT |
| 16 | COX10-ND4-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGCTAAAACTAATCGTCCCAACAATTATGTTACTACCACTGACATGGCTTTC<br>CAAAAAACACATGATTTGGATCAACACAACCACCCACAGCCTAATTATTAGCATCATCCCTCTACTATTT |

TABLE 1-continued nucleic acid and polypeptide sequences and SEQ ID NOs

| SEQ | description | sequence |
|---|---|---|
| | | TTTAACCAAATCAACAACAACCTATTTAGCTGTTCCCCAACCTTTTCCTCCGACCCCCTAACAACCCCC<br>CTCCTAATGCTAACTACCTGGCTCCTACCCCTCACAATCATGGCAAGCCAACGCCACTTATCCAGTGA<br>ACCACTATCACGAAAAAAACTCTACCTCTCTATGCTAATCTCCCTACAAATCTCCTTAATTATGACATTC<br>ACAGCCACAGAACTAATCATGTTTTATATCTTCTTCGAAACCACACTTATCCCCACCTTGGCTATCATCA<br>CCCGATGGGGCAACCAGCCAGAACGCCTGAACGCAGGCACATACTTCCTATTCTACACCCTAGTAGG<br>CTCCCTTCCCCTACTCATCGCACTAATTTACACTCACAACACCCTAGGCTCACTAAACATTCTACTACT<br>CACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAATCGCTCATTGCATACTCTTCAATCAGCCAC<br>ATGGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCA |
| 17 | COX10-<br>opt_ND4-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCTCTGACCTGGCTG<br>AGCAAGAAACACATGATCTGGATCAACACCACCACGCACAGCCTGATCATCAGCATCATCCCTCTGCT<br>GTTCTTCAACCAGATCAACAACAACCTGTTCAGCTGCAGCCCCACCTTCAGCAGCGACCCTCTGACAA<br>CACCTCTGCTGATGCTGACCACTCGGCTGCTGCCCCTCACAATCATGGCCTCTCAGAGACACCTGAG<br>CAGCGAGCCCCTGAGCCGGAAGAAACTGTACCTGAGCATGCTGATCTCCCTGCAGATCTCTCTGATC<br>ATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGGCATGATTATGACCAGCAGCATCTGCCTGCGGCAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACAGCAGAATCATGATCCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCCTGAA<br>CATGCTGGTTACAGCCCTGTACTCCCTGTACATGTTCACCACCACACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTAAATAT<br>TACCCAAAATGCTCCCCAAATAAGAAATGCATCAGCTCAGTCAGTGAATACAAAAAAGGAATTATTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCAGCCCCTGTCC<br>TCCCTTCACCCCCATTGCGTATGAGCATTTCAGAACTCCAAGGAGTCACAGGCATCTTTATAGTTCACG<br>TTAACATATAGACACTGTTGGAAGCAGTTCCTTCAAAAGGGTAGCCCTGGACTTAATACCAGCCGGAT<br>ACCTCTGGCCCCCACCCCATTACTGTACCTCTGGAGTCACTACTGTGGGTCGCCACTCCTCTGCTACA<br>CAGCACGGCTTTTTCAAGGCTGTATTGAGAAGGGAAGTTAGGAAGAAGGGTGTGCTGGGCTAACCAG<br>CCCACAGAGCTCACATTCCTGTCCCTTGGGTGAAAAATACATGTCCATCCTGATATCTCCTGAATTCAG<br>AAAATTAGCCTCCACATGTGCAATGGCTTTAAGAGCCAGAAGCAGGGTTCTGGGAATTTTGCAAGTTAC<br>CTGTGGCCAGGTGTGGTCTCGGTTACCAAATACGGTTACCTGCAGCTTTTTAGTCCTTTGTGCTCCCA<br>CGGGTCTACAGAGTCCCATCTGCCCAAAGGTCTTGAAGCTTGACAGGATGTTTTCGATTACTCAGTCT<br>CCCAGGGCACTACTGGTCCGTAGGATTCGATTGGTCGGGTAGGAGAGTTAAACAACATTTAAACAGA<br>GTTCTCTCAAAAATGTCTAAAGGGATTGTAGGTAGATAACATCCAATCACTGTTTGCACTTATCTGAAAT<br>CTTCCCTCTTGGCTGCCCCCAGGTATTTACTGTGGAGAACATTGCATAGGAATGTCTGGAAAAAGCTT<br>CTACAACTTGTTACAGCCTTCACATTTGTAGAAGCTTT |
| 18 | COX10-<br>opt_ND4-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGCTGAAGCTGATCGTGCCCACCATCATGCTGCTGCCTCTGACCTGGCTG<br>AGCAAGAAACACATGATCTGGATCAACACCACCACGCACAGCCTGATCATCAGCATCATCCCTCTGCT |

TABLE 1-continued nucleic acid and polypeptide sequences and SEQ ID NOs

| SEQ | description | sequence |
|---|---|---|
| | | GTTCTTCAACCAGATCAACAACAACCTGTTCAGCTGCAGCCCCACCTTCAGCAGCGACCCTCTGACAA
CACCTCTGCTGATGCTGACCACCTGGCTGCTGCCCCTCACAATCATGGCCTCTCAGAGACACCTGAG
CAGCGAGCCCCTGAGCCGGAAGAAACTGTACCTGAGCATGCTGATCTCCCTGCAGATCTCTCTGATC
ATGACCTTCACCGCCACCGAGCTGATCATGTTCTACATCTTTTTCGAGACAACGCTGATCCCCACACT
GGCCATCATCACCAGATGGGGCAACCAGCCTGAGAGACTGAACGCCGGCACCTACTTTCTGTTCTAC
ACCCTCGTGGGCAGCCTGCCACTGCTGATTGCCCTGATCTACACCCACAACACCCTGGGCTCCCTGA
ACATCCTGCTGCTGACACTGACAGCCCAAGAGCTGAGCAACAGCTGGGCAACAATCTGATGTGGCT
GGCCTACACAATGGCCTTCATGGTCAAGATGCCCCTGTACGGCCTGCACCTGTGGCTGCCTAAAGCT
CATGTGGAAGCCCCTATCGCCGGCTCTATGGTGCTGGCTGCAGTGCTGCTGAAACTCGGCGGCTACG
GCATGATGCGGCTGACCCTGATTCTGAATCCCCTGACCAAGCACATGGCCTATCCATTTCTGGTGCTG
AGCCTGTGGGGCATGATTATGACCAGCAGCATCTGCCTGCGGCAGACCGATCTGAAGTCCCTGATCG
CCTACAGCTCCATCAGCCACATGGCCCTGGTGGTCACCGCCATCCTGATTCAGACCCCTTGGAGCTTT
ACAGGCGCCGTGATCCTGATGATTGCCCACGGCCTGACAAGCAGCCTGCTGTTTTGTCTGGCCAACA
GCAACTACGAGCGGACCCACAGCAGATGATCCTGTCTCAGGGCCTGCAGACCCTCCTGCCTCT
TATGGCTTTTTGGTGGCTGCTGGCCTCTCTGGCCAATCTGGCACTGCCTCCTACCATCAATCTGCTGG
GCGAGCTGAGCGTGCTGGTCACCACATTCAGCTGGTCCAATATCACCCTGCTGCTCACCGGCCTGAA
CATGCTGGTTACAGCCCTGTACTCCCTGTACATGTTCACCACCACACAGTGGGGAAGCCTGACACAC
ACATCAACAATATGAAGCCCAGCTTCACCCGCGAGAACACCCTGATGTTCATGCATCTGAGCCCCATT
CTGCTGCTGTCCCTGAATCCTGATATCATCACCGGCTTCTCCAGCTGAGAGCACTGGGACGCCCACC
GCCCCCTTTCCCTCCGCTGCCAGGCGAGCATGTTGTGGTAATTCTGGAACACAAGAAGAGAAATTGCTG
GGTTTAGAACAAGATTATAAACGAATTCGGTGCTCAGTGATCACTTGACAGTTTTTTTTTTTTTAAATAT
TACCCAAAATGCTCCCAAATAAGAAATGCATCAGCTCAGTCAGTGAATACAAAAAAGGAATTATTTTT
CCCTTTGAGGGTCTTTTATACATCTCTCCTCCAACCCCACCCTCTATTCTGTTTCTTCCTCCTCACATGG
GGGTACACATACACAGCTTCCTCTTTTGGTTCCATCCTTACCACCACACCACACGCACACTCCACATG
CCCAGCAGAGTGGCACTTGGTGGCCAGAAAGTGTGAGCCTCATGATCTGCTGTCTGTAGTTCTGTGA
GCTCAGGTCCCTCAAAGGCCTCGGAGCACCCCCTTCCTTGTGACTGAGCCAGGGCCTGCATTTTTGG
TTTTTCCCCACCCCACACATTCTCAACCATAGTCCTTCTAACAATACCAATAGCTAGGACCCGGCTGCTG
TGCACTGGGACTGGGGATTCCACATGTTTGCCTTGGGAGTCTCAAGCTGGACTGCCA |
| 19 | COX10-
opt_ND4*-
3'UTR | ATGGCCGCATCTCCGCACACTCTCTCCTCACGCCTCCTGACAGGTTGCGTAGGAGGCTCTGTCTGGT
ATCTTGAAAGAAGAACTATGCTGAAGCTGATCGTGCCCACCATCATGCTGCTGCCCCTGACCTGGCTG
AGCAAGAAGCACATGATCTGGATCAACACCACCACCCACAGCCTGATCATCAGCATCATCCCCCTGCT
GTTCTTCAACCAGATCAACAACAACCTGTTCAGCTGCAGCCCCACCTTCAGCAGCGACCCCCTGACCA
CCCCCTGCTGATGCTGACCACCTGGCTGCTGCCCCTGACCATCATGGCCCAGCCAGCGCCACCTGAG
CAGCGAGCCCCTGAGCCGCAAGAAGCTGTACCTGAGCATGCTGATCAGCCTGCAGATCAGCCTGATC
ATGACCTTCACCGCCACCGAGCTGATCATGTTCTACATCTTCTTCGAGACCACCCTGATCCCCACCCT
GGCCATCATCACCCGCTGGGGCAACCAGCCCGAGCGCCTGAACGCCGGCACCTACTTCCTGTTCTAC
ACCCTGGTGGGCAGCCTGCCCCTGCTGATCGCCCTGATCTACACCCACAACACCCTGGGCAGCCTGA
ACATCCTGCTGCTGACCCTGACCGCCCAGGAGCTGAGCAACAGCTGGGCAACAACCTGATGTGGCT
GGCCTACACCATGGCCTTCATGGTGAAGATGCCCCTGTACGGCCTGCACCTGTGGCTGCCCAAGGCC
CACGTGGAGGCCCCCATCGCCGGCAGCATGGTGCTGGCCGCCGTGCTGCTGAAGCTGGGCGGCTAC
GGCATGATGCGCCTGACCCTGATCCTGAACCCCCTGACCAAGCACATGGCCTACCCCTTCCTGGTGC
TGAGCCTGTGGGGCATGATCATGACCAGCAGCATCTGCCTGCGCCAGACCGACCTGAAGAGCCTGAT
CGCCTACAGCAGCATCAGCCACATGGCCCTGGTGGTGACCGCCATCCTGATCCAGACCCCCTGGAGC
TTCACCGGCGCCGTGATCCTGATGATCGCCCACGGCCTGACCAGCAGCCTGCTGTTCTGCCTGGCCA
ACAGCAACTACGAGCGCACCCACAGCCGCATCATGATCCTGAGCCAGGGCCTGCAGACCCTGCTGCC
CCTGATGGCCTTCTGGTGGCTGCTGGCCAGCCTGGCCAACCTGGCCCTGCCCCCCACCATCAACCTG
CTGGGCGAGCTGAGCGTGCTGGTGACCACCTTCAGCTGGAGCAACATCACCCTGCTGCTGACCGGC
CTGAACATGCTGGTGACCGCCCTGTACAGCCTGTACATGTTCACCACCACCCAGTGGGGCAGCCTGA
CCCACCACATCAACAACATGAAGCCCAGCTTCACCCGCGAGAACACCCTGATGTTCATGCACCTGAGC
CCCATCCTGCTGCTGAGCCTGAACCCCGACATCATCACCGGCTTCAGCAGCTAAGCACTGGGACG
CCCACCGCCCCCTTTCCCTCCGCTGCCAGGCGAGCATGTTGTGGTAATTCTGGAACACAAGAAGAGAA
ATTGCTGGGTTTAGAACAAGATTATAAACGAATTCGGTGCTCAGTGATCACTTGACAGTTTTTTTTTTT
TTAAATATTACCCAAAATGCTCCCAAATAAGAAATGCATCAGCTCAGTCAGTGAATACAAAAAAGGAAT
TATTTTTCCCTTTGAGGGTCTTTTATACATCTCTCCTCCAACCCCACCCTCTATTCTGTTTCTTCCTCCT
CACATGGGGGTACACATACACAGCTTCCTCTTTTGGTTCCATCCTTACCACCACACCACACGCACACT
CCACATGCCCAGCAGAGTGGCACTTGGTGGCCAGAAAGTGTGAGCCTCATGATCTGCTGTCTGTAGT
TCTGTGAGCTCAGGTCCCTCAAAGGCCTCGGAGCACCCCCTTCCTTGTGACTGAGCCAGGGCCTGCA
TTTTTGGTTTTTCCCCACCCCACACATTCTCAACCATAGTCCTTCTAACAATACCAATAGCTAGGACCCG
GCTGCTGTGCACTGGGACTGGGGATTCCACATGTTTGCCTTGGGAGTCTCAAGCTGGACTGCCAGCC
CCTGTCCTCCCTTCACCCCCATTGCGTATGAGCATTTCAGAACTCCAAGGAGTCACAGGCATCTTTATA
GTTCACGTTAACATATAGACACTGTTGGAAGCAGTTCCTTCTAAAAGGGTAGCCCTGGACTTAATACCA
GCCGGATACCTCTGGCCCCCACCCCATTACTGTACCTCTGGAGTCACTACTGTGGGTCGCGCCACTCCT
CTGCTACACAGCACGGCTTTTTCAAGGCTGTATTGAGAAGGGAAGTTAGGAAGAAGGGTGTGCTGGG
CTAACCAGCCCACAGAGCTCACATTCCTGTCCCTTGGGTGAAAAATACATGTCCATCCTGATATCTCCT
GAATTCAGAAATTAGCCTCCACATGTGCAATGGCTTTAAGAGCCAGAAGCAGGGTTCTGGGAATTTTG
CAAGTTACCTGTGGCCAGGTGTGGTCTCGGTTACCAAATACGGTTACCTGCAGCTTTTTAGTCCTTTGT
GCTCCCACGGGTCTACAGAGTCCCATCTGCCCAAAGGTCTTGAAGCTTGACAGGATGTTTTCGATTAC
TCAGTCTCCCAGGGCACTACTGGTCCGTAGGATTCGATTGGTCGGGTAGGAGAGTTAAAACAACATTT
AAACAGAGTTCTCTCAAAAATGTCTAAAGGGATTGTAGGTAGATAACATCCAATCACTGTTTGCACTTAT
CTGAAATCTTCCCTCTTGGCTGCCCCCAGGTATTTACTGTGGAGAACATTGCATAGGAATGTCTGGAA
AAAGCTTCTACAACTTGTTACAGCCTTCACATTTGTAGAAGCTTT |
| 20 | COX10-
opt_ND4*-
3'UTR* | ATGGCCGCATCTCCGCACACTCTCTCCTCACGCCTCCTGACAGGTTGCGTAGGAGGCTCTGTCTGGT
ATCTTGAAAGAAGAACTATGCTGAAGCTGATCGTGCCCACCATCATGCTGCTGCCCCTGACCTGGCTG
AGCAAGAAGCACATGATCTGGATCAACACCACCACCCACAGCCTGATCATCAGCATCATCCCCCTGCT |

TABLE 1-continued nucleic acid and polypeptide sequences and SEQ ID NOs

| SEQ | description | sequence |
|---|---|---|
| | | GTTCTTCAACCAGATCAACAACAACCTGTTCAGCTGCAGCCCCACCTTCAGCAGCGACCCCCTGACCA<br>CCCCCCTGCTGATGCTGACCACCTGGCTGCTGCCCCTGACCATCATGGCCAGCCAGCGCCACCTGAG<br>CAGCGAGCCCCTGAGCCGCAAGAAGCTGTACCTGAGCATGCTGATCAGCCTGCAGATCAGCCTGATC<br>ATGACCTTCACCGCCACCGAGCTGATCATGTTCTACATCTTCTTCGAGACCACCCTGATCCCCACCCT<br>GGCCATCATCACCCGCTGGGGCAACCAGCCCGAGCGCCTGAACGCCGGCACCTACTTCCTGTTCTAC<br>ACCCTGGTGGGCAGCCTGCCCCTGCTGATCGCCCTGATCTACACCCACAACACCCTGGGCAGCCTGA<br>CATCCTGCTGCTGACCCTGACCGCCAGGAGCTGAGCAACAGCTGGGCAACAACCTGATGTGGCT<br>GGCCTACACCATGGCCTTCATGGTGAAGATGCCCCTGTACGGCCTGCACCTGTGGCTGCCCAAGGCC<br>CACGTGGAGGCCCCCATCGCCGGCAGCATGGTGCTGGCCGCCGTGCTGCTGAAGCTGGGCGGCTAC<br>GGCATGATGCGCCTGACCCTGATCCTGAACCCCCTGACCAAGCACATGGCCTACCCCTTCCTGGTGC<br>TGAGCCTGTGGGGCATGATCATGACCAGCAGCATCTGCCTGCGCCAGACCGACCTGAAGAGCCTGAT<br>CGCCTACAGCAGCATCAGCCACATGGCCCTGGTGGTGACCGCCATCCTGATCCAGACCCCCTGGAGC<br>TTCACCGGCGCCGTGATCCTGATGATCGCCCACGGCCTGACCAGCAGCCTGCTGTTCTGCCTGGCCA<br>ACAGCAACTACGAGCGCACCCACAGCCGCATCATGATCCTGAGCCAGGGCCTGCAGACCCTGCTGCC<br>CCTGATGGCCTTCTGGTGGCTGCTGGCCAGCCTGGCCAACCTGGCCCTGCCCCCCACCATCAACCTG<br>CTGGGCGAGCTGAGCGTGCTGGTGACCACCTTCAGCTGGAGCAACATCACCCTGCTGCTGACCGGC<br>CTGAACATGCTGGTGACCGCCCTGTACAGCCTGTACATGTTCACCACCACCCAGTGGGGCAGCCTGA<br>CCCACCACATCAACAACATGAAGCCCAGCTTCACCCGCGAGAACACCCTGATGTTCATGCACCTGAGC<br>CCCATCCTGCTGCTGAGCCTGAACCCCGACATCATCACCGGCTTCAGCAGCTAAGAGCACTGGGACG<br>CCCACCGCCCCTTTCCCTCCGCTGCCAGGCGAGCATGTTGTGGTAATTCTGGAACACAAGAAGAGAA<br>ATTGCTGGGTTTAGAACAAGATTATAAACGAATTCGGTGCTCAGTGATCACTTGACAGTTTTTTTTTT<br>TTAAATATTACCCAAAATGCTCCCCAAATAAGAAATGCATCAGCTCAGTCAGTGAATACAAAAAAAGGAA<br>TTATTTTTCCCTTTGAGGGTCTTTTATACATCTCTCCTCCAACCCCACCCTCTATTCTGTTTCTTCCTCCT<br>CACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTGCACTGGGACTGGGGATTCCACATGTTTGCCTTGGGAGTCTCAAGCTGGACTGCCA |
| 21 | COX10-ND6-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGATGTATGCTTTGTTTCTGTTGAGTGTGGGTTTAGTAATGGGGTTTGTGG<br>GGTTTTCTTCTAAGCCTTCTCCTATTTATGGGGGTTTAGTATTGATTGTTAGCGGTGTGGTCGGGTGTG<br>TTATTATTCTGAATTTTGGGGGAGGTTATATGGGTTTAATGGTTTTTTTAATTTATTTAGGGGGAATGAT<br>GGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGGAGCTGGATGATTTATGAAGGAGAGGGG<br>TCAGGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCAGCCCCTGTCCTCCCTTCACCCCCATTGCGTATGAGCATTTCAGAACTCCAAGGAGTCACAGGC<br>ATCTTTATAGTTCACGTTAACATATAGACACTGTTGGAAGCAGTTCCTTCTAAAAGGGTAGCCCTGGAC<br>TTAATACCAGCCGGATACCTCTGGCCCCCACCCCATTACTGTACCTCTGGAGTCACTACTGTGGGTCG<br>CCACTCCTCTGCTACACAGCACGGCTTTTTCAAGGCTGTATTGAGAAGGGAAGTTAGGAAGAAGGGTG<br>TGCTGGGCTAACCAGCCCACAGAGCTCACATTCCTGTCCCTTGGGTGAAAAATACATGTCCATCCTGA<br>TATCTCCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTGGTTACCAAATACGGTTACCTGCAGCTTTTTAG<br>TCCTTTGTGCTCCCACGGGTCTACAGAGTCCCATCTGCCCAAAGGTCTTGAAGCTTGACAGGATGTTT<br>TCGATTACTCAGTCTCCCAGGGCACTACTGGTCCGTAGGATTCGATTGGTCGGGTAGGAGAGTTAAA<br>CAACATTTAAACAGAGTTCTCTCAAAAATGTCTAAAGGGATTGTAGGTAGATAACATCCAATCACTGTTT<br>GCACTTATCTGAAATCTTCCCTCTTGGCTGCCCCAGGTATTTACTGTGGAGAACATTGCATAGGAATG<br>TCTGGAAAAAGCTTCTACAACTTGTTACAGCCTTCACATTTGTAGAAGCTTT |
| 22 | COX10-ND6-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGATGTATGCTTTGTTTCTGTTGAGTGTGGGTTTAGTAATGGGGTTTGTGG<br>GGTTTTCTTCTAAGCCTTCTCCTATTTATGGGGGTTTAGTATTGATTGTTAGCGGTGTGGTCGGGTGTG<br>TTATTATTCTGAATTTTGGGGGAGGTTATATGGGTTTAATGGTTTTTTTAATTTATTTAGGGGGAATGAT<br>GGTTGTCTTTGGATATACTACAGCGATGGCTATTGAGGAGTATCCTGAGGCATGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGGAGCTGGATGATTTATGAAGGAGAGGGG<br>TCAGGGGTTGATTCGGGAGGATCCTATTGGTGCGGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG |

TABLE 1-continued nucleic acid and polypeptide sequences and SEQ ID NOs

| SEQ | description | sequence |
|---|---|---|
| | | GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCA |
| 23 | COX10-<br>opt_ND6-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGATGTACGCCCTGTTCCTGCTGAGCGTGGGCCTGGTGATGGGCTTCGTG<br>GGCTTCAGCAGCAAGCCCAGCCCCATCTACGGCGGCCTGGTGCTGATCGTGAGCGGCGTGGTGGGC<br>TGCGTGATCATCCTGAACTTCGGCGGCGGCTACATGGGCCTGATGGTGTTCCTGATCTACCTGGGCG<br>GCATGATGGTGGTGTTCGGCTACACCACCGCCATGGCCATCGAGGAGTACCCCGAGGCCTGGGGCA<br>GCGGCGTGGAGGTGCTGGTGAGCGTGCTGGTGGGCCTGGCCATGGAGGTGGGCCTGGTGCTGTGG<br>GTGAAGGAGTACGACGGCGTGGTGGTGGTGGTGAACTTCAACAGCGTGGGCAGCTGGATGATCTAC<br>GAGGGCGAGGGCAGCGGCCTGATCCGCGAGGACCCCATCGGCGCCGGCGCCCTGTACGACTACGG<br>CCGCTGGCTGGTGGTGGTGACCGGCTGGACCCTGTTCGTGGGCGTGTACATCGTGATCGAGATCGC<br>CCGCGGCAACTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCAGCCCCTGTCCTCCCTTCACCCCCATTGCTATGAGCATTTCAGAACT<br>CCAAGGAGTCACAGGCATCTTTATAGTTCACGTTAACATATAGACACTGTTGGAAGCAGTTCCTTCTAA<br>AAGGGTAGCCCTGGACTTAATACCAGCCGGATACCTCTGGCCCCCACCCCATTACTGTACCTCTGGA<br>GTCACTACTGTGGGTCGCCACTCCTCTGCTACACAGCACGGCTTTTTCAAGGCTGTATTGAGAAGGGA<br>AGTTAGGAAGAAGGGTGTGCTGGGCTAACCAGCCCACAGAGCTCACATTCCTGTCCCTTGGGTGAAA<br>AATACATGTCCATCCTGATATCTCCTGAATTCAGAAATTAGCCTCCACATGTGCAATGGCTTTAAGAGC<br>CAGAAGCAGGGTTCTGGGAATTTTGCAAGTTACCTGTGGCCAGGTGTGGTCTCGGTTACCAAATACGG<br>TTACCTGCAGCTTTTTAGTCCTTTGTGCTCCCACGGGTCTACAGAGTCCCATCTGCCCAAAGGTCTTGA<br>AGCTTGACAGGATGTTTTCGATTACTCAGTCTCCCAGGGCACTACTGGTCCGTAGGATTCGATTGGTC<br>GGGGTAGGAGAGTTAAACAACATTTAAACAGAGTTCTCTCAAAAATGTCTAAAGGGATTGTAGGTAGAT<br>AACATCCAATCACTGTTTGCACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCTTCACATTTGTAGAAGCTT<br>T |
| 24 | COX10-<br>opt_ND6-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGATGTACGCCCTGTTCCTGCTGAGCGTGGGCCTGGTGATGGGCTTCGTG<br>GGCTTCAGCAGCAAGCCCAGCCCCATCTACGGCGGCCTGGTGCTGATCGTGAGCGGCGTGGTGGGC<br>TGCGTGATCATCCTGAACTTCGGCGGCGGCTACATGGGCCTGATGGTGTTCCTGATCTACCTGGGCG<br>GCATGATGGTGGTGTTCGGCTACACCACCGCCATGGCCATCGAGGAGTACCCCGAGGCCTGGGGCA<br>GCGGCGTGGAGGTGCTGGTGAGCGTGCTGGTGGGCCTGGCCATGGAGGTGGGCCTGGTGCTGTGG<br>GTGAAGGAGTACGACGGCGTGGTGGTGGTGGTGAACTTCAACAGCGTGGGCAGCTGGATGATCTAC<br>GAGGGCGAGGGCAGCGGCCTGATCCGCGAGGACCCCATCGGCGCCGGCGCCCTGTACGACTACGG<br>CCGCTGGCTGGTGGTGGTGACCGGCTGGACCCTGTTCGTGGGCGTGTACATCGTGATCGAGATCGC<br>CCGCGGCAACTAAGAGCACTGGGACGCCCACCGCCCCTTTCCCTCCGCTGCCAGGCGAGCATGTTG<br>TGGTAATTCTGGAACACAAGAAGAGAAATTGCTGGGTTTAGAACAAGATTATAAACGAATTCGGTGCTC<br>AGTGATCACTTGACAGTTTTTTTTTTTTAAATATTACCCAAAATGCTCCCCAAATAAGAAATGCATCAG<br>CTCAGTCAGTGAATACAAAAAAGGAATTATTTTTCCCTTTGAGGGTCTTTTATACATCTCTCCTCCAACC<br>CCACCCTCTATTCTGTTTCTTCCTCCTCACATGGGGGTACACATACACAGCTTCCTCTTTTGGTTCCAT<br>CCTTACCACCACACCACACGCACACTCCACATGCCCAGCAGAGTGGCACTTGGTGGCCAGAAAGTGT<br>GAGCCTCATGATCTGCTGTCTGTAGTTCTGTGAGCTCAGGTCCCTCAAAGGCCTCGGAGCACCCCCTT<br>CCTTGTGACTGAGCCAGGGCCTGCATTTTTGGTTTTCCCCACCCCACACATTCTCAACCATAGTCCTTC<br>TAACAATACCAATAGCTAGGACCCGGCTGCTGTGCACTGGGACTGGGGATTCCACATGTTTGCCTTGG<br>GAGTCTCAAGCTGGACTGCCA |
| 25 | COX10-ND1-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTCCTACTCCTCATTGTACCCATTCTAATCGCAATGGCATTCC<br>TAATGCTTACCGAACGAAAAATTCTAGGGTATATGCAACTACGCAAAGGCCCCAACGTTGTAGGCCCC<br>TACGGGCTACTACAACCCTTCGCTGACGCCATAAAACTCTTCACCAAAGAGCCCCTAAAACCCGCCAC<br>ATCTACCATCACCCTCTACATCACCGCCCCGACCTTAGCTCTCACCATCGCTCTTCTACTATGGACCCC<br>CCTCCCCATGCCCAACCCCCTGGTCAACCTCAACCTAGGCCTCCTATTTATTCTAGCCACCTCTAGCC<br>TAGCCGTTTACTCAATCCTCTGGTCAGGGTGGGCATCAAACTCAACTACGCCCTGATCGGCGCACTG<br>CGAGCAGTAGCCCAAACAATCTCATATGAAGTCACCCTAGCCATCATTCTACTATCAACATTACTAATG<br>AGTGGCTCCTTTAACCTCTCCACCCTTATCACAACACCAAGAACACCTCTGGTTACTCCTGCCATCATGG<br>CCCTTGGCCATGATGTGGTTTATCTCCACACTAGCAGAGACCAACCGAACCCCCTTCGACCTTGCCGA<br>AGGGGAGTCCGAACTAGTCTCAGGCTTCAACATCGAATACGCCGCAGGCCCCTTCGCCCTATTCTTCA<br>TGGCCGAATACACAAACATTATTATGATGAACACCCTCACCACTACAATCTTCCTAGGAACAACATATG<br>ACGCACTCTCCCCTGAACTCTACACAACATATTTGTCACCAAGACCCTACTTCTAACCTCCCTGTTCT<br>TATGGATTCGAACAGCATACCCCCGATTCCGCTACGACCAACTCATGCACCTCCTATGGAAAAACTTC<br>CTACCACTCACCCTAGCATTATGTGGTATGTCATAACATCTCCAGCATTCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC |

TABLE 1-continued nucleic acid and polypeptide sequences and SEQ ID NOs

| SEQ | description | sequence |
|---|---|---|
|  |  | CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCAGCCCCTGTCCTCCCTTCACCCCCATTGCGTATGAGCATTTCAGAACTCCAAG<br>GAGTCACAGGCATCTTTATAGTTCACGTTAACATATAGACACTGTTGGAAGCAGTTCCTTCTAAAAGGG<br>TAGCCCTGGACTTAATACCAGCCGGATACCTCTGGCCCCCACCCCATTACTGTACCTCTGGAGTCACT<br>ACTGTGGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAATACAT<br>GTCCATCCTGATATCTCCTGAATTCAGAAATTAGCCTCCACATGTGCAATGGCTTTAAGAGCCAGAAGC<br>AGGGTTCTGGGAATTTTGCAAGTTACCTGTGGCCAGGTGTGGTCTCGGTTACCAAATACGGTTACCTG<br>CAGCTTTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCGGGGTA<br>GGGAGAGTTAAACAACATTTAAACAGAGTTCTCTCAAAAATGTCTAAAGGGATTGTAGGTAGATAACATC<br>CAATCACTGTTTGCACTTATCTGAAATCTTCCCTCTTGGCTGCCCCCAGGTATTTACTGTGGAGAACAT<br>TGCATAGGAATGTCTGGAAAAAGCTTCTACAACTTGTTACAGCCTTCACATTTGTAGAAGCTTT |
| 26 | COX10-ND1-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTCCTACTCCTCATTGTACCCATTCTAATCGCAATGGCATTCC<br>TAATGCTTACCGAACGAAAAATTCTAGGCTATATGCAACTACGCAAAGGCCCCAACGTTGTAGGCCCC<br>TACGGGCTACTACAACCCTTCGCTGACGCCATAAAACTCTTCACCAAAGAGCCCCTAAAACCCGCCAC<br>ATCTACCATCACCCTCTACATCACCGCCCCGACCTTAGCTCTCACCATCGCTCTTCTACTATGGACCCC<br>CCTCCCCATGCCCAACCCCTGGTCAACCTCAACCTAGGCCTCCTATTTATTCTAGCCACCTCTAGCC<br>TAGCCGTTTACTCAATCCTCTGGTCAGGGTGGGCATCAAACTCAAACTACGCCCTGATCGGCGCACTG<br>CGAGCAGTAGCCCAAACAATCTCATATGAAGTCACCCTAGCCATCATTCTACTATCAACATTACTAATG<br>AGTGGCTCCTTTAACCTCTCCACCCTTATCACAACACAAGAACACCTCTGGTTACTCCTGCCATCATGG<br>CCCTTGGCCATGATGTGGTTTATCTCCACACTAGCAGAGACCAACCGAACCCCCTTCGACCTTGCCGA<br>AGGGGAGTCCGAACTAGTCTCAGGCTTCAACATCGAATACGCCGCAGGCCCCTTCGCCCTATTCTTCA<br>TGGCCGAATACACAAACATTATTATGATGAACACCCTCACCACTACAATCTTCCTAGGAACAACATATG<br>ACGCACTCTCCCCTGAACTCTACACAACATATTTTGTCACCAAGACCCTACTTCTAACCTCCCTGTTCT<br>TATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCA |
| 27 | COX10-<br>opt_ND1-<br>3'UTR | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTGCTGCTGCTGATCGTGCCCATCCTGATCGCCATGGCCTTC<br>CTGATGCTGACCGAGCGCAAGATCCTGGGCTACATGCAGCTGCGCAAGGGCCCCAACGTGGTGGGC<br>CCCTACGGCCTGCTGCAGCCCTTCGCCGACGCCATCAAGCTGTTCACCAAGGAGCCCCTGAAGCCCG<br>CCACCAGCACCATCACCCTGTACATCACCGCCCCCACCCTGGCCCTGACCATCGCCCTGCTGCTGTG<br>GACCCCCCTGCCCATGCCCAACCCCCTGGTGAACCTGAACCTGGGCCTGCTGTTCATCCTGGCCACC<br>AGCAGCCTGGCCGTGTACAGCATCCTGTGGAGCGGCTGGGCCAGCAACAGCAACTACGCCCTGATC<br>GGCGCCCTGCGCGCCGTGGCCCAGACCATCAGCTACGAGGTGACCCTGGCCATCATCCTGCTGAGC<br>ACCCTGCTGATGAGCGGCAGCTTCAACCTGAGCACCCTGATCACCACCCAGGAGCACCTGTGGCTGC<br>TGCTGCCCAGCTGGCCCCTGGCCATGATGTGGTTCATCAGCACCCTGGCCGAGACCAACCGCACCCC<br>CTTCGACCTGGCCGAGGGCGAGAGCGAGCTGGTGAGCGGCTTCAACATCGAGTACGCCGCCGGCCC<br>CTTCGCCCTGTTCTTCATGGCCGAGTACACCAACATCATCATGATGAACACCCTGACCACCACCATCTT<br>CCTCGGCACCACCTACGACGCCCTGAGCCCCGAGCTGTACACCACCTACTTCGTGACCAAGACCCTG<br>CTGCTGACCAGCCTGTTCCTGTGGATCCGCACCGCCTACCCCCGCTTCCGCTACGACCAGCTGATGC<br>ACCTGCTGTGGAAGAACTTCCTGCCCCTGACCCTGGCCCTGCTGATGTGGTACGTGAGCATGCCCAT<br>CACCATCAGCAGCATCCCCCCCAGACCTAAGAGCACTGGGACGCCCACCGCCCCTTTCCCTCCGCT<br>GCCAGGCGAGCATGTTGTGGTAATTCTGGAACACAAGAAGAGAAATTGCTGGGTTTAGAACAAGATTA<br>TAAACGAATTCGGTGCTCAGTGATCACTTGACAGTTTTTTTTTTTAAATATTACCCAAAATGCTCCC<br>CAAATAAGAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACATACACAG<br>CTTCCTCTTTTGGTTCCATCCTTACCACCACACCACACGCACACTCCACATGCCCAGCAGAGTGGCAC<br>TTGGTGGCCAGAAAGTGTGAGCCTCATGATCTGCTGTCTGTAGTTCTGTGAGCTCAGGTCCCTCAAAG<br>GCCTCGGAGCACCCCCTTCCTTGTGACTGAGCCAGGGCCTGCATTTTTGGTTTTCCCACCCCACACA<br>TTCTCAACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCAGCCCCTGTCCTCCCTTCACCCCCATTGC<br>GTATGAGCATTTCAGAACTCCAAGGAGTCACAGGCATCTTTATAGTTCACGTTAACATATAGACACTGT<br>TGGAAGCAGTTCCTTCTAAAAGGGTAGCCCTGGACTTAATACCAGCCGGATACCTCTGGCCCCCACCC<br>CATTACTGTACCTCTGGAGTCACTACTGTGGGTCGCCACTCCTCTGCTACACAGCACGGCTTTTTCAA<br>GGCTGTATTGAGAAGGGAAGTTAGGAAGAAGGGTGTGCTGGGCTAACCAGCCCACAGAGCTCACATT<br>CCTGTCCCTTGGGTGAAAAATACATGTCCATCCTGATATCTCCTGAATTCAGAAATTAGCCTCCACATG<br>TGCAATGGCTTTAAGAGCCAGAAGCAGGGTTCTGGGAATTTTGCAAGTTACCTGTGGCCAGGTGTGGT<br>CTCGGTTACCAAATACGGTTACCTGCAGCTTTTTAGTCCTTTGTGCTCCCACGGGTCTACAGAGTCCC<br>ATCTGCCCAAAGGTCTTGAAGCTTGACAGGATGTTTTCGATTACTCAGTCTCCCAGGGCACTACTGGT |

TABLE 1-continued nucleic acid and polypeptide sequences and SEQ ID NOs

| SEQ | description | sequence |
|---|---|---|
| | | CCGTAGGATTCGATTGGTCGGGGTAGGAGAGTTAAACAACATTTAAACAGAGTTCTCTCAAAAATGTCT<br>AAAGGGATTGTAGGTAGATAACATCCAATCACTGTTTGCACTTATCTGAAATCTTCCCTCTTGGCTGCC<br>CCCAGGTATTTACTGTGGAGAACATTGCATAGGAATGTCTGGAAAAAGCTTCTACAACTTGTTACAGCC<br>TTCACATTTGTAGAAGCTTT |
| 28 | COX10-<br>opt_ND1-<br>3'UTR* | ATGGCCGCATCTCCGCACACTCTCTCCTCACGCCTCCTGACAGGTTGCGTAGGAGGCTCTGTCTGGT<br>ATCTTGAAAGAAGAACTATGGCCAACCTGCTGCTGCTGATCGTGCCCATCCTGATCGCCATGGCCTTC<br>CTGATGCTGACCGAGCGCAAGATCCTGGGCTACATGCAGCTGCGCAAGGGCCCCAACGTGGTGGGC<br>CCCTACGGCCTGCTGCAGCCCTTCGCCGACGCCATCAAGCTGTTCACCAAGGAGCCCCTGAAGCCCG<br>CCACCAGCACCATCACCCTGTACATCACCGCCCCCACCCTGGCCCTGACCATCGCCCTGCTGCTGTG<br>GACCCCCCTGCCCATGCCCAACCCCCTGGTGAACCTGAACCTGGGCCTGCTGTTCATCCTGGCCACC<br>AGCAGCCTGGCCGTGTACAGCATCCTGTGGAGCGGCTGGGCCAGCAACAGCAACTACGCCCTGATC<br>GGCGCCCTGCGCGCCGTGGCCCAGACCATCAGCTACGAGGTGACCCTGGCCATCATCCTGCTGAGC<br>ACCCTGCTGATGAGCGGCAGCTTCAACCTGAGCACCCTGATCACCACCCAGGAGCACCTGTGGCTGC<br>TGCTGCCCAGCTGGCCCCTGGCCATGATGTGGTTCATCAGCACCCTGGCCGAGACCAACCGCACCCC<br>CTTCGACCTGGCCGAGGGCGAGAGCGAGCTGGTGAGCGGCTTCAACATCGAGTACGCCGCCGGCCC<br>CTTCGCCCTGTTCTTCATGGCCGAGTACACCAACATCATCATGATGAACACCCTGACCACCACCATCTT<br>CCTGGGCACCACCTACGACGCCCTGAGCCCCGAGCTGTACACCACCTACTTCGTGACCAAGACCCTG<br>CTGCTGACCAGCCTGTTCCTGTGGATCCGCACCGCCTACCCCCGCTTCCGCTACGACCAGCTGATGC<br>ACCTGCTGTGGAAGAACTTCCTGCCCCTGACCCTGGCCCTGCTGATGTGGTACGTGAGCATGCCCAT<br>CACCATCAGCAGCATCCCCCCCAGACCTAAGAGCACTGGGACGCCCACCGCCCCTTCCCTCCGCT<br>GCCAGGCGAGCATGTTGTGGTAATTCTGGAACACAAGAAGAGAAATTGCTGGGTTTAGAACAAGATTA<br>TAAACGAATTCGGTGCTCAGTGATCACTTGACAGTTTTTTTTTTTTTAAATATTACCCAAAATGCTCCC<br>CAAATAAGAAATGCATCAGCTCAGTCAGTGAATACAAAAAAGGAATTATTTTTCCCTTTGAGGGTCTTTT<br>ATACATCTCTCCTCCAACCCCACCCTCTATTCTGTTTCTTCCTCCTCACATGGGGGTACACATACACAG<br>CTTCCTCTTTTGGTTCCATCCTTACCACCACACCACACGCACACTCCACATGCCCAGCAGAGTGGCAC<br>TTGGTGGCCAGAAAGTGTGAGCCTCATGATCTGCTGTCTGTAGTTCTGTGAGCTCAGGTCCCTCAAAG<br>GCCTCGGAGCACCCCCTTCCTTGTGACTGAGCCAGGGCCTGCATTTTTGGTTTTCCCCACCCCACACA<br>TTCTCAACCATAGTCCTTCTAACAATACCAATAGCTAGGACCCGGCTGCTGTGCACTGGGACTGGGGA<br>TTCCACATGTTTGCCTTGGGAGTCTCAAGCTGGACTGCCA |
| 29 | opt_COX10-<br>ND4-3'UTR | ATGGCCGCCTCTCCACACACACTGAGTAGCAGACTGCTGACCGGCTGTGTTGGCGGCTCTGTGTGGT<br>ATCTGGAACGGCGGACAATGCTAAAACTAATCGTCCCAACAATTATGTTACTACCACTGACATGGCTTT<br>CCAAAAACACATGATTTGGATCAACACAACCACCCACAGCCTAATTATTAGCATCATCCCTCTACTATT<br>TTTTAACCAAATCAACAACAACCTATTTAGCTGTTCCCCAACCTTTTCCTTCCGACCCCCTAACAACCCC<br>CCTCCTAATGCTAACTACCCTGGCTCCTACCCCTCACAATCATGGCAAGCCAACGCCACTTATCCAGTG<br>AACCACTATCACGAAAAAAACTCTACCTCTCTATGCTAATCTCCCTACAAATCTCCTTAATTATGACATT<br>CACAGCCACAGAACTAATCATGTTTTATATCTTCTTCGAAACACACTTATTCCCACCTTGGCTATCATC<br>ACCCGATGGGGCAACCAGCCAGAACGCCTGAACGCAGGCACATACTTCCTATTCTACACCCTAGTAG<br>GCTCCCTTCCCCTACTCATCGCACTAATTTACACTCACAACACCCTAGGCTCACTAAACATTCTACTAC<br>TCACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAAATCGCTCATTGCATACTCTTCAATCAGCCAC<br>ATGGCCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCACAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTTAAATATTACCCAAAATGCTCCCCAAATAAGAAA<br>TGCATCAGCTCAGTCAGTGAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCAGCCCCTGTCCTCCCTTCACCCCCATTGCGTATGAGCATT<br>TCAGAACTCCAAGGAGTCACAGGCATCTTTATAGTTCACGTTAACATATAGACACTGTTGGAAGCAGTT<br>CCTTCTAAAAGGGTAGCCCTGGACTTAATACCAGCCGGATACCTCTGGCCCCCACCCCATTACTGTAC<br>CTCTGGAGTCACTACTGTGGGTCGCCACTCCTCTGCTACACAGCACGGCTTTTTCAAGGCTGTATTGA<br>GAAGGGAAGTTAGGAAGAAGGGTGTGCTGGGCTAACCAGCCCACAGAGCTCACATTCCTGTCCCTTG<br>GGTGAAAAATACATGTCCATCCTGATATCTCCTGAATTCAGAAATTAGCCTCCACATGTGCAATGGCTT<br>TAAGAGCACAGAAGCAGGGTTCTGGGAATTTTGCAAGTTACCTGTGGCCAGGTGTGGTCTCGGTTACCA<br>AATACGGTTACCTGCAGCTTTTTAGTCCTTTGTGCTCCCACGGGTCTACAGAGTCCCATCTGCCCAAA<br>GGTCTTGAAGCTTGACAGGATGTTTTCGATTACTCAGTCCCCAGGGCACTACTGGTCCGTAGGATTC<br>GATTGGTCGGGGTAGGAGAGTTAAACAACATTTAAACAGAGTTCTCTCAAAAATGTCTAAAGGGATTGT<br>AGGTAGATAACATCCAATCACTGTTTGCACTTATCTGAAATCTTCCCTCTTGGCTGCCCCCAGGTATTT<br>ACTGTGGAGAACATTGCATAGGAATGTCTGGAAAAAGCTTCTACAACTTGTTACAGCCTTCACATTTGT<br>AGAAGCTTT |

TABLE 1-continued nucleic acid and polypeptide sequences and SEQ ID NOs

| SEQ | description | sequence |
| --- | --- | --- |
| 30 | opt_COX10-ND4-3'UTR* | ATGGCCGCCTCTCCACACACACTGAGTAGCAGACTGCTGACCGGCTGTGTTGGCGGCTCTGTGTGGT<br>ATCTGGAACGGCGGACAATGCTAAAACTAATCGTCCCAACAATTATGTTACTACCACTGACATGGCTTT<br>CCAAAAAACACATGATTTGGATCAACACAACCACCCACAGCCTAATTATTAGCATCATCCCTCTACTATT<br>TTTTAACCAAATCAACAACAACCTATTTAGCTGTTCCCCAACCTTTTCCTCCGACCCCCTAACAACCCC<br>CCTCCTAATGCTAACTACCTGGCTCCTACCCCTCACAATCATGGCAAGCCAACGCCACTTATCCAGTG<br>AACCACTATCACGAAAAAAACTCTACCTCTCTATGCTAATCTCCCTACAAATCTCCTTAATTATGACATT<br>CACAGCCACAGAACTAATCATGTTTTATATCTTCTTCGAAACCACACTTATCCCCACCTTGGCTATCATC<br>ACCCGATGGGGCAACCAGCCAGAACGCCTGAACGCAGGCACATACTTCCTATTCTACACCCTAGTAG<br>GCTCCCTTCCCCTACTCATCGCACTAATTTACACTCACAACACCCTAGGCTCACTAAACATTCTACTAC<br>TCACTCTCACTGCCCAAGAACTATCAAACTCCTGGGCCAACAACTTAATGTGGCTAGCTTACACAATGG<br>CTTTTATGGTAAAGATGCCTCTTTACGGACTCCACTTATGGCTCCCTAAAGCCCATGTCGAAGCCCCCA<br>TCGCTGGGTCAATGGTACTTGCCGCAGTACTCTTAAAACTAGGCGGCTATGGTATGATGCGCCTCACA<br>CTCATTCTCAACCCCCTGACAAAACACATGGCCTACCCCTTCCTTGTACTATCCCTATGGGGCATGATT<br>ATGACAAGCTCCATCTGCCTACGACAAACAGACCTAAATCGCTCATTGCATACTCTTCAATCAGCCAC<br>ATGGGCCTCGTAGTAACAGCCATTCTCATCCAAACCCCCTGGAGCTTCACCGGCGCAGTCATTCTCAT<br>GATCGCCCACGGGCTTACATCCTCATTACTATTCTGCCTAGCAAACTCAAACTACGAACGCACTCACA<br>GTCGCATCATGATCCTCTCTCAAGGACTTCAAACTCTACTCCCACTAATGGCTTTTTGGTGGCTTCTAG<br>CAAGCCTCGCTAACCTCGCCTTACCCCCCACTATTAACCTACTGGGAGAACTCTCTGTGCTAGTAACC<br>ACGTTCTCCTGGTCAAATATCACTCTCCTACTTACAGGACTCAACATGCTAGTCACAGCCCTATACTCC<br>CTCTACATGTTTACCAACACAATGGGGCTCACTCACCCACCACATTAACAACATGAAACCCTCATTC<br>ACACGAGAAAACACCCTCATGTTCATGCACCTATCCCCCATTCTCCTCCTATCCCTCAACCCCGACATC<br>ATTACCGGGTTTTCCTCTTAAGAGCACTGGGACGCCCACCGCCCCTTTCCCTCCGCTGCCAGGCGAG<br>CATGTTGTGGTAATTCTGGAACACAAGAAGAGAAATTGCTGGGTTTAGAACAAGATTATAAACGAATTC<br>GGTGCTCAGTGATCACTTGACAGTTTTTTTTTTTTAAATATTACCCAAAATGCTCCCAAATAAGAAA<br>TGCATCAGCTCAGTCAGTAATACAAAAAAGGAATTATTTTTCCCTTTGAGGGTCTTTTATACATCTCTC<br>CTCCAACCCCACCCTCTATTCTGTTTCTTCCTCCTCACATGGGGGTACACATACACAGCTTCCTCTTTT<br>GGTTCCATCCTTACCACCACACCACACGCACACTCCACATGCCCAGCAGAGTGGCACTTGGTGGCCA<br>GAAAGTGTGAGCCTCATGATCTGCTGTCTGTAGTTCTGTGAGCTCAGGTCCCTCAAAGGCCTCGGAGC<br>ACCCCCTTCCTTGTGACTGAGCCAGGGCCTGCATTTTTGGTTTTCCCCACCCCACACATTCTCAACCAT<br>AGTCCTTCTAACAATACCAATAGCTAGGACCCGGCTGCTGTGCACTGGGACTGGGGATTCCACATGTT<br>TGCCTTGGGAGTCTCAAGCTGGACTGCCA |
| 31 | opt_COX10-opt_ND4-3'UTR | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCTCTGACCTGGCT<br>GAGCAAGAAACACATGATCTGGATCAACACCACCACGCACAGCCTGATCATCAGCATCATCCCTCTGC<br>TGTTCTTCAACCAGATCAACAACAACCTGTTCAGCTGCAGCCCCACCTTCAGCAGCGACCCTCTGACA<br>ACACCTCTGCTGATGCTGACCACCTGGCTGCTGCCCCTCACAATCATGGCCTCTCAGAGACACCTGA<br>GCAGCGAGCCCCTGAGCCGGAAGAAACTGTACCTGAGCATGCTGATCTCCCTGCAGATCTCTCTGAT<br>CATGACCTTCACCGCCACCGAGCTGATCATGTTCTACATCTTTTTCGAGACAACGCTGATCCCCACACT<br>GGCCATCATCACCAGATGGGGCAACCAGCCTGAGAGACTGAACGCCGGCACCTACTTTCTGTTCTAC<br>ACCCTCGTGGGCAGCCTGCCACTGCTGATTGCCCTGATCTACACCCACAACACCCTGGGCTCCCTGA<br>ACATCCTGCTGCTGACACTGACAGCCCAAGAGCTGAGCAACAGCTGGGCCAACAATCTGATGTGGCT<br>GGCCTACACAATGGCCTTCATGGTCAAGATGCCCCTGTACGGCCTGCACCTGTGGCTGCCTAAAGCT<br>CATGTGGAAGCCCCTATCGCCGGCTCTATGGTGCTGGCTGCAGTGCTGCTGAAACTCGGCGGCTACG<br>GCATGATGCGGCTGACCCTGATTCTGAATCCCCTGACCAAGCACATGGCCTATCCATTTCTGGTGCTG<br>AGCCTGTGGGCATGATTATGACCAGCAGCATCTGCCTGCGACAGACCGATCTGAAGTCCCTGATCG<br>CCTACAGCTCCATCAGCCACATGGCCCTGGTGGTCACCGCCATCCTGATTCAGACCCCTTGGAGCTTT<br>ACAGGCGCCGTGATCCTGATGATTGCCCACGGCCTGACAAGCAGCCTGCTGTTTTGTCTGGCCAACA<br>GCAACTACGAGCGGACCCACACAGCAATCATGATCCTCTGTCTCAGGGCCTGCAGACCCTCCTGCCTCT<br>TATGGCTTTTTGGTGGCTGCTGGCCTCTCTGGCCAATCTGGCACTGCCTCCTACCATCAATCTGCTGG<br>GCGAGCTGAGCGTGCTGGTCACCACATTCAGCTGGTCCAATATCACCCTGCTGCTCACCGGCCTGAA<br>CATGCTGGTTACAGCCCTGTACTCCCTGTACATGTTCACCACCACAGTGGGGAAGCCTGACACACC<br>ACATCAACAATATGAAGCCCAGCTTCACCCGCGAGAACACCCTGATGTTCATGCATCTGAGCCCCATT<br>CTGCTGCTGTCCCTGAATCCTGATATCATCACCGGCTTCTCCAGCTGAGAGCACTGGGACGCCCACC<br>GCCCCTTTCCCTCCGCTGCCAGGCGAGCATGTTGTGGTAATTCTGGAACACAAGAAGAGAAATTGCTG<br>GGTTTAGAACAAGATTATAAACGAATTCGGTGCTCAGTGATCACTTGACAGTTTTTTTTTTTTAAATAT<br>TACCCAAAATGCTCCCAAATAAGAAATGCATCAGCTCAGTCAGTAATACAAAAAAGGAATTATTTTTT<br>CCCTTTGAGGGTCTTTTATACATCTCTCCTCCAACCCCACCCTCTATTCTGTTTCTTCCTCCTCACATGG<br>GGGTACACATACACAGCTTCCTCTTTTGGTTCCATCCTTACCACCACACCACACGCACACTCCACATG<br>CCCAGCAGAGTGGCACTTGGTGGCCAGAAAGTGTGAGCCTCATGATCTGCTGTCTGTAGTTCTGTGA<br>GCTCAGGTCCCTCAAAGGCCTCGGAGCACCCCCTTCCTTGTGACTGAGCCAGGGCCTGCATTTTTGG<br>TTTTCCCCACCCCACACATTCTCAACCATAGTCCTTCTAACAATACCAATAGCTAGGACCCGGCTGCTG<br>TGCACTGGGACTGGGGATTCCACATGTTTGCCTTGGGAGTCTCAAGCTGGACTGCCAGCCCCTGTCC<br>TCCCTTCACCCCCATTGCGTATGAGCATTTCAGAACTCCAAGGAGTCACAGGCATCTTTATAGTTCACG<br>TTAACATATAGACACTGTTGGAAGCAGTTCCTTCAAAAGGGTAGCCCTGGACTTAATACCAGCCGGAT<br>ACCTCTGGCCCCCACCCCATTACTGTACCTCTGGAGTCACTACTGTGGGTCGCCACTCCTCTGCTACA<br>CAGCACGGCTTTTTCAAGGCTGTATTGAGAAGGGAAGTTAGGAAGAAGGGTGTGCTGGGCTAACCAG<br>CCCACAGAGCTCACATTCCTGTCCCTTGGGTGAAAAATACATGTCCATCCTGATATCTCCTGAATTCAG<br>AAATTAGCCTCCACATGTGCAATGGCTTTAAGAGCCAGAAGCAGGGTCTGGGAATTTTGCAAGTTAC<br>CTGTGGCCAGGTGTGGTCTCGGTTACCAAATACGGTTACCTGCAGCTTTTTAGTCCTTTGGTGCTCCA<br>CGGGTCTACAGAGTCCCATCTGCCCAAAGGTCTTGAAGCTTGACAGGATGTTTTCGATTACTCAGTCT<br>CCCAGGGCACTACTGGTCCGTAGGATTCGATTGGTCGGGTAGGAGAGTTAAACAACATTTAAACAGA<br>GTTCTCTCAAAAATGTCTAAAGGGATTGTAGGTAGATAACATCCAATCACTGTTTGCACTTATCTGAAAT<br>CTTCCCTCTTGGCTGCCCCCAGGTATTTACTGTGGAGAACATTGCATAGGAATGTCTGGAAAAGCTT<br>CTACAACTTGTTACAGCCTTCACATTTGTAGAAGCTTT |

TABLE 1-continued nucleic acid and polypeptide sequences and SEQ ID NOs

| SEQ | description | sequence |
|---|---|---|
| 32 | opt_COX10-opt_ND4-3'UTR* | ATGGCCGCCTCTCCACACACACTGAGTAGCAGACTGCTGACCGGCTGTGTTGGCGGCTCTGTGTGGT
ATCTGGAACGGCGGACAATGCTGAAGCTGATCGTGCCCACCATCATGCTGCTGCCCTCTGACCTGGCT
GAGCAAGAAACACATGATCTGGATCAACACCACCACCACGCACAGCCTGATCATCAGCATCATCCCTCTGC
TGTTCTTCAACCAGATCAACAACAACCTGTTCAGCTGCAGCCCCACCTTCAGCAGCGACCCTCTGACA
ACACCTCTGCTGATGCTGACCACCTGGCTGCTGCCCCTCACAATCATGGCCTCTCAGAGACACCTGA
GCAGCGAGCCCCTGAGCCGGAAGAAACTGTACCTGAGCATGCTGATCTCCCTGCAGATCTCTCTGAT
CATGACCTTCACCGCCACCGAGCTGATCATGTTCTACATCTTTTTCGAGACAACGCTGATCCCCACACT
GGCCATCATCACCAGATGGGGCAACCAGCCTGAGAGACTGAACGCCGGCACCTACTTTCTGTTCTAC
ACCCTCGTGGGCAGCCTGCCACTGCTGATTGCCCTGATCTACACCCACAACACCCTGGGCTCCCTGA
ACATCCTGCTGCTGACACTGACAGCCCAAGAGCTGAGCAACAGCTGGGCCAACAATCTGATGTGGCT
GGCCTACACAATGGCCTTCATGGTCAAGATGCCCCTGTACGGCCTGCACCTGTGGCTGCCTAAAGCT
CATGTGGAAGCCCCTATCGCCGGCTCTATGGTGCTGGCTGCCAGTGCTGCTGAAACTCGGCGGCTACG
GCATGATGCGGCTGACCCTGATTCTGAATCCCCTGACCAAGCACATGGCCTATCCATTTCTGGTGCTG
AGCCTGTGGGCATGATTATGACCAGCAGCATCTGCCTGCGGCAGACCGATCTGAAGTCCCTGATCG
CCTACAGCTCCATCAGCCACATGGCCCTGGTGGTCACCGCCATCCTGATTCAGACCCCTTGGAGCTTT
ACAGGCGCCGTGATCCTGATGATTGCCCACGGCCTGACAAGCAGCCTGCTGTTTTGTCTGGCCAACA
GCAACTACGAGCGGACCCACAGCAGAATCATGATCCTGTCTCAGGGCCTGCAGACCCTCCTGCCTCT
TATGGCTTTTTGGTGGCTGCTGGCCTCTCTGGCCAATCTGGCACTGCCTCCTACCATCAATCTGCTGG
GCGAGCTGAGCGTGCTGGTCACCACATTCAGCTGGTCCAATATCACCCTGCTGCTCACCGGCC'TGAA
CATGCTGGTTACAGCCCTGTACTCCCTGTACATGTTCACCACCACAGTGGGGAAGCCTGACACACC
ACATCAACAATATGAAGCCCAGCTTCACCCGCGAGAACACCCTGATGTTCATGCATCTGAGCCCCATT
CTGCTGCTGTCCCTGAATCCTGATATCATCACCGGCTTCTCCAGCTGAGAGCACTGGGACGCCCACC
GCCCCTTTCCCTCCGCTGCCAGGCGAGCATGTTGTGGTAATTCTGGAACACAAGAAGAGAAATTGCTG
GGTTTAGAACAAGATTATAAACGAATTCGGTGCTCAGTGATCACTTGACAGTTTTTTTTTTTTTAAATAT
TACCCAAAATGCTCCCCAAATAAGAAATGCATCAGCTCAGTCAGTGAATACAAAAAAGGAATTATTTTT
CCCTTTGAGGGTCTTTTATACATCTCTCCTCAACCCCACCCTCTATTCTGTTTCTTCCTCCTCACATGG
GGGTACACATACACAGCTTCCTCTTTTGGTTCCATCCTTACCACCACACCACACGCACACTCCACATG
CCCAGCAGAGTGGCACTTGGTGGCCAGAAAGTGTGAGCCTCATGATCTGCTGTCTGTAGTTCTGTGA
GCTCAGGTCCCTCAAAGGCCTCGGAGCACCCCCTTCCTTGTGACTGAGCCAGGGCCTGCATTTTTGG
TTTTTCCCCACCCCACACATTCTCAACCATAGTCCTTCTAACAATACCAATAGCTAGGACCCGGCTGCTG
TGCACTGGGACTGGGGATTCCACATGTTTGCCTTGGGAGTCTCAAGCTGGACTGCCA |
| 33 | opt_COX10-opt_ND4*-3'UTR | ATGGCCGCCTCTCCACACACACTGAGTAGCAGACTGCTGACCGGCTGTGTTGGCGGCTCTGTGTGGT
ATCTGGAACGGCGGACAATGCTGAAGCTGATCGTGCCCACCATCATGCTGCTGCCCCTGACCTGGCT
GAGCAAGAAGCACATGATCTGGATCAACACCACCACCCAGCCTGATCATCAGCATCATCCCCCTGC
TGTTCTTCAACCAGATCAACAACAACCTGTTCAGCTGCAGCCCCACCTTCAGCAGCGACCCCCTGACC
ACCCCCTGCTGATGCTGACCACCTGGCTGCTGCCCCTGACCATCATGGCCAGCAGCGCCACCTGA
GCAGCGAGCCCCTGAGCCGCAAGAAGCTGTACCTGAGCATGCTGATCAGCCTGCAGATCAGCCTGAT
CATGACCTTCACCGCCACCGAGCTGATCATGTTCTACATCTTCTTCGAGACCACCCTGATCCCCACCC
TGGCCATCATCACCCGCTGGGGCAACCAGCCCGAGCGCCTGAACGCCGGCACCTACTTCCTGTTCTA
CACCCTGGTGGGCAGCCTGCCCCTGCTGATCGCCCTGATCTACACCCACAACACCCTGGGCAGCCTG
AACATCCTGCTGCTGACCCTGACCGCCCAGGAGCTGAGCAACAGCTGGGCCAACAACCTGATGTGGC
TGGCCTACACCATGGCCTTCATGGTGAAGATGCCCCTGTACGGCCTGCACCTGTGGCTGCCCAAGGC
CCACGTGGAGGCCCCCATCGCCGGCAGCATGGTGCTGGCCGCCGTGCTGCTGAAGCTGGGCGGCTA
CGGCATGATGCGCCTGACCCTGATCCTGAACCCCCTGACCAAGCACATGGCCTACCCCTTCCTGGTG
CTGAGCCTGTGGGGCATGATCATGACCAGCAGCATCTGCCTGCGCCAGACCGACCTGAAGAGCCTGA
TCGCCTACAGCAGCATCAGCCACATGGCCCTGGTGGTGACCGCCATCCTGATCCAGACCCCCTGGAG
CTTCACCGGCGCCGTGATCCTGATGATCGCCCACGGCCTGACCAGCAGCCTGCTGTTCTGCCTGGCC
AACAGCAACTACGAGCGCACCCACAGCCGCATCATGATCCTGAGCCAGGGCCTGCAGACCCTGCTGC
CCCTGATGGCCTTCTGGTGGCTGCTGGCCAGCCTGGCCAACCTGGCCCTGCCCCCCACCATCAACCT
GCTGGGCGAGCTGAGCGTGCTGGTGACCACCTTCAGCTGGAGCAACATCACCCTGCTGCTGACCGG
CCTGAACATGCTGGTGACCGCCCTGTACAGCCTGTACATGTTCACCACCACCCAGTGGGGCAGCCTG
ACCCACCACATCAACAACATGAAGCCCAGCTTCACCCGCGAGAACACCCTGATGTTCATGCACCTGAG
CCCCATCCTGCTGCTGAGCCTGAACCCCGACATCATCACCGGCTTCAGCAGCTAAGAGCACTGGGAC
GCCCACCGCCCCTTTCCCTCCGCTGCCAGGCGAGCATGTTGTGGTAATTCTGGAACACAAGAAGAGA
AATTGCTGGGTTTAGAACAAGATTATAAACGAATTCGGTGCTCAGTGATCACTTGACAGTTTTTTTTTT
TTTAAATATTACCCAAAATGCTCCCCAAATAAGAAATGCATCAGCTCAGTCAGTGAATACAAAAAAGGA
ATTATTTTTCCCTTTGAGGGTCTTTTATACATCTCTCCTCAACCCCACCCCTCTATTCTGTTTCTTCCTCC
TCACATGGGGGTACACATACACAGCTTCCTCTTTTGGTTCCATCCTTACCACCACACCACACGCACACT
CCACATGCCCAGCAGAGTGGCACTTGGTGGCCAGAAAGTGTGAGCCTCATGATCTGCTGTCTGTAGT
TCTGTGAGCTCAGGTCCCTCAAAGGCCTCGGAGCACCCCCTTCCTTGTGACTGAGCCAGGGCCTGCA
TTTTGGTTTTTCCCCACCCCACAACATTCTCAACCATAGTCCTTCTAACAATACCAATAGCTAGGACCCG
GCTGCTGTGCACTGGGACTGGGGATTCCACATGTTTGCCTTGGGAGTCTCAAGCTGGACTGCCAGCC
CCTGTCCTCCCTTCACCCCCATTGCGTATGAGCATTTCAGAACTCCAAGGAGTCACAGGCATCTTTATA
GTTCACGTTAACATATAGACACTGTTGGAAGCAGTTCCTTCTAAAAGGGTAGCCCTGGACTTAATACCA
GCCGGATACCTCTGGCCCCCACCCCATTACTGTACCTCTGGAGTCACTACTGTGGGTCGCCACTCCT
CTGCTACACAGCACGGCTTTTCAAGGCTGTATTGAGAAGGGAAGTTAGGAAGAAGGGTGTGCTGGG
CTAACCAGCCCACAGAGCTCACATTCCTGTCCCTTGGGTGAAAAATACATGTCCATCCTGATATCTCCT
GAATTCAGAAATTAGCCTCCACATGTGCAATGGCTTTAAGAGCCAGAAGCAGGGTTCTGGGAATTTTG
CAAGTTACCTGTGGCCAGGTGTGGTCTCGGTTACCAGCCAAATACGGTTACCTGCTCTTTTAGTCCTTGT
GCTCCCACGGGTCTACAGAGTCCCATCTGCCCAAAGGTCTTGAAGCTTGACAGGATGTTTTCGATTAC
TCAGTCTCCCAGGGCACTACTGGTCCGTAGGATTCGATTGGTCGGGTAGGAGAGTTAAACAACATTT
AAACAGAGTTCTCTCAAAAATGTCTAAAGGGATTGTAGGTAGATAACATCCAATCACTGTTTGCACTTAT
CTGAAATCTTCCCTCTTGGCTGCCCCCAGGTATTTACTGTGGAGAACATTGCATAGGAATGTCTGGAA
AAAGCTTCTACAACTTGTTACAGCCTTCACATTTGTAGAAGCTTT |

TABLE 1-continued nucleic acid and polypeptide sequences and SEQ ID NOs

| SEQ | description | sequence |
| --- | --- | --- |
| 34 | opt_COX10-<br>opt_ND4*-<br>3'UTR* | ATGGCCGCCTCTCCACACACACTGAGTAGCAGACTGCTGACCGGCTGTGTTGGCGGCTCTGTGTGGT<br>ATCTGGAACGGCGGACAATGCTGAAGCTGATCGTGCCCACCATCATGCTGCTGCCCCTGACCTGGCT<br>GAGCAAGAAGCACATGATCTGGATCAACACCACCACCCACAGCCTGATCATCAGCATCATCCCCCTGC<br>TGTTCTTCAACCAGATCAACAACAACCTGTTCAGCTGCAGCCCCACCTTCAGCAGCGACCCCCTGACC<br>ACCCCCCTGCTGATGCTGACCACCTGGCTGCTGCCCCTGACCATCATGGCCAGCCAGCGCCACCTGA<br>GCAGCGAGCCCCTGAGCCGCAAGAAGCTGTACCTGAGCATGCTGATCAGCCTGCAGATCAGCCTGAT<br>CATGACCTTCACCGCCACCGAGCTGATCATGTTCTACATCTTCTTCGAGACCACCCTGATCCCCACCC<br>TGGCCATCATCACCCGCTGGGGCAACCAGCCCGAGCGCCTGAACGCCGGCACCTACTTCCTGTTCTA<br>CACCCTGGTGGGCAGCCTGCCCCTGCTGATCGCCCTGATCTACACCCACAACACCCTGGGCAGCCTG<br>AACATCCTGCTGCTGACCCTGACCGCCCAGGAGCTGAGCAACAGCTGGGCCAACAACCTGATGTGGC<br>TGGCCTACACCATGGCCTTCATGGTGAAGATGCCCCTGTACGGCCTGCACCTGTGGCTGCCCAAGGC<br>CCACGTGGAGGCCCCCATCGCCGGCAGCATGGTGCTGGCCGCCTGCTGCTGAAGCTGGGCGGCTA<br>CGGCATGATGCGCCTGACCCTGATCCTGAACCCCCTGACCAAGCACATGGCCTACCCCTTCCTGGTG<br>CTGAGCCTGTGGGGCATGATCATGACCAGCAGCATCTGCCTGCGCCAGACCGACCTGAAGAGCCTGA<br>TCGCCTACAGCAGCATCAGCCACATGGCCCTGGTGGTGACCGCCATCCTGATCCAGACCCCCTGGAG<br>CTTCACCGGCGCCGTGATCCTGATGATCGCCCACGGCCTGACCAGCAGCCTGCTGTTCTGCCTGGCC<br>AACAGCAACTACGAGCGCACCCACAGCCGCATCATGATCCTGAGCCAGGGCCTGCAGACCCTGCTGC<br>CCCTGATGGCCTTCTGGTGGCTGCTGGCCAGCCTGGCCAACCTGGCCCTGCCCCCCACCATCAACCT<br>GCTGGGCGAGCTGAGCGTGCTGGTGACCACCTTCAGCTGGAGCAACATCACCCTGCTGCTGACCGG<br>CCTGAACATGCTGGTGACCGCCCTGTACAGCCTGACATGTTCACCACCACCCAGTGGGGCAGCCTG<br>ACCCACCACATCAACAACATGAAGCCCAGCTTCACCCGCGAGAACACCCTGATGTTCATGCACCTGAG<br>CCCCATCCTGCTGCTGAGCCTGAACCCCGACATCATCACCGGCTTCAGCAGCTAAGAGCACTGGGAC<br>GCCCACCGCCCCTTTCCCTCCGCTGCCAGGCGAGCATGTTGTGGTAATTCTGGAACACAAGAAGAGA<br>AATTGCTGGGTTTAGAACAAGATTATAAACGAATTCGGTGCTCAGTGATCACTTGACAGTTTTTTTTTT<br>TTTAAATATTACCCAAAATGCTCCCCAAATAAGAAATGCATCAGCTCAGTCAGTGAATACAAAAAAGGA<br>ATTATTTTTCCCTTTGAGGGTCTTTTATACATCTCTCCTCCAACCCCACCCTCTATTCTGTTTCTTCCTCC<br>TCACATGGGGGTACACATACACAGCTTCCTCTTTTGGTTCCATCCTTACCACCACACCACACGCACACT<br>CCACATGCCCAGCAGAGTGGCACTTGGTGGCCAGAAAGTGTGAGCCTCATGATCTGCTGTCTGTAGT<br>TCTGTGAGCTCAGGTCCCTCAAAGGCCTCGGAGCACCCCCTTCCTTGTGACTGAGCCAGGGCCTGCA<br>TTTTTGGTTTTCCCCACCCCACACATTCTCAACCATAGTCCTTCTAACAATACCAATAGCTAGGACCCG<br>GCTGCTGTCCACTGGGACTGGGGATTCCACATGTTTGCCTTGGGAGTCTCAAGCTGGACTGCCA |
| 35 | opt_COX10-<br>ND6-3'UTR | ATGGCCGCCTCTCCACACACACTGAGTAGCAGACTGCTGACCGGCTGTGTTGGCGGCTCTGTGTGGT<br>ATCTGGAACGGCGGACAATGATGTATGCTTTGTTTCTGTTGAGTGTGGGTTTAGTAATGGGGTTTGTG<br>GGGTTTTCTTCTAAGCCTTCTCCTATTTATGGGGGTTTAGTATTGATTGTTAGCGGTGTGGTCGGGTGT<br>GTTATTATTCTGAATTTTGGGGGAGGTTATATGGGTTTAATGGTTTTTTTAATTTATTTAGGGGGAATGA<br>TGGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGAAGCTGGATGATTTATGAAGGAGAGGGG<br>TCAGGGTTGATTCGGGAGGATCCTATTGGTGCGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTAAATATTACCCAAAATGCTCCCCAAATAAGAAATGCATCAGCTCAGTCAGTGAATACAA<br>AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCAGCCCCTGTCCTCCCTTCACCCCCATTGCGTATGAGCATTTCAGAACTCCAAGGAGTCACAGGC<br>ATCTTTATAGTTCACGTTAACATATAGACACTGTTGGAAGCAGTTCCTTCTAAAAGGGTAGCCCTGGAC<br>TTAATACCAGCCGGATACCTCTGGCCCCCACCCCATTACTGTACCTCTGGAGTCACTACTGTGGGTCG<br>CCACTCCTCTGCTACACAGCACGGCTTTTTCAAGGCTGTATTGAGAAGGGAAGTTAGGAAGAAGGGTG<br>TGCTGGGCTAACCAGCCCACAGAGCTCACATTCCTGTCCCTTGGGTGAAAAATACATGTCCATCCTGA<br>TATCTCCTGAATTCAGAAATTAGCCTCCACATGTGCAATGGCTTTAAGAGCCAGAAGCAGGGTTCTGG<br>GAATTTTGCAAGTTACCTGTGGCCAGGTGTGGTCTCGGTTACCAAATACGGTTACCTGCAGCTTTTTAG<br>TCCTTTGTGCTCCCACGGGTCTACAGAGTCCCATCTGCCCAAAGGTCTTGAAGCTTGACAGGATGTTT<br>TCGATTACTCAGTCTCCCAGGGCACTACTGGTCCGTAGGATTCGATTGGTCGGGGTAGGAGAGTTAAA<br>CAACATTTAAACAGAGTTCTCTCAAAAAATGTCTAAAGGGATTGTAGGTAGATAACATCCAATCACTGTTT<br>GCACTTATCTGAAATCTTCCCTCTTGGCTGCCCCCAGGTATTTACTGTGGAGAACATTGCATAGGAATG<br>TCTGGAAAAAGCTTCTACAACTTGTTACAGCCTTCACATTTGTAGAAGCTTT |
| 36 | opt_COX10-<br>ND6-3'UTR* | ATGGCCGCCTCTCCACACACACTGAGTAGCAGACTGCTGACCGGCTGTGTTGGCGGCTCTGTGTGGT<br>ATCTGGAACGGCGGACAATGATGTATGCTTTGTTTCTGTTGAGTGTGGGTTTAGTAATGGGGTTTGTG<br>GGGTTTTCTTCTAAGCCTTCTCCTATTTATGGGGGTTTAGTATTGATTGTTAGCGGTGTGGTCGGGTGT<br>GTTATTATTCTGAATTTTGGGGGAGGTTATATGGGTTTAATGGTTTTTTTAATTTATTTAGGGGGAATGA<br>TGGTTGTCTTTGGATATACTACAGCGATGGCTATTGAGGAGTATCCTGAGGCATGGGGGTCAGGGGTT<br>GAGGTCTTGGTGAGTGTTTTAGTGGGGTTAGCGATGGAGGTAGGATTGGTGCTGTGGGTGAAAGAGT<br>ATGATGGGGTGGTGGTTGTGGTAAACTTTAATAGTGTAGGAAGCTGGATGATTTATGAAGGAGAGGGG<br>TCAGGGTTGATTCGGGAGGATCCTATTGGTGCGGGGCTTTGTATGATTATGGGCGTTGGTTAGTAGT<br>AGTTACTGGTTGGACATTGTTTGTTGGTGTATATATTGTAATTGAGATTGCTCGGGGGAATTAGGAGCA<br>CTGGGACGCCCACCGCCCCTTTCCCTCCGCTGCCAGGCGAGCATGTTGTGGTAATTCTGGAACACAA<br>GAAGAGAAATTGCTGGGTTTAGAACAAGATTATAAACGAATTCGGTGCTCAGTGATCACTTGACAGTTT<br>TTTTTTTTTTAAATATTACCCAAAATGCTCCCCAAATAAGAAATGCATCAGCTCAGTCAGTGAATACAA |

TABLE 1-continued nucleic acid and polypeptide sequences and SEQ ID NOs

| SEQ | description | sequence |
|---|---|---|
| | | AAAAGGAATTATTTTTCCCTTTGAGGGTCTTTTATACATCTCTCCTCCAACCCCACCCTCTATTCTGTTT<br>CTTCCTCCTCACATGGGGGTACACATACACAGCTTCCTCTTTTGGTTCCATCCTTACCACCACACCACA<br>CGCACACTCCACATGCCCAGCAGAGTGGCACTTGGTGGCCAGAAAGTGTGAGCCTCATGATCTGCTG<br>TCTGTAGTTCTGTGAGCTCAGGTCCCTCAAAGGCCTCGGAGCACCCCCTTCCTTGTGACTGAGCCAG<br>GGCCTGCATTTTTGGTTTTCCCCACCCCACACATTCTCAACCATAGTCCTTCTAACAATACCAATAGCT<br>AGGACCCGGCTGCTGTGCACTGGGACTGGGGATTCCACATGTTTGCCTTGGGAGTCTCAAGCTGGAC<br>TGCCA |
| 37 | opt_COX10-<br>opt_ND6-<br>3'UTR | ATGGCCGCCTCTCCACACACACTGAGTAGCAGACTGCTGACCGGCTGTGTTGGCGGCTCTGTGTGGT<br>ATCTGGAACGGCGGACAATGATGTACGCCCTGTTCCTGCTGAGCGTGGGCCTGGTGATGGGCTTCGT<br>GGGCTTCAGCAGCAAGCCCAGCCCCATCTACGGCGGCCTGGTGCTGATCGTGAGCGGCGTGGTGGG<br>CTGCGTGATCATCCTGAACTTCGGCGGCGGCTACATGGGCCTGATGGTGTTCCTGATCTACCTGGGC<br>GGCATGATGGTGGTGTTCGGCTACACCACCGCCATGGCCATCGAGGAGTACCCCGAGGCCTGGGGC<br>AGCGGCGTGGAGGTGCTGGTGAGCGTGCTGGTGGGCCTGGCCATGGAGGTGGGCCTGGTGCTGTG<br>GGTGAAGGAGTACGACGGCGTGGTGGTGGTGAACTTCAACAGCGTGGGCAGCTGGATGATCTA<br>CGAGGGCGAGGGCAGCGGCCTGATCCGCGAGGACCCCATCGGCGCCGGCGCCCTGTACGACTACG<br>GCCGCTGGCTGGTGGTGGTGACCGGCTGGACCCTGTTCGTGGGCGTGTACATCGTGATCGAGATCG<br>CCCGCGGCAACTAAGAGCACTGGGACGCCCACCGCCCCTTTCCCTCCGCTGCCAGGCGAGCATGTT<br>GTGGTAATTCTGGAACACAAGAAGAGAAATTGCTGGGTTTAGAACAAGATTATAAACGAATTCGGTGCT<br>CAGTGATCACTTGACAGTTTTTTTTTTTTAAATATTACCCAAAATGCTCCCCAAATAAGAAATGCATCA<br>GCTCAGTCAGTGAATACAAAAAAGGAATTATTTTTCCCTTTGAGGGTCTTTTATACATCTCTCCTCCAAC<br>CCCACCCTCTATTCTGTTTCTTCCTCCTCACATGGGGGTACACATACACAGCTTCCTCTTTTGGTTCCA<br>TCCTTACCACCACACCACACGCACACTCCACATGCCCAGCAGAGTGGCACTTGGTGGCCAGAAAGTG<br>TGAGCCTCATGATCTGCTGTCTGTAGTTCTGTGAGCTCAGGTCCCTCAAAGGCCTCGGAGCACCCCCT<br>TCCTTGTGACTGAGCCAGGGCCTGCATTTTTGGTTTTCCCCACCCCACACATTCTCAACCATAGTCCTT<br>CTAACAATACCAATAGCTAGGACCCGGCTGCTGTGCACTGGGACTGGGGATTCCACATGTTTGCCTTG<br>GGAGTCTCAAGCTGGACTGCCAGCCCCTGTCCTCCCTTCACCCCATTGCGTATGAGCATTTCAGAAC<br>TCCAAGGAGTCACAGGCATCTTTATAGTTCACGTTAACATATAGACACTGTTGGAAGCAGTTCCTTCTA<br>AAAGGGTAGCCCTGGACTTAATACCAGCCGGATACCTCTGGCCCCCACCCCATTACTGTACCTCTGGA<br>GTCACTACTGTGGGTCGCCACTCCTCTGCTACACAGCACGGCCTTTTTCAAGGCTGTATTGAGAAGGGA<br>AGTTAGGAAGAGGGTGTGCTGGGCTAACCAGCCCACAGAGCTCACATTCCTGTCCCTTGGGTGAAA<br>AATACATGTCCATCCTGATATCTCCTGAATTCAGAAATTAGCCTCCACATGTGCAATGGCTTTAAGAGC<br>CAGAAGCAGGGTTCTGGGAATTTTGCAAGTTACCTGTGGCCAGGTGTGGTCTCGGTTACCAAATACGG<br>TTACCTGCAGCTTTTTAGTCCTTTGTGCTCCCACGGGTCTACAGAGTCCCATCTGCCCAAAGGTCTTGA<br>AGCTTGACAGGATGTTTTCGATTACTCAGTCTCCCAGGGCACTACTGGTCCGTAGGATTCGATTGGTC<br>GGGGTAGGAGAGTTAAACAACATTTAAACAGAGTTCTCTCAAAAATGTCTAAAGGGATTGTAGGTAGAT<br>AACATCCAATCACTGTTTGCACTTATCTGAAATCTTCCCTCTTGGCTGCCCCCAGGTATTTACTGTGGA<br>GAACATTGCATAGGAATGTCTGGAAAAAGCTTCTACAACTTGTTACAGCCTTCACATTTGTAGAAGCTT<br>T |
| 38 | opt_COX10-<br>opt_ND6-<br>3'UTR* | ATGGCCGCCTCTCCACACACACTGAGTAGCAGACTGCTGACCGGCTGTGTTGGCGGCTCTGTGTGGT<br>ATCTGGAACGGCGGACAATGATGTACGCCCTGTTCCTGCTGAGCGTGGGCCTGGTGATGGGCTTCGT<br>GGGCTTCAGCAGCAAGCCCAGCCCCATCTACGGCGGCCTGGTGCTGATCGTGAGCGGCGTGGTGGG<br>CTGCGTGATCATCCTGAACTTCGGCGGCGGCTACATGGGCCTGATGGTGTTCCTGATCTACCTGGGC<br>GGCATGATGGTGGTGTTCGGCTACACCACCGCCATGGCCATCGAGGAGTACCCCGAGGCCTGGGGC<br>AGCGGCGTGGAGGTGCTGGTGAGCGTGCTGGTGGGCCTGGCCATGGAGGTGGGCCTGGTGCTGTG<br>GGTGAAGGAGTACGACGGCGTGGTGGTGGTGAACTTCAACAGCGTGGGCAGCTGGATGATCTA<br>CGAGGGCGAGGGCAGCGGCCTGATCCGCGAGGACCCCATCGGCGCCGGCGCCCAATACGACTACG<br>GCCGCTGGCTGGTGGTGGTGACCGGCTGGACCCTGTTCGTGGGCGTGTACATCGTGATCGAGATCG<br>CCCGCGGCAACTAAGAGCACTGGGACGCCCACCGCCCCTTTCCCTCCGCTGCCAGGCGAGCATGTT<br>GTGGTAATTCTGGAACACAAGAAGAGAAATTGCTGGGTTTAGAACAAGATTATAAACGAATTCGGTGCT<br>CAGTGATCACTTGACAGTTTTTTTTTTTTAAATATTACCCAAAATGCTCCCCAAATAAGAAATGCATCA<br>GCTCAGTCAGTGAATACAAAAAAGGAATTATTTTTCCCTTTGAGGGTCTTTTATACATCTCTCCTCCAAC<br>CCCACCCTCTATTCTGTTTCTTCCTCCTCACATGGGGGTACACATACACAGCTTCCTCTTTTGGTTCCA<br>TCCTTACCACCACACCACACGCACACTCCACATGCCCAGCAGAGTGGCACTTGGTGGCCAGAAAGTG<br>TGAGCCTCATGATCTGCTGTCTGTAGTTCTGTGAGCTCAGGTCCCTCAAAGGCCTCGGAGCACCCCCT<br>TCCTTGTGACTGAGCCAGGGCCTGCATTTTTGGTTTTCCCCACCCCACACATTCTCAACCATAGTCCTT<br>CTAACAATACCAATAGCTAGGACCCGGCTGCTGTGCACTGGGACTGGGGATTCCACATGTTTGCCTTG<br>GGAGTCTCAAGCTGGACTGCCA |
| 39 | opt_COX10-<br>ND1-3'UTR | ATGGCCGCCTCTCCACACACACTGAGTAGCAGACTGCTGACCGGCTGTGTTGGCGGCTCTGTGTGGT<br>ATCTGGAACGGCGGACAATGGCCAACCTCCTACTCCTCATTGTACCCATTCTAATCGCAATGGCATTC<br>CTAATGCTTACCGAACGAAAAATTCTAGGCTATATGCAACTACGCAAAGGCCCCAACGTTGTAGGCCC<br>CTACGGGCTACTACAACCCTTCGCTGACGCCATAAAACTCTTCACCAAAGAGCCCCTAAAACCCGCCA<br>CATCTACCATCACCCTCTACATCACCGCCCCGACCTTAGCTCTCACCATCGCTCTTCTACTATGGACCC<br>CCCTCCCCATGCCCAACCCCCTGGTCAACCTCAACCTAGGCCTCCTATTTATTCTAGCCACCTCTAGC<br>CTAGCCGTTTACTCAATCCTCTGGTCAGGGTGGGCATCAAACTCAAACTACGCCCTGATCGGCGCACT<br>GCGAGCAGTAGCCCAAACAATCTCATATGAAGTCACCCTAGCCATCATTCTACTATCAAATTACTAAT<br>GAGTGGCTCCTTTAACCTCTCCACCCTTATCACAACACAAGAACACCTCTGGTTACTCCTGCCATCATG<br>GCCCTTGGCCATGATGTGGTTTATCTCCACACTAGCAGAGACCAACCGAACCCCCTTCGACCTTGCCG<br>AAGGGGAGTCCGAACTAGTCTCAGGCTTCAACATCGAATACGCAGGCCCTTCGCCAGGCCCCTATTCTTC<br>ATGGCCAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCCCTGTTC<br>TTATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA |

TABLE 1-continued nucleic acid and polypeptide sequences and SEQ ID NOs

| SEQ | description | sequence |
|---|---|---|
| | | ATTCTGGAACACAAGAAGAGAAATTGCTGGGTTTAGAACAAGATTATAAACGAATTCGGTGCTCAGTGA<br>TCACTTGACAGTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCAGCCCCTGTCCTCCCTTCACCCCCATTGCGTATGAGCATTTCAGAACTCCAAG<br>GAGTCACAGGCATCTTTATAGTTCACGTTAACATATAGACACTGTTGGAAGCAGTTCCTTCTAAAAGGG<br>TAGCCCTGGACTTAATACCAGCCGGATACCTCTGGCCCCCACCCCATTACTGTACCTCTGGAGTCACT<br>ACTGTGGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAATACAT<br>GTCCATCCTGATATCTCCTGAATTCAGAAATTAGCCTCCACATGTGCAATGGCTTTAAGAGCCAGAAGC<br>AGGGTTCTGGGAATTTTGCAAGTTACCTGTGGCCAGGTGTGGTCTCGGTTACCAAATACGGTTACCTG<br>CAGCTTTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCGGGGTA<br>GGGAGAGTTAAACAACATTTAAACAGAGTTCTCTCAAAAATGTCTAAAGGGATTGTAGGTAGATAACATC<br>CAATCACTGTTTGCACTTATCTGAAATCTTCCCTCTTGGCTGCCCCCAGGTATTTACTGTGGAGAACAT<br>TGCATAGGAATGTCTGGAAAAAGCTTCTACAACTTGTTACAGCCTTCACATTTGTAGAAGCTTT |
| 40 | Opt_COX10-<br>ND1-3'UTR* | ATGGCCGCCTCTCCACACACACTGAGTAGCAGACTGCTGACCGGCTGTGTTGGCGGCTCTGTGTGCT<br>ATCTGGAACGGCGGACAATGGCCAACCTCCTACTCCTCATTGTACCCATTCTAATCGCAATGGCATTC<br>CTAATGCTTACCGAACGAAAAATTCTAGGCTATATGCAACTACGCAAAGGCCCCAACGTTGTAGGCCC<br>CTACGGGCTACTACAACCCTTCGCTGACGCCATAAAACTCTTCACCAAAGAGCCCCTAAAACCCGCCA<br>CATCTACCATCACCCTCTACATCACCGCCCCGACCTTAGCTCTCACCATCGCTCTTCTACTATGGACCC<br>CCCTCCCCATGCCCAACCCCCTGGTCAACCTCAACCTAGGCCTCCTATTTATTCTAGCCACCTCTAGC<br>CTAGCCGTTTACTCAATCCTCTGGTCAGGGTGGGCATCAAACTCAAACTACGCCCTGATCGGCGCACT<br>GCGAGCAGTAGCCCAAACAATCTCATATGAAGTCACCCTAGCCATCATTCTACTATCAACATTACTAAT<br>GAGTGGCTCCTTTAACCTCTCCACCCTTATCACAACACAAGAACACCTCTGGTTACTCCTGCCATCATG<br>GCCCTTGGCCATGATGTGGTTTATCTCCACACTAGCAGAGACCAACCGAACCCCCTTCGACCTTGCCG<br>AAGGGGAGTCCGAACTAGTCTCAGGCTTCAACATCGAATACGCCGCAGGCCCCTTCGCCCTATTCTTC<br>ATGGCCGAATACACAAACATTATTATGATGAACACCCTCACCACTACAATCTTCCTAGGAACAACATAT<br>GACGCACTCTCCCCTGAACTCTACACAACATATTTTGTCACCAAGACCCTACTTCTAACCTCCCTGTTC<br>TTATGGATTCGAACAGCATACCCCCGATTCCGCTACGACCAACTCATGCACCTCCTATGGAAAAACTTC<br>CTACCACTCACCCTAGCATTACTTATGTGGTATGTCTCCATGCCCATTACAATCTCCAGCATTCCCCCT<br>CAAACCTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCA |
| 41 | opt_COX10-<br>opt_ND1-<br>3'UTR | ATGGCCGCCTCTCCACACACACTGAGTAGCAGACTGCTGACCGGCTGTGTTGGCGGCTCTGTGTGGT<br>ATCTGGAACGGCGGACAATGGCCAACCTGCTGCTGCTGATCGTGCCCATCCTGATCGCCATGGCCTT<br>CCTGATGCTGACCGAGCGCAAGATCCTGGGCTACATGCAGCTGCGCAAGGGCCCCAACGTGGTGGG<br>CCCCTACGGCCTGCTGCAGCCCTTCGCCGACGCCATCAAGCTGTTCACCAAGGAGCCCCTGAAGCCC<br>GCCACCAGCACCATCACCCTGTACATCACCGCCCCCACCCTGGCCCTGACCATCGCCCTGCTGCTGT<br>GGACCCCCCTGCCCATGCCCAACCCCCTGGTGAACCTGAACCTGGGCCTGCTGTTCATCCTGGCCAC<br>CAGCAGCCTGGCCGTGTACAGCATCCTGTGGAGCGGCTGGGCCAGCAACAGCAACTACGCCCTGAT<br>CGGCGCCCTGCGCGCCGTGGCCCAGACCATCAGCTACGAGGTGACCCTGGCCATCATCCTGCTGAG<br>CACCCTGCTGATGAGCGGCAGCTTCAACCTGAGCACCCTGATCACCACCCAGGAGCACCTGTGGCTG<br>CTGCTGCCCAGCTGGCCCCTGGCCATGATGTGGTTCATCAGCACCCTGGCCGAGACCAACCGCACCC<br>CCTTCGACCTGGCCGAGGGCGAGAGCGAGCTGGTGAGCGGCTTCAACATCGAGTACGCCGCGGCC<br>CCTTCGCCCTGTTCTTCATGGCCGAGTACACCAACACCATCATGATGAACACCCTGACCACCACCATC<br>TTCCTGGGCACCACCTACGACGCCCTGAGCCCCGAGCTGTACACCACCTACTTCGTGACCAAGACCC<br>TGCTGCTGACCAGCCTGTTCCTGTGGATCCGCACCGCCTACCCCGCTTCCGCTACGACCAGCTGAT<br>GCACCTGCTGTGGAAGAAACTTCCTGCCCCTGACCCTGGCCCTGCTGATGTGGTACGTGAGCATGCCC<br>ATCACCATCAGCAGCATCCCCCCCAGACCTAAGAGCACTGGGCCCCACCGCCCCTTTCCCTCCG<br>CTGCCAGGCGAGCATGTTGTGGTAATTCTGGAACACAAGAAGAGAAATTGCTGGGTTTAGAACAAGAT<br>TATAAACGAATTCGGTGCTCAGTGATCACTTGACAGTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCTAACAATACCAATAGCTAGGACCCGGCTGCTGTGCACTGGGACTGGG<br>GATTCCACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATAGACACT<br>GTTGGAAGCAGTTCCTTCTAAAAGGGTAGCCCTGGACTTAATACCAGCCGGATACCTCTGGCCCCCAC<br>CCCATTACTGTACCTCTGGAGTCACTACTGTGGGTCGCCACTCCTCTGCTACACAGCACGGCTTTTTc<br>AAGGCTGTATTGAGAAGGGAAGTTAGGAAGAAGGGTGTGCTGGGCTAACCAGCCCACAGAGCTCACA |

TABLE 1-continued nucleic acid and polypeptide sequences and SEQ ID NOs

| SEQ | description | sequence |
|---|---|---|
| | | TTCCTGTCCCTTGGGTGAAAAATACATGTCCATCCTGATATCTCCTGAATTCAGAAATTAGCCTCCACA
TGTGCAATGGCTTTAAGAGCCAGAAGCAGGGTTCTGGGAATTTTGCAAGTTACCTGTGGCCAGGTGTG
GTCTCGGTTACCAAATACGGTTACCTGCAGCTTTTTAGTCCTTTGTGCTCCCACGGGTCTACAGAGTC
CCATCTGCCCAAAGGTCTTGAAGCTTGACAGGATGTTTTCGATTACTCAGTCTCCCAGGGCACTACTG
GTCCGTAGGATTCGATTGGTCGGGGTAGGAGAGTTAAACAACATTTAAACAGAGTTCTCTCAAAAATGT
CTAAAGGGATTGTAGGTAGATAACATCCAATCACTGTTTGCACTTATCTGAAATCTTCCCTCTTGGCTG
CCCCCAGGTATTTACTGTGGAGAACATTGCATAGGAATGTCTGGAAAAAGCTTCTACAACTTGTTACAG
CCTTCACATTTGTAGAAGCTTT |
| 42 | opt_COX10-
opt_ND1-
3'UTR* | ATGGCCGCCTCTCCACACACACTGAGTAGCAGACTGCTGACCGGCTGTGTTGGCGGCTCTGTGTGG
ATCTGGAACGGCGGACAATGGCCAACCTGCTGCTGCTGATCGTGCCCATCCTGATCGCCATGGCCTT
CCTGATGCTGACCGAGCGCAAGATCCTGGGCTACATGCAGCTGCGCAAGGGCCCCAACGTGGTGGG
CCCCTACGGCCTGCTGCAGCCCTTCGCCGACGCCATCAAGCTGTTCACCAAGGAGCCCCTGAAGCCC
GCCACCAGCACCATCACCCTGTACATCACCGCCCCCACCCTGGCCCTGACCATCGCCCTGCTGCTGT
GGACCCCCCTGCCCATGCCCAACCCCCTGGTGAACCTGAACCTGGGCCTGCTGTTCATCCTGGCCAC
CAGCAGCCTGGCCGTGTACAGCATCCTGTGGAGCGGCTGGGCCAGCAACAGCAACTACGCCCTGAT
CGGCGCCCTGCGCGCCGTGGCCCAGACCATCAGCTACGAGGTGACCCTGGCCATCATCCTGCTGAG
CACCCTGCTGATGAGCGGCAGCTTCAACCTGAGCACCCTGATCACCACCCAGGAGCACCTGTGGCTG
CTGCTGCCCAGCTGGCCCCTGGCCATGATGTGGTTCATCAGCACCCTGGCCGAGACCAACCGCACCC
CCTTCGACCTGGCCGAGGGCGAGAGCGAGCTGGTGAGCGGCTTCAACATCGAGTACGCCGCCGGCC
CCTTCGCCCCTGTTCTTCATGGCCGAGTACACCAACATCATCATGATGAACACCCTGACCACCACCATC
TTCCTGGGCACCACCTACGACGCCCTGAGCCCCCGAGCTGTACACCACCTACTTCGTGACCAAGACCC
TGCTGCTGACCAGCCTGTTCCTGTGGATCCGCACCGCCTACCCCCGCTTCCGCTACGACCAGCTGAT
GCACCTGCTGTGGAAGAACTTCCTGCCCCTGACCCTGGCCCTGCTGATGTGGTACGTGAGCATGCCC
ATCACCATCAGCAGCATCCCCCCCCAGACCTAAGAGCACTGGGACGCCCACCGCCCCTTTCCCTCCG
CTGCCAGGCGAGCATGTTGTGGTAATTCTGGAACACAAGAAGAGAAATTGCTGGGTTTAGAACAAGAT
TATAAACGAATTCGGTGCTCAGTGATCACTTGACAGTTTTTTTTTTTAAATATTACCCAAAATGCTCC
CCAAATAAGAAATGCATCAGCTCAGTCAGTGAATACAAAAAAGGAATTATTTTTCCCTTTGAGGGTCTTT
TATACATCTCTCCTCCAACCCCACCCTCTATTCTGTTTCTTCCTCCTCACATGGGGGTACACATACACA
GCTTCCTCTTTTGGTTCCATCCTTACCACCACACCACACGCACACTCCACATGCCCAGCAGAGTGGCA
CTTGGTGGCCAGAAAGTGTGAGCCTCATGATCTGCTGTCTGTAGTTCTGTGAGCTCAGGTCCCTCAAA
GGCCTCGGAGCACCCCCTTCCTTGTGACTGAGCCAGGGCCTGCATTTTTGGTTTTCCCACCCCACA
CATTCTCAACCATAGTCCTTCTAACAATACCAATAGCTAGGACCCGGCTGCTGTGCACTGGGACTGGG
GATTCCACATGTTTGCCTTGGGAGTCTCAAGCTGGACTGCCA |
| 43 | opt_COX10*-
ND4-3'UTR | ATGGCCGCCAGCCCCCACACCCTGAGCAGCCGCCTGCTGACCGGCTGCGTGGGCGGCAGCGTGTG
GTACCTGGAGCGCCGCACCATGCTAAAACTAATCGTCCCAACAATTATGTTACTACCACTGACATGGC
TTTCCAAAAAACACATGATTTGGATCAACAACAATCCACCCACAGCCTAATTATTAGCATCATCCCTCTACT
ATTTTTTAACCAAATCAACAACAACCTATTTAGCTGTTCCCAACCTTTTCCTCCGACCCCCTAACAACC
CCCCTCCTAATGCTAACTACCTGGCTCCTACCCCTCACAATCATGGCAAGCCAACGCCACTTATCCAG
TGAACCACTATCACGAAAAAAACTCTACCTCTCTATGCTAATCTCCCTACAAATCTCCTTAATTATGACA
TTCACAGCCACAGAACTAATCATGTTTTTATATCTTCTTCGAAACCACACTTATCCCCACCCTTGGCTATCA
TCACCCGATGGGGCAACCAGCCAGAACGCCTGAACGCAGGCACATACTTCCTATTCTACACCCTAGTA
GGCTCCCTTCCCCTACTCATCGCACTAATTTACACTCACAACACCCTAGGCTCACTAAACATTCTACTA
CTCACTCTCACTGCCCAAGAACTATCAAACTCCTGGGCCAACAACTTAATGTGGCTAGCTTACACAATG
GCTTTTATGGTAAAGATGCCTCTTTACGGACTCCACTTATGGCTCCCTAAAGCCCATGTCGAAGCCCC
CATCGCTGGGTCAATGGTACTTGCCGCAGTACTCTTAAAACTAGGCGGCTATGGTATGATGCGCCTCA
CACTCATTCTCAACCCCCTGACAAAACACATGGCCTACCCCTTCCTTGTACTATCCCTATGGGGCATGA
TTATGACAAGCTCCATCTGCCTACGACAAACAGACCTAAAATCGCTCATTGCATACTCTTCAATCAGCC
ACATGGCCCTCGTAGTAACAGCCATTCTCATCCAAACCCCCTGGAGCTTCACCGGCGCAGTCATTCTC
ATGATCGCCCACGGGCTTACATCCTCATTACTATTCTGCCTAGCAAACTCAAACTACGAACGCACTCAC
AGTCGCATCATGATCCTCTCTCAAGGACTTCAAACTCTACTCCCACTAATGGCTTTTTGGTGGCTTCTA
GCAAGCTCGCTAACCTCGCCTTACCCCCACTATTAACCTACTGGGAGAACTCTCTGTGCTAGTAAC
CACGTTCTCCTGGTCAAATATCACTCTCCTACTTACAGGACTCAACATGCTAGTCACAGCCCTATACTC
CCTCTACATGTTTACCACAACACAATGGGGCTCACTCACCCACCACATTAACAACATGAAACCCTCATT
CACACGAGAAAACACCCTCATGTTCATGCACCTATCCCCCATTCTCCTCCTATCCCTCAACCCCGACAT
CATTACCGGGTTTTCCTCTTAAGAGCACTGGGACGCCCACCGCCCCTTTCCCTCCGCTGCCAGGCGA
GCATGTTGTGGTAATTCTGGAACACAAGAAGAGAAATTGCTGGGTTTAGAACAAGATTATAAACGAATT
CGGTGCTCAGTGATCACTTGACAGTTTTTTTTTTTTAAATATTACCCAAAATGCTCCCCAAATAAGAA
ATGCATCAGCTCAGTCAGTGAATACAAAAAAGGAATTATTTTTCCCTTTGAGGGTCTTTTATACATCTCT
CCTCCAACCCCACCCTCTATTCTGTTTCTTCCTCCTCACATGGGGGTACACATACACAGCTTCCTCTTT
TGGTTCCATCCTTACCACCACACCACACGCACACTCCACATGCCCAGCAGAGTGGCACTTGGTGGCC
AGAAAGTGTGAGCCTCATGATCTGCTGTCTGTAGTTCTGTGAGCTCAGGTCCCTCAAAGGCCTCGGAG
CACCCCCTTCCTTGTGACTGAGCCAGGGCCTGCATTTTTGGTTTTCCCACCCCACACATTCTCAACC
ATAGTCCTTCTAACAATACCAATAGCTAGGACCCGGCTGCTGTGCACTGGGACTGGGGATTCCACATG
TTTGCCTTGGGAGTCTCAAGCTGGACTGCCAGCCCCTGTCCTCCCTTCACCCCCATTGCGTATGAGCA
TTTCAGAACTCCAAGGAGTCACAGGCATCTTTATAGTTCACGTTAACATATAGACACTGTTGGAAGCAG
TTCCTTCTAAAAGGGTAGCCCTGGACTTAATACCAGCCGGATACCTCTGGCCCCACCCCATTACTGT
ACCTCTGGAGTCACTACTGTGGGTCGCCACTCCTCTGCTACACAGCACGGCTTTTTCAAGGCTGTATT
GAGAAGGGAAGTTAGGAAGAAGGGTGTGCTGGGCTAACCAGCCCACAGAGCTCACATTCCTGTCCCT
TGGGTGAAAAATACATGTCCATCCTGATATCTCCTGAATTCAGAAATTAGCCTCCACATGTGCAATGGC
TTTAAGAGCCAGAAGCAGGGTTCTGGGAATTTTGCAAGTTACCTGTGGCCAGGTGTGGTCTCGGTTAC
CAAATACGGTTACCTGCAGCTTTTTAGTCCTTTGTGCTCCCACGGGTCTACAGAGTCCCATCTGCCCA
AAGGTCTTGAAGCTTGACAGGATGTTTTCGATTACTCAGTCTCCCAGGGCACTACTGGTCCGTAGGAT
TCGATTGGTCGGGGTAGGAGAGTTAAACAACATTTAAACAGAGTTCTCTCAAWATGTCTAAAGGGATT
GTAGGTAGATAACATCCAATCACTGTTTGCACTTATCTGAAATCTTCCCTCTTGGCTGCCCCCAGGTAT |

TABLE 1-continued nucleic acid and polypeptide sequences and SEQ ID NOs

| SEQ | description | sequence |
|---|---|---|
| | | TTACTGTGGAGAACATTGCATAGGAATGTCTGGAAAAAGCTTCTACAACTTGTTACAGCCTTCACATTT<br>GTAGAAGCTTT |
| 44 | opt_COX10*-<br>ND4-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGCTAAAACTAATCGTCCCAACAATTATGTTACTACCACTGACATGGC<br>TTTCCAAAAAACACATGATTTGGATCAACACAACCACCCACAGCCTAATTATTAGCATCATCCCTCTACT<br>ATTTTTTAACCAAATCAACAACAACCTATTTAGCTGTTCCCCAACCTTTTCCTCCGACCCCCTAACAACC<br>CCCCTCCTAATGCTAACTACCTGGCTCCTACCCCTCACAATCATGGCAAGCCAACGCCACTTATCCAG<br>TGAACCACTACTACGAAAAAAACTCTACCTCTCTATGCTAATCTCCCTACAAATCTCCTTAATTATGACA<br>TTCACAGCCACAGAACTAATCATGTTTTATATCTTCTTGAAACCACACTTATCCCCACCTTGGCTATCA<br>TCACCCGATGGGGCAACCAGCCAGAACGCCTGAACGCAGGCACATACTTCCTATTCTACACCCTAGTA<br>GGCTCCCTTCCCCTACTCATCGCACTAATTTACACTCACAACACCCTAGGCTCACTAAACATTCTACTA<br>CTCACTCTCACTGCCCAAGAACTATCAAACTCCTGGGCCAACTTAATGTGGCTAGCTTACACAATG<br>GCTTTTATGGTAAAGATGCCTCTTTACGGACTCCACTTATGGCTCCCTAAAGCCCATGTCGAAGCCCC<br>CATCGCTGGGTCAATGGTACTTGCCGCAGTACTCTTAAAACTAGGCGGCTATGGTATGATGCGCCTCA<br>CACTCATTCTCAACCCCCTGACAAAACACATGGCCTACCCCTTCCTTGTACTATCCCTATGGGGCATGA<br>TTATGACAAGCTCCATCTGCCTACGACAAACAGACCTAAAATCGCTCATTGCATACTCTTCAATCAGCC<br>ACATGGCCCTCGTAGTAACAGCCATTCTCATCCAAACCCCCTGGAGCTTCACCGGCGCAGTCATTCTC<br>ATGATCGCCCACGGGCTTACATCCTCATTACTATTCTGCCTAGCAAACTCAAACTACGAACGCACTCAC<br>AGTCGCATCATGATCCTCTCTCAAGGACTTCAAACTCTACTCCCACTAATGGCTTTTGGTGGCTTCTA<br>GCAAGCCTCGCTAACCTCGCCTTACCCCCCACTATTAACCTACTGGGAGAACTCTCTGTGCTAGTAAC<br>CACGTTCTCCTGGTCAAATATCACTCTCCTACTTACAGGACTCAACATGCTAGTCACAGCCCTATACTC<br>CCTCTACATGTTTACCACAACACAATGGGGCTCACTCACCCACCACATTAACAACATGAAACCCTCATT<br>CACACGAGAAAACACCCTCATGTTCATGCACCTATCCCCCATTCTCCTCCTATCCCTCAACCCCGACAT<br>CATTACCGGGTTTTCCTCTTAAGAGCACTGGGACGCCCACCGCCCCTTTCCCTCCGCTGCCAGGCGA<br>GCATGTTGTGGTAATTCTGGAACACAAGAAGAGAAATTGCTGGGTTTAGAACAAGATTATAAACGAATT<br>CGGTGCTCAGTGATCACTTGACAGTTTTTTTTTTTTTAAATATTACCCAAAATGCTCCCCAAATAAGAA<br>ATGCATCAGCTCAGTCAGTGAATACAAAAAAGGAATTATTTTTCCCTTTGAGGGTCTTTTATACATCTCT<br>CCTCCAACCCCACCCTCTATTCTGTTTCTTCCTCCTCACATGGGGGTACACATACACAGCTTCCTCTTT<br>TGGTTCCATCCTTACCACCACACCACACGCACACTCCACATGCCCAGCAGAGTGGCACTTGGTGGCC<br>AGAAAGTGTGAGCCTCATGATCTGCTGTCTGTAGTTCTGTGAGCTCAGGTCCCTCAAAGGCCTCGGAG<br>CACCCCCTTCCTTGTGACTGAGCCAGGGCCTGCATTTTTGGTTTTCCCCACCCCACACATTCTCAACC<br>ATAGTCCTTCTAACAATACCAATAGCTAGGACCCGGCTGCTGTGCACTGGGACTGGGGATTCCACATG<br>TTTGCCTTGGGAGTCTCAAGCTGGACTGCCA |
| 45 | opt_COX10*-<br>opt_ND4-<br>3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCTCTGACCTGG<br>CTGAGCAAGAAACACATGATCTGGATCAACACCACCACGCACAGCCTGATCATCAGCATCATCCCTCT<br>GCTGTTCTTCAACCAGATCAACAACAACCTGTTCAGCTGCAGCCCCACCTTCAGCAGCGACCCTCTGA<br>CAACACCTCTGCTGATGCTGACCACCTGGCTGCTGCCCCTCACAATCATGGCCTCTCAGAGACACCTG<br>AGCAGCGAGCCCCTGAGCCGGAAGAAACTGTACCTGAGCATGCTGATCTCCCTGCAGATCTCTCTGA<br>TCATGACCTTCACCGCCACCGAGCTGATCATGTTCTACATCTTTTTCGAGACAACGCTGATCCCCACAC<br>TGGCCATCATCACCAGATGGGGCAACCAGCCTGAGAGACTGAACGCCGGCACCTACTTTCTGTTCTA<br>CACCCTCGTGGGCAGCCTGCCACTGCTGATTGCCCTGATCTACACCCACAACACCCTGGGCTCCCTG<br>AACATCCTGCTGCTGACACTGACAGCCCAAGAGCTGAGCAACAGCTGGGCCAACAATCTGATGTGGC<br>TGGCCTACACAATGGCCTTCATGGTCAAGATGCCCCTGTACGGCCTGCACCTGTGGCTGCCTAAAGC<br>TCATGTGGAAGCCCCTATCGCCGGCTCTATGGTGCTGGCTGCAGTGCTGCTGAAACTCGGCGGCTAC<br>GGCATGATGCGGCTGACCCTGATTCTGAATCCCCTGACCAAGCACATGGCCTATCCATTTCTGGTGCT<br>GAGCCTGTGGGGCATGATTATGACCAGCAGCATCTGCCTGCGGCAGACCGATCTGAAGTCCCTGATC<br>GCCTACAGCTCCATCAGCCACATGGCCCTGGTGGTCAACGCCATCCTGATTCAGACCCCTTGGAGCT<br>TTACAGGCGCCGTGATCCTGATGATTGCCCACGGCCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAATCACATGTCCATCCTGATATCTCTGAATTC<br>AGAAATTAGCCTCCACATGTGCAATGGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC<br>CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA |

TABLE 1-continued nucleic acid and polypeptide sequences and SEQ ID NOs

| SEQ | description | sequence |
|---|---|---|
| | | AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 46 | opt_COX10*-<br>opt_ND4-<br>3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCTCTGACCTGG<br>CTGAGCAAGAAACACATGATCTGGATCAACACCACCACGCACAGCCTGATCATCAGCATCATCCCTCT<br>GCTGTTCTTCAACCAGATCAACAACAACCTGTTCAGCTGCAGCCCCACCTTCAGCAGCGACCCTCTGA<br>CAACACCTCTGCTGATGCTGACCACCTGGCTGCTGCCCCTCACAATCATGGCCTCTCAGAGACACCTG<br>AGCAGCGAGCCCCTGAGCCGGAAGAAACTGTACCTGAGCATGCTGATCTCCCTGCAGATCTCTCTGA<br>TCATGACCTTCACCGCCACCGAGCTGATCATGTTCTACATCTTTTTCGAGACAACGCTGATCCCCACAC<br>TGGCCATCATCACCAGATGGGCAACCAGCCTGAGAGACTGAACGCCGGCACCTACTTTCTGTTCTA<br>CACCCTCGTGGGCAGCCTGCCACTGCTGATTGCCCTGATCTACACCCACAACACCCTGGGCTCCCTG<br>AACATCCTGCTGCTGACACTGACAGCCCAAGAGCTGAGCAACAGCTGGGCCAACAATCTGATGTGGC<br>TGGCCTACACAATGGCCTTCATGGTCAAGATGCCCCTGTACGGCCTGCACCTGTGGCTGCCTAAAGC<br>TCATGTGGAAGCCCCTATCGCCGGCTCTATGGTGCTGGCTGCAGTGCTGCTGAAACTCGGCGGCTAC<br>GGCATGATGCGGCTGACCCTGATTCTGAATCCCCTGACCAAGCACATGGCCTATCCATTTCTGGTGCT<br>GAGCCTGTGGGGCATGATTATGACCAGCAGCATCTGCCTGCGGCAGACCGATCTGAAGTCCCTGATC<br>GCCTACAGCTCCATCAGCCACATGGCCCTGGTGGTCACCGCCATCCTGATTCAGACCCCTTGGAGCT<br>TTACAGGCGCCGTGATCCTGATGATTGCCCACGGCCTGACAAGCAGCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 47 | opt_COX10*-<br>opt_ND4*-<br>3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCCCTGACCTGG<br>CTGAGCAAGAAGCACATGATCTGGATCAACACCACCACCCACAGCCTGATCATCAGCATCATCCCCCT<br>GCTGTTCTTCAACCAGATCAACAACAACCTGTTCAGCTGCAGCCCCACCTTCAGCAGCGACCCCCTGA<br>CCACCCCCCTGCTGATGCTGACCACCTGGCTGCTGCCCCTGACCATCATGGCCAGCAGCGCCACCT<br>GAGCAGCGAGCCCCTGAGCCGCAAGAAGCTGTACCTGAGCATGCTGATCAGCCTGCAGATCAGCCTG<br>ATCATGACCTTCACCGCCACCGAGCTGATCATGTTCTACATCTTCTTCGAGACCACCCTGATCCCCAC<br>CCTGGCCATCATCACCCGCTGGGGCAACCAGCCCGAGCGCCTGAACGCCGGCACCTACTTCCTGTTC<br>TACACCCTGGTGGGCAGCCTGCCCCTGCTGATCGCCCTGATCTACACCCACAACACCCTGGGCAGCC<br>TGAACATCCTGCTGCTGACCCTGACCGCCCAGGAGCTGAGCAACAGCTGGGCCAACAACCTGATGTG<br>GCTGGCCTACACCATGGCCTTCATGGTGAAGATGCCCCTGTACGGCCTGCACCTGTGGCTGCCCAAG<br>GCCCACGTGGAGGCCCCCATCGCCGGCAGCATGGTGCTGGCCGCCGTGCTGCTGAAGCTGGGCGG<br>CTACGGCATGATGCGCCTGACCCTGATCCTGAACCCCCTGACCAAGCACATGGCCTACCCCTTCCTG<br>GTGCTGAGCCTGTGGGGCATGATCATGACCAGCAGCATCTGCCTGCGCCAGACCGACCTGAAGAGC<br>CTGATCGCCTACAGCAGCATCAGCCACATGGCCCTGGTGGTGACCGCCATCCTGATCCAGACCCCCT<br>GGAGCTTCACCGGCGCCGTGATCCTGATGATCGCCCACGGCCTGACCAGCAGCTGCTGTTCTGCCT<br>GGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACTGGCCCTGCCCCCCACCAT<br>CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCCAGTGGGGCA<br>GCCTGACCCACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTAAATATTACCCAAAATGCTCCCCAAATAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCAGCCCCTGTCCTCCCTTCACCCCATTGCGTATGAGCATTTCAGAACTCCAAGGAGTCACAGGCAT<br>CTTTATAGTTCACGTTAACATATAGACACTGTTGGAAGCAGTTCCTTCTAAAAGGGTAGCCCTGGACTT<br>AATACCAGCCGGATACCTCTGGCCCCACCCCATTACTGTACCTCTGGAGTCACTACTGTGGGTCGCC<br>ACTCCTCTGCTACACAGCACGGCTTTTTCAAGGCTGTATTGAGAAGGGAAGTTAGGAAGAAGGGTGTG<br>CTGGGCTAACCAGCCCACAGAGCTCACATTCCTGTCCCTTGGGTGAAAAATCACATGTCCATGCTGATA<br>TCTCCTGAATTCAGAAATTAGCCTCCACATGTGCAATGGCTTTAAGAGCCAGAAGCAGGGTTCTGGGA<br>ATTTTGCAAGTTACCTGTGGCCAGGTGTGGTCTCGGTTACCAAATACGGTTACCTGCAGCTTTTTAGTC<br>CTTTGTGCTCCCACGGGTCTACAGAGTCCCATCTGCCCAAAGGTCTTGAAGCTTGACAGGATGTTTTC<br>GATTACTCAGTCTCCCAGGGCACTACTGGTCCGTAGGATTCGATTGGTCGGGTAGGAGAGTTAAACA<br>ACATTTAAACAGAGTTCTCTCAAAAATGTCTAAAGGGATTGTAGGTAGATAACATCCAATCACTGTTTGC |

TABLE 1-continued nucleic acid and polypeptide sequences and SEQ ID NOs

| SEQ | description | sequence |
|---|---|---|
| | | ACTTATCTGAAATCTTCCCTCTTGGCTGCCCCCAGGTATTTACTGTGGAGAACATTGCATAGGAATGTC<br>TGGAAAAAGCTTCTACAACTTGTTACAGCCTTCACATTTGTAGAAGCTTT |
| 48 | opt_COX10*-<br>opt_ND4*-<br>3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGCTGAAGCTGATCGTGCCCACCATCATGCTGCTGCCCCTGACCTGG<br>CTGAGCAAGAAGCACATGATCTGGATCAACACCACCACCCACAGCCTGATCATCAGCATCATCCCCCT<br>GCTGTTCTTCAACCAGATCAACAACAACCTGTTCAGCTGCAGCCCCACCTTCAGCAGCGACCCCCTGA<br>CCACCCCCTGCTGATGCTGACCACCTGGCTGCTGCCCCTGACCATCATGGCCAGCCAGCGCCACCT<br>GAGCAGCGAGCCCCTGAGCCGCAAGAAGCTGTACCTGAGCATGCTGATCAGCCTGCAGATCAGCCTG<br>ATCATGACCTTCACCGCCACCGAGCTGATCATGTTCTACATCTTCTTCGAGACCACCCTGATCCCCAC<br>CCTGGCCATCATCACCCGCTGGGGCAACCAGCCCGAGCGCCTGAACGCCGGCACCTACTTCCTGTTC<br>TACACCCTGGTGGGCAGCCTGCCCCTGCTGATCGCCCTGATCTACACCCACAACACCCTGGGCAGCC<br>TGAACATCCTGCTGCTGACCCTGACCGCCCAGGAGCTGAGCAACAGCTGGGCCAACAACCTGATGTG<br>GCTGGCCTACACCATGGCCTTCATGGTGAAGATGCCCCTGTACGGCCTGCACCTGTGGCTGCCCAAG<br>GCCCACGTGGAGGCCCCCATCGCCGGCAGCATGGTGCTGGCCGCCGTGCTGCTGAAGCTGGGCGG<br>CTACGGCATGATGCGCCTGACCCTGATCCTGAACCCCCTGACCAAGCACATGGCCTACCCCTTCCTG<br>GTGCTGAGCCTGTGGGGCATGATCATGACCAGCAGCATCTGCCTGCGCCAGACCGACCTGAAGAGC<br>CTGATCGCCTACAGCAGCATCAGCCACATGGCCCTGGTGGTGACCGCCATCCTGATCCAGACCCCCT<br>GGAGCTTCACCGGCGCCGTGATCCTGATGATCGCCCACGGCCTGACCAGCAGCCTGCTGTTCTGCCT<br>GGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACCTGGCCCTGCCCCCCACCAT<br>CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCAGTGGGGCA<br>GCCTGACCCACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTAAATATTACCCAAATGCTCCCCAAATAAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCA |
| 49 | opt_COX10*-<br>ND6-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGATGTATGCTTTGTTTCTGTTGAGTGTGGGTTTAGTAATGGGGTTTG<br>TGGGGTTTTCTTCTAAGCCTTCTCCTATTTATGGGGGTTTAGTATTGATTGTTAGCGGTGTGGTCGGGT<br>GTGTTATTATTCTGAATTTTGGGGGAGGTTATATGGGTTTAATGGTTTTTTTAATTTATTTAGGGGGAAT<br>GATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACTTTAATAGTGTAGGAAGCTGGATGATTTATGAAGGAGAG<br>GGGTCAGGGTTGATTCGGAGGATCCTATTGGTGCGGGGCTTTGTATGATTATGGGCGTTGGTTAG<br>TAGTAGTTACTGGTTGGACATTGTTTGTTGGTGTATATATTGTAATTGAGATTGCTCGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTAAATATTACCCAAATGCTCCCCAAATAAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCAGCCCCTGTCCTCCCTTCACCCCCATTGCGTATGAGCATTTCAGAACTCCAAGGAGTCACAG<br>GCATCTTTATAGTTCACGTTAACATATAGACACTGTTGGAAGCAGTTCCTTCTAAAAGGGTAGCCCTGG<br>ACTTAATACCAGCCGGATACCTCTGGCCCCCACCCCATTACTGTACCTCTGGAGTCACTACTGTGGGT<br>CGCCACTCCTCTGCTACACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGTGGGAAAAATACATGTCCATCC<br>TGATATCTCCTGAATTCAGAAAATTAGCCTCCACATGTGCAATGGCTTTAAGAGCCAGAAGCAGGGTTCT<br>GGGAATTTTGCAAGTTACCTGTGGCCAGGTGTGGTCTCGGTTACCAAATACGGTTACCTGCAGCTTTT<br>TAGTCCTTTGTGCTCCCACGGGTCTACAGAGTCCCATCTGCCCAAAGGTCTTGAAGCTTGACAGGATG<br>TTTTCGATTACTCAGTCTCCCAGGGCACTACTGGTCCGTAGGATTCGATTGGTCGGGGTAGGAGAGTT<br>AAACAACATTTAAACAGAGTTCTCTCAAAAATGTCTAAAGGGATTGTAGGTAGATAACATCCAATCACT<br>GTTTGCACTTATCTGAAATCTTCCCTCTTGGCTGCCCCCAGGTATTTACTGTGGAGAACATTGCATAGG<br>AATGTCTGGAAAAGCTTCTACAACTTGTTACAGCCTTCACATTTGTAGAAGCTTT |
| 50 | opt_COX10*-<br>ND6-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGATGTATGCTTTGTTTCTGTTGAGTGTGGGTTTAGTAATGGGGTTTG<br>TGGGGTTTTCTTCTAAGCCTTCTCCTATTTATGGGGGTTTAGTATTGATTGTTAGCGGTGTGGTCGGGT<br>GTGTTATTATTCTGAATTTTGGGGGAGGTTATATGGGTTTAATGGTTTTTTTAATTTATTTAGGGGGAAT<br>GATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACTTTAATAGTGTAGGAAGCTGGATGATTTATGAAGGAGAG<br>GGGTCAGGGTTGATTCGGAGGATCCTATTGGTGCGGGGCTTTGTATGATTATGGGCGTTGGTTAG<br>TAGTAGTTACTGGTTGGACATTGTTTGTTGGTGTATATATTGTAATTGAGATTGCTCGGGGAATTAGG |

TABLE 1-continued nucleic acid and polypeptide sequences and SEQ ID NOs

| SEQ | description | sequence |
|---|---|---|
| | | AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCA |
| 51 | opt_COX10*-<br>opt_ND6-<br>3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGATGTACGCCCTGTTCCTGCTGAGCGTGGGCCTGGTGATGGGCTTC<br>GTGGGCTTCAGCAGCAAGCCCAGCCCCATCTACGGCGGCCTGGTGCTGATCGTGAGCGGCGTGGTG<br>GGCTGCGTGATCATCCTGAACTTCGGCGGCGGCTACATGGGCCTGATGGTGTTCCTGATCTACCTGG<br>GCGGCATGATGGTGGTGTTCGGCTACACCACCGCCATGGCCATCGAGGAGTACCCCGAGGCCTGGG<br>GCAGCGGCGTGGAGGTGCTGGTGAGCGTGCTGGTGGGCCTGGCCATGGAGGTGGGCCTGGTGCTG<br>TGGGTGAAGGAGTACGACGGCGTGGTGGTGGTGGTGAACTTCAACAGCGTGGGCAGCTGGATGATC<br>TACGAGGGCGAGGGCAGCGGCCTGATCCGCGAGGACCCCATCGGCGCCGGCGCCCTGTACGACTA<br>CGGCCGCTGGCTGGTGGTGGTGACCGGCTGGACCCTGTTCGTGGGCGTGTACATCGTGATCGAGAT<br>CGCCCGCGGCAACTAAGAGCACTGGGACGCCCACCGCCCCTTTCCCTCCGCTGCCAGGCGAGCATG<br>TTGTGGTAATTCTGGAACACAAGAAGAGAAATTGCTGGGTTTAGAACAAGATTATAAACGAATTCGGTG<br>CTCAGTGATCACTTGACAGTTTTTTTTTTTTTAAATATTACCCAAAATGCTCCCCAAAAAAGAAATGCAT<br>CAGCTCAGTCAGTGAATACAAAAAAGGAATTATTTTTCCCTTTGAGGGTCTTTTATACATCTCTCCTCCA<br>ACCCCACCCTCTATTCTGTTTCTTCCTCCTCACATGGGGGTACACATACACAGCTTCCTCTTTTGGTTC<br>CATCCTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGCACCCC<br>CTTCCTTGTGACTGAGCCAGGGCCTGCATTTTTGGTTTTCCCCACCCCACACATTCTCAACCATAGTCC<br>TTCTAACAATACCAATAGCTAGGACCCGGCTGCTGTGCACTGGGACTGGGGATTCCACATGTTTGCCT<br>TGGGAGTCTCAAGCTGGACTGCCAGCCCCTGTCCTCCCTTCACCCCATTGCGTATGAGCATTTCAGA<br>ACTCCAAGGAGTCACAGGCATCTTTATAGTTCACGTTAACATATAGACACTGTTGGAAGCAGTTCCTTC<br>TAAAAGGGTAGCCCTGGACTTAATACCAGCCGGATACCTCTGGCCCCACCCCATTACTGTACCTCTG<br>GAGTCACTACTGTGGGTCGCCACTCCTCTGCTACACAGCACGGCTTTTTCAAGGCTGTATTGAGAAGG<br>GAAGTTAGGAAGAAGGGTGTGCTGGGCTAACCAGCCCACAGAGCTCACATTCTGTCCCTTGGGTGA<br>AAAATACATGTCCATCCTGATATCTCCTGAATTCAGAAATTAGCCTCCACATGTGCAATGGCTTTAAGA<br>GCCAGAAGCAGGGTTCTGGGAATTTTGCAAGTTACCTGTGGCCAGGTGTGGTCTCGGTTACCAAATAC<br>GGTTACCTGCAGCTTTTTAGTCCTTTGTGCTCCCACGGGTCTACAGAGTCCCATCTGCCCAAAGGTCT<br>TGAAGCTTGACAGGATGTTTTCGATTACTCAGTCTCCCAGGGCACTACTGGTCCGTAGGATTCGATTG<br>GTCGGGGTAGGAGAGTTAAAACAACATTTAAACAGAGTTCTCTCAAAAATGTCTAAAGGGATTGTAGGTA<br>GATAACATCCAATCACTGTTTGCACTTATCTGAAATCTTCCCTCTTGGCTGCCCCCAGGTATTTACTGT<br>GGAGAACATTGCATAGGAATGTCTGGAAAAAGCTTCTACAACTTGTTACAGCCTTCACATTTGTAGAAG<br>CTTT |
| 52 | opt_COX10*-<br>opt_ND6-<br>3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGATGTACGCCCTGTTCCTGCTGAGCGTGGGCCTGGTGATGGGCTTC<br>GTGGGCTTCAGCAGCAAGCCCAGCCCCATCTACGGCGGCCTGGTGCTGATCGTGAGCGGCGTGGTG<br>GGCTGCGTGATCATCCTGAACTTCGGCGGCGGCTACATGGGCCTGATGGTGTTCCTGATCTACCTGG<br>GCGGCATGATGGTGGTGTTCGGCTACACCACCGCCATGGCCATCGAGGAGTACCCCGAGGCCTGGG<br>GCAGCGGCGTGGAGGTGCTGGTGAGCGTGCTGGTGGGCCTGGCCATGGAGGTGGGCCTGGTGCTG<br>TGGGTGAAGGAGTACGACGGCGTGGTGGTGGTGGTGAACTTCAACAGCGTGGGCAGCTGGATGATC<br>TACGAGGGCGAGGGCAGCGGCCTGATCCGCGAGGACCCCATCGGCGCCGGCGCCCTGTACGACTA<br>CGGCCGCTGGCTGGTGGTGGTGACCGGCTGGACCCTGTTCGTGGGCGTGTACATCGTGATCGAGAT<br>CGCCCGCGGCAACTAAGAGCACTGGGACGCCCACCGCCCCTTTCCCTCCGCTGCCAGGCGAGCATG<br>TTGTGGTAATTCTGGAACACAAGAAGAGAAATTGCTGGGTTTAGAACAAGATTATAAACGAATTCGGTG<br>CTCAGTGATCACTTGACAGTTTTTTTTTTTTTAAATATTACCCAAAATGCTCCCCAAATAAGAAATGCAT<br>CAGCTCAGTCAGTGAATACAAAAAATTATTTTTCCCTTTGAGGGTCTTTTATACATCTCTCCTCCA<br>ACCCCACCCTCTATTCTGTTTCTTCCTCCTCACATGGGGGTACACATACACAGCTTCCTCTTTTGGTTC<br>CATCCTTACCACCACACCACACGCACACTCCACATGCCCAGCAGAGTGGCACTTGGTGGCCAGAAAG<br>TGTGAGCCTCATGATCTGCTGTCTGTAGTTCTGTGAGCTCAGGTCCCTCAAAGGCCTCGGAGCACCCC<br>CTTCCTTGTGACTGAGCCAGGGCCTGCATTTTTGGTTTTCCCCACCCCACACATTCTCAACCATAGTCC<br>TTCTAACAATACCAATAGCTAGGACCCGGCTGCTGTGCACTGGGACTGGGGATTCCACATGTTTGCCT<br>TGGGAGTCTCAAGCTGGACTGCCA |
| 53 | opt_COX10*-<br>ND1-3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTGTAGGC<br>CCCTACGGGCTACTACAACCCTTCGCTGACGCCATAAAACTCTTCACCAAAGAGCCCCTAAAACCCGC<br>CACATCTACCATCACCCTCTACATCACCGCCCCGACCTTAGCTCTCACCATCGCTCTTCTACTATGGAC<br>CCCCCTCCCCATGCCCAACCCCGTGGTCAACCTCAACCTAGGCCTCCTATTTATTCTAGCCACCTCTA<br>GCCTAGCCGTTTACTCAATCCTCTGGTCAGGGTGGGCATCAAACTCAAACTACGCCCTGATCGGCGCA<br>CTGCGAGCAGTAGCCCAAACAATCTCATATGAAGTCACCCTAGCCATCATTCTACTATCAACATTACTA<br>ATGAGTGGCTCCTTTAACCTCTCCACCCTTATCACAACACAAGAACACCTCTGGTTACTCCTGCCATCA<br>TGGCCCTTGGCCATGATGTGGTTTATCTCCACACTAGCAGAGACCAACCGAACCCCCTTCGACCTTGC<br>CGAAGGGGAGTCCGAACTAGTCTCAGGCTTCAACATCGAATACGCCGCAGGCCCCTTCGCCCTATTC<br>TTCATGGCCGAATACACAAACATTATTATGATGAACACCCTCACCACTACAATCTTCCTAGGAACAACA<br>TATGACGCACTCTCCCCTGAACTCTACACAACATATTTTGTCACcAAGACCCTACTTCTAACCTCCCTG |

TABLE 1-continued nucleic acid and polypeptide sequences and SEQ ID NOs

| SEQ | description | sequence |
|---|---|---|
| | | TTCTTATGGATTCGAACAGCATACCCCCGATTCCGCTACGACCAACTCATGCACCTCCTATGGAAAAAC<br>TTCCTACCACTCACCCTAGCATTACTTATGTGGTATGTCTCCATGCCCATTACAATCTCCAGCATTCCC<br>CCTCAAACCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGTGCTCAG<br>TGATCACTTGACAGTTTTTTTTTTTTTAAATATTACCCAAAATGCTCCCCAAATAAGAAATGCATCAGCT<br>CAGTCAGTGAATACAAAAAGGAATTATTTTTCCCTTTGAGGGTCTTTTATACATCTCTCCTCCAACCCC<br>ACCCTCTATTCTGTTTCTTCCTCCTCACATGGGGGTACACATACACAGCTTCCTCTTTTGGTTCCATCC<br>TTACCACCACACCACACGCACACTCCACATGCCCAGCAGAGTGGCACTTGGTGGCCAGAAAGTGTGA<br>GCCTCATGATCTGCTGTCTGTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATTCTCAACCATAGTCCTTCTA<br>ACAATACCAATAGCTAGGACCCGGCTGCTGTGCACTGGGACTGGGGATTCCACATGTTTGCCTTGGG<br>AGTCTCAAGCTGGACTGCCAGCCCCTGTCCTCCCTTCACCCCCATTGCGTATGAGCATTTCAGAACTC<br>CAAGGAGTCACAGGCATCTTTATAGTTCACGTTAACATATAGACACTGTTGGAAGCAGTTCCTTCTAAA<br>AGGGTAGCCCTGGACTTAATACCAGCCGGATACCTCTGGCCCCCACCCCATTACTGTACCTCTGGAGT<br>CACTACTGTGGGTCGCCACTCCTCTGCTACACAGCACGGCTTTTTCAAGGCTGTATTGAGAAGGGAAG<br>TTAGGAAGAAGGGTGTGCTGGGCTAACCAGCCCACAGAGCTCACATTCCTGTCCCTTGGGTGAAAAAT<br>ACATGTCCATCCTGATATCTCCTGAATTCAGAAATTAGCCTCCACATGTGCAATGGCTTTAAGAGCCAG<br>AAGCAGGGTTCTGGGAATTTTGCAAGTTACCTGTGGCCAGGTGTGGTCTCGGTTACCAAATACGGTTA<br>CCTGCAGCTTTTTAGTCCTTTGTGCTCCCACGGGTCTACAGAGTCCCATCTGCCCAAAGGTCTTGAAG<br>CTTGACAGGATGTTTTCGATTACTCAGTCTCCCAGGGCACTACTGGTCCGTAGGATTCGATTGGTCGG<br>GGTAGGAGAGTTAAAACAACATTTAAACAGAGTTCTCTCAAAAATGTCTAAAGGGATTGTAGGTAGATAA<br>CATCCAATCACTGTTTGCACTTATCTGAAATCTTCCCTCTTGGCTGCCCCCAGGTATTTACTGTGGAGA<br>ACATTGCATAGGAATGTCTGGAAAAAGCTTCTACAACTTGTTACAGCCTTCACATTTGTAGAAGCTTT |
| 54 | opt_COX10*-<br>ND1-3'UTR* | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTCCTACTCCTCATTGTACCCATTCTAATCGCAATGGCAT<br>TCCTAATGCTTACCGAACGAAAAATTCTAGGCTATATGCAACTACGCAAAGGCCCCAACGTTGTAGGC<br>CCCTACGGGCTACTACAACCCTTCGCTGACGCCATAAAACTCTTCACCAAAGAGCCCCTAAAACCCGC<br>CACATCCTACCATCACCCTCTACATCACCGCCCCGACCTTAGCTCTCACCATCGCTCTTCTACTATGGAC<br>CCCCCTCCCCATGCCCAACCCCCTGGTCAACCTCAACCTAGGCCTCCTATTTATTCTAGCCACCTCTA<br>GCCTAGCCGTTTACTCAATCCTCTGGTCAGGGTGGGCATCAAACTCAAACTACGCCCTGATCGGCGCA<br>CTGCGAGCAGTAGCCCAAACAATCTCATATGAAGTCACCCTAGCCATCATTCTACTATCAACATTACTA<br>ATGAGTGGCTCCTTTAACCTCTCCACCCTTATCACAACACAAGAACACCTCTGGTTACTCCTGCCATCA<br>TGGCCCTTGGCCATGATGTGGTTTATCTCCACACTAGCAGAGACCAACCGAACCCCCTTCGACCTTGC<br>CGAAGGGGAGTCCGAACTAGTCTCAGGCTTCAACATCGAATACGCCGCAGGCCCCTTCGCCCTATTC<br>TTCATGGCCGAATACACAAACATTATTATGATGAACACCCTCACCACTACAATCTTCCTAGGAACAACA<br>TATGACGCACTCTCCCCTGAACTCTACACAACATATTTTGTCACCAAGACCCTACTTTCTAACCTCCCTG<br>TTCTTATGGATTCGAACAGCATACCCCCGATTCCGCTACGACCAACTCATGCACCTCCTATGGAAAAAC<br>TTCCTACCACTCACCCTAGCATTACTTATGTGGTATGTCTCCATGCCCATTACAATCTCCAGCATTCCC<br>CCTCAAACCTAAGAGCACTGGGACGCCCACCGCCCCTTTCCCTCCGCTGCCAGGCGAGCATGTTGTG<br>GTAATTCTGGAACACAAGAAGAGAAATTGCTGGGTTTAGAACAAGATTATAAACGAATTCGGTGCTCAG<br>TGATCACTTGACAGTTTTTTTTTTTTTAAATATTACCCAAAATGCTCCCCAAATAAGAAATGCATCAGCT<br>CAGTCAGTGAATACAAAAAGGAATTATTTTTCCCTTTGAGGGTCTTTTATACATCTCTCCTCCAACCCC<br>ACCCTCTATTCTGTTTCTTCCTCCTCACATGGGGGTACACATACACAGCTTCCTCTTTTGGTTCCATCC<br>TTACCACCACACCACACGCACACTCCACATGCCCAGCAGAGTGGCACTTGGTGGCCAGAAAGTGTGA<br>GCCTCATGATCTGCTGTCTGTAGTTCTGTGAGCTCAGGTCCCTCAAAGGCCTCGGAGCACCCCCTTCC<br>TTGTGACTGAGCCAGGGCCTGCATTTTTGGTTTTCCCCACCCCACACATTCTCAACCATAGTCCTTCTA<br>ACAATACCAATAGCTAGGACCCGGCTGCTGTGCACTGGGACTGGGGATTCCACATGTTTGCCTTGGG<br>AGTCTCAAGCTGGACTGCCA |
| 55 | opt_COX10*-<br>opt_ND1-<br>3'UTR | ATGGCCGCCAGCCCCCACACCCTGAGCAGCCGCCTGCTGACCGGCTGCGTGGGCGGCAGCGTGTG<br>GTACCTGGAGCGCCGCACCATGGCCAACCTGCTGCTGATCGTGCCCATCCTGATCGCCATGGCC<br>TTCCTGATGCTGACCGAGCGCAAGATCCTGGGCTACATGCAGCTGCGCAAGGGCCCCAACGTGGTG<br>GGCCCCTACGGCCTGCTGCAGCCCTTCGCCGACGCCATCAAGCTGTTCACCAAGGAGCCCCTGAAG<br>CCCGCCACCAGCACCATCACCCTGTACATCACCGCCCCCACCCTGGCCCTGACCATCGCCCTGCTGC<br>TGTGGACCCCCCTGCCCATGCCCAACCCCCTGGTGAACCTGAACCTGGGCCTGCTGTTCATCCTGGC<br>CACCAGCAGCCTGGCCGTGTACAGCATCCTGTGGAGCGGCTGGGCCAGCAACAGCAACTACGCCCT<br>GATCGGCGCCCTGCGCGCCGTGGCCCAGACCATCAGCTACGAGGTGACCCTGGCCATCATCCTGCT<br>GAGCACCCTGCTGATGAGCGGCAGCTTCAACCTGAGCACCCTGATCACCACCCAGGAGCACCTGTGG<br>CTGCTGCTGCCCAGCTGGCCCCTGGCCATGATGTGGTTCATCAGCACCCTGGCCGAGACCAACCGCA<br>CCCCCTTCGACCTGGCCGAGGGCGAGAGCGAGCTGGTGAGCGGCTTCAACATCGAGTACGCCGCCG<br>GCCCCTTCGCCCTGTTCTTCATGGCCGAGTACACCAACATCATCATGATGAACACCCTGACCACCACC<br>ATCTTCCTGGGCACCACCTACGACGCCCTGAGCCCCGAGCTGTACACCACCTACTTCGTGACCAAGA<br>CCCTGCTGCTGACCAGCCTGTTCCTGTGGATCCGCACCGCCTACCCCCGCTTCCGCTACGACCAGCT<br>GATGCACCTGCTGTGGAAGAACTTCCTGCCCCTGACCCTGGCCCTGCTGATGTGGTACGTGAGCATG<br>CCCATCACCATCAGCAGCATCCCCCCCAGACCTAAGAGCACTGGGACGCCCACCGCCCCTTTCCCT<br>CCGCTGCCAGGCGAGCATGTTGTGGTAATTCTGGAACACAAGAAGAGAAATTGCTGGGTTTAGAACAA<br>GATTATAAACGAATTCGGTGCTCAGTGATCACTTGACAGTTTTTTTTTTTTTAAATATTACCCAAAATGC<br>TCCCCAAATAAGAAATGCATCAGCTCAGTCAGTGAATACAWAAGGAATTATTTTTCCCTTTGAGGGT<br>CTTTTATACATCTCTCCTCCAACCCCACCCTCTATTCTGTTTCTTCCTCCTCACATGGGGGTACACATAC<br>ACAGCTTCCTCTTTTGGTTCCATCCTTACCACCACACCACACGCACACTCCACATGCCCAGCAGAGTG<br>GCACTTGGTGGCCAGAAAGTGTGAGCCTCATGATCTGCTGTCTGTAGTTCTGTGAGCTCAGGTCCCTC<br>AAAGGCCTCGGAGCACCCCCTTCCTTGTGACTGAGCCAGGGCCTGCATTTTTGGTTTTCCCCACCCCA<br>CACATTCTCAACCATAGTCCTTCTAACAATACCAATAGCTAGGACCCGGCTGCTGTGCACTGGGACTG<br>GGGATTCCACATGTTTGCCTTGGGAGTCTCAAGCTGGACTGCCAGCCCCTGTCCTCCCTTCACCCCCA<br>TTGCGTATGAGCATTTCAGAACTCCAAGGAGTCACAGGCATCTTTATAGTTCACGTTAACATATAGACA |

TABLE 1-continued nucleic acid and polypeptide sequences and SEQ ID NOs

| SEQ | description | sequence |
|---|---|---|
| | | CTGTTGGAAGCAGTTCCTTCTAAAAGGGTAGCCCTGGACTTAATACCAGCCGGATACCTCTGGCCCCC
ACCCCATTACTGTACCTCTGGAGTCACTACTGTGGGTCGCCACTCCTCTGCTACACAGCACGGCTTTT
TCAAGGCTGTATTGAGAAGGGAAGTTAGGAAGAAGGGTGTGCTGGGCTAACCAGCCCACAGAGCTCA
CATTCCTGTCCCTTGGGTGAAAAATACATGTCCATCCTGATATCTCCTGAATTCAGAAATTAGCCTCCA
CATGTGCAATGGCTTTAAGAGCCAGAAGCAGGGTTCTGGGAATTTTGCAAGTTACCTGTGGCCAGGTG
TGGTCTCGGTTACCAAATACGGTTACCTGCAGCTTTTTAGTCCTTTGTGCTCCCACGGGTCTACAGAGT
CCCATCTGCCCAAAGGTCTTGAAGCTTGACAGGATGTTTTCGATTACTCAGTCTCCCAGGGCACTACT
GGTCCGTAGGATTCGATTGGTCGGGGTAGGAGAGTTAAACAACATTTAAACAGAGTTCTCTCAAAAT
GTCTAAAGGGATTGTAGGTAGATAACATCCAATCACTGTTTGCACTTATCTGAAATCTTCCCTCTTGGC
TGCCCCCAGGTATTTACTGTGGAGAACATTGCATAGGAATGTCTGGAAAAAGCTTCTACAACTTGTTAC
AGCCTTCACATTTGTAGAAGCTTT |
| 56 | opt_COX10*-
opt_ND1-
3'UTR* | ATGGCCGCCAGCCCCCACACCCTGAGCAGCCGCCTGCTGACCGGCTGCGTGGGCGGCAGCGTGTG
GTACCTGGAGCGCCGCACCATGGCCAACCTGCTGCTGCTGATCGTGCCCATCCTGATCGCCATGGCC
TTCCTGATGCTGACCGAGCGCAAGATCCTGGGCTACATGCAGCTGCGCAAGGGCCCCAACGTGGTG
GGCCCCTACGGCCTGCTGCAGCCCTTCGCCGACGCCATCAAGCTGTTCACCAAGGAGCCCCTGAAG
CCCGCCACCAGCACCATCACCCTGTACATCACCGCCCCCACCCTGGCCCTGCCTGACCATCGCCCTGCTGC
TGTGGACCCCCCTGCCCATGCCCAACCCCCTGGTGAACCTGAACCTGGGCCTGCTGTTCATCCTGGC
CACCAGCAGCCTGGCCGTGTACAGCATCCTGTGGAGCGGCTGGGCCAGCAACAGCAACTACGCCCT
GATCGGCGCCCTGCGCGCCGTGGCCCAGACCATCAGCTACGAGGTGACCCTGGCCATCATCCTGCT
GAGCACCCTGCTGATGAGCGGCAGCTTCAACCTGAGCACCCTGATCACCACCCAGGAGCACCTGTGG
CTGCTGCTGCCCAGCTGGCCCCTGGCCATGATGTGGTTCATCAGCACCCTGGCCGAGACCAACCGCA
CCCCCTTCGACCTGGCCGAGGGCGAGAGCGAGCTGGTGAGCGGCTTCAACATCGAGTACGCCGCCG
GCCCCTTCGCCCTGTTCTTCATGGCCGAGTACACCAACATCATCATGATGAACACCCTGACCACCACC
ATCTTCCTGGGCACCACCTACGACGCCCTGAGCCCCGAGCTGTACACCACCTACTTCGTGACCAAGA
CCCTGCTGCTGACCAGCCTGTTCCTGTGGATCCGCACCGCCTACCCCCGCTTCCGCTACGACCAGCT
GATGCACCTGCTGTGGAAGAACTTCCTGCCCCTGACCCTGGCCCTGCTGATGTGGTACGTGAGCATG
CCCATCACCATCAGCAGCATCCCCCCCAGACCTAAGAGCACTGGGACGCCCACCGCCCCTTTCCCT
CCGCTGCCAGGCGGCGAGCATGTTGTGGTAATTCTGGAACACAAGAAGAGAAATTGCTGGGTTTAGAACAA
GATTATAAACGAATTCGGTGCTCAGTGATCACTTGACAGTTTTTTTTTTTTTAAATATTACCCAAAATGC
TCCCCAAATAAGAAATGCATCAGCTCAGTCAGTGAATACAAAAAAGGAATTATTTTTCCCTTTGAGGGT
CTTTTATACATCTCCTCCAACCCCACCCTCTATTCTGTTTCTTCCTCCTCACATGGGGGTACACATAC
ACAGCTTCCTCTTTTGGTTCCATCCTTACCACCACACCACACGCACACTCCACATGCCCAGCAGAGTG
GCACTTGGTGGCCAGAAAGTGTGAGCCTCATGATCTGCTGTCTGTAGTTCTGTGAGCTCAGGTCCCTC
AAAGGCCTCGGAGCACCCCCTTCCTTGTGACTGAGCCAGGGCCTGCATTTTTGGTTTTCCCCACCCCA
CACATTCTCAACCATAGTCCTTCTAACAATACCAATAGCTAGGACCCGGCTGCTGTGCACTGGGACTG
GGGATTCCACATGTTTGCCTTGGGAGTCTCAAGCTGGACTGCCA |
| 57 | COX8-ND4-
3'UTR | ATGTCCGTCCTGACGCGCCTGCTGCTGCGGGGCTTGACACGGCTCGGCTCGGCGGCTCCAGTGCGG
CGCGCCAGAATCCATTCGTTGATGCTAAAACTAATCGTCCCAACAATTATGTTACTACCACTGACATGG
CTTTCCAAAAAACACATGATTTGGATCAACACAACCACCCACAGCCTAATTATTAGCATCATCCCTCTA
CTATTTTTTAACCAAATCAACAACAACCTATTTAGCTGTTCCCCAACCTTTTCCTCCGACCCCCTAACAA
CCCCCCTCCTAATGCTAACTACCTGGCTCCTACCCCTCACAATCATGGCAAGCCAACGCCACTTATCC
AGTGAACCACTATCACGAAAAAACTCTACCTCTCTATGCTAATCTCCCTACAAATCTCCTTAATTATGA
CATTCACAGCCACAGAACTAATCATGTTTTATATCTTCTTCGAAACCACACTTATCCCCACCTTGGCTAT
CATCACCCGATGGGGCAACCAGCCAGAACGCCTGAACGCAGGCACATACTTCCTATTCTACACCCTA
GTAGGCTCCCTTCCCCTACTCATCGCACTAATTTACACTCACAACACCCTAGGCTCACTAACATTCTA
CTACTACTCTCACTGCCCAAGAACTATCAAACTCCTGGGCCAACAACTTAATGTGGCTAGCTTACACA
ATGGCTTTTATGGTAAAGATGCCTCTTTACGGACTCCACTTATGGCTCCCTAAAGCCCATGTCGAAGCC
CCCATCGCTGGGTCAATGGTACTTGCCGCAGTACTCTTAAAACTAGGCGGCTATGGTATGATGCGCCT
CACACTCATTCTCAACCCCCTGACAAAACACATGGCCTACCCCTTCCTTGTACTATCCCTATGGGGCAT
GATTATGACAAGCTCCATCTGCCTACGACAAACAGACCTAAAATCGCTCATTGCATACTCTTCAATCAG
CCACATGGCCCTCGTAGTAACAGCCATTCTCATCCAAACCCCCTGGAGCTTCACCGGCGCAGTCATTC
TCATGATCGCCCACGGCTTACATCCTCATTACTATTCTGCCTAGCAAACTCAAACTACGAACGCACTC
ACAGTCGCATCATGATCCTCTCTCAAGGACTTCAAACTCTACTCCCACTAATGGCTTTTTGGTGGCTTC
TAGCAAGCCTCGCTAACCTCGCCTTACCCCCCACTATTAACCTACTGGGAGAACTCTCTGTGCTAGTA
ACCACGTTCTCCTGGTCAAATATCACTCTCCTACTTACAGGACTCAACATGCTAGTCACAGCCCTATAC
TCCCTCTACATGTTTACCACAACAATGGGGCTCACTCACCCACCACATTAACAACATGAAACCCTCA
TTCACGAGAAAACACCCTCATGTTCATGCACCTATCCCCCATTCTCCTCCTATCCCTCAACCCCGAC
ATCATTACCGGGTTTTCCTCTTAAGAGCACTGGGACGCCCACCGCCCCTTTCCCTCCGCTGCCAGGC
GAGCATGTTGTGGTAATTCTGGAACACAAGAAGAGAAATTGCTGGGTTTAGAACAAGATTATAAACGAA
TTCGGTGCTCAGTGATCACTTGACAGTTTTTTTTTTTAAATATTACCCAAAATGCTCCCCAAATAAG
AAATGCATCAGCTCAGTCAGTGAATACAAAAAAGGAATTATTTTTCCCTTTGAGGGTCTTTTATACATCT
CTCCTCCAACCCCACCCTCTATTCTGTTTCTTCCTCCTCACATGGGGGTACACATACACAGCTTCCTCT
TTTGGTTCCATCCTTACCACCACACCACACGCACACTCCACATGCCCAGCAGAGTGGCACTTGGTGGC
CAGAAAGTGTGAGCCTCATGATCTGCTGTCTGTAGTTCTGTGAGCTCAGGTCCCTCAAAGGCCTCGGA
GCACCCCCTTCCTTGTGACTGAGCCAGGGCCTGCATTTTTGGTTTTCCCCACCCCACACATTCTCAAC
CATAGTCCTTCTAACAATACCAATAGCTAGGACCCGGCTGCTGTGCACTGGGACTGGGGATTCCACAT
GTTTGCCTTGGGAGTCTCAAGCTGGACTGCCAGCCCCTGTCCTCCCTTCACCCCCATTGCGTATGAGC
ATTTCAGAACTCCAAGGAGTCACAGGCATCTTTATAGTTCACGTTAACATATAGACACTGTTGGAAGCA
GTTCCTTCTAAAAGGGTAGCCCTGGACTTAATACCAGCCGGATACCTCTGGCCCCCACCCCATTACTG
TACCTCTGGAGTCACTACTGTGGGTCGCCACTCCTCTGCTACACAGCACGGCTTTTTCAAGGCTGTAT
TGAGAAGGGAAGTTAGGAAGAAGGGTGTGCTGGGCTAACCAGCCCACAGAGCTCACATTCCTGTCCC
TTGGGTGAAAAATACATGTCCATCCTGATATCTCCTGAATTCAGAAATTAGCCTCCACATGTGCAATGG
CTTTAAGAGCCAGAAGCAGGGTTCTGGGAATTTTGCAAGTTACCTGTGGCCAGGTGTGGTCTCGGTTA
CCAAATACGGTTACCTGCAGCTTTTTAGTCCTTTGTGCTCCCACGGGTCTACAGAGTCCCATCTGCCC |

TABLE 1-continued nucleic acid and polypeptide sequences and SEQ ID NOs

| SEQ | description | sequence |
|---|---|---|
| | | AAAGGTCTTGAAGCTTGACAGGATGTTTTCGATTACTCAGTCTCCCAGGGCACTACTGGTCCGTAGGA<br>TTCGATTGGTCGGGGTAGGAGAGTTAAACAACATTTAAACAGAGTTCTCTCAAAAATGTCTAAAGGGAT<br>TGTAGGGTAGATAACATCCAATCACTGTTTGCACTTATCTGAAATCTTCCCTCTTGGCTGCCCCCAGGTA<br>TTTACTGTGGAGAACATTGCATAGGAATGTCTGGAAAAAGCTTCTACAACTTGTTACAGCCTTCACATT<br>TGTAGAAGCTTT |
| 58 | COX8-ND4-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTAAAACTAATCGTCCCAACAATTATGTTACTACCACTGACATGG<br>CTTTCCAAAAAACACATGATTTGGATCAACACAACCACCCACAGCCTAATTATTAGCATCATCCCTCTA<br>CTATTTTTTAACCAAATCAACAACAACCTATTTAGCTGTTCCCCAACCTTTTCCTCCGACCCCCTAACAA<br>CCCCCCTCCTAATGCTAACTACCTGGCTCCTACCCCTCACAATCATGGCAAGCCAACGCCACTTATCC<br>AGTGAACCACTATCACGAAAAAAACTCTACCTCTCTATGCTAATCTCCCTACAAATCTCCTTAATTATGA<br>CATTCACAGCCACAGAACTAATCATGTTTTATATCTTCTTCGAAACCACACTTATCCCCACCTTGGCTAT<br>CATCACCCGATGGGGCAACCAGCCAGAACGCCTGAACGCAGGCACATACTTCCTATTCTACACCCTA<br>GTAGGCTCCCTTCCCCTACTCATCGCACTAATTTACACTCACAACACCCTAGGCTCACTAAACATTCTA<br>CTACTCACTCTCACTGCCCAAGAACTATCAAACTCCTGGGCCAACAACTTAATGTGGCTAGCTTACACA<br>ATGGCTTTTATGGTAAAGATGCCTCTTTACGGACTCCACTTATGGCTCCCTAAAGCCCATGTCGAAGCC<br>CCCATCGCTGGGTCAATGGTACTTGCCGCAGTACTCTTAAAACTAGGCGGCTATGGTATGATGCGCCT<br>CACACTCATTCTCAACCCCCTGACNVAACACATGGCCTACCCCTTCCTTGTACTATCCCTATGGGGCAT<br>GATTATGACAAGCTCCATCTGCCTACGACAAACAGACCTAAAATCGCTCATTGCATACTCTTCAATCAG<br>CCACATGGCCCTCGTAGTAACAGCCATTCTCATCCAACCCCCTGGAGCTTCACCGGCGCAGTCATTC<br>TCATGATCGCCCACGGGCTTACATCCTCATTACTATTCTGCCTAGCAAACTCAAACTACGAACGCACTC<br>ACAGTCGCATCATGATCCTCTCTCAAGGACTTCAAACTCTACTCCCACTAATGGCTTTTTGGTGGCTTC<br>TAGCAAGCCTCGCTAACCTCGCCTTACCCCCCACTATTAACCTACTGGGAGAACTCTCTGTGCTAGTA<br>ACCACGTTCTCCTGGTCAAATATCACTCTCCTACTTACAGGACTCAACATGCTAGTCACAGCCCTATAC<br>TCCCTCTACATGTTTACCACAACACAATGGGGCTCACTCACCCACCACATTAACAACATGAAACCCTCA<br>TTCACACGAGAAAACCCCTCATGTTCATGCACCTATCCCCCATTCTCCTCCTATCCCTCAACCCCGAC<br>ATCATTACCGGGTTTTCCTCTTAAGAGCACTGGGACGCCCACCGCCCCTTTCCCTCCGCTGCCAGGC<br>GAGCATGTTGTGGTAATTCTGGAACACAAGAAGAGAAATTGCTGGGTTTAGAACAAGATTATAAACGAA<br>TTCGGTGCTCAGTGATCACTTGACAGTTTTTTTTTTTTAAATATTACCCAAAATGCTCCCCAAATAAG<br>AAATGCATCAGCTCAGTCAGTGAATACAAAAAAGGAATTATTTTTCCCTTTGAGGGTCTTTTATACATCT<br>CTCCTCCAACCCCACCCTCTATTCGTTTCTTCCTCCTCACATGGGGGTACACATACACAGCTTCCTCT<br>TTTGGTTCCATCCTTACCACCACCACACGCACACTTCCACATGCCCAGCAGAGTGGCACTTGGTGGC<br>CAGAAAGTGTGAGCCTCATGATCTGCTGTCTGTAGTTCTGTGAGCTCAGGTCCCTCAAAGGCCTCGGA<br>GCACCCCCTTCCTTGTGACTGAGCCAGGGCCTGCATTTTTGGTTTTCCCCACCCCACACATTCTCAAC<br>CATAGTCCTTCTAACAATACCAATAGCTAGGACCCGGCTGCTGTGCACTGGGACTGGGGATTCCACAT<br>GTTTGCCTTGGGAGTCTCAAGCTGGACTGCCA |
| 59 | COX8-<br>opt_ND4-<br>3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCTCTGACCTG<br>GCTGAGCAAGAAACACATGATCTGGATCAACACCACCACGCACAGCCTGATCATCAGCATCATCCCTC<br>TGCTGTTCTTCAACCAGATCAACAACAACCTGTTCAGCTGCGCCCCACCTTCAGCAGCGACCCCTCTG<br>ACAACACCTCTGCTGATGCTGACCACCTGGCTGCTGCCCCTCACAATCATGGCCTCTCAGAGACACCT<br>GAGCAGCGAGCCCTGAGCCGGAAGAAACTGTACCTGAGCATGCTGATCTCCCTGCAGATCTCTCTG<br>ATCATGACCTTCACCGCCACCGAGCTGATCATGTTCTACATCTTTTTCGAGACAACGCTGATCCCCACA<br>CTGGCCATCATCACCAGATGGGGCAACCAGCCTGAGAACGCCTGAACGCCGGCACCTACTTTCTGTTCT<br>ACACCCTCGTGGGCAGCCTGCCACTGCTGATTGCCCTGATCTACACCCACAACACCCTGGGCTCCCT<br>GACACATCCTGCTGCTGACACTGACAGCCCAAGAGCTGAGCAACAGCTGGGCCAACAATCTGATGTGG<br>CTGGCCTACACAATGGCCTTCATGGTCAAGATGCCCCTGTACGGCCTGCACCTGTGGCTGCCTAAAG<br>CTCATGTGGAAGCCCCTATCGCCGGCTCTATGGTGCTGGCTGCAGTGCTGCTGAAACTCGGCGGCTA<br>CGGCATGATGCGGCTGACCCTGATTCTGAATCCCCTGACCAAGCACATGGCCTATCCATTTCTGGTGC<br>TGAGCCTGTGGGGCATGATTATGACCAGCAGCATCTGCCTGCGGCAGACCGATCTGAAGTCCCTGAT<br>CGCCTACAGCTCCATCAGCCACATGGGCCCTGGTGGTCACCGCCATCCTGATTCAGACCCCTTGGAGC<br>TTTACAGGCGCCGTGATCCTGATGATTGCCCACGGCCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCAATATCACCCTGCTGCTCACCGGCCTG<br>AACATGCTGGTTACAGCCCCTGTACTCCCTGTACATGTTCACCACCACACAGTGGGGAAGCCTGACACA<br>CCCATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTAAAT<br>ATTACCCAAAATGCTCCCCAAATAAGAAATGCATCAGCTCAGTCAGTGAATACAAAAAAGGAATTATTTTT<br>TCCCTTTGAGGGTCTTTTATACATCTCTCCTCCAACCCCACCCTCTATTCGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAAATACATGTCCATCCTGATATCTCCTGAATTC<br>AGAAATTAGCCTCCACATGTGCAATGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC |

TABLE 1-continued nucleic acid and polypeptide sequences and SEQ ID NOs

| SEQ | description | sequence |
|---|---|---|
| | | CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA<br>AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 60 | COX8-<br>opt_ND4-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCTCTGACCTG<br>GCTGAGCAAGAAACACATGATCTGGATCAACACCACCACGCACAGCCTGATCATCAGCATCATCCCTC<br>TGCTGTTCTTCAACCAGATCAACAACAACCTGTTCAGCTGCAGCCCCACCTTCAGCAGCGACCCTCTG<br>ACAACACCTCTGCTGATGCTGACCACCTGGCTGCTGCCCCTCACAATCATGGCCTCTCAGAGACACCT<br>GAGCAGCGAGCCCCTGAGCCGGAAGAAACTGTACCTGAGCATGCTGATCTCCCTGCAGATCTCTCTG<br>ATCATGACCTTCACCGCCACCGAGCTGATCATGTTCTACATCTTTTTCGAGACAACGCTGATCCCCACA<br>CTGGCCATCATCACCGATGGGGCAACCAGCCTGAGAGACTGAACGCCGGCACCTACTTTCTGTTCT<br>ACACCCTCGTGGGCAGCCTGCCACTGCTGATTGCCCTGATCTACACCCACAACACCCTGGGCTCCCT<br>GAACATCCTGCTGCTGACACTGACAGCCCAAGAGCTGAGCAACAGCTGGGCCAACAATCTGATGTGG<br>CTGGCCTACACACAATGGCCTTCATGGTCAAGATGCCCCTGTACGGCCTGCACCTGTGGCTGCCTAAAG<br>CTCATGTGGAAGCCCCTATCGCCGGCTCTATGGTGCTGGCTGCAGTGCTGCTGAAACTCGGCGGCTA<br>CGGCATGATGCGGCTGACCCTGATTCTGAATCCCCTGACCAAGCACATGGCCTATCCATTTCTGGTGC<br>TGAGCCTGTGGGGCATGATTATGACCAGCAGCATCTGCCTGCGGCAGACCGATCTGAAGTCCCTGAT<br>CGCCTACAGCTCCATCAGCCACATGGCCCTGGTGGTCACCGCCATCCTGATTCAGACCCCTTGGAGC<br>TTTACAGGCGCCGTGATCCTGATGATTGCCCACGGCTGACAAGCAGCCTGCTGTTTTGTCTGGCCAA<br>CAGCAACTACGAGCGGACCCACAGCAGAATCATGATCCTGTCTCAGGGCCTGCAGACCCTCCTGCCT<br>CTTATGGCTTTTTGGTGGCTGCTGGCCTCTCTGGCCAATCTGGCACTGCCTCCTACCATCAATCTGCT<br>GGGCGAGCTGAGCGTGCTGGTCACCACATTCAGCTGGTCCAATATCACCCTGCTGCTCACCGGCCTG<br>AACATGCTGGTTACAGCCCTGTACTCCCTGTACATGTTCACCACCACACAGTGGGGAAGCCTGACACA<br>CCCACATCAACAATATGAAGCCCAGCTTCACCCGCGAGAACACCCTGATGTTCATGCATCTGAGCCCCA<br>TTCTGCTGCTGTCCCTGAATCCTGATATCATCACCGGCTTCTCCAGCTGAGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTAAAT<br>ATTACCCAAAATGCTCCCCAAATAAGAAATGCATCAGCTCAGTCAGTGAATACAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 61 | COX8-<br>opt_ND4*-<br>3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCCCTGACCT<br>GGCTGAGCAAGAAGCACATGATCTGGATCAACACCACCACCCACAGCCTGATCATCAGCATCATCCCC<br>CTGCTGTTCTTCAACCAGATCAACAACAACCTGTTCAGCTGCAGCCCCACCTTCAGCAGCGACCCCCT<br>GACCACCCCCCTGCTGATGCTGACCACCTGGCTGCTGCCCCTGACCATCATGGCCAGCAGCGACCAC<br>CTGAGCAGCGAGCCCCTGAGCCGCAAGAAGCTGTACCTGAGCATGCTGATCAGCCTGCAGATCAGCC<br>TGATCATGACCTTCACCGCCACCGAGCTGATCATGTTCTACATCTTCTTCGAGACCACCCTGATCCCC<br>ACCCTGGCCATCATCACCCGCTGGGGCAACCAGCCTGCGAGCGCCTGAACGCCGGCACCTACTTCCTGT<br>TCTACACCCTGGTGGGCAGCCTGCCCCTGCTGATCGCCCTGATCTACACCCACAACACCCTGGGCAG<br>CCTGAACATCCTGCTGCTGACCCTGACCGCCCAGGAGCTGAGCAACAGCTGGGCCAACAACCTGATG<br>TGGCTGGCCTACACCATGGCCTTCATGGTGAAGATGCCCCTGTACGGCCTGCACCTGTGGCTGCCCA<br>AGGCCCACGTGGAGGCCCCCATCGCCGGCAGCATGGTGCTGGCCGCCGTGCTGCTGAAGCTGGGC<br>GGCTACGGCATGATGCGCCTGACCCTGATCCTGAACCCCCTGACCAAGCACATGGCCTACCCCTTCC<br>TGGTGCTGAGCCTGTGGGGCATGATCATGACCAGCAGCATCTGCCTGCGCCAGACCGACCTGAAGAG<br>CCTGATCGCCTACAGCAGCATCAGCCACATGGCCCTGGTGGTGACCGCCATCCTGATCCAGACCCCC<br>TGGAGCTTCACCGGCGCCGTGATCCTGATGATCGCCCACGGCCTGACCAGCAGCCTGCTGTTCTGCC<br>TGGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACCTGGCCCTGCCCCCCACCAT<br>CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCCAGTGGGGCA<br>GCCTGAACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTTAAATATTACCCAAAATGCTCCCCAAATAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCAGCCCCTGTCCTCCCTTCACCCCCATTGCGTATGAGCATTTCAGAACTCCAAGGAGTCACAGGCAT<br>CTTTATAGTTCACGTTAACATATAGACAGTTGGAACAGTTCCTTCTAAAAGGGTAGCCCTGGACTT<br>AATACCAGCCGGATACCTCTGGCCCCACCCCATTACTGTACCTCTGGAGTCACTACTGTGGGTCGCC<br>ACTCCTCTGCTACACAGCACGGCTTTTTCAAGGCTGTATTGAGAAGGGAAGTTAGGAAGAAGGGTGTG<br>CTGGGCTAACCAGCCCACAGAGCTCACATTCCTGTCCCTTGGGTGAAAAATACATGTCCATCCTGATA<br>TCTCCTGAATTCAGAAATTAGCCTCCACATGTGCAATGGCTTTAAGAGCCAGAAGCAGGGTTCTGGGA<br>ATTTTGCAAGTTACCTGTGGCCAGGTGTGGTCTCGGTTACCAAATACGGTTACCTGCAGCTTTTTAGTC |

TABLE 1-continued nucleic acid and polypeptide sequences and SEQ ID NOs

| SEQ | description | sequence |
|---|---|---|
| | | CTTTGTGCTCCCACGGGTCTACAGAGTCCCATCTGCCCAAAGGTCTTGAAGCTTGACAGGATGTTTTC<br>GATTACTCAGTCTCCCAGGGCACTACTGGTCCGTAGGATTCGATTGGTCGGGGTAGGAGAGTTAAACA<br>ACATTTAAACAGAGTTCTCTCAAAAATGTCTAAAGGGATTGTAGGTAGATAACATCCAATCACTGTTTGC<br>ACTTATCTGAAATCTTCCCTCTTGGCTGCCCCCAGGTATTTACTGTGGAGAACATTGCATAGGAATGTC<br>TGGAAAAAGCTTCTACAACTTGTTACAGCCTTCACATTTGTAGAAGCTTT |
| 62 | COX8-<br>opt_ND4*-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGCTGAAGCTGATCGTGCCCACCATCATGCTGCTGCCCCTGACcT<br>GGCTGAGCAAGAAGCACATGATCTGGATCAACACCACCACCCACAGCCTGATCATCAGCATCATCCCC<br>CTGCTGTTCTTCAACCAGATCAACAACAACCTGTTCAGCTGCAGCCCCACCTTCAGCAGCGACCCCCT<br>GACCACCCCCCTGCTGATGCTGACCACCTGGCTGCTGCCCCTGACCATCATGGCCAGCCAGCGCCAC<br>CTGAGCAGCGAGCCCCTGAGCCGCAAGAAGCTGTACCTGAGCATGCTGATCAGCCTGCAGATCAGCC<br>TGATCATGACCTTCACCGCCACCGAGCTGATCATGTTCTACATCTTCTTCGAGACCACCCCTGATCCCC<br>ACCCTGGCCATCATCACCCGCTGGGGCAACCAGCCCGAGCGCCTGAACGCCGGCACCTACTTCCTGT<br>TCTACACCCTGGTGGGCAGCCTGCCCCTGCTGATCGCCCTGATCTACACCCACAACACCCTGGGCAG<br>CCTGAACATCCTGCTGCTGACCCTGACCGCCCAGGAGCTGAGCAACAGCTGGGCCAACAACCTGATG<br>TGGCTGGCCTACACCATGGCCTTCATGGTGAAGATGCCCCTGTACGGCCTGCACCTGTGGCTGCCCA<br>AGGCCCACGTGGAGGCCCCCATCGCCGGCAGCATGGTGCTGGCCGCCGTGCTGCTGAAGCTGGGC<br>GGCTACGGCATGATGCGCCTGACCCTGATCCTGAACCCCCTGACCAAGCACATGGCCTACCCCTTCC<br>TGGTGCTGAGCCTGTGGGGCATGATCATGACCAGCAGCATCTGCCTGCGCCAGACCGACCTGAAGAG<br>CCTGATCGCCTACAGCAGCATCAGCCACATGGCCCTGGTGGTGACCGCCATCCTGATCCAGACCCCC<br>TGGAGCTTCACCGGCGCCGTGATCCTGATGATCGCCCACGGCCTGACCAGCAGCCTGCTGTTCTGCC<br>TGGCCAACAGCAACTACGAGCGCACCCACAGCCGCATCATGATCCTGAGCCAGGGCCTGCAGACCCT<br>GCTGCCCCTGATGGCCTTCTGGTGGCTGCTGGCCAGCCTGGCCAACCTGGCCCTGCCCCCCACCAT<br>CAACCTGCTGGGCGAGCTGAGCGTGCTGGTGACCACCTTCAGCTGGAGCAACATCACCCTGCTGCTG<br>ACCGGCCTGAACATGCTGGTGACCGCCCTGTACAGCCTGTACATGTTCACCACCACCCAGTGGGGCA<br>GCCTGACCCACCACATCAACAACATGAAGCCCAGCTTCACCCGCGAGAACACCCTGATGTTCATGCAC<br>CTGAGCCCCATCCTGCTGCTGAGCCTGAACCCCGACATCATCACCGGCTTCAGCAGCTAAGAGCACT<br>GGGACGCCCACCGCCCCTTTCCCTCCGCTGCCAGGCGAGCATGTTGTGGTAATTCTGGAACACAAGA<br>AGAGAAATTGCTGGGTTTAGAACAAGATTATAAACGAATTCGGTGCTCAGTGATCACTTGACAGTTTTT<br>TTTTTTTTTTAAATATTACCCAAAATGCTCCCCAAATAAGAAATGCATCAGCTCAGTCAGTGAATACAAAA<br>AAGGAATTATTTTTCCCTTTGAGGGTCTTTTATACATCTCTCCTCCAACCCCACCCTCTATTCTGTTTCT<br>TCCTCCTCACATGGGGGTACACATACACAGCTTCCTCTTTTGGTTCCATCCTTACCACCACACCACACG<br>CACACTCCACATGCCCAGCAGAGTGGCACTTGGTGGCCAGAAAGTGTGAGCCTCATGATCTGCTGTC<br>TGTAGTTCTGTGAGCTCAGGTCCCTCAAAGGCCTCGGAGCACCCCCTTCCTTGTGACTGAGCCAGGG<br>CCTGCATTTTTGGTTTTCCCCACCCCACACATTCTCAACCATAGTCCTTCTAACAATACCAATAGCTAG<br>GACCCGGCTGCTGTGCACTGGGACTGGGGATTCCACATGTTTGCCTTGGGAGTCTCAAGCTGGACTG<br>CCA |
| 63 | COX3-ND6-<br>3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTATGCTTTGTTTCTGTTGAGTGTGGGTTTAGTAATGGGGTTT<br>GTGGGGTTTTCTTCTAAGCCTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTTTAATTTATTTAGGGGGAA<br>TGATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG<br>AGTATGATGGGGTGGTGGTTGTGGTAAACATTTAATAGTGTAGGAAGCTGGATGATTTATGAAGGAGAG<br>GGGTCAGGGTTGATTCGGGAGGATCCTATTGGTGCGGGGCTTTGTATGATTATGGGCGTTGGTTAG<br>TAGTAGTTACTGGTTGGACATTGTTTGTTGGTGTATATATTGTAATTGAGATTGCTCGGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCTAACAATACCAATAG<br>CTAGGACCCGGCTGCTGTGCACTGGGACTGGGGATTCCACATGTTTGCCTTGGGAGTCTCAAGCTGG<br>ACTGCCAGCCCCTGTCCTCCCTTCACCCCCATTGCGTATGAGCATTTCAGAACTCCAAGGAGTCACAG<br>GCATCTTTATAGTTCACGTTAACATATAGACACTGTTGGAAGCAGTTCCTTCTAAAAGGGTAGCCCTGG<br>ACTTAATACCAGCCGGATACCTCTGGCCCCCACCCCATTACTGTACCTCTGGAGTCACTACTGTGGGT<br>CGCCACTCCTCTGCTACACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTGGGTGAAAAATACATGTCCATCC<br>TGATATCTCCTGAATTCAGAAATTAGCCTCCACATGTGCAATGGCTTTAAGAGCCAGAAGCAGGGTTCT<br>GGGAATTTTGCAAGTTACCTGTGGCCAGGTGTGGTCTCGGTTACCAAATACGGTTACCTGCAGCTTTT<br>TAGTCCTTTGTGCTCCCACGGGTCTACAGAGTCCCATCTGCCCAAAGGTCTTGAAGCTTGACAGGATG<br>TTTTCGATTACTCAGTCTCCCAGGGCACTACTGGTCCGTAGGATTCGATTGGTCGGGGTAGGAGAGTT<br>AAACAACATTTAAACAGAGTTCTCTCAAAAATGTCTAAAGGGATTGTAGGTAGATAACATCCAATCACT<br>GTTTGCACTTATCTGAAATCTTCCCTCTTGGCTGCCCCCAGGTATTTACTGTGGAGAACATTGCATAGG<br>AATGTCTGGAAAAAGCTTCTACAACTTGTTACAGCCTTCACATTTGTAGAAGCTTT |
| 64 | COX8-ND6-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTATGCTTTGTTTCTGTTGAGTGTGGGTTTAGTAATGGGGTTT<br>GTGGGGTTTTCTTCTAAGCCTTCTCCTATTTATGGGGGTTTAGTATTGATTGTTAGCGGTGTGGTCGGG<br>TGTGTTATTATTCTGAATTTTGGGGGAGGTTATATGGGTTTAATGGTTTTTTTAATTTATTTAGGGGGAA<br>TGATGGTTGTCTTTGGATATACTACAGCGATGGCTATTGAGGAGTATCCTGAGGCATGGGGGTCAGGG<br>GTTGAGGTCTTGGTGAGTGTTTTAGTGGGGTTAGCGATGGAGGTAGGATTGGTGCTGTGGGTGAAAG |

TABLE 1-continued nucleic acid and polypeptide sequences and SEQ ID NOs

| SEQ | description | sequence |
|---|---|---|
| | | AGTATGATGGGGTGGTGGTTGTGGTAAACTTTAATAGTGTAGGAAGCTGGATGATTTATGAAGGAGAG<br>GGGTCAGGGTTGATTCGGGAGGATCCTATTGGTGCGGGGGCTTTGTATGATTATGGGCGTTGGTTAG<br>TAGTAGTTACTGGTTGGACATTGTTTGTTGGTGTATATATTGTAATTGAGATTGCTCGGGGGAATTAGG<br>AGCACTGGGACGCCCACCGCCCCTTTCCCTCCGCTGCCAGGCGAGCATGTTGTGGTAATTCTGGAAC<br>ACAAGAAGAGAAATTGCTGGGTTTAGAACAAGATTATAAACGAATTCGGTGCTCAGTGATCACTTGACA<br>GTTTTTTTTTTTTTAAATATTACCCAAAATGCTCCCCAAATAAGAAATGCATCAGCTCAGTCAGTGAATA<br>CAAAAAAGGAATTATTTTTCCCTTTGAGGGTCTTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTTGTGACTGAGCC<br>AGGGCCTGCATTTTTGGTTTTCCCCACCCCACACATTCTCAACCATAGTCCTTCAACAATACCAATAG<br>CTAGGACCCGGCTGCTGTGCACTGGGACTGGGGATTCCACATGTTTGCCTTGGGAGTCTCAAGCTGG<br>ACTGCCA |
| 65 | COX8-<br>opt_ND6-<br>3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTACGCCCTGTTCCTGCTGAGCGTGGGCCTGGTGATGGGCT<br>TCGTGGGCTTCAGCAGCAAGCCCAGCCCCATCTACGGCGGCCTGGTGCTGATCGTGAGCGGCGTGG<br>TGGGCTGCGTGATCATCCTGAACTTCGGCGGCGGCTACATGGGCGTGATGGTGTTCCTGATCTACCT<br>GGGCGGCATGATGGTGGTGTTCGGCTACACCACCGCCATGGCCATCGAGGAGTACCCCGAGGCCTG<br>GGGCAGCGGCGTGGAGGTGCTGGTGAGCGTGCTGGTGGGCCTGGCCATGGAGGTGGGCCTGGTGC<br>TGTGGGTGAAGGAGTACGACGGCGTGGTGGTGGTGAACTTCAACAGCGTGGGCAGCTGGATGA<br>TCTACGAGGGCGAGGGCAGCGGCCTGATCCGCGAGGACCCCATCGGCGCCGGCGCCCTGTACGAC<br>TACGGCCGCTGGCTGGTGGTGGTGACCGGCTGGACCCTGTTCGTGGGCGTGTACATCGTGATCGAG<br>ATCGCCCGCGGCAACTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGAATTCGG<br>TGCTCAGTGATCACTTGACAGTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCAGCCCCTGTCCTCCCTTCACCCCATTGCGTATGAGCATTTCA<br>GAACTCCAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCACCCCATTACTGTACCTC<br>TGGAGTCACTACTGTGGGTCGCCACTCCTCTGCTACACAGCACGGCTTTTTCAAGGCTGTATTGAGAA<br>GGGAAGTTAGGAAGAAAGGGTGTGCTGGGCTAACCAGCCCACAGAGCTCACATTCCTGTCCCTTGGGT<br>GAAAAATACATGTCCATCCTGATATCTCCTGAATTCAGAAATTAGCCTCCACATGTGCAATGGCTTTAA<br>GAGCCAGAAGCAGGGTTCTGGGAATTTTGCAAGTTACCTGTGGCCAGGTGTGGTCTCGGTTACCAAAT<br>ACGGTTACCTGCAGCTTTTTAGTCCTTTGTGCTCCCACGGGTCTACAGAGTCCCATCTGCCCAAAGGT<br>CTTGAAGCTTGACAGGATGTTTTCGATTACTCAGTCTCCCAGGGCACTACTGGTCCGTAGGATTCGAT<br>TGGTCGGGGTAGGAGAGTTAAACAACATTTAAAAGAGTTCTCTCAAAAATGTCTAAAGGGATTGTAG<br>GTAGATAACATCCAATCACTGTTTGCACTTATCTGAAATCTTCCCTCTTGGCTGCCCCCAGGTATTTAC<br>TGTGGAGAACATTGCATAGGAATGTCTGGAAAAAGCTTCTACAACTTGTTACAGCCTTCACATTTGTAG<br>AAGCTTT |
| 66 | COX8-<br>opt_ND6-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGATGTACGCCCTGTTCCTGCTGAGCGTGGGCCTGGTGATGGGCT<br>TCGTGGGCTTCAGCAGCAAGCCCAGCCCCATCTACGGCGGCCTGGTGCTGATCGTGAGCGGCGTGG<br>TGGGCTGCGTGATCATCCTGAACTTCGGCGGCGGCTACATGGGCGTGATGGTGTTCCTGATCTACCT<br>GGGCGGCATGATGGTGGTGTTCGGCTACACCACCGCCATGGCCATCGAGGAGTACCCCGAGGCCTG<br>GGGCAGCGGCGTGGAGGTGCTGGTGAGCGTGCTGGTGGGCCTGGCCATGGAGGTGGGCCTGGTGC<br>TGTGGGTGAAGGAGTACGACGGCGTGGTGGTGGTGAACTTCAACAGCGTGGGCAGCTGGATGA<br>TCTACGAGGGCGAGGGCAGCGGCCTGATCCGCGAGGACCCCATCGGCGCCGGCGCCCTGTACGAC<br>TACGGCCGCTGGCTGGTGGTGGTGACCGGCTGGACCCTGTTCGTGGGCGTGTACATCGTGATCGAG<br>ATCGCCCGCGGCAACTAAGAGCACTGGGACGCCCACCGCCCCTTTCCCTCCGCTGCCAGGCGAGCA<br>TGTTGTGGTAATTCTGGAACACAAGAAGAGAAATTGCTGGGTTTAGAACAAGATTATAAACGAATTCGG<br>TGCTCAGTGATCACTTGACAGTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCA |
| 67 | COX8-ND1-<br>3'UTR | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTCCTACTCCTCATTGTACCCATTCTAATCGCAATGGC<br>ATTCCTAATGCTTACCGAACGAAAAATTCTAGGCTATATGCAACTACGCAAAGGCCCCAACGTTGTAGG<br>CCCCTACGGGCTACTACAACCCTTCGCTGACGCCATAAAACTCTTCACCAAAGAGCCCCTAAAACCCG<br>CCACATCTACCATCACCCTCTACATCACCGCCCCGACCTTAGCTCTCACCATCGCTCTTCTACTATGGA<br>CCCCCCTCCCCATGCCCAACCCCCTGGTCAACCTCAACCTAGGCCTCCTATTTATTCTAGCCACCTCT<br>AGCCTAGCCGTTTACTCAATCCTCTGGTCAGGGTGGGCATCAAACTCAAACTACGCCCTGATCGGCGC<br>ACTGCGAGCAGTAGCCCAAACAATCTCATATGAAGTCACCCTAGCCATCATTCTACTATCAACATTACT<br>AATGAGTGGCTCCTTTAACCTCTCCACCCTTATCACAACACAAGAACACCTCTGGTTACTCCTGCCATC<br>ATGGCCCTTGGCCATGATGTGGTTTATCTCCACACTAGCAGAGACCAACCGAACCCCCTTCGACCTTG |

TABLE 1-continued nucleic acid and polypeptide sequences and SEQ ID NOs

| SEQ | description | sequence |
|---|---|---|
| | | CCGAAGGGGAGTCCGAACTAGTCTCAGGCTTCAACATCGAATACGCCGCAGGCCCCTTCGCCCTATT CTTCATGGCCGAATACACAAACATTATTATGATGAACACCCTCACCACTACAATCTTCCTAGGAACAAC ATATGACGCACTCTCCCCTGAACTCTACACAACATATTTTGTCACCAAGACCCTACTTCTAACCTCCCT GTTCTTATGGATTCGAACAGCATACCCCCGATTCCGCTACGACCAACTCATGCACCTCCTATGGAAAA ACTTCCTACCACTCACCCTAGCATTACTTATGTGGTATGTCTCCATGCCCATTACAATCTCCAGCATTC CCCCTCAAACCTAAGAGCACTGGGACGCCCACCGCCCCTTTCCCTCCGCTGCCAGGCGAGCATGTTG TGGTAATTCTGGAACACAAGAAGAGAAATTGCTGGGTTTAGAACAAGATTATAAACGAATTCGGTGCTC AGTGATCACTTGACAGTTTTTTTTTTTTTAAATATTACCCAAAATGCTCCCCAAATAAGAAATGCATCAG CTCAGTCAGTGAATACAAAAAAGGAATTATTTTTCCCTTTGAGGGTCTTTTATACATCTCTCCTCCAACC CCACCCTCTATTCTGTTTCTTCCTCCTCACATGGGGGTACACATACACAGCTTCCTCTTTTGGTTCCAT CCTTACCACCACACCACACGCACACTCCACATGCCCAGCAGAGTGGCACTTGGTGGCAGAAAGTGT GAGCCTCATGATCTGCTGTCTGTAGTTCTGTGAGCTCAGGTCCCTCAAAGGCCTCGGAGCACCCCCTT CCTTGTGACTGAGCCAGGGCCTGCATTTTTGGTTTTCCCCACCCCACACATTCTCAACCATAGTCCTTC TAACAATACCAATAGCTAGGACCCGGCTGCTGTGCACTGGGACTGGGGATTCCACATGTTTGCCTTGG GAGTCTCAAGCTGGACTGCCAGCCCCTGTCCTCCCTTCACCCCCATTGCGTATGAGCATTTCAGAACT CCAAGGAGTCACAGGCATCTTTATAGTTCACGTTAACATATAGACACTGTTGGAAGCAGTTCCTTCTAA AAGGGTAGCCCTGGACTTAATACCAGCCGGATACCTCTGGCCCCCACCCCATTACTGTACCTCTGGA GTCACTACTGTGGGTCGCCACTCCTCTGCTACACAGCACGGCTTTTTCAAGGCTGTATTGAGAAGGGA AGTTAGGAAGAGGGTGTGCTGGGCTAACCAGCCCACAGAGCTCACATTCCTGTCCCTTGGGTGAAA AATACATGTCCATCCTGATATCTCCTGAATTCAGAAATTAGCCTCCACATGTGCAATGGCTTTAAGAGC CAGAAGCAGGGTTCTGGGAATTTTGCAAGTTACCTGTGGCCAGGTGTGGTCTCGGTTACCAAATACGG TTACCTGCAGCTTTTTAGTCCTTTGTGCTCCCACGGGTCTACAGAGTCCCATCTGCCCAAAGGTCTTGA AGCTTGACAGGATGTTTTCGATTACTCAGTCTCCCAGGGCACTACTGGTCCGTAGGATTCGATTGGTC GGGGTAGGAGAGTTAAACAACATTTAAACAGAGTTCTCTCAAAAATGTCTAAAGGGATTGTAGGTAGAT AACATCCAATCACTGTTTGCACTTATCTGAAATCTTCCCTCTTGGCTGCCCCCAGGTATTTACTGTGGA GAACATTGCATAGGAATGTCTGGAAAAAGCTTCTACAACTTGTTACAGCCTTCACATTTGTAGAAGCTT T |
| 68 | COX8-ND1-3'UTR* | ATGTCCGTCCTGACGCGCCTGCTGCTGCGGGGCTTGACACGGCTCGGCTCGGCGGCTCCAGTGCGG CGCGCCAGAATCCATTCGTTGATGGCCAACCTCCTACTCCTCATTGTACCCATTCTAATCGCAATGGC ATTCCTAATGCTTACCGAACGAAAAATTCTAGGCTATATGCAACTACGCAAAGGCCCCAACGTTGTAGG CCCCTACGGGCTACTACAACCCTTCGCTGACGCCATAAAACTCTTCACCAAAGAGCCCCTAAAACCCG CCACATCTACCATCACCCCTCTACATCACCGCCCCGACCTTAGCTCTCACCATCGCTCTTCTACTATGGA CCCCCCTCCCCATGCCCAACCCCCTGGTCAACCTCAACCTAGGCCTCCTATTTATTCTAGCCACCTCT AGCCTAGCCGTTTACTCAATCCTCTGGTCAGGGTGGGCATCAAACTCAAACTACGCCCTGATCGGCGC ACTGCGAGCAGTAGCCCAAACAATCTCATATGAAGTCACCCTAGCCATCATTCTACTATCAACATTACT AATGAGTGGCTCCTTTAACCTCTCCACCCTTATCACAACACAAGAACACCTCTGGTTACTCCTGCCATC ATGGCCCTTGGCCATGATGTGGTTTATCTCCACACTAGCAGGAGCAACCGAACCCCCTTCGACCTTG CCGAAGGGGAGTCCGAACTAGTCTCAGGCTTCAACATCGAATACGCCGCAGGCCCCTTCGCCCTATT CTTCATGGCCGAATACACAAACATTATTATGATGAACACCCTCACCACTACAATCTTCCTAGGAACAAC ATATGACGCACTCTCCCCTGAACTCTACACAACATATTTTGTCACCAAGACCCTACTTCTAACCTCCCT GTTCTTATGGATTCGAACAGCATACCCCCGATTCCGCTACGACCAACTCATGCACCTCCTATGGAAAA ACTTCCTACCACTCACCCTAGCATTACTTATGTGGTATGTCTCCATGCCCATTACAATCTCCAGCATTC CCCCTCAAACCTAAGAGCACTGGGACGCCCACCGCCCCTTTCCCTCCGCTGCCAGGCGAGCATGTTG TGGTAATTCTGGAACACAAGAAGAGAAATTGCTGGGTTTAGAACAAGATTATAAACGAATTCGGTGCTC AGTGATCACTTGACAGTTTTTTTTTTTTTAAATATTACCCAAAATGCTCCCCAAATAAGAAATGCATCAG CTCAGTCAGTGAATACAAAAAAGGAATTATTTTTCCCTTTGAGGGTCTTTTATACATCTCTCCTCCAACC CCACCCTCTATTCTGTTTCTTCCTCCTCACATGGGGGTACACATACACAGCTTCCTCTTTTGGTTCCAT CCTTACCACCACACCACACGCACACTCCACATGCCCAGCAGAGTGGCACTTGGTGGCAGAAAGTGT GAGCCTCATGATCTGCTGTCTGTAGTTCTGTGAGCTCAGGTCCCTCAAAGGCCTCGGAGCACCCCCTT CCTTGTGACTGAGCCAGGGCCTGCATTTTTGGTTTTCCCCACCCCACACATTCTCAACCATAGTCCTTC TAACAATACCAATAGCTAGGACCCGGCTGCTGTGCACTGGGACTGGGGATTCCACATGTTTGCCTTGG GAGTCTCAAGCTGGACTGCCA |
| 69 | COX8-opt_ND1-3'UTR | ATGTCCGTCCTGACGCGCCTGCTGCTGCGGGGCTTGACACGGCTCGGCTCGGCGGCTCCAGTGCGG CGCGCCAGAATCCATTCGTTGATGGCCAACCTGCTGCTGCTGATCGTGCCCATCCTGATCGCCATGG CCTTCCTGATGCTGACCGAGCGCAAGATCCTGGGCTACATGCAGCTGCGCAAGGGCCCCAACGTGGT GGGGCCCCTACGGCCTGCTGCAGCCCTTCGCCGACGCCATCAAGCTGTTCACCAAGGAGCCCCTGAA GCCCGCCACCAGCACCATCACCCTGTACATCACCGCCCCCACCCTGGCCCTGACCATCGCCCTGCTG CTGTGGACCCCCCTGCCCATGCCCAACCCCCTGGTGAACCTGAACCTGGGCCTGCTGTTCATCCTGG CCACCAGCAGCCTGGCCGTGTACAGCATCCTGTGGAGCGGCTGGGCCAGCAACAGCAACTACGCCC TGATCGGCGCCCTGCGCGCCGTGGCCCAGACCATCAGCTACGAGGTGACCCTGGCCATCATCCTGC TGAGCACCCTGCTGATGAGCGGCAGCTTCAACCTGAGCACCCTGATCACCACCCAGGAGCACCTGTG GCTGCTGCTGCCCAGCTGGCCCCTGGCCATGATGTGGTTCATCAGCACCCTGGCCGAGACCAACCG CACCCCCTTCGACCTGGCCGAGGGCGAGAGCGAGCTGGTGAGCGGCTTCAACATCGAGTACGCCGC CGGCCCCTTCGCCCTGTTCTTCATGGCCGAGTACACCAACATCATCATGATGAACACCCTGACCACCA CCATCTTCCTGGGCACCACCTACGACGCCCTGAGCCCCGAGCTGTACACCACCCTACTTCGTGACCAA GACCCTGCTGCTGACCAGCCTGTTCCTGTGGACCGCACCGCCTACCCCCGCTTCCGCTACGACCAG CTGATGCACCTGCTGTGGAAGAACTTCCTGCCCCTGACCCTGGCCCTGCTGATGTGGTACGTGAGCA TGCCCATCACCATCAGCAGCATCCCCCCCCAGACCTAAGAGCACTGGGACGCCCACCGCCCCTTTCC CTCCGCTGCCAGGCGAGCATGTTGTGGTAATTCTGGAACACAAGAAGAGAAATTGCTGGGTTTAGAAC AAGATTATAAACGAATTCGGTGCTCAGTGATCACTTGACAGTTTTTTTTTTTTTAAATATTACCCAAAAT GCTCCCCAAATAAGAAATGCATCAGCTCAGTCAGTGAATACAAAAAAGGAATTATTTTTCCCTTTGAGG GTCTTTTATACATCTCTCCTCCAACCCCACCCTCTATTCTGTTTCTTCCTCCTCACATGGGGTACACAT ACACAGCTTCCTCTTTTGGTTCCATCCTTACCACCACACCACACGCACACTCCACATGCCCAGCAGAG TGGCACTTGGTGGCAGAAAGTGTGAGCCTCATGATCTGCTGTCTGTAGTTCTGTGAGCTCAGGTCCC |

| SEQ | description | sequence |
|---|---|---|
| | | TCAAAGGCCTCGGAGCACCCCCTTCCTTGTGACTGAGCCAGGGCCTGCATTTTTGGTTTTCCCCACCC<br>CACACATTCTCAACCATAGTCCTTCTAACAATACCAATAGCTAGGACCCGGCTGCTGTGCACTGGGAC<br>TGGGGATTCCACATGTTTGCCTTGGGAGTCTCAAGCTGGACTGCCAGCCCCTGTCCTCCCTTCACCCC<br>CATTGCGTATGAGCATTTCAGAACTCCAAGGAGTCACAGGCATCTTTATAGTTCACGTTAACATATAGA<br>CACTGTTGGAAGCAGTTCCTTCTAAAAGGGTAGCCCTGGACTTAATACCAGCCGGATACCTCTGGCCC<br>CCACCCCATTACTGTACCTCTGGAGTCACTACTGTGGGTCGCCACTCCTCTGCTACACAGCACGGCTT<br>TTTCAAGGCTGTATTGAGAAGGGAAGTTAGGAAGAAGGGTGTGCTGGGCTAACCAGCCCACAGAGCT<br>CACATTCCTGTCCCTTGGGTGAAAAATACATGTCCATCCTGATATCTCCTGAATTCAGAAATTAGCCTC<br>CACATGTGCAATGGCTTTAAGAGCCAGAAGCAGGGTTCTGGGAATTTTGCAAGTTACCTGTGGCCAGG<br>TGTGGTCTCGGTTACCAAATACGGTTACCTGCAGCTTTTTAGTCCTTTGTGCTCCCACGGGTCTACAGA<br>GTCCCATCTGCCCAAAGGTCTTGAAGCTTGACAGGATGTTTTCGATTACTCAGTCTCCCAGGGCACTA<br>CTGGTCCGTAGGATTCGATTGGTCGGGTAGGAGAGTTAAACAACATTTAAACAGAGTTCTCTCAAAA<br>ATGTCTAAAGGGATTGTAGGTAGATAACATCCAATCACTGTTTGCACTTATCTGAAATCTTCCCTCTTG<br>GCTGCCCCCAGGTATTTACTGTGGAGAACATTGCATAGGAATGTCTGGAAAAAGCTTCTACAACTTGTT<br>ACAGCCTTCACATTTGTAGAAGCTTT |
| 70 | COX8-<br>opt_ND1-<br>3'UTR* | ATGTCCGTCCTGACGCGCCTGCTGCTGCGGGGCTTGACACGGCTCGGCTCGGCGGCTCCAGTGCGG<br>CGCGCCAGAATCCATTCGTTGATGGCCAACCTGCTGCTGCTGATCGTGCCCATCCTGATCGCCATGG<br>CCTTCCTGATGCTGACCGAGCGCAAGATCCTGGGCTACATGCAGCTGCGCAAGGGCCCCAACGTGGT<br>GGGCCCCTACGGCCTGCTGCAGCCCTTCGCCGACGCCATCAAGCTGTTCACCAAGGAGCCCCTGAA<br>GCCCGCCACCAGCACCATCACCCTGTACATCACCGCCCCCACCCTGGCCCTGACCATCGCCCTGCTG<br>CTGTGGACCCCCCTGCCCATGCCCAACCCCCTGGTGAACCTGAACCTGGGCCTGCTGTTCATCCTGG<br>CCACCAGCAGCCTGGCCGTGTACAGCATCCTGTGGAGCGGCTGGGCCAGCAACAGCAACTACGCCC<br>TGATCGGCGCCCTGCGCGCCGTGGCCCAGACCATCAGCTACGAGGTGACCCTGGCCATCATCCTGC<br>TGAGCACCCTGCTGATGAGCGGCAGCTTCAACCTGAGCACCCTGATCACCACCCAGGAGCACCTGTG<br>GCTGCTGCTGCCCAGCTGGCCCCTGGCCATGATGTGGTTCATCAGCACCCTGGCCGAGACCAACCG<br>CACCCCCTTCGACCTGCCGAGGGCGAGAGCGAGCTGGTGAGCGGCTTCAACATCGAGTACGCCGC<br>CGGCCCCTTCGCCCTGTTCTTCATGGCCGAGTACACCAACATCATCATGATGAACACCCTGACCACCA<br>CCATCTTCCTGGGCACCACCTACGACGCCCTGAGCCCCGAGCTGTACACCACCTACTTCGTGACCAA<br>GACCCTGCTGCTGACCAGCCTGTTCCTGTGGATCCGCACCGCCTACCCCCGCTTCCGCTACGACCAG<br>CTGATGCACCTGCTGTGGAAGAACTTCCTGCCCCTGACCCTGGCCCTGCTGATGTGGTACGTGAGCA<br>TGCCCATCACCATCAGCAGCATCCCCCCCAGACCTAAGAGCACTGGGACGCCCACCGCCCCTTTCC<br>CTCCGCTGCCAGGCGAGCATGTTGTGGTAATTCTGGAACACAAGAAGAGAAATTGCTGGGTTTAGAAC<br>AAGATTATAAACGAATTCGGTGCTCAGTGATCACTTGACAGTTTTTTTTTTTTAAATATTACCCAAAAT<br>GCTCCCCAAATAAGAAATGCATCAGCTCAGTCAGTGAATACAAAAAAGGAATTATTTTTCCCTTTGAGG<br>GTCTTTTATACATCTCTCCTCCAACCCCACCCTCTATTCTGTTTCTTCCTCCTCACATGGGGGTACACAT<br>ACACAGCTTCCTCTTTTGGTTCCATCCTTACCACCACACCACACGCACACTCCACATGCCCAGCAGAG<br>TGGCACTTGGTGGCCAGAAAGTGTGAGCCTCATGATCTGCTGTCTGTAGTTCTGTGAGCTCAGGTCCC<br>TCAAAGGCCTCGGAGCACCCCCTTCCTTGTGACTGAGCCAGGGCCTGCATTTTTGGTTTTCCCCACCC<br>CACACATTCTCAACCATAGTCCTTCTAACAATACCAATAGCTAGGACCCGGCTGCTGTGCACTGGGAC<br>TGGGGATTCCACATGTTTGCCTTGGGAGTCTCAAGCTGGACTGCCA |
| 71 | OPA1-ND4-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTAAAACTAATCGTCCCAACAATTATGTTACTACCACTGACATGGCTTTCCAAAAAACACATG<br>ATTTGGATCAACACAACCACCCACAGCCTAATTATTAGCATCATCCCTCTACTATTTTTAACCAAATCA<br>ACAACAACCTATTTAGCTGTTCCCCAACCTTTTCCTCCGACCCCCTAACAACCCCCCTCCTAATGCTAA<br>CTACCTGGCTCCTACCCCTCACAATCATGGCAAGCCAACGCCACTTATCCAGTGAACCACTATCACGA<br>AAAAAACTCTACCTCTCTATGCTAATCTCCCTACAAATCTCCTTAATTATGACATTCACAGCCACAGAAC<br>TAATCATGTTTTATATCTTCTTCGAAACCACACTTATCCCCACCTTGGCTATCATCACCCGATGGGGCA<br>ACCAGCCAGAACGCCTGAACGCAGGCACATACTTCCTATTCTACACCCTAGTAGGCTCCCTTCCCCTA<br>CTCATCGCACTAATTACACTCACAACACCCTAGGCTCACTAAACATTCTACTACTCACTCTCACTGCC<br>CAAGAACTATCAAACTCCTGGGCCAACAACTTAATGTGGCTAGCTTACACAATGGCTTTTATGGTAAAG<br>ATGCCTCTTTACGGACTCCACTTATGCTCCCTAAAGCCCATGTCGAAGCCCCCATCGCTGGGTCAAT<br>GGTACTTGCCGCAGTACTCTTAAAACTAGGCGGCTATGGTATGATGCGCCTCACACTCATTCTCAACC<br>CCCTGACAAAACACATGGCCTACCCCTTCCTTGTACTATCCCTATGGGGCATGATTATGACAAGCTCC<br>ATCTGCCTACGACAAAACAGACCTAAAATCGCTCATTGCATACTCTTCAATCAGCCACATGGCCCTCGTA<br>GTAACAGCCATTCTCATCCAAACCCCCTGGAGCTTCACCGGCGCAGTCATTCTCATGATCGCCCACGG<br>GCTTACATCCTCATTACTATTCTGCCTAGCAAACTCAAACTACGAACGCACTCACAGTCGCATCATGAT<br>CCTCTCTCAAGGACTTCAAACTCTACTCCCACTAATGGCTTTTTGGTGGCTTCTAGCAAGCCTCGCTAA<br>CCTCGCCTTACCCCCCACTATTAACCTACTGGGAGAACTCTCTGTGCTAGTAACCACGTTCTCCTGGT<br>CAAATATCACTCTCCTACTTACAGGACTCAACATGCTAGTCACAGCCCTATACTCCCTCTACATGTTTA<br>CCACAACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACCGGGTTT<br>TCCTCTTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCAGCCCCTGTCCTCCCTTCACCCCCATTGCGTATGAGCATTTCAGAACTCCAAG |

TABLE 1-continued nucleic acid and polypeptide sequences and SEQ ID NOs

| SEQ | description | sequence |
|---|---|---|
|  |  | GAGTCACAGGCATCTTTATAGTTCACGTTAACATATAGACACTGTTGGAAGCAGTTCCTTCTAAAAGGG<br>TAGCCCTGGACTTAATACCAGCCGGATACCTCTGGCCCCCACCCCATTACTGTACCTCTGGAGTCACT<br>ACTGTGGGTCGCCACTCCTCTGCTACACAGCACGGCTTTTTCAAGGCTGTATTGAGAAGGGAAGTTAG<br>GAAGAAGGGTGTGCTGGGCTAACCAGCCCACAGAGCTCACATTCCTGTCCCTTGGGTGAAAAATACAT<br>GTCCATCCTGATATCTCCTGAATTCAGAAATTAGCCTCCACATGTGCAATGGCTTTAAGAGCCAGAAGC<br>AGGGTTCTGGGAATTTTGCAAGTTACCTGTGGCCAGGTGTGGTCTCGGTTACCAAATACGGTTACCTG<br>CAGCTTTTTAGTCCTTTGTGCTCCCACGGGTCTACAGAGTCCCATCTGCCCAAAGGTCTTGAAGCTTG<br>ACAGGATGTTTTCGATTACTCAGTCTCCCAGGGCACTACTGGTCCGTAGGATTCGATTGGTCGGGGTA<br>GGAGAGTTAAACAACATTTAAACAGAGTTCTCTCAAAAATGTCTAAAGGGATTGTAGGTAGATAACATC<br>CAATCACTGTTTGCACTTATCTGAAATCTTCCCTCTTGGCTGCCCCCAGGTATTTACTGTGGAGAACAT<br>TGCATAGGAATGTCTGGAAAAAGCTTCTACAACTTGTTACAGCCTTCACATTTGTAGAAGCTTT |
| 72 | OPA1-ND4-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTAAAACTAATCGTCCCAACAATTATGTTACTACCACTGACATGGCTTTCCAAAAACACATG<br>ATTTGGATCAACACAACCACCCACAGCCTAATTATTAGCATCATCCCTCTACTATTTTTAACCAAATCA<br>ACAACAACCTATTTAGCTGTTCCCAACCTTTTCCTCCGACCCCCTAACAACCCCCCTCCTAATGCTAA<br>CTACCTGGCTCCTACCCCTCACAATCATGGCAAGCCAACGCCACTTATCCAGTGAACCACTATCACGA<br>AAAAAACTCTACCTCTCTATGCTAATCTCCCTACAAATTCCTAAAATTATGACATTCACAGCCACAGAAC<br>TAATCATGTTTTATATCTTCTTCGAAACCACACTTATCCCCACCTTGGCTATCATCACCCGATGGGCA<br>ACCAGCCAGAACGCCTGAACGCAGGCACATATTCCTATTCTACACCCTAGTAGGCTCCCTTCCCCTA<br>CTCATCGCACTAATTTACACTCACAACACCCTAGGCTCACTAAACATTCTACTACTCACTCTCACTGCC<br>CAAGAACTATCAAACTCCTGGGCCAACAACTTAATGTGGCTAGCTTACACAATGGCTTTTATGGTAAAG<br>ATGCCTCTTTACGGACTCCACTTATGGCTCCCTAAAGCCCATGTCGAAGCCCCCATCGCTGGGTCAAT<br>GGTACTTGCCGCAGTACTCTTAAAACTAGGCGGCTATGGTATGATGCGCCTCACACTCATTCTCAACC<br>CCCTGACAAAACACATGGCCTACCCCTTCCTTGTACTATCCCTATGGGGCATGATTATGACAAGCTCC<br>ATCTGCTACGACAAACAGACCTAAAATCGCTCATTGCATACTCTTCAATCAGCCACATGGCCCTCGTA<br>GTAACAGCCATTCTCATCCAAACCCCCTGGAGCTTCACCGGCGCAGTCATTCTCATGATCGCCCACGG<br>GCTTACATCCTCATTACTATTCTGCCTAGCAAACTCAAACTACGAACGCACTCACAGTCGCATCATGAT<br>CCTCTCTCAAGGACTTCAAACTCTACTCCCACTAATGGCTTTTTGGTGGCTTCTAGCAAGCCTCGCTAA<br>CCTCGCCTTACCCCCCACTATTAACCTACTGGGAGAACTCTCTGTGCTAGTAACCACGTTCTCCTGGT<br>CAAATATCACTCTCCTACTTACAGGACTCAACATGCTAGTCACAGCCCTATACTCCCTCTACATGTTTA<br>CCACAACACAATGGGGCTCACTCACCCACCACATTAACAACATGAAACCCTCATTCACACGAGAAAAC<br>ACCCTCATGTTCATGCACCTATCCCCCATTCTCCTCCTATCCCTCAACCCCGACATCATTACCGGGTTT<br>TCCTCTTAAGAGCACTGGGACGCCCACCGCCCCTTTCCCTCCGCTGCCAGGCGAGCATGTTGTGGTA<br>ATTCTGGAACACAAGAAGAGAAATTGCTGGGTTTAGAACAAGATTATAAACGAATTCGGTGCTCAGTGA<br>TCACTTGACAGTTTTTTTTTTTTAAATATTACCCAAAATGCTCCCCAAATAAGAAATGCATCAGCTCAG<br>TCAGTGAATACAAAAAAGGAATTATTTTTCCCTTTGAGGGTCTTTTATACATCTCTCCTCCAACCCCACC<br>CTCTATTCTGTTTCTTCCTCCTCACATGGGGGTACACATACACAGCTTCCTCTTTTGGTTCCATCCTTAC<br>CACCACACCACACGCACACTCCACATGCCCAGCAGAGTGGCACTTGGTGGCCAGAAAGTGTGAGCCT<br>CATGATCTGCTGTCTGTAGTTCTGTGAGCTCAGGTCCCTCAAAGGCCTCGGAGCACCCCCTTCCTTGT<br>GACTGAGCCAGGGCCTGCATTTTTGGTTTTCCCACCCCACACATTCTCAACCATAGTCCTTCTAACAA<br>TACCAATAGCTAGGACCCGGCTGCTGTGCACTGGGACTGGGGATTCCACATGTTTGCCTTGGGAGTC<br>TCAAGCTGGACTGCCA |
| 73 | OPA1-<br>opt_ND4-<br>3'UTR | GTGCTGCCCGCCTAGAAAGGGTGAAGTGGTTGTTTcCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCTCTGACCTGGCTGAGCAAGAAACACAT<br>GATCTGGATCAACACCACCACGCACAGCCTGATCATCAGCATCATCCCTCTGCTGTTCTTCAACCAGA<br>TCAACAACAACCTGTTCAGCTGCAGCCCCACCTTCAGCAGCGACCCCTCTGACAACACCTCTGCTGATG<br>CTGACCACCTGGCTGCTGCCCCTCACAATCATGGCCTCTCAGAGACACCTGAGCAGCGAGCCCCTGA<br>GCCGGAAGAAACTGTACCTGAGCATGCTGATCTCCCTGCAGATCTCTCTGATCATGACCTTCACCGCC<br>ACCGAGCTGATCATGTTCTACATCTTTTTCGAGACAACGCTGATCCCCACACTGGCCATCATCACCAG<br>ATGGGGCAACCAGCCTGAGAGACTGAACGCCGGCACCTACTTTCTGTTCTACACCCTCGTGGGCAGC<br>CTGCCACTGCTGATTGCCCTGATCTACACCCCACAACACCCCTGGGCTCCCTGAACATCCTGCTGCTGAC<br>ACTGACAGCCCAAGAGCTGAGCAACAGCTGGGCCAACAATCTGATGTGGCTGGCCTACACAATGGCC<br>TTCATGGTCAAGATGCCCCTGTACGGCCTGCACCTGTGGCTGCCTAAAGCTCATGTGGAAGCCCTAT<br>CGCCGGCTCTATGGTGCTGGCTGCAGTGCTGCTGAAACTCGGCGGCTACGGCATGATGCGGCTGAC<br>CCTGATTCTGAATCCCCTGACCAAGCACATGGCCTATCCATTTCTGGTGCTGAGCCTGTGGGGCATGA<br>TTATGACCAGCAGCATCTGCCTGCGGCAGACCGATCTGAAGTCCCTGATCGCCTACAGCTCCATCAG<br>CCACATGGCCCTGGTGGTCACCGCCATCCTGATTCAGACCCCTTGGAGCTTTACAGGCGCCGTGATC<br>CTGATGATTGCCCACGGCCTGACAAGCAGCCTGCTGTTTTGTCTGGCCAACAGCAACTACGAGCGGA<br>CCCACAGCAGAATCATGATCCTGTCTCAGGGCTGCAGACCCTCCTGCCTCTTATGGCTTTTTGGTGG<br>CTGCTGGCCTCTCTGGCCAATCTGGCACTGCCTCCTACCATCAATCTGCTGGGCGAGCTGAGCGTGC<br>TGGTCACCACATTCAGCTGGTCAATATCACCCCTGCTGCTCACCGGCCTGAACATGCTGGTTACAGCC<br>CTGTACTCCCTGTACATGTTCACCACCACACAGTGGGGAAGCCTGACACACCCACATCAACAATATGAA<br>GCCCAGCTTCACCCGCGAGAACACCCTGATGTTCATGCATCTGAGCCCCATTCTGCTGCTGTCCCTGA<br>ATCCTGATATCATCACCGGCTTCTCCAGCTGAGAGCACTGGGACGCCCACCGCCCCTTTCCCTCCGC<br>TGCCAGGCGAGCATGTTGTGGTAATTCTGGAACACAAGAAGAGAAATTGCTGGGTTTAGAACAAGATT<br>ATAAACGAATTCGGTGCTCAGTGATCACTTGACAGTTTTTTTTTTTTAAATATTACCCAAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA |

TABLE 1-continued nucleic acid and polypeptide sequences and SEQ ID NOs

| SEQ | description | sequence |
|---|---|---|
| | | GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCAAAACAATACCAATAGCTAGGACCCGGCTGCTGTGCACTGGGACTGGG<br>GATTCCACATGTTTGCCTTGGGAGTCTCAAGCTGGACTGCCAGCCCCTGTCCTCCCTTCACCCCCATT<br>GCGTATGAGCATTTCAGAACTCCAAGGAGTCACAGGCATCTTTATAGTTCACGTTAACATATAGACACT<br>GTTGGAAGCAGTTCCTTCTAAAAGGGTAGCCCTGGACTTAATACCAGCCGGATACCTCTGGCCCCCAC<br>CCCATTACTGTACCTCTGGAGTCACTACTGTGGGTCGCCACTCCTCTGCTACACAGCACGGCTTTTTC<br>AAGGCTGTATTGAGAAGGGAAGTTAGGAAGAAGGGTGTGCTGGGCTAACCAGCCCACAGAGCTCACA<br>TTCCTGTCCCTTGGGTGAAAAATACATGTCCATCCTGATATCTCCTGAATTCAGAAATTAGCCTCCACA<br>TGTGCAATGGCTTTAAGAGCCAGAAGCAGGGTTCTGGGAATTTTGCAAGTTACCTGTGGCCAGGTGTG<br>GTCTCGGTTACCAAATACGGTTACCTGCAGCTTTTTAGTCCTTTGTGCTCCCACGGGTCTACAGAGTC<br>CCATCCTGCCCAAAGGTCTTGAAGCTTGACAGGATGTTTTCGATTACTCAGTCTCCCAGGGCACTACTG<br>GTCCGTAGGATTCGATTGGTCGGGGTAGGAGAGTTAAACAACATTTAAACAGAGTTCTCTCAAAAATGT<br>CTAAAGGGATTGTAGGTAGATAACATCCAATCACTGTTTGCACTTATCTGAAATCTTCCCTCTTGGCTG<br>CCCCCAGGTATTTACTGTGGAGAACATTGCATAGGAATGTCTGGAAAAAGCTTCTACAACTTGTTACAG<br>CCTTCACATTTGTAGAAGCTTT |
| 74 | OPA1-<br>opt_ND4-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCTCTGACCTGGCTGAGCAAGAAACACAT<br>GATCTGGATCAACACCACCACGCACAGCCTGATCATCAGCATCATCCCTCTGCTGTTCTTCAACCAGA<br>TCAACAACAACCTGTTCAGCTGCAGCCCCACCTTCAGCAGCGACCCCTCTGACAACACCTCTGCTGATG<br>CTGACCACCTGGCTGCTGCCCCTCACAATCATGGCCTCTCAGAGACACCTGAGCAGCGAGCCCCTGA<br>GCCGGAAGAAACTGTACCTGAGCATGCTGATCTCCCTGCAGATCTCTCTGATCATGACCTTCACCGCC<br>ACCGAGCTGATCATGTTCTACATCTTTTTCGAGACAACGCTGATCCCCACACTGGCCATCATCACCAG<br>ATGGGGCAACCAGCCTGAGAGACTGAACGCCGGCCACCTACTTTCTGTTCTACACCCTCGTGGGCAGC<br>CTGCCACTGCTGATTGCCCTGATCTACACCCCACAACACCCTGGGCTCCCTGAACATCCTGCTGCTGAC<br>ACTGACAGCCCAAGAGCTGAGCAACAGCTGGGCCAACAATCTGATGTGGCTGGCCTACACAATGGCC<br>TTCATGGTCAAGATGCCCCTGTACGGCCTGCACCTGTGGCTGCCTAAAGCTCATGTGGAAGCCCCTAT<br>CGCCGGCTCTATGGTGCTGGCTGCAGTGCTGCTGAAACTCGGCGGCTACGGCATGATGCGGCTGAC<br>CCTGATTCTGAATCCCCTGACCAAGCACATGGCCTATCCATTTCTGGTGCTGAGCCTGTGGGGCATGA<br>TTATGACCAGCAGCATCTGCCTGCGGCAGACCGATCTGAAGTCCCTGATCGCCTACAGCTCCATCAG<br>CCACATGGCCCTGGTGGTCACCGCCATCCTGATTCAGACCCCTTGGAGCTTTACAGGCGCCGTGATC<br>CTGATGATTGCCCACGGCCTGACAAGCAGCCTGCTGTTTTGTCTGGCCAACAGCAACTACGAGCGGA<br>CCCACAGCAGAATCATGATCCTGTCTCAGGGCCTGCAGACCCTCCTGCCTCTTATGCTTTTTTGGTGG<br>CTGCTGGCCTCTCTGGCCAATCTGGCACTGCCTCCTACCATCAATCTGCTGGGCGAGCTGAGCGTGC<br>TGGTCACCACATTCAGCTGGTCCAATATCACCCTGCTGCTCACCGGCCTGAACATGTGGTTACAGCC<br>CTGTACTCCCTGTACATGTTCACCACCACACAGTGGGGAAGCCTGACACACCACATCAACAATATGAA<br>GCCCAGCTTCACCCGCGAGAACACCCTGATGTTCATGCATCTGAGCCCCATTCTGCTGCTGTCCCTGA<br>ATCCTGATATCATCACCGGCTTCTCCAGCTGAGAGCACTGGGACGCCCACCGCCCCTTTCCCTCCGC<br>TGCCAGGCGAGCATGTTGTGGTAATTCTGGAACAAGAAGAGAAATTGCTGGGTTTAGAACAAGATT<br>ATAAACGAATTCGGTGCTCAGTGATCACTTGACAGTTTTTTTTTTTTAAATATTACCCAAATGCTCC<br>CCAAATAAGAAATGCATCAGCTCAGTCAGTGAATACAAAAAAGGAATTATTTTTCCCTTTGAGGGTCTTT<br>TATACATCTCTCCTCCAACCCCACCCTCTATTCTGTTTCTTCCTCCTCACATGGGGGTACACATACACA<br>GCTTCCTCTTTTGGTTCCATCCTTACCACCACACCACACGCACACTCCACATGCCCAGCAGAGTGGCA<br>CTTGGTGGCCAGAAAGTGTGAGCCTCATGATCTGCTGTCTGTAGTTCTGTGAGCTCAGGTCCCTCAAA<br>GGCCTCGGAGCACCCCCTTCCTTGTGACTGAGCCAGGGCCTGCATTTTTGGTTTTCCCCACCCCACA<br>CATTCTCAACCATAGTCCTTCTAACAATACCAATAGCTAGGACCCGGCTGCTGTGCACTGGGACTGGG<br>GATTCCACATGTTTGCCTTGGGAGTCTCAAGCTGGACTGCCA |
| 75 | OPA1-<br>opt_ND4*-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCCCTGACCTGGCTGAGCAAGAAGCACA<br>TGATCTGGATCAACACCACCACACGCACAGCCTGATCATCAGCATCATCCCCCTGCTGTTCTTCAACCAG<br>ATCAACAACAACCTGTTCAGCTGCAGCCCCACCTTCAGCAGCGACCCCCTGACCACCCCCCTGCTGA<br>TGCTGACCACCTGGCTGCTGCCCCTGACCATCATGGCCAGCAGCGCCACTGAGCAGCGAGCCCC<br>TGAGCCGCAAGAAGCTGTACCTGAGCATGCTGATCAGCCTGCAGATCAGCCTGATCATGACCTTCACC<br>GCCACCGAGCTGATCATGTTCTACATCTTCTTCGAGACCACCCTGATCCCCACCCTGGCCATCATCAC<br>CCGCTGGGGCAACCAGCCCGAGCGCCTGAACGCCGGCACCTACTTCCTGTTCTACACCCTGGTGGG<br>CAGCCTGCCCCTGCTGATCGCCCTGATCTACACCCCACAACACCCTGGGCAGCCTGAACATCCTGCTG<br>CTGACCCTGACCGCCCAGGAGCTGAGCAACAGCTGGGCCAACAACCTGATGTGGCTGGCCTACACCA<br>TGGCCTTCATGGTGAAGATGCCCCTGTACGGCCTGCACCTGTGGCTGCCCAAGGCCCACGTGGAGG<br>CCCCCATCGCCGGCAGCATGGTGCTGGCCGCCGTGCTGCTGAAGCTGGGCGGCTACGGCATGATGC<br>GCCTGACCCTGATCCTGAACCCCCTGACCAAGCACATGGCCTACCCCTTCCTGGTGCTGAGCCTGTG<br>GGGCATGATCATGACCAGCAGCATCTGCCTGCGCCAGACCGACCTGAAGAGCCTGATCGCCTACAGC<br>AGCATCAGCCACATGGCCCTGGTGGTGACCGCCATCCTGATCCAGACCCCCTGGAGCTTCACCGGCG<br>CCGTGATCCTGATGATCGCCCACGGCCTGACCAGCAGCCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA |

TABLE 1-continued nucleic acid and polypeptide sequences and SEQ ID NOs

| SEQ | description | sequence |
|---|---|---|
| | | TCAACAACATGAAGCCCAGCTTCACCCGCGAGAACACCCTGATCTTCATGCACCTGAGCCCCATCCTG<br>CTGCTGAGCCTGAACCCCGACATCATCACCGGCTTCAGCAGCTAAGAGCACTGGGACGCCCACCGCC<br>CCTTTCCCTCCGCTGCCAGGCGAGCATGTTGTGGTAATTCTGGAACACAAGAAGAGAAATTGCTGGGT<br>TTAGAACAAGATTATAAACGAATTCGGTGCTCAGTGATCACTTGACAGTTTTTTTTTTTTAAATATTAC<br>CCAAAATGCTCCCCAAATAAGAAATGCATCAGCTCAGTCAGTGAATACAAAAAAGGAATTATTTTTCCC<br>TTTGAGGGTCTTTTATACATCTCTCCTCCAACCCCACCCTCTATTCTGTTTCTTCCTCCTCACATGGGG<br>GTACACATACACAGCTTCCTCTTTTGGTTCCATCCTTACCACCACACCACACGCACACTCCACATGCCC<br>AGCAGAGTGGCACTTGGTGGCCAGAAAGTGTGAGCCTCATGATCTGCTGTCTGTAGTTCTGTGAGCTC<br>AGGTCCCTCAAAGGCCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCTGTGCA<br>CTGGGACTGGGGATTCCACATGTTTGCCTTGGGAGTCTCAAGCTGGACTGCCAGCCCCTGTCCTCCC<br>TTCACCCCCATTGCGTATGAGCATTTCAGAACTCCAAGGAGTCACAGGCATCTTTATAGTTCACGTTAA<br>CATATAGACACTGTTGGAAGCAGTTCCTTCTAAAAGGGTAGCCCTGGACTTAATACCAGCCGGATACC<br>TCTGGCCCCCACCCCATTACTGTACCTCTGGAGTCACTACTGTGGGTCGCCACTCCTCTGCTACACAG<br>CACGGCTTTTTCAAGGCTGTATTGAGAAGGGAAGTTAGGAAGAAGGGTGTGCTGGGCTAACCAGCCC<br>ACAGAGCTCACATTCCTGTCCCTTGGGTGAAAAATACATGTCCATCCTGATATCTCCTGAATTCAGAAA<br>TTAGCCTCCACATGTGCAATGGCTTTAAGAGCCAGAAGCAGGGTTCTGGGAATTTTGCAAGTTACCTG<br>TGGCCAGGTGTGGTCTCGGTTACCAAATACGGTTACCTGCAGCTTTTTAGTCCTTTGTGCTCCCACGG<br>GTCTACAGAGTCCCATCTGCCCAAAGGTCTTGAAGCTTGACAGGATGTTTTCGATTACTCAGTCTCCCA<br>GGGCACTACTGGTCCGTAGGATTCGATTGGTCGGGTAGGAGAGTTAAACAACATTTAAACAGAGTTC<br>TCTCAAAAATGTCTAAAGGGATTGTAGGTAGATAACATCCAATCACTGTTTGCACTTATCTGAAATCTTC<br>CCTCTTGGCTGCCCCCAGGTATTTACTGTGGAGAACATTGCATAGGAATGTCTGGAAAAAGCTTCTAC<br>AACTTGTTACAGCCTTCACATTTGTAGAAGCTTT |
| 76 | OPA1-<br>opt_ND4*-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGCTGAAGCTGATCGTGCCCACCATCATGCTGCTGCCCCTGACCTGGCTGAGCAAGAAGCACA<br>TGATCTGGATCAACACCACCACCCACAGCCTGATCATCAGCATCATCCCCCTGCTGTTCTTCAACCAG<br>ATCAACAACAACCTGTTCAGCTGCAGCCCCACCTTCAGCAGCGACCCCCTGACCACCCCCTGCTGA<br>TGCTGACCACCTGGCTGCTGCCCCTGACCATCATGGGCAGCAGCGCCACCTGAGCAGCGAGCCCC<br>TGAGCCGCCAAGAAGCTGTACCTGAGCATGCTGATCAGCCTGCAGATCAGCCTGATCATGACCTTCACC<br>GCCACCGAGCTGATCATGTTCTACATCTTCTTCGAGACCACCCTGATCCCCACCCTGGCCATCATCAC<br>CCGCTGGGGCAACCAGCCCGAGCGCCTGAACGCCGGCACCTACTTCCTGTTCTACACCCTGGTGGG<br>CAGCCTGCCCCTGCTGATCGCCCTGATCTACACCCACAACACCCTGGGCAGCCTGAACATCCTGCTG<br>CTGACCCTGACCGCCCAGGAGCTGAGCAACAGCTGGGCCAACAACCTGATGTGGCTGGCCTACACCA<br>TGGCCTTCATGGTGAAGATGCCCCTGTACGGCCTGCACCTGTGGCTGCCCAAGGCCCACGTGGAGG<br>CCCCCATCGCCGGCAGCATGGTGCTGGCCGCCGTGCTGCTGAAGCTGGGCGGCTACGGCATGATGC<br>GCCTGACCCTGATCCTGAACCCCCTGACCAAGCACATGGCCTACCCCTTCCTGGTGCTGAGCCTGTG<br>GGGCATGATCATGACCAGCAGCATCTGCCTGCGCCAGACCGACCTGAAGAGCCTGATCGCCTACAGC<br>AGCATCAGCCACATGGCCCTGGTGGTGACCGCCATCCTGATCCAGACCCCCTGGAGCTTCACCGGCC<br>CCGTGATCCTGATGATCGCCCACGGCCTGACCAGCAGCTGCTGTTCTGCCTGGCCAACAGCAACTA<br>CGAGCGCACCCACAGCCGCATCATGATCCTGAGCCAGGGCCTGCAGACCCTGCTGCCCCTGATGGC<br>CTTCTGGTGGCTGCTGGCCAGCCTGGCCAACCTGGCCCTGCCCCCCACCATCAACCTGCTGGGCGA<br>GCTGAGCGTGCTGGTGACCACCTTCAGCTGGAGCAACATCACCCTGCTGCTGACCGGCCTGAACATG<br>CTGGTGACCGCCCTGTACAGCCTGTACATGTTCACCACCACCCAGTGGGGCAGCCTGACCCACCACA<br>TCAACAACATGAAGCCCAGCTTCACCCGCGAGAACACCCTGATGTTCATGCACCTGAGCCCCATCCTG<br>CTGCTGAGCCTGAACCCCGACATCATCACCGGCTTCAGCAGCTAAGAGCACTGGGACGCCCACCGCC<br>CCTTTCCCTCCGCTGCCAGGCGAGCATGTTGTGGTAATTCTGGAACACAAGAAGAGAAATTGCTGGGT<br>TTAGAACAAGATTATAAACGAATTCGGTGCTCAGTGATCACTTGACAGTTTTTTTTTTTTAAATATTAC<br>CCAAAATGCTCCCCAAATAAGAAATGCATCAGCTCAGTCAGTGAATACAAAAAAGGAATTATTTTTCCC<br>TTTGAGGGTCTTTTATACATCTCTCCTCCAACCCCACCCTCTATTCTGTTTCTTCCTCCTCACATGGGG<br>GTACACATACACAGCTTCCTCTTTTGGTTCCATCCTTACCACCACACCACACGCACACTCCACATGCCC<br>AGCAGAGTGGCACTTGGTGGCCAGAAAGTGTGAGCCTCATGATCTGCTGTCTGTAGTTCTGTGAGCTC<br>AGGTCCCTCAAAGGCCTCGGAGCACCCCCTTCCTTGTGACTGAGCCAGGGCCTGCATTTTTGGTTTTC<br>CCCACCCCACACATTCTCAACCATAGTCCTTCTAACAATACCAATAGCTAGGACCCGGCTGCTGTGCA<br>CTGGGACTGGGGATTCCACATGTTTGCCTTGGGAGTCTCAAGCTGGACTGCCA |
| 77 | OPA1-ND6-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTATGCTTTGTTTCTGTTGAGTGTGGGTTTAGTAATGGGGTTTGTGGGGTTTTCTTCTAAG<br>CCTTCTCCTATTTATGGGGTTTAGTATTGATTGTTAGCGGTGTGGTCGGGTGTGTTATTATTCTGAAT<br>TTTGGGGAGGTTATATGGGTTTAATGGTTTTTTTAATTTATTTAGGGGAATGATGGTTGTCTTTGGAT<br>ATACTACAGCGATGGCTATTGAGGAGTATCCTGAGGCATGGGGGTCAGGGGTTGAGGTCTTGGTGAG<br>TGTTTTAGTGGGGTTAGCGATGGAGGTAGGATTGGTGCTGTGGGTGAAAGAGTATGATGGGGTGGTG<br>GTTGTGGTAAACTTTAATAGTGTAGGAAGCTGGATGATTTATGAAGGAGAGGGTCAGGGTTGATTCG<br>GGAGGATCCTATTGGTGCGGGGCTTTGTATGATTATGGGCGTTGGTTAGTAGTAGTTACTGGTTGGA<br>CATTGTTTGTTGGTGTATATATTGTAATTGAGATTGCCTGCGGCAGTTAGGAGCACTGGGACGCCCAC<br>CGCCCCTTTCCCTCCGCTGCCAGGCGAGCATGTTGTGGTAATTCTGGAACAAGAAGAGAAATTGCT<br>GGGTTTAGAACAAGATTATAAACGAATTCGGTGCTCAGTGATCACTTGACAGTTTTTTTTTTTTAAAT<br>ATTACCCAAAATGCTCCCCAAATAAGAAATGCATCAGCTCAGTCAGTGAATACAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT |

TABLE 1-continued nucleic acid and polypeptide sequences and SEQ ID NOs

| SEQ | description | sequence |
|---|---|---|
| | | GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCAGCCCCTGTC<br>CTCCCTTCACCCCCATTGCGTATGAGCATTTCAGAACTCCAAGGAGTCACAGGCATCTTTATAGTTCAC<br>GTTAACATATAGACACTGTTGGAAGCAGTTCCTTCTAAAAGGGTAGCCCTGGACTTAATACCAGCCGG<br>ATACCTCTGGCCCCCACCCCATTACTGTACCTCTGGAGTCACTACTGTGGGTCGCCACTCCTCTGCTA<br>CACAGCACGGCTTTTTCAAGGCTGTATTGAGAAGGGAAGTTAGGAAGAAGGGTGTGCTGGGCTAACC<br>AGCCCACAGAGCTCACATTCCTGTCCCTTGGGTGAAAAATACATGTCCATCCTGATATCTCCTGAATTC<br>AGAAATTAGCCTCCACATGTGCAATGGCTTTAAGAGCCAGAAGCAGGGTTCTGGGAATTTTGCAAGTT<br>ACCTGTGGCCAGGTGTGGTCTCGGTTACCAAATACGGTTACCTGCAGCTTTTTAGTCCTTTGTGCTCC<br>CACGGGTCTACAGAGTCCCATCTGCCCAAAGGTCTTGAAGCTTGACAGGATGTTTTCGATTACTCAGT<br>CTCCCAGGGCACTACTGGTCCGTAGGATTCGATTGGTCGGGGTAGGAGAGTTAAACAACATTTAAACA<br>GAGTTCTCTCAAAAATGTCTAAAGGGATTGTAGGTAGATAACATCCAATCACTGTTTGCACTTATCTGA<br>AATCTTCCCTCTTGGCTGCCCCCAGGTATTTACTGTGGAGAACATTGCATAGGAATGTCTGGAAAAAG<br>CTTCTACAACTTGTTACAGCCTTCACATTTGTAGAAGCTTT |
| 78 | OPA1-ND6-<br>3'UTR* | GTGCTGCCCGCCTAGAAAGGGTGAAGTGGTTGTTGCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGATGTATGCTTTGTTTCTGTTGAGTGTGGGTTTAGTAATGGGGTTTGTGGGGTTTTCTTCTAAG<br>CCTTCTCCTATTTATGGGGGTTTAGTATTGATTGTTAGCGGTGTGGTCGGGTGTGTTATTATTCTGAAT<br>TTTGGGGGAGGTTATATGGGTTTAATGGTTTTTTTAATTTATTTAGGGGGAATGATGGTTGTCTTTGGAT<br>ATACTACAGCGATGGCTATTGAGGAGTATCCTGAGGCATGGGGGTCAGGGGTTGAGGTCTTGGTGAG<br>TGTTTTAGTGGGGTTAGCGATGGAGGTAGGATTGGTGCTGTGGGTGAAAGAGTATGATGGGGTGGTG<br>GTTGTGGTAAACTTTAATAGTGTAGGAAGCTGGATGATTTATGAAGGAGAGGGGTCAGGGTTGATTCG<br>GGAGGATCCTATTGGTGCGGGGCTTTGTATGATTATGGGCGTTGGTTAGTAGTAGTTACTGGTTGGA<br>CATTGTTTGTTGGTGTATATATTGTAATTGAGATTGCTCGGGGGAATTAGGAGCACTGGGACGCCCAC<br>CGCCCCTTTCCCTCCGCTGCCAGGCGAGCATGTTGTGGTAATTCTGGAACACAAGAAGAGAAATTGCT<br>GGGTTTAGAACAAGATTATAAACGAATTCGGTGCTCAGTGATCACTTGACAGTTTTTTTTTTTTTAAAT<br>ATTACCCAAAATGCTCCCCAAATAAGAAATGCATCAGCTCAGTCAGTGAATACAAAAAAGGAATTATTTT<br>TCCCTTTGAGGGTCTTTTATACATCTCTCCTCCAACCCCACCCTCTATTCTGTTTCTTCCTCCTCACATG<br>GGGGTACACATACACAGCTTCCTCTTTTGGTTCCATCCTTACCACCACACCACACGCACACTCCACAT<br>GCCCAGCAGAGTGGCACTTGGTGGCCAGAAAGTGTGAGCCTCATGATCTGCTGTCTGTAGTTCTGTG<br>AGCTCAGGTCCCTCAAAGGCCTCGGAGCACCCCCTTCCTTGTGACTGAGCCAGGGCCTGCATTTTTG<br>GTTTTCCCCACCCCACACATTCTCAACCATAGTCCTTCTAACAATACCAATAGCTAGGACCCGGCTGCT<br>GTGCACTGGGACTGGGGATTCCACATGTTTGCCTTGGGAGTCTCAAGCTGGACTGCCA |
| 79 | OPA1-<br>opt_ND6-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCCGCGTGG<br>CCGTCTCGGCGCCTGCGTGACCTCCCCGCCGGCGGGATGTGGCGACTACGTCGGGCCGCTGTGGC<br>CTGATGATGTACGCCCTGTTCCTGCTGAGCGTGGGCCTGGTGATGGGCTTCGTGGGCTTCAGCAGCA<br>AGCCCAGCCCCATCTACGGCGGCCTGGTGCTGATCGTGAGCGGCGTGGTGGGCTGCGTGATCATCC<br>TGAACTTCGGCGGCGGCTACATGGGCGTGATGGTGTTCCTGATCTACCTGGGCGGCATGATGGTGGT<br>GTTCGGCTACACCACCGCCATGGCCATCGAGGAGTACCCGAGGCCTGGGGCAGCGGCGTGGAGGT<br>GCTGGTGAGCGTGCTGGTGGGCCTGGCCATGAGGTGGGCCTGGTGCTGTGGGTGAAGGAGTACGA<br>CGGCGTGGTGGTGGTGGTGAACTTCAACAGCGTGGGCAGCTGGATGATCTACGAGGGCGAGGGCAG<br>CGGCCTGATCCGCGAGGACCCCATCGGCGCCGGCCCTGTACGACTACGGCCTGCTGGTGGT<br>GGTGACCGGCTGGACCCTGTTCGTGGGCGTGTACATCGTGATCGAGATCGCCCGCGGCAACTAAGA<br>GCACTGGGACGCCCACCGCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTGCTCAGTGATCACTTGACAG<br>TTTTTTTTTTTTTAAATATTACCCAAAATGCTCCCCAAATAAGAAATGCATCAGCTCAGTCAGTGAATAC<br>AAAAAAGGAATTATTTTTCCCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGATCTGC<br>TGTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCAGCCCCTGTCCTCCCTTCACCCCCATTGCGTATGAGCATTTCAGAACTCCAAGGAGTCACAGG<br>CATCTTTATAGTTCACGTTAACATATAGACACTGTTGGAAGCAGTTCCTTCTAAAAGGGTAGCCCTGGA<br>CTTAATACCAGCCGGATACCTCTGGCCCCCACCCCATTACTGTACCTCTGGAGTCACTACTGTGGGTC<br>GCCACTCCTCTGCTACACAGCACGGCTTTTTCAAGGCTGTATTGAGAAGGGAAGTTAGGAAGAAGGGT<br>GTGCTGGGCTAACCAGCCCACAGAGCTCACATTCCTGTCCCTTGGGTGAAAAATACATGTCCATCCTG<br>ATATCTCCTGAATTCAGAAATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATACGGTTACCTGCAGCTTTTTA<br>GTCCTTTGTGCTCCCACGGGTCTACAGAGTCCCATCTGCCCAAAGGTCTTGAAGCTTGACAGGATGTT<br>TTCGATTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAATCACTGTT<br>TGCACTTATCTGAAATCTTCCCTCTTGGCTGCCCCCAGGTATTTACTGTGGAGAACATTGCATAGGAAT<br>GTCTGGAAAAAGCTTCTACAACTTGTTACAGCCTTCACATTTGTAGAAGCTTT |
| 80 | OPA1-<br>opt_ND6-<br>3'UTR* | GTGCTGCCCGCCTAGAAAGGGTGAAGTGGTTGTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG |

TABLE 1-continued nucleic acid and polypeptide sequences and SEQ ID NOs

| SEQ | description | sequence |
|---|---|---|
| | | CCGTCTCGGCGCCTGCGTGACCTCCCCGCCGGCGGGATGTGGCGACTACGTCGGGCCGCTGTGGC<br>CTGATGATGTACGCCCTGTTCCTGCTGAGCGTGGGCCTGGTGATGGGCTTCGTGGGCTTCAGCAGCA<br>AGCCCAGCCCCATCTACGGCGGCCTGGTGCTGATCGTGAGCGGCGTGGTGGGCTGCGTGATCATCC<br>TGAACTTCGGCGGCGGCTACATGGGCCTGATGGTGTTCCTGATCTACCTGGGCGGCATGATGGTGGT<br>GTTCGGCTACACCACCGCCATGGGCATCGAGGAGTACCCCGAGGCCTGGGGCAGCGCGTGGAGGT<br>GCTGGTGAGCGTGCTGGTGGGCCTGGCCATGGAGGTGGGCCTGGTGCTGTGGGTGAAGGAGTACGA<br>CGGCGTGGTGGTGGTGGTGAACTTCAACAGCGTGGGCAGCTGGATGATCTACGAGGGCGAGGGCAG<br>CGGCCTGATCCGCGAGGACCCCATCGGCGCCGGCGCCCTGTACGACTACGGCCGCTGGCTGGTGGT<br>GGTGACCGGCTGGACCCTGTTCGTGGGCGTGTACATCGTGATCGAGATCGCCCGCGCGCAACTAAGA<br>GCACTGGGACGCCCACCGCCCCTTTCCCTCCGCTGCCAGGCGAGCATGTTGTGGTAATTCTGGAACA<br>CAAGAAGAGAAATTGCTGGGTTTAGAACAAGATTATAAACGAATTCGGTGCTCAGTGATCACTTGACAG<br>TTTTTTTTTTTTTAAATATTACCCAAAATGCTCCCCAAATAAGAAATGCATCAGCTCAGTCAGTGAATAC<br>AAAAAAGGAATTATTTTTCCCTTTGAGGGTCTTTTATACATCTCTCCTCCAACCCCACCCTCTATTCTGT<br>TTCTTCCTCCTCACATGGGGGTACACATACACAGCTTCCTCTTTTGGTTCCATCCTTACCACCACACCA<br>CACGCACACTCCACATGCCCAGCAGAGTGGCACTTGGTGGCCAGAAAGTGTGAGCCTCATGATCTGC<br>TGTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCA |
| 81 | OPA1-ND1-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTCCTACTCCTCATTGTACCCATTCTAATCGCAATGGCATTCCTAATGCTTACCGAA<br>CGAAAAATTCTAGGCTATATGCAACTACGCAAAGGCCCCAACGTTGTAGGCCCCTACGGGCTACTACA<br>ACCCTTCGCTGACGCCATAAAAACTCTTCACCAAAGAGCCCCTAAAACCCGCCACATCTACCATCACCC<br>TCTACATCACCGCCCCGACCTTAGCTCTCACCATCGCTCTTCTACTATGGACCCCCCTCCCCATGCCC<br>AACCCCCTGGTCAACCTCAACCTAGGCCTCCTATTTATTCTAGCCACCTCTAGCCTAGCCGTTTACTCA<br>ATCCTCTGGTCAGGGTGGGCATCAAACTCAAACTACGCCCTGATCGGCGCACTGCGAGCAGTAGCCC<br>AAACAATCTCATATGAAGTCACCCTAGCCATCATTCTACTATCAACATTACTAATGAGTGGCTCCTTTAA<br>CCTCTCCACCCTTATCACAACACAAGAACACCTCTGGTTACTCCTGCCATCATGGCCCTTGGCCATGA<br>TGTGGTTTATCTCCACACTAGCAGAGACCAACCGAACCCCCTTCGACCTTGCCAAGGGGAGTCCGA<br>ACTAGTCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCACTCTCCC<br>CTGAACTCTACACAACATATTTTGTCACCAAGACCCTACTTCTAAACCTCCCTGTTCTTATGGATTCGAAC<br>AGCATACCCCCGATTCCGCTACGACCAACTCATGCACCTCCTATGGAAAAACTTCCTACCACTCACCC<br>TAGCATTACTTATGTGGTATGTCTCCATGCCCATTACAATCTCCAGCATTCCCCTCAAACCTAAGAGC<br>ACTGGGACGCCCACCGCCCCTTTCCCTCCGCTGCCAGGCGAGCATGTTGTGGTAATTCTGGAACACA<br>AGAAGAGAAATTGCTGGGTTTAGAACAAGATTATAAACGAATTCGGTGCTCAGTGATCACTTGACAGTT<br>TTTTTTTTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTATTCTGTT<br>TCTTCCTCCTCACATGGGGTACACATACACAGCTTCCTCTTTTGGTTCCATCCTTACCACCACACCAC<br>ACGCACACTCCACATGCCCAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCAGCCCCTGTCCTCCCTTCACCCCCATTGCGTATGAGCATTTCAGAACTCCAAGGAGTCACAGG<br>CATCTTTATAGTTCACGTTAACATATAGACACTGTTGGAAGCAGTTCCTTCTAAAAGGGTAGCCCTGGA<br>CTTAATACCAGCCGGATACCTCTGGCCCCCACCCCATTACTGTACCTCTGGAGTCACTACTGTGGGTC<br>GCCACTCCTCTGCTACACAGCACGGCTTTTTCAAGGCTGTATTGAGAAGGGAAGTTAGGAAGAAGGGT<br>GTGCTGGGCTAACCAGCCCACAGAGCTCACATTCCTGTCCCTTGGGTGAAAAATACATGTCCATCCTG<br>ATATCTCCTGAATTCAGAAATTAGCCTCCACATGTGCAATGGCTTTAAGAGCCAGAAGCAGGGTTCTG<br>GGAATTTTGCAAGTTACCTGTGGCCAGGTGTGGTCTCGGTTACCAAATACGGTTACCTGCAGCTTTTTA<br>GTCCTTTGTGCTCCCACGGGTCTACAGAGTCCCATCTGCCCAAAGGTCTTGAAGCTTGACAGGATGTT<br>TTCGATTACTCAGTCTCCCAGGGCACTACTGGTCCGTAGGATTCGATTGGTCGGGGTAGGAGAGTTAA<br>ACAACATTTAAACAGAGTTCTCTCAAAAATGTCTAAAGGGATTGTAGGTAGATAACATCCAATCACTGTT<br>TGCACTTATCTGAAATCTTCCCTCTTGGCTGCCCCCAGGTATTTACTGTGGAGAACATTGCATAGGAAT<br>GTCTGGAAAAAGCTTCTACAACTTGTTACAGCCTTCACATTTGTAGAAGCTTT |
| 82 | OPA1-ND1-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTCCTACTCCTCATTGTACCCATTCTAATCGCAATGGCATTCCTAATGCTTACCGAA<br>CGAAAAATTCTAGGCTATATGCAACTACGCAAAGGCCCCAACGTTGTAGGCCCCTACGGGCTACTACA<br>ACCCTTCGCTGACGCCATAAAAACTCTTCACCAAAGAGCCCCTAAAACCCGCCACATCTACCATCACCC<br>TCTACATCACCGCCCCGACCTTAGCTCTCACCATCGCTCTTCTACTATGGACCCCCCTCCCCATGCCC<br>AACCCCCTGGTCAACCTCAACCTAGGCCTCCTATTTATTCTAGCCACCTCTAGCCTAGCCGTTTACTCA<br>ATCCTCTGGTCAGGGTGGGCATCAAACTCAAACTACGCCCTGATCGGCGCACTGCGAGCAGTAGCCC<br>AAACAATCTCATATGAAGTCACCCTAGCCATCATTCTACTATCAACATTACTAATGAGTGGCTCCTTTAA<br>CCTCTCCACCCTTATCACAACACAAGAACACCTCTGGTTACTCCTGCCATCATGGCCCTTGGCCATGA<br>TGTGGTTTATCTCCACACTAGCAGAGACCAACCGAACCCCCTTCGACCTTGCCAAGGGGAGTCCGA<br>ACTAGTCTCAGGCTTCAACATCGAATACGCCGCAGGCCCCTTCGCCCTATTCTTCATGGCCGAATACA<br>CAAACATTATTATGATGAACACCCTCACCACTACAATCTTCCTAGGAACAACATATGACGCACTCTCCC<br>CTGAACTCTACACAACATATTTTGTCACCAAGACCCTACTTCTAAACCTCCCTGTTCTTATGGATTCGAAC |

TABLE 1-continued nucleic acid and polypeptide sequences and SEQ ID NOs

| SEQ | description | sequence |
|---|---|---|
| | | AGCATACCCCCGATTCCGCTACGACCAACTCATGCACCTCCTATGGAAAAACTTCCTACCACTCACCC<br>TAGCATTACTTATGTGGTATGTCTCCATGCCCATTACAATCTCCAGCATTCCCCCTCAAACCTAAGAGC<br>ACTGGGACGCCCACCGCCCCTTTCCCTCCGCTGCCAGGCGAGCATGTTGTGGTAATTCTGGAACACA<br>AGAAGAGAAATTGCTGGGTTTAGAACAAGATTATAAACGAATTCGGTGCTCAGTGATCACTTGACAGTT<br>TTTTTTTTTTTTAAATATTACCCAAAATGCTCCCCAAATAAGAAATGCATCAGCTCAGTCAGTGAATACA<br>AAAAAGGAATTATTTTTCCCTTTGAGGGTCTTTTATACATCTCTCCTCCAACCCCACCCTCTATTCTGTT<br>TCTTCCTCCTCACATGGGGGTACACATACACAGCTTCCTCTTTTGGTTCCATCCTTACCACCACACCAC<br>ACGCACACTCCACATGCCCAGCAGAGTGGCACTTGGTGGCCAGAAAGTGTGAGCCTCATGATCTGCT<br>GTCTGTAGTTCTGTGAGCTCAGGTCCCTCAAAGGCCTCGGAGCACCCCCTTCCTTGTGACTGAGCCA<br>GGGCCTGCATTTTTGGTTTTCCCCACCCCACACATTCTCAACCATAGTCCTTCTAACAATACCAATAGC<br>TAGGACCCGGCTGCTGTGCACTGGGACTGGGGATTCCACATGTTTGCCTTGGGAGTCTCAAGCTGGA<br>CTGCCA |
| 83 | OPA1-<br>opt_ND1-<br>3'UTR | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTGCTGCTGCTGATCGTGCCCATCCTGATCGCCATGGCCTTCCTGATGCTGACCG<br>AGCGCAAGATCCTGGGCTACATGCAGCTGCGCAAGGGCCCCAACGTGGTGGGCCCCTACGGCCTGC<br>TGCAGCCCTTCGCCGACGCCATCAAGCTGTTCACCAAGGAGCCCCTGAAGCCCGCCACCAGCACCAT<br>CACCCTGTACATCACCGCCCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGGCCACCAGCAGCCTGGCCG<br>TGTACAGCATCCTGTGGAGCGGCTGGGCCAGCAACAGCAACTACGCCCTGATCGGCGCCCTGCGCG<br>CCGTGGCCCAGACCATCAGCTACGAGGTGACCCTGGCCATCATCCTGCTGAGCACCCTGCTGATGAG<br>CGGCAGCTTCAACCTGAGCACCCTGATCACCACCCAGGAGCACCTGTGGCTGCTGCTGCCCAGCTGG<br>CCCCTGGCCATGATGTGGTTCATCAGCACCCTGGCCGAGACCAACCGCACCCCCTTCGACCTGGCCG<br>AGGGCGAGAGCGAGCTGGTGAGCGGCTTCAACATCGAGTACGCCGCCGGCCCCTTCGCCCTGTTCT<br>TCATGGCCGAGTACACCAACATCATCATGATGAACACCCTGACCACCACCATCTTCCTGGGCACCACC<br>TACGACGCCCTGAGCCCCGAGCTGTACACCACCTACTTCGTGACCAAGACCCTGCTGCTGACCAGCC<br>TGTTCCTGTGGATCCGCACCGCCTACCCCCGCTTCCGCTACGACCAGCTGATGCACCTGCTGTGGAA<br>GAACTTCCTGCCCCTGACCCTGGCCCTGCTGATGTGGTACGTGAGCATGCCCATCACCATCAGCAGC<br>ATCCCCCCCCAGACCTAAGAGCACTGGGACGCCCACCGCCCCTTTCCCTCCGCTGCCAGGCGAGCAT<br>GTTGTGGTAATTCTGGAACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC<br>CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCAGCCCCTGTCCTCCCTTCACCCCCATTGCGTATGAGCATTTCA<br>GAACTCCAAGGAGTCACAGGCATCTTTATAGTTCACGTTAACATATAGACACTGTTGGAAGCAGTTCCT<br>TCTAAAAGGGTAGCCCTGGACTTAATACCAGCCGGATACCTCTGGCCCCACCCCATTACTGTACCTC<br>TGGAGTCACTACTGTGGGTCGCCACTCCTCTGCTACACAGCACGGCTTTTTCAAGGCTGTATTGAGAA<br>GGGAAGTTAGGAAGAAGGGTGTGCTGGGCTAACCAGCCCACAGAGCTCACATTCCTGTCCCTTGGGT<br>GAAAAATACATGTCCATCCTGATATCTCCTGAATTCAGAAATTAGCCTCCACATGTGCAATGGCTTTAA<br>GAGCCAGAAGCAGGGTTCTGGGAATTTTGCAAGTTACCTGTGGCCAGGTGTGGTCTCGGTTACCAAAT<br>ACGGTTACCTGCAGCTTTTTAGTCCTTTGTGCTCCCACGGGTCTACAGAGTCCCATCTGCCCAAAGGT<br>CTTGAAGCTTGACAGGATGTTTTCGATTACTCAGTCTCCCAGGGCACTACTGGTCCGTAGGATTCGAT<br>TGGTCGGGGTAGGAGAGTTAAACAACATTTAAACAGAGTTCTCTCAAAAAATGTCTAAAGGATTGTAG<br>GTAGATAACATCCAATCACTGTTTGCACTTATCTGAAATCTTCCCTCTTGGCTGCCCCCAGGTATTTAC<br>TGTGGAGAACATTGCATAGGAATGTCTGGAAAAAGCTTCTACAACTTGTTACAGCCTTCACATTTGTAG<br>AAGCTTT |
| 84 | OPA1-<br>opt_ND1-<br>3'UTR* | GTGCTGCCCGCCTAGAAAGGGTGAAGTGGTTGTTTCCGTGACGGACTGAGTACGGGTGCCTGTCAGG<br>CTCTTGCGGAAGTCCATGCGCCATTGGGAGGGCCTCGGCCGCGGCTCTGTGCCCTTGCTGCTGAGG<br>GCCACTTCCTGGGTCATTCCTGGACCGGGAGCCGGGCTGGGGCTCACACGGGGGCTCCCGCGTGG<br>CCGTCTCGGCGCCTGCGTGACCTCCCCGCCGGCGGGATGTGGCGACTACGTCGGGCCGCTGTGGC<br>CTGATGGCCAACCTGCTGCTGCTGATCGTGCCCATCCTGATCGCCATGGCCTTCCTGATGCTGACCG<br>AGCGCAAGATCCTGGGCTACATGCAGCTGCGCAAGGGCCCCAACGTGGTGGGCCCCTACGGCCTGC<br>TGCAGCCCTTCGCCGACGCCATCAAGCTGTTCACCAAGGAGCCCCTGAAGCCCGCCACCAGCACCAT<br>CACCCTGTACATCACCGCCCCCACCCTGGCCCTGACCATCGCCCTGCTGCTGTGGACCCCCCTGCCC<br>ATGCCCAACCCCCTGGTGAACCTGAACCTGGGCCTGCTGTTCATCCTGGCCACCAGCAGCCTGGCCG<br>TGTACAGCATCCTGTGGAGCGGCTGGGCCAGCAACAGCAACTACGCCCTGATCGGCGCCCTGCGCG<br>CCGTGGCCCAGACCATCAGCTACGAGGTGACCCTGGCCATCATCCTGCTGAGCACCCTGCTGATGAG<br>CGGCAGCTTCAACCTGAGCACCCTGATCACCACCCAGGAGCACCTGTGGCTGCTGCTGCCCAGCTGG<br>CCCCTGGCCATGATGTGGTTCATCAGCACCCTGGCCGAGACCAACCGCACCCCCTTCGACCTGGCCG<br>AGGGCGAGAGCGAGCTGGTGAGCGGCTTCAACATCGAGTACGCCGCCGGCCCCTTCGCCCTGTTCT<br>TCATGGCCGAGTACACCAACATCATCATGATGAACACCCTGACCACCACCATCTTCCTGGGCACCACC<br>TACGACGCCCTGAGCCCCGAGCTGTACACCACCTACTTCGTGACCAAGACCCTGCTGCTGACCAGCC<br>TGTTCCTGTGGATCCGCACCGCCTACCCCCGCTTCCGCTACGACCAGCTGATGCACCTGCTGTGGAA<br>GAACTTCCTGCCCCTGACCCTGGCCCTGCTGATGTGGTACGTGAGCATGCCCATCACCATCAGCAGC<br>ATCCCCCCCCAGACCTAAGAGCACTGGGACGCCCACCGCCCCTTTCCCTCCGCTGCCAGGCGAGCAT<br>GTTGTGGTAATTCTGGAACACAAGAAGAGAAATTGCTGGGTTTAGAACAAGATTATAAACGAATTCGGT<br>GCTCAGTGATCACTTGACAGTTTTTTTTTTTTTAAATATTACCCAAAATGCTCCCCAAATAAGAAATGC<br>ATCAGCTCAGTCAGTGAATACAAAAAAGGAATTATTTTTCCCTTTGAGGGTCTTTTATACATCTCTCCTC |

TABLE 1-continued nucleic acid and polypeptide sequences and SEQ ID NOs

| SEQ | description | sequence |
|---|---|---|
| | | CAACCCCACCCTCTATTCTGTTTCTTCCTCCTCACATGGGGGTACACATACACAGCTTCCTCTTTTGGT<br>TCCATCCTTACCACCACACCACACGCACACTCCACATGCCCAGCAGAGTGGCACTTGGTGGCCAGAA<br>AGTGTGAGCCTCATGATCTGCTGTCTGTAGTTCTGTGAGCTCAGGTCCCTCAAAGGCCTCGGAGCACC<br>CCCTTCCTTGTGACTGAGCCAGGGCCTGCATTTTTGGTTTTCCCCACCCCACACATTCTCAACCATAGT<br>CCTTCTAACAATACCAATAGCTAGGACCCGGCTGCTGTGCACTGGGACTGGGGATTCCACATGTTTGC<br>CTTGGGAGTCTCAAGCTGGACTGCCA |
| 35 | β-actin-S primer | CGAGATCGTGCGGGACAT |
| 36 | β-actin-A primer | CAGGAAGGAGGGCTGGAAC |
| 87 | ND4-S primer | CTGCCTACGACAAACAGAC |
| 88 | ND4-A primer | AGTGCGTTCGTAGTTTGAG |
| 89 | ND6-F primer | ATGATGTATGCTTTGTTTCTG |
| 90 | ND6-R primer | CTAATTCCCCCGAGCAATCTC |
| 91 | ND6-S primer | AGTGTGGGTTTAGTAATG |
| 92 | ND6-A primer | TGCCTCAGGATACTCCTC |
| 93 | β-actin-F primer | CTCCATCCTGGCCTCGCTGT |
| 94 | β-actin-R primer | GCTGTCACCTTCACCGTTCC |
| 95 | ND6-F primer | GGGTTTTCTTCTAAGCCTTCTCC |
| 96 | ND6-R primer | CCATCATACTCTTTCACCCACAG |
| 97 | opt_ND6-F primer | CGCCTGCTGACCGGCTGCGT |
| 98 | opt_ND6-R | CCAGGCCTCGGGGTACTCCT |
| 99 | ND1-F primer | ATGGCCGCATCTCCGCACACT |
| 100 | ND1-R primer | TTAGGTTTGAGGGGGAATGCT |
| 101 | ND1-F primer | AACCTCAACCTAGGCCTCCTA |
| 102 | ND1-R primer | TGGCAGGAGTAACCAGAGGTG |
| 103 | ND1-F primer | AGGAGGCTCTGTCGTATCTTG |
| 104 | ND1-R primer | TTTTAGGGGCTCTTTGGTGAA |
| 105 | opt-ND1-F primer | GCCGCCTGCTGACCGGCTGCGT |
| 106 | opt-ND1-R primer | TGATGTACAGGGTGATGGTGCTGG |
| 107 | ND4-S primer | GCCAACAGCAACTACGAGC |
| 108 | ND4-A primer | TGATGTTGCTCCAGCTGAAG |
| 109 | opt-ND4-S primer | GCCTGACCCTGATCCTGAAC |
| 110 | opt-ND4-A primerr | GTGCGCTCGTAGTTGCTGTT |
| 111 | hsACO2 | GGGCAGTGCCTCCCCGCCCGCCGCTGGCGTCAAGTTCAGCTCCACGTGTGCCATCAGTGGATCCG<br>ATCCGTCCAGCCATGGCTTCCTATTCCAAGATGGTGTGACCAGACATGCTTCCTGCTCCCCGCTTAGC<br>CCACGGAGTGACTGTGGTTGTGGTGGGGGGTTCTTAAAATAACTTTTTAGCCCCCGTCTTCCTATTTT<br>GAGTTTGGTTCAGATCTTAAGCAGCTCCATGCAACTGTATTTATTTTTGATGACAAGACTCCCATCTAAA<br>GTTTTTCTCCTGCCTGATCATTTCATTGGTGGCTGAAGGATTCTAGAGAACCTTTTGTTCTTGCAAGGA<br>AAACAAGAATCCAAAACCAGTGACTGTTCTGTGA |

TABLE 1-continued nucleic acid and polypeptide sequences and SEQ ID NOs

| SEQ | description | sequence |
|---|---|---|
| 112 | hsATR5B | GGGGTCTTTGTCCTCTGTACTGTCTCTCTCCTTGCCCCTAACCCAAAAAGCTTCATTTTTCTGTGTAGG<br>CTGCACAAGAGCCTTGATTGAAGATATATTCTTTCTGAACAGTATTTAAGGTTTCCAATAAAATGTACAC<br>CCCTCAG |
| 113 | hsAK2 | TGTTGGGTCCAAGAAGGAATTTCTTTCCATCCCTGTGAGGCAATGGGTGGGAATGATAGGACAGGCAA<br>AGAGAAGCTTCCTCAGGCTAGCAAAAATATCATTTGATGTATTGATTAAAAAAGCACTTGCTTGATGTAT<br>CTTTGGCGTGTGTGCTACTCTCATCTGTGTGTATGTGTTGTGTGTGTGTGTGCATGCACATAT<br>GTGTTCACTCTGCTACTTTGTAAGTTTTAGGCTAGGTTGCTTTACCAGCTGTTTACTTCTTTTTTGTTGTT<br>GTTTTGAGACAAGGTTTCGCTCTGCCACCCTGGCTGGAGTGCAGTGGCGTGATCTTGGCTCACGGCA<br>ACCTCTGCCTCCTGGGGCTCAAGCAATTATCCCACCTCAGCCTCCTGAGCAGCTGGGACTACAGGTG<br>CATGCCACAACACCTGGCTGATATTTGTATTTTTTGTAGAGACAGGATTTTGCCAAGTTGCCCAGGCTG<br>GTCTTGAACTCCTAGGCTTAAGCAATCCACCCACCTTGGCCTCCTGAAGTGCCAGGATCACAGACGTG<br>AGCCACTACACCCAGCCCAGCTGTTTACTTCTTTAACCATACTTTTGATTTTATTTTTTGACCAAAATGA<br>ACTAACCCAGGTAATCTTCCAGGGACCGCAATTCCAGAACCTCATAGTATTTCTTCCATTTCCAGCAGC<br>TGATTAGAAGTCCAGGATCATGTGAAGTCAGGCAGGGTCACAGTTCCTGATGGCACATTATGGACAGA<br>GAATTCCATTTTGTTTTCTAACCCATGATGAAAACCCACGTGAGTCAGTGTGTGAACAGGGATCATTAA<br>TTTTTTCCCCCTAGGTGGAAGGTVAAAGGCACTTACTTTGCAGGTTACAGAAATTACTGGGAGAGGAT<br>ATCGTCATAAAAAGAGCCAGGCCAAATTGGAATATTTTGTGATCTGCATCATGATGCTGAAAATAGCA<br>ATTATTTGGGAATTGGGTTTGAAAACTGAATTGTTGCCAGAGAATTAAACCAGGTGAAAGGTCCTTTTG<br>AATTCAGATTGTCTTCTGAACATCCAGGCTGATCATCTGAGAGCAGTCAAATCTACTTCCCCAAAAAGA<br>GACCAGGGTAGGTTTATTTGCTTTTATTTTTAATGTTTGCCTGTGTTTccAAGTCTGAACAAAACAGTGT<br>GTGATCTATTCTTGGATTCATTTTGATCAGTATTTATTCAAACCCAGTCTCTCTCCAGGACATAAAACTG<br>AAATCAGATATGTTCTTTTTAAGCCCAAACCCTCTCCTTTCTAGATCCAACCCTTCACCCCTAATTTTAT<br>GATGGCTATAGCCATGGACTTCCCCAAGAAAAGATCACCCAGAAATAAGACCACCTGTGACAGTTACC<br>AGCTTTTATTCATAACCTTAGCTTCCCAACTATTGAGCATTTTCTAAGGTCCCTGCTGTCTTTTGGTCTC<br>TGGTTTGATTTGTGGCAAACAGATGAAGTAACAGACTGCTATGAAGGACCACAAAAACGGCAGCCTCT<br>GGAAAAACCATTAGAAAGTCAGTGGCAGATCCAGTAAATAATATCGCCAGCCTCAGCATAATCTGCTG<br>CTGACTCGATTCAGTGGACTCTAAAGTGCCCAGCCTCCTGACCTGAGCTCTCCTGCCATCTGTGAGAC<br>TACCAGAGGTCTTATCTGCTGTCCACATGGCAACTGGGCATGAGTACCTGGCCACCTTGCTTCCCTCT<br>TTGCCTGGTCCAAGTGAGTGTCTGCTGCCTCTGTCCTGCCTTGTTTTCCTGGCTCTAAACCAACTCCA<br>CCCACTCTTAATGGAAACTCAGTCTGGCTTTGTGTGTTTCTGGGAAGCACATGACTTCTGGGAATGGG<br>CAAGGAAGAGGAGTGAAACAAAAACTGTCAGCTATGTGTGCCTGGTCTGGGATCCTTCTCTGGGTGAC<br>AGTGGCATCATGAATCTTAGAATCAGCTCCCC |
| 114 | hsALDH2 | GAATCATGCAAGCTTCCTCCCTCAGCCATTGATGGAAAGTTCAGCAAGATCAGCAACAAAACCAAGAA<br>AAATGATCCTTGCGTGCTGAATATCTGAAAAGAGAAATTTTTCCTACAAAATCTCTTGGGTCAAGAAAG<br>TTCTAGAATTTGAATTGATAAACATGGTGGGTTGGCTGAGGGTAAGAGTATATGAGGAACCTTTTAAAC<br>GACAACAATACTGCTAGCTTTCAGGATGATTTTTAAAAAATAGATTCAAATGTGTTATCCTCTCTCTGAA<br>ACGCTTCCTATAACTCGAGTTTATAGGGGAAGAAAAAGCTATTGTTTACAATTATATCACCATTAAGGCA<br>ACTGCTACACCCTGCTTTGTATTCTGGGCTAAGATTCATTAAAAACTAGCTGCTCTTAACTTACA |
| 115 | hsCOX10 | GAGCACTGGGACGCCCACCGCCCCTTTCCCTCCGCTGCCAGGCGAGCATGTTGTGGTAATTCTGGAA<br>CACAAGAAGAGAAATTGCTGGGTTTAGAACAAGATTATAAACGAATTCGGTGCTCAGTGATCACTTGAC<br>AGTTTTTTTTTTTTAAATATTACCCAAAATGCTCCCCAAATAAGAAATGCATCAGCTCAGTCAGTGAAT<br>ACAAAAAAGGAATTATTTTTCCCTTTGAGGGTCTTTATACATCTCTCCTCCAACCCCACCCTCTATTCTG<br>TTTCTTCCTCCTCACATGGGGGTACACATACACAGCTTCCTCTTTTGGTTCCATCCTTACCACCACACC<br>ACACGCACACTCCACATGCCCAGCAGAGTGGCACTTGGTGGCCAGAAAGTGTGAGCCTCATGATCTG<br>CTGTCTGTAGTTCTGTGAGCTCAGGTCCCTCAAAGGCCTCGGAGCACCCCCTTCCTGGTGACTGAGC<br>CAGGGCCTGCATTTTTGGTTTTCCCCACCCCACACATTCTCAACCATAGTCCTTCTAACAATACCAATA<br>GCTAGGACCCGGCTGCTGTGCACTGGGACTGGGGATTCCACATGTTTGCCTTGGGAGTCTCAAGCTG<br>GACTGCCAGCCCCTGTCCTCCCTTCACCCCCATTGCGTATGAGCATTTCAGAACTCCAAGGAGTCACA<br>GGCATCTTTATAGTTCACGTTAACATATAGACACTGTTGGAAGCAGTTCCTTCTAAAAGGGTAGCCCTG<br>GACTTAATACCAGCCGGATACCTCTGGCCCCCACCCCATTACTGTACCTCTGGAGTCACTACTGTGGG<br>TCGCCACTCCTCTGCTACACAGCACGGCTTTTTCAAGGCTGTATTGAGAAGGGAAGTTAGGAAGAAGG<br>GTGTGCTGGGCTAACCAGCCCACAGAGCTCACATTCCTGTCCCTTGGGTGAAAAATACATGTCCATCC<br>TGATATCTCCTGAATTCAGAAAATTAGCCTCCACATGTGCAATGGCTTTAAGAGCCAGAAGCAGGGTTCT<br>GGGAATTTTGCAAGTTATCCTGTGGCCAGGTGTGGTCTCGGTTACCAAATACGGTTACCTGCAGCTTT<br>TTAGTCCTTTGTGCTCCCACGGGTCTGCAGAGTCCCATCTGCCCAAAGGTCTTGAAGCTTGACAGGAT<br>GTTTTCATTACTCAGTCTCCCAGGGCACTGCTGGTCCGTAGGGATTCATTGGTCGGGGTGGGAGAGTT<br>AAACAACATTTAAACAGAGTTCTCTCAAAAATGTCTAAAGGGATTGTAGGTAGATAACATCCAATCACT<br>GTTTGCACTTATCTGAAATCTTCCCTCTTGGCTGCCCCCAGGTATTTACTGTGGAGAACATTGCATAGG<br>AATGTCTGGAAAAAGCCTACAACTTGTTACAGCCTTCACATTTGTACAATTCATTGATTCTCTTTTCC<br>TTCCACAATAAAATGGTATACAAGAAC |
| 116 | hsUQCRFS1 | GAGACTTGGACTCAAGTCATAGGCTTCTTTCAGTCTTTATGTCACCTCAGGAGACTTATTTGAGAGGAA<br>GCCTTCTGTACTTGAAGTTGATTTGAAATATGTAAGAATTGATGATGTATTTGCAAACATTAATGTGAAA<br>TAAATTGAATTTAATGTTGAATACTTTCAGGCATTCACTTAATAAAGACACTGTTAAGCACTGTTATGCT<br>CAGTCATACACGCGAAAGGTACAATGTCTTTTAGCTAATTCTAATTAAAAATTACAGACTGGTGTACAA<br>GATACTTGTG |
| 117 | hsNDUFV1 | CCCACCACCCTGGCCTGCTGTCCTGCGTCTATCCATGTGGAATGCTGGACAATAAAGCGAGTGCTGC<br>CCACCCTCCAGCTGCC |

TABLE 1-continued nucleic acid and polypeptide sequences and SEQ ID NOs

| SEQ | description | sequence |
|---|---|---|
| 118 | hsNDUFV2 | TTTATATTGAACTGTAAATATGTCACTAGAGAAATAAAATATGGACTTCCAATCTACGTAAACTTA |
| 119 | hsSOD2 | ACCACGATCGTTATGCTGAGTATGTTAAGCTCTTTATGACTGTTTTTGTAGTGGTATAGAGTACTGCAG AATACAGTAAGCTGCTCTATTGTAGCATTTCTTGATGTTGCTTAGTCACTTATTTCATAAACAACTTAAT GTTCTGAATAATTTCTTACTAAACATTTTGTTATTGGGCAAGTGATTGAAAATAGTAAATGCTTTGTGTG ATTGA |
| 120 | hsCOX6c | TCTTGGAATATAAAGAATTTCTTCAGGTTGAATTACCTAGAAGTTTGTCACTGACTTGTGTTCCTGAACT ATGCACACATGAATATGTGGGCTAAGAAATAGTTCCTCTTGATAAATAAACAATTAACAAATACTTTGGAC AGTAAGTCTTTCTCAGTTCTTAATGATAATGCAGGGCACTTACTAGCATAAGAATTGGTTTGGGATTTAA CTGTTTATGAAGCTAACTTGATTTCCGTGTTTTGTTAAAATTTCATTGTTCTAGCACATCTTTAACTGTGA TAGTT |
| 121 | hsIRP1 | GAGACGTGCACTTGGTCGTGCGCCCAGGGAGGAAGCCGCACCACCAGCCAGCGCAGGCCCTGGTG GAGAGGCCTCCCTGGCTGCCTCTGGGAGGGGTGCTGCCTTGTAGATGGAGCAAGTGAGCACTGAGG GTCTGGTGCCAATCCTGTAGGCACAAAACCAGAAGTTTCTACATTCTCTATTTTTGTTAATCATCTTCTC TTTTTCCAGAATTTGGAAGCTAGAATGGTGGGAATGTCAGTAGTGCCAGAAAGAGAGAACCAAGCTTG TCTTTAAAGTTACTGATCACAGGACGTTGCTTTTTCACTGTTTCCTATTAATCTTCAGCTGAACACAAGC AAACCTTCTCAGGAGGTGTCTCCTACCCTCTTATTGTTCCTCTTACGCTCTGCTCAATGAAACCTTCCT CTTGAGGGTCATTTTCCTTTCTGTATTAATTATACCAGTGTTAAGTGACATAGATAAGAACTTTGCACAC TTCAAATCAGAGCAGTGATTCTCTCTTCTCTCCCCTTTTCCTTCAGAGTGAATCATCCAGACTCCTCAT GGATAGGTCGGGTGTTAAAGTTGTTTTGATTATGTACCTTTTGATAGATCCACATAAAAAGAAATGTGA AGTTTTCTTTTACTATCTTTTCATTTATCAAGCAGAGACCTTTGTTGGGAGGCGGTTTGGGAGAACACA TTTCTAATTTGAATGAAATGAAATCTATTTTCAGTG |
| 122 | hsRPS12 | CAGAAGAAGTGACGGCTGGGGGCACAGTGGGCTGGGCGCCCCTGCAGAACATGAACCTTCCGCTCC TGGCTGCCACAGGGTCCTCCGATGCTGGCCTTTGCGCCTCTAGAGGCAGCCACTCATGGATTCAAGT CCTGGCTCCGCCTCTTCCATCAGGACCACT |
| 123 | hsATP5J2 | AGAGGACACACTCTGCACCCCCCCACCCCACGACCTTGGCCCGAGCCCCTCCGTGAGGAA |
| 124 | rnSOD2 | AGCCCTTCCGCCAGGCTGTGTGTCAGGCCCGTGGTGGGTGTTTTGTAGTAGTGTAGAGCATTGCA |
| 125 | hsOXA1L | CTTATGTTCTGTGCGCATTCTGGCAGGAATTCTGTCTCTTCAGAGACTCATCCTCAAAACAAGACTTGA CACTGTGTCCTTGCCCCAGTCCTAGGAACTGTGGCACACAGAGATGTTCATTTTAAAAACGGATTTCAT GAAACACTCTTGTACTTATGTTTATAAGAGAGCACTGGGTAGCCAAGTGATCTTCCCATTCACAGAGTT AGTAAACCTCTGTACTACATGCTG |
| 126 | TS-COX10 | MAASPHTLSSRLLTGCVGGSVWYLERRT |
| 127 | TS-COX8 | MSVLTRLLLRGLTRLGSAAPVRRARIHSL |
| 128 | TS-OPA1 | MWRLRRAAVA |
| 129 | hsCOX10 | MAASPHTLSSRLLTGCVGGSVWYLERRT |
| 130 | scRP2 | MAFKSFIYSKGYHRSAAQKKTATSFFDSSYQYLRQNQGLVNSDPVLHASHLHPHPVVVANVNYNNVDDILH PHDLDSSINNTNNPLTHEELLYNQNVSLRSLKQQQSTNYVNNNNNNQHRYY |
| 131 | lcSirt5 | MRKRSLRCHLWSANASLSPRKDEVTSRKESENLVKGKKNKKSHLHLLLFTASKIGTDSVFDVQKSKECCKE LGLLFTSLIHSIGSFPFDEEPKAAAVFLPGSLPQLTVLVLAPGSGSCPTGKSTPHLAASGRNAELLRPQNSMI VRQFTCRGTISSHLCAHLRKPHDSRNMARP |
| 132 | tbNDUS7 | MLRRTSFNFTGRAMISRGSPEWSHRLDLKKGKKTTMMHKLGTSKPNNALQYAQMTL |
| 133 | neQCR2 | MISRSALSRGSQLALRRPAAAKTAQRGFAAAAASPAASYEPTTIAG |
| 134 | hsATP5G2 | MPELILYVAITLSVAERLVGPGHACAEPSFRSSRCSAPLCLLCSGSSSPATAPHPLKFACSKFVSTPSLVK STSQLLSRPLSAVVLKRPEILTDESLSSLAVSCPLTSLVSSRSFQTSAISRDIDTA |
| 135 | hsLACTB | MYRLMSAVTARAAAPGGLASSCGRRGVHQRAGLPPLGHGWVGGLGLGLGLALGVKLAGGLRGAAPAQS PAAPDPEASPLAEPPQEQSLAPWSPQTPAPPCSRCFARAIESSRDLL |
| 136 | spilv1 | MTVLAPLRRLHTRAAFSSYGREIALQKRFLNLNSCSAVRRYGTGFSNNLRIKKLKNAFGVVRANSTKSTSTV TTASPIKYDSSFVGKTGGEIFHDMMLKHNVKHVFGYPGGAILPVFDAIYRSPHFEFILPRHEQAAGHA |
| 137 | gmCOX2 | MILCPLEAFIVQHILTISVMGLLSCFRSTVLRKCSKGSSGMSRFLYTNNFQRNLISSGGNESYYGYFNRRSY TSLYMGTGTVGGITSARIRVPNVGCEGFMCSSHLSITQRNSRLIHSTSKIVPN |
| 138 | crATP6 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNM |
| 139 | hsOPA1 | MWRLRRAAVACEVCQSLVKHSSGIKGSLPLQKLHLVSRSIYHSHHPTLKLQRPQLRTSFQQFSSLTNLPLR KLKFSPIKYGYQPRRN |

TABLE 1-continued nucleic acid and polypeptide sequences and SEQ ID NOs

| SEQ | description | sequence |
|---|---|---|
| 140 | hsSDHD | MAVLWRLSAVCGALGGRALLLRTPVVRPAHISAFLQDRPIPEWCGVQHIHLSPSHH |
| 141 | hsADCK3 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHAHSEGPAPAYVASGPFREAGFPGQASSPLGRA NGRLFANPRDSFSAMGFQRRF |
| 142 | osP0644B06. 24-2 | MALLLRHSPKLRRAHAILGCERGTVVRHFSSSTCSSLVKEDTVSSSNLHPEYAKKIGGSDFSHDRQSGKEL QNFKVSPQEASRASNFMRASKYGMPITANGVHSLFSCGQVVPSRCF |
| 143 | *Neurospora crassa* ATP9 (ncATP9) | MASTRVLASRLASQMAASAKVARPAVRVAQVSKRTIQTGSPLQTLKRTQMTSIVNATTRQAFQKRA |
| 144 | hsGHIT | MLAARLVCLRTLPSRVFHPAFTKASPVVKNSITKNQWLLTPSRE |
| 145 | hsNDUFAB1 | MASRVLSAYVSRLPAAFAPLPRVRMLAVARPLSTALCSAGTQTRLGTLQPALVLAQVPGRVTQLCRQY |
| 146 | hsATP5G3 | MFACAKLACTPSLIRAGSRVAYRPISASVLSRPEASRTGEGSTVFNGAQNGVSQLIQREFQTSAISR |
| 147 | crATP6_ hsADCK3 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNMGGMAAILGDTIMVAKGLVKLTQAAVETHLQHL GIGGELIMAARALQSTAVEQIGMFLGKVQGQDKHEEYFAENFGGPEGEFHFSVPHAAGASTDFSSASAPD QSAPPSLGHAHSEGPAPAYVASGPFREAGFPGQASSPLGRANGRLFANPRDSFSAMGFQRRFGG |
| 148 | neATP9_ncAT P9 | MASTRVLASRLASQMAASAKVARPAVRVAQVSKRTIQTGSPLQTLKRTQMTSIVNATTRQAFQKRAAST RVLASRLASQMAASAKVARPAVRVAQVSKRTIQTGSPLQTLKRTQMTSIVNATTRQAFQKRA |
| 149 | zm LOC100282174 | MALLRAAVSELRRRGRGALTPLPALSSILSSLSPRSPASTRPEPNNPHADRRHVIALRRCPPLPASAVLAPE LLHARGLLPRHWSHASPLSTSSSSSRPADKAQLTWVDKWIPEAARPY |
| 150 | neATP9_zm LOC100282174_ spilv1_ncAT P9 | MASTRVLASRLASQMAASAKVARPAVRVAQVSKRTIQTGSPLQTLKRTQMTSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPYMTVLAPLRRLHTRAAFSSYGREIALQKRF LNLNSCSAVRRYGTGFSNNLRIKKLKNAFGVVRANSTKSTSTVTTASPIKYDSSFVGKTGGEIFHDMMLKH NVKHVFGYPGGAILPVFDAIYRSPHFEFILPRHEQAAGHAMASTRVLASRLASQMAASAKVARPAVRVAQV SKRTIQTGSPLQTLKRTQMTSIVNATTRQAFQKRA |
| 151 | zm LOC100282174_ hsADCK3_ cr ATP6_ hsTP5G3 | MALLRAASELRRRGRGALTPLPALSSLLSSISPRSPASTRPEPNNPHADRRHVIALRRCPPLPASAVLAPE LLHARGLLPRHWSHASPLSTSSSSSRPADKAQLTWVDKWIPEAARPYMAAILGDTIMVAKGLVKLTQAAVE THLQHLGIGGELIMAARALQSTAVEQIGMFLGKVQGQDKHEEYFAENFGGPEGEFHFSVPHAAGASTDFS SASAPDQSAPPSLGHAHSEGPAPAYVASGPFREAGFPGQASSPLGRANGRLFANPRDSFSAMGFQRRF MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQMNMMFACAKLACTPSLIRAGSRVAYRPISASVLSR PEASRTGEGSTVFNGAQNGVSQLICREFQTSAISR |
| 152 | zm LOC100282174_ hsADCK3_ hsATP5G3 | MALLRAAVSELRRRGRGALTPLPALSSLLSSLSPRSPASTRPEPNNPHADRRHVIALRRCPPLPASAVLAPE LLHARGLLPRHWSHASPLSTSSSSSRPADKAQLTWVDKWIPEAARPYMAAILGDTIMVAKGLVKLTQAAVE THLQHLGIGGELIMAARALQSTAVEQIGMFLGKVQGQDKHEEYFAENFGGPEGEFHFSVPHAAGASTDFS SASAPDQSAPPSLGHAHSEGPAPAYVASGPFREAGFPGQASSPLGRANGRLFANPRDSFSAMGFQRRF MFACAKLACTPSLIRAGSRVAYRPISASVLSRPEASRTGEGSTVFNGAQNGVSQLIQREFQTSAISR |
| 153 | ncATP9_ zm LOC100282174 | MASTRVLASRLASQMAASAKVARPAVRVAQVSKRTIQTGSPLQTLKRTQMTSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPY |
| 154 | hsADCK3_ zm LOC100282174_ cr ATP6_ hsATP5G3 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHARSEGPAPAYVASGPFREAGFPGQASSPLGRA NGRLFANPRDSFSAMGFQRRFMALLRAAVSELRRRGRGALTPLPALSSLLSSLSPRSPASTRPEPNNPHA DRRHVIALRRCPPLPASAVLAPELLHARGLLPRHWSHASPLSTSSSSSRPADKAQLTWVDKWIPEAARRY MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQAMNMMFACAKLACTPSLIRAGSRVAYRPISASVLSR PEASRTGEGSTVFNGAQNGVSQLIQREFQTSAISR |
| 155 | crATP6_ hsADCK3_ zm LOC100282174_ hsATP5G3 | MALQQAAPRVFGLLGRAPVALGQSGILTGSSGFKNQGFNGSLQSVENHVYAQAFSTSSQEEQAAPSIQGA SGMKLPGMAGSMLLGKSRSGLRTGSMVPFAAQQMNMMAAILGDTIMVAKGLVKLTQAAVETHLQHLGIG GELIMAARALQSTAVEQIGMFLGKVQGQDKHEEYFAENFGGPEGEFHFSVPHAAGASTDFSSASAPDQSA PPSLGHAHSEGPAPAYVASGPFREAGFPGQASSPLGRANGRLFANPRDSFSAMGFQRRFMALLRAAVSE LRRRGRGALTPLPALSSLLSSLSPRSPASTRPEPNNPHADRRHVIALRRCPPLPASAVLAPELLHARGLLPR HWSHASPLSTSSSSSRPADKAQLTWVDKWIPEAAREPYMFACAKLACTPSLIRAGSRVAYRPISASVLSRPE ASRTGEGSTVFNGAQNGVSQLIQREFQTSAISR |
| 156 | hsADCK3_ zm LOC100282174 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHAHSEGPAPAYVASGPFREAGFPGQASSPLGRA NGRLFANPRDSFSAMGFQRRFGGMALLRAAVSELRRRGRGALTPLPALSSLLSSLSPRSPASTRPEPNNP HADRRHVIALRRCPPLPASAVLAPELLHARGLLPRHWSHASPLSTSSSSSRPADKAQLTWVDKWIPEAARP YGG |

TABLE 1-continued nucleic acid and polypeptide sequences and SEQ ID NOs

| SEQ | description | sequence |
|---|---|---|
| 157 | hsADCK3_zm LOC100282174_crATP6 | MAAILGDTIMVAKGLVKLTQAAVETHLQHLGIGGELIMAARALQSTAVEQIGMFLGKVQGQDKHEEYFAENF GGPEGEFHFSVPHAAGASTDFSSASAPDQSAPPSLGHAHSEGPAPAYVASGPFREAGFPGQASSPLGRA NGRLFANPRDSFSAMGFQRRFGGMALLRAAVSELRRGRGALTPLPALSSLLSSLSPRSPASTRPEPNNP HADRRHVIALRRCPPLPASAVLAPELLHARGLLPRHWSHASPLSTSSSSSRPADKAQLTWVDKWIPEAARP YGGMALQQAAPRVFGLLGRAPVALGQSGILTGSSGFKNQGFNGSLQSVENHVYAQAFSTSSQEEQAAPSI QGASGMKLPGAGSMLLGKSRSGLRTGSMVPFAAQQMNMMGG |
| 158 | ncATP9_zm LOC100282174_spilv1_GNFP_ncATP79 | MASTRVLASRLASQMAASAKVARPAVRVAQVSKRTIQTGSPLQTLKRTQMTSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPYMTVLAPLRRLHTRAAFSSYGREIALQKRF LNLNSCSAVRRYGTGFSNNLRIKKLKNAFGVVRANSTKSTSTVTTASPIKYDSSFVGKTGGEIFHDMMLKH NVKHVFGYPGGAILPVFDAIYRSPHFEFILPRHEQAAGHAVSGEGDATYGKLTLKFICTTGKLPVPWPTLVT TLTGVGVQCFSRYPDHKQHDFFKSAMPEGYVQERTIFFKDDGNYKTRAEVKFEGDTLVNRIELKGIDFKED GNILGHKLEYNYNSHNVYIMADKQKNGIKVNFKIRHNIEDGSVQLADHYQQNTPIGDGPVLLPDNHYLSTQS ALSKDPNEMASTRVLASRLASQMAASAKVARPAVRVAQVSKRTIQTGSPLQTLKRTQMTSIVNATTRQAFQ KRA |
| 159 | ncATP9_zm LOC100282174_spilv1_lcSirt5_osP0644B06.24-2_hsATP5G2_ncATP9 | MASTRVLASRLASQMAASAKVARPAVRVAQVSKRTIQTGSPLQTLKRTQMTSIVNATTRQAFQKRAMALLR AAVSELRRRGRGALTPLPALSSLLSSLSPRSPASTRPEPNNPHADRRHVIALRRCPPLPASAVLAPELLHAR GLLPRHWSHASPLSTSSSSSRPADKAQLTWVDKWIPEAARPYMTVLAPLRRLHTRAAFSSYGREIALQKRF LNLNSCSAVRRYGTGFSNNLRIKKLKNAFGVVRANSTKSTSTVTTASPIKYDSSFVGKTGGEIFHDMMLKH NVKHVFGYPGGAILPVFDAIYRSPHFEFILPRHEQAAGHAMRKRSLRCHLWSANASLSPRKDEVTSRKESE NLVKGKKNKKSHLHLLLFTASKIGTDSVPDVQKSKECCKELGLLFTSLIHSIGSFPFDEEPKAAAVFLPGSLP QLTVLVLAPGSGSCPTGKSTPHLAASGRNAELLRPQNSMIVRQFTCRGTISSHLCAHLRKPHDSRNMARP MALLLRHSPKLRRAHAILGCERGTVVRHFSSSTCSSLVKEDTVSSSNLHPEYAKKIGGSDFSHDRQSGKEL QNFKVSPQEASRASNFRMASKYGMPITANGVHSLFSCGQVVPSRCFMPELILYVAITLSVAERLVGPGHAC AEPSFRSSRCSAPLCLLCSGSSSPATAPHPLKMFACSKFVSTPSLVKSTSQLLSRPLSAVVLKRPEILTDES LSSLAVSCPLTSLVSSRSFQTSAISRDIDTAMASTRVLASRLASQMAASAKVARPAVRVAQVSKRTIQTGSP LQTLKRTQMTSIVNATTRQAFQKRA |
| 160 | ND4 | MLKLIVPTIMLLPLTWLSKKHMIWINTTTHSLIISIIPLLFFNQINNNLFSCSPTFSSDPLTTPLLMLTTWLLPLTI MASQRHLSSEPLSRKKLYLSMLISLQISLIMTFTATELIMFYIFFETTLIPTLAIITRWGNQPERLNAGTYFLFYT LVGSLPLLIALIYTHNTLGSLNILLLTLTAQELSNSWANNLMWLAYTMAFMVKMPLYGLHLWLPKAHVEAPIA GSMVLAAVLLKLGGYGMMRLTLILNPLTKHMAYPFLVLSLWGMIMTSSICLRQTDLKSLIAYSSISHMALVVT AILIQTPWSFTGAVILMIAHGLTSSLLFCLANSNYERTHSRIMILSQGLQTLLPLMAFWWLLASLANLALPPTIN LLGELSVLVTTFSWSNITLLLTGLNMLVTALYSLYMVFTTTQWGSLTHHINNMKPSFTRENTLMFMHLSPILLL SLNRPDIITGFSS |
| 161 | ND6 | MMYALFLLSVGLVMGFVGFSSKPSPIYGGLVLIVSGVVGCVIILNFGGGYMGLMVFLIYLGGMMVVFGYTTA MAIEEYPEAWGSGVEVLVSVLVGLAMEVGLVLWVKEYDGVVVVVNFNSVGSWMIYEGEGSGLIREDPIGA GALYDYGRWLVVVTGWTLFVGVYIVIEIARGN |
| 162 | ND1 | MANLLLLIVPILIAMAFLMLTERKILGYMQLRKGPNVVGPYGLLQPFADAIKLFTKEPLKPATSTITLYITAPTLA LTIALLLWTPLPMPNPLVNLNLGLLFILATSSLAVYSILWSGWASNSNYALIGALRAVAQTISYEVTLAIILLSTL LMSGSFNLSTLITTQEHLWLLLPSWPLAMMWFISTLAETNRTPFDLAEGESELVSGFNIEYAAGPFALFFMA EYTNIIMMNTLTTTIFLGTTYDALSPELYTTYFVTKTLLLTSLFLWIRTAYPRFRYDQLMHLLWKNFLPLTLALL MWYVSMPITISSIPPQT |

Adeno-Associated Virus (AAV)

Adeno-associated virus (AAV) is a small virus that infects humans and some other primate species. The compositions disclosed herein comprises firstly an adeno-associated virus (AAV) genome or a derivative thereof.

An AAV genome is a polynucleotide sequence which encodes functions needed for production of an AAV viral particle. These functions include those operating in the replication and packaging cycle for AAV in a host cell, including encapsidation of the AAV genome into an AAV viral particle. Naturally occurring AAV viruses are replication-deficient and rely on the provision of helper functions in trans for completion of a replication and packaging cycle. Accordingly, the AAV genome of the vector of the invention is typically replication-deficient.

The AAV genome can be in single-stranded form, either positive or negative-sense, or alternatively in double-stranded form. The use of a double-stranded form allows bypass of the DNA replication step in the target cell and so can accelerate transgene expression.

The AAV genome may be from any naturally derived serotype or isolate or Glade of AAV. Thus, the AAV genome may be the full genome of a naturally occurring AAV virus. As is known to the skilled person, AAV viruses occurring in nature may be classified according to various biological systems.

Commonly, AAV viruses are referred to in terms of their serotype. A serotype corresponds to a variant subspecies of AAV which owing to its profile of expression of capsid surface antigens has a distinctive reactivity which can be used to distinguish it from other variant subspecies. Typically, a virus having a particular AAV serotype does not efficiently cross-react with neutralising antibodies specific for any other AAV serotype. AAV serotypes include AAV1, AAV2, AAV3, AAV4, AAV5, AAV6, AAV7, AAV8, AAV9, AAV10, AAV11, AAV12. AAV13, AAV14, AAV15, and AAV16, also recombinant serotypes, such as Rec2 and Rec3, recently identified from primate brain.

A preferred serotype of AAV for use in the invention is AAV2. Other serotypes of particular interest for use in the invention include AAV4, AAV5 and AAV8 which efficiently transduce tissue in the eye, such as the retinal pigmented epithelium. The serotype of AAV which is used can be an AAV serotype which is not AAV4. Reviews of AAV serotypes may be found in Choi et al (Curr Gene Ther. 2005; 5(3); 299-310) and Wu et al (Molecular Therapy. 2006; 14(3), 316-327). The sequences of AAV genomes or of elements of AAV genomes including ITR sequences, rep or cap genes for use in the invention may be derived from the following accession numbers for AAV whole genome sequences: Adeno-associated virus 1 NC_002077, AF063497; Adeno-associated virus 2 NC_001401; Adeno-associated virus 3 NC_001729; Adeno-associated virus 3B NC_001863; Adeno-associated virus 4 NC_001829; Adeno-associated virus 5 Y18065, AF085716; Adeno-associated virus 6 NC_001862; Avian AAV ATCC VR-865 AY186198, AY629583, NC_004828; Avian AAV strain DA-1 NC 006263, AY629583; Bovine AAV NC_005889, AY388617.

AAV viruses may also be referred to in terms of clades or clones. This refers to the phylogenetic relationship of naturally derived AAV viruses, and typically to a phylogenetic group of AAV viruses which can be traced back to a common ancestor, and includes all descendants thereof. Additionally, AAV viruses may be referred to in terms of a specific isolate, i.e. a genetic isolate of a specific AAV virus found in nature. The term genetic isolate describes a population of AAV viruses which has undergone limited genetic mixing with other naturally occurring AAV viruses, thereby defining a recognisably distinct population at a genetic level.

Examples of clades and isolates of AAV that may be used in the invention include: Clade A: AAV1 NC_002077, AF063497, AAV6 NC_001862, Hu. 48 AY530611, Hu 43 AY530606, Hu 44 AY530607, Hu 46 AY530609; Clade B: Hu. 19 AY530584, Hu. 20 AY530586, Hu 23 AY530589, Hu22 AY530588, Hu24 AY530590, Hu21 AY530587, Hu27 AY530592, Hu28 AY530593, Hu 29 AY530594, Hu63 AY530624, Hu64 AY530625, Hu13 AY530578, Hu56 AY530618, Hu57 AY530619, Hu49 AY530612. Hu58 AY530620, Hu34 AY530598, Hu35 AY530599, AAV2 NC_001401, Hu45 AY530608, Hu47 AY530610, Hu51 AY530613, Hu52 AY530614, Hu T41 AY695378, Hu S17 AY695376, Hu T88 AY695375, Hu T71 AY695374, Hu T70 AY695373, Hu T40 AY695372, Hu T32 AY695371, Hu T17 AY695370, Hu LG15 AY695377; Clade C: Hu9 AY530629, Hu10 AY530576, Hu11 AY530577, Hu53 AY530615, Hu55 AY530617, Hu54 AY530616, Hu7 AY530628, Hu18 AY530583, Hu15 AY530580, Hu16 AY530581, Hu25 AY530591, Hu60 AY530622, Ch5 AY243021, Hu3 AY530595, Hu1 AY530575, Hu4 AY530602 Hu2, AY530585, Hu61 AY530623; Clade D: Rh62 AY530573, Rh48 AY530561. Rh54 AY530567. Rh55 AY530568, Cy2 AY243020, AAV7 AF513851, Rh35 AY243000, Rh37 AY242998, Rh36 AY242999, Cy6 AY243016, Cy4 AY243018, Cy3 AY243019, Cy5 AY243017, Rh13 AY243013; Clade E: Rh38 AY530558, Hu66 AY530626, Hu42 AY530605, Hu67 AY530627, Hu40 AY530603, Hu41 AY530604, Hu37 AY530600, Rh40 AY530559, Rh2 AY243007. Bb1 AY243023, Bb2 AY243022, Rh10 AY243015, Hu17 AY530582, Hu6 AY530621, Rh25 AY530557, Pi2 AY530554. Pi1 AY530553, Pi3 AY530555, Rh57 AY530569, Rh50 AY530563, Rh49 AY530562, Hu39 AY530601, Rh58 AY530570, Rh61 AY530572, Rh52 AY530565, Rh53 AY530566, Rh51 AY530564, Rh64 AY530574, Rh43 AY530560, AAV8 AF513852, Rh8 AY242997, Rh1 AY530556; Clade F: Hu14 (AAV9) AY530579, Hu31 AY530596, Hu32 AY530597. Clonal Isolate AAV5 Y18065, AF085716, AAV 3 NC_001729, AAV 3B NC_001863, AAV4 NC_001829, Rh34 AY243001, Rh33 AY243002, Rh32 AY243003.

The skilled person can select an appropriate serotype, Glade, clone or isolate of AAV for use in the present invention on the basis of their common general knowledge. For instance, the AAV5 capsid has been shown to transduce primate cone photoreceptors efficiently as evidenced by the successful correction of an inherited color vision defect (Mancuso et al., Nature 2009, 461:784-7).

It should be understood however that the invention also encompasses use of an AAV genome of other serotypes that may not yet have been identified or characterised. The AAV serotype determines the tissue specificity of infection (or tropism) of an AAV virus. Accordingly, preferred AAV serotypes for use in AAV viruses administered to patients in accordance with the invention are those which have natural tropism for or a high efficiency of infection of target cells within eye in LHON. Thus, AAV serotypes for use in AAV viruses administered to patients can be ones which infect cells of the neurosensory retina and retinal pigment epithelium.

Typically, the AAV genome of a naturally derived serotype or isolate or Glade of AAV comprises at least one inverted terminal repeat sequence (ITR). An ITR sequence acts in cis to provide a functional origin of replication, and allows for integration and excision of the vector from the genome of a cell. In preferred embodiments, one or more ITR sequences flank the polynucleotide sequence encoding ND4, ND6, or ND1 or a variant thereof. Preferred ITR sequences are those of AAV2, and variants thereof. The AAV genome typically also comprises packaging genes, such as rep and/or cap genes which encode packaging functions for an AAV viral particle. The rep gene encodes one or more of the proteins Rep78, Rep68, Rep52 and Rep40 or variants thereof. The cap gene encodes one or more capsid proteins such as VP1, VP2 and VP3 or variants thereof. These proteins make up the capsid of an AAV viral particle. Capsid variants are discussed below.

A promoter will be operably linked to each of the packaging genes. Specific examples of such promoters include the p5, p19 and p40 promoters (Laughlin et al., 1979, PNAS, 76:5567-5571). For example, the p5 and p19 promoters are generally used to express the rep gene, while the p40 promoter is generally used to express the cap gene.

As discussed above, the AAV genome used in the vector of the invention may therefore be the full genome of a naturally occurring AAV virus. For example, a vector comprising a full AAV genome may be used to prepare AAV virus in vitro. However, while such a vector may in principle be administered to patients, this will be done rarely in practice. Preferably the AAV genome will be derivatised for the purpose of administration to patients. Such derivatisation is standard in the art and the present invention encompasses the use of any known derivative of an AAV genome, and derivatives which could be generated by applying techniques known in the art. Derivatisation of the AAV genome and of the AAV capsid are reviewed in Coura and Nardi (Virology Journal, 2007, 4:99), and in Choi et al and Wu et al, referenced above.

Derivatives of an AAV genome include any truncated or modified forms of an AAV genome which allow for expression of a ND4, ND6, or ND1 transgene from a vector of the invention in vivo. Typically, it is possible to truncate the AAV genome significantly to include minimal viral sequence yet retain the above function. This is preferred for safety reasons to reduce the risk of recombination of the vector with wild-type virus, and also to avoid triggering a cellular immune response by the presence of viral gene proteins in the target cell.

Typically, a derivative will include at least one inverted terminal repeat sequence (ITR), preferably more than one ITR, such as two ITRs or more. One or more of the ITRs may be derived from AAV genomes having different serotypes, or may be a chimeric or mutant ITR. A preferred mutant ITR is one having a deletion of a trs (terminal resolution site). This deletion allows for continued replication of the genome to generate a single-stranded genome which contains both coding and complementary sequences i.e. a self-complementary AAV genome. This allows for bypass of DNA replication in the target cell, and so enables accelerated transgene expression.

The one or more ITRs will preferably flank the polynucleotide sequence encoding ND4, ND6, ND1, or a variant thereof at either end. The inclusion of one or more ITRs is preferred to aid concatamer formation of the vector of the invention in the nucleus of a host cell, for example following the conversion of single-stranded vector DNA into double-stranded DNA by the action of host cell DNA polymerases. The formation of such episomal concatamers protects the vector construct during the life of the host cell, thereby allowing for prolonged expression of the transgene in vivo.

In preferred embodiments, ITR elements will be the only sequences retained from the native AAV genome in the derivative. Thus, a derivative will preferably not include the rep and/or cap genes of the native genome and any other sequences of the native genome. This is preferred for the reasons described above, and also to reduce the possibility of integration of the vector into the host cell genome. Additionally, reducing the size of the AAV genome allows for increased flexibility in incorporating other sequence elements (such as regulatory elements) within the vector in addition to the transgene.

With reference to the AAV2 genome, the following portions could therefore be removed in a derivative of the invention: One inverted terminal repeat (ITR) sequence, the replication (rep) and capsid (cap) genes (NB: the rep gene in the wildtype AAV genome should not to be confused with ND4, ND6, or ND1, the human gene affected in LHON). However, in some embodiments, including in vitro embodiments, derivatives may additionally include one or more rep and/or cap genes or other viral sequences of an AAV genome. Naturally occurring AAV virus integrates with a high frequency at a specific site on human chromosome 19, and shows a negligible frequency of random integration, such that retention of an integrative capacity in the vector may be tolerated in a therapeutic setting.

Where a derivative genome comprises genes encoding capsid proteins i.e. VP1, VP2 and/or VP3, the derivative may be a chimeric, shuffled or capsid-modified derivative of one or more naturally occurring AAV viruses. In particular, the invention encompasses the provision of capsid protein sequences from different serotypes, clades, clones, or isolates of AAV within the same vector i.e. pseudotyping.

Chimeric, shuffled or capsid-modified derivatives will be typically selected to provide one or more desired functionalities for the viral vector. Thus, these derivatives may display increased efficiency of gene delivery, decreased immunogenicity (humoral or cellular), an altered tropism range and/or improved targeting of a particular cell type compared to an AAV viral vector comprising a naturally occurring AAV genome, such as that of AAV2. Increased efficiency of gene delivery may be effected by improved receptor or co-receptor binding at the cell surface, improved internalisation, improved trafficking within the cell and into the nucleus, improved uncoating of the viral particle and improved conversion of a single-stranded genome to double-stranded form. Increased efficiency may also relate to an altered tropism range or targeting of a specific cell population, such that the vector dose is not diluted by administration to tissues where it is not needed.

Chimeric capsid proteins include those generated by recombination between two or more capsid coding sequences of naturally occurring AAV serotypes. This may be performed for example by a marker rescue approach in which non-infectious capsid sequences of one serotype are cotransfected with capsid sequences of a different serotype, and directed selection is used to select for capsid sequences having desired properties. The capsid sequences of the different serotypes can be altered by homologous recombination within the cell to produce novel chimeric capsid proteins.

Chimeric capsid proteins also include those generated by engineering of capsid protein sequences to transfer specific capsid protein domains, surface loops or specific amino acid residues between two or more capsid proteins, for example between two or more capsid proteins of different serotypes.

Shuffled or chimeric capsid proteins may also be generated by DNA shuffling or by error-prone PCR. Hybrid AAV capsid genes can be created by randomly fragmenting the sequences of related AAV genes e.g. those encoding capsid proteins of multiple different serotypes and then subsequently reassembling the fragments in a self-priming polymerase reaction, which may also cause crossovers in regions of sequence homology. A library of hybrid AAV genes created in this way by shuffling the capsid genes of several serotypes can be screened to identify viral clones having a desired functionality. Similarly, error prone PCR may be used to randomly mutate AAV capsid genes to create a diverse library of variants which may then be selected for a desired property.

The sequences of the capsid genes may also be genetically modified to introduce specific deletions, substitutions or insertions with respect to the native wild-type sequence. In particular, capsid genes may be modified by the insertion of a sequence of an unrelated protein or peptide within an open reading frame of a capsid coding sequence, or at the N- and/or C-terminus of a capsid coding sequence.

The unrelated protein or peptide may advantageously be one which acts as a ligand for a particular cell type, thereby conferring improved binding to a target cell or improving the specificity of targeting of the vector to a particular cell population. An example might include the use of RGD peptide to block uptake in the retinal pigment epithelium and thereby enhance transduction of surrounding retinal tissues (Cronin et al., 2008 ARVO Abstract: D1048). The unrelated protein may also be one which assists purification of the viral particle as part of the production process i.e. an epitope or affinity tag. The site of insertion will typically be selected so as not to interfere with other functions of the viral particle e.g. internalisation, trafficking of the viral particle. The skilled person can identify suitable sites for insertion based on their common general knowledge. Particular sites are disclosed in Choi et al, referenced above.

The invention additionally encompasses the provision of sequences of an AAV genome in a different order and configuration to that of a native AAV genome. The invention also encompasses the replacement of one or more AAV sequences or genes with sequences from another virus or with chimeric genes composed of sequences from more than one virus. Such chimeric genes may be composed of sequences from two or more related viral proteins of different viral species.

The vector of the invention takes the form of a polynucleotide sequence comprising an AAV genome or derivative thereof and a sequence encoding ND4, ND6, ND1 or a variant thereof.

For the avoidance of doubt, the invention also provides an AAV viral particle comprising a vector of the invention. The AAV particles of the invention include transcapsidated forms wherein an AAV genome or derivative having an ITR of one serotype is packaged in the capsid of a different serotype. The AAV particles of the invention also include mosaic forms wherein a mixture of unmodified capsid proteins from two or more different serotypes makes up the viral envelope. The AAV particle also includes chemically modified forms bearing ligands adsorbed to the capsid surface. For example, such ligands may include antibodies for targeting a particular cell surface receptor.

The invention additionally provides a host cell comprising a vector or AAV viral particle of the invention.

Recombinant Nucleic Acid Sequences

Also disclosed herein are recombinant nucleic acid sequences comprising a polynucleotide sequence encoding a NADH dehydrogenase subunit-4 (ND4), NADH dehydrogenase subunit-1 (ND1) and NADH dehydrogenase subunit-6 (ND6) polypeptide or a variant thereof.

The polynucleotide sequence for ND4 is shown in SEQ ID NO: 6 and encodes the protein shown in SEQ ID NO: 160. Further nucleic acid sequences for ND4 are SEQ ID NO: 7 and 8. The polynucleotide sequence for ND6 is shown in SEQ ID NO: 9 and encodes the protein shown in SEQ ID NO: 161. A further nucleic acid sequence for ND6 is SEQ ID NO: 10. The polynucleotide sequence for ND1 is shown in SEQ ID NO: 11 and encodes the protein shown in SEQ ID NO: 162. A further nucleic acid sequence for ND1 is SEQ ID NO: 12.

A variant of any one of SEQ ID NO: 160, 161, or 162 may comprise truncations, mutants or homologues thereof, and any transcript variants thereof which encode a functional ND4, ND6, or ND1 polypeptide. Any homologues mentioned herein are typically at least 70% homologous to a relevant region of ND4, ND6, or ND1, and can functionally compensate for the polypeptide deficiency.

Homology can be measured using known methods. For example the UWGCG Package provides the BESTFIT program which can be used to calculate homology (for example used on its default settings) (Devereux et at (1984) Nucleic Acids Research 12, 387-395). The PILEUP and BLAST algorithms can be used to calculate homology or line up sequences (typically on their default settings), for example as described in Altschul S. F. (1993) J Mol Evol 36:290-300; Altschul, S, F et at (1990) J Mol Biol 215:403-10. Software for performing BLAST analyses is publicly available through the National Center for Biotechnology Information (http://www.ncbi.nlm.nih.gov/).

In preferred embodiments, a recombinant nucleic acid sequence may encode a polypeptide which is at least 55%, 65%, 70%, 75%, 80%, 85%, 90% and more preferably at least 95%, 97%, 99%, 99.5%, or 100% homologous to a relevant region of ND4, ND6, or ND (SEQ ID NO: 160, 161, or 162) over at least 20, preferably at least 30, for instance at least 40, 60, 100, 200, 300, 400 or more contiguous amino acids, or even over the entire sequence of the recombinant nucleic acid. The relevant region will be one which provides for functional activity of ND4, ND6, or ND1.

Alternatively, and preferably the recombinant nucleic acid sequence may encode a polypeptide having at least 70%, 75%, 80%, 85%, 90% and more preferably at least 95%, 97%, 99%, 99.5%, or 100% homologous to full-length ND4, ND6, or ND1 (SEQ ID NO: 160, 161, or 162) over its entire sequence. Typically the recombinant nucleic acid sequence differs from the relevant region of ND4, ND6, or ND1 (SEQ ID NO: 160, 161, or 162) by at least, or less than, 2, 5, 10, 20, 40, 50 or 60 mutations (each of which can be substitutions, insertions or deletions).

A recombinant nucleic acid ND4, ND6, or ND polypeptide may have a percentage identity with a particular region of SEQ ID NO: 160, 161, or 162 which is the same as any of the specific percentage homology values (i.e. it may have at least 70%, 80% or 90% and more preferably at least 95%, 97%, 99% identity) across any of the lengths of sequence mentioned above.

Variants of ND4, ND6, or ND1 (SEQ ID NO: 160, 161, or 162) also include truncations. Any truncation may be used so long as the variant is still functional. Truncations will typically be made to remove sequences that are non-essential for the protein activity and/or do not affect conformation of the folded protein, in particular folding of the active site. Appropriate truncations can routinely be identified by systematic truncation of sequences of varying length from the N- or C-terminus. Preferred truncations are N-terminal and may remove all other sequences except for the catalytic domain.

Variants of ND4, ND6, or ND1 (SEQ ID NO: 160, 161, or 162) further include mutants which have one or more, for example, 2, 3, 4, 5 to 10, 10 to 20, 20 to 40 or more, amino acid insertions, substitutions or deletions with respect to a particular region of ND4, ND6, or ND1 (SEQ ID NO: 160, 161, or 162). Deletions and insertions are made preferably outside of the catalytic domain as described below. Substitutions are also typically made in regions that are non-essential for protease activity and/or do not affect conformation of the folded protein.

Substitutions preferably introduce one or more conservative changes, which replace amino acids with other amino acids of similar chemical structure, similar chemical properties or similar side-chain volume. The amino acids introduced may have similar polarity, hydrophilicity, hydrophobicity, basicity, acidity, neutrality or charge to the amino acids they replace. Alternatively, the conservative change may introduce another amino acid that is aromatic or aliphatic in the place of a pre-existing aromatic or aliphatic amino acid. Conservative amino acid changes are well known in the art and may be selected in accordance with the properties of the amino acids.

Similarly, preferred variants of the polynucleotide sequence of ND4, ND6, or ND1 (SEQ ID NO: 6, 9, or 11) include polynucleotides having at least 70%, 75%, 80%, 85%, 90% and more preferably at least 95%, 96%, 97%, 9, 9%, 99%, or 99.5% homologous to a relevant region of ND4, ND6, or ND1 (SEQ ID NO: 6, 9, or 11). Preferably the variant displays these levels of homology to full-length ND4, ND6, or ND1 (SEQ ID NO: 6, 9, or 11) over its entire sequence.

Mitochondrial targeting sequences (MTSs) and three prime untranslated regions (3'UTRs) can be used to target proteins or mRNA to the mitochondria. The charge, length, and structure of the MTS can be important for protein import into the mitochondria. Particular 3'UTRs may drive mRNA localization to the mitochondrial surface and thus facilitate cotranslational protein import into the mitochondria.

The polynucleotide sequence for a mitochondrial targeting sequence can encode a polypeptide selected from hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa*

ATP9 (ncATP9), hsGHITM, hsNDUFAB1, hsATPSG3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3 zmLOC100282174_crATP6_hsATP5G3, crATP6_hsADCK3 zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9 (see Table 1 for SEQ ID NO). In one example, the polynucleotide sequences, COX10 (SEQ ID NO: 1, 2, or 3) can encode the mitochondrial targeting sequence, MTS-COX10 (SEQ ID NO: 126). In another example, the polynucleotide sequences, COX8 (SEQ ID NO: 4) can encode the mitochondrial targeting sequence, MTS-COX8 (SEQ ID NO: 127). In another example, the polynucleotide sequences, OPA1 (SEQ ID NO: 5) can encode the mitochondrial targeting sequence, MTS-OPA1 (SEQ ID NO: 128).

The 3'UTR nucleic acid sequence can be selected from hsACO2 (SEQ ID NO: 111), hsATP5B (SEQ ID NO: 112), hsAK2 (SEQ ID NO: 113), hsALDH2 (SEQ ID NO: 114), hsCOX10 (SEQ ID NO: 115), hsUQCRFS1 (SEQ ID NO: 116), hsNDUFV1 (SEQ ID NO: 117), hsNDUFV2 (SEQ ID NO: 118), hsSOD2 (SEQ ID NO: 119), hsCOX6c (SEQ ID NO: 120), hsIRP1 (SEQ ID NO: 121), hsMRPS12 (SEQ ID NO: 122), hsATP5J2 (SEQ ID NO: 123), mSOD2 (SEQ ID NO: 124), and hsOXA1L (SEQ ID NO: 125). The 3'UTR nucleic acid sequence can also be a variant having at least 70%, 75%, 80%, 85%, 90% and more preferably at least 95%, 96%, 97%, 98%, 99%, 99.5%, or 100% homologous to any 3'UTR nucleic acid sequence listed here. For example, the 3'UTR nucleic acid sequence can be SEQ ID NO: 13 or 14.

Also disclosed herein are recombinant nucleic acid sequences comprising a mitochondrial targeting sequence, a mitochondrial protein coding sequence, and a 3'UTR nucleic acid sequence. For example, the recombinant nucleic acid sequence can be selected from SEQ ID NO: 15-84. The recombinant nucleic acid sequence can also be a variant having at least 70%, 75%, 80%, 85%, 90% and more preferably at least 95%, 96%, 97%, 98%, 99%, 99.5%, or 100% homologous to any recombinant nucleic acid sequence listed here.

Promoters and Regulatory Sequences

The vector of the invention also includes elements allowing for the expression of the disclosed transgene in vitro or in vivo. Thus, the vector typically comprises a promoter sequence operably linked to the polynucleotide sequence encoding the ND4, ND6, or ND1 transgene or a variant thereof.

Any suitable promoter may be used. The promoter sequence may be constitutively active i.e. operational in any host cell background, or alternatively may be active only in a specific host cell environment, thus allowing for targeted expression of the transgene in a particular cell type. The promoter may show inducible expression in response to presence of another factor, for example a factor present in a host cell. In any event, where the vector is administered for therapy, the promoter must be functional in a retinal cell background.

In some embodiments, it is preferred that the promoter shows retinal-cell specific expression in order to allow for the transgene to only be expressed in retinal cell populations. Thus, expression from the promoter may be retinal-cell specific, for example confined only to cells of the neurosensory retina and retinal pigment epithelium.

Preferred promoters for the ND4, ND6, or ND transgene include the chicken beta-actin (CBA) promoter, optionally in combination with a cytomegalovirus (CME) enhancer element. In some cases, the preferred promoters for the ND4, ND6, or ND1 transgene comprises the CAG promoter. A particularly preferred promoter is a hybrid CBA/CAG promoter, for example the promoter used in the rAVE expression cassette. Examples of promoters based on human sequences that would induce retina specific gene expression include rhodospin kinase for rods and cones (Allocca et al., 2007. J Viol 81:11372-80), PR2.1 for cones only (Mancuso et al. 2009. Nature) and/or RPE65 for the retinal pigment epithelium (Bainbridge et al., 2008, N Eng J Med).

The vector of the invention may also comprise one or more additional regulatory sequences with may act pre- or post-transcriptionally. The regulatory sequence may be part of the native ND4, ND6, or ND1 gene locus or may be a heterologous regulatory sequence. The vector of the invention may comprise portions of the 5'UTR or 3'UTR from the native ND4, ND6, or ND1 transcript.

Regulatory sequences are any sequences which facilitate expression of the transgene i.e. act to increase expression of a transcript, improve nuclear export of mRNA or enhance its stability. Such regulatory sequences include for example enhancer elements, postregulatory elements and polyadenylation sites. A preferred polyadenylation site is the Bovine Growth Hormone poly-A signal. In the context of the vector of the invention such regulatory sequences will be cis-acting. However, the invention also encompasses the use of trans-acting regulatory sequences located on additional genetic constructs.

A preferred postregulatory element for use in a vector of the invention is the woodchuck hepatitis postregulatory element (WPRE) or a variant thereof. Another regulatory sequence which may be used in a vector of the present invention is a scaffold-attachment region (SAR). Additional regulatory sequences may be selected by the skilled person on the basis of their common general knowledge.

Preparation of Vector

The vector of the invention may be prepared by standard means known in the art for provision of vectors for gene therapy. Thus, well established public domain transfection, packaging and purification methods can be used to prepare a suitable vector preparation.

As discussed above, a vector of the invention may comprise the full genome of a naturally occurring AAV virus in addition to a polynucleotide sequence encoding ND4, ND6, or ND1 or a variant thereof. However, commonly a derivatised genome will be used, for instance a derivative which has at least one inverted terminal repeat sequence (ITR), but which may lack any AAV genes such as rep or cap.

In such embodiments, in order to provide for assembly of the derivatised genome into an AAV viral particle, additional genetic constructs providing AAV and/or helper virus functions will be provided in a host cell in combination with the derivatised genome. These additional constructs will typically contain genes encoding structural AAV capsid proteins i.e. cap, VP1, VP2, VP3, and genes encoding other functions required for the AAV life cycle, such as rep. The selection of structural capsid proteins provided on the additional construct will determine the serotype of the packaged viral vector.

A particularly preferred packaged viral vector for use in the invention comprises a derivatised genome of AAV2 in combination with AAV5 or AAV8 capsid proteins. This packaged viral vector typically comprises one or more AAV2 ITRs.

As mentioned above, AAV viruses are replication incompetent and so helper virus functions, preferably adenovirus helper functions will typically also be provided on one or more additional constructs to allow for AAV replication.

All of the above additional constructs may be provided as plasmids or other episomal elements in the host cell, or alternatively one or more constructs may be integrated into the genome of the host cell.

In these aspects, the invention provides a method for production of a vector of the invention. The method comprises providing a vector which comprises an adeno-associated virus (AAV) genome or a derivative thereof and a polynucleotide sequence encoding ND4, ND6, or ND1 or a variant thereof in a host cell, and providing means for replication and assembly of the vector into an AAV viral particle. Preferably, the method comprises providing a vector comprising a derivative of an AAV genome and a polynucleotide sequence encoding ND4, ND6, or ND1 or a variant thereof, together with one or more additional genetic constructs encoding AAV and/or helper virus functions. Typically, the derivative of an AAV genome comprises at least one ITR. Optionally, the method further comprises a step of purifying the assembled viral particles. Additionally, the method may comprise a step of formulating the viral particles for therapeutic use.

Methods of Therapy and Medical Uses

As discussed above, the present inventors have surprisingly demonstrated that a vector of the invention may be used to address the cellular dysfunction underlying LHON. In particular, they have shown that use of the vector can correct the defect associated with LHON. This provides a means whereby the degenerative process of the disease can be treated, arrested, palliated or prevented.

The invention therefore provides a method of treating or preventing LHON in a patient in need thereof, comprising administering a therapeutically effective amount of a vector of the invention to the patient by direct retinal, subretinal or intravitreal injection. Accordingly, LHON is thereby treated or prevented in the patient.

In a related aspect, the invention provides for use of a vector of the invention in a method of treating or preventing LHON by administering said vector to a patient by direct retinal, subretinal or intravitreal injection. Additionally, the invention provides the use of a vector of the invention in the manufacture of a medicament for treating or preventing LHON by direct retinal, subretinal or intravitreal injection.

In all these embodiments, the vector of the invention may be administered in order to prevent the onset of one or more symptoms of LHON. The patient may be asymptomatic. The subject may have a predisposition to the disease. The method or use may comprise a step of identifying whether or not a subject is at risk of developing, or has, LHON. A prophylactically effective amount of the vector is administered to such a subject. A prophylactically effective amount is an amount which prevents the onset of one or more symptoms of the disease.

Alternatively, the vector may be administered once the symptoms of the disease have appeared in a subject i.e. to cure existing symptoms of the disease. A therapeutically effective amount of the antagonist is administered to such a subject. A therapeutically effective amount is an amount which is effective to ameliorate one or more symptoms of the disease. Such an amount may also arrest, slow or reverse some loss of peripheral vision associated with LHON. Such an amount may also arrest, slow or reverse onset of LHON.

A typical single dose is between $10^{10}$ and $10^{12}$ genome particles, depending on the amount of remaining retinal tissue that requires transduction. A genome particle is defined herein as an AAV capsid that contains a single stranded DNA molecule that can be quantified with a sequence specific method (such as real-time PCR). That dose may be provided as a single dose, but may be repeated for the fellow eye or in cases where vector may not have targeted the correct region of retina for whatever reason (such as surgical complication). The treatment is preferably a single permanent treatment for each eye, but repeat injections, for example in future years and/or with different AAV serotypes may be considered.

The invention also provides a method of monitoring treatment or prevention of LHON in a patient comprising measuring activity ex vivo in retinal cells obtained from said patient following administration of the AAV vector of the invention by direct retinal, subretinal or intravitreal injection. This method can allow for determination of the efficacy of treatment.

Pharmaceutical Compositions

The vector of the invention can be formulated into pharmaceutical compositions. These compositions may comprise, in addition to the vector, a pharmaceutically acceptable excipient, carrier, buffer, stabiliser or other materials well known to those skilled in the art. Such materials should be non-toxic and should not interfere with the efficacy of the active ingredient. The precise nature of the carrier or other material may be determined by the skilled person according to the route of administration, i.e. here direct retinal, subretinal or intravitreal injection.

The pharmaceutical composition is typically in liquid form. Liquid pharmaceutical compositions generally include a liquid carrier such as water, petroleum, animal or vegetable oils, mineral oil or synthetic oil. Physiological saline solution, magnesium chloride, dextrose or other saccharide solution or glycols such as ethylene glycol, propylene glycol or polyethylene glycol may be included. In some cases, a surfactant, such as pluronic acid (PF68) 0.001% may be used.

For injection at the site of affliction, the active ingredient will be in the form of an aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

For delayed release, the vector may be included in a pharmaceutical composition which is formulated for slow release, such as in microcapsules formed from biocompatible polymers or in liposomal carrier systems according to methods known in the art.

Samples

Samples that are suitable for use in the methods described herein can be nucleic acid samples from a subject. A "nucleic acid sample" as used herein can include RNA or DNA, or a combination thereof. In another embodiment, a "polypeptide sample" (e.g., peptides or proteins, or fragments therefrom) can be used to ascertain information that an amino acid change has occurred, which is the result of a genetic variant. Nucleic acids and polypeptides can be extracted from one or more samples including but not limited to, blood, saliva, urine, mucosal scrapings of the lining of the mouth, expectorant, serum, tears, skin, tissue, or hair. A nucleic acid sample can be assayed for nucleic acid information. "Nucleic acid information," as used herein, includes a nucleic acid sequence itself, the presence/absence of genetic variation in the nucleic acid sequence, a physical property which varies depending on the nucleic acid sequence (e.g., Tm), and the amount of the nucleic acid (e.g., number of mRNA copies). A "nucleic acid" means any one of DNA. RNA. DNA including artificial nucleotides, or RNA including artificial nucleotides. As used herein, a "purified nucleic acid" includes cDNAs, fragments of genomic nucleic acids, nucleic acids produced using the polymerase chain reaction (PCR), nucleic acids formed by restriction enzyme treatment of genomic nucleic acids, recombinant nucleic acids, and chemically synthesized nucleic acid molecules. A "recombinant" nucleic acid molecule includes a nucleic acid molecule made by an artificial combination of two otherwise separated segments of sequence, e.g., by chemical synthesis or by the manipulation of isolated segments of nucleic acids by genetic engineering techniques. As used herein, a "polypeptide" includes proteins, fragments of proteins, and peptides, whether isolated from natural sources, produced by recombinant techniques, or chemically synthesized. A polypeptide may have one or more modifications, such as a post-translational modification (e.g., glycosylation, phosphorylation, etc.) or any other modification (e.g., pegylation, etc.). The polypeptide may contain one or more non-naturally-occurring amino acids (e.g., such as an amino acid with a side chain modification).

In some embodiments, the nucleic acid sample can comprise cells or tissue, for example, cell lines. Exemplary cell types from which nucleic acids can be obtained using the methods described herein include, but are not limited to, the following: a blood cell such as a B lymphocyte, T lymphocyte, leukocyte, erythrocyte, macrophage, or neutrophil; a muscle cell such as a skeletal cell, smooth muscle cell or cardiac muscle cell; a germ cell, such as a sperm or egg; an epithelial cell; a connective tissue cell, such as an adipocyte, chondrocyte; fibroblast or osteoblast; a neuron; an astrocyte; a stromal cell; an organ specific cell, such as a kidney cell, pancreatic cell, liver cell, or a keratinocyte; a stem cell; or any cell that develops therefrom. A cell from which nucleic acids can be obtained can be a blood cell or a particular type of blood cell including, for example, a hematopoietic stem cell or a cell that arises from a hematopoietic stem cell such as a red blood cell, B lymphocyte, T lymphocyte, natural killer cell, neutrophil, basophil, eosinophil, monocyte, macrophage, or platelet. Generally, any type of stem cell can be used including, without limitation, an embryonic stem cell, adult stem cell, or pluripotent stem cell.

In some embodiments, a nucleic acid sample can be processed for RNA or DNA isolation, for example, RNA or DNA in a cell or tissue sample can be separated from other components of the nucleic acid sample. Cells can be harvested from a nucleic acid sample using standard techniques, for example, by centrifuging a cell sample and resuspending the pelleted cells, for example, in a buffered solution, for example, phosphate-buffered saline (PBS). In some embodiments, after centrifuging the cell suspension to obtain a cell pellet, the cells can be lysed to extract DNA. In some embodiments, the nucleic acid sample can be concentrated and/or purified to isolate DNA. All nucleic acid samples obtained from a subject, including those subjected to any sort of further processing, are considered to be obtained from the subject. In some embodiments, standard techniques and kits known in the art can be used to extract RNA or DNA from a nucleic acid sample, including, for example, phenol extraction, a QIAAMP® Tissue Kit (Qiagen, Chatsworth, Calif.), a WIZARD® Genomic DNA purification kit (Promega), or a Qiagen Autopure method using Puregene chemistry, which can enable purification of highly stable DNA well-suited for archiving.

In some embodiments, determining the identity of an allele or determining copy number can, but need not, include obtaining a nucleic acid sample comprising RNA and/or DNA from a subject, and/or assessing the identity, copy number, presence or absence of one or more genetic variations and their chromosomal locations within the genomic DNA (i.e. subject's genome) derived from the nucleic acid sample.

The individual or organization that performs the determination need not actually carry out the physical analysis of a nucleic acid sample from a subject. In some embodiments, the methods can include using information obtained by analysis of the nucleic acid sample by a third party. In some embodiments, the methods can include steps that occur at more than one site. For example, a nucleic acid sample can be obtained from a subject at a first site, such as at a health care provider or at the subject's home in the case of a self-testing kit. The nucleic acid sample can be analyzed at the same or a second site, for example, at a laboratory or other testing facility.

Nucleic Acids

The nucleic acids and polypeptides described herein can be used in methods and kits of the present disclosure. In some embodiments, aptamers that specifically bind the nucleic acids and polypeptides described herein can be used in methods and kits of the present disclosure. As used herein, a nucleic acid can comprise a deoxyribonucleotide (DNA) or ribonucleotide (RNA), whether singular or in polymers, naturally occurring or non-naturally occurring, double-stranded or single-stranded, coding, for example a translated gene, or non-coding, for example a regulatory region, or any fragments, derivatives, mimetics or complements thereof. In some embodiments, nucleic acids can comprise oligonucleotides, nucleotides, polynucleotides, nucleic acid sequences, genomic sequences, complementary DNA (cDNA), anti-sense nucleic acids, DNA regions, probes, primers, genes, regulatory regions, introns, exons, open-reading frames, binding sites, target nucleic acids and allele-specific nucleic acids.

A "probe," as used herein, includes a nucleic acid fragment for examining a nucleic acid in a specimen using the hybridization reaction based on the complementarity of nucleic acid.

A "hybrid" as used herein, includes a double strand formed between any one of the abovementioned nucleic acid, within the same type, or across different types, including DNA-DNA, DNA-RNA, RNA-RNA or the like.

"Isolated" nucleic acids, as used herein, are separated from nucleic acids that normally flank the gene or nucleotide sequence (as in genomic sequences) and/or has been completely or partially purified from other transcribed sequences (e.g., as in an RNA library). For example, isolated nucleic acids of the disclosure can be substantially isolated with respect to the complex cellular milieu in which it naturally occurs, or culture medium when produced by recombinant techniques, or chemical precursors or other chemicals when chemically synthesized. In some instances, the isolated material can form part of a composition, for example, a crude extract containing other substances, buffer system or reagent mix. In some embodiments, the material can be purified to essential homogeneity using methods known in the art, for example, by polyacrylamide gel electrophoresis (PAGE) or column chromatography (e.g., HPLC). With regard to genomic DNA (gDNA), the term "isolated" also can refer to nucleic acids that are separated from the chromosome with which the genomic DNA is naturally associated. For example, the isolated nucleic acid molecule can contain less than about 250 kb, 200 kb, 150 kb, 100 kb, 75 kb, 50 kb, 25 kb, 10 kb, 5 kb, 4 kb, 3 kb, 2 kb, 1 kb, 0.5 kb or 0.1 kb of the nucleotides that flank the nucleic acid molecule in the gDNA of the cell from which the nucleic acid molecule is derived.

Nucleic acids can be fused to other coding or regulatory sequences can be considered isolated. For example, recombinant DNA contained in a vector is included in the definition of "isolated" as used herein. In some embodiments, isolated nucleic acids can include recombinant DNA molecules in heterologous host cells or heterologous organisms, as well as partially or substantially purified DNA molecules in solution. Isolated nucleic acids also encompass in vivo and in vitro RNA transcripts of the DNA molecules of the present disclosure. An isolated nucleic acid molecule or nucleotide sequence can be synthesized chemically or by recombinant means. Such isolated nucleotide sequences can be useful, for example, in the manufacture of the encoded polypeptide, as probes for isolating homologous sequences (e.g., from other mammalian species), for gene mapping (e.g., by in situ hybridization with chromosomes), or for detecting expression of the gene, in tissue (e.g., human tissue), such as by Northern blot analysis or other hybridization techniques disclosed herein. The disclosure also pertains to nucleic acid sequences that hybridize under high stringency hybridization conditions, such as for selective hybridization, to a nucleotide sequence described herein Such nucleic acid sequences can be detected and/or isolated by allele- or sequence-specific hybridization (e.g., under high stringency conditions). Stringency conditions and methods for nucleic acid hybridizations are well known to the skilled person (see, e.g., Current Protocols in Molecular Biology, Ausubel. F. et al., John Wiley & Sons, (1998), and Kraus, M. and Aaronson. S., Methods Enzymol., 200:546-556 (1991), the entire teachings of which are incorporated by reference herein.

Calculations of "identity" or "percent identity" between two or more nucleotide or amino acid sequences can be determined by aligning the sequences for optimal comparison purposes (e.g., gaps can be introduced in the sequence of a first sequence). The nucleotides at corresponding positions are then compared, and the percent identity between the two sequences is a function of the number of identical positions shared by the sequences (i.e. % identity=# of identical positions/total # of positions×100). For example, a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

In some embodiments, the length of a sequence aligned for comparison purposes is at least 30%, at least 40%, at least 50%, at least 60%, at least 70%, at least 80%, at least 90%, or at least 95%, of the length of the reference sequence. The actual comparison of the two sequences can be accomplished by well-known methods, for example, using a mathematical algorithm. A non-limiting example of such a mathematical algorithm is described in Karlin, S. and Altschul, S., Proc. Natl. Acad. Sci. USA, 90-5873-5877 (1993). Such an algorithm is incorporated into the NBLAST and XBLAST programs (version 2.0), as described in Altschul, S. et al., Nucleic Acids Res., 25:3389-3402 (1997). When utilizing BLAST and Gapped BLAST programs, any relevant parameters of the respective programs (e.g., NBLAST) can be used. For example, parameters for sequence comparison can be set at score=100, word length=12, or can be varied (e.g., W=5 or W=20). Other examples include the algorithm of Myers and Miller, CABIOS (1989), ADVANCE, ADAM, BLAT, and FASTA. In some embodiments, the percent identity between two amino acid sequences can be accomplished using, for example, the GAP program in the GCG software package (Accelrys, Cambridge, UK).

"Probes" or "primers" can be oligonucleotides that hybridize in a base-specific manner to a complementary strand of a nucleic acid molecule. Probes can include primers, which can be a single-stranded oligonucleotide probe that can act as a point of initiation of template-directed DNA synthesis using methods including but not limited to, polymerase chain reaction (PCR) and ligase chain reaction (LCR) for amplification of a target sequence. Oligonucleotides, as described herein, can include segments or fragments of nucleic acid sequences, or their complements. In some embodiments, DNA segments can be between 5 and 10,000 contiguous bases, and can range from 5, 10, 12, 15, 20, or 25 nucleotides to 10, 15, 20, 25, 30, 40, 50, 100, 200, 500, 1000 or 10,000 nucleotides. In addition to DNA and RNA, probes and primers can include polypeptide nucleic acids (PNA), as described in Nielsen, P. et al., Science 254: 1497-1500 (1991). A probe or primer can comprise a region of nucleotide sequence that hybridizes to at least about 15, typically about 20-25, and in certain embodiments about 40, 50, 60 or 75, consecutive nucleotides of a nucleic acid molecule.

The present disclosure also provides isolated nucleic acids, for example, probes or primers, that contain a fragment or portion that can selectively hybridize to a nucleic acid that comprises, or consists of, a nucleotide sequence, wherein the nucleotide sequence can comprise at least one polymorphism or polymorphic allele contained in the genetic variations described herein or the wild-type nucleotide that is located at the same position, or the complements thereof. In some embodiments, the probe or primer can be at least 70% identical, at least 80% identical, at least 85% identical, at least 90% identical, or at least 95% identical, to the contiguous nucleotide sequence or to the complement of the contiguous nucleotide sequence.

In some embodiments, a nucleic acid probe can be an oligonucleotide capable of hybridizing with a complementary region of a gene associated with a condition (e.g., LHON) containing a genetic variation described herein. The nucleic acid fragments of the disclosure can be used as probes or primers in assays such as those described herein.

The nucleic acids of the disclosure, such as those described above, can be identified and isolated using standard molecular biology techniques well known to the skilled person. In some embodiments, DNA can be amplified and/or can be labeled (e.g., radiolabeled, fluorescently labeled) and used as a probe for screening, for example, a cDNA library derived from an organism. cDNA can be derived from mRNA and can be contained in a suitable vector. For example, corresponding clones can be isolated, DNA obtained following in vivo excision, and the cloned insert can be sequenced in either or both orientations by art-recognized methods to identify the correct reading frame encoding a polypeptide of the appropriate molecular weight.

Using these or similar methods, the polypeptide and the DNA encoding the polypeptide can be isolated, sequenced and further characterized.

In some embodiments, nucleic acid can comprise one or more polymorphisms, variations, or mutations, for example, single nucleotide polymorphisms (SNPs), single nucleotide variations (SNVs), copy number variations (CNVs), for example, insertions, deletions, inversions, and translocations. In some embodiments, nucleic acids can comprise analogs, for example, phosphorothioates, phosphoramidates, methyl phosphonate, chiralmethyl phosphonates, 2-0-methyl ribonucleotides, or modified nucleic acids, for example, modified backbone residues or linkages, or nucleic acids combined with carbohydrates, lipids, polypeptide or other materials, or peptide nucleic acids (PNAs), for example, chromatin, ribosomes, and transcriptosomes. In some embodiments nucleic acids can comprise nucleic acids in various structures, for example, A DNA, B DNA, Z-form DNA, siRNA, tRNA, and ribozymes. In some embodiments, the nucleic acid may be naturally or non-naturally polymorphic, for example, having one or more sequence differences, for example, additions, deletions and/or substitutions, as compared to a reference sequence. In some embodiments, a reference sequence can be based on publicly available information, for example, the U.C. Santa Cruz Human Genome Browser Gateway (genome.ucsc.edu/cgi-bin/hg-Gateway) or the NCBI website (www.ncbi.nlm.nih.gov). In some embodiments, a reference sequence can be determined by a practitioner of the present disclosure using methods well known in the art, for example, by sequencing a reference nucleic acid.

In some embodiments, a probe can hybridize to an allele, SNP, SNV, or CNV as described herein. In some embodiments, the probe can bind to another marker sequence associated with LHON as described herein.

One of skill in the art would know how to design a probe so that sequence specific hybridization can occur only if a particular allele is present in a genomic sequence from a test nucleic acid sample. The disclosure can also be reduced to practice using any convenient genotyping method, including commercially available technologies and methods for genotyping particular genetic variations.

Control probes can also be used, for example, a probe that binds a less variable sequence, for example, a repetitive DNA associated with a centromere of a chromosome, can be used as a control. In some embodiments, probes can be obtained from commercial sources. In some embodiments, probes can be synthesized, for example, chemically or in vitro, or made from chromosomal or genomic DNA through standard techniques. In some embodiments sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification using PCR.

One or more nucleic acids for example, a probe or primer, can also be labeled, for example, by direct labeling, to comprise a detectable label. A detectable label can comprise any label capable of detection by a physical, chemical, or a biological process for example, a radioactive label, such as 32P or 3H, a fluorescent label, such as FITC, a chromophore label, an affinity-ligand label, an enzyme label, such as alkaline phosphatase, horseradish peroxidase, or I2 galactosidase, an enzyme cofactor label, a hapten conjugate label, such as digoxigenin or dinitrophenyl, a Raman signal generating label, a magnetic label, a spin label, an epitope label, such as the FLAG or HA epitope, a luminescent label, a heavy atom label, a nanoparticle label, an electrochemical label, a light scattering label, a spherical shell label, semiconductor nanocrystal label, such as quantum dots (described in U.S. Pat. No. 6,207,392), and probes labeled with any other signal generating label known to those of skill in the art, wherein a label can allow the probe to be visualized with or without a secondary detection molecule. A nucleotide can be directly incorporated into a probe with standard techniques, for example, nick translation, random priming, and PCR labeling. A "signal," as used herein, include a signal suitably detectable and measurable by appropriate means, including fluorescence, radioactivity, chemiluminescence, and the like.

Non-limiting examples of label moieties useful for detection include, without limitation, suitable enzymes such as horseradish peroxidase, alkaline phosphatase, beta-galactosidase, or acetylcholinesterase; members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, Texas Red, dichlorotriazinylamine fluorescein, dansyl chloride, phycoerythrin, fluorescent lanthanide complexes such as those including Europium and Terbium, cyanine dye family members, such as Cy3 and Cy5, molecular beacons and fluorescent derivatives thereof, as well as others known in the art as described, for example, in Principles of Fluorescence Spectroscopy, Joseph R. Lakowicz (Editor), Plenum Pub Corp. 2nd edition (July 1999) and the 6th Edition of the Molecular Probes Handbook by Richard P. Hoagland; a luminescent material such as luminol; light scattering or plasmon resonant materials such as gold or silver particles or quantum dots; or radioactive material include 14C, 123I, 124I, 125I, Tc99m, 32P, 33P, 35S or 3H.

Other labels can also be used in the methods of the present disclosure, for example, backbone labels. Backbone labels comprise nucleic acid stains that bind nucleic acids in a sequence independent manner. Non-limiting examples include intercalating dyes such as phenanthridine and acridines (e.g., ethidium bromide, propidium iodide, hexidium iodide, dihydroethidium, ethidium homodimer-1 and -2, ethidium monoazide, and ACMA); some minor grove binders such as indoles and imidazoles (e.g., Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc. Still other examples of nucleic acid stains include the following dyes from Molecular Probes: cyanine dyes such as SYTOX Blue, SYTOX Green, SYTOX Orange. POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82. - 83, -84, -85 (orange), SYTO-64, -17, -59, -61, -62, -60, -63 (red).

In some embodiments, fluorophores of different colors can be chosen, for example, 7-amino-4-methylcoumarin-3-acetic acid (AMCA), 5-(and-6)-carboxy-X-rhodamine, lissamine rhodamine B, 5-(and-6)-carboxyfluorescein, fluorescein-5-isothiocyanate (FITC), 7-diethylaminocoumarin-3-carboxylic acid, tetramethylrhodamine-5-(and-6)-isothiocyanate, 5-(and-6)-carboxytetramethylrhodamine, 7-hydroxycoumarin-3-carboxylic acid, 6-[fluorescein 5-(and-6)-carboxamido]hexanoic acid, N-(4,4-difluoro-5,7-dimethyl-4-bora-3a,4a diaza-3-indacenepropionic acid, eosin-5-isothiocyanate, erythrosin-5-isothiocyanate, TRITC, rhodamine, tetramethylrhodamine, R-phycoerythrin, Cy-3, Cy-5, Cy-7, Texas Red, Phar-Red, allophycocyanin (APC), and CASCADE™ blue acetylazide, such that each probe in or not in a set can be distinctly visualized. In some embodiments, fluorescently labeled probes can be viewed with a fluorescence microscope and an appropriate filter for each fluorophore, or by using dual or triple band-pass filter sets to observe multiple fluorophores. In some embodiments, techniques such as flow cytometry can be used to examine the hybridization pattern of the probes.

In other embodiments, the probes can be indirectly labeled, for example, with biotin or digoxygenin, or labeled with radioactive isotopes such as 32P and/or 3H. As a non-limiting example, a probe indirectly labeled with biotin can be detected by avidin conjugated to a detectable marker. For example, avidin can be conjugated to an enzymatic marker such as alkaline phosphatase or horseradish peroxidase. In some embodiments, enzymatic markers can be detected using colorimetric reactions using a substrate and/or a catalyst for the enzyme. In some embodiments, catalysts for alkaline phosphatase can be used, for example, 5-bromo-4-chloro-3-indolylphosphate and nitro blue tetrazolium. In some embodiments, a catalyst can be used for horseradish peroxidase, for example, diaminobenzoate.

Formulations, Routes of Administration, and Effective Doses

Yet another aspect of the present disclosure relates to formulations, routes of administration and effective doses for pharmaceutical compositions comprising an agent or combination of agents of the instant disclosure. Such pharmaceutical compositions can be used to treat a condition (e.g., LHON) as described above.

Compounds of the disclosure can be administered as pharmaceutical formulations including those suitable for oral (including buccal and sub-lingual), rectal, nasal, topical, transdermal patch, pulmonary, vaginal, suppository, or parenteral (including intraocular, intravitreal, intramuscular, intraarterial, intrathecal, intradermal, intraperitoneal, subcutaneous and intravenous) administration or in a form suitable for administration by aerosolization, inhalation or insufflation. General information on drug delivery systems can be found in Ansel et al., Pharmaceutical Dosage Forms and Drug Delivery Systems (Lippencott Williams & Wilkins, Baltimore Md. (1999).

In various embodiments, the pharmaceutical composition includes carriers and excipients (including but not limited to buffers, carbohydrates, mannitol, polypeptides, amino acids, antioxidants, bacteriostats, chelating agents, suspending agents, thickening agents and/or preservatives), water, oils including those of petroleum, animal, vegetable or synthetic origin, such as peanut oil, soybean oil, mineral oil, sesame oil and the like, saline solutions, aqueous dextrose and glycerol solutions, flavoring agents, coloring agents, detackifiers and other acceptable additives, adjuvants, or binders, other pharmaceutically acceptable auxiliary substances to approximate physiological conditions, such as pH buffering agents, tonicity adjusting agents, emulsifying agents, wetting agents and the like. Examples of excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. In some embodiments, the pharmaceutical preparation is substantially free of preservatives. In other embodiments, the pharmaceutical preparation can contain at least one preservative. General methodology on pharmaceutical dosage forms is found in Ansel et al., Pharmaceutical Dosage Forms and Drug Delivery Systems (Lippencott, Williams, & Wilkins, Baltimore Md. (1999)). It can be recognized that, while any suitable carrier known to those of ordinary skill in the art can be employed to administer the compositions of this disclosure, the type of carrier can vary depending on the mode of administration.

Compounds can also be encapsulated within liposomes using well-known technology. Biodegradable microspheres can also be employed as carriers for the pharmaceutical compositions of this disclosure. Suitable biodegradable microspheres are disclosed, for example, in U.S. Pat. Nos. 4,897,268, 5,075,109, 5,928,647, 5,811,128, 5,820,883, 5,853,763, 5,814,344 and 5,942,252.

The compound can be administered in liposomes or microspheres (or microparticles). Methods for preparing liposomes and microspheres for administration to a subject are well known to those of skill in the art. U.S. Pat. No. 4,789,734, the contents of which are hereby incorporated by reference, describes methods for encapsulating biological materials in liposomes. Essentially, the material is dissolved in an aqueous solution, the appropriate phospholipids and lipids added, and along with surfactants if required, and the material dialyzed or sonicated, as necessary. A review of known methods is provided by G. Gregoriadis, Chapter 14, "Liposomes," Drug Carriers in Biology and Medicine, pp. 2. sup. 87-341 (Academic Press, 1979).

Microspheres formed of polymers or polypeptides are well known to those skilled in the art, and can be tailored for passage through the gastrointestinal tract directly into the blood stream. Alternatively, the compound can be incorporated and the microspheres, or composite of microspheres, implanted for slow release over a period of time ranging from days to months. See, for example, U.S. Pat. Nos. 4,906,474, 4,925,673 and 3,625,214, and Jein, TIPS 19:155-157 (1998), the contents of which are hereby incorporated by reference.

The concentration of drug can be adjusted, the pH of the solution buffered and the isotonicity adjusted to be compatible with intraocular or intravitreal injection.

The compounds of the disclosure can be formulated as a sterile solution or suspension, in suitable vehicles. The pharmaceutical compositions can be sterilized by conventional, well-known sterilization techniques, or can be sterile filtered. The resulting aqueous solutions can be packaged for use as is, or lyophilized, the lyophilized preparation being combined with a sterile solution prior to administration. Suitable formulations and additional carriers are described in Remington "The Science and Practice of Pharmacy" (20th Ed., Lippincott Williams & Wilkins, Baltimore Md.), the teachings of which are incorporated by reference in their entirety herein.

The agents or their pharmaceutically acceptable salts can be provided alone or in combination with one or more other agents or with one or more other forms. For example, a formulation can comprise one or more agents in particular proportions, depending on the relative potencies of each agent and the intended indication. For example, in compositions for targeting two different host targets, and where potencies are similar, about a 1:1 ratio of agents can be used. The two forms can be formulated together, in the same dosage unit e.g., in one cream, suppository, tablet, capsule, aerosol spray, or packet of powder to be dissolved in a beverage; or each form can be formulated in a separate unit, e.g., two creams, two suppositories, two tablets, two capsules, a tablet and a liquid for dissolving the tablet, two aerosol sprays, or a packet of powder and a liquid for dissolving the powder, etc.

The term "pharmaceutically acceptable salt" means those salts which retain the biological effectiveness and properties of the agents used in the present disclosure, and which are not biologically or otherwise undesirable.

Typical salts are those of the inorganic ions, such as, for example, sodium, potassium, calcium, magnesium ions, and the like. Such salts include salts with inorganic or organic acids, such as hydrochloric acid, hydrobromic acid, phosphoric acid, nitric acid, sulfuric acid, methanesulfonic acid, p toluenesulfonic acid, acetic acid, fumaric acid, succinic acid, lactic acid, mandelic acid, malic acid, citric acid, tartaric acid or maleic acid. In addition, if the agent(s) contain a carboxyl group or other acidic group, it can be converted into a pharmaceutically acceptable addition salt with inorganic or organic bases. Examples of suitable bases include sodium hydroxide, potassium hydroxide, ammonia, cyclohexylamine, dicyclohexyl-amine, ethanolamine, diethanolamine, triethanolamine, and the like.

A pharmaceutically acceptable ester or amide refers to those which retain biological effectiveness and properties of the agents used in the present disclosure, and which are not biologically or otherwise undesirable. Typical esters include ethyl, methyl, isobutyl, ethylene glycol, and the like. Typical amides include unsubstituted amides, alkyl amides, dialkyl amides, and the like.

In some embodiments, an agent can be administered in combination with one or more other compounds, forms, and/or agents, e.g., as described above. Pharmaceutical compositions with one or more other active agents can be formulated to comprise certain molar ratios. For example, molar ratios of about 99:1 to about 1:99 of a first active agent to the other active agent can be used. In some subset of the embodiments, the range of molar ratios of a first active agent: other active agents are selected from about 80:20 to about 20:80; about 75:25 to about 25:75, about 70:30 to about 30:70, about 66:33 to about 33:66, about 60:40 to about 40:60; about 50:50; and about 90:10 to about 10:90. The molar ratio of a first active: other active agents can be about 1:9, and in some embodiments can be about 1:1. The two agents, forms and/or compounds can be formulated together, in the same dosage unit e.g., in one cream, suppository, tablet, capsule, or packet of powder to be dissolved in a beverage; or each agent, form, and/or compound can be formulated in separate units, e.g., two creams, suppositories, tablets, two capsules, a tablet and a liquid for dissolving the tablet, an aerosol spray a packet of powder and a liquid for dissolving the powder, etc.

If necessary or desirable, the agents and/or combinations of agents can be administered with still other agents. The choice of agents that can be co-administered with the agents and/or combinations of agents of the instant disclosure can depend, at least in part, on the condition being treated.

The agent(s) (or pharmaceutically acceptable salts, esters or amides thereof) can be administered per se or in the form of a pharmaceutical composition wherein the active agent(s) is in an admixture or mixture with one or more pharmaceutically acceptable carriers. A pharmaceutical composition, as used herein, can be any composition prepared for administration to a subject. Pharmaceutical compositions for use in accordance with the present disclosure can be formulated in conventional manner using one or more physiologically acceptable carriers, comprising excipients, diluents, and/or auxiliaries, e.g., which facilitate processing of the active agents into preparations that can be administered. Proper formulation can depend at least in part upon the route of administration chosen. The agent(s) useful in the present disclosure, or pharmaceutically acceptable salts, esters, or amides thereof, can be delivered to a subject using a number of routes or modes of administration, including oral, buccal, topical, rectal, transdermal, transmucosal, subcutaneous, intravenous, intraocular, intravitreal, and intramuscular applications, as well as by inhalation.

In some embodiments, oils or non-aqueous solvents can be used to bring the agents into solution, due to, for example, the presence of large lipophilic moieties. Alternatively, emulsions, suspensions, or other preparations, for example, liposomal preparations, can be used. With respect to liposomal preparations, any known methods for preparing liposomes for treatment of a condition can be used. See, for example, Bangham et al., J. Mol. Biol. 23: 238-252 (1965) and Szoka et al., Proc. Natl Acad. Sci. USA 75: 4194-4198 (1978), incorporated herein by reference. Ligands can also be attached to the liposomes to direct these compositions to particular sites of action. Agents of this disclosure can also be integrated into foodstuffs, e.g., cream cheese, butter, salad dressing, or ice cream to facilitate solubilization, administration, and/or compliance in certain subject populations.

The compounds of the disclosure can be formulated for parenteral administration (e.g., by injection, for example, intraocular or intravitreal injection) and can be presented in unit dose form in ampoules, pre-filled syringes, small volume infusion or in multi-dose containers with an added preservative. The compositions can take such forms as suspensions, solutions, or emulsions in oily or aqueous vehicles, for example, solutions in aqueous polyethylene glycol.

For injectable formulations, the vehicle can be chosen from those known in art to be suitable, including aqueous solutions or oil suspensions, or emulsions, with sesame oil, corn oil, cottonseed oil, or peanut oil, as well as elixirs, mannitol, dextrose, or a sterile aqueous solution, and similar pharmaceutical vehicles. The formulation can also comprise polymer compositions which are biocompatible, biodegradable, such as poly(lactic-co-glycolic)acid. These materials can be made into micro or nanospheres, loaded with drug and further coated or derivatized to provide superior sustained release performance. Vehicles suitable for periocular or intraocular injection include, for example, suspensions of therapeutic agent in injection grade water, liposomes and vehicles suitable for lipophilic substances. Other vehicles for periocular or intraocular injection are well known in the art.

In some embodiments, the composition is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

When administration is by injection, the active compound can be formulated in aqueous solutions, specifically in physiologically compatible buffers such as Hanks solution, Ringer's solution, or physiological saline buffer. The solution can contain formulatory agents such as suspending, stabilizing and/or dispersing agents. Alternatively, the active compound can be in powder form for constitution with a suitable vehicle, e.g., sterile pyrogen-free water, before use. In some embodiments, the pharmaceutical composition does not comprise an adjuvant or any other substance added to enhance the immune response stimulated by the peptide. In some embodiments, the pharmaceutical composition comprises a substance that inhibits an immune response to the peptide. Methods of formulation are known in the art, for example, as disclosed in Remington's Pharmaceutical Sciences, latest edition, Mack Publishing Co., Easton P.

In some embodiments, eye disorders can be effectively treated with ophthalmic solutions, suspensions, ointments or inserts comprising an agent or combination of agents of the present disclosure. Eye drops can be prepared by dissolving the active ingredient in a sterile aqueous solution such as physiological saline, buffering solution, etc., or by combining powder compositions to be dissolved before use. Other vehicles can be chosen, as is known in the art, including but not limited to: balance salt solution, saline solution, water soluble polyethers such as polyethyene glycol, polyvinyls, such as polyvinyl alcohol and povidone, cellulose derivatives such as methylcellulose and hydroxypropyl methylcellulose, petroleum derivatives such as mineral oil and white petrolatum, animal fats such as lanolin, polymers of acrylic acid such as carboxypolymethylene gel, vegetable fats such as peanut oil and polysaccharides such as dextrans, and glycosaminoglycans such as sodium hyaluronate. If desired, additives ordinarily used in the eye drops can be added. Such additives include isotonizing agents (e.g., sodium chloride, etc.), buffer agent (e.g., boric acid, sodium monohydrogen phosphate, sodium dihydrogen phosphate, etc.), preservatives (e.g., benzalkonium chloride, benzethonium chloride, chlorobutanol, etc.), thickeners (e.g., saccharide such as lactose, mannitol, maltose, etc.; e.g., hyaluronic acid or its salt such as sodium hyaluronate, potassium hyaluronate, etc., e.g., mucopolysaccharide such as chondroitin sulfate, etc.; e.g., sodium polyacrylate, carboxyvinyl polymer, cross-linked polyacrylate, polyvinyl alcohol, polyvinyl pyrrolidone, methyl cellulose, hydroxy propyl methylcellulose, hydroxyethyl cellulose, carboxymethyl cellulose, hydroxy propyl cellulose or other agents known to those skilled in the art).

The solubility of the components of the present compositions can be enhanced by a surfactant or other appropriate co-solvent in the composition. Such cosolvents include polysorbate 20, 60, and 80, Pluronic F68, F-84 and P-103, cyclodextrin, or other agents known to those skilled in the art. Such co-solvents can be employed at a level of from about 0.01% to 2% by weight.

The compositions of the disclosure can be packaged in multidose form. Preservatives can be preferred to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M. or other agents known to those skilled in the art. In the prior art ophthalmic products, such preservatives can be employed at a level of from 0.004% to 0.02%. In the compositions of the present application the preservative, preferably benzalkonium chloride, can be employed at a level of from 0.001% to less than 0.01%. e.g., from 0.001% to 0.008%, preferably about 0.005% by weight. It has been found that a concentration of benzalkonium chloride of 0.005% can be sufficient to preserve the compositions of the present disclosure from microbial attack.

In some embodiments, the agents of the present disclosure are delivered in soluble rather than suspension form, which allows for more rapid and quantitative absorption to the sites of action. In general, formulations such as jellies, creams, lotions, suppositories and ointments can provide an area with more extended exposure to the agents of the present disclosure, while formulations in solution, e.g., sprays, provide more immediate, short-term exposure.

It is envisioned additionally, that the compounds of the disclosure can be attached releasably to biocompatible polymers for use in sustained release formulations on, in or attached to inserts for topical, intraocular, periocular, or systemic administration. The controlled release from a biocompatible polymer can be utilized with a water soluble polymer to form an instillable formulation, as well. The controlled release from a biocompatible polymer, such as for example, PLGA microspheres or nanospheres, can be utilized in a formulation suitable for intra ocular implantation or injection for sustained release administration, as well any suitable biodegradable and biocompatible polymer can be used.

EXAMPLES

The following exemplary embodiments further describe the present invention. It should be understood that these examples are only intended to illustrate the invention, but not to limit the scope of the present invention. Unless otherwise indicated, the methods and conditions disclosed in e.g., sambrook et al, molecular cloning: a laboratory manual (New York: cold spring harbor laboratory press, 1989) or the conditions recommended by the manufacturer can be used in the examples below.

Example 1—ND4 Plasmid and Virus Preparation 1.1 Plasmid Preparation

The nucleotide sequence for human ND4 (SEQ ID NO: 6) was obtained based on US National Center for Biotechnology Information reference sequence yp_003024035.1. The sequences for the non-optimized mitochondrial targeting sequence COX10 is SEQ ID NO: 1. The optimized sequences for the mitochondrial targeting sequence COX10 (opt_COX10, SEQ ID NO: 2) and the coding sequence of human ND4 (opt_ND4, SEQ ID NO: 7) were designed to improve the transcription efficiency and the translation efficiency. The optimized COX10-ND4 sequence, which is about 75.89% homology to the non-optimized COX10-ND4, was followed by a three prime untranslated region (i.e., 3'UTR, SEQ ID NO: 13) to a recombinant nucleic acid, opt_COX10-opt_ND4-3'UTR (as shown in SEQ ID NO: 31).

The synthesized recombinant nucleic acid, opt_COX10-opt_ND4-3'UTR, was incorporated into an adeno-associated virus (AAV) vector by PCR amplification (FIG. 1). The opt_COX10-opt_ND4-3'UTR was cut by the EcoRI/SalI restriction enzymes to form cohesive ends, and then embedded into an AAV vector with EcoRI/SalI restriction sites, such as the pSNaV vector, to generate the pSNaV/rAAV2/2-ND4 plasmid (i.e., the pAAV2-optimized ND4 plasmid). The pAAV2-opt_ND4 plasmid was compared to the non-optimized pAAV2-ND4 plasmid.

The recon screening and identifying steps were similar to the CN102634527B: the plasmid was cultured at 37° C. in a LB plate. Blue colonies and white colonies were appeared, where white colonies were recombinant clones. The white colonies were picked, added to 100 mg/L ampicillin-containing LB culture medium, cultured at 37° C., 200 rpm for 8 hours and then the plasmid were extracted from the cultured bacterial medium based on the Biomiga plasmid extraction protocol. The identification of the plasmid was confirmed using the EcoRI/SalI restriction enzymes.

1.2 Cell Transfection

One day before transfection, HEK293 cells were inoculated to 225 $cm^2$ cell culture bottle: at the inoculation density of $3.0 \times 10^7$ cells/ml, the culture medium was the Dulbecco's Modified Eagle Medium (DMEM) with 10% bovine serum, at 37° C. in a 5% $CO_2$ incubator overnight. The culture medium were replaced with fresh DMEM with 10% bovine serum on the day of transfection.

After the cells grow to 80-90%, discard the culture medium and transfect the cells with the pAAV2-ND4 and pAAV2-opt_ND4 plasmid, using the PlasmidTrans (VGTC) transfection kit. The detailed transfection protocol was described in CN102634527B example 1. The cells were collected 48 h after the transfection.

1.3 Collection, Concentration and Purification of the Recombinant Adeno-Associated Virus Virus collection: 1) dry ice ethanol bath (or liquid nitrogen) and a 37° C. water bath were prepared; 2) the transfected cells along with media were collected in a 15 ml centrifuge tube; 3) the cells were centrifuged for 3 minutes at 1000 rpm/min; the cells and supernatant were separated; the supernatant were stored separately; and the cells were re-suspended in 1 ml of PBS; 4) the cell suspension were transferred between the dry ice-ethanol bath and 37° C. water bath repeatedly, freeze thawing for four times for 10 minutes each, slightly shaking after each thawing.

Virus concentration: 1) cell debris were removed with 10,000 g centrifugation; the centrifugal supernatant was transferred to a new centrifuge tube; 2) impurities were removed by filtering with a 0.45 μm filter; 3) each ½ volume of IM NaCl and 10% PEG 8000 solution were added in the sample, uniformly mixed, and stored at 4° C. overnight; 4) supernatant was discarded after 12,000 rpm centrifugation for 2 h; after the virus precipitate was completely dissolving in an appropriate amount of PBS solution, sterilizing the sample with a 0.22 μm filter; 5) adding benzonase nuclease was added to remove residual plasmid DNA (final concentration at 50 U/ml). The tube was inverted several times to mix thoroughly and then incubated at 37° C. for 30 minutes: 6) the sample was filtered with a 0.45 μm filtration head; the filtrate is the concentrated rAAV2 virus.

Virus purification: 1) CsCl was added to the concentrated virus solution until a density of 1.41 g/ml (refraction index at 1.372); 2) the sample was added to in the ultracentrifuge tube and filled the tube with pre-prepared 1.41 g/ml CsCl solution; 3) centrifuged at 175,000 g for 24 hours to form a density gradient. Sequential collection of different densities of the sample was performed. The enriched rAAV2 particles were collected; 4) repeating the process one more time. The virus was loaded to a 100 kDa dialysis bag and dialyzed/desalted at 4° C. overnight. The concentrated and purified recombinant adeno-associated virus were rAAV2-ND4 and rAAV2-optimized ND4.

Similarly, other mitochondrial targeting sequences (MTS), such as OPA1 (SEQ ID NO: 5) can be used to replace COX10 in the above example and create AAV with recombinant plasmids.

Example 2—Intravitreal Injection of rAAV2 in Rabbit Eyes

Twelve rabbits were divided into 2 group: rAAV2-ND4 and rAAV2-optimized ND4. Virus solution ($1 \times 10^{10}$ vg/0.05 mL) was punctured into the vitreous cavity from 3 mm outside the corneal limbus at the pars plana. After the intravitreal injection, the eyes were examined using slit lamp exam and fundus photography inspection. Injection for 30 days. RT-PCR detection and immunoblotting were carried out in each group respectively.

Example 3—Real-Time PCR for the Expression of ND4

The RNAs from the transfected rAAV2-ND4 and rAAV2-optimized ND4 rabbit optic nerve cells were extracted using the TRIZOL total RNA extraction kit. cDNA templates were synthesized by reverse transcription of the extracted RNA.

The NCBI conserved structural domain analysis software were used to analyze the conservative structure of ND4, ensuring that the designed primers amplified fragments were located at non-conserved region; then primers were designed according to the fluorescent quantitative PCR primer design principle:

β-actin-S:
(SEQ ID NO: 85)
CGAGATCGTGCGGGACAT;

β-actin-A:
(SEQ ID NO: 86)
CAGGAAGGAGGGCTGGAAC;

ND4-S:
(SEQ ID NO: 87)
CTGCCTACGACAAACAGAC;

ND4-A:
(SEQ ID NO: 88)
AGTGCGTTCGTAGTTTGAG;

The fluorescent quantitative PCR reaction and protocol: fluorescence quantitative PCR were measured in a real-time PCR detection system. In a 0.2 ml PCR reaction tube, SYBR green mix 12.5 μl, $ddH_2O$ 8 μl, 1 μl of each primer, and the cDNA sample 2.5 μl, were added to an overall volume of 25 μl. Each sample was used for amplification of the target gene and amplifying the reference gene β-actin, and each amplification were repeated three times. The common reagents were added together and then divided separately to minimize handling variation. The fluorescent quantitative PCR were carried out: pre-denaturation at 95° C. for 1 s, denaturation at 94° C. for 15 s, annealing at 55° C. for 15 sec, extension at 72° C. for 45 s. A total of 40 cycles of amplification reaction were performed and fluorescence signal acquisition was done at the extension phase of each cycle. After the reaction, a 94° C. to 55° C. melting curve analysis was done. By adopting a relative quantitative method research of gene expression level difference to beta-actin was used as an internal reference gene.

Figure 2:
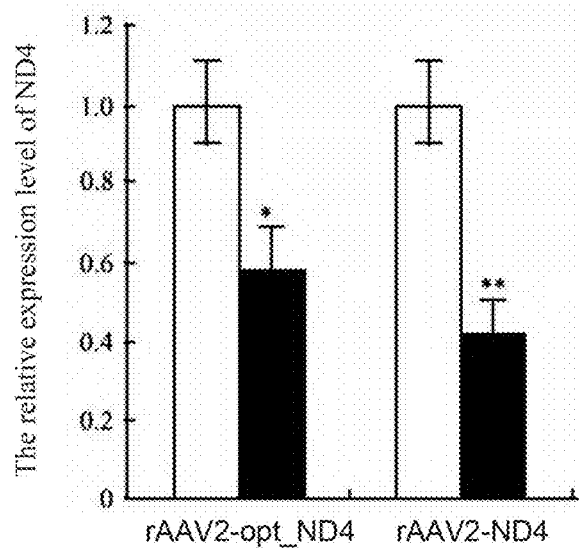
FIG. 2 shows the relative expression level comparison using qPCR between the rAAV2-opt_ND4 (left black column) and rAAV2-ND4 (right black column). β-actin is the internal reference gene (white column).

As shown in FIG. 2, the relative expression level (mRNA level) of the rAAV2-ND4 and rAAV2-optimized ND4 were 0.42±0.23 and 0.57±0.62, respectively (p<0.05, FIG. 2). The results unexpectedly show that the optimized ND4 (opt_ND4, SEQ ID NO: 7) coding nucleic acid sequence and the corresponding recombinant nucleic acid (opt_COX10-opt_ND4-3'UTR, SEQ ID NO: 31) surprisingly increased the transcription efficiency, increasing the expression of the rAAV2-optimized ND4 by about 36%. The results showed that the transcription efficiency of the rAAV2-optimized ND4 is significantly higher.

Example 4—Immunoblotting Detection of ND4 Expression

The ND4 protein was purified from the rabbit nerve cells transfected by rAAV2-optimized ND4 and rAAV2-ND4, respectively. After a 10% polyacrylamide gel electrophoresis, and transferred to a polyvinylidene difluoride membrane (Bio-Rad, HER-hercules, CA, USA) for immune detection. β-actin was used as an internal reference gene. The film strip was observed on an automatic image analysis instrument (Li-Cor; Lincoln, Nebr., USA) and analyzed using the integrated optical density of the protein band with integral normalization method, so as to obtain the same sample corresponding optical density value. The statistical analysis software SPSS 19.0 was used for the data analysis.

Figure 3:
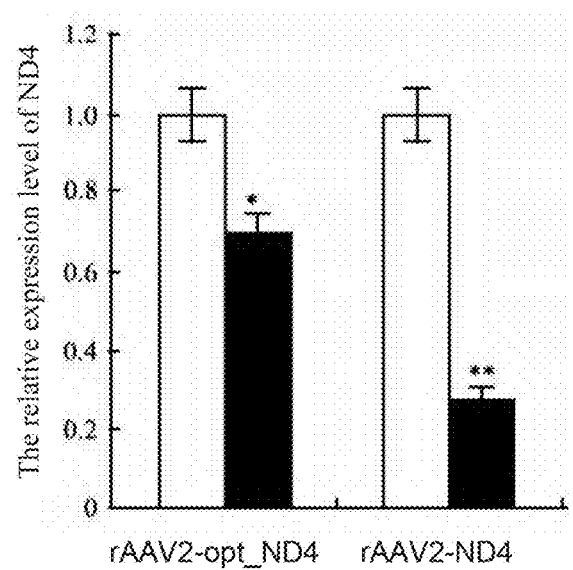
FIG. 3 shows the relative expression level comparison using immunoblotting between the rAAV2-opt_ND4 (left black column) and rAAV2-ND4 (right black column). β-actin is the internal reference gene (white column).

The results was shown in FIG. 3. The average relative protein expression level of ND4 for rAAV2-optimized ND4 (left black column) and rAAV2-ND4 was 0.32±0.11 and 0.68±0.20, respectively (p<0.01, FIG. 3). The results unexpectedly show that the optimized ND4 coding nucleic acid sequence (opt_ND4, SEQ ID NO: 7) and the corresponding recombinant nucleic acid (opt_COX10-opt_ND4-3'UTR, SEQ ID NO: 31) surprisingly increased the translation efficiency, increasing the expression of the rAAV2-optimized ND4 by about 112%. The results showed that the translation efficiency of the rAAV2-optimized ND4 is also significantly higher.

Example 5—Rabbits Intraocular Pressure and Eye-Ground Photography

Slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 4:
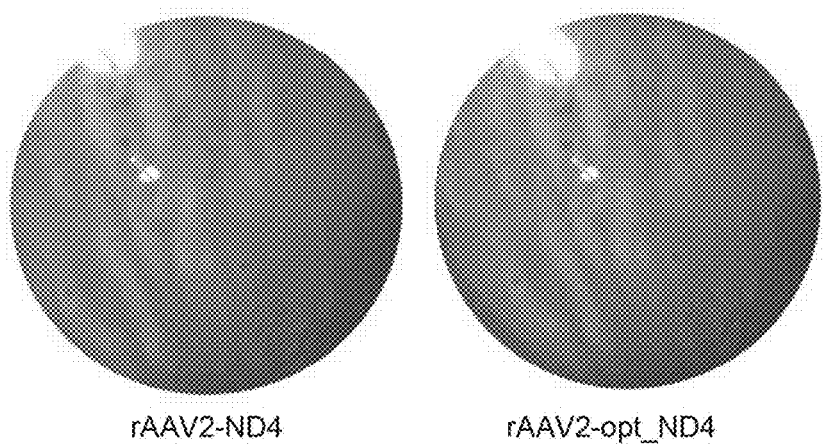
FIG. 4 shows the fundus photographic results for rabbits injected with rAAV2-opt_ND4 (right) and rAAV2-ND4 (left), respectively.

The fundus photographic results were shown in FIG. 4. No obvious damage or complication to the optic nerve and retinal vascular of the rabbits, indicating the standard intravitreal injection is safe without noticeable inflammation reaction or other complications.

Example 6—Human Clinical Trial

Two groups of patients were tested: 1) between 2011 and 2012, 9 patients received intravitreal injection of $1\times10^{10}$ vg/0.05 mL rAAV2-ND4 in a single eye, as a control group; and 2) between 2017 and January 2018, 20 patients received intravitreal injection of $1\times10^{10}$ vg/0.05 mL rAAV2-optimized ND4 in a single eye, as an experimental group. The results of the clinical trial were analyzed using the statistical analysis SPSS 19.0.

Figure 5:
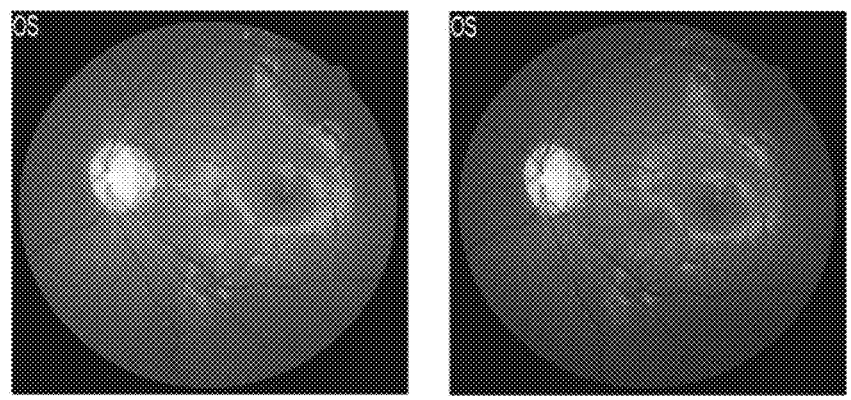
FIG. 5 shows the fundus photographic results for a patient before (left) and after (right) the injection with rAAV2-optimized ND4.

The comparison of the two groups is shown in Table 2. The fastest eyesight improving time was 1 month in the experimental group, which was significantly faster than the control group at 3 months (p<0.01); the optimal recovery of vision for the experimental group was 1.0, which was obviously higher than the control group at 0.8 (p<0.01); the average recovery of vision in the experimental group was 0.582±0.086, which was obviously higher than the control group at 0.344±0.062 (p<0.01). The fundus photographic results were shown in FIG. 5. No obvious damage or complication to the optic nerve and retinal vascular of the patients in the experimental and control groups, indicating the safety of the intravitreal injection of rAAV2-optimized ND4 and rAAV2-ND4.

TABLE 2

The comparison of rAAV2-optimized ND4 and rAAV2-ND4 in LHON gene therapy

| group | Patient number | Fastest eyesight improving time (month) | Number of patients with improved vision | optimal recovery of vision | average recovery of vision |
|---|---|---|---|---|---|
| control | 9 | 3 | 6 (67%) | 0.8 | 0.344 ± 0.062 |
| experimental | 20 | 1 | 15 (75%) | 1.0 | 0.582 ± 0.086 |
| P value | | <0.01 | <0.01 | <0.01 | <0.01 |

Example 7—OPA1 as the Mitochondrial Targeting Sequences

The COX10 and 3'UTR sequences in the recombinant nucleic acid (opt_COX10-opt_ND4-3'UTR, SEQ ID NO: 31) in examples 1-6 were replaced with another mitochondrial targeted sequence, OPA1 (SEQ ID NO: 5) and another 3'UTR sequence, 3'UTR* (SEQ ID NO: 14) respectively, to generate a new recombinant nucleic acid, OPA1-opt_ND4-3'UTR* (SEQ ID NO: 74).

Experimental methods were the same as examples 1-6, where the recombinant nucleic acid opt_COX10-opt_ND4-3'UTR (SEQ ID NO: 31) was replaced by OPA1-opt_ND4-3'UTR* (SEQ ID NO: 74). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 8—Optimized ND4 Sequence Opt_ND4*

Similar experimental methods in examples 1-6 were followed using the nucleic acid, opt_COX10*-opt_ND4*-3'UTR (SEQ ID NO: 47). Follow the similar procedures as in example 1, virus tagged with a fluorescent protein, EGFP, was prepared as rAAV2-ND4-EGFP and rAAV2-opt_ND4*-EGFP.

The frozen 293T cell was resuscitated and allowed to grow in a T75 flask to about 90%. The cells were precipitated and resuspended in DMEM complete medium to a cell density of $5\times10^{4}$ cells/mL. The cells were resuspended.

Figure 6:
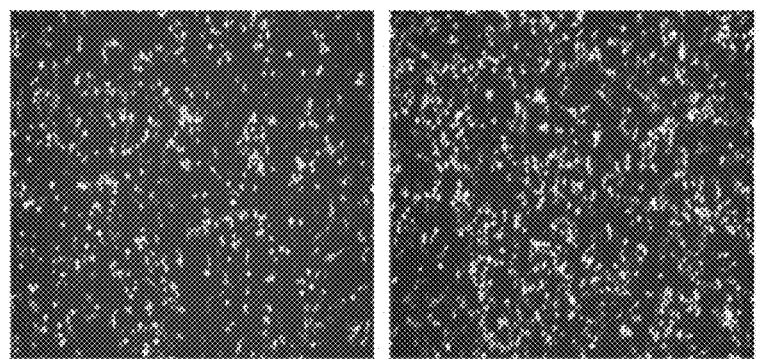
FIG. 6 shows EGFP expression levels of rAAV2-ND4 (left) and rAAV2-opt_ND4* (right).

About 100 μl of the cell suspension (about 5000 cells) were added in each well of a 96 well plate. The cells were cultured and grown to 50% under 37° C. and 5% $CO_2$. About 0.02 μl PBS was mixed with $2\times10^{10}$ vg/0.02 μl of the virus rAAV2-ND4-EGFP and rAAV2-opt_ND4*-EGFP, respectively. After 48 hours, fluorescence microscopy and RT-PCR detection and immunoblotting experiments were performed. As shown in FIG. 6, EGFP was successfully expressed, indicating that rAAV carrying the EGFP gene was successfully transfected in the 293T cells and rAAV2-ND4-EGFP and rAAV2-opt_ND4*-EGFP were successfully expressed.

Real-time PCR tests similar to example 3 was following using the following primers:

```
β-actin-S:
                                  (SEQ ID NO: 85)
CGAGATCGTGCGGGACAT;

β-actin-A:
                                  (SEQ ID NO: 86)
CAGGAAGGAGGGCTGGAAC;

ND4-S:
                                  (SEQ ID NO: 107)
GCCAACAGCAACTACGAGC;

ND4-A:
                                  (SEQ ID NO: 108)
TGATGTTGCTCCAGCTGAAG;
```

The results unexpectedly show that the optimized ND4* (opt_ND4, SEQ ID NO: 8) coding nucleic acid sequence and the corresponding recombinant nucleic acid (opt_COX10*-opt_ND4*-3'UTR, SEQ ID NO: 47) surprisingly increased the transcription efficiency, increasing the expression of the rAAV2-opt_ND4 by about 20%. The results showed that the transcription efficiency of the rAAV2-opt_ND4 is significantly higher.

Figure 7:
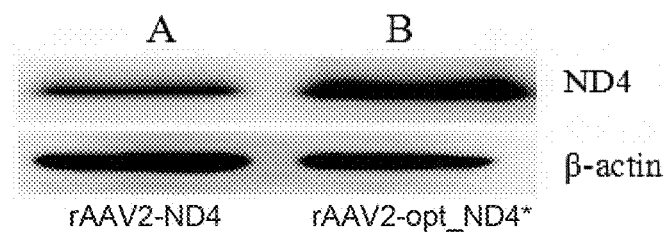
FIG. 7 shows the ND4 expression in 293T cells: rAAV2-ND4 (left) and rAAV2-opt_ND4* (right).
Figure 8:
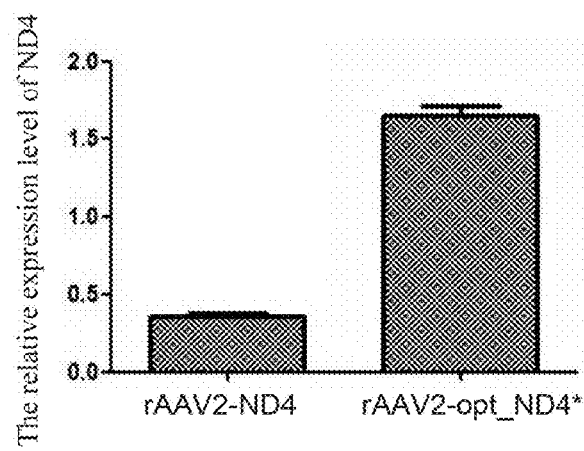
FIG. 8 shows the relative ND4 expression in 293T cells: rAAV2-ND4 (left) and rAAV2-opt_ND4* (right).

FIG. 7 shows the ND4 expression in 293T cells. The average expression of ND4 protein for rAAV2-ND4 is 0.36, while the average expression of ND4 protein for rAAV2-opt_ND4* is 1.65, which is about 4.6 times higher than the rAAV2-ND4 group (p<0.01) (see FIG. 8).

Figure 9:
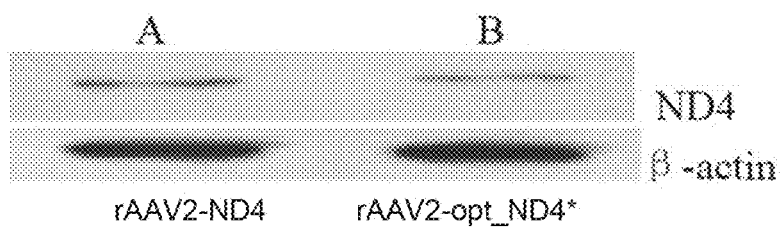
FIG. 9 shows the ND4 expression in rabbit optic nerve cells: rAAV2-ND4 (left) and rAAV2-opt_ND4* (right).
Figure 10:
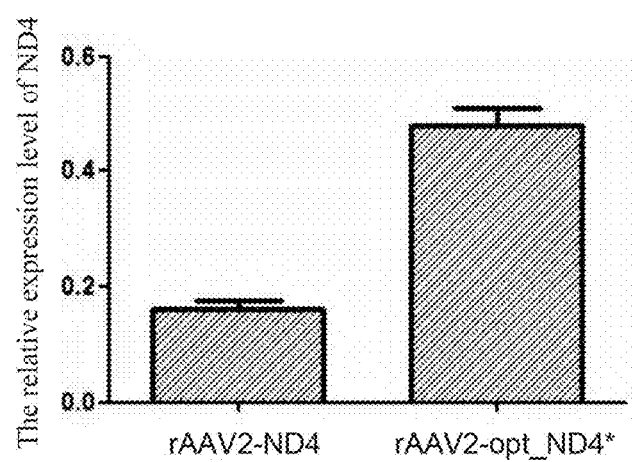
FIG. 10 shows the relative ND4 expression in rabbit optic nerve cells: rAAV2-ND4 (left) and rAAV2-opt_ND4* (right).

FIG. 9 shows the ND4 expression in rabbit optic nerve cells. The average expression of ND4 protein for rAAV2-ND4 is 0.16, while the average expression of ND4 protein for rAAV2-opt_ND4* is 0.48, which is about 3 times higher than the rAAV2-ND4 group (p<0.01) (see FIG. 10).

Similar to example 5, slit lamp examination and intraocular pressure measurement was performed on both groups of rabbits at 1, 3, 7, and 30 days after the surgery. No obviously abnormality, conjunctival congestion, secretions, or endophthalmitis were observed and the intraocular pressure were not elevated in all the rabbits.

Figure 11:
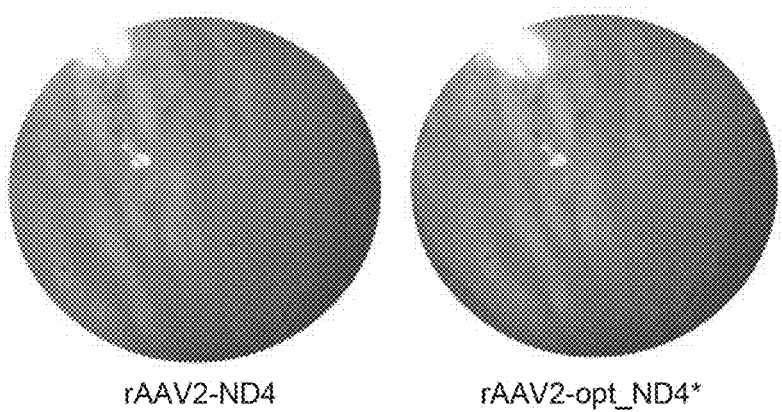
FIG. 11 shows the fundus photographic results for rAAV2-ND4 (left) and rAAV2-opt_ND4* (right).

The fundus photographic results for rAAV2-ND4 and rAAV2-opt_ND4* were shown in FIG. 11. No obvious damage or complication to the optic nerve and retinal vascular of the rabbits, indicating the standard intravitreal injection is safe without noticeable inflammation reaction or other complications.

Figure 12:
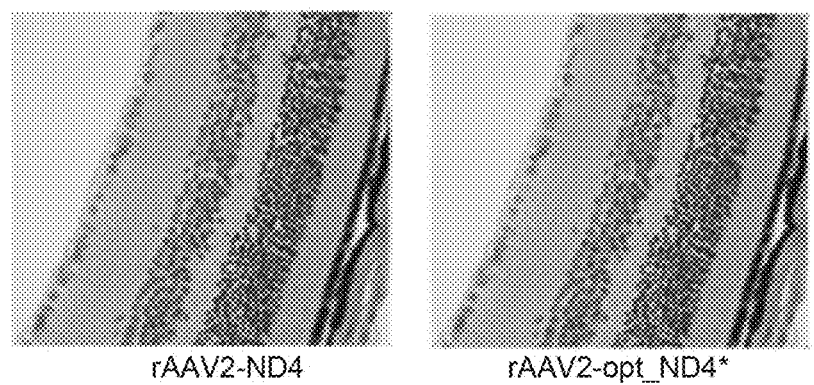
FIG. 12 shows the microscope inspection (HE staining) results for rAAV2-ND4 (left) and rAAV2-opt_ND4* (right).

Eye balls from both rabbit groups were removed after the slit lamp examination and intraocular pressure measurement. Eye balls were fixed, and dehydrated using paraffin. Tissues were pathologically sectioned along the direction of optic nerves. After further dehydration, the tissue sample was dyed using hematoxylin and eosin. The microscope inspection result is referred to FIG. 12. As shown in the HE staining results, the rabbit retinal ganglion fiber layer was not damaged and the number of ganglion cells was not reduced, indicating the intravitreal injection did not produce retinal toxicity or nerve damage, and can be used safely.

Experimental methods were the same as example 8, where the recombinant nucleic acid opt_COX10*-opt_ND4*-3'UTR (SEQ ID NO: 47) was replaced by OPA1-opt_ND4*-3'UTR* (SEQ ID NO: 76). It was found that, the optimized ND4 sequence has significantly improved transcription and translation efficiencies, expression levels, as well as higher efficacy and safety in treating LHON when compared to non-optimized ND4 (COX10-ND4-3'UTR, SEQ ID NO: 15).

Example 9—ND6 Sequence

Similar experimental methods in examples 1-6 were followed using the nucleic acid, COX10-ND6-3'UTR (SEQ ID NO: 21), which is the combination (5' to 3') of COX10 (SEQ ID NO: 1), ND6 (SEQ ID NO: 9), and 3'UTR (SEQ ID NO: 13).

The plasmid screening for COX10-ND6-3'UTR (SEQ ID NO: 21) used the following primers:

```
ND6-F:
                                  (SEQ ID NO: 89)
ATGATGTATGCTTTGTTTCTG,

ND6-R:
                                  (SEQ ID NO: 90)
CTAATTCCCCCGAGCAATCTC,
```

Figure 13:
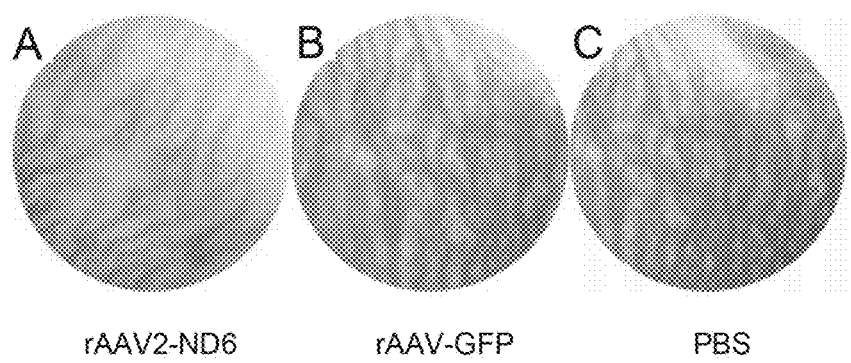
FIG. 13 shows the fundus photographic results for rabbits injected with rAAV2-ND6 (A), rAAV-GFP (B) and PBS, respectively.

The transfected and screened virus rAAV2-ND6 had a viral titer of $2.0\times10^{11}$ vg/mL. Similar to example 5, slit lamp examination and intraocular pressure measurement was performed on three groups of rabbits (A: rAAV2-ND6; B: rAAV-GFP; C: PBS) at 1, 7, and 30 days after the surgery (FIG. 13). No obviously abnormality, conjunctival congestion, secretions, or endophthalmitis were observed and the intraocular pressure were not elevated in all the rabbits.

Real-time PCR tests similar to example 3 was following using the following primers:

```
β-actin-S:
                                  (SEQ ID NO: 85)
CGAGATCGTGCGGGACAT;

β-actin-A:
                                  (SEQ ID NO: 86)
CAGGAAGGAGGGCTGGAAC;

ND6-S:
                                  (SEQ ID NO: 91)
AGTGTGGGTTTAGTAATG;

ND4-A:
                                  (SEQ ID NO: 92)
TGCCTCAGGATACTCCTC;
```

The results show that the expression of ND6 for rAAV2-ND6 and control (PBS) was 0.59±0.06 and 0.41±0.03, respectively. The results showed that the transcription efficiency of the rAAV2-ND6 is higher than the control group (p<0.01).

Example 10— Optimized Opt_ND6 Sequence

Similar experimental methods in examples 1-6 were followed using the nucleic acid, opt_COX10*-opt_ND6-3'UTR (SEQ ID NO: 51), which is the combination (5' to 3') of opt_COX10* (SEQ ID NO: 3), opt_ND6 (SEQ ID NO: 10), and 3'UTR (SEQ ID NO: 13).

Figure 14:
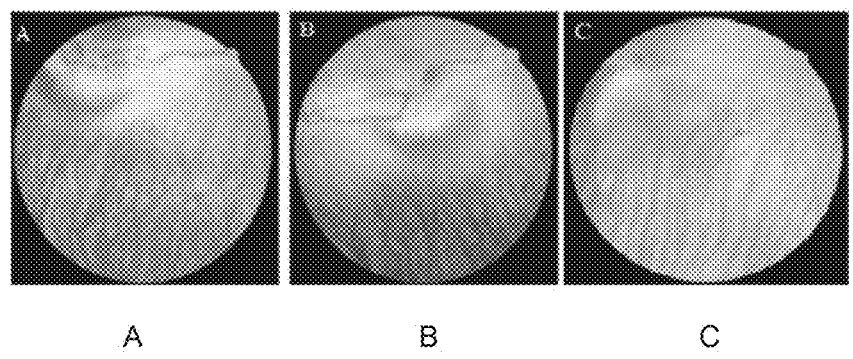
FIG. 14 shows the fundus photographic results for rabbits injected with rAAV2-opt_ND6 (A), rAAV2-ND6 (B), rAAV-EGFP (C), respectively.

Three groups of rabbits were injected: A: $10^{10}$ vg/50 μl of rAAV2-opt_ND6. B: $10^{10}$ vg/50 μl of rAAV2-ND6 (example 9), and C: $10^{10}$ vg/50 μl of rAAV2-EGFP. FIG. 14 shows the fundus photographic results for rabbits injected with rAAV2-opt_ND6 (A), rAAV2-ND6 (B), rAAV-EGFP (C), respectively. No obviously abnormality, conjunctival congestion, secretions, or endophthalmitis were observed and the intraocular pressure were not elevated in all the rabbits.

Figure 15:
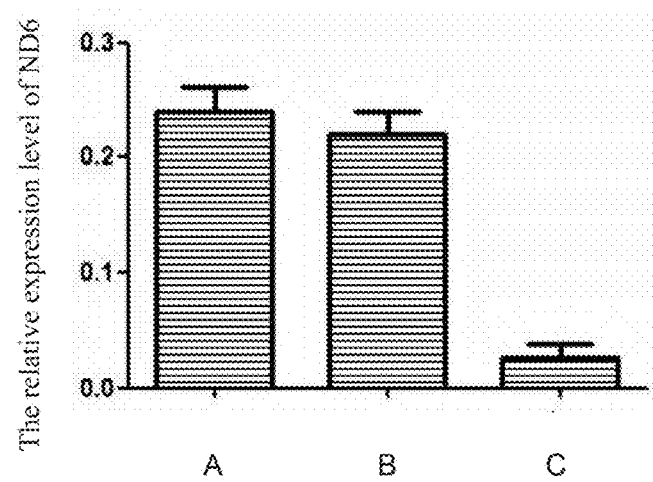
FIG. 15 shows the relative ND6 expression in rabbit optic nerve cells: rAAV2-opt_ND6 (A), rAAV2-ND6 (B), and rAAV-EGFP (C).
Figure 16:
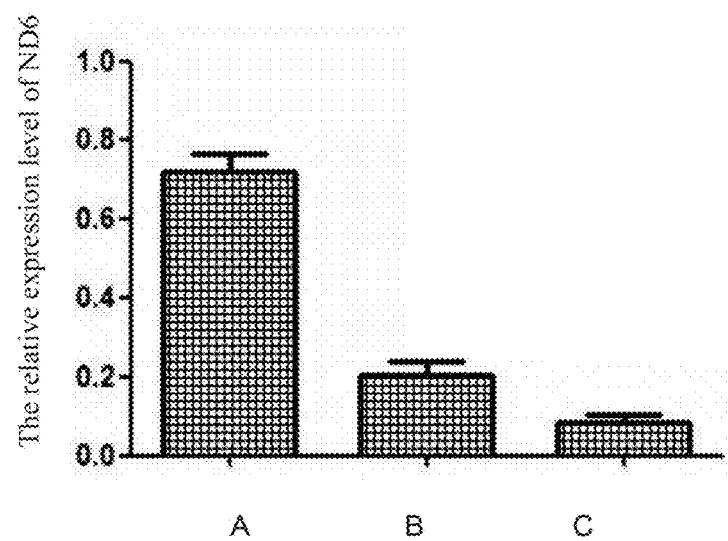
FIG. 16 shows the relative ND6 expression by western blot: rAAV2-opt_ND6 (A), rAAV2-ND6 (B), and rAAV-EGFP (C).

Real-time PCR tests similar to example 3 was following using the following primers:

β-actin-F:
(SEQ ID NO: 93)
CTCCATCCTGGCCTCGCTGT;

β-actin-R:
(SEQ ID NO: 94)
GCTGTCACCTTCACCGTTCC;

ND6-F:
(SEQ ID NO: 95)
GGGTTTTCTTCTAAGCCTTCTCC;

ND6-R:
(SEQ ID NO: 96)
CCATCATACTCTTTCACCCACAG;

opt_ND6-F:
(SEQ ID NO: 97)
CGCCTGCTGACCGGCTGCGT;

opt_ND6-R:
(SEQ ID NO: 98)
CCAGGCCTCGGGGTACTCCT;

As shown in FIG. 15, rAAV2-opt_ND6 (A) and rAAV2-ND6 (B) both had higher (p<0.05) relative ND6 expression levels than the control group (C), rAAV2-opt_ND6 (A) had a little higher relative ND6 expression levels than rAAV2-ND6 (B). As shown in the western blot in FIG. 16, rAAV2-opt_ND6 (A) had more than 3 times higher relative ND6 expression levels than rAAV2-ND6 (B).

Experimental methods were the same as example 8, where the recombinant nucleic acids, COX10-ND6-3'UTR (SEQ ID NO: 21) and opt_COX10*-opt_ND6-3'UTR (SEQ ID NO: 51), were replaced by OPA1-ND6-3'UTR (SEQ ID NO: 77) and OPA1-opt_ND6-3'UTR (SEQ ID NO: 79). It was found that, the optimized ND6 sequence has significantly improved transcription and translation efficiencies, expression levels, as well as higher efficacy and safety in treating LHON.

Example 11—ND1 and Opt_ND1 Sequences

Similar experimental methods in examples 1-6 were followed using rAAV2-ND1, COX10-ND1-3'UTR (SEQ ID NO: 25), which is the combination (5' to 3') of COX10 (SEQ ID NO: 1), ND1 (SEQ ID NO: 11), and 3'UTR (SEQ ID NO: 13); and rAAV2-opt_ND1, opt_COX10*-opt_ND1-3'UTR (SEQ ID NO: 55), which is the combination (5' to 3') of opt_COX10* (SEQ ID NO: 3), opt_ND1 (SEQ ID NO: 12), and 3'UTR (SEQ ID NO: 13).

The plasmid screening for COX10-ND1-3'UTR (SEQ ID NO: 25) used the following primers:

ND1-F:
(SEQ ID NO: 99)
ATGGCCGCATCTCCGCACACT,

ND1-R:
(SEQ ID NO: 100)
TTAGGTTTGAGGGGGAATGCT,

The plasmid screening for opt_COX10*-opt_ND1-3'UTR (SEQ ID NO: 55) used the following primers:

ND1-F:
(SEQ ID NO: 101)
AACCTCAACCTAGGCCTCCTA,

ND1-R:
(SEQ ID NO: 102)
TGGCAGGAGTAACCAGAGGTG,

Three groups of rabbits were injected: A: $10^{10}$ vg/50 μl of rAAV2-opt_ND1. B: $10^{10}$ vg/50 μl of rAAV2-ND1 (example 9), and C: $10^{10}$ vg/50 μl of rAAV2-EGFP. No obviously abnormality, conjunctival congestion, secretions, or endophthalmitis were observed and the intraocular pressure were not elevated in all the rabbits.

Figure 17:
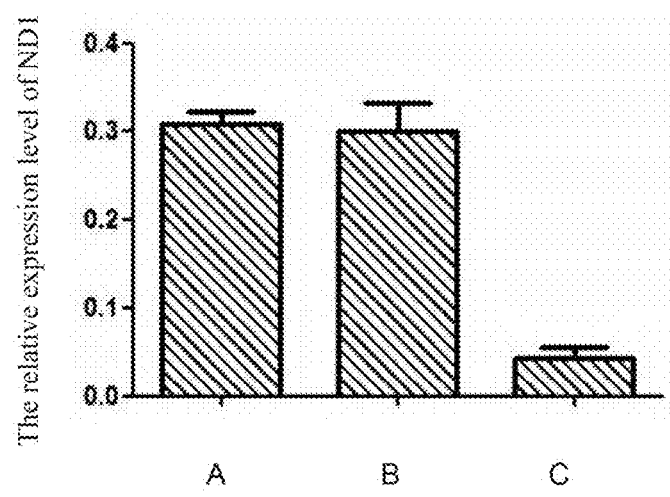
FIG. 17 shows the relative ND1 expression in rabbit optic nerve cells: rAAV2-opt_ND1 (A), rAAV2-ND1 (B), and rAAV-EGFP (C).
Figure 18:
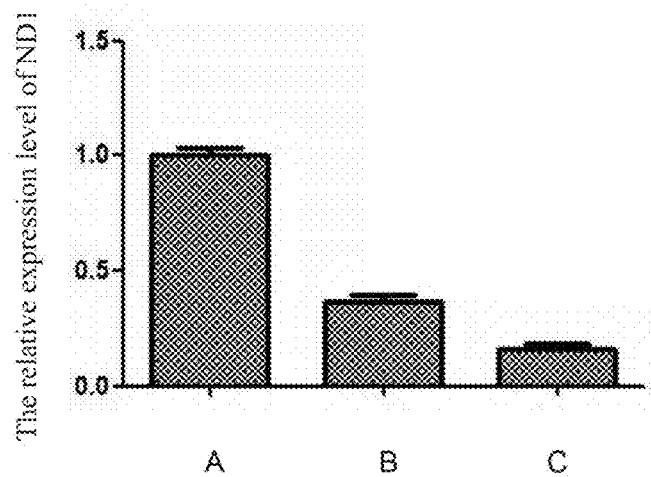
FIG. 18 shows the relative ND1 expression by western blot: rAAV2-opt_ND1 (A), rAAV2-ND1 (B), and rAAV-EGFP (C).

Real-time PCR tests similar to example 3 was following using the following primers:

ND1-F:
(SEQ ID NO: 103)
AGGAGGCTCTGTCTGGTATCTTG;

ND1-R:
(SEQ ID NO: 104)
TTTTAGGGGCTCTTTGGTGAA;

opt_ND1-F:
(SEQ ID NO: 105)
GCCGCCTGCTGACCGGCTGCGT;

opt_ND1-R:
(SEQ ID NO: 106)
TGATGTACAGGGTGATGGTGCTGG;

As shown in FIG. 17, rAAV2-opt_ND1 (A) and rAAV2-ND1 (B) both had higher (p<0.05) relative ND1 expression levels than the control group (C). As shown in the western blot in FIG. 18, rAAV2-opt_ND1 (A) had more than 2 times higher relative ND6 expression levels than rAAV2-ND1 (B).

Experimental methods were the same as example 8, where the recombinant nucleic acids, COX10-ND1-3'UTR (SEQ ID NO: 25) and opt_COX10*-opt_ND1-3'UTR (SEQ ID NO: 55), were replaced by OPA1-ND1-3'UTR (SEQ ID NO: 81) and OPA1-opt_ND1-3'UTR (SEQ ID NO: 83). It was found that, the optimized ND1 sequence has significantly improved transcription and translation efficiencies, expression levels, as well as higher efficacy and safety in treating LHON.

Example 12—Other Fusion Proteins

Similar experimental methods in examples 1-6 can be followed using other fusion proteins as set forth in SEQ ID NO: 15-84. And similar results are expected to be achieved.

Example 13—Formulation Development

AAV2 virus samples were used to screen different AAV formulations. The stability of the different AAV formulations were evaluated using the StepOnePlus real-time PCR system. The viral titer of each formulation under a freeze/thaw cycle condition was measured.

First, three different formulations were tested under 1, 2, 3, 4, and 5 freeze/thaw cycles and the viral titers were measured and summarized in Table 3. The three formulations tested were: A: phosphate-buffered saline (PBS); B: 1% α,α-trehalose dehydrate, 1% L-histidine monohydrochloride monohydrate, and 1% polysorbate 20; and C: 180 mM NaCl, 10 mM $NaH_2PO_4/Na_2$—$HPO_4$, and 0.001% poloxamer 188, pH 7.3. As shown in Table 3, formulation C has the lowest relative standard deviation (RSD) after 5 freeze/thaw cycles, indicating superior stability as an AAV formulation.

TABLE 3 the viral titers of formulations A, B, and C

| viral titers | 0 cycle | 1 cycle | 2 cycles | 3 cycles | 4 cycles | 5 cycles | RSD |
|---|---|---|---|---|---|---|---|
| A | 1.15E+11 | 9.48E+10 | 6.16E+10 | 2.90E+10 | 1.56E+10 | 5.26E+09 | 83.18 |
| B | 4.25E+11 | 5.12E+11 | 6.66E+11 | 4.30E+11 | 4.77E+11 | 4.20E+11 | 19.30 |
| C | 4.96E+11 | 6.91E+11 | 7.69E+11 | 6.82E+11 | 6.83E+11 | 7.27E+11 | 13.90 |

As shown in Table 3, formulation C has the lowest relative standard deviation (RSD) after 5 freeze/thaw cycles, indicating superior stability as an AAV formulation.

Second, another group of three different formulations were tested under 1, 2, 3, 4, and 5 freeze/thaw cycles and the viral titers were measured and summarized in Table 4. The three formulations tested were: D: phosphate-buffered saline (PBS), pH 7.2-7.4; E: PBS and 0.001% poloxamer 188, pH 7.2-7.4; and F: 80 mM NaCl, 5 mM $NaH_2PO_4$, 40 mM $Na_2HPO_4$, 5 mM $KH_2PO_4$ and 0.001% poloxamer 188, 7.2-7.4.

TABLE 4 the viral titers of formulations D, E, and F

| viral titers | 0 cycle | 1 cycle | 2 cycles | 3 cycles | 4 cycles | 5 cycles | RSD |
|---|---|---|---|---|---|---|---|
| D | 1.13E+10 | 4.62E+09 | 2.25E+09 | 1.25E+09 | 1.01E+09 | 9.48E+08 | 113.25 |
| E | 4.72E+10 | 5.48E+10 | 5.33E+10 | 5.33E+10 | 4.94E+10 | 4.08E+10 | 10.53 |
| F | 6.61E+10 | 6.08E+10 | 6.47E+10 | 6.84E+10 | 6.52E+10 | 6.05E+10 | 4.81 |

As shown in Table 4, formulation F has the lowest relative standard deviation (RSD) after 5 freeze/thaw cycles, indicating superior stability as an AAV formulation. Overall, formulation F also has the lowest RSD among all tested formulations and can be used as the AAV formulation for future development.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A recombinant nucleic acid, comprising:
a mitochondrial targeting sequence;
a mitochondrial protein coding sequence comprising a sequence that is at least 90% identical to a sequence selected from the group consisting of SEQ ID NO: 7, 10, and 12; and
a 3'UTR nucleic acid sequence.

2. The recombinant nucleic acid of claim 1, wherein said mitochondrial targeting sequence encodes a polypeptide comprising a peptide sequence that is at least 90% identical to a sequence selected from the group consisting of SEQ ID NO: 129-159.

3. The recombinant nucleic acid of claim 1, wherein said mitochondrial targeting sequence comprises a sequence that is at least 90% identical to a sequence selected from the group consisting of SEQ ID NO: 2-5.

4. The recombinant nucleicacid of claim 1, wherein said mitochondrial targeting sequence comprises a sequence that encodes a polypeptide selected from the group consisting of hsCOX10, hsCOX8, scRPM2, lcSirt5, tbNDUS7, ncQCR2, hsATP5G2, hsLACTB, spilv1, gmCOX2, crATP6, hsOPA1, hsSDHD, hsADCK3, osP0644B06.24-2, *Neurospora crassa* ATP9 (ncATP9), hsGHITM, hsNDUFAB1, hsATPSG3, crATP6_hsADCK3, ncATP9_ncATP9, zmLOC100282174, ncATP9_zmLOC100282174_spilv1_ncATP9, zmLOC100282174_hsADCK3_crATP6_hsATP5G3, zmLOC100282174_hsADCK3_hsATP5G3, ncATP9_zmLOC100282174, hsADCK3_zmLOC100282174_crATP6_hsATP5G3, crATP6_hsADCK3_zmLOC100282174_hsATP5G3, hsADCK3_zmLOC100282174, hsADCK3_zmLOC100282174_crATP6, ncATP9_zmLOC100282174_spilv1_GNFP_ncATP9, and ncATP9_zmLOC100282174_spilv1_lcSirt5_osP0644B06.24-2_hsATP5G2_ncATP9.

5. The recombinant nucleic acid of claim 1, wherein said mitochondrial protein is selected from a group consisting of NADH dehydrogenase 4 (ND4), NADH dehydrogenase 6 (ND6), NADH dehydrogenase 1 (ND1), and a variant thereof.

6. The recombinant nucleic acid of claim 5, wherein said mitochondrial protein comprises NADH dehydrogenase 4 (ND4), or a variant thereof.

7. The recombinant nucleic acid of claim 6, wherein said mitochondrial protein coding sequence comprises a sequence that is at least 99% identical to a sequence as set forth in SEQ ID NO: 7.

8. The recombinant nucleic acid of claim 5, wherein said mitochondrial protein comprises NADH dehydrogenase 6 (ND6), or a variant thereof.

9. The recombinant nucleic acid of claim 8, wherein said mitochondrial protein coding sequence comprises a sequence that is at least 90% identical to a sequence as set forth in SEQ ID NO: 10.

10. The recombinant nucleic acid of claim 5, wherein said mitochondrial protein comprises NADH dehydrogenase 1 (ND1), or a variant thereof.

11. The recombinant nucleic acid of claim 10, wherein said mitochondrial protein coding sequence comprises a sequence that is at least 90% identical to a sequence as set forth in SEQ ID NO: 12.

12. The recombinant nucleic acid of claim 1, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

13. The recombinant nucleic acid of claim 1, wherein said 3'UTR nucleic acid sequence comprises a sequence selected from the group consisting of hsACO2, hsATP5B, hsAK2, hsALDH2, hsCOX10, hsUQCRFS1, hsNDUFV1, hsNDUFV2, hsSOD2, hsCOX6c, hsIRP1, hsMRPS12, hsATP5J2, rnSOD2, and hsOXA1L.

14. The recombinant nucleic acid of claim 1, wherein said 3'UTR nucleic acid sequence comprises a sequence that is at least 90% identical to a sequence selected from the group consisting of SEQ ID NO: 111-125.

15. An adeno-associated viral (AAV) vector comprising a recombinant nucleic acid, comprising: a mitochondrial targeting sequence; a mitochondrial protein coding sequence comprising a sequence that is at least 90% identical to a sequence selected from the group consisting of SEQ ID NO: 7, 10, and 12; and a 3'UTR nucleic acid sequence.

16. The AAV vector of claim 15, wherein said AAV vector is a recombinant AAV (rAAV) vector.

17. The AAV vector of claim 16, wherein said rAAV vector is rAAV2 vector.

18. A pharmaceutical composition, comprising an adeno-associated virus (AAV) comprising a recombinant nucleic acid and a pharmaceutically acceptable excipient thereof, wherein said recombinant nucleic acid comprises: a mitochondrial targeting sequence; a mitochondrial protein coding sequence comprising a sequence that is at least 90% identical to a sequence selected from the group consisting of SEQ ID NO: 7, 10, and 12; and a 3'UTR nucleic acid sequence.

19. The pharmaceutical composition of claim 18, wherein said pharmaceutically acceptable excipient comprises phosphate-buffered saline (PBS), α,α-trehalose dihydrate, L-histidine monohydrochloride monohydrate, polysorbate 20, NaCl, $NaH_2PO_4$, $Na_2HPO_4$, $KH_2PO_4$, $K_2HPO_4$, poloxamer 188, or any combination thereof.

20. The pharmaceutical composition of claim 19, wherein said pharmaceutically acceptable excipient comprises poloxamer 188.

21. The pharmaceutical composition of claim 20, wherein said pharmaceutically acceptable excipient comprises 0.0001%-0.01% poloxamer 188.

22. The pharmaceutical composition of claim 18, wherein said pharmaceutical composition has a viral titer of at least $5.0 \times 10^{10}$ vg/mL.

23. The pharmaceutical composition of claim 18, when said pharmaceutical composition is subject to five freeze/thaw cycles, said pharmaceutical composition retains at least 60%, 70%, 80%, or 90% of a viral titer as compared to the viral titer prior to the five freeze/thaw cycles.

* * * * *

SEQUENCE LISTING

<160> NUMBER OF SEQ ID NOS: 162

<210> SEQ ID NO 1
<211> LENGTH: 84
<212> TYPE: DNA
<213> ORGANISM: Homo sapiens

<400> SEQUENCE: 1
atggccgcat ctccgcacac tctctcctca cgcctcctga caggttgcgt aggaggctct    60
gtctggtatc ttgaaagaag aact    84

```
<210> SEQ ID NO 2
<211> LENGTH: 84
<212> TYPE: DNA
<213> ORGANISM: Artificial Sequence
<220> FEATURE:
<223> OTHER INFORMATION: opt_COX10

<400> SEQUENCE: 2
atggccgcct ctccacacac actgagtagc agactgctga ccggctgtgt tggcggctct      60
gtgtggtatc tggaacggcg gaca                                            84

<210> SEQ ID NO 3
<211> LENGTH: 84
<212> TYPE: DNA
<213> ORGANISM: Artificial Sequence
<220> FEATURE:
<223> OTHER INFORMATION: opt_COX10*

<400> SEQUENCE: 3
atggccgcca gccccacac cctgagcagc cgcctgctga ccggctgcgt gggcggcagc      60
gtgtggtacc tggagcgccg cacc                                            84

<210> SEQ ID NO 4
<211> LENGTH: 87
<212> TYPE: DNA
<213> ORGANISM: Artificial Sequence
<220> FEATURE:
<223> OTHER INFORMATION: COX8

<400> SEQUENCE: 4
atgtccgtcc tgacgcgcct gctgctgcgg ggcttgacac ggctcggctc ggcggctcca      60
gtgcggcgcg ccagaatcca ttcgttg                                         87

<210> SEQ ID NO 5
<211> LENGTH: 266
<212> TYPE: DNA
<213> ORGANISM: Homo sapiens

<400> SEQUENCE: 5
gtgctgcccg cctagaaagg gtgaagtggt tgtttccgtg acggactgag tacgggtgcc      60
tgtcaggctc ttgcggaagt ccatgcgcca ttgggagggc tcggccgcg gctctgtgcc     120 cttgctgctg agggccactt cctgggtcat tcctggaccg ggagccgggc tggggctcac     180 acggggggctc ccgcgtggcc gtctcggcgc ctgcgtgacc tccccgccgg cgggatgtgg     240
cgactacgtc gggccgctgt ggcctg                                          266

<210> SEQ ID NO 6
<211> LENGTH: 1380
<212> TYPE: DNA
<213> ORGANISM: Homo sapiens

<400> SEQUENCE: 6
atgctaaaac taatcgtccc aacaattatg ttactaccac tgacatggct ttccaaaaaa      60
cacatgattt ggatcaacac aaccacccac agcctaatta ttagcatcat ccctctacta     120 tttttaacc aaatcaacaa caacctattt agctgttccc caacctttc ctccgacccc      180 ctaacaaccc cctcctaat gctaactacc tggctcctac cctcacaat catggcaagc      240 caacgccact tatccagtga accactatca cgaaaaaaac tctacctctc tatgctaatc     300
tccctacaaa tctccttaat tatgacattc acagccacag aactaatcat gttttatatc     360
```

```
ttcttcgaaa ccacacttat ccccaccttg gctatcatca cccgatgggg caaccagcca      420
gaacgcctga acgcaggcac atacttccta ttctacaccc tagtaggctc ccttcccta       480 ctcatcgcac taatttacac tcacaacacc ctaggctcac taaacattct actactcact      540
ctcactgccc aagaactatc aaactcctgg gccaacaact taatgtggct agcttacaca      600
atggctttta tggtaaagat gcctctttac ggactccact tatggctccc taaagcccat      660
gtcgaagccc ccatcgctgg gtcaatggta cttgccgcag tactcttaaa actaggcggc      720
tatggtatga tgcgcctcac actcattctc aacccctga caaaacacat ggcctacccc       780
ttccttgtac tatccctatg gggcatgatt atgacaagct ccatctgcct acgacaaaca      840
gacctaaaat cgctcattgc atactcttca atcagccaca tggccctcgt agtaacagcc      900
attctcatcc aaaccccctg gagcttcacc ggcgcagtca ttctcatgat cgcccacggg      960
cttacatcct cattactatt ctgcctagca aactcaaact acgaacgcac tcacagtcgc     1020
atcatgatcc tctctcaagg acttcaaact ctactcccac taatggcttt ttggtggctt     1080
ctagcaagcc tcgctaacct cgccttaccc cccactatta acctactggg agaactctct     1140
gtgctagtaa ccacgttctc ctggtcaaat atcactctcc tacttacagg actcaacatg     1200
ctagtcacag ccctatactc cctctacatg tttaccacaa cacaatgggg ctcactcacc     1260
caccacatta acaacatgaa accctcattc acacgagaaa acaccctcat gttcatgcac     1320
ctatccccca ttctcctcct atccctcaac cccgacatca ttaccgggtt ttcctcttaa     1380
```

<210> SEQ ID NO 7
<211> LENGTH: 1380
<212> TYPE: DNA
<213> ORGANISM: Artificial Sequence
<220> FEATURE:
<223> OTHER INFORMATION: opt_ND4

<400> SEQUENCE: 7

```
atgctgaagc tgatcgtgcc caccatcatg ctgctgcctc tgacctggct gagcaagaaa       60
cacatgatct ggatcaacac caccacgcac agcctgatca tcagcatcat ccctctgctg      120
ttcttcaacc agatcaacaa caacctgttc agctgcagcc ccaccttcag cagcgaccct      180
ctgacaacac ctctgctgat gctgaccacc tggctgctgc ccctcacaat catggcctct      240
cagagacacc tgagcagcga gcccctgagc cggaagaaac tgtacctgag catgctgatc      300
tccctgcaga tctctctgat catgaccttc accgccaccg agctgatcat gttctacatc      360
tttttcgaga caacgctgat ccccacactg gccatcatca ccagatgggg caaccagcct      420
gagagactga acgccggcac ctactttctg ttctacaccc tcgtgggcag cctgccactg      480
ctgattgccc tgatctacac ccacaacacc ctgggctccc tgaacatcct gctgctgaca      540
ctgacagccc aagagctgag caacagctgg gccaacaatc tgatgtggct ggcctacaca      600
atggccttca tggtcaagat gcccctgtac ggcctgcacc tgtggctgcc taaagctcat      660
gtggaagccc ctatcgccgg ctctatggtg ctggctgcag tgctgctgaa actcggcggc      720
tacggcatga tgcggctgac cctgattctg aatcccctga ccaagcacat ggcctatcca      780
tttctggtgc tgagcctgtg gggcatgatt atgaccagca gcatctgcct gcggcagacc      840
gatctgaagt ccctgatcgc ctacagctcc atcagccaca tggccctggt ggtcaccgcc      900
atcctgattc agacccccttg gagctttaca ggcgccgtga tcctgatgat tgcccacggc      960
ctgacaagca gcctgctgtt tgtctctgcc aacagcaact acgagcggac ccacagcaga     1020
atcatgatcc tgtctcaggg cctgcagacc ctcctgcctc ttatggcttt tggtggctg     1080
```

```
ctggcctctc tggccaatct ggcactgcct cctaccatca atctgctggg cgagctgagc    1140
gtgctggtca ccacattcag ctggtccaat atcaccctgc tgctcaccgg cctgaacatg    1200
ctggttacag ccctgtactc cctgtacatg ttcaccacca cacagtgggg aagcctgaca    1260
caccacatca acaatatgaa gcccagcttc acccgcgaga acaccctgat gttcatgcat    1320
ctgagcccca ttctgctgct gtccctgaat cctgatatca tcaccggctt ctccagctga    1380
```

<210> SEQ ID NO 8
<211> LENGTH: 1380
<212> TYPE: DNA
<213> ORGANISM: Artificial Sequence
<220> FEATURE:
<223> OTHER INFORMATION: opt_ND4*

<400> SEQUENCE: 8

```
atgctgaagc tgatcgtgcc caccatcatg ctgctgcccc tgacctggct gagcaagaag     60
cacatgatct ggatcaacac caccacccac agcctgatca tcagcatcat ccccctgctg    120
ttcttcaacc agatcaacaa caacctgttc agctgcagcc ccaccttcag cagcgacccc    180
ctgaccaccc ccctgctgat gctgaccacc tggctgctgc ccctgaccat catggccagc    240
cagcgccacc tgagcagcga gcccctgagc cgcaagaagc tgtacctgag catgctgatc    300
agcctgcaga tcagcctgat catgaccttc accgccaccg agctgatcat gttctacatc    360
ttcttcgaga ccaccctgat ccccaccctg gccatcatca cccgctgggg caaccagccc    420
gagcgcctga cgccggcac ctacttcctg ttctacaccc tggtgggcag cctgcccctg    480
ctgatcgccc tgatctacac ccacaacacc ctgggcagcc tgaacatcct gctgctgacc    540
ctgaccgccc aggagctgag caacagctgg gccaacaacc tgatgtggct ggcctacacc    600
atggccttca tggtgaagat gcccctgtac ggcctgcacc tgtggctgcc caaggcccac    660
gtggaggccc ccatcgccgg cagcatggtg ctggccgccg tgctgctgaa gctgggcggc    720
tacggcatga tgcgcctgac cctgatcctg aaccccctga ccaagcacat ggcctacccc    780
ttcctggtgc tgagcctgtg gggcatgatc atgaccagca gcatctgcct gcgccagacc    840
gacctgaaga gcctgatcgc ctacagcagc atcagccaca tggccctggt ggtgaccgcc    900
atcctgatcc agacccccctg gagcttcacc ggcgccgtga tcctgatgat cgcccacggc    960
ctgaccagca gcctgctgtt ctgcctggcc aacagcaact acgagcgcac ccacagccgc   1020
atcatgatcc tgagccaggg cctgcagacc ctgctgcccc tgatggcctt ctggtggctg   1080
ctggccagct ggccaacct ggccctgccc ccaccatca acctgctggg cgagctgagc   1140
gtgctggtga ccaccttcag ctggagcaac atcaccctgc tgctgaccgg cctgaacatg   1200
ctggtgaccg ccctgtacag cctgtacatg ttcaccacca cccagtgggg cagcctgacc   1260
caccacatca acaacatgaa gcccagcttc acccgcgaga acaccctgat gttcatgcac   1320
ctgagcccca tcctgctgct gagcctgaac cccgacatca tcaccggctt cagcagctaa   1380
```

<210> SEQ ID NO 9
<211> LENGTH: 525
<212> TYPE: DNA
<213> ORGANISM: Homo sapiens

<400> SEQUENCE: 9

```
atgatgtatg ctttgtttct gttgagtgtg ggtttagtaa tggggtttgt ggggttttct     60
tctaagcctt ctcctatttta tggggggttta gtattgattg ttagcggtgt ggtcgggtgt    120
```

| | |
|---|---|
| gttattattc tgaattttgg gggaggttat atgggtttaa tggttttttt aatttattta | 180 |
| ggggaatga tggttgtctt tggatatact acagcgatgg ctattgagga gtatcctgag | 240 |
| gcatggggt caggggttga ggtcttggtg agtgttttag tggggttagc gatggaggta | 300 |
| ggattggtgc tgtgggtgaa agagtatgat ggggtggtgg ttgtggtaaa ctttaatagt | 360 |
| gtaggaagct ggatgattta tgaaggagag gggtcagggt tgattcggga ggatcctatt | 420 |
| ggtgcggggg ctttgtatga ttatgggcgt tggttagtag tagttactgg ttggacattg | 480 |
| tttgttggtg tatatattgt aattgagatt gctcggggga attag | 525 |

<210> SEQ ID NO 10
<211> LENGTH: 525
<212> TYPE: DNA
<213> ORGANISM: Artificial Sequence
<220> FEATURE:
<223> OTHER INFORMATION: opt_ND6

<400> SEQUENCE: 10

| | |
|---|---|
| atgatgtacg ccctgttcct gctgagcgtg ggcctggtga tgggcttcgt gggcttcagc | 60 |
| agcaagccca gccccatcta cggcggcctg gtgctgatcg tgagcggcgt ggtgggctgc | 120 |
| gtgatcatcc tgaacttcgg cggcggctac atgggcctga tggtgttcct gatctacctg | 180 |
| gcggcatga tggtggtgtt cggctacacc accgccatgg ccatcgagga gtaccccgag | 240 |
| gcctggggca gcggcgtgga ggtgctggtg agcgtgctgg tgggcctggc catggaggtg | 300 |
| ggcctggtgc tgtgggtgaa ggagtacgac ggcgtggtgg tggtggtgaa cttcaacagc | 360 |
| gtgggcagct ggatgatcta cgagggcgag ggcagcggcc tgatccgcga ggaccccatc | 420 |
| ggcgccggcg ccctgtacga ctacggccgc tggctggtgg tggtgaccgg ctggaccctg | 480 |
| ttcgtgggcg tgtacatcgt gatcgagatc gcccgcggca actaa | 525 |

<210> SEQ ID NO 11
<211> LENGTH: 951
<212> TYPE: DNA
<213> ORGANISM: Homo sapiens

<400> SEQUENCE: 11

| | |
|---|---|
| atggccaacc tcctactcct cattgtaccc attctaatcg caatggcatt cctaatgctt | 60 |
| accgaacgaa aaattctagg ctatatgcaa ctacgcaaag cccccaacgt tgtaggcccc | 120 |
| tacgggctac tacaacccttt cgctgacgcc ataaaactct tcaccaaaga gcccctaaaa | 180 |
| cccgccacat ctaccatcac cctctacatc accgccccga ccttagctct caccatcgct | 240 |
| cttctactat ggacccccct ccccatgccc aaccccctgg tcaacctcaa cctaggcctc | 300 |
| ctatttattc tagccacctc tagcctagcc gtttactcaa tcctctggtc agggtgggca | 360 |
| tcaaactcaa actacgccct gatcggcgca ctgcgagcag tagcccaaac aatctcatat | 420 |
| gaagtcaccc tagccatcat tctactatca acattactaa tgagtggctc ctttaacctc | 480 |
| tccacccttta tcacaacaca agaacacctc tggttactcc tgccatcatg gcccttggcc | 540 |
| atgatgtggt ttatctccac actagcagag accaaccgaa ccccttcga ccttgccgaa | 600 |
| ggggagtccg aactagtctc aggcttcaac atcgaatacg ccgcaggccc cttcgcccta | 660 |
| ttcttcatgg ccgaatacac aaacattatt atgatgaaca ccctcaccac tacaatcttc | 720 |
| ctaggaacaa catatgacgc actctcccct gaactctaca acaatatttt tgtcaccaag | 780 |
| accctacttc taacctcccct gttcttatgg attcgaacag catacccccg attccgctac | 840 |
| gaccaactca tgcacctcct atggaaaaac ttcctaccac tcaccctagc attacttatg | 900 |

```
tggtatgtct ccatgcccat acaatctcc agcattcccc ctcaaaccta a              951
```

```
<210> SEQ ID NO 12
<211> LENGTH: 951
<212> TYPE: DNA
<213> ORGANISM: Artificial Sequence
<220> FEATURE:
<223> OTHER INFORMATION: opt_ND1

<400> SEQUENCE: 12
atggccaacc tgctgctgct gatcgtgccc atcctgatcg ccatggcctt cctgatgctg    60
accgagcgca agatcctggg ctacatgcag ctgcgcaagg cccccaacgt ggtgggcccc   120
tacggcctgc tgcagccctt cgccgacgcc atcaagctgt tcaccaagga gcccctgaag   180
cccgccacca gcaccatcac cctgtacatc ccgcccccca ccctggcccct gaccatcgcc   240
ctgctgctgt ggaccccct gcccatgccc aacccctgg tgaacctgaa cctgggcctg    300
ctgttcatcc tggccaccag cagcctggcc gtgtacagca cctgtggag cggctgggcc   360
agcaacagca actacgccct gatcggcgcc ctgcgcgccg tggcccagac catcagctac   420
gaggtgaccc tggccatcat cctgctgagc accctgctga tgagcggcag cttcaacctg   480
agcaccctga tcaccaccca ggagcacctg tggctgctgc tgcccagctg gccctggcc    540
atgatgtggt tcatcagcac cctggccgag accaaccgca cccccttcga cctggccgag   600
ggcgagagcg agctggtgag cggcttcaac atcgagtacg ccgccggccc cttcgccctg   660
ttcttcatgg ccgagtacac caacatcatc atgatgaaca ccctgaccac caccatcttc   720
ctgggcacca cctacgacgc cctgagcccc gagctgtaca ccacctactt cgtgaccaag   780
accctgctgc tgaccagcct gttcctgtgg atccgcaccg cctaccccg cttccgctac   840
gaccagctga tgcacctgct gtggaagaac ttcctgcccc tgaccctggc cctgctgatg   900
tggtacgtga gcatgcccat caccatcagc agcatccccc cccagaccta a            951
```

```
<210> SEQ ID NO 13
<211> LENGTH: 1425
<212> TYPE: DNA
<213> ORGANISM: Homo sapiens

<400> SEQUENCE: 13
gagcactggg acgccaccg ccccctttccc tccgctgcca ggcgagcatg ttgtggtaat    60
tctggaacac aagaagagaa attgctgggt ttagaacaag attataaacg aattcggtgc   120
tcagtgatca cttgacagtt tttttttttt taaatatta cccaaaatgc tccccaaata    180
agaaatgcat cagctcagtc agtgaataca aaaaggaat tatttttccc tttgagggtc    240
ttttatacat ctctcctcca accccaccct ctattctgtt tcttcctcct cacatggggg   300
tacacataca cagcttcctc ttttggttcc atccttacca ccacaccaca cgcacactcc   360
acatgcccag cagagtggca cttggtggcc agaaagtgtg agcctcatga tctgctgtct   420
gtagttctgt gagctcaggt ccctcaaagg cctcggagca ccccttcct tgtgactgag   480
ccagggcctg catttttggt ttccccacc ccacacattc tcaaccatag tccttctaac   540
aataccaata gctaggaccc ggctgctgtg cactgggact ggggattcca catgtttgcc   600
ttgggagtct caagctggac tgccagcccc tgtcctccct tcaccccat gcgtatgag    660
catttcagaa ctccaaggag tcacaggcat ctttatagtt cacgttaaca tatagacact   720
gttggaagca gttccttcta aagggtagc cctggactta ataccagccg gatacctctg   780
```

| | |
|---|---|
| gcccccaccc cattactgta cctctggagt cactactgtg ggtcgccact cctctgctac | 840 |
| acagcacggc tttttcaagg ctgtattgag aagggaagtt aggaagaagg gtgtgctggg | 900 |
| ctaaccagcc cacagagctc acattcctgt cccttgggtg aaaaatacat gtccatcctg | 960 |
| atatctcctg aattcagaaa ttagcctcca catgtgcaat ggctttaaga gccagaagca | 1020 |
| gggttctggg aattttgcaa gttacctgtg gccaggtgtg gtctcggtta ccaaatacgg | 1080 |
| ttacctgcag cttttagtc ctttgtgctc ccacgggtct acagagtccc atctgcccaa | 1140 |
| aggtcttgaa gcttgacagg atgttttcga ttactcagtc tcccagggca ctactggtcc | 1200 |
| gtaggattcg attggtcggg gtaggagagt taaacaacat ttaaacagag ttctctcaaa | 1260 |
| aatgtctaaa gggattgtag gtagataaca tccaatcact gtttgcactt atctgaaatc | 1320 |
| ttccctcttg gctgccccca ggtatttact gtggagaaca ttgcatagga atgtctggaa | 1380 |
| aaagcttcta caacttgtta cagccttcac atttgtagaa gcttt | 1425 |

<210> SEQ ID NO 14
<211> LENGTH: 625
<212> TYPE: DNA
<213> ORGANISM: Homo sapiens

<400> SEQUENCE: 14

| | |
|---|---|
| gagcactggg acgcccaccg ccccttccc tccgctgcca ggcgagcatg ttgtggtaat | 60 |
| tctggaacac aagaagagaa attgctgggt ttagaacaag attataaacg aattcggtgc | 120 |
| tcagtgatca cttgacagtt ttttttttt ttaaatatta cccaaaatgc tccccaaata | 180 |
| agaaatgcat cagctcagtc agtgaataca aaaaggaat tattttttccc tttgagggtc | 240 |
| ttttatacat ctctcctcca accccaccct ctattctgtt tcttcctcct cacatgggg | 300 |
| tacacataca cagcttcctc ttttggttcc atccttacca ccacaccaca cgcacactcc | 360 |
| acatgcccag cagagtggca cttggtggcc agaaagtgtg agcctcatga tctgctgtct | 420 |
| gtagttctgt gagctcaggt ccctcaaagg cctcggagca cccccttcct tgtgactgag | 480 |
| ccagggcctg catttttggt tttccccacc ccacacattc tcaaccatag tccttctaac | 540 |
| aataccaata gctaggaccc ggctgctgtg cactgggact ggggattcca catgtttgcc | 600 |
| ttgggagtct caagctggac tgcca | 625 |

<210> SEQ ID NO 15
<211> LENGTH: 2889
<212> TYPE: DNA
<213> ORGANISM: Artificial Sequence
<220> FEATURE:
<223> OTHER INFORMATION: COX10-ND4-3'UTR

<400> SEQUENCE: 15

| | |
|---|---|
| atggccgcat ctccgcacac tctctcctca cgcctcctga caggttgcgt aggaggctct | 60 |
| gtctggtatc ttgaaagaag aactatgcta aaactaatcg tcccaacaat tatgttacta | 120 |
| ccactgacat ggctttccaa aaaacacatg atttggatca acacaaccac ccacagccta | 180 |
| attattagca tcatccctct actatttttt aaccaaatca caacaaccct atttagctgt | 240 |
| tccccaacct tttcctccga ccccctaaca acccccctcc taatgctaac tacctggctc | 300 |
| ctaccctca caatcatggc aagccaacgc acttatcca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatccccac cttggctatc | 480 |
| atcacccgat ggggcaacca gccagaacgc ctgaacgcag gcacatactt cctattctac | 540 |

```
accctagtag gctcccttcc cctactcatc gcactaattt acactcacaa caccctaggc    600
tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
gtcattctca tgatcgccca cgggcttaca tcctcattac tattctgcct agcaaactca   1080
aactacgaac gcactcacag tcgcatcatg atcctctctc aaggacttca aactctactc   1140
ccactaatgg cttttggtg gcttctagca agcctcgcta acctcgcctt ccccccact     1200
attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgccctt tccctccgct   1500
gccaggcgag catgttgtgg taattctgga acacaagaag agaaattgct gggtttagaa   1560
caagattata aacgaattcg gtgctcagtg atcacttgac agtttttttt tttttaaat    1620
attacccaaa atgctcccca ataagaaat gcatcagctc agtcagtgaa tacaaaaaag    1680
gaattatttt tcccttttgag ggtcttttat acatctctcc tccaaccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggc cctgcatttt tggttttccc caccccacac    1980
attctcaacc atagtccttc taacaatacc aatagctagg accggctgc tgtgcactgg     2040
gactggggat tccacatgtt tgccttggga gtctcaagct ggactgccag cccctgtcct    2100
cccttcaccc ccattgcgta tgagcatttc agaactccaa ggagtcacag gcatctttat    2160
agttcacgtt aacatataga cactgttgga agcagttcct tctaaagggg tagccctgga    2220
cttaatacca gccggatacc tctggccccc accccattac tgtacctctg gagtcactac    2280
tgtgggtcgc cactcctctg ctacacagca cggctttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
```

| | |
|---|---:|
| agaagcttt | 2889 |

<210> SEQ ID NO 16
<211> LENGTH: 2089
<212> TYPE: DNA
<213> ORGANISM: Artificial Sequence
<220> FEATURE:
<223> OTHER INFORMATION: COX10-ND4-3'UTR*

<400> SEQUENCE: 16

| | |
|---|---:|
| atggccgcat ctccgcacac tctctcctca cgcctcctga caggttgcgt aggaggctct | 60 |
| gtctggtatc ttgaaagaag aactatgcta aaactaatcg tcccaacaat tatgttacta | 120 |
| ccactgacat ggcttttccaa aaaacacatg atttggatca cacaaccac ccacagccta | 180 |
| attattagca tcatccctct actattttt aaccaaatca caacaacct atttagctgt | 240 |
| tccccaacct tttcctccga ccccctaaca accccctcc taatgctaac tacctggctc | 300 |
| ctaccccctca caatcatggc aagccaacgc acttatcca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatccccac cttggctatc | 480 |
| atcacccgat ggggcaacca gccagaacgc ctgaacgcag gcatacttt cctattctac | 540 |
| accctagtag gctcccttcc cctactcatc gcactaattt acactcacaa cccctaggc | 600 |
| tcactaaaca ttctactact cactctcact gcccaagaac tatcaaactc ctgggccaac | 660 |
| aacttaatgt ggctagctta cacaatggct tttatggtaa agatgcctct ttacggactc | 720 |
| cacttatggc tccctaaagc ccatgtcgaa gccccccatcg ctgggtcaat ggtacttgcc | 780 |
| gcagtactct taaaactagg cggctatggt atgatgcgcc tcacactcat tctcaacccc | 840 |
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg cttttttggtg gcttctagca agcctcgcta acctcgcctt accccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact cacccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgcccctt tcctccgct | 1500 |
| gccaggcgag catgttgtgg taattctgga acacaagaag agaaattgct gggtttagaa | 1560 |
| caagattata aacgaattcg gtgctcagtg atcacttgac agttttttt ttttttaaat | 1620 |
| attacccaaa atgctcccca aataagaaat gcatcagctc agtcagtgaa tacaaaaaag | 1680 |
| gaattatttt tccctttgag ggtcttttat acatctctcc tccaacccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcaccccct tccttgtgac tgagccaggg cctgcatttt tggttttccc cacccacac | 1980 |
| attctcaacc atagtccttc taacaatacc aatagctagg accggctgc tgtgcactgg | 2040 |

| | |
|---|---|
| gactggggat tccacatgtt tgccttggga gtctcaagct ggactgcca | 2089 |

<210> SEQ ID NO 17
<211> LENGTH: 2889
<212> TYPE: DNA
<213> ORGANISM: Artificial Sequence
<220> FEATURE:
<223> OTHER INFORMATION: COX10-opt_ND4-3'UTR

<400> SEQUENCE: 17

| | |
|---|---|
| atggccgcat ctccgcacac tctctcctca cgcctcctga caggttgcgt aggaggctct | 60 |
| gtctggtatc ttgaaagaag aactatgctg aagctgatcg tgcccaccat catgctgctg | 120 |
| cctctgacct ggctgagcaa gaaacacatg atctggatca acaccaccac gcacagcctg | 180 |
| atcatcagca tcatccctct gctgttcttc aaccagatca caacaaccct gttcagctgc | 240 |
| agccccacct tcagcagcga ccctctgaca cacctctgc tgatgctgac cacctggctg | 300 |
| ctgccccctca caatcatggc ctctcagaga cacctgagca gcgagcccct gagccggaag | 360 |
| aaactgtacc tgagcatgct gatctccctg cagatctctc tgatcatgac cttcaccgcc | 420 |
| accgagctga tcatgttcta catctttttc gagacaacgc tgatccccac actggccatc | 480 |
| atcaccagat ggggcaacca gcctgagaga ctgaacgccg gcacctactt tctgttctac | 540 |
| accctcgtgg gcagcctgcc actgctgatt gccctgatct acacccacaa cacccctgggc | 600 |
| tccctgaaca tcctgctgct gacactgaca gcccaagagc tgagcaacag ctgggccaac | 660 |
| aatctgatgt ggctggccta cacaatggcc ttcatggtca agatgcccct gtacggcctg | 720 |
| cacctgtggc tgcctaaagc tcatgtggaa gcccctatcg ccggctctat ggtgctggct | 780 |
| gcagtgctgc tgaaactcgg cggctacggc atgatgcggc tgaccctgat tctgaatccc | 840 |
| ctgaccaagc acatggccta tccatttctg gtgctgagcc tgtggggcat gattatgacc | 900 |
| agcagcatct gcctgcggca gaccgatctg aagtccctga tcgcctacag ctccatcagc | 960 |
| cacatggccc tggtggtcac cgccatcctg attcagaccc cttggagctt tacaggcgcc | 1020 |
| gtgatcctga tgattgccca cggcctgaca agcagcctgc tgttttgtct ggccaacagc | 1080 |
| aactacgagc ggacccacag cagaatcatg atcctgtctc agggcctgca gaccctcctg | 1140 |
| cctcttatgg cttttggtg gctgctggcc tctctggcca atctggcact gcctcctacc | 1200 |
| atcaatctgc tgggcgagct gagcgtgctg gtcaccacat tcagctggtc caatatcacc | 1260 |
| ctgctgctca ccggcctgaa catgctggtt acagccctgt actccctgta catgttcacc | 1320 |
| accacacagt ggggaagcct gacacaccac atcaacaata tgaagcccag cttcacccgc | 1380 |
| gagaacaccc tgatgttcat gcatctgagc cccattctgc tgctgtccct gaatcctgat | 1440 |
| atcatcaccg gcttctccag ctgagagcac tgggacgccc accgccccttt tccctccgct | 1500 |
| gccaggcgag catgttgtgg taattctgga acacaagaag agaaattgct gggtttagaa | 1560 |
| caagattata aacgaattcg gtgctcagtg atcacttgac agttttttt tttttaaat | 1620 |
| attacccaaa atgctcccca aataagaaat gcatcagctc agtcagtgaa tacaaaaaag | 1680 |
| gaattatttt tccctttgag ggtcttttat acatctctcc tccaaccca ccctctattc | 1740 |
| tgtttcttcc tcctcacatg ggggtacaca tacacagctt cctctttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtcccctca aaggcctcgg | 1920 |
| agcaccccct tccttgtgac tgagccaggg cctgcatttt tggttttccc caccccacac | 1980 |

| | |
|---|---|
| attctcaacc atagtccttc taacaatacc aatagctagg acccggctgc tgtgcactgg | 2040 |
| gactggggat tccacatgtt tgccttggga gtctcaagct ggactgccag cccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaaaggg tagccctgga | 2220 |
| cttaatacca gccggatacc tctggccccc accccattac tgtacctctg gagtcactac | 2280 |
| tgtgggtcgc cactcctctg ctacacagca cggcttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagcttttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 18
<211> LENGTH: 2089
<212> TYPE: DNA
<213> ORGANISM: Artificial Sequence
<220> FEATURE:
<223> OTHER INFORMATION: COX10-opt_ND4-3'UTR*

<400> SEQUENCE: 18

| | |
|---|---|
| atggccgcat ctccgcacac tctctcctca cgcctcctga caggttgcgt aggaggctct | 60 |
| gtctggtatc ttgaaagaag aactatgctg aagctgatcg tgcccaccat catgctgctg | 120 |
| cctctgacct ggctgagcaa gaaacacatg atctggatca acaccaccac gcacagcctg | 180 |
| atcatcagca tcatccctct gctgttcttc aaccagatca caacaaccct gttcagctgc | 240 |
| agccccacct tcagcagcga ccctctgaca acacctctgc tgatgctgac cacctggctg | 300 |
| ctgcccctca caatcatggc ctctcagaga cacctgagca gcgagcccct gagcggaag | 360 |
| aaactgtacc tgagcatgct gatctccctg cagatctctc tgatcatgac cttcaccgcc | 420 |
| accgagctga tcatgttcta catcttttc gagacaacgc tgatccccac actggccatc | 480 |
| atcaccagat ggggcaacca gcctgagaga ctgaacgccg gcacctactt tctgttctac | 540 |
| accctcgtgg gcagcctgcc actgctgatt gccctgatct acacccacaa ccctgggc | 600 |
| tccctgaaca tcctgctgct gacactgaca gcccaagagc tgagcaacag ctgggccaac | 660 |
| aatctgatgt ggctggccta cacaatggcc ttcatggtca agatgcccct gtacggcctg | 720 |
| cacctgtggc tgcctaaagc tcatgtggaa gccctatcg ccggctctat ggtgctggct | 780 |
| gcagtgctgc tgaaactcgg cggctacggc atgatgcggc tgaccctgat tctgaatccc | 840 |
| ctgaccaagc acatggccta tccatttctg tgctgagcc tgtggggcat gattatgacc | 900 |
| agcagcatct gcctgcggca gaccgatctg aagtccctga tcgcctacag ctccatcagc | 960 |
| cacatggccc tggtggtcac cgccatcctg attcagaccc cttggagctt acaggcgcc | 1020 |
| gtgatcctga tgattgccca cggcctgaca agcagcctgc tgttttgtct ggccaacagc | 1080 |
| aactacgagc ggacccacag cagaatcatg atcctgtctc agggcctgca gaccctcctg | 1140 |

```
cctcttatgg cttttt ggtg gctgctggcc tctctggcca atctggcact gcctcctacc    1200
atcaatctgc tgggcgagct gagcgtgctg gtcaccacat tcagctggtc caatatcacc    1260
ctgctgctca ccggcctgaa catgctggtt acagccctgt actccctgta catgttcacc    1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agtttttttt tttttttaaat    1620 attacccaaa atgctcccca aataagaaat gcatcagctc agtcagtgaa tacaaaaaag    1680
gaattatttt tccctttgag ggtcttttat acatctctcc tccaaccca ccctctattc     1740 tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc cacccacac     1980 attctcaacc atagtccttc taacaatacc aatagctagg acccggctgc tgtgcactgg    2040
gactggggat tccacatgtt tgccttggga gtctcaagct ggactgcca                2089

<210> SEQ ID NO 19
<211> LENGTH: 2889
<212> TYPE: DNA
<213> ORGANISM: Artificial Sequence
<220> FEATURE:
<223> OTHER INFORMATION: COX10-opt_ND4*-3'UTR

<400> SEQUENCE: 19
atggccgcat ctccgcacac tctctcctca cgcctcctga caggttgcgt aggaggctct      60
gtctggtatc ttgaaagaag aactatgctg aagctgatcg tgcccaccat catgctgctg     120
cccctgacct ggctgagcaa gaagcacatg atctggatca acaccaccac ccacagcctg     180
atcatcagca tcatccccct gctgttcttc aaccagatca acaacaacct gttcagctgc     240
agccccacct tcagcagcga ccccctgacc acccccctgc tgatgctgac cacctggctg     300
ctgcccctga ccatcatggc cagccagcgc cacctgagca gcgagcccct gagccgcaag     360
aagctgtacc tgagcatgct gatcagcctg cagatcagcc tgatcatgac cttcaccgcc     420
accgagctga tcatgttcta catcttcttc gagaccaccc tgatcccac cctggccatc      480 atcacccgct ggggcaacca gcccgagcgc ctgaacgccg gcacctactt cctgttctac     540
accctggtgg gcagcctgcc cctgctgatc gccctgatct acacccacaa cccctgggc     600 agcctgaaca tcctgctgct gaccctgacc gcccaggagc tgagcaacag ctgggccaac     660
aacctgatgt ggctggccta caccatggcc ttcatggtga agtgcccct gtacggcctg     720 cacctgtggc tgcccaaggc ccacgtggag gcccccatcg ccggcagcat ggtgctggcc     780
gccgtgctgc tgaagctggg cggctacggc atgatgcgcc tgaccctgat cctgaacccc     840
ctgaccaagc acatggccta cccccttcctg gtgctgagcc tgtggggcat gatcatgacc     900
agcagcatct gcctgcgcca gaccgacctg aagagcctga tcgcctacag cagcatcagc     960
cacatggccc tggtggtgac cgccatcctg atccagaccc cctggagctt caccggcgcc    1020
gtgatcctga tgatcgccca cggcctgacc agcagcctgc tgttctgcct ggccaacagc    1080
```

| | |
|---|---|
| aactacgagc gcacccacag ccgcatcatg atcctgagcc agggcctgca gaccctgctg | 1140 |
| cccctgatgg ccttctggtg gctgctggcc agcctggcca acctggccct gcccccacc | 1200 |
| atcaacctgc tgggcgagct gagcgtgctg gtgaccacct tcagctggag caacatcacc | 1260 |
| ctgctgctga ccggcctgaa catgctggtg accgccctgt acagcctgta catgttcacc | 1320 |
| accacccagt ggggcagcct gacccaccac atcaacaaca tgaagcccag cttcacccgc | 1380 |
| gagaacaccc tgatgttcat gcacctgagc cccatcctgc tgctgagcct gaaccccgac | 1440 |
| atcatcaccg gcttcagcag ctaagagcac tgggacgccc accgcccctt tccctccgct | 1500 |
| gccaggcgag catgttgtgg taattctgga acacaagaag agaaattgct gggtttagaa | 1560 |
| caagattata acgaattcg tgctcagtg atcacttgac agtttttttt tttttaaat | 1620 |
| attacccaaa atgctcccca aataagaaat gcatcagctc agtcagtgaa tacaaaaaag | 1680 |
| gaattatttt tcccctttgag ggtctttttat acatctctcc tccaaccca ccctctattc | 1740 |
| tgtttcttcc tcctcacatg ggggtacaca tacacagctt cctctttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcaccccct tccttgtgac tgagccaggg cctgcatttt tggttttccc caccccacac | 1980 |
| attctcaacc atagtccttc taacaatacc aatagctagg acccggctgc tgtgcactgg | 2040 |
| gactggggat tccacatgtt tgccttggga gtctcaagct ggactgccag ccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaagggg tagccctgga | 2220 |
| cttaatacca gccggatacc tctggccccc accccattac tgtacctctg gagtcactac | 2280 |
| tgtgggtcgc cactcctctg ctacacagca cggctttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaattt gcaagttacc tgtggccagg | 2520 |
| tgtggtctcg gttaccaaat acggttacct gcagcttttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 20
<211> LENGTH: 2089
<212> TYPE: DNA
<213> ORGANISM: Artificial Sequence
<220> FEATURE:
<223> OTHER INFORMATION: COX10-opt_ND4*-3'UTR*

<400> SEQUENCE: 20

| | |
|---|---|
| atggccgcat ctccgcacac tctctcctca cgcctcctga caggttgcgt aggaggctct | 60 |
| gtctggtatc ttgaaagaag aactatgctg aagctgatcg tgcccaccat catgctgctg | 120 |
| cccctgaccg gctgagcaa gaagcacatg atctggatca acaccaccac ccacagcctg | 180 |
| atcatcagca tcatccccct gctgttcttc aaccagatca caacaacct gttcagctgc | 240 |

```
agccccacct tcagcagcga cccccctgacc acccccctgc tgatgctgac cacctggctg    300
ctgcccctga ccatcatggc cagccagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatcccac cctggccatc    480 atcacccgct ggggcaacca gcccgagcgc ctgaacgccg gcacctactt cctgttctac    540
accctggtgg gcagcctgcc cctgctgatc gccctgatct acacccacaa caccctgggc    600
agcctgaaca tcctgctgct gaccctgacc gcccaggagc tgagcaacag ctgggccaac    660
aacctgatgt ggctggccta ccatggccttcatggtga agatgcccct gtacggcctg    720
cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta cccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gcccccacc    1200 atcaacctgc tgggcgagct gagcgtgctg gtgaccacct cagctggag caacatcacc   1260 ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgcccctt tccctccgct   1500
gccaggcgag catgttgtgg taattctgga acacaagaag agaaattgct gggtttagaa   1560
caagattata acgaattcg gtgctcagtg atcacttgac agttttttt tttttttaaat   1620 attacccaaa atgctcccca ataagaaat gcatcagctc agtcagtgaa tacaaaaaag   1680
gaattatttt tcccctttgag ggtctttat acatctctcc tccaccccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc caccccacac   1980
attctcaacc atagtccttc taacaatacc aatagctagg acccggctgc tgtgcactgg   2040
gactggggat ccacatgtt tgccttggga gtctcaagct ggactgcca                2089

<210> SEQ ID NO 21
<211> LENGTH: 2034
<212> TYPE: DNA
<213> ORGANISM: Artificial Sequence
<220> FEATURE:
<223> OTHER INFORMATION: COX10-ND6-3'UTR

<400> SEQUENCE: 21
atggccgcat ctccgcacac tctctcctca cgcctcctga caggttgcgt aggaggctct     60
gtctggtatc ttgaaagaag aactatgatg tatgctttgt ttctgttgag tgtgggttta    120
gtaatggggt ttgtggggtt ttcttctaag ccttctccta tttatggggg tttagtattg    180
```

```
attgttagcg gtgtggtcgg gtgtgttatt attctgaatt ttgggggagg ttatatgggt    240
ttaatggttt ttttaatttta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agagggtca    480 gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc cccttcccct ccgctgccag gcgagcatgt    660
tgtggtaatt ctgaacacaa agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttccct    840 ttgagggtct tttatacatc tctcctccaa ccccaccctc tattctgttt cttcctcctc    900 acatggggt acacatacac agcttcctct tttggttcca tccttaccac cacaccacac    960
gcacactcca catgcccagc agagtggcac ttggtggcca gaaagtgtga gcctcatgat   1020
ctgctgtctg tagttctgtg agctcaggtc cctcaaaggc ctcggagcac ccccttcctt   1080
gtgactgagc cagggcctgc atttttggtt ttccccaccc cacacattct caaccatagt   1140
ccttctaaca ataccaatag ctaggacccg gctgctgtgc actgggactg gggattccac   1200
atgtttgcct tgggagtctc aagctggact gccagcccct gtcctcccttt caccccattt   1260 gcgtatgagc atttcagaac tccaaggagt cacaggcatc tttatagttc acgttaacat   1320
atagacactg ttggaagcag ttccttctaa aagggtagcc ctggacttaa taccagccgg   1380
atacctctgg cccccaccc attactgtac ctctggagtc actactgtgg gtcgccactc   1440
ctctgctaca cagcacggct ttttcaaggc tgtattgaga agggaagtta ggaagaaggg   1500
tgtgctgggc taaccagccc acagagctca cattcctgtc ccttgggtga aaaatacatg   1560
tccatcctga tatctcctga attcagaaat tagcctccac atgtgcaatg ctttaagag   1620 ccagaagcag ggttctggga attttgcaag ttacctgtgg ccaggtgtgg tctcggttac   1680
caaatacggt tacctgcagc ttttttagtcc tttgtgctcc cacgggtcta cagagtccca   1740
tctgcccaaa ggtcttgaag cttgacagga tgttttcgat tactcagtct cccagggcac   1800
tactggtccg taggattcga ttggtcgggg taggagagtt aaacaacatt taaacagagt   1860
tctctcaaaa atgtctaaag ggattgtagg tagataacat ccaatcactg tttgcactta   1920
tctgaaatct tccctcttgg ctgccccag gtatttactg tggagaacat tgcataggaa   1980
tgtctggaaa aagcttctac aacttgttac agccttcaca tttgtagaag cttt         2034
```

<210> SEQ ID NO 22
<211> LENGTH: 1234
<212> TYPE: DNA
<213> ORGANISM: Artificial Sequence
<220> FEATURE:
<223> OTHER INFORMATION: COX10-ND6-3'UTR*

<400> SEQUENCE: 22

```
atggccgcat ctccgcacac tctctcctca cgcctcctga caggttgcgt aggaggctct     60
gtctggtatc ttgaaagaag aactatgatg tatgctttgt ttctgttgag tgtgggttta    120
gtaatggggt ttgtggggtt ttcttctaag ccttctccta tttatggggg tttagtattg    180
attgttagcg gtgtggtcgg gtgtgttatt attctgaatt ttgggggagg ttatatgggt    240
```

```
ttaatggttt ttttaattta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agagggtca    480 gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc cccctttccct ccgctgccag gcgagcatgt    660
tgtggtaatt ctggaacaca agaagagaaa ttgctgggtt tagaacaaga ttataaacga    720
attcggtgct cagtgatcac ttgacagttt ttttttttt taaatattac ccaaaatgct    780
ccccaaataa gaaatgcatc agctcagtca gtgaatacaa aaaggaatt attttttccct    840 ttgagggtct tttatacatc tctcctccaa ccccacccctc tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat   1020
ctgctgtctg tagttctgtg agctcaggtc cctcaaaggc ctcggagcac cccttcctt   1080 gtgactgagc cagggcctgc atttttggtt ttccccaccc cacacattct caaccatagt   1140
ccttctaaca ataccaatag ctaggacccg gctgctgtgc actgggactg gggattccac   1200
atgtttgcct tgggagtctc aagctggact gcca                              1234

<210> SEQ ID NO 23
<211> LENGTH: 2034
<212> TYPE: DNA
<213> ORGANISM: Artificial Sequence
<220> FEATURE:
<223> OTHER INFORMATION: COX10-opt_ND6-3'UTR

<400> SEQUENCE: 23
atggccgcat ctccgcacac tctctcctca cgcctcctga caggttgcgt aggaggctct     60
gtctggtatc ttgaaagaag aactatgatg tacgccctgt tcctgctgag cgtgggcctg    120
gtgatgggct tcgtgggctt cagcagcaag cccagcccca tctacggcgg cctggtgctg    180
atcgtgagcg gcgtggtggg ctgcgtgatc atcctgaact tcggcggcgg ctacatgggc    240
ctgatggtgt tcctgatcta cctgggcggc atgatggtgg tgttcggcta caccaccgcc    300
atggccatcg aggagtaccc cgaggcctgg ggcagcggcg tggaggtgct ggtgagcgtg    360 ctggtggggcc tggccatgga ggtgggcctg gtgctgtggg tgaaggagta cgacggcgtg    420
gtggtggtgg tgaacttcaa cagcgtgggc agctggatga tctacgaggg cgagggcagc    480
ggcctgatcc gcgaggaccc catcggcgcc ggcgccctgt acgactacgg ccgctggctg    540
gtggtggtga ccggctggac cctgttcgtg ggcgtgtaca tcgtgatcga gatcgcccgc    600
ggcaactaag agcactggga cgcccaccgc cccctttccct ccgctgccag gcgagcatgt    660
tgtggtaatt ctggaacaca agaagagaaa ttgctgggtt tagaacaaga ttataaacga    720
attcggtgct cagtgatcac ttgacagttt ttttttttt taaatattac ccaaaatgct    780
ccccaaataa gaaatgcatc agctcagtca gtgaatacaa aaaggaatt attttttccct    840 ttgagggtct tttatacatc tctcctccaa ccccacccctc tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat   1020
```

```
ctgctgtctg tagttctgtg agctcaggtc cctcaaaggc ctcggagcac cccttccctt    1080
gtgactgagc cagggcctgc attttttggtt ttccccaccc cacacattct caaccatagt    1140
ccttctaaca ataccaatag ctaggacccg gctgctgtgc actgggactg gggattccac    1200
atgtttgcct tgggagtctc aagctggact gccagcccct gtcctccctt caccccatt     1260 gcgtatgagc atttcagaac tccaaggagt cacaggcatc tttatagttc acgttaacat    1320
atagacactg ttggaagcag ttccttctaa aagggtagcc ctggacttaa taccagccgg    1380
atacctctgg cccccacccc attactgtac ctctggagtc actactgtgg gtcgccactc    1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag    1620 ccagaagcag ggttctggga attttgcaag ttacctgtgg ccaggtgtgg tctcggttac    1680
caaatacggt tacctgcagc ttttagtcc tttgtgctcc cacgggtcta cagagtccca    1740
tctgcccaaa ggtcttgaag cttgacagga tgttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgccccag gtatttactg tggagaacat tgcataggaa    1980
tgtctggaaa aagcttctac aacttgttac agccttcaca tttgtagaag cttt          2034

<210> SEQ ID NO 24
<211> LENGTH: 1234
<212> TYPE: DNA
<213> ORGANISM: Artificial Sequence
<220> FEATURE:
<223> OTHER INFORMATION: COX10-opt_ND6-3'UTR*

<400> SEQUENCE: 24
atggccgcat ctccgcacac tctctcctca cgcctcctga caggttgcgt aggaggctct     60
gtctggtatc ttgaaagaag aactatgatg tacgccctgt tcctgctgag cgtgggcctg    120
gtgatgggct tcgtgggctt cagcagcaag cccagcccca tctacggcgg cctggtgctg    180
atcgtgagcg gcgtggtggg ctgcgtgatc atcctgaact tcggcggcgg ctacatgggc    240
ctgatggtgt tcctgatcta cctgggcggc atgatggtgg tgttcggcta caccaccgcc    300
atggccatcg aggagtaccc cgaggcctgg ggcagcggcg tggaggtgct ggtgagcgtg    360 ctggtggggcc tggccatgga ggtgggcctg gtgctgtggg tgaaggagta cgacggcgtg    420
gtggtggtgg tgaacttcaa cagcgtgggc agctggatga tctacgaggg cgagggcagc    480
ggcctgatcc gcaggacccc catcggcgcc ggcgccctgt acgactacgg ccgctggctg    540
gtggtggtga ccggctggac cctgttcgtg ggcgtgtaca tcgtgatcga gatcgcccgc    600
ggcaactaag agcactggga cgcccaccgc ccctttccct ccgctgccag gcgagcatgt    660
tgtggtaatt ctgaacacac agaagagaaa ttgctgggtt tagaacaaga ttataaacga    720
attcggtgct cagtgatcac ttgacagttt ttttttttt taaatattac ccaaaatgct    780
ccccaaataa gaaatgcatc agctcagtca gtgaatacaa aaaaggaatt attttttccct    840 ttgagggtct tttatacatc tctcctccaa ccccacccctc tattctgttt cttcctcctc    900
acatgggggt acacatacac agcttcctct tttggttcca tccttaccac cacaccacac    960
gcacactcca catgcccagc agagtggcac ttggtggcca gaaagtgtga gcctcatgat    1020
ctgctgtctg tagttctgtg agctcaggtc cctcaaaggc ctcggagcac cccttccctt    1080
```

-continued

| | |
|---|---|
| gtgactgagc cagggcctgc atttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 25
<211> LENGTH: 2460
<212> TYPE: DNA
<213> ORGANISM: Artificial Sequence
<220> FEATURE:
<223> OTHER INFORMATION: COX10-ND1-3'UTR

<400> SEQUENCE: 25

| | |
|---|---|
| atggccgcat ctccgcacac tctctcctca cgcctcctga caggttgcgt aggaggctct | 60 |
| gtctggtatc ttgaaagaag aactatggcc aacctcctac tcctcattgt acccattcta | 120 |
| atcgcaatgg cattcctaat gcttaccgaa cgaaaaattc taggctatat gcaactacgc | 180 |
| aaaggcccca acgttgtagg cccctacggg ctactacaac ccttcgctga cgccataaaa | 240 |
| ctcttcacca aagagcccct aaaacccgcc acatctacca tcaccctcta catcaccgcc | 300 |
| ccgaccttag ctctcaccat cgctcttcta ctatggaccc cctcccccat gcccaacccc | 360 |
| ctggtcaacc tcaacctagg cctcctattt attctagcca cctctagcct agccgtttac | 420 |
| tcaatcctct ggtcagggtg ggcatcaaac tcaaactacg ccctgatcgg cgcactgcga | 480 |
| gcagtagccc aaacaatctc atatgaagtc accctagcca tcattctact atcaacatta | 540 |
| ctaatgagtg gctcctttaa cctctccacc cttatcacaa cacaagaaca cctctggtta | 600 |
| ctcctgccat catggcccctt ggccatgatg tggtttatct ccacactagc agagaccaac | 660 |
| cgaacccccct tcgaccttgc cgaaggggag tccgaactag tctcaggctt caacatcgaa | 720 |
| tacgccgcag gccccttcgc cctattcttc atggccgaat acacaaacat tattatgatg | 780 |
| aacaccctca ccactacaat cttcctagga caacatatg acgcactctc ccctgaactc | 840 |
| tacacaacat attttgtcac caagacccta cttctaacct ccctgttctt atggattcga | 900 |
| acagcatacc cccgattccg ctacgaccaa ctcatgcacc tcctatggaa aaacttccta | 960 |
| ccactcaccc tagcattact tatgtggtat gtctccatgc ccattacaat ctccagcatt | 1020 |
| cccccctcaaa cctaagagca ctgggacgcc caccgcccct ttccctccgc tgccaggcga | 1080 |
| gcatgttgtg gtaattctgg aacacaagaa gagaaattgc tgggtttaga acaagattat | 1140 |
| aaacgaattc ggtgctcagt gatcacttga cagttttttt tttttttaaa tattacccaa | 1200 |
| aatgctcccc aaataagaaa tgcatcagct cagtcagtga atacaaaaaa ggaattattt | 1260 |
| ttcccttga gggtctttta tacatctctc ctccaacccc ccctctatt ctgtttcttc | 1320 |
| ctcctcacat gggggtacac atacacagct tcctcttttg gttccatcct taccaccaca | 1380 |
| ccacacgcac actccacatg cccagcagag tggcacttgg tggccagaaa gtgtgagcct | 1440 |
| catgatctgc tgtctgtagt tctgtgagct caggtccctc aaaggcctcg gagcaccccc | 1500 |
| ttccttgtga ctgagccagg gcctgcattt ttggttttcc ccaccccaca cattctcaac | 1560 |
| catagtcctt ctaacaatac caatagctag gacccggctg ctgtgcactg ggactggggga | 1620 |
| ttccacatgt ttgccttggg agtctcaagc tggactgcca gccctgtcc tcccttcacc | 1680 |
| cccattgcgt atgagcattt cagaactcca aggagtcaca ggcatcttta tagttcacgt | 1740 |
| taacatatag acactgttgg aagcagttcc ttctaaaagg gtagccctgg acttaatacc | 1800 |
| agccggatac ctctggcccc caccccatta ctgtacctct ggagtcacta ctgtgggtcg | 1860 |

```
ccactcctct gctacacagc acggctttt caaggctgta ttgagaaggg aagttaggaa    1920
gaagggtgtg ctgggctaac cagcccacag agctcacatt cctgtccctt gggtgaaaaa    1980
tacatgtcca tcctgatatc tcctgaattc agaaattagc ctccacatgt gcaatggctt    2040
taagagccag aagcagggtt ctgggaattt tgcaagttac ctgtggccag gtgtggtctc    2100
ggttaccaaa tacggttacc tgcagctttt tagtccttg tgctcccacg ggtctacaga    2160
gtcccatctg cccaaaggtc ttgaagcttg acaggatgtt ttcgattact cagtctccca    2220
gggcactact ggtccgtagg attcgattgg tcggggtagg agagttaaac aacatttaaa    2280
cagagttctc tcaaaaatgt ctaaagggat tgtaggtaga taacatccaa tcactgtttg    2340
cacttatctg aaatcttccc tcttggctgc ccccaggtat ttactgtgga gaacattgca    2400
taggaatgtc tggaaaaagc ttctacaact tgttacagcc ttcacatttg tagaagcttt    2460
```

<210> SEQ ID NO 26
<211> LENGTH: 1660
<212> TYPE: DNA
<213> ORGANISM: Artificial Sequence
<220> FEATURE:
<223> OTHER INFORMATION: COX10-ND1-3'UTR*

<400> SEQUENCE: 26

```
atggccgcat ctccgcacac tctctcctca cgcctcctga caggttgcgt aggaggctct      60
gtctggtatc ttgaaagaag aactatggcc aacctcctac tcctcattgt acccattcta     120
atcgcaatgg cattcctaat gcttaccgaa cgaaaaattc taggctatat gcaactacgc     180
aaaggcccca acgttgtagg cccctacggg ctactacaac ccttcgctga cgccataaaa     240
ctcttcacca agagcccct aaaacccgcc acatctacca tcaccctcta catcaccgcc     300
ccgaccttag ctctcaccat cgctcttcta ctatggaccc cctccccat gcccaacccc     360 ctggtcaacc tcaacctagg cctcctattt attctagcca cctctagcct agccgtttac     420
tcaatcctct ggtcagggtg gcatcaaac tcaaactacg ccctgatcgg cgcactgcga     480
gcagtagccc aaacaatctc atatgaagtc accctagcca tcattctact atcaacatta     540
ctaatgagtg gctcctttaa cctctccacc cttatcacaa cacaagaaca cctctggtta     600
ctcctgccat catggccctt ggccatgatg tggtttatct ccacactagc agagaccaac     660
cgaaccccct tcgaccttgc cgaaggggag tccgaactag tctcaggctt caacatcgaa     720
tacgccgcag gccccttcgc cctattcttc atggccgaat acacaaacat tattatgatg     780 aacacccctca ccactacaat cttcctagga acaacatatg acgcactctc ccctgaactc     840
tacacaacat attttgtcac caagacccta cttctaacct ccctgttctt atggattcga     900
acagcatacc cccgattccg ctacgaccaa ctcatgcacc tcctatggaa aaacttccta     960
ccactcaccc tagcattact tatgtggtat gtctccatgc ccattacaat ctccagcatt    1020 cccctcaaa cctaagagca ctgggacgcc caccgcccct ttccctccgc tgccaggcga    1080
gcatgttgtg gtaattctgg aacacaagaa gagaaattgc tgggtttaga acaagattat    1140
aaacgaattc ggtgctcagt gatcacttga cagtttttt tttttttaaa tattacccaa    1200
aatgctcccc aaataagaaa tgcatcagct cagtcagtga atacaaaaaa ggaattattt    1260
ttccctttga gggtctttta tacatctctc ctccaacccc accctctatt ctgtttcttc    1320
ctcctcacat ggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcacccc    1500
```

```
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca                         1660
```

<210> SEQ ID NO 27
<211> LENGTH: 2460
<212> TYPE: DNA
<213> ORGANISM: Artificial Sequence
<220> FEATURE:
<223> OTHER INFORMATION: COX10-opt_ND1-3'UTR

<400> SEQUENCE: 27

```
atggccgcat ctccgcacac tctctcctca cgcctcctga caggttgcgt aggaggctct      60
gtctggtatc ttgaaagaag aactatggcc aacctgctgc tgctgatcgt gcccatcctg     120
atcgccatgg ccttcctgat gctgaccgag cgcaagatcc tgggctacat gcagctgcgc     180
aagggcccca cgtggtgggc ccctacggc ctgctgcagc ccttcgccga cgccatcaag      240
ctgttcacca aggagcccct gaagcccgcc accagcacca tcaccctgta catcaccgcc     300
cccaccctgg ccctgaccat cgccctgctg ctgtggaccc cctgcccat gcccaacccc     360 ctggtgaacc tgaacctggg cctgctgttc atcctggcca ccagcagcct ggccgtgtac     420
agcatcctgt ggagcggctg ggccagcaac agcaactacg ccctgatcgg cgccctgcgc     480
gccgtggccc agaccatcag ctacgaggtg accctggcca tcatcctgct gagcaccctg     540
ctgatgagcg gcagcttcaa cctgagcacc ctgatcacca cccaggagca cctgtggctg     600
ctgctgccca gctggcccct ggccatgatg tggttcatca gcaccctggc cgagaccaac     660
cgcaccccct tcgacctggc cgagggcgag agcgagctgg tgagcggctt caacatcgag     720
tacgccgccg gccccttcgc cctgttcttc atggccgagt acaccaacat catcatgatg     780 aacacccctga ccaccaccat cttcctgggc accacctacg acgccctgag ccccgagctg     840 tacaccaccct acttcgtgac caagaccctg ctgctgacca gcctgttcct gtggatccgc     900 accgctacc cccgcttccg ctacgaccag ctgatgcacc tgctgtggaa gaacttcctg     960
cccctgaccc tggccctgct gatgtggtac gtgagcatgc ccatcaccat cagcagcatc    1020 ccccccagata cctaagagca ctgggacgcc caccgcccct ttccctccgc tgccaggcga    1080
gcatgttgtg gtaattctgg aacacaagaa gagaaattgc tgggtttaga caagattat    1140 aaacgaattc ggtgctcagt gatcacttga cagttttttt ttttttttaaa tattacccaa    1200 aatgctcccc aaataagaaa tgcatcagct cagtcagtga atacaaaaaa ggaattattt    1260
ttccctttga gggtctttta tacatctctc ctccaacccc ccctctatt ctgtttcttc    1320 ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca gccccgtcc tcccttcacc    1680 cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc caccccatta ctgtacctct ggagtcacta ctgtgggtcg    1860
```

-continued

| | |
|---|---|
| ccactcctct gctacacagc acggcttttt caaggctgta ttgagaaggg aagttaggaa | 1920 |
| gaagggtgtg ctgggctaac cagcccacag agctcacatt cctgtccctt gggtgaaaaa | 1980 |
| tacatgtcca tcctgatatc tcctgaattc agaaattagc ctccacatgt gcaatggctt | 2040 |
| taagagccag aagcagggtt ctgggaattt tgcaagttac ctgtggccag gtgtggtctc | 2100 |
| ggttaccaaa tacggttacc tgcagctttt tagtcctttg tgctcccacg ggtctacaga | 2160 |
| gtcccatctg cccaaaggtc ttgaagcttg acaggatgtt ttcgattact cagtctccca | 2220 |
| gggcactact ggtccgtagg attcgattgg tcggggtagg agagttaaac aacatttaaa | 2280 |
| cagagttctc tcaaaaatgt ctaaagggat tgtaggtaga taacatccaa tcactgtttg | 2340 |
| cacttatctg aaatcttccc tcttggctgc ccccaggtat ttactgtgga gaacattgca | 2400 |
| taggaatgtc tggaaaaagc ttctacaact tgttacagcc ttcacatttg tagaagcttt | 2460 |

<210> SEQ ID NO 28
<211> LENGTH: 1660
<212> TYPE: DNA
<213> ORGANISM: Artificial Sequence
<220> FEATURE:
<223> OTHER INFORMATION: COX10-opt_ND1-3'UTR*

<400> SEQUENCE: 28

| | |
|---|---|
| atggccgcat ctccgcacac tctctcctca cgcctcctga caggttgcgt aggaggctct | 60 |
| gtctggtatc ttgaaagaag aactatggcc aacctgctgc tgctgatcgt gcccatcctg | 120 |
| atcgccatgg ccttcctgat gctgaccgag cgcaagatcc tgggctacat gcagctgcgc | 180 |
| aagggcccca cgtggtgggc ccctacggc ctgctgcagc ccttcgccga cgccatcaag | 240 |
| ctgttcacca aggagcccct gaagcccgcc accagcacca tcaccctgta catcaccgcc | 300 |
| cccaccctgg ccctgaccat cgccctgctg ctgtggaccc cctgcccat gcccaacccc | 360 |
| ctggtgaacc tgaacctggg cctgctgttc atcctggcca ccagcagcct ggccgtgtac | 420 |
| agcatcctgt ggagcggctg ggccagcaac agcaactacg ccctgatcgg cgccctgcgc | 480 |
| gccgtggccc agaccatcag ctacgaggtg accctggcca tcatcctgct gagcaccctg | 540 |
| ctgatgagcg gcagcttcaa cctgagcacc ctgatcacca cccaggagca cctgtggctg | 600 |
| ctgctgccca gctggcccct ggccatgatg tggttcatca gcaccctggc cgagaccaac | 660 |
| cgcacccccc tcgacctggc cgagggcgag agcgagctgg tgagcggctt caacatcgag | 720 |
| tacgccgccg gcccctttcgc cctgttcttc atggccgagt acaccaacat catcatgatg | 780 |
| aacacccctga ccaccaccat cttcctgggc accacctacg acgccctgag ccccgagctg | 840 |
| tacaccacct acttcgtgac caagaccctg ctgctgacca gcctgttcct gtggatccgc | 900 |
| accgcctacc cccgcttccg ctacgaccag ctgatgcacc tgctgtggaa gaacttcctg | 960 |
| cccctgaccc tggccctgct gatgtggtac gtgagcatgc ccatcaccat cagcagcatc | 1020 |
| cccccccaga cctaagagca ctgggacgcc accgcccct ttccctccgc tgccaggcga | 1080 |
| gcatgttgtg gtaattctgg aacacaagaa gagaaattgc tgggtttaga acaagattat | 1140 |
| aaacgaattc ggtgctcagt gatcacttga cagttttttt tttttttaaa tattacccaa | 1200 |
| aatgctcccc aaataagaaa tgcatcagct cagtcagtga atacaaaaaa ggaattattt | 1260 |
| ttcccttttga gggtctttta tacatctctc ctccaacccc accctctatt ctgtttcttc | 1320 |
| ctcctcacat gggggtacac atacacagct tcctcttttg gttccatcct taccaccaca | 1380 |
| ccacacgcac actccacatg cccagcagag tggcacttgg tggccagaaa gtgtgagcct | 1440 |
| catgatctgc tgtctgtagt tctgtgagct caggtccctc aaaggcctcg agcaccccc | 1500 |

-continued

| | |
|---|---|
| ttccttgtga ctgagccagg gcctgcattt ttggttttcc ccaccccaca cattctcaac | 1560 |
| catagtcctt ctaacaatac caatagctag gacccggctg ctgtgcactg ggactgggga | 1620 |
| ttccacatgt ttgccttggg agtctcaagc tggactgcca | 1660 |

<210> SEQ ID NO 29
<211> LENGTH: 2889
<212> TYPE: DNA
<213> ORGANISM: Artificial Sequence
<220> FEATURE:
<223> OTHER INFORMATION: opt_COX10-ND4-3'UTR

<400> SEQUENCE: 29

| | |
|---|---|
| atggccgcct ctccacacac actgagtagc agactgctga ccggctgtgt tggcggctct | 60 |
| gtgtggtatc tggaacggcg gacaatgcta aaactaatcg tcccaacaat tatgttacta | 120 |
| ccactgacat ggcttttccaa aaaacacatg atttggatca acacaaccac ccacagccta | 180 |
| attattagca tcatccctct actatttttt aaccaaatca caacaaccct atttagctgt | 240 |
| tccccaacct tttcctccga ccccctaaca acccccctcc taatgctaac tacctggctc | 300 |
| ctaccctca caatcatggc aagccaacgc cacttatcca gtgaaccact atcacgaaaa | 360 |
| aaactctacc tctctatgct aatctcccta caaatctcct taattatgac attcacagcc | 420 |
| acagaactaa tcatgtttta tatcttcttc gaaaccacac ttatcccac cttggctatc | 480 |
| atcacccgat ggggcaacca gccagaacgc ctgaacgcag gcacatactt cctattctac | 540 |
| accctagtag gctcccttcc cctactcatc gcactaattt acactcacaa caccctaggc | 600 |
| tcactaaaca ttctactact cactctcact gcccaagaac tatcaaactc ctgggccaac | 660 |
| aacttaatgt ggctagctta cacaatggct tttatggtaa agatgcctct ttacggactc | 720 |
| cacttatggc tccctaaagc ccatgtcgaa gccccatcg ctgggtcaat ggtacttgcc | 780 |
| gcagtactct taaaactagg cggctatggt atgatgcgcc tcacactcat tctcaacccc | 840 |
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg ctttttggtg gcttctagca agcctcgcta acctcgcctt acccccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact caccccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgcccctt tcctccgct | 1500 |
| gccaggcgag catgttgtgg taattctgga acacaagaag agaaattgct gggtttagaa | 1560 |
| caagattata aacgaattcg gtgctcagtg atcacttgac agttttttttt tttttttaaat | 1620 |
| attcccaaa atgctcccca aataagaaat gcatcagctc agtcagtgaa tacaaaaaag | 1680 |
| gaattatttt tcccttttgag ggtcttttat acatctctcc tccaacccca ccctctattc | 1740 |
| tgtttcttcc tcctcacatg gggtacaca tacacagctt cctcttttgg ttccatcctt | 1800 |
| accaccacac cacacgcaca ctccacatgc ccagcagagt ggcacttggt ggccagaaag | 1860 |

```
tgtgagcctc atgatctgct gtctgtagtt ctgtgagctc aggtccctca aaggcctcgg    1920
agcaccccct tccttgtgac tgagccaggg cctgcatttt tggttttccc caccccacac    1980
attctcaacc atagtccttc taacaatacc aatagctagg acccggctgc tgtgcactgg    2040
gactggggat ccacatgtt tgccttggga gtctcaagct ggactgccag ccctgtcct     2100 cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                           2889

<210> SEQ ID NO 30
<211> LENGTH: 2089
<212> TYPE: DNA
<213> ORGANISM: Artificial Sequence
<220> FEATURE:
<223> OTHER INFORMATION: opt_COX10-ND4-3'UTR*

<400> SEQUENCE: 30
atggccgcct ctccacacac actgagtagc agactgctga ccggctgtgt tggcggctct      60
gtgtggtatc tggaacggcg gacaatgcta aaactaatcg tcccaacaat tatgttacta     120
ccactgacat ggcttcccaa aaaacacatg atttggatca acacaaccac ccacagccta     180
attattagca tcatccctct actatttttt aaccaaatca caacaaccct atttagctgt     240
tccccaacct tttcctccga ccccctaaca acccccctcc taatgctaac tacctggctc     300 ctaccctca caatcatggc aagccaacgc cacttatcca gtgaaccact atcacgaaaa     360
aaactctacc tctctatgct aatctcccta caaatctcct taattatgac attcacagcc     420
acagaactaa tcatgtttta tatcttcttc gaaaccacac ttatcccac ttggctatc      480 atcacccgat ggggcaacca gccagaacgc tgaacgcag gcacatactt cctattctac     540
accctagtag ctccccttcc cctactcatc gcactaattt acactcacaa cccctaggc      600 tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gccccatcg ctgggtcaat ggtacttgcc     780
gcagtactct taaaactagg cggctatggt atgatgcgcc tcacactcat tctcaacccc    840
ctgacaaaac acatggccta ccccttcctt gtactatccc tatggggcat gattatgaca    900
agctccatct gcctacgaca aacagaccta aaatcgctca ttgcatactc ttcaatcagc    960
cacatggccc tcgtagtaac agccattctc atccaaaccc cctggagctt caccggcgca   1020
```

```
gtcattctca tgatcgccca cgggcttaca tcctcattac tatttctgcct agcaaactca   1080 aactacgaac gcactcacag tcgcatcatg atcctctctc aaggacttca aactctactc   1140
ccactaatgg cttttttggtg gcttctagca agcctcgcta acctcgcctt acccccact   1200 attaacctac tgggagaact ctctgtgcta gtaaccacgt tctcctggtc aaatatcact   1260
ctcctactta caggactcaa catgctagtc acagccctat actccctcta catgtttacc   1320
acaacacaat ggggctcact cacccaccac attaacaaca tgaaaccctc attcacacga   1380
gaaaacaccc tcatgttcat gcacctatcc cccattctcc tcctatccct caaccccgac   1440
atcattaccg ggttttcctc ttaagagcac tgggacgccc accgcccctt tccctccgct   1500
gccaggcgag catgttgtgg taattctgga acacaagaag agaaattgct gggtttagaa   1560
caagattata aacgaattcg gtgctcagtg atcacttgac agttttttt ttttttaaat   1620 attacccaaa atgctcccca ataagaaat gcatcagctc agtcagtgaa tacaaaaaag   1680
gaattatttt tccctttgag ggtcttttat acatctctcc tccaacccca ccctctattc   1740
tgtttcttcc tcctcacatg ggggtacaca tacacagctt cctcttttgg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920 agcacccct tccttgtgac tgagccaggg cctgcatttt tggttttccc caccccacac   1980
attctcaacc atagtccttc taacaatacc aatagctagg acccggctgc tgtgcactgg   2040
gactggggat tccacatgtt tgccttggga gtctcaagct ggactgcca              2089
```

```
<210> SEQ ID NO 31
<211> LENGTH: 2889
<212> TYPE: DNA
<213> ORGANISM: Artificial Sequence
<220> FEATURE:
<223> OTHER INFORMATION: opt_COX10-opt_ND4-3'UTR

<400> SEQUENCE: 31
```

```
atggccgcct ctccacacac actgagtagc agactgctga ccggctgtgt tggcggctct     60
gtgtggtatc tggaacggcg gacaatgctg aagctgatcg tgcccaccat catgctgctg    120
cctctgacct ggctgagcaa gaaacacatg atctggatca acaccaccac gcacagcctg    180
atcatcagca tcatccctct gctgttcttc aaccagatca caacaacct gttcagctgc    240 agccccacct tcagcagcga ccctctgaca cacctctgc tgatgctgac cacctggctg    300 ctgccctca caatcatggc ctctcagaga cacctgagca gcgagcccct gagccggaag    360
aaactgtacc tgagcatgct gatctccctg cagatctctc tgatcatgac cttcaccgcc    420
accgagctga tcatgttcta catcttttc gagacaacgc tgatcccac actggccatc    480 atcaccagat ggggcaacca gcctgagaga ctgaacgccg gcacctactt tctgttctac    540
accctcgtgg gcagcctgcc actgctgatt gccctgatct acacccacaa cccctgggc    600 tccctgaaca tcctgctgct gacactgaca gcccaagagc tgagcaacag ctgggccaac    660
aatctgatgt ggctggccta cacaatggcc ttcatggtca agatgccct gtacggcctg    720 cacctgtggc tgcctaaagc tcatgtggaa gcccctatcg ccggctctat ggtgctggct    780
gcagtgctgc tgaaactcgg cggctacggc atgatgcggc tgaccctgat tctgaatccc    840
ctgaccaagc acatggccta tccatttctg gtgctgagcc tgtggggcat gattatgacc    900
agcagcatct gcctgcggca gaccgatctg aagtccctga tcgcctacag ctccatcagc    960
```

```
cacatggccc tggtggtcac cgccatcctg attcagaccc cttggagctt tacaggcgcc    1020
gtgatcctga tgattgccca cggcctgaca agcagcctgc tgttttgtct ggccaacagc    1080
aactacgagc ggacccacag cagaatcatg atcctgtctc agggcctgca gaccctcctg    1140
cctcttatgg cttttggtg gctgctggcc tctctggcca atctggcact gcctcctacc    1200
atcaatctgc tgggcgagct gagcgtgctg gtcaccacat tcagctggtc caatatcacc    1260
ctgctgctca ccggcctgaa catgctggtt acagccctgt actccctgta catgttcacc    1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgccctt tccctccgct    1500 gccaggcgag catgttgtgg taattctgga acacaagaag agaaattgct gggtttagaa    1560
caagattata aacgaattcg gtgctcagtg atcacttgac agtttttttt tttttttaaat    1620 attacccaaa atgctcccca aataagaaat gcatcagctc agtcagtgaa tacaaaaaag    1680
gaattatttt tcccttgag ggtctttat acatctctcc tccaaccca ccctctattc       1740 tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc cacccacac     1980 attctcaacc atagtccttc taacaatacc aatagctagg accggctgc tgtgcactgg     2040 gactggggat tccacatgtt tgccttggga gtctcaagct ggactgccag cccctgtcct    2100
cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc acccccattac tgtacctctg gagtcactac    2280
tgtgggtcgc cactcctctg ctacacagca cggctttttc aaggctgtat tgagaaggga    2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taaagggatt gtaggtagat aacatccaat    2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889
```

<210> SEQ ID NO 32
<211> LENGTH: 2089
<212> TYPE: DNA
<213> ORGANISM: Artificial Sequence
<220> FEATURE:
<223> OTHER INFORMATION: opt_COX10-opt_ND4-3'UTR*

<400> SEQUENCE: 32

```
atggccgcct ctccacacac actgagtagc agactgctga ccggctgtgt tggcggctct     60
gtgtggtatc tggaacggcg gacaatgctg aagctgatcg tgcccaccat catgctgctg    120
```

```
cctctgacct ggctgagcaa gaaacacatg atctggatca acaccaccac gcacagcctg      180
atcatcagca tcatccctct gctgttcttc aaccagatca acaacaacct gttcagctgc      240
agccccacct tcagcagcga ccctctgaca cacctctgc tgatgctgac cacctggctg      300
ctgcccctca caatcatggc ctctcagaga cacctgagca gcgagcccct gagccggaag      360
aaactgtacc tgagcatgct gatctccctg cagatctctc tgatcatgac cttcaccgcc      420
accgagctga tcatgttcta catcttttc gagacaacgc tgatcccac actggccatc      480 atcaccagat ggggcaacca gcctgagaga ctgaacgccg gcacctactt tctgttctac      540
accctcgtgg gcagcctgcc actgctgatt gccctgatct acacccacaa caccctgggc      600
tccctgaaca tcctgctgct gacactgaca gcccaagagc tgagcaacag ctgggccaac      660
aatctgatgt ggctggccta cacaatggcc ttcatggtca agatgcccct gtacggcctg      720
cacctgtggc tgcctaaagc tcatgtggaa gcccctatcg ccggctctat ggtgctggct      780
gcagtgctgc tgaaactcgg cggctacggg atgatgcggc tgaccctgat tctgaatccc      840
ctgaccaagc acatggccta tccatttctg gtgctgagcc tgtggggcat gattatgacc      900
agcagcatct gcctgcggca gaccgatctg aagtccctga tcgcctacag ctccatcagc      960
cacatggccc tggtggtcac cgccatcctg attcagaccc cttggagctt tacaggcgcc     1020
gtgatcctga tgattgccca cggcctgaca agcagcctgc tgttttgtct ggccaacagc     1080
aactacgagc ggacccacag cagaatcatg atcctgtctc agggcctgca gaccctcctg     1140
cctcttatgg cttttggtg gctgctggcc tctctggcca atctggcact gcctcctacc     1200
atcaatctgc tgggcgagct gagcgtgctg gtcaccacat tcagctggtc caatatcacc     1260
ctgctgctca ccggcctgaa catgctggtt acagccctgt actccctgta catgttcacc     1320
accacacagt gggaagcct gacacaccac atcaacaata tgaagcccag cttcacccgc     1380
gagaacaccc tgatgttcat gcatctgagc cccattctgc tgctgtccct gaatcctgat     1440
atcatcaccg gcttctccag ctgagagcac tgggacgccc accgcccctt tccctccgct     1500
gccaggcgag catgttgtgg taattctgga acacaagaag agaaattgct gggtttagaa     1560
caagattata acgaattcg gtgctcagtg atcacttgac agttttttt tttttaaat       1620 attacccaaa atgctcccca aataagaaat gcatcagctc agtcagtgaa tacaaaaaag     1680
gaattatttt tcccttgag ggtctttat acatctctcc tccaacccca ccctctattc      1740
tgtttcttcc tcctcacatg ggggtacaca tacacagctt cctcttttgg ttccatcctt     1800
accaccacac cacacgcaca ctccacatgc ccagcagagt ggcacttggt ggccagaaag     1860
tgtgagcctc atgatctgct gtctgtagtt ctgtgagctc aggtccctca aaggcctcgg     1920 agcacccct tccttgtgac tgagccaggg cctgcatttt tggttttccc caccccacac     1980
attctcaacc atagtccttc taacaatacc aatagctagg acccggctgc tgtgcactgg     2040
gactgtggat tccacatgtt tgccttggga gtctcaagct ggactgcca                2089

<210> SEQ ID NO 33
<211> LENGTH: 2889
<212> TYPE: DNA
<213> ORGANISM: Artificial Sequence
<220> FEATURE:
<223> OTHER INFORMATION: opt_COX10-opt_ND4*-3'UTR

<400> SEQUENCE: 33
atggccgcct ctccacacac actgagtagc agactgctga ccggctgtgt tggcggctct       60
```

```
gtgtggtatc tggaacggcg acaatgctg  aagctgatcg tgcccaccat catgctgctg    120
cccctgacct ggctgagcaa gaagcacatg atctggatca acaccaccac ccacagcctg    180
atcatcagca tcatccccct gctgttcttc aaccagatca caacaacct  gttcagctgc    240 agccccacct tcagcagcga ccccctgacc acccccctgc tgatgctgac cacctggctg    300
ctgcccctga ccatcatggc cagccagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatccccac cctggccatc    480
atcacccgct ggggcaacca gcccgagcgc ctgaacgccg gcacctactt cctgttctac    540
accctggtgg gcagcctgcc cctgctgatc gccctgatct acacccacaa cccctgggc    600 agcctgaaca tcctgctgct gaccctgacc gcccaggagc tgagcaacag ctgggccaac    660
aacctgatgt ggctggccta caccatggcc ttcatggtga gatgcccct  gtacggcctg    720 cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta cccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gccccccacc   1200
atcaacctgc tgggcgagct gagcgtgctg gtgaccacct tcagctggag caacatcacc   1260
ctgctgctga ccgcctgaa  catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
atcatcaccg gcttcagcag ctaagagcac tgggacgccc accgccccctt tccctccgct   1500 gccaggcgag catgttgtgg taattctgga acacaagaag agaaattgct gggtttagaa   1560
caagattata acgaattcg  gtgctcagtg atcacttgac agttttttt  tttttaaat    1620 attacccaaa atgctcccca ataagaaat  gcatcagctc agtcagtgaa tacaaaaaag   1680
gaattatttt tcccttgag  ggtcttttat acatctctcc tccaacccca ccctctattc   1740
tgtttcttcc tcctcacatg ggggtacaca tacacagctt cctctttggg ttccatcctt   1800
accaccacac cacacgcaca ctccacatgc ccagcagagt ggcacttggt ggccagaaag   1860
tgtgagcctc atgatctgct gtctgtagtt ctgtgagctc aggtccctca aaggcctcgg   1920
agcaccccct tccttgtgac tgagccaggg cctgcatttt tggttttccc caccccacac   1980
attctcaacc atagtccttc taacaatacc aatagctagg accggctgc  tgtgcactgg   2040 gactggggat tccacatgtt tgccttggga gtctcaagct ggactgccag cccctgtcct   2100
cccttcaccc ccattgcgta tgagcatttc agaactccaa ggagtcacag gcatctttat   2160
agttcacgtt aacatataga cactgttgga agcagttcct tctaaaaggg tagccctgga   2220
cttaatacca gccggatacc tctggccccc accccattac tgtacctctg gagtcactac   2280
tgtgggtcgc cactcctctg ctacacagca cggcttttc  aaggctgtat tgagaaggga   2340
agttaggaag aagggtgtgc tgggctaacc agccacagaa gctcacattc tgtcccttg    2400 ggtgaaaaat acatgtccat cctgatatct cctgaattca gaaattagcc tccacatgtg   2460
```

| | |
|---|---|
| caatggcttt aagagccaga agcagggttc tgggaatttt gcaagttacc tgtggccagg | 2520 |
| tgtggtctcg gttaccaaat acggttacct gcagctttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 34
<211> LENGTH: 2089
<212> TYPE: DNA
<213> ORGANISM: Artificial Sequence
<220> FEATURE:
<223> OTHER INFORMATION: opt_COX10-opt_ND4*-3'UTR*

<400> SEQUENCE: 34

| | |
|---|---|
| atggccgcct ctccacacac actgagtagc agactgctga ccggctgtgt tggcggctct | 60 |
| gtgtggtatc tggaacggcg gacaatgctg aagctgatcg tgcccaccat catgctgctg | 120 |
| cccctgacct ggctgagcaa gaagcacatg atctggatca acaccaccac ccacagcctg | 180 |
| atcatcagca tcatccccct gctgttcttc aaccagatca caacaaccct gttcagctgc | 240 |
| agccccacct tcagcagcga ccccctgacc accccctgc tgatgctgac cacctggctg | 300 |
| ctgcccctga ccatcatggc cagccagcgc cacctgagca gcgagcccct gagccgcaag | 360 |
| aagctgtacc tgagcatgct gatcagcctg cagatcagcc tgatcatgac cttcaccgcc | 420 |
| accgagctga tcatgttcta catcttcttc gagaccaccc tgatccccac cctggccatc | 480 |
| atcacccgct ggggcaacca gcccgagcgc ctgaacgccg gcacctactt cctgttctac | 540 |
| accctggtgg gcagcctgcc cctgctgatc gccctgatct acacccacaa caccctgggc | 600 |
| agcctgaaca tcctgctgct gaccctgacc gcccaggagc tgagcaacag ctgggccaac | 660 |
| aacctgatgt ggctggccta caccatggcc ttcatggtga agatgcccct gtacggcctg | 720 |
| cacctgtggc tgcccaaggc ccacgtggag gccccatcg ccggcagcat ggtgctggcc | 780 |
| gccgtgctgc tgaagctggg cggctacggc atgatgcgcc tgaccctgat cctgaacccc | 840 |
| ctgaccaagc acatggccta ccccttcctg gtgctgagcc tgtggggcat gatcatgacc | 900 |
| agcagcatct gcctgcgcca gaccgacctg aagagcctga tcgcctacag cagcatcagc | 960 |
| cacatggccc tggtggtgac cgccatcctg atccagaccc cctggagctt caccggcgcc | 1020 |
| gtgatcctga tgatcgccca cggcctgacc agcagcctgc tgttctgcct ggccaacagc | 1080 |
| aactacgagc gcacccacag ccgcatcatg atcctgagcc agggcctgca gaccctgctg | 1140 |
| cccctgatgg ccttctggtg gctgctggcc agcctggcca acctggccct gcccccacc | 1200 |
| atcaacctgc tgggcgagct gagcgtgctg gtgaccacct cagctggag caacatcacc | 1260 |
| ctgctgctga ccggcctgaa catgctggtg accgccctgt acagcctgta catgttcacc | 1320 |
| accacccagt ggggcagcct gacccaccac atcaacaaca tgaagcccag cttcacccgc | 1380 |
| gagaacaccc tgatgttcat gcacctgagc cccatcctgc tgctgagcct gaaccccgac | 1440 |
| atcatcaccg gcttcagcag ctaagagcac tgggacgccc accgcccctt tccctccgct | 1500 |
| gccaggcgag catgttgtgg taattctgga acacaagaag agaaattgct gggtttagaa | 1560 |

| | |
|---|---|
| caagattata aacgaattcg gtgctcagtg atcacttgac agtttttttt tttttttaaat | 1620 |
| attacccaaa atgctcccca aataagaaat gcatcagctc agtcagtgaa tacaaaaaag | 1680 |
| gaattatttt tcccttttgag ggtcttttat acatctctcc tccaacccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcaccccct tccttgtgac tgagccaggg cctgcatttt tggttttccc caccccacac | 1980 |
| attctcaacc atagtccttc taacaatacc aatagctagg accggctgc tgtgcactgg | 2040 |
| gactggggat tccacatgtt tgccttggga gtctcaagct ggactgcca | 2089 |

<210> SEQ ID NO 35
<211> LENGTH: 2034
<212> TYPE: DNA
<213> ORGANISM: Artificial Sequence
<220> FEATURE:
<223> OTHER INFORMATION: opt_COX10-ND6-3'UTR

<400> SEQUENCE: 35

| | |
|---|---|
| atggccgcct ctccacacac actgagtagc agactgctga ccggctgtgt tggcggctct | 60 |
| gtgtggtatc tggaacggcg gacaatgatg tatgctttgt ttctgttgag tgtgggttta | 120 |
| gtaatggggt ttgtggggtt ttcttctaag ccttctccta tttatggggg tttagtattg | 180 |
| attgttagcg gtgtggtcgg gtgtgttatt attctgaatt tggggggagg ttatatgggt | 240 |
| ttaatggttt ttttaatta tttagggga atgatggttg tctttggata tactacagcg | 300 |
| atggctattg aggagtatcc tgaggcatgg gggtcagggg ttgaggtctt ggtgagtgtt | 360 |
| ttagtggggt tagcgatgga ggtaggattg gtgctgtggg tgaaagagta tgatggggtg | 420 |
| gtggttgtgg taaactttaa tagtgtagga agctggatga tttatgaagg agagggtca | 480 |
| gggttgattc gggaggatcc tattggtgcg ggggctttgt atgattatgg gcgttggtta | 540 |
| gtagtagtta ctggttggac attgtttgtt ggtgtatata ttgtaattga gattgctcgg | 600 |
| gggaattagg agcactggga cgcccaccgc ccctttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac cccttcctt | 1080 |
| gtgactgagc cagggcctgc atttttggtt tccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctccctt cacccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg ccccaccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |

```
tccatcctga tatctcctga attcagaaat tagcctccac atgtgcaatg gctttaagag    1620
ccagaagcag ggttctggga attttgcaag ttacctgtgg ccaggtgtgg tctcggttac    1680
caaatacggt tacctgcagc ttttagtcc tttgtgctcc cacgggtcta cagagtccca    1740
tctgcccaaa ggtcttgaag cttgacagga tgttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgcccccag gtatttactg tggagaacat tgcataggaa    1980
tgtctggaaa aagcttctac aacttgttac agccttcaca tttgtagaag cttt          2034
```

<210> SEQ ID NO 36
<211> LENGTH: 1234
<212> TYPE: DNA
<213> ORGANISM: Artificial Sequence
<220> FEATURE:
<223> OTHER INFORMATION: opt_COX10-ND6-3'UTR*

<400> SEQUENCE: 36

```
atggccgcct ctccacacac actgagtagc agactgctga ccggctgtgt tggcggctct     60
gtgtggtatc tggaacggcg gacaatgatg tatgctttgt ttctgttgag tgtgggttta    120
gtaatggggt ttgtggggtt ttcttctaag ccttctccta tttatggggg tttagtattg    180
attgttagcg gtgtggtcgg gtgtgttatt attctgaatt ttggggagg ttatatgggt    240 ttaatggttt ttttaattta tttaggggga atgatggttg tctttggata tactacagcg    300
atggctattg aggagtatcc tgaggcatgg gggtcagggg ttgaggtctt ggtgagtgtt    360
ttagtggggt tagcgatgga ggtaggattg gtgctgtggg tgaaagagta tgatggggtg    420
gtggttgtgg taaactttaa tagtgtagga agctggatga tttatgaagg agagggtca    480 gggttgattc gggaggatcc tattggtgcg ggggctttgt atgattatgg gcgttggtta    540
gtagtagtta ctggttggac attgtttgtt ggtgtatata ttgtaattga gattgctcgg    600
gggaattagg agcactggga cgcccaccgc ccctttccct ccgctgccag gcgagcatgt    660
tgtggtaatt ctggaacaca agaagagaaa ttgctgggtt tagaacaaga ttataaacga    720
attcggtgct cagtgatcac ttgacagttt ttttttttt taaatattac ccaaaatgct    780
ccccaaataa gaaatgcatc agctcagtca gtgaatacaa aaaaggaatt attttttccct    840 ttgagggtct tttatacatc tctcctccaa ccccacccte tattctgttt cttcctcctc     900
acatgggggt acacatacac agcttcctct tttggttcca tccttaccac cacaccacac    960
gcacactcca catgcccagc agagtggcac ttggtggcca gaaagtgtga gcctcatgat    1020
ctgctgtctg tagttctgtg agctcaggtc cctcaaaggc ctcggagcac cccttcctt    1080 gtgactgagc cagggcctgc atttttggtt ttccccaccc cacacattct caaccatagt    1140
ccttctaaca ataccaatag ctaggacccg gctgctgtgc actgggactg gggattccac    1200
atgtttgcct tgggagtctc aagctggact gcca                                 1234
```

<210> SEQ ID NO 37
<211> LENGTH: 2034
<212> TYPE: DNA
<213> ORGANISM: Artificial Sequence
<220> FEATURE:
<223> OTHER INFORMATION: opt_COX10-opt_ND6-3'UTR

<400> SEQUENCE: 37

| | |
|---|---:|
| atggccgcct ctccacacac actgagtagc agactgctga ccggctgtgt tggcggctct | 60 |
| gtgtggtatc tggaacggcg gacaatgatg tacgccctgt tcctgctgag cgtgggcctg | 120 |
| gtgatgggct tcgtgggctt cagcagcaag cccagcccca tctacggcgg cctggtgctg | 180 |
| atcgtgagcg gcgtggtggg ctgcgtgatc atcctgaact tcggcggcgg ctacatgggc | 240 |
| ctgatggtgt tcctgatcta cctgggcggc atgatggtgg tgttcggcta caccaccgcc | 300 |
| atggccatcg aggagtaccc cgaggcctgg ggcagcggcg tggaggtgct ggtgagcgtg | 360 |
| ctggtgggcc tggccatgga ggtgggcctg gtgctgtggg tgaaggagta cgacggcgtg | 420 |
| gtggtggtgg tgaacttcaa cagcgtgggc agctggatga tctacgaggg cgagggcagc | 480 |
| ggcctgatcc gcgaggaccc catcggcgcc ggcgccctgt acgactacgg ccgctggctg | 540 |
| gtggtggtga ccggctggac cctgttcgtg ggcgtgtaca tcgtgatcga gatcgcccgc | 600 |
| ggcaactaag agcactggga cgcccaccgc cccttccct ccgctgccag gcgagcatgt | 660 |
| tgtggtaatt ctggaacaca agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccacccctc tattctgttt cttcctcctc | 900 |
| acatgggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctccctt cacccccatt | 1260 |
| gcgtatgagc atttcagaac tccaaggagt cacaggcatc tttatagttc acgttaacat | 1320 |
| atagacactg ttggaagcag ttccttctaa aagggtagcc ctggacttaa taccagccgg | 1380 |
| atacctctgg ccccaccccc attactgtac ctctggagtc actactgtgg gtcgccactc | 1440 |
| ctctgctaca cagcacggct ttttcaaggc tgtattgaga agggaagtta ggaagaaggg | 1500 |
| tgtgctgggc taaccagccc acagagctca cattcctgtc ccttgggtga aaaatacatg | 1560 |
| tccatcctga tatctcctga attcagaaat tagcctccac atgtgcaatg ctttaagag | 1620 |
| ccagaagcag ggttctggga attttgcaag ttacctgtgg ccaggtgtgg tctcggttac | 1680 |
| caaatacggt tacctgcagc ttttttagtcc tttgtgctcc cacgggtcta cagagtccca | 1740 |
| tctgcccaaa ggtcttgaag cttgacagga tgttttcgat tactcagtct cccagggcac | 1800 |
| tactggtccg taggattcga ttggtcgggg taggagagtt aaacaacatt taaacagagt | 1860 |
| tctctcaaaa atgtctaaag ggattgtagg tagataacat ccaatcactg tttgcactta | 1920 |
| tctgaaatct tccctcttgg ctgccccccag gtatttactg tggagaacat tgcataggaa | 1980 |
| tgtctggaaa aagcttctac aacttgttac agccttcaca tttgtagaag cttt | 2034 |

<210> SEQ ID NO 38
<211> LENGTH: 1234
<212> TYPE: DNA
<213> ORGANISM: Artificial Sequence
<220> FEATURE:
<223> OTHER INFORMATION: opt_COX10-opt_ND6-3'UTR*

<400> SEQUENCE: 38

| | |
|---|---:|
| atggccgcct ctccacacac actgagtagc agactgctga ccggctgtgt tggcggctct | 60 |

```
gtgtggtatc tggaacggcg acaatgatg tacgccctgt tcctgctgag cgtgggcctg      120
gtgatgggct tcgtgggctt cagcagcaag cccagcccca tctacggcgg cctggtgctg      180
atcgtgagcg gcgtggtggg ctgcgtgatc atcctgaact tcggcggcgg ctacatgggc      240
ctgatggtgt tcctgatcta cctgggcggc atgatggtgg tgttcggcta caccaccgcc      300
atggccatcg aggagtaccc cgaggcctgg ggcagcggcg tggaggtgct ggtgagcgtg      360
ctggtgggcc tggccatgga ggtgggcctg gtgctgtggg tgaaggagta cgacggcgtg      420
gtggtggtgg tgaacttcaa cagcgtgggc agctggatga tctacgaggg cgagggcagc      480
ggcctgatcc gcgaggaccc catcggcgcc ggcgccctgt acgactacgg ccgctggctg      540
gtggtggtga ccggctggac cctgttcgtg ggcgtgtaca tcgtgatcga gatcgcccgc      600
ggcaactaag agcactggga cgcccaccgc cccttccct ccgctgccag gcgagcatgt      660
tgtggtaatt ctggaacaca agaagagaaa ttgctgggtt tagaacaaga ttataaacga      720
attcggtgct cagtgatcac ttgacagttt tttttttttt taaatattac ccaaaatgct      780
ccccaaataa gaaatgcatc agctcagtca gtgaatacaa aaaggaatt attttttccct      840 ttgagggtct tttatacatc tctcctccaa ccccaccctc tattctgttt cttcctcctc      900 acatggggt acacatacac agcttcctct tttggttcca tccttaccac cacaccacac      960
gcacactcca catgcccagc agagtggcac ttggtggcca gaaagtgtga gcctcatgat      1020
ctgctgtctg tagttctgtg agctcaggtc cctcaaaggc ctcggagcac ccccttcctt      1080
gtgactgagc cagggcctgc attttttggtt ttccccaccc cacacattct caaccatagt      1140
ccttctaaca ataccaatag ctaggacccg gctgctgtgc actgggactg gggattccac      1200
atgtttgcct tgggagtctc aagctggact gcca                                  1234
```

<210> SEQ ID NO 39
<211> LENGTH: 2460
<212> TYPE: DNA
<213> ORGANISM: Artificial Sequence
<220> FEATURE:
<223> OTHER INFORMATION: opt_COX10-ND1-3'UTR

<400> SEQUENCE: 39

```
atggccgcct ctccacacac actgagtagc agactgctga ccggctgtgt tggcggctct       60
gtgtggtatc tggaacggcg acaatggcc aacctcctac tcctcattgt acccattcta      120
atcgcaatgg cattcctaat gcttaccgaa cgaaaaattc taggctatat gcaactacgc      180
aaaggcccca acgttgtagg cccctacggg ctactacaac ccttcgctga cgccataaaa      240
ctcttcacca aagagcccct aaaacccgcc acatctacca tcaccctcta catcaccgcc      300
ccgaccttag ctctcaccat cgctcttcta ctatggaccc cctcccccat gcccaacccc      360
ctggtcaacc tcaacctagg cctcctattt attctagcca cctctagcct agccgtttac      420
tcaatcctct ggtcagggtg ggcatcaaac tcaaactacg ccctgatcgg cgcactgcga      480
gcagtagccc aaacaatctc atatgaagtc accctagcca tcattctact atcaacatta      540
ctaatgagtg gctcctttaa cctctccacc cttatcacaa cacaagaaca cctctggtta      600
ctcctgccat catggccctt ggccatgatg tggtttatct ccacactagc agagaccaac      660
cgaaccccct tcgaccttgc cgaagggag tccgaactag tctcaggctt caacatcgaa      720
tacgccgcag gccccttcgc cctattcttc atggccgaat acacaaacat tattatgatg      780
aacaccctca ccactacaat cttcctagga acaacatatg acgcactctc ccctgaactc      840
```

```
tacacaacat attttgtcac caagacccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt   1020 cccctcaaa cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagttttttt tttttttaaa tattacccaa   1200
aatgctcccc aaataagaaa tgcatcagct cagtcagtga atacaaaaaa ggaattattt   1260 ttcccttga gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca gcccctgtcc tcccttcacc   1680
cccattgcgt atgagcattt cagaactcca aggagtcaca ggcatcttta tagttcacgt   1740
taacatatag acactgttgg aagcagttcc ttctaaaagg gtagccctgg acttaatacc   1800
agccggatac ctctggcccc cacccccatta ctgtacctct ggagtcacta ctgtgggtcg   1860
ccactcctct gctacacagc acggcttttt caaggctgta ttgagaaggg aagttaggaa   1920
gaagggtgtg ctgggctaac cagcccacag agctcacatt cctgtccctt gggtgaaaaa   1980
tacatgtcca tcctgatatc tcctgaattc agaaattagc ctccacatgt gcaatggctt   2040
taagagccag aagcagggtt ctgggaattt tgcaagttac ctgtggccag gtgtggtctc   2100
ggttaccaaa tacggttacc tgcagctttt tagtcctttg tgctcccacg ggtctacaga   2160
gtcccatctg cccaaaggtc ttgaagcttg acaggatgtt ttcgattact cagtctccca   2220
gggcactact ggtccgtagg attcgattgg tcggggtagg agagttaaac aacatttaaa   2280
cagagttctc tcaaaaatgt ctaaagggat tgtaggtaga taacatccaa tcactgtttg   2340
cacttatctg aaatcttccc tcttggctgc ccccaggtat ttactgtgga gaacattgca   2400
taggaatgtc tggaaaaagc ttctacaact tgttacagcc ttcacatttg tagaagcttt   2460
```

<210> SEQ ID NO 40
<211> LENGTH: 1660
<212> TYPE: DNA
<213> ORGANISM: Artificial Sequence
<220> FEATURE:
<223> OTHER INFORMATION: opt_COX10-ND1-3'UTR*

<400> SEQUENCE: 40

```
atggccgcct ctccacacac actgagtagc agactgctga ccggctgtgt tggcggctct     60
gtgtggtatc tggaacggcg acaatggcc aacctcctac tcctcattgt acccattcta    120
atcgcaatgg cattcctaat gcttaccgaa cgaaaaattc taggctatat gcaactacgc    180
aaaggcccca acgttgtagg cccctacggg ctactacaac ccttcgctga cgccataaaa    240
ctcttcacca aagagcccct aaaacccgcc acatctacca tcaccctcta catcaccgcc    300
ccgaccttag ctctcaccat cgctcttcta ctatggaccc cctcccccat gcccaacccc    360
ctggtcaacc tcaacctagg cctcctattt attctagcca cctctagcct agccgtttac    420
tcaatcctct ggtcagggtg ggcatcaaac tcaaactacg ccctgatcgg cgcactgcga    480
```

```
gcagtagccc aaacaatctc atatgaagtc accctagcca tcattctact atcaacatta    540
ctaatgagtg gctcctttaa cctctccacc cttatcacaa acaagaaaca cctctggtta    600
ctcctgccat catggccctt ggccatgatg tggtttatct ccacactagc agagaccaac    660
cgaacccccT tcgaccttgc cgaaggggag tccgaactag tctcaggctt caacatcgaa    720
tacgccgcag gccccttcgc cctattcttc atggccgaat acacaaacat tattatgatg    780
aacaccctca ccactacaat cttcctagga acaacatatg acgcactctc ccctgaactc    840
tacacaacat attttgtcac aagaccccta cttctaacct ccctgttctt atggattcga    900
acagcatacc cccgattccg ctacgaccaa ctcatgcacc tcctatggaa aaacttccta    960
ccactcaccc tagcattact tatgtggtat gtctccatgc ccattacaat ctccagcatt   1020 cccctcaaa cctaagagca ctgggacgcc caccgcccct ttccctccgc tgccaggcga   1080
gcatgttgtg gtaattctgg aacacaagaa gagaaattgc tgggtttaga acaagattat   1140
aaacgaattc ggtgctcagt gatcacttga cagtttttt tttttttaaa tattacccaa   1200
aatgctcccc aaataagaaa tgcatcagct cagtcagtga atacaaaaaa ggaattattt   1260 ttcccttga gggtcttta tacatctctc ctccaacccc accctctatt ctgtttcttc   1320
ctcctcacat gggggtacac atacacagct tcctcttttg gttccatcct taccaccaca   1380
ccacacgcac actccacatg cccagcgaga tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcatt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca                          1660

<210> SEQ ID NO 41
<211> LENGTH: 2460
<212> TYPE: DNA
<213> ORGANISM: Artificial Sequence
<220> FEATURE:
<223> OTHER INFORMATION: opt_COX10-opt_ND1-3'UTR

<400> SEQUENCE: 41
atggccgcct ctccacacac actgagtagc agactgctga ccggctgtgt tggcggctct     60
gtgtggtatc tggaacggcg gacaatggcc aacctgctgc tgctgatcgt gcccatcctg    120
atcgccatgg ccttcctgat gctgaccgag cgcaagatcc tgggctacat gcagctgcgc    180
aagggcccca acgtggtggg ccCCtacggc ctgctgcagc ccttcgccga cgccatcaag    240
ctgttcacca aggagcccct gaagcccgcc accagcacca tcaccctgta catcaccgcc    300 ccaccctgg ccctgaccat cgccctgctg ctgtggaccc cctgcccat gccaaccccc    360 ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
gccgtggccc agaccatcag ctacgaggtg accctggcca tcatcctgct gagcacCctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660
cgcaccccct tcgacctggc cgagggcgag agcgagctgg tgagcggctt caacatcgag    720
tacgccgccg gccccttcgc cctgttcttc atggccgagt acaccaacat catcatgatg    780
aacacCCtga ccaccaccat cttcctgggc accacctacg acgccctgag ccccgagctg    840
```

```
tacaccacct acttcgtgac caagaccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020
cccccccaga cctaagagca ctgggacgcc accgcccct ttccctccgc tgccaggcga    1080
gcatgttgtg gtaattctgg aacacaagaa gagaaattgc tgggtttaga acaagattat   1140
aaacgaattc ggtgctcagt gatcacttga cagttttttt ttttttttaaa tattacccaa   1200 aatgctcccc aaataagaaa tgcatcagct cagtcagtga atacaaaaaa ggaattattt   1260 ttcccttga gggtctttta tacatctctc ctccaacccc accctctatt ctgtttcttc    1320
ctcctcacat gggggtacac atacacagct tcctcttttg gttccatcct taccaccaca   1380
ccacacgcac actccacatg cccagcgagg tggcacttgg tggccagaaa gtgtgagcct   1440
catgatctgc tgtctgtagt tctgtgagct caggtccctc aaaggcctcg gagcacccc    1500 ttccttgtga ctgagccagg gcctgcattt ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca gccctgtcc tcccttcacc    1680 cccattgcgt atgagcattt cagaactcca aggagtcaca ggcatcttta tagttcacgt   1740
taacatatag acactgttgg aagcagttcc ttctaaaagg gtagccctgg acttaatacc   1800
agccggatac ctctggcccc caccccatta ctgtacctct ggagtcacta ctgtgggtcg   1860
ccactcctct gctacacagc acggcttttt caaggctgta ttgagaaggg aagttaggaa   1920
gaagggtgtg ctgggctaac cagcccacag agctcacatt cctgtccctt gggtgaaaaa   1980
tacatgtcca tcctgatatc tcctgaattc agaaattagc ctccacatgt gcaatggctt   2040
taagagccag aagcagggtt ctgggaattt tgcaagttac ctgtggccag gtgtggtctc   2100
ggttaccaaa tacggttacc tgcagctttt tagtcctttg tgctcccacg ggtctacaga   2160
gtcccatctg cccaaaggtc ttgaagcttg acaggatgtt ttcgattact cagtctccca   2220
gggcactact ggtccgtagg attcgattgg tcggggtagg agagttaaac aacatttaaa   2280
cagagttctc tcaaaaatgt ctaaagggat tgtaggtaga taacatccaa tcactgtttg   2340
cacttatctg aaatcttccc tcttggctgc ccccaggtat ttactgtgga gaacattgca   2400
taggaatgtc tggaaaaagc ttctacaact tgttacagcc ttcacatttg tagaagcttt   2460
```

<210> SEQ ID NO 42
<211> LENGTH: 1660
<212> TYPE: DNA
<213> ORGANISM: Artificial Sequence
<220> FEATURE:
<223> OTHER INFORMATION: opt_COX10-opt_ND1-3'UTR*

<400> SEQUENCE: 42

```
atggccgcct ctccacacac actgagtagc agactgctga ccggctgtgt tggcggctct     60
gtgtggtatc tggaacggcg gacaatggcc aacctgctgc tgctgatcgt gcccatcctg    120
atcgccatgg ccttcctgat gctgaccgag cgcaagatcc tgggctacat gcagctgcgc    180
aagggcccca acgtggtggg ccctacggc ctgctgcagc ccttcgccga cgccatcaag     240
ctgttcacca aggagcccct gaagcccgcc accagcacca tcaccctgta catcaccgcc    300
cccaccctgg ccctgaccat cgccctgctg ctgtggaccc cctgcccat gccaacccc     360 ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
```

```
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660 cgcacccct  tcgacctggc cgagggcgag agcgagctgg tgagcggctt caacatcgag    720
tacgccgccg gccccttcgc cctgttcttc atggccgagt acaccaacat catcatgatg    780
aacaccctga ccaccaccat cttcctgggc accacctacg acgccctgag ccccgagctg    840
tacaccacct acttcgtgac caagaccctg ctgctgacca gcctgttcct gtggatccgc    900
accgcctacc cccgcttccg ctacgaccag ctgatgcacc tgctgtggaa gaacttcctg    960
cccctgaccc tggccctgct gatgtggtac gtgagcatgc ccatcaccat cagcagcatc   1020 ccccccccaga cctaagagca ctgggacgcc caccgcccct tccctccgc  tgccaggcga   1080 gcatgttgtg gtaattctgg aacacaagaa gagaaattgc tgggtttaga caagattat    1140 aaacgaattc ggtgctcagt gatcacttga cagttttttt ttttttttaaa tattacccaa   1200 aatgctcccc aaataagaaa tgcatcagct cagtcagtga atacaaaaaa ggaattattt   1260 ttcccttga  gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcacccc    1500 ttccttgtga ctgagccagg gcctgcatt  ttggttttcc ccaccccaca cattctcaac   1560
catagtcctt ctaacaatac caatagctag gacccggctg ctgtgcactg ggactgggga   1620
ttccacatgt ttgccttggg agtctcaagc tggactgcca                         1660
```

<210> SEQ ID NO 43
<211> LENGTH: 2889
<212> TYPE: DNA
<213> ORGANISM: Artificial Sequence
<220> FEATURE:
<223> OTHER INFORMATION: opt_COX10*-ND4-3'UTR

<400> SEQUENCE: 43

```
atggccgcca gccccacac  cctgagcagc cgcctgctga ccggctgcgt gggcggcagc     60
gtgtggtacc tggagcgccg caccatgcta aaactaatcg tcccaacaat tatgttacta    120
ccactgacat ggcttcccaa aaaacacatg atttggatca acacaaccac ccacagccta    180
attattagca tcatccctct actattttt  aaccaaatca caacaaccct atttagctgt    240
tccccaacct tttcctccga ccccctaaca acccccctcc taatgctaac tacctggctc    300
ctacccctca caatcatggc aagccaacgc acttatccag gtgaaccact atcacgaaaa    360
aaactctacc tctctatgct aatctcccta caaatctcct aattatgac  attcacagcc    420 acagaactaa tcatgtttta tatcttcttc gaaaccacac ttatcccac  cttggctatc    480 atcacccgat ggggcaacca gccagaacgc ctgaacgcag gcacatactt cctattctac    540
accctagtag gctcccttcc cctactcatc gcactaattt acactcacaa cccctaggc    600 tcactaaaca ttctactact cactctcact gcccaagaac tatcaaactc ctgggccaac    660
aacttaatgt ggctagctta cacaatggct tttatggtaa agatgcctct ttacggactc    720
cacttatggc tccctaaagc ccatgtcgaa gcccccatcg ctgggtcaat ggtacttgcc    780
gcagtactct taaaactagg cggctatggt atgatgcgcc tcacactcat tctcaacccc    840
```

| | |
|---|---|
| ctgacaaaac acatggccta ccccttcctt gtactatccc tatggggcat gattatgaca | 900 |
| agctccatct gcctacgaca aacagaccta aaatcgctca ttgcatactc ttcaatcagc | 960 |
| cacatggccc tcgtagtaac agccattctc atccaaaccc cctggagctt caccggcgca | 1020 |
| gtcattctca tgatcgccca cgggcttaca tcctcattac tattctgcct agcaaactca | 1080 |
| aactacgaac gcactcacag tcgcatcatg atcctctctc aaggacttca aactctactc | 1140 |
| ccactaatgg cttttggtg gcttctagca agcctcgcta acctcgcctt accccccact | 1200 |
| attaacctac tgggagaact ctctgtgcta gtaaccacgt tctcctggtc aaatatcact | 1260 |
| ctcctactta caggactcaa catgctagtc acagccctat actccctcta catgtttacc | 1320 |
| acaacacaat ggggctcact cacccaccac attaacaaca tgaaaccctc attcacacga | 1380 |
| gaaaacaccc tcatgttcat gcacctatcc cccattctcc tcctatccct caaccccgac | 1440 |
| atcattaccg ggttttcctc ttaagagcac tgggacgccc accgccctt tcctccgct | 1500 |
| gccaggcgag catgttgtgg taattctgga acacaagaag agaaattgct gggtttagaa | 1560 |
| caagattata aacgaattcg gtgctcagtg atcacttgac agttttttt tttttaaat | 1620 |
| attacccaaa atgctcccca aataagaaat gcatcagctc agtcagtgaa tacaaaaaag | 1680 |
| gaattatttt tcccttgag ggtcttttat acatctctcc tccaaccccca ccctctattc | 1740 |
| tgtttcttcc tcctcacatg ggggtacaca tacacagctt cctcttttgg ttccatcctt | 1800 |
| accaccacac cacacgcaca ctccacatgc ccagcagagt ggcacttggt ggccagaaag | 1860 |
| tgtgagcctc atgatctgct gtctgtagtt ctgtgagctc aggtccctca aaggcctcgg | 1920 |
| agcacccct tccttgtgac tgagccaggg cctgcatttt tggttttccc caccccacac | 1980 |
| attctcaacc atagtccttc taacaatacc aatagctagg acccggctgc tgtgcactgg | 2040 |
| gactggggat tccacatgtt tgccttggga gtctcaagct ggactgccag ccctgtcct | 2100 |
| cccttcaccc ccattgcgta tgagcatttc agaactccaa ggagtcacag gcatctttat | 2160 |
| agttcacgtt aacatataga cactgttgga agcagttcct tctaaaaggg tagccctgga | 2220 |
| cttaatacca gccggatacc tctggccccc accccattac tgtacctctg gagtcactac | 2280 |
| tgtgggtcgc cactcctctg ctacacagca cggcttttc aaggctgtat tgagaaggga | 2340 |
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagctttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 44
<211> LENGTH: 2089
<212> TYPE: DNA
<213> ORGANISM: Artificial Sequence
<220> FEATURE:
<223> OTHER INFORMATION: opt_COX10*-ND4-3'UTR*

<400> SEQUENCE: 44

```
atggccgcca gcccccacac cctgagcagc cgcctgctga ccggctgcgt gggcggcagc      60
gtgtggtacc tggagcgccg caccatgcta aaactaatcg tcccaacaat tatgttacta     120
ccactgacat ggcttccaa aaacacatg atttggatca acacaaccac ccacagccta      180
attattagca tcatccctct actatttttt aaccaaatca caacaaccct atttagctgt     240
tccccaacct tttcctccga ccccctaaca accccctcc taatgctaac tacctggctc      300
ctacccctca caatcatggc aagccaacgc acttatccga gtgaaccact atcacgaaaa     360
aaactctacc tctctatgct aatctcccta caaatctcct taattatgac attcacagcc     420
acagaactaa tcatgtttta tatcttcttc gaaaccacac ttatccccac cttggctatc     480
atcacccgat ggggcaacca gccagaacgc ctgaacgcag gcacatactt cctattctac     540
accctagtag ctccccttcc cctactcatc gcactaattt acactcacaa cccctaggc      600
tcactaaaca ttctactact cactctcact gcccaagaac tatcaaactc ctgggccaac     660
aacttaatgt ggctagctta cacaatggct tttatggtaa agatgcctct ttacggactc     720
cacttatggc tccctaaagc ccatgtcgaa gcccccatcg ctgggtcaat ggtacttgcc     780
gcagtactct taaaactagg cggctatggt atgatgcgcc tcacactcat tctcaaccc     840
ctgacaaaac acatggccta ccccttcctt gtactatccc tatggggcat gattatgaca     900
agctccatct gcctacgaca aacagaccta aaatcgctca ttgcatactc ttcaatcagc     960
cacatggccc tcgtagtaac agccattctc atccaaaccc cctggagctt caccggcgca    1020
gtcattctca tgatcgccca cgggcttaca tcctcattac tattctgcct agcaaactca    1080
aactacgaac gcactcacag tcgcatcatg atcctctctc aaggacttca aactctactc    1140
ccactaatgg cttttttggtg gcttctagca agcctcgcta acctcgcctt acccccccact    1200
attaacctac tgggagaact ctctgtgcta gtaaccacgt tctcctggtc aaatatcact    1260
ctcctactta caggactcaa catgctagtc acagccctat actccctcta catgtttacc    1320
acaacacaat ggggctcact cacccaccac attaacaaca tgaaaccctc attcacacga    1380
gaaaacaccc tcatgttcat gcacctatcc cccattctcc tcctatccct caaccccgac    1440
atcattaccg ggttttcctc ttaagagcac tgggacgccc accgccctt tccctccgct     1500
gccaggcgag catgttgtgg taattctgga acacaagaag agaaattgct gggtttagaa    1560
caagattata aacgaattcg gtgctcagtg atcacttgac agtttttttt tttttttaaat    1620
attacccaaa atgctcccca aataagaaat gcatcagctc agtcagtgaa tacaaaaaag    1680
gaattatttt tcccttgag ggtcttttat acatctctcc tccaacccca ccctctattc     1740
tgtttcttcc tcctcacatg ggggtacaca tacacagctt cctctttgg ttccatcctt      1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggttttccc cacccccac     1980
attctcaacc atagtccttc taacaatacc aatagctagg acccggctgc tgtgcactgg    2040
gactggggat tccacatgtt tgccttggga gtctcaagct ggactgcca                2089
```

<210> SEQ ID NO 45
<211> LENGTH: 2889
<212> TYPE: DNA
<213> ORGANISM: Artificial Sequence
<220> FEATURE:
<223> OTHER INFORMATION: opt_COX10*-opt_ND4-3'UTR

```
<400> SEQUENCE: 45
atggccgcca gccccacac cctgagcagc cgcctgctga ccggctgcgt gggcggcagc      60
gtgtggtacc tggagcgccg caccatgctg aagctgatcg tgcccaccat catgctgctg     120
cctctgacct ggctgagcaa gaaacacatg atctggatca acaccaccac gcacagcctg     180
atcatcagca tcatccctct gctgttcttc aaccagatca caacaaccct gttcagctgc     240
agccccacct tcagcagcga ccctctgaca cacctctgc tgatgctgac cacctggctg      300
ctgcccctca caatcatggc ctctcagaga cacctgagca gcgagcccct gagccggaag     360
aaactgtacc tgagcatgct gatctccctg cagatctctc tgatcatgac cttcaccgcc     420
accgagctga tcatgttcta catctttttc gagacaacgc tgatccccac actggccatc     480
atcaccagat ggggcaacca gcctgagaga ctgaacgccg gcacctactt tctgttctac     540
accctcgtgg gcagcctgcc actgctgatt gccctgatct acacccacaa caccctgggc     600
tccctgaaca tcctgctgct gacactgaca gcccaagagc tgagcaacag ctgggccaac     660
aatctgatgt ggctggccta cacaatggcc ttcatggtca gatgcccct gtacggcctg      720
cacctgtggc tgcctaaagc tcatgtggaa gcccctatcg ccggctctat ggtgctggct     780
gcagtgctgc tgaaactcgg cggctacggc atgatgcggc tgaccctgat tctgaatccc     840
ctgaccaagc acatggccta tccatttctg gtgctgagcc tgtggggcat gattatgacc     900
agcagcatct gcctgcggca gaccgatctg aagtccctga tcgcctacag ctccatcagc     960
cacatggccc tggtggtcac cgccatcctg attcagaccc cttggagctt acaggcgcc     1020
gtgatcctga tgattgccca cggcctgaca agcagcctgc tgttttgtct ggccaacagc    1080
aactacgagc ggacccacag cagaatcatg atcctgtctc agggcctgca gaccctcctg    1140
cctcttatgc cttttggtg gctgctggcc tctctggcca atctggcact gcctcctacc     1200
atcaatctgc tgggcgagct gagcgtgctg gtcaccacat tcagctggtc caatatcacc    1260
ctgctgctca ccgcctgaa catgctggtt acagccctgt actccctgta catgttcacc     1320
accacacagt ggggaagcct gacacaccac atcaacaata tgaagcccag cttcacccgc    1380
gagaacaccc tgatgttcat gcatctgagc cccattctgc tgctgtccct gaatcctgat    1440
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata acgaattcg gtgctcagtg atcacttgac agttttttt ttttttaaat      1620
attacccaaa atgctcccca ataagaaat gcatcagctc agtcagtgaa tacaaaaaag     1680
gaattatttt tcccctttgag ggtctttttat acatctctcc tccaaccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920
agcaccccct tccttgtgac tgagccaggg cctgcatttt tggtttcccc caccccacac    1980
attctcaacc atagtccttc taacaatacc aatagctagg accggctgc tgtgcactgg     2040
gactggggat tccacatgtt tgccttggga gtctcaagct ggactgccag ccctgtcct    2100
cccttcaccc ccattgcgta tgagcatttc agaactccaa ggagtcacag gcatctttat    2160
agttcacgtt aacatataga cactgttgga agcagttcct tctaaaaggg tagccctgga    2220
cttaatacca gccggatacc tctggccccc acccattac tgtacctctg gagtcactac     2280
tgtgggtcgc cactcctctg ctacacagca cggcttttc aaggctgtat tgagaaggga     2340
```

| | |
|---|---|
| agttaggaag aagggtgtgc tgggctaacc agcccacaga gctcacattc ctgtcccttg | 2400 |
| ggtgaaaaat acatgtccat cctgatatct cctgaattca gaaattagcc tccacatgtg | 2460 |
| caatggcttt aagagccaga agcagggttc tgggaatttt gcaagttacc tgtggccagg | 2520 |
| tgtggtctcg gttaccaaat acggttacct gcagctttt agtcctttgt gctcccacgg | 2580 |
| gtctacagag tcccatctgc ccaaaggtct tgaagcttga caggatgttt tcgattactc | 2640 |
| agtctcccag ggcactactg gtccgtagga ttcgattggt cggggtagga gagttaaaca | 2700 |
| acatttaaac agagttctct caaaaatgtc taaagggatt gtaggtagat aacatccaat | 2760 |
| cactgtttgc acttatctga aatcttccct cttggctgcc cccaggtatt tactgtggag | 2820 |
| aacattgcat aggaatgtct ggaaaaagct tctacaactt gttacagcct tcacatttgt | 2880 |
| agaagcttt | 2889 |

<210> SEQ ID NO 46
<211> LENGTH: 2089
<212> TYPE: DNA
<213> ORGANISM: Artificial Sequence
<220> FEATURE:
<223> OTHER INFORMATION: opt_COX10*-opt_ND4-3'UTR*

<400> SEQUENCE: 46

| | |
|---|---|
| atggccgcca gccccacac cctgagcagc cgcctgctga ccggctgcgt gggcggcagc | 60 |
| gtgtggtacc tggagcgccg caccatgctg aagctgatcg tgcccaccat catgctgctg | 120 |
| cctctgacct ggctgagcaa gaaacacatg atctggatca acaccaccac gcacagcctg | 180 |
| atcatcagca tcatccctct gctgttcttc aaccagatca caacaaccct gttcagctgc | 240 |
| agccccacct tcagcagcga ccctctgaca acacctctgc tgatgctgac cacctggctg | 300 |
| ctgcccctca caatcatggc ctctcagaga cacctgagca gcgagcccct gagccggaag | 360 |
| aaactgtacc tgagcatgct gatctccctg cagatctctc tgatcatgac cttcaccgcc | 420 |
| accgagctga tcatgttcta catctttttc gagacaacgc tgatccccac actggccatc | 480 |
| atcaccagat ggggcaacca gcctgagaga ctgaacgccg gcacctactt tctgttctac | 540 |
| accctcgtgg gcagcctgcc actgctgatt gccctgatca cacccacaa cacccctgggc | 600 |
| tccctgaaca tcctgctgct gacactgaca gcccaagagc tgagcaacag ctgggccaac | 660 |
| aatctgatgt ggctggccta cacaatggcc ttcatggtca agatgcccct gtacggcctg | 720 |
| cacctgtggc tgcctaaagc tcatgtggaa gcccctatcg ccggctctat ggtgctggct | 780 |
| gcagtgctgc tgaaactcgg cggctacggc atgatgcggc tgaccctgat tctgaatccc | 840 |
| ctgaccaagc acatggccta tccatttctg gtgctgagcc tgtggggcat gattatgacc | 900 |
| agcagcatct gcctgcggca gaccgatctg aagtccctga tcgcctacag ctccatcagc | 960 |
| cacatggccc tggtggtcac cgccatcctg attcagaccc cttggagctt tacaggcgcc | 1020 |
| gtgatcctga tgattgccca cggcctgaca agcagcctgc tgttttgtct ggccaacagc | 1080 |
| aactacgagc ggacccacag cagaatcatg atcctgtctc agggcctgca gaccctcctg | 1140 |
| cctcttatgg cttttggtg gctgctggcc tctctggcca atctggcact gcctcctacc | 1200 |
| atcaatctgc tgggcgagct gagcgtgctg gtcaccacat tcagctggtc caatatcacc | 1260 |
| ctgctgctca ccggcctgaa catgctggtt acagccctgt actccctgta catgttcacc | 1320 |
| accacacagt ggggaagcct gacacaccac atcaacaata tgaagcccag cttcacccgc | 1380 |
| gagaacaccc tgatgttcat gcatctgagc cccattctgc tgctgtccct gaatcctgat | 1440 |

```
atcatcaccg gcttctccag ctgagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agttttttt ttttttaaat     1620 attacccaaa atgctcccca aataagaaat gcatcagctc agtcagtgaa tacaaaaaag    1680
gaattatttt tcccttgag ggtcttttat acatctctcc tccaacccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc cacccacac     1980 attctcaacc atagtccttc taacaatacc aatagctagg accggctgc tgtgcactgg    2040 gactggggat tccacatgtt tgccttggga gtctcaagct ggactgcca                2089

<210> SEQ ID NO 47
<211> LENGTH: 2889
<212> TYPE: DNA
<213> ORGANISM: Artificial Sequence
<220> FEATURE:
<223> OTHER INFORMATION: opt_COX10*-opt_ND4*-3'UTR

<400> SEQUENCE: 47
atggccgcca gccccacac cctgagcagc cgcctgctga ccggctgcgt gggcggcagc      60
gtgtggtacc tggagcgccg caccatgctg aagctgatcg tgcccaccat catgctgctg    120
cccctgacct ggctgagcaa gaagcacatg atctggatca caccaccac ccacagcctg    180 atcatcagca tcatcccct gctgttcttc aaccagatca caacaacct gttcagctgc     240 agccccacct tcagcagcga ccccctgacc acccccctgc tgatgctgac cacctggctg    300
ctgcccctga ccatcatggc cagccagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatccccac cctggccatc    480
atcacccgct ggggcaacca gcccgagcgc ctgaacgccg gcacctactt cctgttctac    540
accctggtgg gcagcctgcc cctgctgatc gccctgatct acacccacaa caccctgggc    600
agcctgaaca tcctgctgct gaccctgacc gcccaggagc tgagcaacag ctgggccaac    660
aacctgatgt ggctggccta caccatggcc ttcatggtga agatgccct gtacggcctg    720 cacctgtggc tgcccaaggc ccacgtggag gcccccatcg ccggcagcat ggtgctggcc    780
gccgtgctgc tgaagctggg cggctacggc atgatgcgcc tgaccctgat cctgaacccc    840
ctgaccaagc acatggccta ccccttcctg gtgctgagcc tgtggggcat gatcatgacc    900
agcagcatct gcctgcgcca gaccgacctg aagagcctga tcgcctacag cagcatcagc    960
cacatggccc tggtggtgac cgccatcctg atccagaccc cctggagctt caccggcgcc   1020
gtgatcctga tgatcgccca cggcctgacc agcagcctgc tgttctgcct ggccaacagc   1080
aactacgagc gcacccacag ccgcatcatg atcctgagcc agggcctgca gaccctgctg   1140
cccctgatgg ccttctggtg gctgctggcc agcctggcca acctggccct gccccccacc   1200
atcaacctgc tgggcgagct gagcgtgctg gtgaccacct cagctggag caacatcacc   1260 ctgctgctga ccggcctgaa catgctggtg accgccctgt acagcctgta catgttcacc   1320
accacccagt ggggcagcct gacccaccac atcaacaaca tgaagcccag cttcacccgc   1380
gagaacaccc tgatgttcat gcacctgagc cccatcctgc tgctgagcct gaaccccgac   1440
```

```
atcatcaccg gcttcagcag ctaagagcac tgggacgccc accgcccctt tccctccgct    1500
gccaggcgag catgttgtgg taattctgga acacaagaag agaaattgct gggtttagaa    1560
caagattata aacgaattcg gtgctcagtg atcacttgac agttttttt tttttaaat     1620 attacccaaa atgctcccca aataagaaat gcatcagctc agtcagtgaa tacaaaaaag    1680
gaattatttt tcccttgag ggtcttttat acatctctcc tccaacccca ccctctattc    1740
tgtttcttcc tcctcacatg ggggtacaca tacacagctt cctcttttgg ttccatcctt    1800
accaccacac cacacgcaca ctccacatgc ccagcagagt ggcacttggt ggccagaaag    1860
tgtgagcctc atgatctgct gtctgtagtt ctgtgagctc aggtccctca aaggcctcgg    1920 agcacccct tccttgtgac tgagccaggg cctgcatttt tggttttccc caccccacac     1980
attctcaacc atagtccttc taacaatacc aatagctagg acccggctgc tgtgcactgg    2040
gactggggat tccacatgtt tgccttggga gtctcaagct ggactgccag cccctgtcct    2100
cccttcaccc ccattgcgta tgagcatttc agaactccaa ggagtcacag gcatctttat    2160
agttcacgtt aacatataga cactgttgga agcagttcct tctaaagggg tagccctgga    2220
cttaatacca gccggatacc tctggccccc accccattac tgtacctctg gagtcactac    2280
tgtgggtcgc cactcctctg ctacacagca cggcttttc aaggctgtat tgagaaggga     2340
agttaggaag aagggtgtgc tgggctaacc agcccacaga gctcacattc ctgtcccttg    2400
ggtgaaaaat acatgtccat cctgatatct cctgaattca gaaattagcc tccacatgtg    2460
caatggcttt aagagccaga agcagggttc tgggaatttt gcaagttacc tgtggccagg    2520
tgtggtctcg gttaccaaat acggttacct gcagcttttt agtcctttgt gctcccacgg    2580
gtctacagag tcccatctgc ccaaaggtct tgaagcttga caggatgttt tcgattactc    2640
agtctcccag ggcactactg gtccgtagga ttcgattggt cggggtagga gagttaaaca    2700
acatttaaac agagttctct caaaaatgtc taagggatt gtaggtagat aacatccaat     2760
cactgtttgc acttatctga aatcttccct cttggctgcc cccaggtatt tactgtggag    2820
aacattgcat aggaatgtct ggaaaaagct tctacaactt gttacagcct tcacatttgt    2880
agaagcttt                                                            2889
```

<210> SEQ ID NO 48
<211> LENGTH: 2089
<212> TYPE: DNA
<213> ORGANISM: Artificial Sequence
<220> FEATURE:
<223> OTHER INFORMATION: opt_COX10*-opt_ND4*-3'UTR*

<400> SEQUENCE: 48

```
atggccgcca gccccacac cctgagcagc cgcctgctga ccggctgcgt gggcggcagc      60
gtgtggtacc tggagcgccg caccatgctg aagctgatcg tgcccaccat catgctgctg    120
cccctgacct ggctgagcaa gaagcacatg atctggatca caccaccac ccacagcctg    180 atcatcagca tcatccccct gctgttcttc aaccagatca caacaacct gttcagctgc    240 agccccacct tcagcagcga ccccctgacc acccccctgc tgatgctgac cacctggctg    300
ctgcccctga ccatcatggc cagcagcgc cacctgagca gcgagcccct gagccgcaag    360
aagctgtacc tgagcatgct gatcagcctg cagatcagcc tgatcatgac cttcaccgcc    420
accgagctga tcatgttcta catcttcttc gagaccaccc tgatcccac cctggccatc    480 atcacccgct ggggcaacca gcccgagcgc ctgaacgccg gcacctactt cctgttctac    540
```

| | | |
|---|---|---|
| accctggtgg gcagcctgcc cctgctgatc gccctgatct acacccacaa caccctgggc | 600 | |
| agcctgaaca tcctgctgct gaccctgacc gcccaggagc tgagcaacag ctgggccaac | 660 | |
| aacctgatgt ggctggccta caccatggcc ttcatggtga agatgcccct gtacggcctg | 720 | |
| cacctgtggc tgcccaaggc ccacgtggag gcccccatcg ccggcagcat ggtgctggcc | 780 | |
| gccgtgctgc tgaagctggg cggctacggc atgatgcgcc tgaccctgat cctgaacccc | 840 | |
| ctgaccaagc acatggccta ccccttcctg gtgctgagcc tgtggggcat gatcatgacc | 900 | |
| agcagcatct gcctgcgcca gaccgacctg aagagcctga tcgcctacag cagcatcagc | 960 | |
| cacatggccc tggtggtgac cgccatcctg atccagaccc cctggagctt caccggcgcc | 1020 | |
| gtgatcctga tgatcgccca cggcctgacc agcagcctgc tgttctgcct ggccaacagc | 1080 | |
| aactacgagc gcacccacag ccgcatcatg atcctgagcc agggcctgca gaccctgctg | 1140 | |
| cccctgatgg ccttctggtg gctgctggcc agcctggcca acctggccct gcccccacc | 1200 | |
| atcaacctgc tgggcgagct gagcgtgctg gtgaccacct tcagctggag caacatcacc | 1260 | |
| ctgctgctga ccggcctgaa catgctggtg accgccctgt acagcctgta catgttcacc | 1320 | |
| accacccagt ggggcagcct gacccaccac atcaacaaca tgaagcccag cttcacccgc | 1380 | |
| gagaacaccc tgatgttcat gcacctgagc cccatcctgc tgctgagcct gaaccccgac | 1440 | |
| atcatcaccg gcttcagcag ctaagagcac tgggacgccc accgccctt tccctccgct | 1500 | |
| gccaggcgag catgttgtgg taattctgga acacaagaag agaaattgct gggtttagaa | 1560 | |
| caagattata acgaattcg gtgctcagtg atcacttgac agttttttt ttttttaaat | 1620 | |
| attacccaaa atgctcccca aataagaaat gcatcagctc agtcagtgaa tacaaaaaag | 1680 | |
| gaattatttt tcccttgag ggtctttat acatctctcc tccaacccca ccctctattc | 1740 | |
| tgtttcttcc tcctcacatg ggggtacaca tacacagctt cctcttttgg ttccatcctt | 1800 | |
| accaccacac cacacgcaca ctccacatgc ccagcagagt ggcacttggt ggccagaaag | 1860 | |
| tgtgagcctc atgatctgct gtctgtagtt ctgtgagctc aggtccctca aaggcctcgg | 1920 | |
| agcaccccct tccttgtgac tgagccaggg cctgcatttt tggttttccc caccccacac | 1980 | |
| attctcaacc atagtccttc taacaatacc aatagctagg accggctgc tgtgcactgg | 2040 | |
| gactggggat tccacatgtt tgccttggga gtctcaagct ggactgcca | 2089 | |

<210> SEQ ID NO 49
<211> LENGTH: 2034
<212> TYPE: DNA
<213> ORGANISM: Artificial Sequence
<220> FEATURE:
<223> OTHER INFORMATION: opt_COX10*-ND6-3'UTR

<400> SEQUENCE: 49

| | | |
|---|---|---|
| atggccgcca gccccacac cctgagcagc cgcctgctga ccggctgcgt gggcggcagc | 60 | |
| gtgtggtacc tggagcgccg caccatgatg tatgctttgt ttctgttgag tgtgggttta | 120 | |
| gtaatggggt ttgtggggtt ttcttctaag ccttctccta tttatggggg tttagtattg | 180 | |
| attgttagcg gtgtggtcgg gtgtgttatt attctgaatt ttgggggagg ttatatgggt | 240 | |
| ttaatggttt ttttaattta tttaggggga atgatggttg tctttggata tactacagcg | 300 | |
| atggctattg aggagtatcc tgaggcatgg ggtcagggg ttgaggtctt ggtgagtgtt | 360 | |
| ttagtggggt tagcgatgga ggtaggattg gtgctgtggg tgaaagagta tgatggggtg | 420 | |
| gtggttgtgt taaactttaa tagtgtagga agctggatga tttatgaagg agaggggtca | 480 | |
| gggttgattc gggaggatcc tattggtgcg ggggctttgt atgattatgg gcgttggtta | 540 | |

```
gtagtagtta ctggttggac attgtttgtt ggtgtatata ttgtaattga gattgctcgg    600
gggaattagg agcactggga cgcccaccgc cccttccct ccgctgccag gcgagcatgt     660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttcccct     840
ttgagggtct tttatacatc tctcctccaa ccccaccctc tattctgttt cttcctcctc    900
acatggggt acacatacac agcttcctct tttggttcca tccttaccac cacaccacac     960
gcacactcca catgcccagc agagtggcac tggtggcca gaaagtgtga gcctcatgat     1020
ctgctgtctg tagttctgtg agctcaggtc cctcaaaggc ctcggagcac ccccttcctt    1080
gtgactgagc cagggcctgc attttggtt ttccccaccc cacacattct caaccatagt     1140
ccttctaaca ataccaatag ctaggacccg gctgctgtgc actgggactg gggattccac    1200
atgtttgcct tgggagtctc aagctggact gccagcccct gtcctcctt cacccccatt     1260
gcgtatgagc atttcagaac tccaaggagt cacaggcatc tttatagttc acgttaacat    1320
atagacactg ttggaagcag ttccttctaa aagggtagcc ctggacttaa taccagccgg    1380
atacctctgg ccccaccc attactgtac ctctggagtc actactgtgg gtcgccactc      1440
ctctgctaca cagcacggct ttttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag     1620
ccagaagcag ggttctggga attttgcaag ttacctgtgg ccaggtgtgg tctcggttac    1680
caaatacggt tacctgcagc ttttagtcc tttgtgctcc cacgggtcta cagagtccca     1740
tctgcccaaa ggtcttgaag cttgacagga tgttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgccccag gtatttactg tggagaacat tgcataggaa     1980
tgtctggaaa aagcttctac aacttgttac agccttcaca tttgtagaag cttt          2034

<210> SEQ ID NO 50
<211> LENGTH: 1234
<212> TYPE: DNA
<213> ORGANISM: Artificial Sequence
<220> FEATURE:
<223> OTHER INFORMATION: opt_COX10*-ND6-3'UTR*

<400> SEQUENCE: 50
atggccgcca gccccacac cctgagcagc cgcctgctga ccggctgcgt gggcggcagc      60
gtgtggtacc tggagcgccg caccatgatg tatgctttgt ttctgttgag tgtgggttta    120
gtaatggggt ttgtgggtt ttcttctaag ccttctccta tttatggggg tttagtattg     180
attgttagcg gtgtggtcgg gtgtgttatt attctgaatt tgggggagg ttatatgggt     240
ttaatggttt ttttaattta tttaggggga atgatggttg tctttggata tactacagcg    300
atggctattg aggagtatcc tgaggcatgg ggtcagggg ttgaggtctt ggtgagtgtt     360
ttagtggggt tagcgatgga ggtaggattg gtgctgtggg tgaaagagta tgatgggtg     420
gtggttgtgg taaactttaa tagtgtagga agctggatga tttatgaagg agaggggtca    480
gggttgattc gggaggatcc tattggtgcg ggggctttgt atgattatgg gcgttggtta    540
```

| | |
|---|---|
| gtagtagtta ctggttggac attgtttgtt ggtgtatata ttgtaattga gattgctcgg | 600 |
| gggaattagg agcactggga cgcccaccgc ccctttccct ccgctgccag gcgagcatgt | 660 |
| tgtggtaatt ctgaacacag agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatggggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gcca | 1234 |

<210> SEQ ID NO 51
<211> LENGTH: 2034
<212> TYPE: DNA
<213> ORGANISM: Artificial Sequence
<220> FEATURE:
<223> OTHER INFORMATION: opt_COX10*-opt_ND6-3'UTR

<400> SEQUENCE: 51

| | |
|---|---|
| atggccgcca gccccacac cctgagcagc cgcctgctga ccggctgcgt gggcggcagc | 60 |
| gtgtggtacc tggagcgccg caccatgatg tacgccctgt tcctgctgag cgtgggcctg | 120 |
| gtgatgggct tcgtgggctt cagcagcaag cccagcccca tctacggcgg cctggtgctg | 180 |
| atcgtgagcg cgctggtggg ctgcgtgatc atcctgaact tcggcggcgg ctacatgggc | 240 |
| ctgatggtgt tcctgatcta cctgggcggc atgatggtgg tgttcggcta caccaccgcc | 300 |
| atggccatcg aggagtaccc cgaggcctgg ggcagcggcg tggaggtgct ggtgagcgtg | 360 |
| ctggtggggcc tggccatgga ggtgggcctg gtgctgtggg tgaaggagta cgacggcgtg | 420 |
| gtggtggtgg tgaacttcaa cagcgtgggc agctggatga tctacgaggg cgagggcagc | 480 |
| ggcctgatcc gcgaggaccc catcggcgcc ggcgccctgt acgactacgg ccgctggctg | 540 |
| gtggtggtga ccggctggac cctgttcgtg ggcgtgtaca tcgtgatcga gatcgcccgc | 600 |
| ggcaactaag agcactggga cgcccaccgc ccctttccct ccgctgccag gcgagcatgt | 660 |
| tgtggtaatt ctgaacacag agaagagaaa ttgctgggtt tagaacaaga ttataaacga | 720 |
| attcggtgct cagtgatcac ttgacagttt tttttttttt taaatattac ccaaaatgct | 780 |
| ccccaaataa gaaatgcatc agctcagtca gtgaatacaa aaaggaatt attttttccct | 840 |
| ttgagggtct tttatacatc tctcctccaa ccccaccctc tattctgttt cttcctcctc | 900 |
| acatggggggt acacatacac agcttcctct tttggttcca tccttaccac cacaccacac | 960 |
| gcacactcca catgcccagc agagtggcac ttggtggcca gaaagtgtga gcctcatgat | 1020 |
| ctgctgtctg tagttctgtg agctcaggtc cctcaaaggc ctcggagcac ccccttcctt | 1080 |
| gtgactgagc cagggcctgc attttttggtt ttccccaccc cacacattct caaccatagt | 1140 |
| ccttctaaca ataccaatag ctaggacccg gctgctgtgc actgggactg gggattccac | 1200 |
| atgtttgcct tgggagtctc aagctggact gccagcccct gtcctccctt caccccatt | 1260 |
| gcgtatgagc atttcagaac tccaaggagt cacaggcatc tttatagttc acgttaacat | 1320 |
| atagacactg ttgaagcag ttccttctaa aagggtagcc ctggacttaa taccagccgg | 1380 |

-continued

```
atacctctgg ccccccccc attactgtac ctctggagtc actactgtgg gtcgccactc    1440
ctctgctaca cagcacggct tttcaaggc tgtattgaga agggaagtta ggaagaaggg    1500
tgtgctgggc taaccagccc acagagctca cattcctgtc ccttgggtga aaaatacatg    1560
tccatcctga tatctcctga attcagaaat tagcctccac atgtgcaatg ctttaagag    1620 ccagaagcag ggttctggga attttgcaag ttacctgtgg ccaggtgtgg tctcggttac    1680
caaatacggt tacctgcagc tttttagtcc tttgtgctcc cacgggtcta cagagtccca    1740
tctgcccaaa ggtcttgaag cttgacagga tgtttttcgat tactcagtct cccagggcac    1800
tactggtccg taggattcga ttggtcgggg taggagagtt aaacaacatt taaacagagt    1860
tctctcaaaa atgtctaaag ggattgtagg tagataacat ccaatcactg tttgcactta    1920
tctgaaatct tccctcttgg ctgcccccag gtatttactg tggagaacat tgcataggaa    1980
tgtctggaaa aagcttctac aacttgttac agccttcaca tttgtagaag cttt        2034
```

<210> SEQ ID NO 52
<211> LENGTH: 1234
<212> TYPE: DNA
<213> ORGANISM: Artificial Sequence
<220> FEATURE:
<223> OTHER INFORMATION: opt_COX10*-opt_ND6-3'UTR*

<400> SEQUENCE: 52

```
atggccgcca gccccacac cctgagcagc cgcctgctga ccggctgcgt gggcggcagc     60
gtgtggtacc tggagcgccg caccatgatg tacgccctgt cctgctgag cgtgggcctg    120 gtgatgggct tcgtgggctt cagcagcaag cccagcccca tctacggcgg cctggtgctg    180
atcgtgagcg gcgtggtggg ctgcgtgatc atcctgaact tcggcggcgg ctacatgggc    240
ctgatggtgt tcctgatcta cctgggcggc atgatggtgg tgttcggcta caccaccgcc    300
atggccatcg aggagtaccc cgaggcctgg ggcagcggcg tggaggtgct ggtgagcgtg    360
ctggtgggcc tggccatgga ggtgggcctg gtgctgtggg tgaaggagta cgacggcgtg    420
gtggtggtgg tgaacttcaa cagcgtgggc agctggatga tctacgaggg cgagggcagc    480
ggcctgatcc gcgaggaccc catcggcgcc ggcgccctgt acgactacgg ccgctggctg    540
gtggtggtga ccggctggac cctgttcgtg ggcgtgtaca tcgtgatcga gatcgcccgc    600
ggcaactaag agcactggga cgcccaccgc cccttttccct ccgctgccag gcgagcatgt    660
tgtggtaatt ctggaacaca agaagagaaa ttgctgggtt tagaacaaga ttataaacga    720
attcggtgct cagtgatcac ttgacagttt tttttttttt taaatattac ccaaaatgct    780
ccccaaataa gaaatgcatc agctcagtca gtgaatacaa aaaggaatt attttttcccct    840 ttgagggtct tttatacatc tctcctccaa ccccacccctc tattctgttt cttcctcctc    900 acatggggggt acacatacac agcttcctct tttggtcca tccttaccac cacaccacac    960
gcacactcca catgcccagc agagtggcac ttggtggcca gaaagtgtga gcctcatgat   1020
ctgctgtctg tagttctgtg agctcaggtc cctcaaaggc ctcggagcac cccttcctt    1080 gtgactgagc cagggcctgc atttttggtt tccccaccccc cacacattct caaccatagt   1140
ccttctaaca ataccaatag ctaggacccg gctgctgtgc actgggactg gggattccac    1200
atgtttgcct tgggagtctc aagctggact gcca                                1234
```

<210> SEQ ID NO 53
<211> LENGTH: 2460
<212> TYPE: DNA

<213> ORGANISM: Artificial Sequence
<220> FEATURE:
<223> OTHER INFORMATION: opt_COX10*-ND1-3'UTR

<400> SEQUENCE: 53

```
atggccgcca gccccacac cctgagcagc cgcctgctga ccggctgcgt gggcggcagc      60
gtgtggtacc tggagcgccg caccatggcc aacctcctac tcctcattgt acccattcta     120
atcgcaatgg cattcctaat gcttaccgaa cgaaaaattc taggctatat gcaactacgc     180
aaaggcccca acgttgtagg cccctacggg ctactacaac ccttcgctga cgccataaaa     240
ctcttcacca aagagcccct aaacccgcc acatctacca tcaccctcta catcaccgcc      300
ccgaccttag ctctcaccat cgctcttcta ctatggaccc cctccccat gcccaacccc      360
ctggtcaacc tcaacctagg cctcctattt attctagcca cctctagcct agccgtttac     420
tcaatcctct ggtcaggtg ggcatcaaac tcaaactacg ccctgatcgg cgcactgcga      480
gcagtagccc aaacaatctc atatgaagtc accctagcca tcattctact atcaacatta     540
ctaatgagtg gctcctttaa cctctccacc cttatcacaa caagaaaca cctctggtta      600
ctcctgccat catggccctt ggccatgatg tggtttatct ccacactagc agagaccaac     660
cgaaccccct tcgaccttgc cgaaggggag tccgaactag tctcaggctt caacatcgaa     720
tacgccgcag gccccttcgc cctattcttc atggccgaat acacaaacat tattatgatg     780
aacaccctca ccactacaat cttcctagga acaacatatg acgcactctc ccctgaactc     840
tacacaacat attttgtcac caagacccta cttctaacct ccctgttctt atggattcga     900
acagcatacc cccgattccg ctacgaccaa ctcatgcacc tcctatggaa aaacttccta     960
ccactcaccc tagcattact tatgtgggtat gtctccatgc ccattacaat ctccagcatt    1020
cccctcaaa cctaagagca ctgggacgcc caccgcccct ttcctccgc tgccaggcga      1080
gcatgttgtg gtaattctgg aacacaagaa gagaaattgc tgggtttaga caagattat     1140
aaacgaattc ggtgctcagt gatcacttga cagttttttt tttttttaaa tattacccaa    1200
aatgctcccc aaataagaaa tgcatcagct cagtcagtga atacaaaaaa ggaattattt    1260
ttccctttga gggtctttta tacatctctc ctccaacccc accctctatt ctgtttcttc    1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt ttggttttcc ccaccccaca cattctcaac    1560
catagtcctt ctaacaatac caatagctag gacccggctg ctgtgcactg ggactgggga    1620
ttccacatgt ttgccttggg agtctcaagc tggactgcca gccctgtcc tcccttcacc     1680
cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc cacccattt ctgtacctct ggagtcacta ctgtgggtcg     1860
ccactcctct gctacacagc acggcttttt caaggctgta ttgagaaggg aagttaggaa    1920
gaagggtgtg ctgggctaac cagcccacag agctcacatt cctgtcccct gggtgaaaaa    1980
tacatgtcca tcctgatatc tcctgaattc agaaattagc ctccacatgt gcaatggctt    2040
taagagccag aagcagggtt ctgggaattt tgcaagttac ctgtggccag gtgtggtctc    2100
ggttaccaaa tacggttacc tgcagctttt tagtcctttg tgctcccacg ggtctacaga    2160
gtcccatctg cccaaaggtc ttgaagcttg acaggatgtt ttcgattact cagtctccca    2220
```

```
gggcactact ggtccgtagg attcgattgg tcggggtagg agagttaaac aacatttaaa    2280
cagagttctc tcaaaaatgt ctaaagggat tgtaggtaga taacatccaa tcactgtttg    2340
cacttatctg aaatcttccc tcttggctgc ccccaggtat ttactgtgga aacattgca     2400 taggaatgtc tggaaaaagc ttctacaact tgttacagcc ttcacatttg tagaagcttt    2460
```

<210> SEQ ID NO 54
<211> LENGTH: 1660
<212> TYPE: DNA
<213> ORGANISM: Artificial Sequence
<220> FEATURE:
<223> OTHER INFORMATION: opt_COX10*-ND1-3'UTR*

<400> SEQUENCE: 54

```
atggccgcca gccccacac cctgagcagc cgcctgctga ccggctgcgt gggcggcagc      60
gtgtggtacc tggagcgccg caccatggcc aacctcctac tcctcattgt acccattcta    120
atcgcaatgg cattcctaat gcttaccgaa cgaaaaattc taggctatat gcaactacgc    180
aaaggcccca acgttgtagg ccctacggg ctactacaac ccttcgctga cgccataaaa     240
ctcttcacca aagagcccct aaacccgcc acatctacca tcaccctcta catcaccgcc    300
ccgaccttag ctctcaccat cgctcttcta ctatggaccc cctccccat gcccaacccc    360 ctggtcaacc tcaacctagg cctcctattt attctagcca cctctagcct agccgtttac    420
tcaatcctct ggtcagggtg ggcatcaaac tcaaactacg cctgatcgg cgcactgcga     480 gcagtagccc aaacaatctc atatgaagtc accctagcca tcattctact atcaacatta    540
ctaatgagtg gctcctttaa cctctccacc cttatcacaa cacaagaaca cctctggtta    600
ctcctgccat catggccctt ggccatgatg tggtttatct ccacactagc agagaccaac    660
cgaaccccct tcgaccttgc cgaaggggag tccgaactag tctcaggctt caacatcgaa    720
tacgccgcag gccccttcgc cctattcttc atggccgaat acacaaacat tattatgatg    780
aacaccctca ccactacaat cttcctagga acaacatatg acgcactctc ccctgaactc    840
tacacaacat attttgtcac caagacccta cttctaacct ccctgttctt atggattcga    900
acagcatacc cccgattccg ctacgaccaa tcatgcacc tcctatggaa aaacttccta    960
ccactcaccc tagcattact tatgtggtat gtctccatgc ccattacaat ctccagcatt   1020 cccctcaaa cctaagagca ctgggacgcc caccgcccct ttccctccgc tgccaggcga    1080
gcatgttgtg gtaattctgg aacacaagaa gagaaattgc tgggtttaga acaagattat    1140
aaacgaattc ggtgctcagt gatcacttga cagttttttt tttttttaaa tattacccaa   1200
aatgctcccc aaataagaaa tgcatcagct cagtcagtga atacaaaaaa ggaattattt    1260 ttcccttga gggtctttta tacatctctc ctccaaccc accctctatt ctgtttcttc     1320
ctcctcacat gggggtacac atacacagct tcctcttttg gttccatcct taccaccaca   1380
ccacacgcac actccacatg cccagcagag tggcacttgg tggccagaaa gtgtgagcct    1440
catgatctgc tgtctgtagt tctgtgagct caggtccctc aaaggcctcg gagcacccc     1500 ttccttgtga ctgagccagg gcctgcattt ttggttttcc ccaccccaca cattctcaac    1560
catagtcctt ctaacaatac caatagctag gacccggctg ctgtgcactg ggactgggga   1620
ttccacatgt ttgccttggg agtctcaagc tggactgcca                          1660
```

<210> SEQ ID NO 55
<211> LENGTH: 2460
<212> TYPE: DNA

<213> ORGANISM: Artificial Sequence
<220> FEATURE:
<223> OTHER INFORMATION: opt_COX10*-opt_ND1-3'UTR

<400> SEQUENCE: 55

```
atggccgcca gccccacac cctgagcagc cgcctgctga ccggctgcgt gggcggcagc      60
gtgtggtacc tggagcgccg caccatggcc aacctgctgc tgctgatcgt gcccatcctg     120
atcgccatgg ccttcctgat gctgaccgag cgcaagatcc tgggctacat gcagctgcgc     180
aagggcccca acgtggtggg ccctacggc ctgctgcagc ccttcgccga cgccatcaag     240
ctgttcacca aggagcccct gaagcccgcc accagcacca tcaccctgta catcaccgcc     300
cccaccctgg ccctgaccat cgccctgctg ctgtggaccc cctgcccat gcccaacccc      360
ctggtgaacc tgaacctggg cctgctgttc atcctggcca ccagcagcct ggccgtgtac     420
agcatcctgt ggagcggctg ggccagcaac agcaactacg ccctgatcgg cgccctgcgc     480
gccgtggccc agaccatcag ctacgaggtg accctggcca tcatcctgct gagcaccctg     540
ctgatgagcg gcagcttcaa cctgagcacc ctgatcacca cccaggagca cctgtggctg     600
ctgctgccca gctggcccct ggccatgatg tggttcatca gcaccctggc cgagaccaac     660
cgcaccccct tcgacctggc cgagggcgag agcgagctgg tgagcggctt caacatcgag     720
tacgccgccg ccccttcgc cctgttcttc atggccgagt acaccaacat catcatgatg     780
aacaccctga ccaccaccat cttcctgggc accacctacg acgccctgag ccccgagctg     840
tacaccacct acttcgtgac caagaccctg ctgctgacca gcctgttcct gtggatccgc     900
accgcctacc ccgcttccg ctacgaccag ctgatgcacc tgctgtggaa gaacttcctg      960
cccctgaccc tggccctgct gatgtggtac gtgagcatgc ccatcaccat cagcagcatc    1020
cccccccaga cctaagagca ctgggacgcc caccgccct ttccctccgc tgccaggcga     1080
gcatgttgtg gtaattctgg aacacaagaa gagaaattgc tgggtttaga acaagattat    1140
aaacgaattc ggtgctcagt gatcacttga cagttttttt ttttttttaaa tattacccaa   1200
aatgctcccc aaataagaaa tgcatcagct cagtcagtga atacaaaaaa ggaattattt    1260
ttcccttttga gggtctttta tacatctctc ctccaacccc accctctatt ctgtttcttc   1320
ctcctcacat gggggtacac atacacagct tcctcttttg gttccatcct taccaccaca    1380
ccacacgcac actccacatg cccagcagag tggcacttgg tggccagaaa gtgtgagcct    1440
catgatctgc tgtctgtagt tctgtgagct caggtccctc aaaggcctcg gagcaccccc    1500
ttccttgtga ctgagccagg gcctgcattt tggttttcc ccaccccaca cattctcaac     1560
catagtcctt ctaacaatac caatagctag gaccggctg ctgtgcactg ggactgggga     1620
ttccacatgt ttgccttggg agtctcaagc tggactgcca gcccctgtcc tcccttcacc    1680
cccattgcgt atgagcattt cagaactcca aggagtcaca ggcatcttta tagttcacgt    1740
taacatatag acactgttgg aagcagttcc ttctaaaagg gtagccctgg acttaatacc    1800
agccggatac ctctggcccc caccccatta ctgtacctct ggagtcacta ctgtgggtcg    1860
ccactcctct gctacacagc acggcttttt caaggctgta ttgagaaggg aagttaggaa    1920
gaagggtgtg ctgggctaac cagcccacag agctcacatt cctgtccctt gggtgaaaaa    1980
tacatgtcca tcctgatatc tcctgaattc agaaattagc ctccacatgt gcaatggctt    2040
taagagccag aagcagggtt ctgggaattt tgcaagttac ctgtggccag gtgtggtctc    2100
ggttaccaaa tacggttacc tgcagctttt tagtcctttg tgctcccacg ggtctacaga    2160
gtcccatctg cccaaaggtc ttgaagcttg acaggatgtt ttcgattact cagtctccca    2220
```

```
gggcactact ggtccgtagg attcgattgg tcggggtagg agagttaaac aacatttaaa    2280
cagagttctc tcaaaaatgt ctaaagggat tgtaggtaga taacatccaa tcactgtttg    2340
cacttatctg aaatcttccc tcttggctgc ccccaggtat ttactgtgga gaacattgca    2400
taggaatgtc tggaaaaagc ttctacaact tgttacagcc ttcacatttg tagaagcttt    2460
```

<210> SEQ ID NO 56
<211> LENGTH: 1660
<212> TYPE: DNA
<213> ORGANISM: Artificial Sequence
<220> FEATURE:
<223> OTHER INFORMATION: opt_COX10*-opt_ND1-3'UTR*

<400> SEQUENCE: 56

```
atggccgcca gccccacac cctgagcagc cgcctgctga ccggctgcgt gggcggcagc      60
gtgtggtacc tggagcgccg caccatggcc aacctgctgc tgctgatcgt gcccatcctg    120
atcgccatgg ccttcctgat gctgaccgag cgcaagatcc tggctacat gcagctgcgc     180 aagggcccca acgtggtggg ccctacggc ctgctgcagc ccttcgccga cgccatcaag     240
ctgttcacca aggagcccct gaagcccgcc accagcacca tcaccctgta catcaccgcc    300
cccaccctgg ccctgaccat cgccctgctg ctgtggaccc cctgcccat gcccaacccc     360 ctggtgaacc tgaacctggg cctgctgttc atcctggcca ccagcagcct ggccgtgtac    420
agcatcctgt ggagcggctg ggccagcaac agcaactacg ccctgatcgg cgccctgcgc    480
gccgtggccc agaccatcag ctacgaggtg accctggcca tcatcctgct gagcaccctg    540
ctgatgagcg gcagcttcaa cctgagcacc ctgatcacca cccaggagca cctgtggctg    600
ctgctgccca gctggcccct ggccatgatg tggttcatca gcaccctggc cgagaccaac    660 cgcacccccct tcgacctggc cgagggcgag agcgagctgg tgagcggctt caacatcgag    720
tacgccgccg ccccctcgc cctgttcttc atggccgagt acaccaacat catcatgatg    780
aacaccctga ccaccaccat cttcctgggc accacctacg acgccctgag ccccgagctg    840
tacaccacct acttcgtgac caagaccctg ctgctgacca gcctgttcct gtggatccgc    900
accgcctacc ccgcttccg ctacgaccag ctgatgcacc tgctgtggaa gaacttcctg    960
cccctgaccc tggccctgct gatgtggtac gtgagcatgc ccatcaccat cagcagcatc   1020 ccccccaga cctaagagca ctgggacgcc caccgccct ttccctccgc tgccaggcga     1080
gcatgttgtg gtaattctgg aacacaagaa gagaaattgc tgggtttaga acaagattat   1140
aaacgaattc ggtgctcagt gatcacttga cagtttttttt ttttttaaa tattacccaa   1200 aatgctcccc aaataagaaa tgcatcagct cagtcagtga atacaaaaaa ggaattattt   1260
ttcccttgta gggtctttta tacatctctc ctccaacccc accctctatt ctgtttcttc   1320
ctcctcacat gggggtacac atacacagct tcctcttttg gttccatcct taccaccaca   1380
ccacacgcac actccacatg cccagcagag tggcacttgg tggccagaaa gtgtgagcct   1440
catgatctgc tgtctgtagt tctgtgagct caggtccctc aaaggcctcg gagcaccccc   1500
ttccttgtga ctgagccagg gcctgcattt ttggttttcc ccaccccaca cattctcaac   1560
catagtcctt ctaacaatac caatagctag gaccggctg ctgtgcactg ggactgggga   1620
ttccacatgt ttgccttggg agtctcaagc tggactgcca                        1660
```

<210> SEQ ID NO 57
<211> LENGTH: 2892
<212> TYPE: DNA

<213> ORGANISM: Artificial Sequence
<220> FEATURE:
<223> OTHER INFORMATION: COX8-ND4-3'UTR

<400> SEQUENCE: 57

```
atgtccgtcc tgacgcgcct gctgctgcgg ggcttgacac ggctcggctc ggcggctcca      60
gtgcggcgcg ccagaatcca ttcgttgatg ctaaaactaa tcgtcccaac aattatgtta     120
ctaccactga catggctttc caaaaaacac atgatttgga tcaacacaac cacccacagc     180
ctaattatta gcatcatccc tctactattt tttaaccaaa tcaacaacaa cctatttagc     240
tgttccccaa ccttttcctc cgacccccta acaacccccc tcctaatgct aactacctgg     300
ctcctacccc tcacaatcat ggcaagccaa cgccacttat ccagtgaacc actatcacga     360
aaaaaactct acctctctat gctaatctcc ctacaaatct ccttaattat gacattcaca     420
gccacagaac taatcatgtt ttatatcttc ttcgaaacca cacttatccc caccttggct     480
atcatcaccc gatggggcaa ccagccagaa cgcctgaacg caggcacata cttcctattc     540
tacaccctag taggctccct tcccctactc atcgcactaa tttacactca caacacccta     600
ggctcactaa acattctact actcactctc actgcccaag aactatcaaa ctcctgggcc     660
aacaacttaa tgtggctagc ttacacaatg cttttatgg taaagatgcc tctttacgga     720
ctccacttat ggctccctaa agcccatgtc gaagccccca tcgctgggtc aatggtactt     780
gccgcagtac tcttaaaact aggcggctat ggtatgatgc cctcacact cattctcaac      840
cccctgacaa acacatggc ctaccccttc cttgtactat ccctatgggg catgattatg      900
acaagctcca tctgcctacg acaaacagac ctaaaatcgc tcattgcata ctcttcaatc     960
agccacatgg ccctcgtagt aacagccatt ctcatccaaa cccctggag cttcaccggc    1020
gcagtcattc tcatgatcgc ccacgggctt acatcctcat tactattctg cctagcaaac    1080
tcaaactacg aacgcactca cagtcgcatc atgatcctct ctcaaggact tcaaactcta    1140
ctcccactaa tggcttttg gtggcttcta gcaagcctcg ctaacctcgc cttaccccc     1200
actattaacc tactgggaga actctctgtg ctagtaacca cgttctcctg gtcaaatatc    1260
actctcctac ttacaggact caacatgcta gtcacagccc tatactccct ctacatgttt    1320
accacaacac aatggggctc actcacccac cacattaaca acatgaaacc ctcattcaca    1380
cgagaaaaca ccctcatgtt catgcaccta tcccccattc tcctcctatc cctcaaccc     1440
gacatcatta ccgggttttc ctcttaagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt ttttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtggccaga    1860
aagtgtgagc tcatgatct gctgtctgta gttctgtgag ctcaggtccc tcaaaggcct     1920
cggagcaccc ccttccttgt gactgagcca gggcctgcat ttttggtttt ccccaccca     1980
cacattctca accatagtcc ttctaacaat accaatagct aggaccggc tgctgtgcac     2040
tgggactggg gattccacat gtttgccttg ggagtctcaa gctggactgc agcccctgt     2100
cctcccttca cccccattgc gtatgagcat ttcagaactc caaggagtca caggcatctt    2160
tatagttcac gttaacatat agacactgtt ggaagcagtt ccttctaaaa gggtagccct    2220
```

```
ggacttaata ccagccggat acctctggcc cccaccccat tactgtacct ctggagtcac    2280
tactgtgggt cgccactcct ctgctacaca gcacggcttt ttcaaggctg tattgagaag    2340
ggaagttagg aagaagggtg tgctgggcta accagcccac agagctcaca ttcctgtccc    2400
ttgggtgaaa aatacatgtc catcctgata tctcctgaat tcagaaatta gcctccacat    2460
gtgcaatggc tttaagagcc agaagcaggg ttctgggaat tttgcaagtt acctgtggcc    2520
aggtgtggtc tcggttacca aatacggtta cctgcagctt tttagtcctt tgtgctccca    2580
cgggtctaca gagtcccatc tgcccaaagg tcttgaagct tgacaggatg ttttcgatta    2640
ctcagtctcc cagggcacta ctggtccgta ggattcgatt ggtcggggta ggagagttaa    2700
acaacattta aacagagttc tctcaaaaat gtctaagggg attgtaggta gataacatcc    2760
aatcactgtt tgcacttatc tgaaatcttc cctcttggct gcccccaggt atttactgtg    2820
gagaacattg cataggaatg tctggaaaaa gcttctacaa cttgttacag ccttcacatt    2880
tgtagaagct tt                                                        2892
```

<210> SEQ ID NO 58
<211> LENGTH: 2092
<212> TYPE: DNA
<213> ORGANISM: Artificial Sequence
<220> FEATURE:
<223> OTHER INFORMATION: COX8-ND4-3'UTR*

<400> SEQUENCE: 58

```
atgtccgtcc tgacgcgcct gctgctgcgg ggcttgacac ggctcggctc ggcggctcca      60
gtgcggcgcg ccagaatcca ttcgttgatg ctaaaactaa tcgtcccaac aattatgtta     120
ctaccactga catggctttc caaaaaacac atgatttgga tcaacacaac cacccacagc     180
ctaattatta gcatcatccc tctactattt tttaaccaaa tcaacaacaa cctatttagc     240
tgttccccaa cctttcctc cgaccccct acaacccccc tcctaatgct aactacctgg     300
ctcctacccc tcacaatcat ggcaagccaa cgccacttat ccagtgaacc actatcacga     360
aaaaaactct acctctctat gctaatctcc ctacaaatct ccttaattat gacattcaca     420
gccacagaac taatcatgtt ttatatcttc ttcgaaacca cacttatccc caccttggct     480
atcatcaccc gatggggcaa ccagccagaa cgcctgaacg caggcacata cttcctattc     540
tacaccctag taggctccct tccctactc atcgcactaa tttacactca aacacccta     600 ggctcactaa acattctact actcactctc actgcccaag aactatcaaa ctcctgggcc     660
aacaacttaa tgtggctagc ttacacaatg gcttttatgg taaagatgcc tctttacgga     720
ctccacttat ggctccctaa agcccatgtc gaagccccca tcgctgggtc aatggtactt     780
gccgcagtac tcttaaaact aggcggctat ggtatgatgc gcctcacact cattctcaac     840
cccctgacaa aacacatggc ctacccttc cttgtactat ccctatgggg catgattatg     900
acaagctcca tctgcctacg acaaacagac taaaatcgc tcattgcata tcttcaatc     960 agccacatgg ccctcgtagt aacagccatt ctcatccaaa cccctggag cttcaccggc    1020 gcagtcattc tcatgatcgc ccacgggctt acatcctcat tactattctg cctagcaaac    1080
tcaaactacg aacgcactca cagtcgcatc atgatcctct ctcaaggact tcaaactcta    1140
ctcccactaa tggcttttg gtggcttcta gcaagcctcg ctaacctcgc cttaccccc     1200 actattaacc tactgggaga actctctgtg ctagtaacca cgttctcctg gtcaaatatc    1260
actctcctac ttacaggact caacatgcta gtcacagccc tatactccct ctacatgttt    1320
```

```
accacaacac aatggggctc actcacccac cacattaaca acatgaaacc ctcattcaca    1380
cgagaaaaca ccctcatgtt catgcaccta tcccccattc tcctcctatc cctcaacccc    1440
gacatcatta ccgggttttc ctcttaagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt tttttttta    1620 aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtggccaga    1860
aagtgtgagc ctcatgatct gctgtctgta gttctgtgag ctcaggtccc tcaaaggcct    1920
cggagcaccc ccttccttgt gactgagcca gggcctgcat ttttggtttt ccccacccca    1980
cacattctca accatagtcc ttctaacaat accaatagct aggacccggc tgctgtgcac    2040
tgggactggg gattccacat gtttgccttg ggagtctcaa gctggactgc ca           2092

<210> SEQ ID NO 59
<211> LENGTH: 2892
<212> TYPE: DNA
<213> ORGANISM: Artificial Sequence
<220> FEATURE:
<223> OTHER INFORMATION: COX8-opt_ND4-3'UTR

<400> SEQUENCE: 59
atgtccgtcc tgacgcgcct gctgctgcgg ggcttgacac ggctcggctc ggcggctcca      60
gtgcggcgcg ccagaatcca ttcgttgatg ctgaagctga tcgtgcccac catcatgctg     120
ctgcctctga cctggctgag caagaaacac atgatctgga tcaacaccac cacgcacagc     180
ctgatcatca gcatcatccc tctgctgttc ttcaaccaga tcaacaacaa cctgttcagc     240
tgcagcccca ccttcagcag cgaccctctg acaacacctc tgctgatgct gaccaccctgg    300 ctgctgcccc tcacaatcat ggcctctcag agacacctga gcagcgagcc cctgagccgg     360
aagaaactgt acctgagcat gctgatctcc ctgcagatct ctctgatcat gaccttcacc     420
gccaccgagc tgatcatgtt ctacatcttt ttcgagacaa cgctgatccc cacactggcc     480
atcatcacca gatggggcaa ccagcctgag agactgaacg ccggcaccta ctttctgttc     540
tacaccctcg tgggcagcct gccactgctg attgccctga tctacaccca caacaccctg     600
ggctccctga acatcctgct gctgacactg acagcccaag agctgagcaa cagctgggcc     660
aacaatctga tgtggctggc ctacacaatg gccttcatgg tcaagatgcc cctgtacggc     720
ctgcacctgt ggctgcctaa agctcatgtg aagcccccta tcgccggctc tatggtgctg     780
gctgcagtgc tgctgaaaaact cggcggctac ggcatgatgc ggctgaccct gattctgaat     840
cccctgacca agcacatggc ctatccattt ctggtgctga gctgtgggg catgattatg     900 accagcagca tctgcctgcg gcagaccgat ctgaagtccc tgatcgccta cagctccatc     960
agccacatgg ccctggtggt caccgccatc ctgattcaga ccccttggag ctttacaggc    1020
gccgtgatcc tgatgattgc ccacggcctg acaagcagcc tgctgttttg tctggccaac    1080
agcaactacg agcggaccca cagcagaatc atgatcctgt ctcagggcct gcagaccctc    1140
ctgcctctta tggctttttg gtggctgctg gcctctctgg ccaatctggc actgcctcct    1200
accatcaatc tgctgggcga gctgagcgtg ctggtcacca cattcagctg gtccaatatc    1260
accctgctgc tcaccggcct gaacatgctg gttacagccc tgtactccct gtacatgttc    1320
```

```
accaccacac agtggggaag cctgacacac cacatcaaca atatgaagcc cagcttcacc    1380
cgcgagaaca ccctgatgtt catgcatctg agccccattc tgctgctgtc cctgaatcct    1440
gatatcatca ccggcttctc cagctgagag cactgggacg cccaccgccc ctttccctcc    1500
gctgccaggc gagcatgttg tggtaattct ggaacacaag aagagaaatt gctgggttta    1560
gaacaagatt ataaacgaat tcggtgctca gtgatcactt gacagttttt ttttttttta    1620
aatattaccc aaaatgctcc ccaaataaga aatgcatcag ctcagtcagt gaatacaaaa    1680
aaggaattat ttttcccttt gagggtcttt tatacatctc tcctccaacc ccaccctcta    1740
ttctgtttct tcctcctcac atgggggtac acatacacag cttcctcttt tggttccatc    1800
cttaccacca caccacacgc acactccaca tgcccagcag agtggcactt ggtggccaga    1860
aagtgtgagc ctcatgatct gctgtctgta gttctgtgag ctcaggtccc tcaaaggcct    1920
cggagcaccc ccttccttgt gactgagcca gggcctgcat ttttggtttt ccccaccccca   1980
cacattctca accatagtcc ttctaacaat accaatagct aggacccggc tgctgtgcac    2040
tgggactggg gattccacat gtttgccttg ggagtctcaa gctggactgc cagcccctgt    2100
cctcccttca cccccattgc gtatgagcat ttcagaactc caaggagtca caggcatctt    2160
tatagttcac gttaacatat agacactgtt ggaagcagtt ccttctaaaa gggtagccct    2220
ggacttaata ccagccggat acctctggcc cccaccccat tactgtacct ctggagtcac    2280
tactgtgggt cgccactcct ctgctacaca gcacggcttt tcaaggctg tattgagaag    2340
ggaagttagg aagaagggtg tgctgggcta accagcccac agagctcaca ttcctgtccc    2400
ttgggtgaaa aatacatgtc catcctgata tctcctgaat tcagaaatta gcctccacat    2460
gtgcaatggc tttaagagcc agaagcaggg ttctgggaat tttgcaagtt acctgtggcc    2520
aggtgtggtc tcggttacca aatacggtta cctgcagctt tttagtcctt tgtgctccca    2580
cgggtctaca gagtcccatc tgcccaaagg tcttgaagct tgacaggatg ttttcgatta    2640
ctcagtctcc cagggcacta ctggtccgta ggattcgatt ggtcggggta ggagagttaa    2700
acaacattta aacagagttc tctcaaaaat gtctaaaggg attgtaggta gataacatcc    2760
aatcactgtt tgcacttatc tgaaatcttc cctcttggct gccccaggt atttactgtg    2820
gagaacattg cataggaatg tctggaaaaa gcttctacaa cttgttacag ccttcacatt    2880
tgtagaagct tt                                                       2892
```

<210> SEQ ID NO 60
<211> LENGTH: 2092
<212> TYPE: DNA
<213> ORGANISM: Artificial Sequence
<220> FEATURE:
<223> OTHER INFORMATION: COX8-opt_ND4-3'UTR*

<400> SEQUENCE: 60

```
atgtccgtcc tgacgcgcct gctgctgcgg ggcttgacac ggctcggctc ggcggctcca      60
gtgcggcgcg ccagaatcca ttcgttgatg ctgaagctga tcgtgcccac catcatgctg     120
ctgcctctga cctggctgag caagaaacac atgatctgga tcaacaccac cacgcacagc     180
ctgatcatca gcatcatccc tctgctgttc ttcaaccaga tcaacaacaa cctgttcagc     240
tgcagcccca ccttcagcag cgaccctctg acaacacctc tgctgatgct gaccacctgg     300
ctgctgcccc tcacaatcat ggcctctcag agacacctga gcagcgagcc cctgagccgg     360
aagaaactgt acctgagcat gctgatctcc ctgcagatct ctctgatcat gaccttcacc     420
```

```
gccaccgagc tgatcatgtt ctacatcttt ttcgagacaa cgctgatccc cacactggcc      480
atcatcacca gatggggcaa ccagcctgag agactgaacg ccggcaccta ctttctgttc      540
tacaccctcg tgggcagcct gccactgctg attgccctga tctacaccca caacaccctg      600
ggctccctga acatcctgct gctgacactg acagccaag agctgagcaa cagctgggcc       660
aacaatctga tgtggctggc ctacacaatg gccttcatgg tcaagatgcc cctgtacggc      720
ctgcacctgt ggctgcctaa agctcatgtg gaagccccta tcgccggctc tatggtgctg      780
gctgcagtgc tgctgaaaact cggcggctac ggcatgatgc ggctgaccct gattctgaat     840
cccctgacca agcacatggc ctatccattt ctggtgctga gcctgtgggg catgattatg      900
accagcagca tctgcctgcg gcagaccgat ctgaagtccc tgatcgccta cagctccatc      960
agccacatgg ccctggtggt caccgccatc ctgattcaga ccccttggag ctttacaggc     1020
gccgtgatcc tgatgattgc ccacggcctg acaagcagcc tgctgttttg tctggccaac     1080
agcaactacg agcggaccca cagcagaatc atgatcctgt ctcagggcct gcagaccctc     1140
ctgcctctta tggctttttg gtggctgctg gcctctctgg ccaatctggc actgcctcct     1200
accatcaatc tgctgggcga ctgagcgtg ctggtcacca cattcagctg gtccaatatc      1260
accctgctgc tcaccggcct gaacatgctg gttacagccc tgtactccct gtacatgttc     1320
accaccacac agtggggaag cctgacacac cacatcaaca atatgaagcc cagcttcacc     1380
cgcgagaaca ccctgatgtt catgcatctg agccccattc tgctgctgtc cctgaatcct     1440
gatatcatca ccggcttctc cagctgagag cactgggacg cccaccgccc ctttccctcc     1500
gctgccaggc gagcatgttg tggtaattct ggaacacaag aagagaaatt gctgggttta     1560
gaacaagatt ataacgaat tcggtgctca gtgatcactt gacagttttt ttttttttta      1620
aatattaccc aaaatgctcc ccaaataaga aatgcatcag ctcagtcagt gaatacaaaa     1680
aaggaattat ttttcccttt gagggtcttt tatacatctc tcctccaacc ccaccctcta     1740
ttctgtttct tcctcctcac atgggggtac acatacacag cttcctcttt tggttccatc     1800
cttaccacca caccacacgc acactccaca tgcccagcag agtggcactt ggtggccaga     1860
aagtgtgagc ctcatgatct gctgtctgta gttctgtgag ctcaggtccc tcaaaggcct     1920
cggagcaccc ccttccttgt gactgagcca gggcctgcat ttttggtttt ccccaccca      1980 cacattctca accatagtcc ttctaacaat accaatagct aggacccggc tgctgtgcac     2040
tgggactggg gattccacat gttttgccttg ggagtctcaa gctggactgc ca            2092
```

<210> SEQ ID NO 61
<211> LENGTH: 2892
<212> TYPE: DNA
<213> ORGANISM: Artificial Sequence
<220> FEATURE:
<223> OTHER INFORMATION: COX8-opt_ND4*-3'UTR

<400> SEQUENCE: 61

```
atgtccgtcc tgacgcgcct gctgctgcgg ggcttgacac ggctcggctc ggcggctcca       60
gtgcggcgcg ccagaatcca ttcgttgatg ctgaagctga tcgtgcccac catcatgctg      120
ctgcccctga cctggctgag caagaagcac atgatctgga tcaacaccac cacccacagc      180
ctgatcatca gcatcatccc cctgctgttc ttcaaccaga tcaacaacaa cctgttcagc      240
tgcagcccca ccttcagcag cgaccccctg accaccccc tgctgatgct gaccacctgg      300
ctgctgcccc tgaccatcat ggccagccag cgccacctga gcagcgagcc cctgagccgc      360
aagaagctgt acctgagcat gctgatcagc ctgcagatca gcctgatcat gaccttcacc      420
```

-continued

```
gccaccgagc tgatcatgtt ctacatcttc ttcgagacca ccctgatccc caccctggcc      480
atcatcaccc gctggggcaa ccagcccgag cgcctgaacg ccggcaccta cttcctgttc      540
tacaccctgg tgggcagcct gcccctgctg atcgccctga tctacaccca caacaccctg      600
ggcagcctga acatcctgct gctgaccctg accgccaggg agctgagcaa cagctgggcc      660
aacaacctga tgtggctggc ctacaccatg gccttcatgg tgaagatgcc cctgtacggc      720
ctgcacctgt ggctgcccaa ggcccacgtg gaggcccca tcgccggcag catggtgctg       780
gccgccgtgc tgctgaagct gggcggctac ggcatgatgc gcctgaccct gatcctgaac      840
cccctgacca gcacatggc ctaccccttc tggtgctga gctgtgggg catgatcatg         900 accagcagca tctgcctgcg ccagaccgac ctgaagagcc tgatcgccta cagcagcatc      960
agccacatgg ccctggtggt gaccgccatc ctgatccaga ccccctggag cttcaccggc     1020
gccgtgatcc tgatgatcgc ccacggcctg accagcagcc tgctgttctg cctggccaac     1080
agcaactacg agcgcaccca cagccgcatc atgatcctga ccagggcct gcagaccctg      1140 ctgcccctga tggccttctg gtggctgctg gccagcctgg ccaacctggc cctgcccccc     1200
accatcaacc tgctgggcga gctgagcgtg ctggtgacca ccttcagctg gagcaacatc     1260
accctgctgc tgaccggcct gaacatgctg gtgaccgccc tgtacagcct gtacatgttc     1320
accaccaccc agtggggcag cctgacccac acatcaaca acatgaagcc cagcttcacc      1380
cgcgagaaca ccctgatgtt catgcacctg agccccatcc tgctgctgag cctgaacccc     1440
gacatcatca ccggcttcag cagctaagag cactgggacg cccaccgccc ctttccctcc     1500
gctgccaggc gagcatgttg tggtaattct ggaacacaag aagagaaatt gctgggttta     1560
gaacaagatt ataaacgaat tcggtgctca gtgatcactt gacagttttt ttttttttta     1620
aatattaccc aaaatgctcc ccaaataaga aatgcatcag ctcagtcagt gaatacaaaa     1680
aaggaattat ttttcccttt gagggtcttt tatacatctc tcctccaacc ccaccctcta     1740
ttctgtttct tcctcctcac atgggggtac acatacacag cttcctcttt tggttccatc     1800
cttaccacca caccacacgc acactccaca tgcccagcag agtggcactt ggtggccaga     1860
aagtgtgagc ctcatgatct gctgtctgta gttctgtgag ctcaggtccc tcaaaggcct     1920
cggagcaccc ccttccttgt gactgagcca gggcctgcat ttttggtttt ccccacccca     1980
cacattctca accatagtcc ttctaacaat accaatagct aggacccggc tgctgtgcac     2040
tgggactggg gattccacat gtttgccttg ggagtctcaa gctggactgc cagcccctgt     2100
cctcccttca cccccattgc gtatgagcat ttcagaactc caaggagtca caggcatctt     2160
tatagttcac gttaacatat agacactgtt ggaagcagtt ccttctaaaa gggtagccct     2220
ggacttaata ccagccggat acctctggcc cccaccccat tactgtacct ctggagtcac     2280
tactgtgggt cgccactcct ctgctacaca gcacggcttt ttcaaggctg tattgagaag     2340
ggaagttagg aagaagggtg tgctgggcta accagcccac agagctcaca ttcctgtccc     2400
ttgggtgaaa aatacatgtc catcctgata tctcctgaat tcagaaatta gcctccacat     2460
gtgcaatggc tttaagagcc agaagcaggg ttctgggaat tttgcaagtt acctgtggcc     2520
aggtgtggtc tcggttacca aatacggtta cctgcagctt tttagtcctt tgtgctccca     2580
cgggtctaca gagtcccatc tgcccaaagg tcttgaagct tgacaggatg ttttcgatta     2640
ctcagtctcc cagggcacta ctggtccgta ggattcgatt ggtcggggta ggagagttaa     2700
acaacattta aacagagttc tctcaaaaat gtctaaaggg attgtaggta gataacatcc     2760
```

| aatcactgtt tgcacttatc tgaaatcttc cctcttggct gccccaggt atttactgtg | 2820 |
| gagaacattg cataggaatg tctggaaaaa gcttctacaa cttgttacag ccttcacatt | 2880 |
| tgtagaagct tt | 2892 |

<210> SEQ ID NO 62
<211> LENGTH: 2092
<212> TYPE: DNA
<213> ORGANISM: Artificial Sequence
<220> FEATURE:
<223> OTHER INFORMATION: COX8-opt_ND4*-3'UTR*

<400> SEQUENCE: 62

| atgtccgtcc tgacgcgcct gctgctgcgg ggcttgacac ggctcggctc ggcggctcca | 60 |
| gtgcggcgcg ccagaatcca ttcgttgatg ctgaagctga tcgtgcccac catcatgctg | 120 |
| ctgcccctga cctggctgag caagaagcac atgatctgga tcaacaccac cacccacagc | 180 |
| ctgatcatca gcatcatccc cctgctgttc ttcaaccaga tcaacaacaa cctgttcagc | 240 |
| tgcagcccca ccttcagcag cgacccctg accacccccc tgctgatgct gaccacctgg | 300 |
| ctgctgcccc tgaccatcat ggccagccag cgccacctga gcagcgagcc cctgagccgc | 360 |
| aagaagctgt acctgagcat gctgatcagc ctgcagatca gcctgatcat gaccttcacc | 420 |
| gccaccgagc tgatcatgtt ctacatcttc ttcgagacca ccctgatccc caccctggcc | 480 |
| atcatcaccc gctggggcaa ccagcccgag cgcctgaacg ccggcaccta cttcctgttc | 540 |
| tacaccctgg tgggcagcct gcccctgctg atcgccctga tctacaccca caacaccctg | 600 |
| ggcagcctga acatcctgct gctgacccctg accgccagg agctgagcaa cagctgggcc | 660 |
| aacaacctga tgtggctggc ctacaccatg gccttcatgg tgaagatgcc cctgtacggc | 720 |
| ctgcacctgt ggctgcccaa ggcccacgtg gaggccccca tcgccggcag catggtgctg | 780 |
| gccgccgtgc tgctgaagct gggcggctac ggcatgatgc gcctgaccct gatcctgaac | 840 |
| cccctgacca gcacatggc ctacccctc ctggtgctga gcctgtgggg catgatcatg | 900 |
| accagcagca tctgcctgcg ccagaccgac ctgaagagcc tgatcgccta cagcagcatc | 960 |
| agccacatgg ccctggtggt gaccgccatc ctgatccaga ccccctggag cttcaccggc | 1020 |
| gccgtgatcc tgatgatcgc ccacggcctg accagcagcc tgctgttctg cctggccaac | 1080 |
| agcaactacg agcgcaccca cagccgcatc atgatcctga ccagggcct gcagaccctg | 1140 |
| ctgcccctga tggccttctg gtggctgctg gccagcctgg ccaacctggc cctgcccccc | 1200 |
| accatcaacc tgctgggcga gctgagcgtg ctggtgacca ccttcagctg gagcaacatc | 1260 |
| accctgctgc tgaccggcct gaacatgctg gtgaccgccc tgtacagcct gtacatgttc | 1320 |
| accaccaccc agtggggcag cctgacccac cacatcaaca acatgaagcc cagcttcacc | 1380 |
| cgcgagaaca ccctgatgtt catgcacctg agccccatcc tgctgctgag cctgaacccc | 1440 |
| gacatcatca ccggcttcag cagctaagag cactgggacg cccaccgccc ctttccctcc | 1500 |
| gctgccaggc gagcatgttg tggtaattct ggaacacaag aagagaaatt gctgggttta | 1560 |
| gaacaagatt ataaacgaat tcggtgctca gtgatcactt gacagttttt tttttttta | 1620 |
| aatattaccc aaaatgctcc ccaaataaga aatgcatcag ctcagtcagt gaatacaaaa | 1680 |
| aaggaattat ttttcccttt gagggtcttt tatacatctc tcctccaacc ccaccctcta | 1740 |
| ttctgtttct tcctcctcac atgggggtac acatacacag cttcctcttt tggttccatc | 1800 |
| cttaccacca caccacacgc acactccaca tgcccagcag agtggcactt ggtggccaga | 1860 |
| aagtgtgagc tcatgatct gctgtctgta gttctgtgag ctcaggtccc tcaaaggcct | 1920 |

| cggagcaccc ccttccttgt gactgagcca gggcctgcat ttttggtttt ccccaccccca | 1980 |
| cacattctca accatagtcc ttctaacaat accaatagct aggacccggc tgctgtgcac | 2040 |
| tgggactggg gattccacat gtttgccttg ggagtctcaa gctggactgc ca | 2092 |

<210> SEQ ID NO 63
<211> LENGTH: 2037
<212> TYPE: DNA
<213> ORGANISM: Artificial Sequence
<220> FEATURE:
<223> OTHER INFORMATION: COX8-ND6-3'UTR

<400> SEQUENCE: 63

| atgtccgtcc tgacgcgcct gctgctgcgg ggcttgacac ggctcggctc ggcggctcca | 60 |
| gtgcggcgcg ccagaatcca ttcgttgatg atgtatgctt tgtttctgtt gagtgtgggt | 120 |
| ttagtaatgg ggtttgtggg gttttcttct aagccttctc ctatttatgg gggtttagta | 180 |
| ttgattgtta gcggtgtggt cgggtgtgtt attattctga attttggggg aggttatatg | 240 |
| ggtttaatgg ttttttttaat ttatttaggg ggaatgatgg ttgtctttgg atatactaca | 300 |
| gcgatggcta ttgaggagta tcctgaggca tgggggtcag gggttgaggt cttggtgagt | 360 |
| gttttagtgg ggttagcgat ggaggtagga ttggtgctgt gggtgaaaga gtatgatggg | 420 |
| gtggtggttg tggtaaactt taatagtgta ggaagctgga tgatttatga aggagagggg | 480 |
| tcagggttga ttcgggagga tcctattggt gcggggcctt tgtatgatta tgggcgttgg | 540 |
| ttagtagtag ttactggttg gacattgttt gttggtgtat atattgtaat tgagattgct | 600 |
| cggggggaatt aggagcactg ggacgcccac cgccccttc cctccgctgc caggcgagca | 660 |
| tgttgtggta attctggaac acaagaagag aaattgctgg gtttagaaca agattataaa | 720 |
| cgaattcggt gctcagtgat cacttgacag ttttttttttt ttttaaatat tacccaaaat | 780 |
| gctccccaaa taagaaatgc atcagctcag tcagtgaata caaaaaagga attattttttc | 840 |
| cctttgaggg tctttttatac atctctcctc caaccccacc ctctattctg tttcttcctc | 900 |
| ctcacatggg ggtacacata cacagcttcc tcttttggtt ccatccttac caccacacca | 960 |
| cacgcacact ccacatgccc agcagagtgg cacttggtgg ccagaaagtg tgagcctcat | 1020 |
| gatctgctgt ctgtagttct gtgagctcag gtccctcaaa ggcctcggag cacccccttc | 1080 |
| cttgtgactg agccagggcc tgcatttttg gttttcccca ccccacacat tctcaaccat | 1140 |
| agtccttcta acaataccaa tagctaggac ccggctgctg tgcactggga ctggggattc | 1200 |
| cacatgtttg ccttgggagt ctcaagctgg actgccagcc cctgtcctcc cttcacccccc | 1260 |
| attgcgtatg agcatttcag aactccaagg agtcacaggc atctttatag ttcacgttaa | 1320 |
| catatagaca ctgttggaag cagttccttc taaaagggta gccctggact taataccagc | 1380 |
| cggataccct tggcccccac cccattactg tacctctgga gtcactactg tgggtcgcca | 1440 |
| ctcctctgct acacagcacg gcttttcaa ggctgtattg agaagggaag ttaggaagaa | 1500 |
| gggtgtgctg ggctaaccag cccacagagc tcacattcct gtcccttggg tgaaaaatac | 1560 |
| atgtccatcc tgatatctcc tgaattcaga aattagcctc cacatgtgca atggctttaa | 1620 |
| gagccagaag cagggttctg ggaattttgc aagttacctg tggccaggtg tggtctcggt | 1680 |
| taccaaatac ggttacctgc agcttttttag tcctttgtgc tcccacgggt ctacagagtc | 1740 |
| ccatctgccc aaaggtcttg aagcttgaca ggatgttttc gattactcag tctcccaggg | 1800 |
| cactactggt ccgtaggatt cgattggtcg gggtaggaga gttaaacaac atttaaacag | 1860 |

| agttctctca aaaatgtcta aagggattgt aggtagataa catccaatca ctgtttgcac | 1920 |
| ttatctgaaa tcttccctct tggctgcccc caggtattta ctgtggagaa cattgcatag | 1980 |
| gaatgtctgg aaaaagcttc tacaacttgt tacagccttc acatttgtag aagcttt | 2037 |

<210> SEQ ID NO 64
<211> LENGTH: 1237
<212> TYPE: DNA
<213> ORGANISM: Artificial Sequence
<220> FEATURE:
<223> OTHER INFORMATION: COX8-ND6-3'UTR*

<400> SEQUENCE: 64

| atgtccgtcc tgacgcgcct gctgctgcgg ggcttgacac ggctcggctc ggcggctcca | 60 |
| gtgcggcgcg ccagaatcca ttcgttgatg atgtatgctt tgtttctgtt gagtgtgggt | 120 |
| ttagtaatgg ggtttgtggg gttttcttct aagccttctc ctatttatgg gggtttagta | 180 |
| ttgattgtta gcggtgtggt cgggtgtgtt attattctga attttggggg aggttatatg | 240 |
| ggtttaatgg ttttttttaat ttatttaggg ggaatgatgg ttgtctttgg atatactaca | 300 |
| gcgatggcta ttgaggagta tcctgaggca tggggtcag gggttgaggt cttggtgagt | 360 |
| gttttagtgg ggttagcgat ggaggtagga ttggtgctgt gggtgaaaga gtatgatggg | 420 |
| gtggtggttg tggtaaactt taatagtgta ggaagctgga tgatttatga aggagagggg | 480 |
| tcagggttga ttcgggagga tcctattggt gcggggcctt tgtatgatta tgggcgttgg | 540 |
| ttagtagtag ttactggttg gacattgttt gttggtgtat atattgtaat tgagattgct | 600 |
| cgggggaatt aggagcactg ggacgcccac cgccccttc cctccgctgc caggcgagca | 660 |
| tgttgtggta attctggaac acaagaagag aaattgctgg gtttagaaca agattataaa | 720 |
| cgaattcggt gctcagtgat cacttgacag tttttttttt ttttaaatat acccaaaat | 780 |
| gctccccaaa taagaaatgc atcagctcag tcagtgaata caaaaaagga attattttc | 840 |
| cctttgaggg tcttttatac atctctcctc caaccccacc ctctattctg tttcttcctc | 900 |
| ctcacatggg ggtacacata cacagcttcc tcttttggtt ccatccttac caccacacca | 960 |
| cacgcacact ccacatgccc agcagagtgg cacttggtgg ccagaaagtg tgagcctcat | 1020 |
| gatctgctgt ctgtagttct gtgagctcag gtccctcaaa ggcctcggag cacccccttc | 1080 |
| cttgtgactg agccagggcc tgcattttg gttttcccca ccccacacat tctcaaccat | 1140 |
| agtccttcta acaataccaa tagctaggac ccggctgctg tgcactggga ctggggattc | 1200 |
| cacatgtttg ccttgggagt ctcaagctgg actgcca | 1237 |

<210> SEQ ID NO 65
<211> LENGTH: 2037
<212> TYPE: DNA
<213> ORGANISM: Artificial Sequence
<220> FEATURE:
<223> OTHER INFORMATION: COX8-opt_ND6-3'UTR

<400> SEQUENCE: 65

| atgtccgtcc tgacgcgcct gctgctgcgg ggcttgacac ggctcggctc ggcggctcca | 60 |
| gtgcggcgcg ccagaatcca ttcgttgatg atgtacgccc tgttcctgct gagcgtgggc | 120 |
| ctggtgatgg gcttcgtggg cttcagcagc aagcccagcc ccatctacgg cggcctggtg | 180 |
| ctgatcgtga gcggcgtggt gggctgcgtg atcatcctga acttcggcgg cggctacatg | 240 |
| ggcctgatgg tgttcctgat ctacctgggc ggcatgatgg tggtgttcgg ctacaccacc | 300 |
| gccatggcca tcgaggagta ccccgaggcc tggggcagcg gcgtggaggt gctggtgagc | 360 |

```
gtgctggtgg gcctggccat ggaggtgggc ctggtgctgt gggtgaagga gtacgacggc    420
gtggtggtgg tggtgaactt caacagcgtg ggcagctgga tgatctacga gggcgagggc    480
agcggcctga tccgcgagga ccccatcggc gccggcgccc tgtacgacta cggccgctgg    540
ctggtggtgg tgaccggctg gaccctgttc gtgggcgtgt acatcgtgat cgagatcgcc    600
cgcggcaact aagagcactg gacgcccac cgccccttc cctccgctgc caggcgagca     660
tgttgtggta attctggaac acaagaagag aaattgctgg gtttagaaca agattataaa    720
cgaattcggt gctcagtgat cacttgacag tttttttttt ttttaaatat tacccaaaat    780
gctccccaaa taagaaatgc atcagctcag tcagtgaata caaaaaagga attatttttc    840
cctttgaggg tcttttatac atctctcctc caaccccacc ctctattctg tttcttcctc    900
ctcacatggg ggtacacata cacagcttcc tcttttggtt ccatccttac caccacacca    960
cacgcacact ccacatgccc agcagagtgg cacttggtgg ccagaaagtg tgagcctcat   1020
gatctgctgt ctgtagttct gtgagctcag gtccctcaaa ggcctcggag cacccccttc   1080
cttgtgactg agccagggcc tgcattttg gttttcccca ccccacacat tctcaaccat    1140
agtccttcta acaataccaa tagctaggac ccggctgctg tgcactggga ctggggattc   1200
cacatgtttg ccttgggagt ctcaagctgg actgccagcc cctgtcctcc cttcacccc    1260 attgcgtatg agcatttcag aactccaagg agtcacaggc atctttatag ttcacgttaa   1320
catatagaca ctgttggaag cagttccttc taaaagggta gccctggact taataccagc   1380 cggataccte tggcccccac cccattactg tacctctgga gtcactactg tgggtcgcca   1440
ctcctctgct acacagcacg gcttttttcaa ggctgtattg agaagggaag ttaggaagaa   1500
gggtgtgctg ggctaaccag cccacagagc tcacattcct gtcccttggg tgaaaaatac   1560
atgtccatcc tgatatctcc tgaattcaga aattagcctc cacatgtgca atggctttaa   1620
gagccagaag cagggttctg ggaattttgc aagttacctg tggccaggtg tggtctcggt   1680
taccaaatac ggttacctgc agcttttag tcctttgtgc tcccacgggt ctacagagtc    1740
ccatctgccc aaaggtcttg aagcttgaca ggatgttttc gattactcag tctcccaggg   1800
cactactggt ccgtaggatt cgattggtcg gggtaggaga gttaaacaac atttaaacag   1860
agttctctca aaaatgtcta aagggattgt aggtagataa catccaatca ctgtttgcac   1920
ttatctgaaa tcttccctct tggctgcccc caggtattta ctgtggagaa cattgcatag   1980
gaatgtctgg aaaaagcttc tacaacttgt tacagccttc acatttgtag aagcttt      2037
```

<210> SEQ ID NO 66
<211> LENGTH: 1237
<212> TYPE: DNA
<213> ORGANISM: Artificial Sequence
<220> FEATURE:
<223> OTHER INFORMATION: COX8-opt_ND6-3'UTR*

<400> SEQUENCE: 66

```
atgtccgtcc tgacgcgcct gctgctgcgg ggcttgacac ggctcggctc ggcggctcca     60
gtgcggcgcg ccagaatcca ttcgttgatg atgtacgccc tgttcctgct gagcgtgggc    120
ctggtgatgg gcttcgtggg cttcagcagc aagcccagcc ccatctacgg cggcctggtg    180
ctgatcgtga gcggcgtggt gggctgcgtg atcatcctga acttcggcgg cggctacatg    240
ggcctgatgg tgttcctgat ctacctgggc ggcatgatgg tggtgttcgg ctacaccacc    300
gccatggcca tcgaggagta ccccgaggcc tgggcagcg gcgtggaggt gctggtgagc    360
```

```
gtgctggtgg gcctggccat ggaggtgggc ctggtgctgt gggtgaagga gtacgacggc      420
gtggtggtgg tggtgaactt caacagcgtg ggcagctgga tgatctacga gggcgagggc      480
agcggcctga tccgcgagga ccccatcggc gccggcgccc tgtacgacta cggccgctgg      540
ctggtggtgt gaccggctg gaccctgttc gtgggcgtgt acatcgtgat cgagatcgcc       600
cgcggcaact aagagcactg gacgcccac cgccccttc cctccgctgc caggcgagca        660
tgttgtggta attctggaac acaagaagag aaattgctgg gtttagaaca agattataaa      720
cgaattcggt gctcagtgat cacttgacag tttttttttt ttttaaatat tacccaaaat      780
gctccccaaa taagaaatgc atcagctcag tcagtgaata caaaaaagga attattttc       840 cctttgaggg tcttttatac atctctcctc caaccccacc ctctattctg tttcttcctc      900
ctcacatggg ggtacacata cacagcttcc tcttttggtt ccatccttac caccacacca     960
cacgcacact ccacatgccc agcagagtgg cacttggtgg ccagaaagtg tgagcctcat     1020
gatctgctgt ctgtagttct gtgagctcag gtccctcaaa ggcctcggag cacccccttc    1080
cttgtgactg agccagggcc tgcatttttg gttttcccca ccccacacat tctcaaccat    1140
agtccttcta acaataccaa tagctaggac ccggctgctg tgcactggga ctggggattc    1200
cacatgtttg ccttgggagt ctcaagctgg actgcca                            1237

<210> SEQ ID NO 67
<211> LENGTH: 2463
<212> TYPE: DNA
<213> ORGANISM: Artificial Sequence
<220> FEATURE:
<223> OTHER INFORMATION: COX8-ND1-3'UTR

<400> SEQUENCE: 67
atgtccgtcc tgacgcgcct gctgctgcgg ggcttgacac ggctcggctc ggcggctcca        60
gtgcggcgcg ccagaatcca ttcgttgatg gccaacctcc tactcctcat tgtacccatt      120
ctaatcgcaa tggcattcct aatgcttacc gaacgaaaaa ttctaggcta tatgcaacta      180
cgcaaaggcc ccaacgttgt aggcccctac gggctactac aacccttcgc tgacgccata      240
aaactcttca ccaaagagcc cctaaaaccc gccacatcta ccatcaccct ctacatcacc      300
gccccgacct tagctctcac catcgctctt ctactatgga ccccccctccc catgcccaac    360 cccctggtca acctcaacct aggcctccta tttattctag ccacctctag cctagccgtt      420
tactcaatcc tctggtcagg gtgggcatca aactcaaact acgccctgat cggcgcactg      480
cgagcagtag cccaaacaat ctcatatgaa gtcaccctag ccatcattct actatcaaca     540
ttactaatga gtggctcctt taacctctcc accttatca caacacaaga cacctctgg       600 ttactcctgc catcatggcc cttggccatg atgtggttta ctccacact agcagagacc      660 aaccgaaccc ccttcgacct gccgaaggg gagtccgaac tagtctcagg cttcaacatc      720
gaatacgccg caggcccctt cgccctattc ttcatggccg aatacacaaa cattattatg     780
atgaacaccc tcaccactac aatcttccta ggaacaacat atgacgcact cccctgaa      840 ctctacacaa catattttgt caccaagacc ctacttctaa cctccctgtt cttatggatt   900
cgaacagcat accccgatt ccgctacgac caactcatgc acctcctatg gaaaaacttc     960
ctaccactca ccctagcatt acttatgtgg tatgtctcca tgcccattac aatctccagc   1020 attcccctc aaacctaaga gcactgggac gccaccgcc cctttccctc cgctgccagg    1080
cgagcatgtt gtggtaattc tggaacacaa gaagagaaat tgctgggttt agaacaagat    1140
tataaacgaa ttcggtgctc agtgatcact tgacagtttt tttttttttt aaatattacc    1200
```

```
caaaatgctc cccaaataag aaatgcatca gctcagtcag tgaatacaaa aaaggaatta    1260 ttttccctt tgagggtctt ttatacatct ctcctccaac cccaccctct attctgtttc     1320
ttcctcctca catggggta cacatacaca gcttcctctt ttggttccat ccttaccacc     1380
acaccacacg cacactccac atgcccagca gagtggcact tggtggccag aaagtgtgag    1440
cctcatgatc tgctgtctgt agttctgtga gctcaggtcc ctcaaaggcc tcggagcacc    1500
cccttccttg tgactgagcc agggcctgca ttttggttt tccccacccc acacattctc     1560
aaccatagtc cttctaacaa taccaatagc taggacccgg ctgctgtgca ctgggactgg    1620
ggattccaca tgtttgcctt gggagtctca agctggactg ccagccctg tcctcccttc     1680 accccattg cgtatgagca tttcagaact ccaaggagtc acaggcatct ttatagttca     1740
cgttaacata tagacactgt tggaagcagt tccttctaaa agggtagccc tggacttaat    1800
accagccgga tacctctggc ccccacccca ttactgtacc tctggagtca ctactgtggg    1860
tcgccactcc tctgctacac agcacggctt tttcaaggct gtattgagaa gggaagttag    1920
gaagaagggt gtgctgggct aaccagccca cagagctcac attcctgtcc cttgggtgaa    1980
aaatacatgt ccatcctgat atctcctgaa ttcagaaatt agcctccaca tgtgcaatgg    2040
ctttaagagc cagaagcagg gttctgggaa ttttgcaagt tacctgtggc caggtgtggt    2100
ctcggttacc aaatacggtt acctgcagct ttttagtcct ttgtgctccc acgggtctac    2160
agagtcccat ctgcccaaag gtcttgaagc ttgacaggat gttttcgatt actcagtctc    2220
ccagggcact actggtccgt aggattcgat tggtcggggt aggagagtta acaacatt    2280 aaacagagtt ctctcaaaaa tgtctaaagg gattgtaggt agataacatc caatcactgt    2340
ttgcacttat ctgaaatctt ccctcttggc tgccccagg tatttactgt ggagaacatt     2400
gcataggaat gtctggaaaa agcttctaca acttgttaca gccttcacat ttgtagaagc    2460
ttt                                                                  2463

<210> SEQ ID NO 68
<211> LENGTH: 1663
<212> TYPE: DNA
<213> ORGANISM: Artificial Sequence
<220> FEATURE:
<223> OTHER INFORMATION: COX8-ND1-3'UTR*

<400> SEQUENCE: 68
atgtccgtcc tgacgcgcct gctgctgcgg ggcttgacac ggctcggctc ggcggctcca      60
gtgcggcgcg ccagaatcca ttcgttgatg gccaacctcc tactcctcat tgtacccatt    120
ctaatcgcaa tggcattcct aatgcttacc gaacgaaaaa ttctaggcta tatgcaacta    180
cgcaaaggcc ccaacgttgt aggccctac gggctactac aaccttcgc tgacgccata      240 aaactcttca ccaaagagcc cctaaaaccc gccacatcta ccatcaccct ctacatcacc    300
gccccgacct tagctctcac catcgctctt ctactatgga ccccctccc catgcccaac    360 cccctggtca acctcaacct aggcctccta tttattctag ccacctctag cctagccgtt    420
tactcaatcc tctggtcagg gtgggcatca aactcaaact acgccctgat cggcgcactg    480
cgagcagtag cccaaacaat ctcatatgaa gtcaccctag ccatcattct actatcaaca    540
ttactaatga gtggctcctt taacctctcc acccttatca aacacaaga acacctctgg    600 ttactcctgc catcatggcc cttggccatg atgtggttta tctccacact agcagagacc    660
aaccgaaccc ccttcgacct tgccgaaggg gagtccgaac tagtctcagg cttcaacatc    720
```

```
gaatacgccg caggcccctt cgccctattc ttcatggccg aatacacaaa cattattatg    780
atgaacaccc tcaccactac aatcttccta ggaacaacat atgacgcact ctcccctgaa    840
ctctacacaa catattttgt caccaagacc ctacttctaa cctccctgtt cttatggatt    900
cgaacagcat accccgatt ccgctacgac caactcatgc acctcctatg gaaaaacttc     960
ctaccactca ccctagcatt acttatgtgg tatgtctcca tgcccattac aatctccagc   1020 attcccctc aaacctaaga gcactggac gcccaccgcc cctttccctc cgctgccagg    1080
cgagcatgtt gtggtaattc tggaacacaa gaagagaaat tgctgggttt agaacaagat   1140
tataaacgaa ttcggtgctc agtgatcact tgacagtttt ttttttttt aaatattacc    1200 caaaatgctc cccaaataag aaatgcatca gctcagtcag tgaatacaaa aaaggaatta   1260 ttttttccctt tgagggtctt ttatacatct ctcctccaac cccacccctct attctgtttc  1320 ttcctcctca catggggta cacatacaca gcttcctctt ttggttccat ccttaccacc   1380
acaccacacg cacactccac atgcccagca gagtggcact tggtggccag aaagtgtgag   1440
cctcatgatc tgctgtctgt agttctgtga gctcaggtcc ctcaaaggcc tcggagcacc   1500
cccttccttg tgactgagcc agggcctgca ttttggttt tccccacccc acacattctc    1560
aaccatagtc cttctaacaa taccaatagc taggacccgg ctgctgtgca ctgggactgg   1620
ggattccaca tgtttgcctt gggagtctca agctggactg cca                    1663
```

<210> SEQ ID NO 69
<211> LENGTH: 2463
<212> TYPE: DNA
<213> ORGANISM: Artificial Sequence
<220> FEATURE:
<223> OTHER INFORMATION: COX8-opt_ND1-3'UTR

<400> SEQUENCE: 69

```
atgtccgtcc tgacgcgcct gctgctgcgg ggcttgacac ggctcggctc ggcggctcca     60
gtgcggcgcg ccagaatcca ttcgttgatg gccaacctgc tgctgctgat cgtgcccatc    120
ctgatcgcca tggccttcct gatgctgacc gagcgcaaga tcctgggcta catgcagctg    180
cgcaagggcc caacgtggt gggcccctac ggctgctgc agcccttcgc cgacgccatc      240
aagctgttca ccaaggagcc cctgaagccc gccaccagca ccatcaccct gtacatcacc    300
gcccccaccc tggccctgac catcgccctg ctgctgtgga cccccctgcc catgcccaac   360
cccctggtga acctgaacct gggcctgctg ttcatcctgg ccaccagcag cctggccgtg    420
tacagcatcc tgtggagcgg ctgggccagc aacagcaact acgccctgat cggcgccctg   480
cgcgccgtgg cccagaccat cagctacgag gtgaccctgg ccatcatcct gctgagcacc   540
ctgctgatga cggcagctt caacctgagc accctgatca ccacccagga gcacctgtgg    600
ctgctgctgc ccagctggcc cctggccatg atgtggttca tcagcacccct ggccgagacc   660 aaccgcaccc ccttcgacct ggccgaggc gagagcgagc tggtgagcgg cttcaacatc    720
gagtacgccg ccggcccctt cgccctgttc ttcatggccg agtacaccaa catcatcatg    780
atgaacaccc tgaccaccac catcttcctg ggcaccacct acgacgccct gagccccgag   840
ctgtacacca cctacttcgt gaccaagacc ctgctgctga ccagcctgtt cctgtggatc    900
cgcaccgcct accccgctt ccgctacgac cagctgatgc acctgctgtg gaagaacttc    960 ctgccctga ccctggccct gctgatgtgg tacgtgagca tgcccatcac catcagcagc   1020
atcccccccc agacctaaga gcactggac gcccaccgcc cctttccctc cgctgccagg   1080
cgagcatgtt gtggtaattc tggaacacaa gaagagaaat tgctgggttt agaacaagat   1140
```

| | |
|---|---|
| tataaacgaa ttcggtgctc agtgatcact tgacagtttt ttttttttt aaatattacc | 1200 |
| caaaatgctc cccaaataag aaatgcatca gctcagtcag tgaatacaaa aaaggaatta | 1260 |
| ttttcccctt tgagggtctt ttatacatct ctcctccaac cccaccctct attctgtttc | 1320 |
| ttcctcctca catgggggta cacatacaca gcttcctctt ttggttccat ccttaccacc | 1380 |
| acaccacacg cacactccac atgcccagca gagtggcact tggtggccag aaagtgtgag | 1440 |
| cctcatgatc tgctgtctgt agttctgtga gctcaggtcc ctcaaaggcc tcggagcacc | 1500 |
| cccttccttg tgactgagcc agggcctgca ttttggttt tccccacccc acacattctc | 1560 |
| aaccatagtc cttctaacaa taccaatagc taggacccgg ctgctgtgca ctgggactgg | 1620 |
| ggattccaca tgtttgcctt gggagtctca agctggactg ccagcccctg tcctcccttc | 1680 |
| accccattg cgtatgagca tttcagaact ccaaggagtc acaggcatct ttatagttca | 1740 |
| cgttaacata tagacactgt tggaagcagt tccttctaaa agggtagccc tggacttaat | 1800 |
| accagccgga tacctctggc ccccacccca ttactgtacc tctggagtca ctactgtggg | 1860 |
| tcgccactcc tctgctacac agcacggctt tttcaaggct gtattgagaa gggaagttag | 1920 |
| gaagaagggt gtgctgggct aaccagccca cagagctcac attcctgtcc cttgggtgaa | 1980 |
| aaatacatgt ccatcctgat atctcctgaa ttcagaaatt agcctccaca tgtgcaatgg | 2040 |
| ctttaagagc cagaagcagg gttctgggaa ttttgcaagt tacctgtggc caggtgtggt | 2100 |
| ctcggttacc aaatacggtt acctgcagct ttttagtcct ttgtgctccc acgggtctac | 2160 |
| agagtcccat ctgcccaaag gtcttgaagc ttgacaggat gttttcgatt actcagtctc | 2220 |
| ccagggcact actggtccgt aggattcgat tggtcggggt aggagagtta acaacattt | 2280 |
| aaacagagtt ctctcaaaaa tgtctaaagg gattgtaggt agataacatc caatcactgt | 2340 |
| ttgcacttat ctgaaatctt ccctcttggc tgccccagg tatttactgt ggagaacatt | 2400 |
| gcataggaat gtctggaaaa agcttctaca acttgttaca gccttcacat ttgtagaagc | 2460 |
| ttt | 2463 |

<210> SEQ ID NO 70
<211> LENGTH: 1663
<212> TYPE: DNA
<213> ORGANISM: Artificial Sequence
<220> FEATURE:
<223> OTHER INFORMATION: COX8-opt_ND1-3'UTR*

<400> SEQUENCE: 70

| | |
|---|---|
| atgtccgtcc tgacgcgcct gctgctgcgg ggcttgacac ggctcggctc ggcggctcca | 60 |
| gtgcggcgcg ccagaatcca ttcgttgatg gccaacctgc tgctgctgat cgtgcccatc | 120 |
| ctgatcgcca tggccttcct gatgctgacc gagcgcaaga tcctgggcta catgcagctg | 180 |
| cgcaagggcc ccaacgtggt gggcccctac ggcctgctgc agcccttcgc cgacgccatc | 240 |
| aagctgttca ccaaggagcc cctgaagccc gccaccagca ccatcaccct gtacatcacc | 300 |
| gcccccaccc tggccctgac catcgccctg ctgctgtgga cccccctgcc catgcccaac | 360 |
| cccctggtga acctgaacct gggcctgctg ttcatcctgg ccaccagcag cctggccgtg | 420 |
| tacagcatcc tgtggagcgg ctgggccagc aacagcaact acgccctgat cggcgccctg | 480 |
| cgcgccgtgg cccagaccat cagctacgag gtgaccctgg ccatcatcct gctgagcacc | 540 |
| ctgctgatga cgcggcagct tcaacctgagc accctgatca ccacccagga gcacctgtgg | 600 |
| ctgctgctgc ccagctggcc cctggccatg atgtggttca tcagcaccct ggccgagacc | 660 |

| | |
|---|---|
| aaccgcaccc ccttcgacct ggccgagggc gagagcgagc tggtgagcgg cttcaacatc | 720 |
| gagtacgccg ccggcccctt cgccctgttc ttcatggccg agtacaccaa catcatcatg | 780 |
| atgaacaccc tgaccaccac catcttcctg gcaccacct acgacgccct gagccccgag | 840 |
| ctgtacacca cctacttcgt gaccaagacc ctgctgctga ccagcctgtt cctgtggatc | 900 |
| cgcaccgcct accccgctt ccgctacgac cagctgatgc acctgctgtg gaagaacttc | 960 |
| ctgcccctga ccctggccct gctgatgtgg tacgtgagca tgcccatcac catcagcagc | 1020 |
| atcccccccc agacctaaga gcactgggac gcccaccgcc cctttccctc cgctgccagg | 1080 |
| cgagcatgtt gtggtaattc tggaacacaa gaagagaaat tgctgggttt agaacaagat | 1140 |
| tataaacgaa ttcggtgctc agtgatcact tgacagtttt ttttttttt aaatattacc | 1200 |
| caaaatgctc cccaaataag aaatgcatca gctcagtcag tgaatacaaa aaaggaatta | 1260 |
| ttttccctt tgagggtctt ttatacatct ctcctccaac cccaccctct attctgtttc | 1320 |
| ttcctcctca catgggggta cacatacaca gcttcctctt ttggttccat ccttaccacc | 1380 |
| acaccacacg cacactccac atgcccagca gagtggcact tggtggccag aaagtgtgag | 1440 |
| cctcatgatc tgctgtctgt agttctgtga gctcaggtcc ctcaaaggcc tcggagcacc | 1500 |
| cccttccttg tgactgagcc agggcctgca ttttggttt tccccacccc acacattctc | 1560 |
| aaccatagtc cttctaacaa taccaatagc taggacccgg ctgctgtgca ctgggactgg | 1620 |
| ggattccaca tgtttgcctt gggagtctca agctggactg cca | 1663 |

<210> SEQ ID NO 71
<211> LENGTH: 3071
<212> TYPE: DNA
<213> ORGANISM: Artificial Sequence
<220> FEATURE:
<223> OTHER INFORMATION: OPA1-ND4-3'UTR

<400> SEQUENCE: 71

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggggctc ccgcgtggcc gtctcggcgc ctgcgtgacc tccccgccgg cgggatgtgg | 240 |
| cgactacgtc gggccgctgt ggcctgatgc taaaactaat cgtcccaaca attatgttac | 300 |
| taccactgac atggctttcc aaaaaacaca tgatttggat caacacaacc acccacagcc | 360 |
| taattattag catcatccct ctactatttt ttaaccaaat caacaacaac ctatttagct | 420 |
| gttccccaac cttttcctcc gaccccctaa caacccccct cctaatgcta actacctggc | 480 |
| tcctaccccct cacaatcatg gcaagccaac gccacttatc cagtgaacca ctatcacgaa | 540 |
| aaaaactcta cctctctatg ctaatctccc tacaaatctc cttaattatg acattcacag | 600 |
| ccacagaact aatcatgttt tatatcttct tcgaaccac acttatcccc accttggcta | 660 |
| tcatcacccg atggggcaac cagccagaac gcctgaacgc aggcacatac ttcctattct | 720 |
| acaccctagt aggctcccctt cccctactca tcgcactaat ttacactcac aacaccctag | 780 |
| gctcactaaa cattctacta ctcactctca ctgcccaaga actatcaaac tcctgggcca | 840 |
| acaacttaat gtggctagct tacacaatgg cttttatggt aaagatgcct ctttacggac | 900 |
| tccacttatg gctccctaaa gcccatgtcg aagcccccat cgctgggtca atggtacttg | 960 |
| ccgcagtact cttaaaacta ggcggctatg gtatgatgcg cctcacactc attctcaacc | 1020 |
| ccctgacaaa acacatggcc tacccccttcc ttgtactatc cctatggggc atgattatga | 1080 |

```
caagctccat ctgcctacga caaacagacc taaaatcgct cattgcatac tcttcaatca    1140
gccacatggc cctcgtagta acagccattc tcatccaaac ccctggagc ttcaccggcg     1200 cagtcattct catgatcgcc cacgggctta catcctcatt actattctgc ctagcaaact    1260
caaactacga acgcactcac agtcgcatca tgatcctctc tcaaggactt caaactctac    1320
tcccactaat ggcttttgg tggcttctag caagcctcgc taacctcgcc ttaccccca     1380 ctattaacct actgggagaa ctctctgtgc tagtaaccac gttctcctgg tcaaatatca    1440
ctctcctact tacaggactc aacatgctag tcacagccct atactccctc tacatgttta    1500
ccacaacaca atggggctca ctcacccacc acattaacaa catgaaaccc tcattcacac    1560
gagaaaacac cctcatgttc atgcacctat ccccattct cctcctatcc ctcaaccccg     1620
acatcattac cgggttttcc tcttaagagc actgggacgc ccaccgcccc tttccctccg    1680
ctgccaggcg agcatgttgt ggtaattctg gaacacaaga agagaaattg ctgggtttag    1740
aacaagatta taaacgaatt cggtgctcag tgatcacttg acagtttttt tttttttaa     1800 atattaccca aaatgctccc caaataagaa atgcatcagc tcagtcagtg aatacaaaaa    1860
aggaattatt tttcccttg agggtctttt atacatctct cctccaaccc caccctctat     1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac     2160 acattctcaa ccatagtcct tctaacaata ccaatagcta ggacccggct gctgtgcact    2220
gggactgggg attccacatg tttgccttgg gagtctcaag ctggactgcc agccctgtc     2280 ctcccttcac ccccattgcg tatgagcatt tcagaactcc aaggagtcac aggcatcttt    2340
atagttcacg ttaacatata gacactgttg gaagcagttc cttctaaaag ggtagccctg    2400
gacttaatac cagccggata cctctggccc ccacccatt actgtacctc tggagtcact     2460
actgtgggtc gccactcctc tgctacacag cacggctttt tcaaggctgt attgagaagg    2520
gaagttagga agaagggtgt gctgggctaa ccagcccaca gagctcacat tcctgtccct    2580
tgggtgaaaa atacatgtcc atcctgatat ctcctgaatt cagaaattag cctccacatg    2640
tgcaatggct ttaagagcca gaagcagggt tctgggaatt ttgcaagtta cctgtggcca    2700
ggtgtggtct cggttaccaa atacggttac ctgcagcttt ttagtccttt gtgctcccac    2760
gggtctacag agtcccatct gcccaaaggt cttgaagctt acaggatgt tttcgattac      2820 tcagtctccc agggcactac tggtccgtag gattcgattg gtcggggtag gagagttaaa    2880 caacattta acagagttct ctcaaaaatg tctaaaggga ttgtaggtag ataacatcca     2940
atcactgttt gcacttatct gaaatcttcc ctcttggctg ccccaggta tttactgtgg     3000 agaacattgc ataggaatgt ctggaaaaag cttctacaac ttgttacagc cttcacattt    3060
gtagaagctt t                                                          3071
```

<210> SEQ ID NO 72
<211> LENGTH: 2271
<212> TYPE: DNA
<213> ORGANISM: Artificial Sequence
<220> FEATURE:
<223> OTHER INFORMATION: OPA1-ND4-3'UTR*

<400> SEQUENCE: 72

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggcte ccgcgtggcc gtctcggcgc ctgcgtgacc tccccgccgg cgggatgtgg      240
cgactacgtc gggccgctgt ggcctgatgc taaaactaat cgtcccaaca attatgttac     300
taccactgac atggctttcc aaaaaacaca tgatttggat caacacaacc acccacagcc     360
taattattag catcatccct ctactatttt ttaaccaaat caacaacaac ctatttagct     420
gttccccaac cttttcctcc gaccccctaa caaccccccct cctaatgcta actacctggc    480
tcctacccct cacaatcatg gcaagccaac gccacttatc cagtgaacca ctatcacgaa     540
aaaaactcta cctctctatg ctaatctccc tacaaatctc cttaattatg acattcacag     600
ccacagaact aatcatgttt tatatcttct tcgaaaccac acttatcccc accttggcta     660
tcatcacccg atggggcaac cagccagaac gcctgaacgc aggcacatac ttcctattct     720
acaccctagt aggctccctt cccctactca tcgcactaat ttacactcac aacaccctag     780
gctcactaaa cattctacta ctcactctca ctgcccaaga actatcaaac tcctgggcca     840
acaacttaat gtggctagct tacacaatgg cttttatggt aaagatgcct ctttacggac     900
tccacttatg gctccctaaa gcccatgtcg aagcccccat cgctgggtca atggtacttg     960
ccgcagtact cttaaaacta gcggctatg gtatgatgcg cctcacactc attctcaacc    1020
ccctgacaaa acacatggcc taccccttcc ttgtactatc cctatggggc atgattatga   1080
caagctccat ctgcctacga caaacagacc taaaatcgct cattgcatac tcttcaatca   1140
gccacatggc cctcgtagta acagccattc tcatccaaac ccctggagc ttcaccggcg    1200
cagtcattct catgatcgcc cacgggctta catcctcatt actattctgc ctagcaaact   1260
caaactacga acgcactcac agtcgcatca tgatcctctc tcaaggactt caaactctac   1320
tcccactaat ggcttttttgg tggcttctag caagcctcgc taacctcgcc ttaccccca    1380
ctattaaccct actgggagaa ctctctgtgc tagtaaccac gttctcctgg tcaaatatca   1440
ctctcctact tacaggactc aacatgctag tcacagccct atactccctc tacatgttta   1500
ccacaacaca atggggctca ctcacccacc acattaacaa catgaaaccc tcattcacac   1560
gagaaaacac cctcatgttc atgcacctat cccccattct cctcctatcc ctcaaccccg   1620
acatcattac cgggttttcc tcttaagagc actgggacgc ccaccgcccc tttccctccg   1680
ctgccaggcg agcatgttgt ggtaattctg gaacacaaga agagaaattg ctgggtttag   1740
aacaagatta taaacgaatt cggtgctcag tgatcacttg acagttttt tttttttaa     1800
atattaccca aaatgctccc caaataagaa atgcatcagc tcagtcagtg aatacaaaaa    1860
aggaattatt tttcccttg agggtctttt atacatctct cctccaaccc caccctctat    1920
tctgtttctt cctcctcaca tgggggtaca catacacagc ttcctctttt ggttccatcc   1980
ttaccaccac accacacgca cactccacat gcccagcaga gtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc ccacccccac   2160
acattctcaa ccatagtcct tctaacaata ccaatagcta ggacccggct gctgtgcact   2220
gggactgggg attccacatg tttgccttgg gagtctcaag ctggactgcc a            2271
```

<210> SEQ ID NO 73
<211> LENGTH: 3071

<212> TYPE: DNA
<213> ORGANISM: Artificial Sequence
<220> FEATURE:
<223> OTHER INFORMATION: OPA1-opt_ND4-3'UTR

<400> SEQUENCE: 73

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggGCTC ccgcgtggcc gtctcggcgc ctgcgtgacc tccccgccgg cgggatgtgg     240
cgactacgtc gggccgctgt ggcctgatgc tgaagctgat cgtgcccacc atcatgctgc     300
tgcctctgac ctggctgagc aagaaacaca tgatctggat caacaccacc acgcacagcc     360
tgatcatcag catcatccct ctgctgttct caaccagat caacaacaac ctgttcagct     420
gcagccccac cttcagcagc gaccctctga caacacctct gctgatgctg accacctggc     480
tgctgccccT cacaatcatg gcctctcaga gacacctgag cagcgagccc ctgagccgga     540
agaaactgta cctgagcatg ctgatctccc tgcagatctc tctgatcatg accttcaccg     600
ccaccgagct gatcatgttc tacatctttt tcgagacaac gctgatcccc acactggcca     660
tcatcaccag atggggcaac cagcctgaga gactgaacgc cggcacctac tttctgttct     720
acaccctcgt gggcagcctg ccactgctga ttgccctgat ctacacccac aacaccctgg     780
gctccctgaa catcctgctg ctgacactga gcccaaga gctgagcaac agctgggcca     840
acaatctgat gtggctggcc tacacaatgg ccttcatggt caagatgccc ctgtacggcc     900
tgcacctgtg gctgcctaaa gctcatgtgg aagcccctat cgccggctct atggtgctgg     960
ctgcagtgct gctgaaactc ggcggctacg catgatgcg gctgaccctg attctgaatc    1020
ccctgaccaa gcacatggcc tatccatttc tggtgctgag cctgtggggc atgattatga    1080
ccagcagcat ctgcctgcgg cagaccgatc tgaagtccct gatcgcctac agctccatca    1140
gccacatggc cctggtggtc accgccatcc tgattcagac cccttggagc tttacaggcg    1200
ccgtgatcct gatgattgcc cacggcctga caagcagcct gctgttttgt ctggccaaca    1260
gcaactacga gcggacccac agcagaatca tgatcctgtc tcagggcctg cagaccctcc    1320
tgcctcttat ggcttttggg tggctgctgg cctctctggc caatctggca ctgcctccta    1380
ccatcaatct gctgggcgag ctgagcgtgc tggtcaccac attcagctgg tccaatatca    1440
ccctgctgct caccggcctg aacatgctgg ttacagccct gtactccctg tacatgttca    1500
ccaccacaca gtggggaagc ctgacacacc acatcaacaa tatgaagccc agcttcaccc    1560
gcgagaacac cctgatgttc atgcatctga gccccattct gctgctgtcc ctgaatcctg    1620
atatcatcac cggcttctcc agctgagagc actgggacgc ccaccgcccc tttccctccg    1680
ctgccaggcg agcatgttgt ggtaattctg gaacacaaga gagaaattg ctgggtttag     1740
aacaagatta taaacgaatt cggtgctcag tgatcacttg acagttttttt tttttttaa    1800
atattaccca aaatgctccc caaataagaa atgcatcagc tcagtcagtg aatacaaaaa    1860
aggaattatt tttcccttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac     2160
```

```
acattctcaa ccatagtcct tctaacaata ccaatagcta ggacccggct gctgtgcact    2220
gggactgggg attccacatg tttgccttgg gagtctcaag ctggactgcc agcccctgtc    2280
ctcccttcac ccccattgcg tatgagcatt tcagaactcc aaggagtcac aggcatcttt    2340
atagttcacg ttaacatata gacactgttg gaagcagttc cttctaaaag ggtagccctg    2400
gacttaatac cagccggata cctctggccc ccaccccatt actgtacctc tggagtcact    2460
actgtgggtc gccactcctc tgctacacag cacggctttt tcaaggctgt attgagaagg    2520
gaagttagga agaagggtgt gctgggctaa ccagcccaca gagctcacat tcctgtccct    2580
tgggtgaaaa atacatgtcc atcctgatat ctcctgaatt cagaaattag cctccacatg    2640
tgcaatggct ttaagagcca gaagcagggt tctgggaatt ttgcaagtta cctgtggcca    2700
ggtgtggtct cggttaccaa atacggttac ctgcagcttt ttagtccttt gtgctcccac    2760
gggtctacag agtcccatct gcccaaaggt cttgaagctt gacaggatgt tttcgattac    2820
tcagtctccc agggcactac tggtcctag gattcgattg gtcggggtag gagagttaaa    2880
caacatttaa acagagttct ctcaaaaatg tctaaaggga ttgtaggtag ataacatcca    2940
atcactgttt gcacttatct gaaatcttcc ctcttggctg ccccaggta tttactgtgg    3000 agaacattgc ataggaatgt ctggaaaaag cttctacaac ttgttacagc cttcacattt    3060
gtagaagctt t    3071
```

<210> SEQ ID NO 74
<211> LENGTH: 2271
<212> TYPE: DNA
<213> ORGANISM: Artificial Sequence
<220> FEATURE:
<223> OTHER INFORMATION: OPA1-opt_ND4-3'UTR*

<400> SEQUENCE: 74

```
gtgctgcccg cctagaaagg gtgaagtggt tgtttccgtg acggactgag tacgggtgcc     60
tgtcaggctc ttgcggaagt ccatgcgcca ttgggagggc ctcggccgcg gctctgtgcc    120
cttgctgctg agggccactt cctgggtcat tcctggaccg ggagccgggc tggggctcac    180 acggggctc ccgcgtggcc gtctcggcgc ctgcgtgacc tccccgccgg cgggatgtgg    240
cgactacgtc gggccgctgt ggcctgatgc tgaagctgat cgtgcccacc atcatgctgc    300
tgcctctgac ctggctgagc aagaaacaca tgatctggat caacaccacc acgcacagcc    360
tgatcatcag catcatccct ctgctgttct tcaaccagat caacaacaac ctgttcagct    420
gcagccccac cttcagcagc gaccctctga caacacctct gctgatgctg accacctggc    480
tgctgcccct cacaatcatg gcctctcaga gacacctgag cagcgagccc ctgagccgga    540
agaaactgta cctgagcatg ctgatctccc tgcagatctc tctgatcatg accttcaccg    600
ccaccgagct gatcatgttc tacatctttt tcgagacaac gctgatcccc acactggcca    660
tcatcaccag atggggcaac cagcctgaga gactgaacgc cggcacctac tttctgttct    720 acacctcgt gggcagcctg ccactgctga ttgccctgat ctacacccac aacaccctgg    780
gctccctgaa catcctgctg ctgacactga gcccaagga gctgagcaac agctgggcca    840
acaatctgat gtggctggcc tacacaatgg ccttcatggt caagatgccc ctgtacggcc    900
tgcacctgtg gctgcctaaa gctcatgtgg aagccctat cgccggctct atggtgctgg    960
ctgcagtgct gctgaaactc ggcggctacg gcatgatgcg gctgaccctg attctgaatc   1020
ccctgaccaa gcacatggcc tatccatttc tggtgctgag cctgtggggc atgattatga   1080
ccagcagcat ctgcctgcgg cagaccgatc tgaagtccct gatcgcctac agctccatca   1140
```

```
gccacatggc cctggtggtc accgccatcc tgattcagac cccttggagc tttacaggcg    1200
ccgtgatcct gatgattgcc cacggcctga caagcagcct gctgttttgt ctggccaaca    1260
gcaactacga gcggacccac agcagaatca tgatcctgtc tcagggcctg cagaccctcc    1320
tgcctcttat ggcttttttgg tggctgctgg cctctctggc caatctggca ctgcctccta    1380
ccatcaatct gctgggcgag ctgagcgtgc tggtcaccac attcagctgg tccaatatca    1440
ccctgctgct caccggcctg aacatgctgg ttacagccct gtactccctg tacatgttca    1500
ccaccacaca gtggggaagc ctgacacacc acatcaacaa tatgaagccc agcttcaccc    1560
gcgagaacac cctgatgttc atgcatctga gccccattct gctgctgtcc ctgaatcctg    1620
atatcatcac cggcttctcc agctgagagc actgggacgc ccaccgcccc tttccctccg    1680
ctgccaggcg agcatgttgt ggtaattctg aacacaagag agagaaattg ctgggtttag    1740
aacaagatta taaacgaatt cggtgctcag tgatcacttg acagttttt tttttttaa    1800 atattaccca aaatgctccc caaataagaa atgcatcagc tcagtcagtg aatacaaaaa    1860
aggaattatt tttcccttg agggtctttt atacatctct cctccaaccc caccctctat    1920
tctgtttctt cctcctcaca tgggggtaca catacacagc ttcctctttt ggttccatcc    1980
ttaccaccac accacacgca cactccacat gcccagcaga gtggcacttg gtggccagaa    2040
agtgtgagcc tcatgatctg ctgtctgtag ttctgtgagc tcaggtccct caaaggcctc    2100
ggagcacccc cttccttgtg actgagccag ggcctgcatt tttggttttc cccacccac    2160 acattctcaa ccatagtcct tctaacaata ccaatagcta ggacccggct gctgtgcact    2220
gggactgggg attccacatg tttgccttgg gagtctcaag ctggactgcc a             2271
```

<210> SEQ ID NO 75
<211> LENGTH: 3071
<212> TYPE: DNA
<213> ORGANISM: Artificial Sequence
<220> FEATURE:
<223> OTHER INFORMATION: OPA1-opt_ND4*-3'UTR

<400> SEQUENCE: 75

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg     240
cgactacgtc gggccgctgt ggcctgatgc tgaagctgat cgtgcccacc atcatgctgc     300
tgcccctgac ctggctgagc aagaagcaca tgatctggat caacaccacc acccacagcc     360
tgatcatcag catcatcccc ctgctgttct tcaaccagat caacaacaac ctgttcagct     420
gcagccccac cttcagcagc gacccctga ccaccccct gctgatgctg accacctggc     480 tgctgccct gaccatcatg gccagccagc gccacctgag cagcgagccc ctgagccgca     540
agaagctgta cctgagcatg ctgatcagcc tgcagatcag cctgatcatg accttcaccg     600
ccaccgagct gatcatgttc tacatcttct tcgagaccac cctgatcccc acctggccca     660
tcatcacccg ctggggcaac cagcccgagc gcctgaacgc cggcacctac ttcctgttct     720
acacccgtgt gggcagcctg ccctgctga tcgccctgat ctacacccac aacaccctgg     780
gcagcctgaa catcctgctg ctgacccga ccgccagga gctgagcaac agctgggcca     840
acaacctgat gtggctggcc tacaccatgg ccttcatggt gaagatgccc ctgtacggcc     900
```

| | |
|---|---|
| tgcacctgtg gctgcccaag gcccacgtgg aggcccccat cgccggcagc atggtgctgg | 960 |
| ccgccgtgct gctgaagctg ggcggctacg gcatgatgcg cctgaccctg atcctgaacc | 1020 |
| ccctgaccaa gcacatggcc tacccttcc tggtgctgag cctgtggggc atgatcatga | 1080 |
| ccagcagcat ctgcctgcgc cagaccgacc tgaagagcct gatcgcctac agcagcatca | 1140 |
| gccacatggc cctggtggtg accgccatcc tgatccagac cccctggagc ttcaccggcg | 1200 |
| ccgtgatcct gatgatcgcc cacggcctga ccagcagcct gctgttctgc ctggccaaca | 1260 |
| gcaactacga gcgcacccac agccgcatca tgatcctgag ccagggcctg cagaccctgc | 1320 |
| tgcccctgat ggccttctgg tggctgctgg ccagcctggc caacctggcc ctgcccccca | 1380 |
| ccatcaacct gctgggcgag ctgagcgtgc tggtgaccac cttcagctgg agcaacatca | 1440 |
| ccctgctgct gaccggcctg aacatgctgg tgaccgccct gtacagcctg tacatgttca | 1500 |
| ccaccaccca gtggggcagc ctgacccacc acatcaacaa catgaagccc agcttcaccc | 1560 |
| gcgagaacac cctgatgttc atgcacctga gccccatcct gctgctgagc ctgaaccccg | 1620 |
| acatcatcac cggcttcagc agctaagagc actgggacgc ccaccgcccc tttccctccg | 1680 |
| ctgccaggcg agcatgttgt ggtaattctg gaacacaaga gagaaattg ctgggtttag | 1740 |
| aacaagatta taaacgaatt cggtgctcag tgatcacttg acagtttttt ttttttttaa | 1800 |
| atattaccca aaatgctccc caaataagaa atgcatcagc tcagtcagtg aatacaaaaa | 1860 |
| aggaattatt tttcccttg agggtctttt atacatctct cctccaaccc caccctctat | 1920 |
| tctgtttctt cctcctcaca tgggggtaca catacacagc ttcctctttt ggttccatcc | 1980 |
| ttaccaccac accacacgca cactccacat gcccagcaga gtggcacttg gtggccagaa | 2040 |
| agtgtgagcc tcatgatctg ctgtctgtag ttctgtgagc tcaggtccct caaaggcctc | 2100 |
| ggagcacccc cttccttgtg actgagccag ggcctgcatt tttggttttc ccacccccac | 2160 |
| acattctcaa ccatagtcct tctaacaata ccaatagcta ggacccggct gctgtgcact | 2220 |
| gggactgggg attccacatg tttgccttgg gagtctcaag ctggactgcc agcccctgtc | 2280 |
| ctcccttcac ccccattgcg tatgagcatt tcagaactcc aaggagtcac aggcatcttt | 2340 |
| atagttcacg ttaacatata gacactgttg gaagcagttc cttctaaaag ggtagccctg | 2400 |
| gacttaatac cagccggata cctctggccc ccaccccatt actgtacctc tggagtcact | 2460 |
| actgtgggtc gccactcctc tgctacacag cacggctttt tcaaggctgt attgagaagg | 2520 |
| gaagttagga agaagggtgt gctgggctaa ccagcccaca gagctcacat tcctgtccct | 2580 |
| tgggtgaaaa atacatgtcc atcctgatat ctcctgaatt cagaaattag cctccacatg | 2640 |
| tgcaatggct ttaagagcca gaagcagggt tctgggaatt ttgcaagtta cctgtggcca | 2700 |
| ggtgtggtct cggttaccaa atacggttac ctgcagcttt ttagtccttt gtgctcccac | 2760 |
| gggtctacag agtcccatct gcccaaaggt cttgaagctt gacaggatgt tttcgattac | 2820 |
| tcagtctccc agggcactac tggtccgtag gattcgattg gtcggggtag gagagttaaa | 2880 |
| caacatttaa acagagttct ctcaaaaatg tctaaaggga ttgtaggtag ataacatcca | 2940 |
| atcactgttt gcacttatct gaaatcttcc ctcttggctg ccccaggta tttactgtgg | 3000 |
| agaacattgc ataggaatgt ctggaaaaag cttctacaac ttgttacagc cttcacattt | 3060 |
| gtagaagctt t | 3071 |

<210> SEQ ID NO 76
<211> LENGTH: 2271
<212> TYPE: DNA
<213> ORGANISM: Artificial Sequence
<220> FEATURE:
<223> OTHER INFORMATION: OPA1-opt_ND4*-3'UTR*

<400> SEQUENCE: 76

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
acggggctc ccgcgtggcc gtctcggcgc ctgcgtgacc tccccgccgg cgggatgtgg      240
cgactacgtc gggccgctgt ggcctgatgc tgaagctgat cgtgcccacc atcatgctgc     300
tgcccctgac ctggctgagc aagaagcaca tgatctggat caacaccacc acccacagcc     360
tgatcatcag catcatcccc ctgctgttct caaccagat caacaacaac ctgttcagct      420
gcagccccac cttcagcagc gaccccctga ccaccccct gctgatgctg accacctggc      480
tgctgcccct gaccatcatg ccagccagc gccacctgag cagcgagccc ctgagccgca      540
agaagctgta cctgagcatg ctgatcagcc tgcagatcag cctgatcatg accttcaccg     600
ccaccgagct gatcatgttc tacatcttct tcgagaccac cctgatcccc accctggcca     660
tcatcacccg ctgggggcaac cagcccgagc cctgaacgc cggcacctac ttcctgttct     720
acaccctggt gggcagcctg cccctgctga tcgccctgat ctacacccac aacaccctgg    780
gcagcctgaa catcctgctg ctgacccctga ccgcccagga gctgagcaac agctgggcca    840
acaacctgat gtggctggcc tacaccatgg ccttcatggt gaagatgccc ctgtacggcc     900
tgcacctgtg gctgcccaag gcccacgtgg aggcccccat cgccggcagc atggtgctgg     960
ccgccgtgct gctgaagctg gcggctacg gcatgatgcg cctgaccctg atcctgaacc    1020
ccctgaccaa gcacatggcc taccccttcc tggtgctgag cctgtggggc atgatcatga   1080
ccagcagcat ctgcctgcgc cagaccgacc tgaagagcct gatcgcctac agcagcatca   1140
gccacatggc cctggtggtg accgccatcc tgatccagac ccctggagc ttcaccggcg    1200
ccgtgatcct gatgatcgcc cacggcctga ccagcagcct gctgttctgc ctggccaaca   1260
gcaactacga gcgcacccac agccgcatca tgatcctgag ccagggcctg cagaccctgc   1320
tgccctgat ggccttctgg tggctgctgg ccagcctggc caacctggcc ctgcccccca    1380
ccatcaacct gctgggcgag ctgagcgtgc tggtgaccac cttcagctgg agcaacatca   1440
ccctgctgct gaccggcctg aacatgctgg tgaccgccct gtacagcctg tacatgttca   1500
ccaccaccca gtggggcagc ctgacccacc acatcaacaa catgaagccc agcttcaccc   1560
gcgagaacac cctgatgttc atgcacctga gccccatcct gctgctgagc ctgaaccccg   1620
acatcatcac cggcttcagc agctaagagc actgggacgc ccaccgcccc tttccctccg   1680
ctgccaggcg agcatgttgt ggtaattctg aacacaaga agagaaattg ctgggtttag    1740
aacaagatta taaacgaatt cggtgctcag tgatcacttg acagtttttt ttttttttaa   1800
atattaccca aaatgctccc caaataagaa atgcatcagc tcagtcagtg aatacaaaaa   1860
aggaattatt tttccctttg agggtctttt atacatctct cctccaaccc caccctctat   1920
tctgtttctt cctcctcaca tggggtaca catacacagc ttcctctttt ggttccatcc    1980
ttaccaccac accacacgca cactccacat gccagcagga tgtggcacttg gtggccagaa   2040
agtgtgagcc tcatgatctg ctgtctgtag ttctgtgagc tcaggtccct caaaggcctc   2100
ggagcacccc cttccttgtg actgagccag ggcctgcatt tttggttttc cccacccac    2160
acattctcaa ccatagtcct tctaacaata ccaatagcta ggaccggct gctgtgcact    2220
```

```
gggactgggg attccacatg tttgccttgg gagtctcaag ctggactgcc a        2271
```

<210> SEQ ID NO 77
<211> LENGTH: 2216
<212> TYPE: DNA
<213> ORGANISM: Artificial Sequence
<220> FEATURE:
<223> OTHER INFORMATION: OPA1-ND6-3'UTR

<400> SEQUENCE: 77

```
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180
acggggctc ccgcgtggcc gtctcggcgc ctgcgtgacc tccccgccgg cgggatgtgg    240
cgactacgtc gggccgctgt ggcctgatga tgtatgcttt gtttctgttg agtgtgggtt   300
tagtaatggg gtttgtgggg ttttcttcta agccttctcc tatttatggg ggtttagtat   360
tgattgttag cggtgtggtc gggtgtgtta ttattctgaa ttttggggga ggttatatgg   420
gtttaatggt ttttttaatt tatttagggg gaatgatggt tgtctttgga tatactacag   480
cgatggctat tgaggagtat cctgaggcat ggggtcagg ggttgaggtc ttggtgagtg    540
ttttagtggg gttagcgatg gaggtaggat tggtgctgtg ggtgaaagag tatgatgggg   600
tggtggttgt ggtaaacttt aatagtgtag gaagctggat gatttatgaa ggagaggggt   660
cagggttgat tcgggaggat cctattggtg cggggctttt gtatgattat gggcgttggt   720
tagtagtagt tactggttgg acattgtttg ttggtgtata tattgtaatt gagattgctc   780
ggggaatta ggagcactgg gacgcccacc gccccttttcc ctccgctgcc aggcgagcat   840
gttgtggtaa ttctggaaca caagaagaga aattgctggg tttagaacaa gattataaac   900
gaattcggtg ctcagtgatc acttgacagt tttttttttt tttaaatatt acccaaaatg   960
ctccccaaat aagaaatgca tcagctcagt cagtgaatac aaaaaaggaa ttatttttcc  1020
ctttgagggt cttttataca tctctcctcc aacccaccc tctattctgt ttcttcctcc   1080
tcacatgggg gtacacatac acagcttcct cttttggttc catccttacc accacaccac  1140
acgcacactc cacatgccca gcagagtggc acttggtggc cagaaagtgt gagcctcatg  1200
atctgctgtc tgtagttctg tgagctcagg tccctcaaag gcctcggagc accccttcc   1260
ttgtgactga gccagggcct gcatttttgg ttttcccac cccacacatt ctcaaccata   1320
gtccttctaa cataccaat agctaggacc cggctgctgt gcactgggac tggggattcc   1380
acatgtttgc cttgggagtc tcaagctgga ctgccagccc ctgtcctccc ttcaccccca  1440
ttgcgtatga gcatttcaga actccaagga gtcacaggca tctttatagt tcacgttaac  1500
atatagacac tgttggaagc agttccttct aaaagggtag ccctggactt aataccagcc  1560
ggatacctct ggccccccacc ccattactgt acctctggag tcactactgt gggtcgccac  1620
tcctctgcta cacagcacgg cttttttcaag gctgtattga aagggaagt taggaagaag   1680
ggtgtgctgg gctaaccagc ccacagagct cacattcctg tcccttgggt gaaaaataca  1740
tgtccatcct gatatctcct gaattcagaa attagcctcc acatgtgcaa tggctttaag  1800
agccagaagc agggttctgg gaattttgca agttacctgt ggccaggtgt ggtctcggtt  1860
accaaatacg gttacctgca gcttttttagt cctttgtgct cccacgggtc tacagagtcc  1920
catctgccca aaggtcttga agcttgacag gatgttttcg attactcagt ctcccagggc  1980
actactggtc cgtaggattc gattggtcgg ggtaggagag ttaaacaaca tttaaacaga  2040
```

```
gttctctcaa aaatgtctaa agggattgta ggtagataac atccaatcac tgtttgcact    2100
tatctgaaat cttccctctt ggctgccccc aggtatttac tgtggagaac attgcatagg    2160
aatgtctgga aaaagcttct acaacttgtt acagccttca catttgtaga agcttt        2216
```

<210> SEQ ID NO 78
<211> LENGTH: 1416
<212> TYPE: DNA
<213> ORGANISM: Artificial Sequence
<220> FEATURE:
<223> OTHER INFORMATION: OPA1-ND6-3'UTR*

<400> SEQUENCE: 78

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggctc ccgcgtggcc gtctcggcgc ctgcgtgacc tccccgccgg cgggatgtgg     240
cgactacgtc gggccgctgt ggcctgatga tgtatgcttt gtttctgttg agtgtgggtt     300
tagtaatggg gtttgtgggg ttttcttcta agccttctcc tatttatggg ggtttagtat     360
tgattgttag cggtgtggtc gggtgtgtta ttattctgaa ttttggggga ggttatatgg     420
gtttaatggt tttttaatt tatttagggg gaatgatggt tgtctttgga tatactacag      480
cgatggctat tgaggagtat cctgaggcat gggggtcagg ggttgaggtc ttggtgagtg     540
ttttagtggg gttagcgatg gaggtaggat tggtgctgtg ggtgaaagag tatgatgggg     600
tggtggttgt ggtaaacttt aatagtgtag gaagctggat gatttatgaa ggagaggggt     660
cagggttgat tcgggaggat cctattggtg cggggctt gtatgattat gggcgttggt       720
tagtagtagt tactggttgg acattgtttg ttggtgtata tattgtaatt gagattgctc     780 ggggggaatta ggagcactgg gacgcccacc gccccttttcc ctccgctgcc aggcgagcat    840
gttgtggtaa ttctggaaca caagaagaga aattgctggg tttagaacaa gattataaac     900
gaattcggtg ctcagtgatc acttgacagt ttttttttt tttaaatatt acccaaaatg     960
ctccccaaat aagaaatgca tcagctcagt cagtgaatac aaaaaaggaa ttatttttcc    1020
ctttgagggt ctttatacat ctctcctcc aacccacccc tctattctgt ttcttcctcc    1080
tcacatgggg gtacacatac acagcttcct cttttggttc catccttacc accacaccac    1140
acgcacactc cacatgccca gcagagtggc acttggtggc cagaaagtgt gagcctcatg    1200
atctgctgtc tgtagttctg tgagctcagg tccctcaaag gctcggagc accccctcc      1260 ttgtgactga gccagggcct gcatttttgg ttttccccac cccacacatt ctcaaccata    1320
gtccttctaa caataccaat agctaggacc cggctgctgt gcactgggac tggggattcc    1380
acatgtttgc cttgggagtc tcaagctgga ctgcca                              1416
```

<210> SEQ ID NO 79
<211> LENGTH: 2216
<212> TYPE: DNA
<213> ORGANISM: Artificial Sequence
<220> FEATURE:
<223> OTHER INFORMATION: OPA1-opt_ND6-3'UTR

<400> SEQUENCE: 79

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
```

```
cttgctgctg agggccactt cctgggtcat tcctggaccg ggagccgggc tggggctcac    180
acggggctc ccgcgtggcc gtctcggcgc ctgcgtgacc tccccgccgg cgggatgtgg    240
cgactacgtc gggccgctgt ggcctgatga tgtacgccct gttcctgctg agcgtgggcc    300
tggtgatggg cttcgtgggc ttcagcagca agcccagccc catctacggc ggcctggtgc    360
tgatcgtgag cggcgtggtg ggctgcgtga tcatcctgaa cttcggcggc ggctacatgg    420
gcctgatggt gttcctgatc tacctgggcg gcatgatggt ggtgttcggc tacaccaccg    480
ccatggccat cgaggagtac cccgaggcct ggggcagcgg cgtggaggtg ctggtgagcg    540
tgctggtggg cctggccatg gaggtgggcc tggtgctgtg ggtgaaggag tacgacggcg    600
tggtggtggt ggtgaacttc aacagcgtgg gcagctggat gatctacgag ggcgagggca    660
gcggcctgat ccgcgaggac cccatcggcc cggcgccct gtacgactac ggccgctggc    720
tggtggtggt gaccggctgg accctgttcg tgggcgtgta catcgtgatc gagatcgccc    780
gcggcaacta gagcactgg gacgccacc gcccctttcc ctccgctgcc aggcgagcat    840
gttgtggtaa ttctggaaca caagaagaga aattgctggg tttagaacaa gattataaac    900
gaattcggtg ctcagtgatc acttgacagt ttttttttt tttaaatatt acccaaaatg    960
ctccccaaat aagaaatgca tcagctcagt cagtgaatac aaaaaaggaa ttattttcc   1020
ctttgagggt cttttataca tctctcctcc aaccccaccc tctattctgt ttcttcctcc   1080
tcacatgggg gtacacatac acagcttcct cttttggttc catccttacc accacaccac   1140
acgcacactc cacatgccca gcagagtggc acttggtggc cagaaagtgt gagcctcatg   1200
atctgctgtc tgtagttctg tgagctcagg tccctcaaag gcctcggagc accccttcc   1260
ttgtgactga gccagggcct gcattttgg ttttccccac cccacacatt ctcaaccata   1320
gtccttctaa caataccaat agctaggacc cggctgctgt gcactgggac tggggattcc   1380
acatgtttgc cttgggagtc tcaagctgga ctgccagccc ctgtcctccc ttcaccccca   1440
ttgcgtatga gcatttcaga actccaagga gtcacaggca tctttatagt tcacgttaac   1500
atatagacac tgttggaagc agttccttct aaaagggtag ccctggactt aataccagcc   1560
ggatacctct ggcccccacc ccattactgt acctctggag tcactactgt gggtcgccac   1620
tcctctgcta cacagcacgg cttttttcaag gctgtattga aagggaagt taggaagaag   1680
ggtgtgctgg gctaaccagc ccacagagct cacattcctg tcccttgggt gaaaaataca   1740
tgtccatcct gatatctcct gaattcagaa attagcctcc acatgtgcaa tggctttaag   1800
agccagaagc agggttctgg gaattttgca agttacctgt ggccaggtgt ggtctcggtt   1860
accaaatacg gttacctgca gcttttagt cctttgtgct cccacgggtc tacagagtcc   1920
catctgccca aggtcttga agcttgacag gatgttttcg attactcagt ctcccagggc   1980
actactggtc cgtaggattc gattggtcgg ggtaggagag ttaaacaaca tttaaacaga   2040
gttctctcaa aaatgtctaa agggattgta ggtagataac atccaatcac tgtttgcact   2100
tatctgaaat cttccctctt ggctgcccc aggtatttac tgtggagaac attgcatagg   2160
aatgtctgga aaaagcttct acaacttgtt acagccttca catttgtaga agcttt       2216
```

<210> SEQ ID NO 80
<211> LENGTH: 1416
<212> TYPE: DNA
<213> ORGANISM: Artificial Sequence
<220> FEATURE:
<223> OTHER INFORMATION: OPA1-opt_ND6-3'UTR*

<400> SEQUENCE: 80

```
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180 acggggctc ccgcgtggcc gtctcggcgc ctgcgtgacc tccccgccgg cgggatgtgg    240
cgactacgtc gggccgctgt ggcctgatga tgtacgccct gttcctgctg agcgtgggcc   300
tggtgatggg cttcgtgggc ttcagcagca agcccagccc catctacggc ggcctggtgc   360
tgatcgtgag cggcgtggtg ggctgcgtga tcatcctgaa cttcggcggc ggctacatgg   420
gcctgatggt gttcctgatc tacctgggcg gcatgatggt ggtgttcggc tacaccaccg   480
ccatggccat cgaggagtac cccgaggcct ggggcagcgg cgtggaggtg ctggtgagcg   540
tgctggtggg cctggccatg gaggtgggcc tggtgctgtg ggtgaaggag tacgacggcg   600
tggtggtggt ggtgaacttc aacagcgtgg gcagctggat gatctacgag ggcgagggca   660
gcggcctgat ccgcgaggac cccatcgcg ccggcgccct gtacgactac ggccgctggc    720
tggtggtggt gaccggctgg accctgttcg tgggcgtgta catcgtgatc gagatcgccc   780
gcggcaacta gagcactgg gacgcccacc gccccttcc ctccgctgcc aggcgagcat    840
gttgtggtaa ttctggaaca caagaagaga aattgctggg tttagaacaa gattataaac   900
gaattcggtg ctcagtgatc acttgacagt ttttttttt tttaaatatt acccaaaatg    960
ctccccaaat aagaaatgca tcagctcagt cagtgaatac aaaaaaggaa ttatttttcc  1020 cttgagggt cttttataca tctctcctcc aacccaccc tctattctgt ttcttcctcc    1080
tcacatgggg gtacacatac acagcttcct cttttggttc catccttacc accacaccac  1140
acgcacactc cacatgccca gcagagtggc acttggtggc cagaaagtgt gagcctcatg  1200
atctgctgtc tgtagttctg tgagctcagg tccctcaaag gcctcggagc accccttcc   1260 ttgtgactga gccagggcct gcattttgg ttttccccac cccacacatt ctcaaccata   1320
gtccttctaa caataccaat agctaggacc cggctgctgt gcactgggac tggggattcc  1380
acatgtttgc cttgggagtc tcaagctgga ctgcca                            1416
```

<210> SEQ ID NO 81
<211> LENGTH: 2642
<212> TYPE: DNA
<213> ORGANISM: Artificial Sequence
<220> FEATURE:
<223> OTHER INFORMATION: OPA1-ND1-3'UTR

<400> SEQUENCE: 81

```
gtgctgcccg cctagaaagg gtgaagtggt tgtttccgtg acggactgag tacgggtgcc    60
tgtcaggctc ttgcggaagt ccatgcgcca ttgggagggc ctcggccgcg gctctgtgcc   120
cttgctgctg agggccactt cctgggtcat tcctggaccg ggagccgggc tggggctcac   180 acggggctc ccgcgtggcc gtctcggcgc ctgcgtgacc tccccgccgg cgggatgtgg    240
cgactacgtc gggccgctgt ggcctgatgg ccaacctcct actcctcatt gtacccattc   300
taatcgcaat ggcattccta atgcttaccg aacgaaaaat tctaggctat atgcaactac   360
gcaaaggccc caacgttgta ggcccctacg ggctactaca accttcgct gacgccataa    420 aactcttcac caaagagccc ctaaaacccg ccacatctac catcaccctc tacatcaccg   480
ccccgacctt agctctcacc atcgctcttc tactatggac ccccctcccc atgcccaacc   540
ccctggtcaa cctcaaccta ggcctcctat ttattctagc cacctctagc ctagccgttt   600
```

```
actcaatcct ctggtcaggg tgggcatcaa actcaaacta cgccctgatc ggcgcactgc    660
gagcagtagc ccaaacaatc tcatatgaag tcaccctagc catcattcta ctatcaacat    720
tactaatgag tggctccttt aacctctcca cccttatcac aacacaagaa cacctctggt    780
tactcctgcc atcatggccc ttggccatga tgtggtttat ctccacacta gcagagacca    840
accgaacccc cttcgacctt gccgaagggg agtccgaact agtctcaggc ttcaacatcg    900
aatacgccgc aggccccttc gccctattct tcatggccga atacacaaac attattatga    960
tgaacaccct caccactaca atcttcctag gaacaacata tgacgcactc tcccctgaac   1020
tctacacaac atattttgtc accaagaccc tacttctaac ctccctgttc ttatggattc   1080
gaacagcata ccccgattc cgctacgacc aactcatgca cctcctatgg aaaaacttcc   1140
taccactcac cctagcatta cttatgtggt atgtctccat gcccattaca atctccagca   1200 ttcccctca aacctaagag cactgggacg cccaccgccc ctttccctcc gctgccaggc   1260
gagcatgttg tggtaattct ggaacacaag aagagaaatt gctgggttta gaacaagatt   1320
ataaacgaat tcggtgctca gtgatcactt gacagttttt ttttttttta aatattaccc   1380
aaaatgctcc ccaaataaga aatgcatcag ctcagtcagt gaatacaaaa aaggaattat   1440
ttttcccttt gagggtcttt tatacatctc tcctccaacc ccaccctcta ttctgtttct   1500
tcctcctcac atggggtac acatacacag cttcctcttt tggttccatc cttaccacca   1560
caccacacgc acactccaca tgcccagcag agtggcactt ggtggccaga aagtgtgagc   1620
ctcatgatct gctgtctgta gttctgtgag ctcaggtccc tcaaaggcct cggagcaccc   1680
ccttccttgt gactgagcca gggcctgcat ttttggtttt ccccacccca cacattctca   1740
accatagtcc ttctaacaat accaatagct aggacccggc tgctgtgcac tgggactggg   1800
gattccacat gtttgccttg ggagtctcaa gctggactgc cagcccctgt cctcccttca   1860 ccccccattgc gtatgagcat ttcagaactc caaggagtca caggcatctt tatagttcac   1920
gttaacatat agacactgtt ggaagcagtt ccttctaaaa gggtagccct ggacttaata   1980
ccagccggat acctctggcc cccacccat tactgtacct ctggagtcac tactgtgggt   2040
cgccactcct ctgctacaca gcacggcttt ttcaaggctg tattgagaag ggaagttagg   2100
aagaagggtg tgctgggcta accagcccac agagctcaca ttcctgtccc ttgggtgaaa   2160
aatacatgtc catcctgata tctcctgaat tcagaaatta gcctccacat gtgcaatggc   2220
tttaagagcc agaagcaggg ttctgggaat tttgcaagtt acctgtggcc aggtgtggtc   2280
tcggttacca aatacggtta cctgcagctt tttagtcctt tgtgctccca cgggtctaca   2340
gagtcccatc tgcccaaagg tcttgaagct tgacaggatg ttttcgatta ctcagtctcc   2400
cagggcacta ctggtccgta ggattcgatt ggtcggggta ggagagttaa acaacattta   2460
aacagagttc tctcaaaaat gtctaaaggg attgtaggta gataacatcc aatcactgtt   2520
tgcacttatc tgaaatcttc cctcttggct gccccaggt atttactgtg gagaacattg   2580
cataggaatg tctggaaaaa gcttctacaa cttgttacag ccttcacatt tgtagaagct   2640
tt                                                                  2642
```

<210> SEQ ID NO 82
<211> LENGTH: 1842
<212> TYPE: DNA
<213> ORGANISM: Artificial Sequence
<220> FEATURE:
<223> OTHER INFORMATION: OPA1-ND1-3'UTR*

<400> SEQUENCE: 82

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180 acggggggctc ccgcgtggcc gtctcggcgc ctgcgtgacc tccccgccgg cgggatgtgg    240
cgactacgtc gggccgctgt ggcctgatgg ccaacctcct actcctcatt gtacccattc     300
taatcgcaat ggcattccta atgcttaccg aacgaaaaat tctaggctat atgcaactac     360
gcaaaggccc caacgttgta ggcccctacg gctactaca cccttcgct gacgccataa       420 aactcttcac caaagagccc ctaaaacccg ccacatctac catcaccctc tacatcaccg     480
ccccgacctt agctctcacc atcgctcttc tactatggac ccccctcccc atgcccaacc    540
ccctggtcaa cctcaaccta ggcctcctat ttattctagc cacctctagc ctagccgttt    600
actcaatcct ctggtcaggg tgggcatcaa actcaaacta cgccctgatc ggcgcactgc    660
gagcagtagc ccaaacaatc tcatatgaag tcaccctagc catcattcta ctatcaacat    720
tactaatgag tggctccttt aacctctcca cccttatcac aacacaagaa cacctctggt    780
tactcctgcc atcatggccc ttggccatga tgtggtttat ctccacacta gcagagacca    840
accgaacccc cttcgacctt gccgaagggg agtccgaact agtctcaggc ttcaacatcg    900
aatacgccgc aggccccttc gccctattct tcatggccga atacaaaac attattatga     960 tgaacaccct caccactaca atcttcctag gaacaacata tgacgcactc tcccctgaac   1020
tctacacaac atattttgtc accaagaccc tacttctaac ctccctgttc ttatggattc   1080
gaacagcata ccccgattc cgctacgacc aactcatgca cctcctatgg aaaaacttcc    1140
taccactcac cctagcatta cttatgtggt atgtctccat gcccattaca atctccagca   1200
ttccccctca aacctaagag cactgggacg cccaccgccc ctttcctcc gctgccaggc    1260 gagcatgttg tggtaattct ggaacacaag aagagaaatt gctgggttta gaacaagatt   1320
ataaacgaat tcggtgctca gtgatcactt gacagttttt ttttttttta aatattaccc    1380
aaaatgctcc ccaaataaga aatgcatcag ctcagtcagt gaatacaaaa aaggaattat    1440 ttttccttt gagggtcttt tatacatctc tcctccaacc ccaccctcta ttctgtttct    1500
tcctcctcac atgggggtac acatacacag cttcctcttt tggttccatc cttaccacca   1560
caccacacgc acactccaca tgcccagcag agtggcactt ggtggccaga aagtgtgagc   1620
ctcatgatct gctgtctgta gttctgtgag ctcaggtccc tcaaaggcct cggagcaccc   1680
ccttccttgt gactgagcca gggctgcat ttttggtttt ccccaccca cacattctca     1740 accatagtcc ttctaacaat accaatagct aggacccggc tgctgtgcac tgggactggg   1800
gattccacat gtttgccttg ggagtctcaa gctggactgc ca                      1842
```

<210> SEQ ID NO 83
<211> LENGTH: 2642
<212> TYPE: DNA
<213> ORGANISM: Artificial Sequence
<220> FEATURE:
<223> OTHER INFORMATION: OPA1-opt_ND1-3'UTR

<400> SEQUENCE: 83

```
gtgctgcccg cctagaaagg gtgaagtggt tgtttccgtg acggactgag tacgggtgcc      60
tgtcaggctc ttgcggaagt ccatgcgcca ttgggagggc ctcggccgcg gctctgtgcc     120
cttgctgctg agggccactt cctgggtcat tcctggaccg ggagccgggc tggggctcac     180
```

```
acgggggctc ccgcgtggcc gtctcggcgc ctgcgtgacc tccccgccgg cgggatgtgg        240
cgactacgtc gggccgctgt ggcctgatgg ccaacctgct gctgctgatc gtgcccatcc        300
tgatcgccat ggccttcctg atgctgaccg agcgcaagat cctgggctac atgcagctgc        360
gcaagggccc caacgtggtg ggcccctacg gcctgctgca gccctccgcc gacgccatca        420
agctgttcac caaggagccc ctgaagcccg ccaccagcac catcaccctg tacatcaccg        480
cccccaccct ggccctgacc atcgccctgc tgctgtggac cccctgccc atgcccaacc         540
ccctggtgaa cctgaacctg ggcctgctgt tcatcctggc caccagcagc ctggccgtgt        600
acagcatcct gtggagcggc tgggccagca cagcaacta cgccctgatc ggcgccctgc         660
gcgccgtggc ccagaccatc agctacgagg tgaccctggc catcatcctg ctgagcaccc        720
tgctgatgag cggcagcttc aacctgagca ccctgatcac cacccaggag cacctgtggc       780
tgctgctgcc cagctggccc ctggccatga tgtggttcat cagcaccctg gccgagacca        840
accgcacccc cttcgacctg gccgagggcg agagcgagct ggtgagcggc ttcaacatcg        900
agtacgccgc cggccccttc gccctgttct tcatggccga gtacaccaac atcatcatga        960
tgaacaccct gaccaccacc atcttcctgg gcaccaccta cgacgccctg agccccgagc       1020
tgtacaccac ctacttcgtg accaagaccc tgctgctgac cagcctgttc ctgtggatcc       1080
gcaccgccta cccccgcttc cgctacgacc agctgatgca cctgctgtgg aagaacttcc       1140
tgcccctgac cctggccctg ctgatgtggt acgtgagcat gcccatcacc atcagcagca       1200
tccccccca gacctaagag cactgggacg cccaccgccc ctttccctcc gctgccaggc        1260
gagcatgttg tggtaattct ggaacacaag aagagaaatt gctgggttta gaacaagatt       1320
ataaacgaat tcggtgctca gtgatcactt gacagttttt ttttttttta aatattaccc       1380
aaaatgctcc ccaaataaga aatgcatcag ctcagtcagt gaatacaaaa aaggaattat       1440
ttttcccttt gagggtcttt tatacatctc tcctccaacc ccaccctcta ttctgtttct       1500
tcctcctcac atgggggtac acatacacag cttcctcttt tggttccatc cttaccacca       1560
caccacacgc acactccaca tgcccagcag agtggcactt ggtggccaga agtgtgagc        1620
ctcatgatct gctgtctgta gttctgtgag ctcaggtccc tcaaaggcct cggagcaccc       1680
ccttccttgt gactgagcca gggcctgcat ttttggtttt ccccaccca cacattctca        1740
accatagtcc ttctaacaat accaatagct aggacccggc tgctgtgcac tgggactggg       1800
gattccacat gtttgccttg ggagtctcaa gctggactgc cagcccctgt cctcccttca       1860
cccccattgc gtatgagcat ttcagaactc caaggagtca caggcatctt tatagttcac       1920
gttaacatat agacactgtt ggaagcagtt ccttctaaaa gggtagccct ggacttaata       1980
ccagccggat acctctggcc cccacccat tactgtacct ctggagtcac tactgtgggt        2040
cgccactcct ctgctacaca gcacggcttt ttcaaggctg tattgagaag ggaagttagg       2100
aagaagggtg tgctgggcta accagcccac agagctcaca ttcctgtccc ttgggtgaaa       2160
aatacatgtc catcctgata tctcctgaat tcagaaatta gcctccacat gtgcaatggc       2220
tttaagagcc agaagcaggg ttctgggaat tttgcaagtt acctgtggcc aggtgtggtc       2280
tcggttacca aatacggtta cctgcagctt tttagtcctt tgtgctccca cgggtctaca       2340
gagtcccatc tgcccaaagg tcttgaagct tgacaggatg ttttcgatta ctcagtctcc       2400
cagggcacta ctggtccgta ggattcgatt ggtcggggta ggagagttaa acaacattta       2460
aacagagttc tctcaaaaat gtctaaaggg attgtaggta gataacatcc aatcactgtt       2520
tgcacttatc tgaaatcttc cctcttggct gccccaggt atttactgtg gagaacattg        2580
```

| | |
|---|---|
| cataggaatg tctggaaaaa gcttctacaa cttgttacag ccttcacatt tgtagaagct | 2640 |
| tt | 2642 |

<210> SEQ ID NO 84
<211> LENGTH: 1842
<212> TYPE: DNA
<213> ORGANISM: Artificial Sequence
<220> FEATURE:
<223> OTHER INFORMATION: OPA1-opt_ND1-3'UTR*

<400> SEQUENCE: 84

| | |
|---|---|
| gtgctgcccg cctagaaagg gtgaagtggt tgtttccgtg acggactgag tacgggtgcc | 60 |
| tgtcaggctc ttgcggaagt ccatgcgcca ttgggagggc ctcggccgcg gctctgtgcc | 120 |
| cttgctgctg agggccactt cctgggtcat tcctggaccg ggagccgggc tggggctcac | 180 |
| acggggggctc ccgcgtggcc gtctcggcgc ctgcgtgacc tccccgccgg cgggatgtgg | 240 |
| cgactacgtc gggccgctgt ggcctgatgg ccaacctgct gctgctgatc gtgcccatcc | 300 |
| tgatcgccat ggccttcctg atgctgaccg agcgcaagat cctgggctac atgcagctgc | 360 |
| gcaagggccc caacgtggtg ggcccctacg gcctgctgca gccctttcgcc gacgccatca | 420 |
| agctgttcac caaggagccc ctgaagcccg ccaccagcac catcaccctg tacatcaccg | 480 |
| cccccacccct ggccctgacc atcgccctgc tgctgtggac ccccctgccc atgcccaacc | 540 |
| ccctggtgaa cctgaacctg gcctgctgt tcatcctggc caccagcagc ctggccgtgt | 600 |
| acagcatcct gtggagcggc tgggccagca cagcaacta cgccctgatc ggcgccctgc | 660 |
| gcgccgtggc ccagaccatc agctacgagg tgaccctggc catcatcctg ctgagcaccc | 720 |
| tgctgatgag cggcagcttc aacctgagca ccctgatcac cacccaggag cacctgtggc | 780 |
| tgctgctgcc cagctggccc ctggccatga tgtggttcat cagcaccctg gccgagacca | 840 |
| accgcacccc cttcgacctg gccgagggcg agagcgagct ggtgagcggc ttcaacatcg | 900 |
| agtacgccgc cggcccctcc gccctgttct tcatggccga gtacaccaac atcatcatga | 960 |
| tgaacaccct gaccaccacc atcttcctgg gcaccaccta cgacgccctg agccccgagc | 1020 |
| tgtacaccac ctacttcgtg accaagaccc tgctgctgac cagcctgttc ctgtggatcc | 1080 |
| gcaccgccta cccccgcttc cgctacgacc agctgatgca cctgctgtgg aagaacttcc | 1140 |
| tgcccctgac cctggccctg ctgatgtggt acgtgagcat gcccatcacc atcagcagca | 1200 |
| tcccccccca gacctaagag cactgggacg cccaccgccc ctttccctcc gctgccaggc | 1260 |
| gagcatgttg tggtaattct ggaacacaag aagagaaatt gctgggttta gaacaagatt | 1320 |
| ataaacgaat tcggtgctca gtgatcactt gacagttttt ttttttttta aatattaccc | 1380 |
| aaaatgctcc ccaaataaga aatgcatcag ctcagtcagt gaatacaaaa aaggaattat | 1440 |
| ttttcccttt gagggtcttt tatacatctc tcctccaacc ccaccctcta ttctgtttct | 1500 |
| tcctcctcac atgggggtac acatacacag cttcctcttt tggttccatc cttaccacca | 1560 |
| caccacacgc acactccaca tgcccagcag agtggcactt ggtggccaga aagtgtgagc | 1620 |
| ctcatgatct gctgtctgta gttctgtgag ctcaggtccc tcaaaggcct cggagcaccc | 1680 |
| ccttccttgt gactgagcca gggcctgcat ttttggtttt ccccaccccca cacattctca | 1740 |
| accatagtcc ttctaacaat accaatagct aggacccggc tgctgtgcac tgggactggg | 1800 |
| gattccacat gtttgccttg ggagtctcaa gctggactgc ca | 1842 |

<210> SEQ ID NO 85

```
<211> LENGTH: 18
<212> TYPE: DNA
<213> ORGANISM: Artificial Sequence
<220> FEATURE:
<223> OTHER INFORMATION: beta-actin-S primer

<400> SEQUENCE: 85
cgagatcgtg cgggacat                                                18

<210> SEQ ID NO 86
<211> LENGTH: 19
<212> TYPE: DNA
<213> ORGANISM: Artificial Sequence
<220> FEATURE:
<223> OTHER INFORMATION: beta-actin-A primer

<400> SEQUENCE: 86
caggaaggag ggctggaac                                               19

<210> SEQ ID NO 87
<211> LENGTH: 19
<212> TYPE: DNA
<213> ORGANISM: Artificial Sequence
<220> FEATURE:
<223> OTHER INFORMATION: ND4-S primer

<400> SEQUENCE: 87
ctgcctacga caaacagac                                               19

<210> SEQ ID NO 88
<211> LENGTH: 19
<212> TYPE: DNA
<213> ORGANISM: Artificial Sequence
<220> FEATURE:
<223> OTHER INFORMATION: ND4-A primer

<400> SEQUENCE: 88
agtgcgttcg tagtttgag                                               19

<210> SEQ ID NO 89
<211> LENGTH: 21
<212> TYPE: DNA
<213> ORGANISM: Artificial Sequence
<220> FEATURE:
<223> OTHER INFORMATION: ND6-F primer

<400> SEQUENCE: 89
atgatgtatg ctttgtttct g                                            21

<210> SEQ ID NO 90
<211> LENGTH: 21
<212> TYPE: DNA
<213> ORGANISM: Artificial Sequence
<220> FEATURE:
<223> OTHER INFORMATION: ND6-R primer

<400> SEQUENCE: 90
ctaattcccc cgagcaatct c                                            21

<210> SEQ ID NO 91
<211> LENGTH: 18
<212> TYPE: DNA
<213> ORGANISM: Artificial Sequence
<220> FEATURE:
<223> OTHER INFORMATION: ND6-S primer

<400> SEQUENCE: 91
```
agtgtgggtt tagtaatg                                              18

<210> SEQ ID NO 92
<211> LENGTH: 18
<212> TYPE: DNA
<213> ORGANISM: Artificial Sequence
<220> FEATURE:
<223> OTHER INFORMATION: ND6-A  primer

<400> SEQUENCE: 92
tgcctcagga tactcctc                                              18

<210> SEQ ID NO 93
<211> LENGTH: 20
<212> TYPE: DNA
<213> ORGANISM: Artificial Sequence
<220> FEATURE:
<223> OTHER INFORMATION: beta-actin-F primer

<400> SEQUENCE: 93
ctccatcctg gcctcgctgt                                            20

<210> SEQ ID NO 94
<211> LENGTH: 20
<212> TYPE: DNA
<213> ORGANISM: Artificial Sequence
<220> FEATURE:
<223> OTHER INFORMATION: beta-actin-R primer

<400> SEQUENCE: 94
gctgtcacct tcaccgttcc                                            20

<210> SEQ ID NO 95
<211> LENGTH: 23
<212> TYPE: DNA
<213> ORGANISM: Artificial Sequence
<220> FEATURE:
<223> OTHER INFORMATION: ND6-F primer

<400> SEQUENCE: 95
gggttttctt ctaagccttc tcc                                        23

<210> SEQ ID NO 96
<211> LENGTH: 23
<212> TYPE: DNA
<213> ORGANISM: Artificial Sequence
<220> FEATURE:
<223> OTHER INFORMATION: ND6-R primer

<400> SEQUENCE: 96
ccatcatact ctttcaccca cag                                        23

<210> SEQ ID NO 97
<211> LENGTH: 20
<212> TYPE: DNA
<213> ORGANISM: Artificial Sequence
<220> FEATURE:
<223> OTHER INFORMATION: opt_ND6-F primer

<400> SEQUENCE: 97
cgcctgctga ccggctgcgt                                            20

<210> SEQ ID NO 98
<211> LENGTH: 20
<212> TYPE: DNA

```
<213> ORGANISM: Artificial Sequence
<220> FEATURE:
<223> OTHER INFORMATION: opt_ND6-R

<400> SEQUENCE: 98
ccaggcctcg gggtactcct                                                   20

<210> SEQ ID NO 99
<211> LENGTH: 21
<212> TYPE: DNA
<213> ORGANISM: Artificial Sequence
<220> FEATURE:
<223> OTHER INFORMATION: ND1-F primer

<400> SEQUENCE: 99
atggccgcat ctccgcacac t                                                 21

<210> SEQ ID NO 100
<211> LENGTH: 21
<212> TYPE: DNA
<213> ORGANISM: Artificial Sequence
<220> FEATURE:
<223> OTHER INFORMATION: ND1-R primer

<400> SEQUENCE: 100
ttaggtttga gggggaatgc t                                                 21

<210> SEQ ID NO 101
<211> LENGTH: 21
<212> TYPE: DNA
<213> ORGANISM: Artificial Sequence
<220> FEATURE:
<223> OTHER INFORMATION: ND1-F primer

<400> SEQUENCE: 101
aacctcaacc taggcctcct a                                                 21

<210> SEQ ID NO 102
<211> LENGTH: 21
<212> TYPE: DNA
<213> ORGANISM: Artificial Sequence
<220> FEATURE:
<223> OTHER INFORMATION: ND1-R primer

<400> SEQUENCE: 102
tggcaggagt aaccagaggt g                                                 21

<210> SEQ ID NO 103
<211> LENGTH: 23
<212> TYPE: DNA
<213> ORGANISM: Artificial Sequence
<220> FEATURE:
<223> OTHER INFORMATION: ND1-F primer

<400> SEQUENCE: 103
aggaggctct gtctggtatc ttg                                               23

<210> SEQ ID NO 104
<211> LENGTH: 21
<212> TYPE: DNA
<213> ORGANISM: Artificial Sequence
<220> FEATURE:
<223> OTHER INFORMATION: ND1-R primer

<400> SEQUENCE: 104
ttttaggggc tctttggtga a                                                 21
```

<210> SEQ ID NO 105
<211> LENGTH: 22
<212> TYPE: DNA
<213> ORGANISM: Artificial Sequence
<220> FEATURE:
<223> OTHER INFORMATION: opt-ND1-F primer

<400> SEQUENCE: 105
gccgcctgct gaccggctgc gt                                              22

<210> SEQ ID NO 106
<211> LENGTH: 24
<212> TYPE: DNA
<213> ORGANISM: Artificial Sequence
<220> FEATURE:
<223> OTHER INFORMATION: opt-ND1-R primer

<400> SEQUENCE: 106
tgatgtacag ggtgatggtg ctgg                                            24

<210> SEQ ID NO 107
<211> LENGTH: 19
<212> TYPE: DNA
<213> ORGANISM: Artificial Sequence
<220> FEATURE:
<223> OTHER INFORMATION: ND4-S primer

<400> SEQUENCE: 107
gccaacagca actacgagc                                                  19

<210> SEQ ID NO 108
<211> LENGTH: 20
<212> TYPE: DNA
<213> ORGANISM: Artificial Sequence
<220> FEATURE:
<223> OTHER INFORMATION: ND4-A  primer

<400> SEQUENCE: 108
tgatgttgct ccagctgaag                                                 20

<210> SEQ ID NO 109
<211> LENGTH: 20
<212> TYPE: DNA
<213> ORGANISM: Artificial Sequence
<220> FEATURE:
<223> OTHER INFORMATION: opt-ND4-S primer

<400> SEQUENCE: 109
gcctgaccct gatcctgaac                                                 20

<210> SEQ ID NO 110
<211> LENGTH: 20
<212> TYPE: DNA
<213> ORGANISM: Artificial Sequence
<220> FEATURE:
<223> OTHER INFORMATION: opt-ND4-A primer

<400> SEQUENCE: 110
gtgcgctcgt agttgctgtt                                                 20

<210> SEQ ID NO 111
<211> LENGTH: 376
<212> TYPE: DNA
<213> ORGANISM: Homo sapiens

```
<400> SEQUENCE: 111
gggcagtgcc tccccgcccc gccgctggcg tcaagttcag ctccacgtgt gccatcagtg      60
gatccgatcc gtccagccat ggcttcctat tccaagatgg tgtgaccaga catgcttcct     120 gctcccccgct tagcccacgg agtgactgtg gttgtggtgg ggggttctt aaaataactt     180 tttagccccc gtcttcctat tttgagtttg gttcagatct taagcagctc catgcaactg     240
tatttatttt tgatgacaag actcccatct aaagttttc tcctgcctga tcatttcatt     300
ggtggctgaa ggattctaga gaaccttttg ttcttgcaag gaaaacaaga atccaaaacc     360
agtgactgtt ctgtga                                                    376

<210> SEQ ID NO 112
<211> LENGTH: 146
<212> TYPE: DNA
<213> ORGANISM: Homo sapiens

<400> SEQUENCE: 112
ggggtctttg tcctctgtac tgtctctctc cttgccccta acccaaaaag cttcattttt      60
ctgtgtaggc tgcacaagag ccttgattga agatatattc tttctgaaca gtatttaagg     120
tttccaataa aatgtacacc cctcag                                         146

<210> SEQ ID NO 113
<211> LENGTH: 1956
<212> TYPE: DNA
<213> ORGANISM: Homo sapiens

<400> SEQUENCE: 113
tgttgggtcc aagaaggaat ttctttccat ccctgtgagg caatgggtgg gaatgatagg      60
acaggcaaag agaagcttcc tcaggctagc aaaaatatca tttgatgtat tgattaaaaa     120
agcacttgct tgatgtatct ttggcgtgtg tgctactctc atctgtgtgt atgtgtgttg     180
tgtgtgtgtg tgtgtgcatg cacatatgtg ttcactctgc tactttgtaa gttttaggct     240
aggttgcttt accagctgtt tacttctttt ttgttgttgt tttgagacaa ggtttcgctc     300
tgccaccctg gctggagtgc agtggcgtga tcttggctca cggcaacctc tgcctcctgg     360
ggctcaagca attatcccac ctcagcctcc tgagcagctg ggactacagg tgcatgccac     420
aacacctggc tgatatttgt attttttgta gagacaggat tttgccaagt tgcccaggct     480
ggtcttgaac tcctaggctt aagcaatcca cccaccttgg cctcctgaag tgccaggatc     540
acagacgtga gccactacac ccagcccagc tgtttacttc tttaaccata cttttgattt     600 tatttttttga ccaaaatgaa ctaacccagg taatcttcca gggaccgcaa ttccagaacc     660
tcatagtatt tcttccatt ccagcagctg attagaagtc caggatcatg tgaagtcagg     720
cagggtcaca gttcctgatg gcacattatg acagagaat tccattttgt tttctaaccc     780
atgatgaaaa cccacgtgag tcagtgtgtg aacaggatc attaattttt tccccctagg     840
tggaaggaaa aaggcactta ctttgcaggt tacagaaatt actgggagag gatatcgtca     900
taaaaagagc caggccaaat tggaatattt ttgtgatctg catcatgatg ctgaaaatag     960
caattatttg ggaattgggt ttgaaaactg aattgttgcc agagaattaa accaggtgaa    1020 aggtccttt gaattcagat tgtcttctga acatccaggc tgatcatctg agagcagtca    1080
aatctacttc cccaaaaaga gaccagggta ggtttatttg cttttatttt taatgtttgc    1140 ctgtgttcc aagtgtgaac aaaacagtgt gtgatctatt cttggattca ttttgatcag    1200
tatttattca aacccagtct ctctccagga cataaaactg aaatcagata tgttctttt    1260
```

| | | | | |
|---|---|---|---|---|
| aagcccaaac | cctctccttt | ctagatccaa | cccttcaccc | ctaatttat gatggctata | 1320 |
| gccatggact | tccccaagaa | aagatcaccc | agaaataaga | ccacctgtga cagttaccag | 1380 |
| cttttattca | taaccttagc | ttcccaacta | ttgagcattt | tctaaggtcc ctgctgtctt | 1440 |
| ttggtctctg | gtttgatttg | tggcaaacag | atgaagtaac | agactgctat gaaggaccac | 1500 |
| aaaaacggca | gcctctggaa | aaaccattag | aaagtcagtg | gcagatccag taaataatat | 1560 |
| cgccagcctc | agcataatct | gctgctgact | cgattcagtg | gactctaaag tgcccagcct | 1620 |
| cctgacctga | gctctcctgc | catctgtgag | actaccagag | gtcttatctg ctgtccacat | 1680 |
| ggcaactggg | catgagtacc | tggccacctt | gcttccctct | ttgcctggtc caagtgagtg | 1740 |
| tctgctgcct | ctgtcctgcc | ttgttttcct | ggctctaaac | caactccacc cactcttaat | 1800 |
| ggaaactcag | tctggctttg | tgtgtttctg | ggaagcacat | gacttctggg aatgggcaag | 1860 |
| gaagaggagt | gaaacaaaaa | ctgtcagcta | tgtgtgcctg | gtctgggatc cttctctggg | 1920 |
| tgacagtggc | atcatgaatc | ttagaatcag | ctcccc | | 1956 |

<210> SEQ ID NO 114
<211> LENGTH: 411
<212> TYPE: DNA
<213> ORGANISM: Homo sapiens

<400> SEQUENCE: 114

| | | | | |
|---|---|---|---|---|
| gaatcatgca | agcttcctcc | ctcagccatt | gatggaaagt | tcagcaagat cagcaacaaa | 60 |
| accaagaaaa | atgatcccttg | cgtgctgaat | atctgaaaag | agaaattttt cctacaaaat | 120 |
| ctcttgggtc | aagaaagttc | tagaatttga | attgataaac | atggtgggtt ggctgagggt | 180 |
| aagagtatat | gaggaacctt | taaaacgaca | acaatactgc | tagctttcag gatgattttt | 240 |
| aaaaaataga | ttcaaatgtg | ttatcctctc | tctgaaacgc | ttcctataac tcgagtttat | 300 |
| aggggaagaa | aaagctattg | tttacaatta | tatcaccatt | aaggcaactg ctacaccctg | 360 |
| cttttgtattc | tgggctaaga | ttcattaaaa | actagctgct | cttaacttac a | 411 |

<210> SEQ ID NO 115
<211> LENGTH: 1465
<212> TYPE: DNA
<213> ORGANISM: Homo sapiens

<400> SEQUENCE: 115

| | | | | |
|---|---|---|---|---|
| gagcactggg | acgcccaccg | cccctttccc | tccgctgcca | ggcgagcatg ttgtggtaat | 60 |
| tctggaacac | aagaagagaa | attgctgggt | ttagaacaag | attataaacg aattcggtgc | 120 |
| tcagtgatca | cttgacagtt | tttttttttt | ttaaatatta | cccaaaatgc tccccaaata | 180 |
| agaaatgcat | cagctcagtc | agtgaataca | aaaaaggaat | tatttttccc tttgagggtc | 240 |
| tttatacatc | tctcctccaa | ccccacccctc | tattctgttt | cttcctcctc acatgggggt | 300 |
| acacatacac | agcttcctct | tttggttcca | tccttaccac | cacaccacac gcacactcca | 360 |
| catgcccagc | agagtggcac | ttggtggcca | gaaagtgtga | gcctcatgat ctgctgtctg | 420 |
| tagttctgtg | agctcaggtc | cctcaaaggc | ctcggagcac | cccttcctg gtgactgagc | 480 |
| cagggcctgc | attttggtt | tcccccaccc | cacacattct | caaccatagt ccttctaaca | 540 |
| ataccaatag | ctaggacccg | gctgctgtgc | actgggactg | gggattccac atgtttgcct | 600 |
| tgggagtctc | aagctggact | gccagcccct | gtcctccctt | cacccccatt gcgtatgagc | 660 |
| atttcagaac | tccaaggagt | cacaggcatc | tttatagttc | acgttaacat atagacactg | 720 |

```
ttggaagcag ttccttctaa aagggtagcc ctggacttaa taccagccgg atacctctgg      780
cccccacccc attactgtac ctctggagtc actactgtgg gtcgccactc ctctgctaca      840
cagcacggct ttttcaaggc tgtattgaga agggaagtta ggaagaaggg tgtgctgggc      900
taaccagccc acagagctca cattcctgtc ccttgggtga aaaatacatg tccatcctga      960
tatctcctga attcagaaat tagcctccac atgtgcaatg gctttaagag ccagaagcag     1020
ggttctggga attttgcaag ttatcctgtg gccaggtgtg gtctcggtta ccaaatacgg     1080
ttacctgcag ctttttagtc ctttgtgctc ccacgggtct gcagagtccc atctgcccaa     1140
aggtcttgaa gcttgacagg atgttttcat tactcagtct cccagggcac tgctggtccg     1200
tagggattca ttggtcgggg tgggagagtt aaacaacatt taaacagagt tctctcaaaa     1260
atgtctaaag ggattgtagg tagataacat ccaatcactg tttgcactta tctgaaatct     1320
tccctcttgg ctgcccccag gtatttactg tggagaacat tgcataggaa tgtctggaaa     1380
aagcctctac aacttgttac agccttcaca tttgtacaat tcattgattc tcttttcctt     1440
ccacaataaa atggtataca agaac                                           1465
```

<210> SEQ ID NO 116
<211> LENGTH: 288
<212> TYPE: DNA
<213> ORGANISM: Homo sapiens

<400> SEQUENCE: 116

```
gagacttgga ctcaagtcat aggcttcttt cagtctttat gtcacctcag gagacttatt       60
tgagaggaag ccttctgtac ttgaagttga tttgaaatat gtaagaattg atgatgtatt      120
tgcaaacatt aatgtgaaat aaattgaatt taatgttgaa tactttcagg cattcactta      180
ataaagacac tgttaagcac tgttatgctc agtcatacac gcgaaaggta caatgtcttt      240
tagctaattc taattaaaaa ttacagactg gtgtacaaga tacttgtg                   288
```

<210> SEQ ID NO 117
<211> LENGTH: 83
<212> TYPE: DNA
<213> ORGANISM: Homo sapiens

<400> SEQUENCE: 117

```
cccaccaccc tggcctgctg tcctgcgtct atccatgtgg aatgctggac aataaagcga       60
gtgctgccca ccctccagct gcc                                              83
```

<210> SEQ ID NO 118
<211> LENGTH: 66
<212> TYPE: DNA
<213> ORGANISM: Homo sapiens

<400> SEQUENCE: 118

```
tttatattga actgtaaata tgtcactaga gaaataaaat atggacttcc aatctacgta       60
aactta                                                                 66
```

<210> SEQ ID NO 119
<211> LENGTH: 214
<212> TYPE: DNA
<213> ORGANISM: Homo sapiens

<400> SEQUENCE: 119

```
accacgatcg ttatgctgag tatgttaagc tctttatgac tgttttgta gtggtataga       60 gtactgcaga atacagtaag ctgctctatt gtagcatttc ttgatgttgc ttagtcactt      120
```
atttcataaa caacttaatg ttctgaataa tttcttacta aacattttgt tattgggcaa    180
gtgattgaaa atagtaaatg ctttgtgtga ttga                                214

<210> SEQ ID NO 120
<211> LENGTH: 286
<212> TYPE: DNA
<213> ORGANISM: Homo sapiens

<400> SEQUENCE: 120
tcttggaata taaagaattt cttcaggttg aattacctag aagtttgtca ctgacttgtg     60
ttcctgaact atgacacatg aatatgtggg ctaagaaata gttcctcttg ataaataaac    120
aattaacaaa tactttggac agtaagtctt tctcagttct taatgataat gcagggcact    180
tactagcata agaattggtt tgggatttaa ctgtttatga agctaacttg atttccgtgt    240
tttgttaaaa tttcattgtt ctagcacatc tttaactgtg atagtt                   286

<210> SEQ ID NO 121
<211> LENGTH: 721
<212> TYPE: DNA
<213> ORGANISM: Homo sapiens

<400> SEQUENCE: 121
gagacgtgca cttggtcgtg cgcccaggga ggaagccgca ccaccagcca gcgcaggccc     60
tggtggagag gcctccctgg ctgcctctgg gaggggtgct gccttgtaga tggagcaagt    120
gagcactgag ggtctggtgc caatcctgta ggcacaaaac cagaagtttc tacattctct    180 attttgtta atcatcttct ctttttccag aatttggaag ctagaatggt gggaatgtca     240
gtagtgccag aaagagagaa ccaagcttgt ctttaaagtt actgatcaca ggacgttgct    300
ttttcactgt ttcctattaa tcttcagctg aacacaagca aaccttctca ggaggtgtct    360
cctaccctct tattgttcct cttacgctct gctcaatgaa accttcctct tgagggtcat    420
tttcctttct gtattaatta taccagtgtt aagtgacata gataagaact ttgcacactt    480
caaatcagag cagtgattct ctcttctctc ccctttcct tcagagtgaa tcatccagac     540
tcctcatgga taggtcgggt gttaaagttg ttttgattat gtacctttg atagatccac     600 ataaaaagaa atgtgaagtt ttcttttact atcttttcat ttatcaagca gagacctttg    660
ttgggaggcg gtttgggaga acacatttct aatttgaatg aaatgaaatc tattttcagt    720
g                                                                    721

<210> SEQ ID NO 122
<211> LENGTH: 163
<212> TYPE: DNA
<213> ORGANISM: Homo sapiens

<400> SEQUENCE: 122
cagaagaagt gacggctggg ggcacagtgg gctgggcgcc cctgcagaac atgaaccttc     60
cgctcctggc tgccacaggg tcctccgatg ctggcctttg cgcctctaga ggcagccact    120
catggattca agtcctggct ccgcctcttc catcaggacc act                      163

<210> SEQ ID NO 123
<211> LENGTH: 60
<212> TYPE: DNA
<213> ORGANISM: Homo sapiens

<400> SEQUENCE: 123
agaggacaca ctctgcaccc ccccacccca cgaccttggc ccgagcccct ccgtgaggaa    60

<210> SEQ ID NO 124
<211> LENGTH: 65
<212> TYPE: DNA
<213> ORGANISM: Rattus norvegicus

<400> SEQUENCE: 124
agcccttccg ccaggctgtg tgtcaggccc gtggtgggtg ttttgtagta gtgtagagca    60
ttgca                                                                65

<210> SEQ ID NO 125
<211> LENGTH: 231
<212> TYPE: DNA
<213> ORGANISM: Homo sapiens

<400> SEQUENCE: 125
cttatgttct gtgcgcattc tggcaggaat tctgtctctt cagagactca tcctcaaaac    60
aagacttgac actgtgtcct tgccccagtc ctaggaactg tggcacacag agatgttcat   120
tttaaaaacg gatttcatga aacactcttg tacttatgtt tataagagag cactgggtag   180
ccaagtgatc ttcccattca cagagttagt aaacctctgt actacatgct g            231

<210> SEQ ID NO 126
<211> LENGTH: 28
<212> TYPE: PRT
<213> ORGANISM: Homo sapiens

<400> SEQUENCE: 126

Met Ala Ala Ser Pro His Thr Leu Ser Ser Arg Leu Leu Thr Gly Cys
1               5                   10                  15

Val Gly Gly Ser Val Trp Tyr Leu Glu Arg Arg Thr
            20                  25

<210> SEQ ID NO 127
<211> LENGTH: 29
<212> TYPE: PRT
<213> ORGANISM: Homo sapiens

<400> SEQUENCE: 127

Met Ser Val Leu Thr Arg Leu Leu Leu Arg Gly Leu Thr Arg Leu Gly
1               5                   10                  15

Ser Ala Ala Pro Val Arg Arg Ala Arg Ile His Ser Leu
            20                  25

<210> SEQ ID NO 128
<211> LENGTH: 10
<212> TYPE: PRT
<213> ORGANISM: Homo sapiens

<400> SEQUENCE: 128

Met Trp Arg Leu Arg Arg Ala Ala Val Ala
1               5                   10

<210> SEQ ID NO 129
<211> LENGTH: 28
<212> TYPE: PRT
<213> ORGANISM: Homo sapiens

<400> SEQUENCE: 129

Met Ala Ala Ser Pro His Thr Leu Ser Ser Arg Leu Leu Thr Gly Cys
1               5                   10                  15

```
Val Gly Gly Ser Val Trp Tyr Leu Glu Arg Arg Thr
            20                  25
```

<210> SEQ ID NO 130
<211> LENGTH: 122
<212> TYPE: PRT
<213> ORGANISM: Saccharomyces cerevisiae

<400> SEQUENCE: 130

```
Met Ala Phe Lys Ser Phe Ile Tyr Ser Lys Gly Tyr His Arg Ser Ala
1               5                   10                  15

Ala Gln Lys Lys Thr Ala Thr Ser Phe Phe Asp Ser Tyr Gln Tyr
            20                  25                  30

Leu Arg Gln Asn Gln Gly Leu Val Asn Ser Asp Pro Val Leu His Ala
            35                  40                  45

Ser His Leu His Pro His Pro Val Val Ala Asn Val Asn Tyr Asn
        50                  55                  60

Asn Val Asp Asp Ile Leu His Pro His Asp Leu Asp Ser Ser Ile Asn
65                  70                  75                  80

Asn Thr Asn Asn Pro Leu Thr His Glu Glu Leu Leu Tyr Asn Gln Asn
                85                  90                  95

Val Ser Leu Arg Ser Leu Lys Gln Gln Gln Ser Thr Asn Tyr Val Asn
            100                 105                 110

Asn Asn Asn Asn Asn Gln His Arg Tyr Tyr
            115                 120
```

<210> SEQ ID NO 131
<211> LENGTH: 174
<212> TYPE: PRT
<213> ORGANISM: Larimichthys crocea

<400> SEQUENCE: 131

```
Met Arg Lys Arg Ser Leu Arg Cys His Leu Trp Ser Ala Asn Ala Ser
1               5                   10                  15

Leu Ser Pro Arg Lys Asp Glu Val Thr Ser Arg Lys Glu Ser Glu Asn
            20                  25                  30

Leu Val Lys Gly Lys Asn Lys Ser His Leu His Leu Leu
            35                  40                  45

Phe Thr Ala Ser Lys Ile Gly Thr Asp Ser Val Phe Asp Val Gln Lys
        50                  55                  60

Ser Lys Glu Cys Cys Lys Glu Leu Gly Leu Leu Phe Thr Ser Leu Ile
65                  70                  75                  80

His Ser Ile Gly Ser Phe Pro Phe Asp Glu Glu Pro Lys Ala Ala Ala
                85                  90                  95

Val Phe Leu Pro Gly Ser Leu Pro Gln Leu Thr Val Leu Val Leu Ala
            100                 105                 110

Pro Gly Ser Gly Ser Cys Pro Thr Gly Lys Ser Thr Pro His Leu Ala
            115                 120                 125

Ala Ser Gly Arg Asn Ala Glu Leu Leu Arg Pro Gln Asn Ser Met Ile
        130                 135                 140

Val Arg Gln Phe Thr Cys Arg Gly Thr Ile Ser Ser His Leu Cys Ala
145                 150                 155                 160

His Leu Arg Lys Pro His Asp Ser Arg Asn Met Ala Arg Pro
                165                 170
```

<210> SEQ ID NO 132

```
<211> LENGTH: 56
<212> TYPE: PRT
<213> ORGANISM: Trypanosoma brucei

<400> SEQUENCE: 132

Met Leu Arg Arg Thr Ser Phe Asn Phe Thr Gly Arg Ala Met Ile Ser
1               5                   10                  15

Arg Gly Ser Pro Glu Trp Ser His Arg Leu Asp Leu Lys Lys Gly Lys
            20                  25                  30

Lys Thr Thr Met Met His Lys Leu Gly Thr Ser Lys Pro Asn Asn Ala
        35                  40                  45

Leu Gln Tyr Ala Gln Met Thr Leu
    50                  55

<210> SEQ ID NO 133
<211> LENGTH: 46
<212> TYPE: PRT
<213> ORGANISM: Neurospora crassa

<400> SEQUENCE: 133

Met Ile Ser Arg Ser Ala Leu Ser Arg Gly Ser Gln Leu Ala Leu Arg
1               5                   10                  15

Arg Pro Ala Ala Ala Lys Thr Ala Gln Arg Gly Phe Ala Ala Ala Ala
            20                  25                  30

Ala Ser Pro Ala Ala Ser Tyr Glu Pro Thr Thr Ile Ala Gly
        35                  40                  45

<210> SEQ ID NO 134
<211> LENGTH: 128
<212> TYPE: PRT
<213> ORGANISM: Homo sapiens

<400> SEQUENCE: 134

Met Pro Glu Leu Ile Leu Tyr Val Ala Ile Thr Leu Ser Val Ala Glu
1               5                   10                  15

Arg Leu Val Gly Pro Gly His Ala Cys Ala Glu Pro Ser Phe Arg Ser
            20                  25                  30

Ser Arg Cys Ser Ala Pro Leu Cys Leu Leu Cys Ser Gly Ser Ser Ser
        35                  40                  45

Pro Ala Thr Ala Pro His Pro Leu Lys Met Phe Ala Cys Ser Lys Phe
    50                  55                  60

Val Ser Thr Pro Ser Leu Val Lys Ser Thr Ser Gln Leu Leu Ser Arg
65                  70                  75                  80

Pro Leu Ser Ala Val Val Leu Lys Arg Pro Glu Ile Leu Thr Asp Glu
            85                  90                  95

Ser Leu Ser Ser Leu Ala Val Ser Cys Pro Leu Thr Ser Leu Val Ser
        100                 105                 110

Ser Arg Ser Phe Gln Thr Ser Ala Ile Ser Arg Asp Ile Asp Thr Ala
    115                 120                 125

<210> SEQ ID NO 135
<211> LENGTH: 115
<212> TYPE: PRT
<213> ORGANISM: Homo sapiens

<400> SEQUENCE: 135

Met Tyr Arg Leu Met Ser Ala Val Thr Ala Arg Ala Ala Ala Pro Gly
1               5                   10                  15

Gly Leu Ala Ser Ser Cys Gly Arg Arg Gly Val His Gln Arg Ala Gly
```

```
                 20                  25                  30

Leu Pro Pro Leu Gly His Gly Trp Val Gly Gly Leu Gly Leu Gly Leu
            35                  40                  45

Gly Leu Ala Leu Gly Val Lys Leu Ala Gly Gly Leu Arg Gly Ala Ala
         50                  55                  60

Pro Ala Gln Ser Pro Ala Ala Pro Asp Pro Glu Ala Ser Pro Leu Ala
 65                  70                  75                  80

Glu Pro Pro Gln Glu Gln Ser Leu Ala Pro Trp Ser Pro Gln Thr Pro
                 85                  90                  95

Ala Pro Pro Cys Ser Arg Cys Phe Ala Arg Ala Ile Glu Ser Ser Arg
             100                 105                 110

Asp Leu Leu
        115

<210> SEQ ID NO 136
<211> LENGTH: 140
<212> TYPE: PRT
<213> ORGANISM: Schizosaccharomyces pombe

<400> SEQUENCE: 136

Met Thr Val Leu Ala Pro Leu Arg Arg Leu His Thr Arg Ala Ala Phe
 1               5                  10                  15

Ser Ser Tyr Gly Arg Glu Ile Ala Leu Gln Lys Arg Phe Leu Asn Leu
             20                  25                  30

Asn Ser Cys Ser Ala Val Arg Arg Tyr Gly Thr Gly Phe Ser Asn Asn
         35                  40                  45

Leu Arg Ile Lys Lys Leu Lys Asn Ala Phe Gly Val Val Arg Ala Asn
     50                  55                  60

Ser Thr Lys Ser Thr Ser Thr Val Thr Thr Ala Ser Pro Ile Lys Tyr
 65                  70                  75                  80

Asp Ser Ser Phe Val Gly Lys Thr Gly Gly Glu Ile Phe His Asp Met
                 85                  90                  95

Met Leu Lys His Asn Val Lys His Val Phe Gly Tyr Pro Gly Gly Ala
             100                 105                 110

Ile Leu Pro Val Phe Asp Ala Ile Tyr Arg Ser Pro His Phe Glu Phe
         115                 120                 125

Ile Leu Pro Arg His Glu Gln Ala Ala Gly His Ala
     130                 135                 140

<210> SEQ ID NO 137
<211> LENGTH: 125
<212> TYPE: PRT
<213> ORGANISM: Glycine max

<400> SEQUENCE: 137

Met Ile Leu Cys Pro Leu Glu Ala Phe Ile Val Gln His Ile Leu Thr
 1               5                  10                  15

Ile Ser Val Met Gly Leu Leu Ser Cys Phe Arg Ser Val Leu Arg
             20                  25                  30

Lys Cys Ser Lys Gly Ser Ser Gly Met Ser Arg Phe Leu Tyr Thr Asn
         35                  40                  45

Asn Phe Gln Arg Asn Leu Ile Ser Gly Gly Asn Glu Ser Tyr Tyr
     50                  55                  60

Gly Tyr Phe Asn Arg Arg Ser Tyr Thr Ser Leu Tyr Met Gly Thr Gly
 65                  70                  75                  80

Thr Val Gly Gly Ile Thr Ser Ala Arg Ile Arg Val Pro Asn Val Gly
```

```
                    85                  90                  95

Cys Glu Gly Phe Met Cys Ser Ser His Leu Ser Ile Thr Gln Arg Asn
                100                 105                 110

Ser Arg Leu Ile His Ser Thr Ser Lys Ile Val Pro Asn
        115                 120                 125

<210> SEQ ID NO 138
<211> LENGTH: 107
<212> TYPE: PRT
<213> ORGANISM: Chlamydomonas reinhardtii

<400> SEQUENCE: 138

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met
            100                 105

<210> SEQ ID NO 139
<211> LENGTH: 87
<212> TYPE: PRT
<213> ORGANISM: Homo sapiens

<400> SEQUENCE: 139

Met Trp Arg Leu Arg Arg Ala Ala Val Ala Cys Glu Val Cys Gln Ser
1               5                   10                  15

Leu Val Lys His Ser Ser Gly Ile Lys Gly Ser Leu Pro Leu Gln Lys
            20                  25                  30

Leu His Leu Val Ser Arg Ser Ile Tyr His Ser His Pro Thr Leu
        35                  40                  45

Lys Leu Gln Arg Pro Gln Leu Arg Thr Ser Phe Gln Gln Phe Ser Ser
    50                  55                  60

Leu Thr Asn Leu Pro Leu Arg Lys Leu Lys Phe Ser Pro Ile Lys Tyr
65                  70                  75                  80

Gly Tyr Gln Pro Arg Arg Asn
                85

<210> SEQ ID NO 140
<211> LENGTH: 56
<212> TYPE: PRT
<213> ORGANISM: Homo sapiens

<400> SEQUENCE: 140

Met Ala Val Leu Trp Arg Leu Ser Ala Val Cys Gly Ala Leu Gly Gly
1               5                   10                  15

Arg Ala Leu Leu Leu Arg Thr Pro Val Val Arg Pro Ala His Ile Ser
            20                  25                  30

Ala Phe Leu Gln Asp Arg Pro Ile Pro Glu Trp Cys Gly Val Gln His
        35                  40                  45
```

```
Ile His Leu Ser Pro Ser His His
    50                  55
```

<210> SEQ ID NO 141
<211> LENGTH: 162
<212> TYPE: PRT
<213> ORGANISM: Homo sapiens

<400> SEQUENCE: 141

```
Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe
```

<210> SEQ ID NO 142
<211> LENGTH: 117
<212> TYPE: PRT
<213> ORGANISM: Oryza sativa

<400> SEQUENCE: 142

```
Met Ala Leu Leu Leu Arg His Ser Pro Lys Leu Arg Arg Ala His Ala
1               5                   10                  15

Ile Leu Gly Cys Glu Arg Gly Thr Val Val Arg His Phe Ser Ser Ser
            20                  25                  30

Thr Cys Ser Ser Leu Val Lys Glu Asp Thr Val Ser Ser Asn Leu
        35                  40                  45

His Pro Glu Tyr Ala Lys Lys Ile Gly Gly Ser Asp Phe Ser His Asp
    50                  55                  60

Arg Gln Ser Gly Lys Glu Leu Gln Asn Phe Lys Val Ser Pro Gln Glu
65                  70                  75                  80

Ala Ser Arg Ala Ser Asn Phe Met Arg Ala Ser Lys Tyr Gly Met Pro
                85                  90                  95

Ile Thr Ala Asn Gly Val His Ser Leu Phe Ser Cys Gly Gln Val Val
            100                 105                 110

Pro Ser Arg Cys Phe
        115
```

<210> SEQ ID NO 143
<211> LENGTH: 66

```
<212> TYPE: PRT
<213> ORGANISM: Neurospora crassa

<400> SEQUENCE: 143

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
                20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
        50                  55                  60

Arg Ala
65

<210> SEQ ID NO 144
<211> LENGTH: 44
<212> TYPE: PRT
<213> ORGANISM: Homo sapiens

<400> SEQUENCE: 144

Met Leu Ala Ala Arg Leu Val Cys Leu Arg Thr Leu Pro Ser Arg Val
1               5                   10                  15

Phe His Pro Ala Phe Thr Lys Ala Ser Pro Val Val Lys Asn Ser Ile
                20                  25                  30

Thr Lys Asn Gln Trp Leu Leu Thr Pro Ser Arg Glu
            35                  40

<210> SEQ ID NO 145
<211> LENGTH: 68
<212> TYPE: PRT
<213> ORGANISM: Homo sapiens

<400> SEQUENCE: 145

Met Ala Ser Arg Val Leu Ser Ala Tyr Val Ser Arg Leu Pro Ala Ala
1               5                   10                  15

Phe Ala Pro Leu Pro Arg Val Arg Met Leu Ala Val Ala Arg Pro Leu
                20                  25                  30

Ser Thr Ala Leu Cys Ser Ala Gly Thr Gln Thr Arg Leu Gly Thr Leu
            35                  40                  45

Gln Pro Ala Leu Val Leu Ala Gln Val Pro Gly Arg Val Thr Gln Leu
        50                  55                  60

Cys Arg Gln Tyr
65

<210> SEQ ID NO 146
<211> LENGTH: 67
<212> TYPE: PRT
<213> ORGANISM: Homo sapiens

<400> SEQUENCE: 146

Met Phe Ala Cys Ala Lys Leu Ala Cys Thr Pro Ser Leu Ile Arg Ala
1               5                   10                  15

Gly Ser Arg Val Ala Tyr Arg Pro Ile Ser Ala Ser Val Leu Ser Arg
                20                  25                  30

Pro Glu Ala Ser Arg Thr Gly Glu Gly Ser Thr Val Phe Asn Gly Ala
            35                  40                  45

Gln Asn Gly Val Ser Gln Leu Ile Gln Arg Glu Phe Gln Thr Ser Ala
        50                  55                  60
```

```
Ile Ser Arg
65

<210> SEQ ID NO 147
<211> LENGTH: 273
<212> TYPE: PRT
<213> ORGANISM: Artificial Sequence
<220> FEATURE:
<223> OTHER INFORMATION: crATP6_hsADCK3

<400> SEQUENCE: 147

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

Phe Lys Asn Gln Gly Phe Asn Gly Ser Leu Gln Ser Val Glu Asn His
        35                  40                  45

Val Tyr Ala Gln Ala Phe Ser Thr Ser Ser Gln Glu Glu Gln Ala Ala
    50                  55                  60

Pro Ser Ile Gln Gly Ala Ser Gly Met Lys Leu Pro Gly Met Ala Gly
65                  70                  75                  80

Ser Met Leu Leu Gly Lys Ser Arg Ser Gly Leu Arg Thr Gly Ser Met
                85                  90                  95

Val Pro Phe Ala Ala Gln Gln Ala Met Asn Met Gly Gly Met Ala Ala
            100                 105                 110

Ile Leu Gly Asp Thr Ile Met Val Ala Lys Gly Leu Val Lys Leu Thr
        115                 120                 125

Gln Ala Ala Val Glu Thr His Leu Gln His Leu Gly Ile Gly Gly Glu
    130                 135                 140

Leu Ile Met Ala Ala Arg Ala Leu Gln Ser Thr Ala Val Glu Gln Ile
145                 150                 155                 160

Gly Met Phe Leu Gly Lys Val Gln Gly Gln Asp Lys His Glu Glu Tyr
                165                 170                 175

Phe Ala Glu Asn Phe Gly Gly Pro Glu Gly Glu Phe His Phe Ser Val
            180                 185                 190

Pro His Ala Ala Gly Ala Ser Thr Asp Phe Ser Ser Ala Ser Ala Pro
        195                 200                 205

Asp Gln Ser Ala Pro Pro Ser Leu Gly His Ala His Ser Glu Gly Pro
    210                 215                 220

Ala Pro Ala Tyr Val Ala Ser Gly Pro Phe Arg Glu Ala Gly Phe Pro
225                 230                 235                 240

Gly Gln Ala Ser Ser Pro Leu Gly Arg Ala Asn Gly Arg Leu Phe Ala
                245                 250                 255

Asn Pro Arg Asp Ser Phe Ser Ala Met Gly Phe Gln Arg Arg Phe Gly
            260                 265                 270

Gly

<210> SEQ ID NO 148
<211> LENGTH: 132
<212> TYPE: PRT
<213> ORGANISM: Artificial Sequence
<220> FEATURE:
<223> OTHER INFORMATION: ncATP9_ncATP9

<400> SEQUENCE: 148

Met Ala Ser Thr Arg Val Leu Ala Ser Arg Leu Ala Ser Gln Met Ala
1               5                   10                  15
```

```
Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
         35                  40                  45

Gln Met Thr Ser Ile Val Asn Ala Thr Thr Arg Gln Ala Phe Gln Lys
 50                  55                  60

Arg Ala Met Ala Ser Thr Arg Val Leu Ala Ser Arg Leu Ala Ser Gln
 65                  70                  75                  80

Met Ala Ala Ser Ala Lys Val Ala Arg Pro Ala Val Arg Val Ala Gln
                 85                  90                  95

Val Ser Lys Arg Thr Ile Gln Thr Gly Ser Pro Leu Gln Thr Leu Lys
            100                 105                 110

Arg Thr Gln Met Thr Ser Ile Val Asn Ala Thr Thr Arg Gln Ala Phe
         115                 120                 125

Gln Lys Arg Ala
    130

<210> SEQ ID NO 149
<211> LENGTH: 119
<212> TYPE: PRT
<213> ORGANISM: Zea mays

<400> SEQUENCE: 149

Met Ala Leu Leu Arg Ala Ala Val Ser Glu Leu Arg Arg Gly Arg
 1               5                  10                  15

Gly Ala Leu Thr Pro Leu Pro Ala Leu Ser Ser Leu Leu Ser Ser Leu
             20                  25                  30

Ser Pro Arg Ser Pro Ala Ser Thr Arg Pro Glu Pro Asn Asn Pro His
         35                  40                  45

Ala Asp Arg Arg His Val Ile Ala Leu Arg Arg Cys Pro Pro Leu Pro
 50                  55                  60

Ala Ser Ala Val Leu Ala Pro Glu Leu Leu His Ala Arg Gly Leu Leu
 65                  70                  75                  80

Pro Arg His Trp Ser His Ala Ser Pro Leu Ser Thr Ser Ser Ser Ser
                 85                  90                  95

Ser Arg Pro Ala Asp Lys Ala Gln Leu Thr Trp Val Asp Lys Trp Ile
            100                 105                 110

Pro Glu Ala Ala Arg Pro Tyr
        115

<210> SEQ ID NO 150
<211> LENGTH: 391
<212> TYPE: PRT
<213> ORGANISM: Artificial Sequence
<220> FEATURE:
<223> OTHER INFORMATION: ncATP9_zmLOC100282174_spilv1_ncATP9

<400> SEQUENCE: 150

Met Ala Ser Thr Arg Val Leu Ala Ser Arg Leu Ala Ser Gln Met Ala
 1               5                  10                  15

Ala Ser Ala Lys Val Ala Arg Pro Ala Val Arg Val Ala Gln Val Ser
             20                  25                  30

Lys Arg Thr Ile Gln Thr Gly Ser Pro Leu Gln Thr Leu Lys Arg Thr
         35                  40                  45

Gln Met Thr Ser Ile Val Asn Ala Thr Thr Arg Gln Ala Phe Gln Lys
 50                  55                  60
```

Arg Ala Met Ala Leu Leu Arg Ala Val Ser Glu Leu Arg Arg Arg
65                  70                  75                  80

Gly Arg Gly Ala Leu Thr Pro Leu Pro Ala Leu Ser Ser Leu Leu Ser
            85                  90                  95

Ser Leu Ser Pro Arg Ser Pro Ala Ser Thr Arg Pro Glu Pro Asn Asn
        100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
        130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Ala Ser Thr Arg Val Leu Ala Ser Arg Leu
                325                 330                 335

Ala Ser Gln Met Ala Ala Ser Ala Lys Val Ala Arg Pro Ala Val Arg
            340                 345                 350

Val Ala Gln Val Ser Lys Arg Thr Ile Gln Thr Gly Ser Pro Leu Gln
        355                 360                 365

Thr Leu Lys Arg Thr Gln Met Thr Ser Ile Val Asn Ala Thr Thr Arg
    370                 375                 380

Gln Ala Phe Gln Lys Arg Ala
385                 390

<210> SEQ ID NO 151
<211> LENGTH: 455
<212> TYPE: PRT
<213> ORGANISM: Artificial Sequence
<220> FEATURE:
<223> OTHER INFORMATION: zmLOC100282174_hsADCK3_crATP6 _hsATP5G3

<400> SEQUENCE: 151

Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

```
Ser Pro Arg Ser Pro Ala Ser Thr Arg Pro Glu Pro Asn Asn Pro His
         35                  40                  45

Ala Asp Arg Arg His Val Ile Ala Leu Arg Arg Cys Pro Pro Leu Pro
 50                      55                  60

Ala Ser Ala Val Leu Ala Pro Glu Leu Leu His Ala Arg Gly Leu Leu
 65                  70                  75                  80

Pro Arg His Trp Ser His Ala Ser Pro Leu Ser Thr Ser Ser Ser Ser
                 85                  90                  95

Ser Arg Pro Ala Asp Lys Ala Gln Leu Thr Trp Val Asp Lys Trp Ile
             100                 105                 110

Pro Glu Ala Ala Arg Pro Tyr Met Ala Ala Ile Leu Gly Asp Thr Ile
             115                 120                 125

Met Val Ala Lys Gly Leu Val Lys Leu Thr Gln Ala Ala Val Glu Thr
130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                 165                 170                 175

Val Gln Gly Gln Asp Lys His Glu Glu Tyr Phe Ala Glu Asn Phe Gly
             180                 185                 190

Gly Pro Glu Gly Glu Phe His Phe Ser Val Pro His Ala Ala Gly Ala
             195                 200                 205

Ser Thr Asp Phe Ser Ser Ala Ser Ala Pro Asp Gln Ser Ala Pro Pro
210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                 245                 250                 255

Leu Gly Arg Ala Asn Gly Arg Leu Phe Ala Asn Pro Arg Asp Ser Phe
             260                 265                 270

Ser Ala Met Gly Phe Gln Arg Arg Phe Met Ala Leu Gln Gln Ala Ala
             275                 280                 285

Pro Arg Val Phe Gly Leu Leu Gly Arg Ala Pro Val Ala Leu Gly Gln
290                 295                 300

Ser Gly Ile Leu Thr Gly Ser Ser Gly Phe Lys Asn Gln Gly Phe Asn
305                 310                 315                 320

Gly Ser Leu Gln Ser Val Glu Asn His Val Tyr Ala Gln Ala Phe Ser
                 325                 330                 335

Thr Ser Ser Gln Glu Glu Gln Ala Ala Pro Ser Ile Gln Gly Ala Ser
             340                 345                 350

Gly Met Lys Leu Pro Gly Met Ala Gly Ser Met Leu Leu Gly Lys Ser
             355                 360                 365

Arg Ser Gly Leu Arg Thr Gly Ser Met Val Pro Phe Ala Ala Gln Gln
370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                 405                 410                 415

Val Leu Ser Arg Pro Glu Ala Ser Arg Thr Gly Glu Gly Ser Thr Val
             420                 425                 430

Phe Asn Gly Ala Gln Asn Gly Val Ser Gln Leu Ile Gln Arg Glu Phe
             435                 440                 445

Gln Thr Ser Ala Ile Ser Arg
```

<210> SEQ ID NO 152
<211> LENGTH: 348
<212> TYPE: PRT
<213> ORGANISM: Artificial Sequence
<220> FEATURE:
<223> OTHER INFORMATION: zmLOC100282174_hsADCK3_hsATP5G3

<400> SEQUENCE: 152

```
Met Ala Leu Leu Arg Ala Ala Val Ser Glu Leu Arg Arg Arg Gly Arg
1               5                   10                  15

Gly Ala Leu Thr Pro Leu Pro Ala Leu Ser Ser Leu Leu Ser Ser Leu
            20                  25                  30

Ser Pro Arg Ser Pro Ala Ser Thr Arg Pro Glu Pro Asn Asn Pro His
        35                  40                  45

Ala Asp Arg Arg His Val Ile Ala Leu Arg Arg Cys Pro Pro Leu Pro
    50                  55                  60

Ala Ser Ala Val Leu Ala Pro Glu Leu Leu His Ala Arg Gly Leu Leu
65                  70                  75                  80

Pro Arg His Trp Ser His Ala Ser Pro Leu Ser Thr Ser Ser Ser Ser
                85                  90                  95

Ser Arg Pro Ala Asp Lys Ala Gln Leu Thr Trp Val Asp Lys Trp Ile
            100                 105                 110

Pro Glu Ala Ala Arg Pro Tyr Met Ala Ala Ile Leu Gly Asp Thr Ile
        115                 120                 125

Met Val Ala Lys Gly Leu Val Lys Leu Thr Gln Ala Ala Val Glu Thr
130                 135                 140

His Leu Gln His Leu Gly Ile Gly Gly Glu Leu Ile Met Ala Ala Arg
145                 150                 155                 160

Ala Leu Gln Ser Thr Ala Val Glu Gln Ile Gly Met Phe Leu Gly Lys
                165                 170                 175

Val Gln Gly Gln Asp Lys His Glu Glu Tyr Phe Ala Glu Asn Phe Gly
            180                 185                 190

Gly Pro Glu Gly Glu Phe His Phe Ser Val Pro His Ala Ala Gly Ala
        195                 200                 205

Ser Thr Asp Phe Ser Ser Ala Ser Ala Pro Asp Gln Ser Ala Pro Pro
    210                 215                 220

Ser Leu Gly His Ala His Ser Glu Gly Pro Ala Pro Ala Tyr Val Ala
225                 230                 235                 240

Ser Gly Pro Phe Arg Glu Ala Gly Phe Pro Gly Gln Ala Ser Ser Pro
                245                 250                 255

Leu Gly Arg Ala Asn Gly Arg Leu Phe Ala Asn Pro Arg Asp Ser Phe
            260                 265                 270

Ser Ala Met Gly Phe Gln Arg Phe Met Phe Ala Cys Ala Lys Leu
        275                 280                 285

Ala Cys Thr Pro Ser Leu Ile Arg Ala Gly Ser Arg Val Ala Tyr Arg
    290                 295                 300

Pro Ile Ser Ala Ser Val Leu Ser Arg Pro Glu Ala Ser Arg Thr Gly
305                 310                 315                 320

Glu Gly Ser Thr Val Phe Asn Gly Ala Gln Asn Gly Val Ser Gln Leu
                325                 330                 335

Ile Gln Arg Glu Phe Gln Thr Ser Ala Ile Ser Arg
            340                 345
```

-continued

```
<210> SEQ ID NO 153
<211> LENGTH: 185
<212> TYPE: PRT
<213> ORGANISM: Artificial Sequence
<220> FEATURE:
<223> OTHER INFORMATION: ncATP9_zmLOC100282174

<400> SEQUENCE: 153
```

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr
            180                 185

```
<210> SEQ ID NO 154
<211> LENGTH: 455
<212> TYPE: PRT
<213> ORGANISM: Artificial Sequence
<220> FEATURE:
<223> OTHER INFORMATION: hsADCK3_zmLOC100282174_crATP6 _hsATP5G3

<400> SEQUENCE: 154
```

Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
            130                 135                 140

Leu Phe Ala Asn Pro Arg Asp Ser Phe Ser Ala Met Gly Phe Gln Arg
145                 150                 155                 160

Arg Phe Met Ala Leu Leu Arg Ala Ala Val Ser Glu Leu Arg Arg Arg
                165                 170                 175

Gly Arg Gly Ala Leu Thr Pro Leu Pro Ala Leu Ser Ser Leu Leu Ser
            180                 185                 190

Ser Leu Ser Pro Arg Ser Pro Ala Ser Thr Arg Pro Glu Pro Asn Asn
        195                 200                 205

Pro His Ala Asp Arg Arg His Val Ile Ala Leu Arg Arg Cys Pro Pro
210                 215                 220

Leu Pro Ala Ser Ala Val Leu Ala Pro Glu Leu Leu His Ala Arg Gly
225                 230                 235                 240

Leu Leu Pro Arg His Trp Ser His Ala Ser Pro Leu Ser Thr Ser Ser
                245                 250                 255

Ser Ser Ser Arg Pro Ala Asp Lys Ala Gln Leu Thr Trp Val Asp Lys
            260                 265                 270

Trp Ile Pro Glu Ala Ala Arg Pro Tyr Met Ala Leu Gln Gln Ala Ala
        275                 280                 285

Pro Arg Val Phe Gly Leu Leu Gly Arg Ala Pro Val Ala Leu Gly Gln
    290                 295                 300

Ser Gly Ile Leu Thr Gly Ser Ser Gly Phe Lys Asn Gln Gly Phe Asn
305                 310                 315                 320

Gly Ser Leu Gln Ser Val Glu Asn His Val Tyr Ala Gln Ala Phe Ser
                325                 330                 335

Thr Ser Ser Gln Glu Glu Gln Ala Ala Pro Ser Ile Gln Gly Ala Ser
            340                 345                 350

Gly Met Lys Leu Pro Gly Met Ala Gly Ser Met Leu Leu Gly Lys Ser
        355                 360                 365

Arg Ser Gly Leu Arg Thr Gly Ser Met Val Pro Phe Ala Ala Gln Gln
    370                 375                 380

Ala Met Asn Met Met Phe Ala Cys Ala Lys Leu Ala Cys Thr Pro Ser
385                 390                 395                 400

Leu Ile Arg Ala Gly Ser Arg Val Ala Tyr Arg Pro Ile Ser Ala Ser
                405                 410                 415

Val Leu Ser Arg Pro Glu Ala Ser Arg Thr Gly Glu Gly Ser Thr Val
            420                 425                 430

Phe Asn Gly Ala Gln Asn Gly Val Ser Gln Leu Ile Gln Arg Glu Phe
        435                 440                 445

Gln Thr Ser Ala Ile Ser Arg
    450                 455

<210> SEQ ID NO 155
<211> LENGTH: 455
<212> TYPE: PRT
<213> ORGANISM: Artificial Sequence
<220> FEATURE:
<223> OTHER INFORMATION: crATP6 _hsADCK3_zmLOC100282174_hsATP5G3

<400> SEQUENCE: 155

Met Ala Leu Gln Gln Ala Ala Pro Arg Val Phe Gly Leu Leu Gly Arg
1               5                   10                  15

Ala Pro Val Ala Leu Gly Gln Ser Gly Ile Leu Thr Gly Ser Ser Gly
            20                  25                  30

-continued

```
Phe Lys Asn Gln Gly Phe Asn Gly Ser Leu Gln Ser Val Glu Asn His
         35                  40                  45
Val Tyr Ala Gln Ala Phe Ser Thr Ser Ser Gln Glu Glu Gln Ala Ala
 50                  55                  60
Pro Ser Ile Gln Gly Ala Ser Gly Met Lys Leu Pro Gly Met Ala Gly
 65                  70                  75                  80
Ser Met Leu Leu Gly Lys Ser Arg Ser Gly Leu Arg Thr Gly Ser Met
                 85                  90                  95
Val Pro Phe Ala Ala Gln Gln Ala Met Asn Met Met Ala Ala Ile Leu
                100                 105                 110
Gly Asp Thr Ile Met Val Ala Lys Gly Leu Val Lys Leu Thr Gln Ala
             115                 120                 125
Ala Val Glu Thr His Leu Gln His Leu Gly Ile Gly Gly Glu Leu Ile
130                 135                 140
Met Ala Ala Arg Ala Leu Gln Ser Thr Ala Val Glu Gln Ile Gly Met
145                 150                 155                 160
Phe Leu Gly Lys Val Gln Gly Gln Asp Lys His Glu Glu Tyr Phe Ala
                 165                 170                 175
Glu Asn Phe Gly Gly Pro Glu Gly Glu Phe His Phe Ser Val Pro His
             180                 185                 190
Ala Ala Gly Ala Ser Thr Asp Phe Ser Ser Ala Ser Ala Pro Asp Gln
         195                 200                 205
Ser Ala Pro Pro Ser Leu Gly His Ala His Ser Glu Gly Pro Ala Pro
     210                 215                 220
Ala Tyr Val Ala Ser Gly Pro Phe Arg Glu Ala Gly Phe Pro Gly Gln
225                 230                 235                 240
Ala Ser Ser Pro Leu Gly Arg Ala Asn Gly Arg Leu Phe Ala Asn Pro
                 245                 250                 255
Arg Asp Ser Phe Ser Ala Met Gly Phe Gln Arg Arg Phe Met Ala Leu
             260                 265                 270
Leu Arg Ala Ala Val Ser Glu Leu Arg Arg Arg Gly Arg Gly Ala Leu
         275                 280                 285
Thr Pro Leu Pro Ala Leu Ser Ser Leu Leu Ser Ser Leu Ser Pro Arg
     290                 295                 300
Ser Pro Ala Ser Thr Arg Pro Glu Pro Asn Asn Pro His Ala Asp Arg
305                 310                 315                 320
Arg His Val Ile Ala Leu Arg Arg Cys Pro Pro Leu Pro Ala Ser Ala
                 325                 330                 335
Val Leu Ala Pro Glu Leu Leu His Ala Arg Gly Leu Leu Pro Arg His
             340                 345                 350
Trp Ser His Ala Ser Pro Leu Ser Thr Ser Ser Ser Ser Arg Pro
         355                 360                 365
Ala Asp Lys Ala Gln Leu Thr Trp Val Asp Lys Trp Ile Pro Glu Ala
     370                 375                 380
Ala Arg Pro Tyr Met Phe Ala Cys Ala Lys Leu Ala Cys Thr Pro Ser
385                 390                 395                 400
Leu Ile Arg Ala Gly Ser Arg Val Ala Tyr Arg Pro Ile Ser Ala Ser
                 405                 410                 415
Val Leu Ser Arg Pro Glu Ala Ser Arg Thr Gly Glu Gly Ser Thr Val
             420                 425                 430
Phe Asn Gly Ala Gln Asn Gly Val Ser Gln Leu Ile Gln Arg Glu Phe
         435                 440                 445
Gln Thr Ser Ala Ile Ser Arg
```

<210> SEQ ID NO 156
<211> LENGTH: 285
<212> TYPE: PRT
<213> ORGANISM: Artificial Sequence
<220> FEATURE:
<223> OTHER INFORMATION: hsADCK3_zmLOC100282174

<400> SEQUENCE: 156

```
Met Ala Ala Ile Leu Gly Asp Thr Ile Met Val Ala Lys Gly Leu Val
1               5                   10                  15

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
    50                  55                  60

Glu Glu Tyr Phe Ala Glu Asn Phe Gly Gly Pro Glu Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly
        275                 280                 285
```

<210> SEQ ID NO 157
<211> LENGTH: 394
<212> TYPE: PRT
<213> ORGANISM: Artificial Sequence
<220> FEATURE:
<223> OTHER INFORMATION: hsADCK3_zmLOC100282174_crATP6

<400> SEQUENCE: 157

```
Met Ala Ala Ile Leu Gly Asp Thr Ile Met Val Ala Lys Gly Leu Val
1               5                   10                  15
```

Lys Leu Thr Gln Ala Ala Val Glu Thr His Leu Gln His Leu Gly Ile
            20                  25                  30

Gly Gly Glu Leu Ile Met Ala Ala Arg Ala Leu Gln Ser Thr Ala Val
        35                  40                  45

Glu Gln Ile Gly Met Phe Leu Gly Lys Val Gln Gly Gln Asp Lys His
50                  55                  60

Glu Glu Tyr Phe Ala Glu Asn Phe Gly Gly Pro Gly Glu Phe His
65                  70                  75                  80

Phe Ser Val Pro His Ala Ala Gly Ala Ser Thr Asp Phe Ser Ser Ala
                85                  90                  95

Ser Ala Pro Asp Gln Ser Ala Pro Pro Ser Leu Gly His Ala His Ser
            100                 105                 110

Glu Gly Pro Ala Pro Ala Tyr Val Ala Ser Gly Pro Phe Arg Glu Ala
        115                 120                 125

Gly Phe Pro Gly Gln Ala Ser Ser Pro Leu Gly Arg Ala Asn Gly Arg
    130                 135                 140

Leu Phe Ala Asn Pro Arg Asp Ser Phe Ser Ala Met Gly Phe Gln Arg
145                 150                 155                 160

Arg Phe Gly Gly Met Ala Leu Leu Arg Ala Ala Val Ser Glu Leu Arg
                165                 170                 175

Arg Arg Gly Arg Gly Ala Leu Thr Pro Leu Pro Ala Leu Ser Ser Leu
            180                 185                 190

Leu Ser Ser Leu Ser Pro Arg Ser Pro Ala Ser Thr Arg Pro Glu Pro
        195                 200                 205

Asn Asn Pro His Ala Asp Arg Arg His Val Ile Ala Leu Arg Arg Cys
    210                 215                 220

Pro Pro Leu Pro Ala Ser Ala Val Leu Ala Pro Glu Leu Leu His Ala
225                 230                 235                 240

Arg Gly Leu Leu Pro Arg His Trp Ser His Ala Ser Pro Leu Ser Thr
                245                 250                 255

Ser Ser Ser Ser Ser Arg Pro Ala Asp Lys Ala Gln Leu Thr Trp Val
            260                 265                 270

Asp Lys Trp Ile Pro Glu Ala Ala Arg Pro Tyr Gly Gly Met Ala Leu
        275                 280                 285

Gln Gln Ala Ala Pro Arg Val Phe Gly Leu Leu Gly Arg Ala Pro Val
    290                 295                 300

Ala Leu Gly Gln Ser Gly Ile Leu Thr Gly Ser Ser Gly Phe Lys Asn
305                 310                 315                 320

Gln Gly Phe Asn Gly Ser Leu Gln Ser Val Glu Asn His Val Tyr Ala
                325                 330                 335

Gln Ala Phe Ser Thr Ser Ser Gln Glu Glu Gln Ala Ala Pro Ser Ile
            340                 345                 350

Gln Gly Ala Ser Gly Met Lys Leu Pro Gly Met Ala Gly Ser Met Leu
        355                 360                 365

Leu Gly Lys Ser Arg Ser Gly Leu Arg Thr Gly Ser Met Val Pro Phe
    370                 375                 380

Ala Ala Gln Gln Ala Met Asn Met Gly Gly
385                 390

<210> SEQ ID NO 158
<211> LENGTH: 574
<212> TYPE: PRT
<213> ORGANISM: Artificial Sequence
<220> FEATURE:
<223> OTHER INFORMATION: ncATP9_zmLOC100282174_spilv1_GNFP_ncATP9

<400> SEQUENCE: 158

```
Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
            35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg
65                  70                  75                  80

Gly Arg Gly Ala Leu Thr Pro Leu Pro Ala Leu Ser Ser Leu Leu Ser
                85                  90                  95

Ser Leu Ser Pro Arg Ser Pro Ala Ser Thr Arg Pro Glu Pro Asn Asn
                100                 105                 110

Pro His Ala Asp Arg Arg His Val Ile Ala Leu Arg Arg Cys Pro Pro
            115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Ser Thr Ser Ser
145                 150                 155                 160

Ser Ser Ser Arg Pro Ala Asp Lys Ala Gln Leu Thr Trp Val Asp Lys
                165                 170                 175

Trp Ile Pro Glu Ala Ala Arg Pro Tyr Met Thr Val Leu Ala Pro Leu
            180                 185                 190

Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Val Ser Gly Glu Gly Asp Ala Thr Tyr Gly Lys
                325                 330                 335

Leu Thr Leu Lys Phe Ile Cys Thr Thr Gly Lys Leu Pro Val Pro Trp
            340                 345                 350

Pro Thr Leu Val Thr Thr Leu Thr Tyr Gly Val Gln Cys Phe Ser Arg
        355                 360                 365

Tyr Pro Asp His Met Lys Gln His Asp Phe Phe Lys Ser Ala Met Pro
    370                 375                 380

Glu Gly Tyr Val Gln Glu Arg Thr Ile Phe Phe Lys Asp Asp Gly Asn
385                 390                 395                 400

Tyr Lys Thr Arg Ala Glu Val Lys Phe Glu Gly Asp Thr Leu Val Asn
```

```
                    405                 410                 415
Arg Ile Glu Leu Lys Gly Ile Asp Phe Lys Glu Asp Gly Asn Ile Leu
            420                 425                 430

Gly His Lys Leu Glu Tyr Asn Tyr Asn Ser His Asn Val Tyr Ile Met
            435                 440                 445

Ala Asp Lys Gln Lys Asn Gly Ile Lys Val Asn Phe Lys Ile Arg His
    450                 455                 460

Asn Ile Glu Asp Gly Ser Val Gln Leu Ala Asp His Tyr Gln Gln Asn
465                 470                 475                 480

Thr Pro Ile Gly Asp Gly Pro Val Leu Pro Asp Asn His Tyr Leu
            485                 490                 495

Ser Thr Gln Ser Ala Leu Ser Lys Asp Pro Asn Glu Met Ala Ser Thr
            500                 505                 510

Arg Val Leu Ala Ser Arg Leu Ala Ser Gln Met Ala Ala Ser Ala Lys
            515                 520                 525

Val Ala Arg Pro Ala Val Arg Val Ala Gln Val Ser Lys Arg Thr Ile
            530                 535                 540

Gln Thr Gly Ser Pro Leu Gln Thr Leu Lys Arg Thr Gln Met Thr Ser
545                 550                 555                 560

Ile Val Asn Ala Thr Thr Arg Gln Ala Phe Gln Lys Arg Ala
            565                 570

<210> SEQ ID NO 159
<211> LENGTH: 810
<212> TYPE: PRT
<213> ORGANISM: Artificial Sequence
<220> FEATURE:
<223> OTHER INFORMATION:
      ncATP9_zmLOC100282174_spilv1_lcSirt5_osP0644B06.24-2_hsATP5G2_ncA
      TP9

<400> SEQUENCE: 159

Met Ala Ser Thr Arg Val Leu Ala Ser Arg Leu Ala Ser Gln Met Ala
1               5                   10                  15

Ala Ser Ala Lys Val Ala Arg Pro Ala Val Arg Val Ala Gln Val Ser
            20                  25                  30

Lys Arg Thr Ile Gln Thr Gly Ser Pro Leu Gln Thr Leu Lys Arg Thr
        35                  40                  45

Gln Met Thr Ser Ile Val Asn Ala Thr Thr Arg Gln Ala Phe Gln Lys
    50                  55                  60

Arg Ala Met Ala Leu Leu Arg Ala Ala Val Ser Glu Leu Arg Arg
65              70                  75                  80

Gly Arg Gly Ala Leu Thr Pro Leu Pro Ala Leu Ser Ser Leu Leu Ser
            85                  90                  95

Ser Leu Ser Pro Arg Ser Pro Ala Ser Thr Arg Pro Glu Pro Asn Asn
            100                 105                 110

Pro His Ala Asp Arg Arg His Val Ile Ala Leu Arg Arg Cys Pro Pro
        115                 120                 125

Leu Pro Ala Ser Ala Val Leu Ala Pro Glu Leu Leu His Ala Arg Gly
    130                 135                 140

Leu Leu Pro Arg His Trp Ser His Ala Ser Pro Leu Thr Ser Ser
145             150                 155                 160

Ser Ser Ser Arg Pro Ala Asp Lys Ala Gln Leu Thr Trp Val Asp Lys
            165                 170                 175

Trp Ile Pro Glu Ala Ala Arg Pro Tyr Met Thr Val Leu Ala Pro Leu
            180                 185                 190
```

```
Arg Arg Leu His Thr Arg Ala Ala Phe Ser Ser Tyr Gly Arg Glu Ile
        195                 200                 205

Ala Leu Gln Lys Arg Phe Leu Asn Leu Asn Ser Cys Ser Ala Val Arg
    210                 215                 220

Arg Tyr Gly Thr Gly Phe Ser Asn Asn Leu Arg Ile Lys Lys Leu Lys
225                 230                 235                 240

Asn Ala Phe Gly Val Val Arg Ala Asn Ser Thr Lys Ser Thr Ser Thr
                245                 250                 255

Val Thr Thr Ala Ser Pro Ile Lys Tyr Asp Ser Ser Phe Val Gly Lys
            260                 265                 270

Thr Gly Gly Glu Ile Phe His Asp Met Met Leu Lys His Asn Val Lys
        275                 280                 285

His Val Phe Gly Tyr Pro Gly Gly Ala Ile Leu Pro Val Phe Asp Ala
    290                 295                 300

Ile Tyr Arg Ser Pro His Phe Glu Phe Ile Leu Pro Arg His Glu Gln
305                 310                 315                 320

Ala Ala Gly His Ala Met Arg Lys Arg Ser Leu Arg Cys His Leu Trp
                325                 330                 335

Ser Ala Asn Ala Ser Leu Ser Pro Arg Lys Asp Glu Val Thr Ser Arg
            340                 345                 350

Lys Glu Ser Glu Asn Leu Val Lys Gly Lys Lys Asn Lys Lys Ser His
        355                 360                 365

Leu His Leu Leu Leu Phe Thr Ala Ser Lys Ile Gly Thr Asp Ser Val
    370                 375                 380

Phe Asp Val Gln Lys Ser Lys Glu Cys Cys Lys Glu Leu Gly Leu Leu
385                 390                 395                 400

Phe Thr Ser Leu Ile His Ser Ile Gly Ser Phe Pro Phe Asp Glu Glu
                405                 410                 415

Pro Lys Ala Ala Ala Val Phe Leu Pro Gly Ser Leu Pro Gln Leu Thr
            420                 425                 430

Val Leu Val Leu Ala Pro Gly Ser Gly Ser Cys Pro Thr Gly Lys Ser
        435                 440                 445

Thr Pro His Leu Ala Ala Ser Gly Arg Asn Ala Glu Leu Leu Arg Pro
    450                 455                 460

Gln Asn Ser Met Ile Val Arg Gln Phe Thr Cys Arg Gly Thr Ile Ser
465                 470                 475                 480

Ser His Leu Cys Ala His Leu Arg Lys Pro His Asp Ser Arg Asn Met
                485                 490                 495

Ala Arg Pro Met Ala Leu Leu Leu Arg His Ser Pro Lys Leu Arg Arg
            500                 505                 510

Ala His Ala Ile Leu Gly Cys Glu Arg Gly Thr Val Val Arg His Phe
        515                 520                 525

Ser Ser Ser Thr Cys Ser Ser Leu Val Lys Glu Asp Thr Val Ser Ser
    530                 535                 540

Ser Asn Leu His Pro Glu Tyr Ala Lys Lys Ile Gly Gly Ser Asp Phe
545                 550                 555                 560

Ser His Asp Arg Gln Ser Gly Lys Glu Leu Gln Asn Phe Lys Val Ser
                565                 570                 575

Pro Gln Glu Ala Ser Arg Ala Ser Asn Phe Met Arg Ala Ser Lys Tyr
            580                 585                 590

Gly Met Pro Ile Thr Ala Asn Gly Val His Ser Leu Phe Ser Cys Gly
        595                 600                 605
```

```
Gln Val Val Pro Ser Arg Cys Phe Met Pro Glu Leu Ile Leu Tyr Val
    610                 615                 620

Ala Ile Thr Leu Ser Val Ala Glu Arg Leu Val Gly Pro Gly His Ala
625                 630                 635                 640

Cys Ala Glu Pro Ser Phe Arg Ser Ser Arg Cys Ser Ala Pro Leu Cys
                645                 650                 655

Leu Leu Cys Ser Gly Ser Ser Pro Ala Thr Ala Pro His Pro Leu
                660                 665                 670

Lys Met Phe Ala Cys Ser Lys Phe Val Ser Thr Pro Ser Leu Val Lys
                675                 680                 685

Ser Thr Ser Gln Leu Leu Ser Arg Pro Leu Ser Ala Val Val Leu Lys
690                 695                 700

Arg Pro Glu Ile Leu Thr Asp Glu Ser Leu Ser Ser Leu Ala Val Ser
705                 710                 715                 720

Cys Pro Leu Thr Ser Leu Val Ser Ser Arg Ser Phe Gln Thr Ser Ala
                725                 730                 735

Ile Ser Arg Asp Ile Asp Thr Ala Met Ala Ser Thr Arg Val Leu Ala
                740                 745                 750

Ser Arg Leu Ala Ser Gln Met Ala Ala Ser Ala Lys Val Ala Arg Pro
                755                 760                 765

Ala Val Arg Val Ala Gln Val Ser Lys Arg Thr Ile Gln Thr Gly Ser
770                 775                 780

Pro Leu Gln Thr Leu Lys Arg Thr Gln Met Thr Ser Ile Val Asn Ala
785                 790                 795                 800

Thr Thr Arg Gln Ala Phe Gln Lys Arg Ala
                805                 810

<210> SEQ ID NO 160
<211> LENGTH: 459
<212> TYPE: PRT
<213> ORGANISM: Homo sapiens

<400> SEQUENCE: 160

Met Leu Lys Leu Ile Val Pro Thr Ile Met Leu Leu Pro Leu Thr Trp
1               5                   10                  15

Leu Ser Lys Lys His Met Ile Trp Ile Asn Thr Thr His Ser Leu
                20                  25                  30

Ile Ile Ser Ile Ile Pro Leu Leu Phe Phe Asn Gln Ile Asn Asn Asn
                35                  40                  45

Leu Phe Ser Cys Ser Pro Thr Phe Ser Ser Asp Pro Leu Thr Thr Pro
    50                  55                  60

Leu Leu Met Leu Thr Thr Trp Leu Leu Pro Leu Thr Ile Met Ala Ser
65                  70                  75                  80

Gln Arg His Leu Ser Ser Glu Pro Leu Ser Arg Lys Lys Leu Tyr Leu
                85                  90                  95

Ser Met Leu Ile Ser Leu Gln Ile Ser Leu Ile Met Thr Phe Thr Ala
                100                 105                 110

Thr Glu Leu Ile Met Phe Tyr Ile Phe Phe Glu Thr Thr Leu Ile Pro
            115                 120                 125

Thr Leu Ala Ile Ile Thr Arg Trp Gly Asn Gln Pro Glu Arg Leu Asn
    130                 135                 140

Ala Gly Thr Tyr Phe Leu Phe Tyr Thr Leu Val Gly Ser Leu Pro Leu
145                 150                 155                 160

Leu Ile Ala Leu Ile Tyr Thr His Asn Thr Leu Gly Ser Leu Asn Ile
                165                 170                 175
```

Leu Leu Leu Thr Leu Thr Ala Gln Glu Leu Ser Asn Ser Trp Ala Asn
            180                 185                 190

Asn Leu Met Trp Leu Ala Tyr Thr Met Ala Phe Met Val Lys Met Pro
        195                 200                 205

Leu Tyr Gly Leu His Leu Trp Leu Pro Lys Ala His Val Glu Ala Pro
    210                 215                 220

Ile Ala Gly Ser Met Val Leu Ala Ala Val Leu Leu Lys Leu Gly Gly
225                 230                 235                 240

Tyr Gly Met Met Arg Leu Thr Leu Ile Leu Asn Pro Leu Thr Lys His
                245                 250                 255

Met Ala Tyr Pro Phe Leu Val Leu Ser Leu Trp Gly Met Ile Met Thr
            260                 265                 270

Ser Ser Ile Cys Leu Arg Gln Thr Asp Leu Lys Ser Leu Ile Ala Tyr
        275                 280                 285

Ser Ser Ile Ser His Met Ala Leu Val Val Thr Ala Ile Leu Ile Gln
    290                 295                 300

Thr Pro Trp Ser Phe Thr Gly Ala Val Ile Leu Met Ile Ala His Gly
305                 310                 315                 320

Leu Thr Ser Ser Leu Leu Phe Cys Leu Ala Asn Ser Asn Tyr Glu Arg
                325                 330                 335

Thr His Ser Arg Ile Met Ile Leu Ser Gln Gly Leu Gln Thr Leu Leu
            340                 345                 350

Pro Leu Met Ala Phe Trp Trp Leu Leu Ala Ser Leu Ala Asn Leu Ala
        355                 360                 365

Leu Pro Pro Thr Ile Asn Leu Leu Gly Glu Leu Ser Val Leu Val Thr
    370                 375                 380

Thr Phe Ser Trp Ser Asn Ile Thr Leu Leu Thr Gly Leu Asn Met
385                 390                 395                 400

Leu Val Thr Ala Leu Tyr Ser Leu Tyr Met Phe Thr Thr Gln Trp
                405                 410                 415

Gly Ser Leu Thr His His Ile Asn Asn Met Lys Pro Ser Phe Thr Arg
            420                 425                 430

Glu Asn Thr Leu Met Phe Met His Leu Ser Pro Ile Leu Leu Leu Ser
        435                 440                 445

Leu Asn Pro Asp Ile Ile Thr Gly Phe Ser Ser
    450                 455

<210> SEQ ID NO 161
<211> LENGTH: 174
<212> TYPE: PRT
<213> ORGANISM: Homo sapiens

<400> SEQUENCE: 161

Met Met Tyr Ala Leu Phe Leu Leu Ser Val Gly Leu Val Met Gly Phe
1               5                   10                  15

Val Gly Phe Ser Ser Lys Pro Ser Pro Ile Tyr Gly Gly Leu Val Leu
            20                  25                  30

Ile Val Ser Gly Val Val Gly Cys Val Ile Ile Leu Asn Phe Gly Gly
        35                  40                  45

Gly Tyr Met Gly Leu Met Val Phe Leu Ile Tyr Leu Gly Gly Met Met
    50                  55                  60

Val Val Phe Gly Tyr Thr Thr Ala Met Ala Ile Glu Glu Tyr Pro Glu
65                  70                  75                  80

Ala Trp Gly Ser Gly Val Glu Val Leu Val Ser Val Leu Val Gly Leu

```
                     85                  90                  95
Ala Met Glu Val Gly Leu Val Leu Trp Val Lys Glu Tyr Asp Gly Val
                100                 105                 110

Val Val Val Asn Phe Asn Ser Val Gly Ser Trp Met Ile Tyr Glu
            115                 120                 125

Gly Glu Gly Ser Gly Leu Ile Arg Glu Asp Pro Ile Gly Ala Gly Ala
        130                 135                 140

Leu Tyr Asp Tyr Gly Arg Trp Leu Val Val Thr Gly Trp Thr Leu
145                 150                 155                 160

Phe Val Gly Val Tyr Ile Val Ile Glu Ile Ala Arg Gly Asn
                165                 170

<210> SEQ ID NO 162
<211> LENGTH: 316
<212> TYPE: PRT
<213> ORGANISM: Homo sapiens

<400> SEQUENCE: 162

Met Ala Asn Leu Leu Leu Ile Val Pro Ile Leu Ile Ala Met Ala
1               5                   10                  15

Phe Leu Met Leu Thr Glu Arg Lys Ile Leu Gly Tyr Met Gln Leu Arg
            20                  25                  30

Lys Gly Pro Asn Val Val Gly Pro Tyr Gly Leu Leu Gln Pro Phe Ala
        35                  40                  45

Asp Ala Ile Lys Leu Phe Thr Lys Glu Pro Leu Lys Pro Ala Thr Ser
    50                  55                  60

Thr Ile Thr Leu Tyr Ile Thr Ala Pro Thr Leu Ala Leu Thr Ile Ala
65                  70                  75                  80

Leu Leu Leu Trp Thr Pro Leu Pro Met Pro Asn Pro Leu Val Asn Leu
                85                  90                  95

Asn Leu Gly Leu Leu Phe Ile Leu Ala Thr Ser Ser Leu Ala Val Tyr
            100                 105                 110

Ser Ile Leu Trp Ser Gly Trp Ala Ser Asn Ser Asn Tyr Ala Leu Ile
        115                 120                 125

Gly Ala Leu Arg Ala Val Ala Gln Thr Ile Ser Tyr Glu Val Thr Leu
    130                 135                 140

Ala Ile Ile Leu Leu Ser Thr Leu Leu Met Ser Gly Ser Phe Asn Leu
145                 150                 155                 160

Ser Thr Leu Ile Thr Thr Gln Glu His Leu Trp Leu Leu Pro Ser
                165                 170                 175

Trp Pro Leu Ala Met Met Trp Phe Ile Ser Thr Leu Ala Glu Thr Asn
            180                 185                 190

Arg Thr Pro Phe Asp Leu Ala Glu Gly Glu Ser Glu Leu Val Ser Gly
        195                 200                 205

Phe Asn Ile Glu Tyr Ala Ala Gly Pro Phe Ala Leu Phe Phe Met Ala
    210                 215                 220

Glu Tyr Thr Asn Ile Ile Met Met Asn Thr Leu Thr Thr Thr Ile Phe
225                 230                 235                 240

Leu Gly Thr Thr Tyr Asp Ala Leu Ser Pro Glu Leu Tyr Thr Thr Tyr
                245                 250                 255

Phe Val Thr Lys Thr Leu Leu Leu Thr Ser Leu Phe Leu Trp Ile Arg
            260                 265                 270

Thr Ala Tyr Pro Arg Phe Arg Tyr Asp Gln Leu Met His Leu Leu Trp
        275                 280                 285
```

-continued

```
Lys Asn Phe Leu Pro Leu Thr Leu Ala Leu Leu Met Trp Tyr Val Ser
    290                 295                 300
Met Pro Ile Thr Ile Ser Ser Ile Pro Pro Gln Thr
305                 310                 315
```